United States Patent
Keating et al.

(10) Patent No.: US 12,258,565 B2
(45) Date of Patent: Mar. 25, 2025

(54) COMPLEMENT COMPONENT C3 iRNA COMPOSITIONS AND METHODS OF USE THEREOF

(71) Applicant: Alnylam Pharmaceuticals, Inc., Cambridge, MA (US)

(72) Inventors: Mark Keating, Weston, MA (US); James D. McIninch, Burlington, MA (US); Elane Fishilevich, Rochester, MA (US); Kristina Yucius, Burlington, MA (US); Sarah Solomon, Cambridge, MA (US); Mark K. Schlegel, Boston, MA (US); Adam Castoreno, Framingham, MA (US); Charalambos Kaittanis, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 18/594,132

(22) Filed: Mar. 4, 2024

(65) Prior Publication Data
US 2024/0209369 A1    Jun. 27, 2024

Related U.S. Application Data

(60) Division of application No. 17/721,530, filed on Apr. 15, 2022, which is a continuation of application No. PCT/US2020/056563, filed on Oct. 21, 2020.

(60) Provisional application No. 62/924,210, filed on Oct. 22, 2019.

(51) Int. Cl.
C07H 21/04        (2006.01)
C12N 15/113       (2010.01)
C12N 15/66        (2006.01)

(52) U.S. Cl.
CPC ............ *C12N 15/113* (2013.01); *C12N 15/66* (2013.01); *C12N 2310/3125* (2013.01); *C12N 2310/315* (2013.01); *C12N 2310/321* (2013.01)

(58) Field of Classification Search
None
See application file for complete search history.

(56) References Cited

U.S. PATENT DOCUMENTS

| | | |
|---|---|---|
| 10,465,194 B2 | 11/2019 | Borodovsky et al. |
| 11,186,842 B2 | 11/2021 | Borodovsky et al. |
| 2003/0096775 A1 | 5/2003 | Graham et al. |
| 2007/0088154 A1 | 4/2007 | Khvorova et al. |
| 2007/0123484 A1 | 5/2007 | Bhat |
| 2008/0113351 A1 | 5/2008 | Naito et al. |
| 2009/0239814 A1 | 9/2009 | Manoharan et al. |
| 2009/0306178 A1 | 12/2009 | Bhat et al. |
| 2013/0217756 A1 | 8/2013 | Cancilla et al. |
| 2013/0281511 A1 | 10/2013 | Bettencourt et al. |
| 2016/0222389 A1 | 8/2016 | Grossman |
| 2017/0159055 A1 | 6/2017 | Prakash et al. |
| 2020/0263183 A1 | 8/2020 | Borodovsky et al. |
| 2020/0339998 A1 | 10/2020 | Borodovsky et al. |
| 2022/0364088 A1 | 11/2022 | Keating et al. |
| 2023/0257749 A1 | 8/2023 | McIninch et al. |
| 2023/0272382 A1 | 8/2023 | Keating et al. |
| 2024/0018515 A1 | 1/2024 | McIninch et al. |

FOREIGN PATENT DOCUMENTS

| | | |
|---|---|---|
| EP | 1752536 A1 | 2/2007 |
| WO | WO-2003/066805 A2 | 8/2003 |
| WO | WO-2006/047673 A2 | 5/2006 |
| WO | WO-2007/064846 A2 | 6/2007 |
| WO | WO-2007/089375 A2 | 8/2007 |
| WO | WO-2008/036841 A2 | 3/2008 |
| WO | WO-2010/048352 A2 | 4/2010 |
| WO | WO-2012/037254 A1 | 3/2012 |
| WO | WO-2013/067076 A2 | 5/2013 |
| WO | WO-2013/074974 A2 | 5/2013 |
| WO | WO-2014/107763 A1 | 7/2014 |
| WO | WO-2015/038939 A2 | 3/2015 |
| WO | WO-2015/089368 A2 | 6/2015 |
| WO | WO-2015/168635 A2 | 11/2015 |
| WO | WO-2017/040078 A1 | 3/2017 |
| WO | WO-2018/075373 A1 | 4/2018 |
| WO | WO-2019/027015 A1 | 2/2019 |
| WO | WO-2019/089922 A1 | 5/2019 |
| WO | WO-2020/104669 A1 | 5/2020 |
| WO | WO-2021/081026 A1 | 4/2021 |
| WO | WO-2021/178607 A1 | 9/2021 |
| WO | WO-2021/222549 A1 | 11/2021 |

(Continued)

OTHER PUBLICATIONS

U.S. Appl. No. 15/176,231 U.S. Pat. No. 10,465,194, filed Jun. 8, 2016 Nov. 5, 2019, US 20160298124, Granted.
U.S. Appl. No. 16/574,158 U.S. Pat. No. 11,186,842, filed Sep. 18, 2019 Nov. 30, 2021, US 20200263183, Granted.
U.S. Appl. No. 16/925,463, filed Jul. 10, 2020, US 20200339998, Abandoned.
U.S. Appl. No. 17/405,199, filed Aug. 18, 2021, US 20220213486, Abandoned.
U.S. Appl. No. 18/405,281, filed Jan. 5, 2024, Pending.
PCT/US2014/069951, Dec. 12, 2014, WO 2015/089368, Completed.
U.S. Appl. No. 16/760,593 U.S. Pat. No. 11,866,701, filed Apr. 30, 2020 Jan. 9, 2024, US 20210261959, Granted.
U.S. Appl. No. 18/519,295, filed Nov. 27, 2023, Pending.

(Continued)

*Primary Examiner* — Kimberly Chong
(74) *Attorney, Agent, or Firm* — McCarter & English, LLP; Maria Laccotripe Zacharakis; Deborah L. Nagle

(57) ABSTRACT

The present invention relates to RNAi agents, e.g., double stranded RNA (dsRNA) agents, targeting the complement component C3 gene (C3). The invention also relates to methods of using such RNAi agents to inhibit expression of a C3 gene and to methods of preventing and treating a C3-associated disorder, e.g., cold agglutinin disease (CAD), warm autoimmune hemolytic anemia, and paroxysmal nocturnal hemoglobinuria (PNH), lupus nephritis (LN), bullous pemphigoid, *pemphigus*, e.g., *pemphigus vulgaris* (PV) and *pemphigus foliaceus* (PF), and C3 glomerulopathy.

28 Claims, 10 Drawing Sheets
Specification includes a Sequence Listing.

(56) References Cited

FOREIGN PATENT DOCUMENTS

| WO | WO-2023/044370 A2 | 3/2023 |
| WO | WO-2023/076451 A1 | 5/2023 |

OTHER PUBLICATIONS

PCT/US2018/058705, Nov. 1, 2018, WO 2019/089922, Completed.
U.S. Appl. No. 17/721,530, filed Apr. 15, 2022, US 20220364088, Published.
PCT/US2021/029872, Apr. 29, 2021, WO 2021/222549, Completed.
PCT/US2021/020777, Mar. 4, 2021, WO 2021/178607, Completed.
PCT/US2022/076464, Sep. 15, 2022, WO 2023/044370, Published.
Watts et al., "Gene silencing by siRNAs and antisense oligonucleotides in the laboratory and the clinic", J Pathol 2012; 226: 365-379.
Bora et al., Complement activation via alternative pathway is critical in the development of laser-induced choroidal neovascularization: role of factor B and factor H. J Immunol. Aug. 1, 2006;177(3):1872-8.
Borodovsky et al., Development of RNAi Therapeutics Targeting the Complement Pathway. Blood. 2013;122(21)2471.
Cheng et al., [Effect of C5-siRNA silencing receptor C5 on myocardial ischemia injury in rats]. Nan Fang Yi Ke Da Xue Xue Bao. Jun. 2010;30(6):1486-8.
International Search Report and Written Opinion for Application No. PCT/US2014/069951, dated Jul. 6, 2015.
Zheng et al., "Preventing Renal Ischemia-Reperfusion Injury Using Small Interfering RNA by Targeting Complement 3 Gene," American Journal of Transplantation 2006; 6: 2099-2108.
Zheng et al., "Protection of Renal Ischemia Injury using Combination Gene Silencing of Complement 3 and Caspase 3 Genes," *Transplantation* 2006;82: 1781-1786.
International Search Report and Written Opinion from PCT/US2018/058705, mailed on Mar. 1, 2019.
Vickers et al., Efficient reduction of target RNAs by small interfering RNA and RNase H-dependent antisense agents. A comparative analysis. J Biol Chem. Feb. 28, 2003;278(9):7108-18.
International Search Report and Written Opinion from PCT/US2020/056563, mailed on Mar. 22, 2021.
International Search Report and Written Opinion from PCT/US2021/020777, mailed on Aug. 16, 2021.
Wang et al., "Protecting neurons from cerebral ischemia/reperfusion injury via nanoparticle-mediated delivery of an siRNA to inhibit microglial neurotoxicity", Biomaterials 161 (2018) 95-105.
Ricklin et al, "Complement component C3—The "Swiss Army Knife" of innate immunity and host defense", Immunol Rev. Nov. 2016:274(1):33-58.
Riihila, et al. "Complement Component C3 and Complement Factor B Promote Growth of Cutaneous Squamous Cell Carcinoma" Am. J. Path. 187(5):1186-1197, 2017.
Reynolds et al., Rational siRNA design for RNA interference. Nat Biotechnol. Mar. 2004;22(3):326-30.
PCT/US2020/056563, filed Oct. 21, 2020, WO 2021/081026, Completed.
U.S. Appl. No. 17/974,598, filed Oct. 27, 2022, US 20240018515, Published.
U.S. Appl. No. 17/900,919, filed Sep. 1, 2022, US 20230272382, Published.
U.S. Appl. No. 18/187,741 U.S. Pat. No. 11,965,166, filed Mar. 22, 2023 Apr. 23, 2024, US 20230257749, Granted.
U.S. Appl. No. 18/598,006, filed Mar. 7, 2024, Pending.
PCT/US2022/047987, Oct. 27, 2022, WO 2023/076451, Completed.

| Group# | Test Article | Number of Females | Dose (mg/kg) |
|---|---|---|---|
| 1 | AD-565541 | 3 | 3 |
| 2 | AD-569164 | 3 | 3 |
| 3 | AD-569272 | 3 | 3 |
| 4 | AD-567315 | 3 | 3 |
| 5 | AD-567700 | 3 | 3 |
| 6 | AD-571298 | 3 | 3 |
| 7 | AD-569164 | 3 | 25 |
| 8 | AD-567315 | 3 | 25 |

- Dosing on Day 1 for Groups 1-5; Dosing on Day 71 for Groups 6-8
- Observation: 1 animal from group 3 had hunched posture & decreased activity at day 35
- Group 8: 1 animal euthanized due to moribund

FIG. 5

| Group# | Test Article | Number of Females | Dose (mg/kg) |
|---|---|---|---|
| 1 | AD-564742 | 2 | 3 |
| 2 | AD-567066 | 2 | 3 |
| 3 | AD-567304 | 2 | 3 |
| 4 | AD-568586 | 2 | 3 |
| 5 | AD-568978 | 2 | 3 |
| 6 | AD-570714 | 2 | 3 |
| 7 | AD-571826 | 2 | 3 |
| 8 | AD-572040 | 2 | 3 |
| 9 | AD-572110 | 2 | 3 |
| 10 | AD-572387 | 2 | 3 |

Group 6 was dosed again at 3mg/kg on day 55

FIG. 7

| Group No. | siRNA | Day(s) of Dosing | Dose (mg/kg) | Liver biopsy |
|---|---|---|---|---|
| 1 | AD-1181519 | Day 1 | 3 | |
| 2 | AD-1181519 | Day 1 | 9 | |
| 3 | AD-1181519 | Days 1, 29, and 57 | 3 x 3 | |
| 4 | AD-569268 | Day 1 | 3 | |
| 5 | AD-569268 | Day 1 | 9 | |
| 6 | AD-569268 | Days 1, 29, and 57 | 3 x 3 | |
| 7 | AD-570714 | Day 1 | 3 | |
| 8 | AD-570714 | Day 1 | 9 | |
| 9 | AD-570714 | Days 1, 29, and 57 | 3 x 3 | |
| 10 | AD-570714 | Day 1 | 25 | Day -21 and 29 |

FIG. 9

COMPLEMENT COMPONENT C3 iRNA COMPOSITIONS AND METHODS OF USE THEREOF

RELATED APPLICATIONS

This application is a divisional of Ser. No. 17/721,530, filed on Apr. 15, 2022, which is a 35 § U.S.C. 111 (a) continuation application which claims the benefit of priority to PCT/US2020/056563, filed on Oct. 21, 2020, which claims the benefit of priority to U.S. Provisional Application No. 62/924,210, filed on Oct. 22, 2019. The entire contents of each of the foregoing applications are incorporated herein by reference.

SEQUENCE LISTING

The instant application contains a Sequence Listing which has been filed electronically in XML file format and is hereby incorporated by reference in its entirety. Said XML copy, created on Mar. 1, 2024, is named 121301_10503_SL.xml and is 28,525,134 bytes in size.

BACKGROUND OF THE INVENTION

Complement was first discovered in the 1890s when it was found to aid or "complement" the killing of bacteria by heat-stable antibodies present in normal serum (Walport, M. J. (2001) *N Engl J Med.* 344:1058). The complement system consists of more than 30 proteins that are either present as soluble proteins in the blood or are present as membrane-associated proteins. Activation of complement leads to a sequential cascade of enzymatic reactions, known as complement activation pathways resulting in the formation of the potent anaphylatoxins C3a and C5a that elicit a plethora of physiological responses that range from chemoattraction to apoptosis. Initially, complement was thought to play a major role in innate immunity where a robust and rapid response is mounted against invading pathogens. However, recently it is becoming increasingly evident that complement also plays an important role in adaptive immunity involving T and B cells that help in elimination of pathogens (Dunkelberger J R and Song W C. (2010) *Cell Res.* 20:34; Molina H, et al. (1996) *Proc Natl Acad Sci USA.* 93:3357), in maintaining immunologic memory preventing pathogenic re-invasion, and is involved in numerous human pathological states (Qu, H, et al. (2009) *Mol Immunol.* 47:185; Wagner, E. and Frank M M. (2010) *Nat Rev Drug Discov.* 9:43).

Complement activation is known to occur through three different pathways: alternate, classical and lectin (FIG. 1) involving proteins that mostly exist as inactive zymogens that are then sequentially cleaved and activated.

The classical pathway is often activated by antibody-antigen complexes or by the C-reactive protein (CRP), both of which interact with complement component C1q. In addition, the classical pathway can be activated by phosphatidyl serine present in apoptotic bodies in the absence of immune complexes.

The lectin pathway is initiated by the mannose-binding lectins (MBL) that bind to complex carbohydrate residues on the surface of pathogens. The activation of the classical pathway or the lectin pathway leads to activation of the (C4b2b) C3 convertase.

The alternate pathway is activated by the binding of C3b, which is spontaneously generated by the hydrolysis of C3, on targeted surfaces. This surface-bound C3b is then recognized by factor B, forming the complex C3bB. The C3bB complex, in turn, is cleaved by factor D to yield the active form of the C3 convertase of the AP (C3bBb). Both types of C3 convertases will cleave C3, forming C3b. C3b then either binds to more factor B, enhancing the complement activation through the AP (the so-called alternative or amplification loop), or leads to the formation of the active C5 convertase (C3bBbC3b or C4bC2bC3b), which cleaves C5 and triggers the late events that result in the formation of the membrane attack complex (MAC) (C5b-9).

Inappropriate activation of the complement system is responsible for propagating and/or initiating pathology in many different diseases, including, for example, paroxysmal nocturnal hemoglobinuria (PNH), atypical hemolytic uremic syndrome (aHUS), neuromyelitis optica (NMO), multifocal motor neuropathy (MMN), myasthenia gravis (MG), C3 glomerulonephritis, systemic lupus erythmatosis, rheumatoid arthritis, ischemia-reperfusion injuries and neurodegenerative diseases.

There are limited therapies available for the treatment of complement component C3-associated diseases which require time-consuming and invasive administration at a high cost. Accordingly, there is a need in the art for alternative therapies and combination therapies for subjects having a complement component C3-associated disease.

SUMMARY OF THE INVENTION

The present invention provides iRNA compositions which affect the RNA-induced silencing complex (RISC)-mediated cleavage of RNA transcripts of a gene encoding complement component C3. The complement component C3 may be within a cell, e.g., a cell within a subject, such as a human subject.

In an aspect, the invention provides a double stranded ribonucleic acid (dsRNA) agent for inhibiting expression of complement component C3 in a cell, wherein the dsRNA agent comprises a sense strand and an antisense strand forming a double stranded region, wherein the sense strand comprises at least 15 contiguous nucleotides differing by no more than 0, 1, 2, or 3 nucleotides from the nucleotide sequence of SEQ ID NO:1 and the antisense strand comprises at least 15 contiguous nucleotides differing by no more than 1, 2, or 3 nucleotides from the nucleotide sequence of SEQ ID NO:5.

In another aspect, the present invention provides a double stranded ribonucleic acid (dsRNA) for inhibiting expression of complement component C3 in a cell, wherein said dsRNA comprises a sense strand and an antisense strand forming a double stranded region, wherein the antisense strand comprises a region of complementarity to an mRNA encoding complement component C3, and wherein the region of complementarity comprises at least 15 contiguous nucleotides differing by no more than 0, 1, 2, or 3 nucleotides from any one of the antisense nucleotide sequences in any one of Tables 2-7, 15, 18, 20-23, 30, and 31.

In one aspect, the present invention provides a double stranded ribonucleic acid (dsRNA) for inhibiting expression of complement component C3 in a cell, wherein said dsRNA comprises a sense strand and an antisense strand forming a double stranded region, wherein the sense strand comprises at least 15 contiguous nucleotides differing by no more than 0, 1, 2, or 3 nucleotides from any one of the nucleotide sequence of nucleotides 475-497, 487-509, 490-512, 491-513, 705-727, 809-831, 813-835, 1147-1169, 1437-1459, 1439-1461, 1447-1469, 2596-2618, 2634-2656, 3012-3034, 3334-3356, 3611-3633, 3614-3636, 3622-3655, 3809-3831, 3846-3868, 3847-3869, 3920-3942, 4047-4069, 4061-4083, 4156-4178, 4157-4177, 4162-4184, 4178-4200, 4226-4248, 4369-4391, 4392-4414, 4521-4543, 4522-4544, 4523-4545, 5012-5034 of the nucleotide sequence of SEQ ID NO:1, and the antisense strand comprises at least 19 contiguous nucleotides from the corresponding nucleotide sequence of SEQ ID NO:5.

In one embodiment, the sense strand comprises at least 15 contiguous nucleotides differing by no more than 0, 1, 2, or 3 nucleotides from any one of the nucleotide sequence of nucleotides 705-727, 809-831, or 634-2656 of SEQ ID NO:1. In another embodiment, the sense strand comprises at least 15 contiguous nucleotides differing by no more than 0, 1, 2, or 3 nucleotides from the nucleotide sequence of nucleotides 634-2656 of SEQ ID NO:1.

In one embodiment, the antisense strand comprises at least 15 contiguous nucleotides differing by nor more than 0, 1, 2, or 3 nucleotides from any one of the antisense strand nucleotide sequences of a duplex selected from the group consisting of AD-565541.2, AD-564742, AD-567304, AD-568978, AD-569164, AD-569272.2, AD-569765.2, AD-564730.2, AD-567315, AD-564745.2, AD-571715.2, AD-570714, AD-571826, AD-572041.2, AD-572039.2, AD-572387, AD-568586.2, AD-566837.2, AD-566444.2, AD-567700.2, AD-567814.2, AD-568003.2, AD-569164.2, AD-569763.2, AD-565281.2, AD-571539.2, AD-572389.2, AD-567315.2, AD-571752.2, AD-568026.2, AD-571298, AD-572110.2, AD-572062.2, AD-572388.2, AD-572040.2, AD-567713.2, AD-567521.2, AD-567066.2, AD-1181519, AD-569268, or AD-570714.

In one embodiment, the antisense strand comprises at least 15 contiguous nucleotides differing by nor more than 0, 1, 2, or 3 nucleotides from any one of the antisense strand nucleotide sequences of a duplex selected from the group consisting of AD-1181519, AD-569268, or AD-570714. In another embodiment, the antisense strand comprises at least 15 contiguous nucleotides differing by nor more than 0, 1, 2, or 3 nucleotides from the antisense strand nucleotide sequences of a AD-570714.

In one embodiment, the dsRNA agent comprises at least one modified nucleotide.

In one embodiment, substantially all of the nucleotides of the sense strand; substantially all of the nucleotides of the antisense strand comprise a modification; or substantially all of the nucleotides of the sense strand and substantially all of the nucleotides of the antisense strand comprise a modification.

In one embodiment, all of the nucleotides of the sense strand comprise a modification; all of the nucleotides of the antisense strand comprise a modification; or all of the nucleotides of the sense strand and all of the nucleotides of the antisense strand comprise a modification.

In one embodiment, at least one of the modified nucleotides is selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, a nucleotide comprising a 5'-phosphate mimic, a thermally destabilizing nucleotide, a glycol modified nucleotide (GNA), and a 2-O—(N-methylacetamide) modified nucleotide; and combinations thereof.

In one embodiment, the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, and glycol; and combinations thereof.

In one embodiment, at least one of the modified nucleotides is selected from the group consisting of a deoxy-nucleotide, a 2'-O-methyl modified nucleotide, a 2'-fluoro modified nucleotide, a 2'-deoxy-modified nucleotide, a glycol modified nucleotide (GNA), e.g., Ggn, Cgn, Tgn, or Agn, and, a vinyl-phosphonate nucleotide; and combinations thereof.

In another embodiment, at least one of the modifications on the nucleotides is a thermally destabilizing nucleotide modification.

In one embodiment, the thermally destabilizing nucleotide modification is selected from the group consisting of an abasic modification; a mismatch with the opposing nucleotide in the duplex; and destabilizing sugar modification, a 2'-deoxy modification, an acyclic nucleotide, an unlocked nucleic acids (UNA), and a glycerol nucleic acid (GNA)

The double stranded region may be 19-30 nucleotide pairs in length; 19-25 nucleotide pairs in length; 19-23 nucleotide pairs in length; 23-27 nucleotide pairs in length; or 21-23 nucleotide pairs in length.

In one embodiment, each strand is independently no more than 30 nucleotides in length.

In one embodiment, the sense strand is 21 nucleotides in length and the antisense strand is 23 nucleotides in length.

The region of complementarity may be at least 17 nucleotides in length; between 19 and 23 nucleotides in length; or 19 nucleotides in length.

In one embodiment, at least one strand comprises a 3' overhang of at least 1 nucleotide. In another embodiment, at least one strand comprises a 3' overhang of at least 2 nucleotides.

In one embodiment, the dsRNA agent further comprises a ligand.

In one embodiment, the ligand is conjugated to the 3' end of the sense strand of the dsRNA agent.

In one embodiment, the ligand is an N-acetylgalactosamine (GalNAc) derivative.

In one embodiment, the ligand is one or more GalNAc derivatives attached through a monovalent, bivalent, or trivalent branched linker.

In one embodiment the ligand is

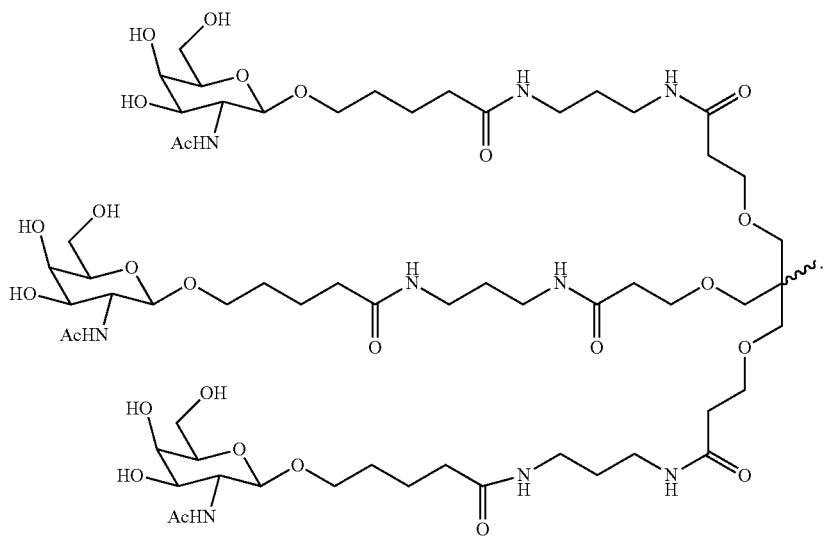 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the dsRNA agent is conjugated to the ligand as shown in the following schematic

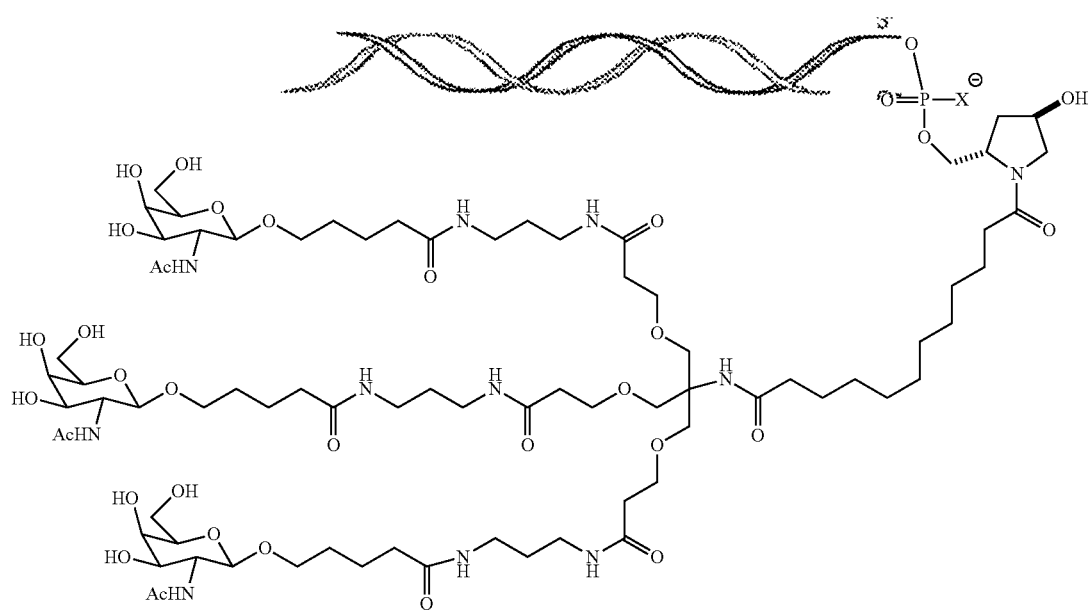

and, wherein X is O or S.

In one embodiment, the X is O.

In one embodiment, the dsRNA agent further comprises at least one phosphorothioate or methylphosphonate internucleotide linkage.

In one embodiment, the phosphorothioate or methylphosphonate internucleotide linkage is at the 3'-terminus of one strand, e.g., the antisense strand or the sense strand.

In another embodiment, the phosphorothioate or methylphosphonate internucleotide linkage is at the 5'-terminus of one strand, e.g., the antisense strand or the sense strand.

In one embodiment, the phosphorothioate or methylphosphonate internucleotide linkage is at the both the 5'- and 3'-terminus of one strand. In one embodiment, the strand is the antisense strand.

In one embodiment, the base pair at the 1 position of the 5'-end of the antisense strand of the duplex is an AU base pair.

The present invention also provides cells containing any of the dsRNA agents of the invention and pharmaceutical compositions comprising any of the dsRNA agents of the invention.

The pharmaceutical composition of the invention may include dsRNA agent in an unbuffered solution, e.g., saline or water, or the pharmaceutical composition of the invention may include the dsRNA agent is in a buffer solution, e.g., a buffer solution comprising acetate, citrate, prolamine, carbonate, or phosphate or any combination thereof; or phosphate buffered saline (PBS).

In one aspect, the present invention provides a method of inhibiting expression of a complement component C3 gene in a cell. The method includes contacting the cell with any of the dsRNAs of the invention or any of the pharmaceutical compositions of the invention, thereby inhibiting expression of the complement component C3 gene in the cell.

In one embodiment, the cell is within a subject, e.g., a human subject, e.g., a subject having a complement component C3-associated disorder, such as a complement component C3-associated disorder selected from the group consisting of cold agglutinin disease (CAD), warm autoimmune hemolytic anemia, and paroxysmal nocturnal hemoglobinuria (PNH), lupis nephritis (LN), bullous pemphigoid, *pemphigus*, e.g., *pemphigus vulgaris* (PV) and *pemphigus foliaceus* (PF), and C3 glomerulopathy.

In one embodiment, contacting the cell with the dsRNA agent inhibits the expression of complement component C3 by at least 50%, 60%, 70%, 80%, 90%, or 95%.

In one embodiment, inhibiting expression of complement component C3 decreases complement component C3 protein level in serum of the subject by at least 50%, 60%, 70%, 80%, 90%, or 95%.

In one aspect, the present invention provides a method of treating a subject having a disorder that would benefit from reduction in complement component C3 expression. The method includes administering to the subject a therapeutically effective amount of any of the dsRNAs of the invention or any of the pharmaceutical compositions of the invention, thereby treating the subject having the disorder that would benefit from reduction in complement component C3 expression.

In another aspect, the present invention provides a method of preventing at least one symptom in a subject having a disorder that would benefit from reduction in complement component C3 expression. The method includes administering to the subject a prophylactically effective amount of any of the dsRNAs of the invention or any of the pharmaceutical compositions of the invention, thereby preventing at least one symptom in the subject having the disorder that would benefit from reduction in complement component C3 expression.

In one embodiment, the disorder is a complement component C3-associated disorder, e.g., a complement component C3-associated disorder is selected from the group consisting of cold agglutinin disease (CAD), warm autoimmune hemolytic anemia, and paroxysmal nocturnal hemoglobinuria (PNH), lupis nephritis (LN), bullous pemphigoid, *pemphigus*, e.g., *pemphigus vulgaris* (PV) and *pemphigus foliaceus* (PF), and C3 glomerulopathy.

In one embodiment, the complement component C3-associated disorder is cold agglutinin disease (CAD).

In one embodiment, the subject is human.

In one embodiment, the administration of the agent to the subject causes a decrease in hemolysis and/or a decrease in C3 protein accumulation.

In one embodiment, the dsRNA agent is administered to the subject at a dose of about 0.01 mg/kg to about 50 mg/kg.

In one embodiment, the dsRNA agent is administered to the subject subcutaneously.

In one embodiment, the methods of the invention include further determining the level of complement component C3 in a sample(s) from the subject.

In one embodiment, the level of complement component C3 in the subject sample(s) is a complement component C3 protein level in a blood or serum sample(s).

In one embodiment, the methods of the invention further include administering to the subject an additional therapeutic agent for treatment of hemolysis.

The present invention also provides kits comprising any of the dsRNAs of the invention or any of the pharmaceutical compositions of the invention, and optionally, instructions for use.

BRIEF DESCRIPTION OF THE DRAWINGS

FIG. 5 is a Table depicting the treatment groups of *Cynomolgus* monkeys subcutaneously administered a single 3 mg/kg or 25 mg/kg dose of the indicated dsRNA duplexes.

FIG. 7 is a Table depicting the treatment groups of *Cynomolgus* monkeys subcutaneously administered a single 3 mg/kg dose of the indicated dsRNA duplexes.

FIG. 9 is a Table depicting the treatment groups and timing of administration and biopsy of *Cynomolgus* monkeys subcutaneously administered a single 3 mg/kg, 9 mg/kg, or 25 mg/kg dose, or a multi-dose of 3 mg/kg (3×3) of the indicated dsRNA duplexes.

DETAILED DESCRIPTION OF THE INVENTION

Figure 1:
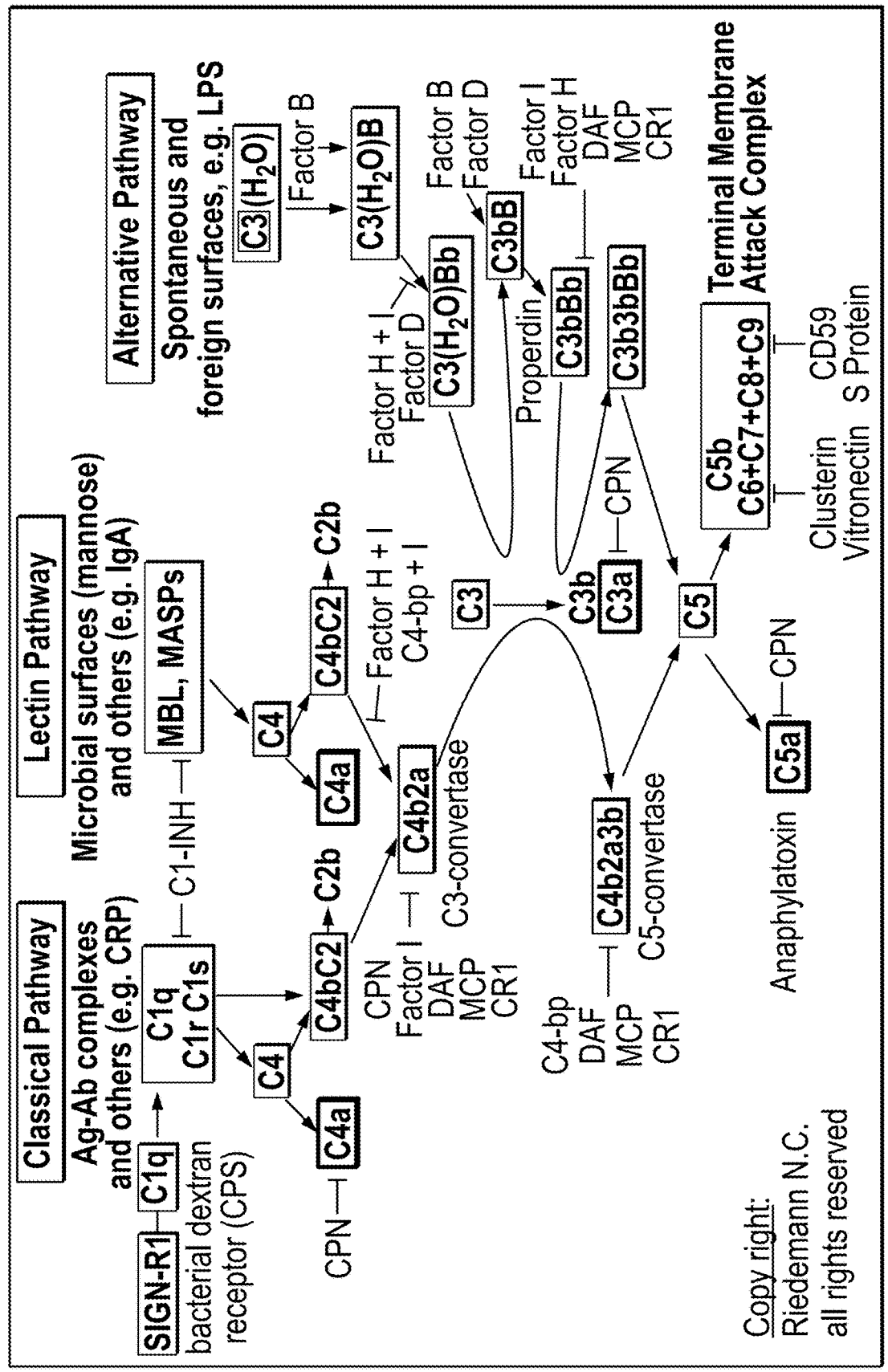
FIG. 1 schematically depicts the three complement pathways: alternative, classical and lectin.

The present invention provides iRNA compositions which effect the RNA-induced silencing complex (RISC)-mediated cleavage of RNA transcripts of a complement component C3 gene. The gene may be within a cell, e.g., a cell within a subject, such as a human. The use of these iRNAs enables the targeted degradation of mRNAs of the corresponding gene (complement component C3 gene) in mammals.

The iRNAs of the invention have been designed to target the human complement component C3 gene, including portions of the gene that are conserved in the complement component C3 orthologs of other mammalian species. Without intending to be limited by theory, it is believed that a combination or sub-combination of the foregoing properties and the specific target sites or the specific modifications in these iRNAs confer to the iRNAs of the invention improved efficacy, stability, potency, durability, and safety.

Accordingly, the present invention provides methods for treating and preventing a complement component C3-associated disorder, e.g., cold agglutinin disease (CAD), warm autoimmune hemolytic anemia, and paroxysmal nocturnal hemoglobinuria (PNH), lupis nephritis (LN), bullous pemphigoid, *pemphigus*, e.g., *pemphigus vulgaris* (PV) and *pemphigus foliaceus* (PF), and C3 glomerulopathy, using iRNA compositions which effect the RNA-induced silencing complex (RISC)-mediated cleavage of RNA transcripts of a complement component C3 gene.

The iRNAs of the invention include an RNA strand (the antisense strand) having a region which is up to about 30 nucleotides or less in length, e.g., 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of a complement component C3 gene.

In certain embodiments, one or both of the strands of the double stranded RNAi agents of the invention is up to 66 nucleotides in length, e.g., 36-66, 26-36, 25-36, 31-60, 22-43, 27-53 nucleotides in length, with a region of at least 19 contiguous nucleotides that is substantially complementary to at least a part of an mRNA transcript of a complement component C3 gene. In some embodiments, such iRNA agents having longer length antisense strands preferably may include a second RNA strand (the sense strand) of 20-60 nucleotides in length wherein the sense and antisense strands form a duplex of 18-30 contiguous nucleotides.

The use of iRNAs of the invention enables the targeted degradation of mRNAs of the corresponding gene (complement component C3 gene) in mammals. Using in vitro and in vivo assays, the present inventors have demonstrated that iRNAs targeting a C3 gene can potently mediate RNAi, resulting in significant inhibition of expression of a C3 gene. Thus, methods and compositions including these iRNAs are useful for treating a subject having a complement component C3-associated disorder, e.g., cold agglutinin disease (CAD), warm autoimmune hemolytic anemia, and paroxysmal nocturnal hemoglobinuria (PNH), lupis nephritis (LN), bullous pemphigoid, *pemphigus*, e.g., *pemphigus vulgaris* (PV) and *pemphigus foliaceus* (PF), and C3 glomerulopathy.

Accordingly, the present invention provides methods and combination therapies for treating a subject having a disorder that would benefit from inhibiting or reducing the expression of a C3 gene, e.g., a complement component C3-associated disease, such as cold agglutinin disease (CAD), warm autoimmune hemolytic anemia, and paroxysmal nocturnal hemoglobinuria (PNH), lupis nephritis (LN), bullous pemphigoid, *pemphigus*, e.g., *pemphigus vulgaris* (PV) and *pemphigus foliaceus* (PF), and C3 glomerulopathy, using iRNA compositions which effect the RNA-induced silencing complex (RISC)-mediated cleavage of RNA transcripts of a C3 gene.

The present invention also provides methods for preventing at least one symptom in a subject having a disorder that would benefit from inhibiting or reducing the expression of a C3 gene, e.g., cold agglutinin disease (CAD), warm autoimmune hemolytic anemia, and paroxysmal nocturnal hemoglobinuria (PNH), lupis nephritis (LN), bullous pemphigoid, *pemphigus*, e.g., *pemphigus vulgaris* (PV) and *pemphigus foliaceus* (PF), and C3 glomerulopathy.

For example, in a subject having cold agglutinin disease (CAD), the methods of the present invention may prevent at least one symptom in the subject including, e.g., hemolysis, MAC deposition and tissue damage, inflammation (e.g., chronic inflammation); in a subject having warm autoimmune hemolytic anemia, the methods of the present invention may prevent at least one symptom in the subject including, e.g., hemolysis, inflammation (e.g., chronic inflammation), and MAC tissue damage; in a subject having paroxysmal nocturnal hemoglobinuria (PNH), the methods of the present invention may prevent at least one symptom in the subject including, e.g., hemolysis, inflammation (e.g., chronic inflammation), thrombosis, and deficient hematopoiesis; in a subject having lupis nephritis (LN), the methods of the present invention may prevent at least one symptom in the subject including, e.g., inflammation (e.g., chronic inflammation), hematuria, proteinuria, edema, hypertension, and renal failure; in a subject having bullous pemphigoid, the methods of the present invention may prevent at least one symptom in the subject including, e.g., blister formation, inflammation (e.g., chronic inflammation), C3 deposition, and MAC tissue damage; in a subject having *pemphigus*, e.g., *pemphigus vulgaris* (PV) and *pemphigus foliaceus* (PF), the methods of the present invention may prevent at least one symptom in the subject including, e.g., blister formation, inflammation (e.g., chronic inflammation), C3 deposition, and MAC tissue damage; and in a subject having C3 glomerulopathy, the methods of the present invention may prevent at least one symptom in the subject including, e.g., inflammation (e.g., chronic inflammation), hematuria, proteinuria, edema, hypertension, and renal failure.

The following detailed description discloses how to make and use compositions containing iRNAs to inhibit the expression of a complement component C3 gene as well as compositions, uses, and methods for treating subjects that would benefit from inhibition and/or reduction of the expression of a complement component C3 gene, e.g., subjects susceptible to or diagnosed with a complement component C3-associated disorder.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise. For example, "sense strand or antisense strand" is understood as "sense strand or antisense strand or sense strand and antisense strand."

The term "about" is used herein to mean within the typical ranges of tolerances in the art. For example, "about" can be understood as about 2 standard deviations from the mean. In certain embodiments, about means±10%. In certain embodiments, about means±5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 19 nucleotides of a 21 nucleotide nucleic acid molecule" means that 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range. As used herein, ranges include both the upper and lower limit.

In the event of a conflict between a sequence and its indicated site on a transcript or other sequence, the nucleotide sequence recited in the specification takes precedence.

As used herein, the term "Complement Component 3," used interchangeably with the term "C3," refers to the well-known gene and polypeptide, also known in the art as ARMD9, C3a Anaphylatoxin, ASP, Complement Component C3a, C3a, Complement Component C3b, C3b, prepro-C3, Acylation-Stimulating Protein Cleavage Product, CPAMD1, Complement C3, C3 And PZP-Like Alpha-2-Macroglobulin Domain-Containing Protein 1, Complement Component C3, and AHUS5. The term "C3" includes human C3, the amino acid and nucleotide sequence of which may be found in, for example, GenBank Accession No. NM_000064.3 (GI:726965399; SEQ ID NO:1); mouse C3, the amino acid and nucleotide sequence of which may be found in, for example, GenBank Accession No. NM_009778.3 (GI:773669943; SEQ ID NO:2); and rat C3, the amino acid and nucleotide sequence of which may be found in, for example, GenBank Accession No. NM_016994.2 (GI:158138560; SEQ ID NO:3).

The term "C3" also includes *Macaca fascicularis* C3, the amino acid and nucleotide sequence of which may be found in, for example, GenBank Accession No. XM_005587719.2 (GI:982312947; SEQ ID NO:4) and in the entry for the gene, ENSP00000245907 (locus=chr19:6921416:6963034), in the Macaca genome project web site (http://macaque.genomics.org.cn/page/species/index.jsp).

Additional examples of C3 mRNA sequences are readily available using, e.g., GenBank, UniProt, OMIM, and the Macaca genome project web site.

Exemplary C3 nucleotide sequences may also be found in SEQ ID NOs:1-8. SEQ ID NOs:5-8 are the reverse complement sequences of SEQ ID NOs:1-4, respectively.

Further information on C3 is provided, for example in the NCBI Gene database at http://www.ncbi.nlm.nih.gov/gene/718.

The entire contents of each of the foregoing GenBank Accession numbers and the Gene database numbers are incorporated herein by reference as of the date of filing this application.

The terms "complement component C3" and "C3," as used herein, also refers to naturally occurring DNA sequence variations of the C3 gene. Numerous sequence variations within the C3 gene have been identified and may be found at, for example, NCBI dbSNP and UniProt (see, e.g., http://www.ncbi.nlm.nih.gov/snp?LinkName=gene_snp&from_uid=718, the entire contents of which is incorporated herein by reference as of the date of filing this application.

As used herein, "target sequence" refers to a contiguous portion of the nucleotide sequence of an mRNA molecule formed during the transcription of a complement component C3 gene, including mRNA that is a product of RNA processing of a primary transcription product. The target portion of the sequence will be at least long enough to serve as a substrate for iRNA-directed cleavage at or near that portion of the nucleotide sequence of an mRNA molecule formed during the transcription of a complement component C3 gene. In one embodiment, the target sequence is within the protein coding region of complement component C3.

The target sequence may be from about 19-36 nucleotides in length, e.g., preferably about 19-30 nucleotides in length. For example, the target sequence can be about 19-30 nucleotides, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T," and "U" each generally stand for a nucleotide that contains guanine, cytosine, adenine, thymidine, and uracil as a base, respectively. However, it will be understood that the term "ribonucleotide" or "nucleotide" can also refer to a modified nucleotide, as further detailed below, or a surrogate replacement moiety (see, e.g., Table 1). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of a complement component C3 gene in a cell, e.g., a cell within a subject, such as a mammalian subject.

In one embodiment, an RNAi agent of the invention includes a single stranded RNA that interacts with a target RNA sequence, e.g., a complement component C3 target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., a complement component C3 gene. Accordingly, the term "siRNA" is also used herein to refer to an iRNA as described above.

In certain embodiments, the RNAi agent may be a single-stranded siRNA (ssRNAi) that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150:883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150:883-894.

In certain embodiments, an "iRNA" for use in the compositions, uses, and methods of the invention is a double stranded RNA and is referred to herein as a "double stranded RNA agent," "double stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a complement component C3 gene. In some embodiments of the invention, a double stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide or a modified nucleotide. In addition, as used in this specification, an "iRNA" may include ribonucleotides with chemical modifications; an iRNA may include substantial modifications at multiple nucleotides. As used herein, the term "modified nucleotide" refers to a nucleotide having, independently, a modified sugar moiety, a modified internucleotide linkage, or modified nucleobase, or any combination thereof. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "iRNA" or "RNAi agent" for the purposes of this specification and claims.

The duplex region may be of any length that permits specific degradation of a desired target RNA through a RISC pathway, and may range from about 19 to 36 base pairs in length, e.g., about 19-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, 3, 4, 5, 6, 7, 8, 9, 10, 20, 23 or more unpaired nucleotides. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides.

Where the two substantially complementary strands of a dsRNA are comprised by separate RNA molecules, those molecules need not be, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In certain embodiments, an iRNA agent of the invention is a dsRNA, each strand of which comprises 19-23 nucleotides, that interacts with a target RNA sequence, e.g., a complement component C3 gene, to direct cleavage of the target RNA.

In some embodiments, an iRNA of the invention is a dsRNA of 24-30 nucleotides that interacts with a target RNA sequence, e.g., a complement component C3 target mRNA sequence, to direct the cleavage of the target RNA.

As used herein, the term "nucleotide overhang" refers to at least one unpaired nucleotide that protrudes from the duplex structure of a double stranded iRNA. For example, when a 3-end of one strand of a dsRNA extends beyond the 5-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5'-end, 3'-end, or both ends of either an antisense or sense strand of a dsRNA.

In certain embodiments, the antisense strand of a dsRNA has a 1-10 nucleotides, e.g., a 1, 2, 3, 4, 5, 6, 7, 8, 9, or 10 nucleotide, overhang at the 3'-end or the 5'-end. In certain embodiments, the overhang on the sense strand or the antisense strand, or both, can include extended lengths longer than 10 nucleotides, e.g., 1-30 nucleotides, 2-30 nucleotides, 10-30 nucleotides, 10-25 nucleotides, 10-20 nucleotides, or 10-15 nucleotides in length. In certain embodiments, an extended overhang is on the sense strand of the duplex. In certain embodiments, an extended overhang is present on the 3' end of the sense strand of the duplex. In certain embodiments, an extended overhang is present on the 5' end of the sense strand of the duplex. In certain embodiments, an extended overhang is on the antisense strand of the duplex. In certain embodiments, an extended overhang is present on the 3' end of the antisense strand of the duplex. In certain embodiments, an extended overhang is present on the 5' end of the antisense strand of the duplex. In certain embodiments, one or more of the nucleotides in the extended overhang is replaced with a nucleoside thiophosphate. In certain embodiments, the overhang includes a self-complementary portion such that the overhang is capable of forming a hairpin structure that is stable under physiological conditions.

"Blunt" or "blunt end" means that there are no unpaired nucleotides at that end of the double stranded RNA agent, i.e., no nucleotide overhang. A "blunt ended" double stranded RNA agent is double stranded over its entire length, i.e., no nucleotide overhang at either end of the molecule. The RNAi agents of the invention include RNAi agents with no nucleotide overhang at one end (i.e., agents with one overhang and one blunt end) or with no nucleotide overhangs at either end. Most often such a molecule will be double-stranded over its entire length.

The term "antisense strand" or "guide strand" refers to the strand of an iRNA, e.g., a dsRNA, which includes a region that is substantially complementary to a target sequence, e.g., a complement component C3 mRNA.

As used herein, the term "region of complementarity" refers to the region on the antisense strand that is substantially complementary to a sequence, for example a target sequence, e.g., a complement component C3 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, or 3 nucleotides of the 5'- or 3'-end of the iRNA. In some embodiments, a double stranded RNA agent of the invention includes a nucleotide mismatch in the antisense strand. In some embodiments, the antisense strand of the double stranded RNA agent of the invention includes no more than 4 mismatches with the target mRNA, e.g., the antisense strand includes 4, 3, 2, 1, or 0 mismatches with the target mRNA. In some embodiments, the antisense strand double stranded RNA agent of the invention includes no more than 4 mismatches with the sense strand, e.g., the antisense strand includes 4, 3, 2, 1, or 0 mismatches with the sense strand. In some embodiments, a double stranded RNA agent of the invention includes a nucleotide mismatch in the sense strand. In some embodiments, the sense strand of the double stranded RNA agent of the invention includes no more than 4 mismatches with the antisense strand, e.g., the sense strand includes 4, 3, 2, 1, or 0 mismatches with the antisense strand. In some embodiments, the nucleotide mismatch is, for example, within 5, 4, 3 nucleotides from the 3'-end of the iRNA. In another embodiment, the nucleotide mismatch is, for example, in the 3'-terminal nucleotide of the iRNA agent. In some embodiments, the mismatch(s) is not in the seed region.

Thus, an RNAi agent as described herein can contain one or more mismatches to the target sequence. In one embodiment, a RNAi agent as described herein contains no more than 3 mismatches (i.e., 3, 2, 1, or 0 mismatches). In one embodiment, an RNAi agent as described herein contains no more than 2 mismatches. In one embodiment, an RNAi agent as described herein contains no more than 1 mismatch. In one embodiment, an RNAi agent as described herein contains 0 mismatches. In certain embodiments, if the antisense strand of the RNAi agent contains mismatches to the target sequence, the mismatch can optionally be restricted to be within the last 5 nucleotides from either the 5'- or 3'-end of the region of complementarity. For example, in such embodiments, for a 23 nucleotide RNAi agent, the strand which is complementary to a region of a C3 gene, generally does not contain any mismatch within the central 13 nucleotides. The methods described herein or methods known in the art can be used to determine whether an RNAi agent containing a mismatch to a target sequence is effective in inhibiting the expression of a C3 gene. Consideration of the efficacy of RNAi agents with mismatches in inhibiting expression of a C3 gene is important, especially if the particular region of complementarity in a C3 gene is known to have polymorphic sequence variation within the population.

The term "sense strand" or "passenger strand" as used herein, refers to the strand of an iRNA that includes a region that is substantially complementary to a region of the antisense strand as that term is defined herein.

As used herein, "substantially all of the nucleotides are modified" are largely but not wholly modified and can include not more than 5, 4, 3, 2, or 1 unmodified nucleotides.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3, or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of a double stranded RNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding a complement component C3 gene). For example, a polynucleotide is complementary to at least a part of a complement component C3 mRNA if the sequence is substantially complementary to a non-interrupted portion of an mRNA encoding a complement component C3 gene.

Accordingly, in some embodiments, the antisense polynucleotides disclosed herein are fully complementary to the target complement component C3 sequence. In other embodiments, the antisense polynucleotides disclosed herein are substantially complementary to the target complement component C3 sequence and comprise a contiguous nucleotide sequence which is at least 80% complementary over its entire length to the equivalent region of the nucleotide sequence of any one of SEQ ID NOs:1-4, or a fragment of any one of SEQ ID NOs:1-4, such as about 85%, about 90%, about 91%, about 92%, about 93%, about 94%, about 95%, about 96%, about 97%, about 98%, or about 99% complementary.

In some embodiments, the antisense polynucleotides disclosed herein are substantially complementary to a fragment of a target complement component C3 sequence and comprise a contiguous nucleotide sequence which is at least 80% complementary over its entire length to a fragment of SEQ ID NO: 1 selected from the group of nucleotides 475-497, 487-509, 490-512, 491-513, 705-727, 809-831, 813-835, 1147-1169, 1437-1459, 1439-1461, 1447-1469, 2596-2618, 2634-2656, 3012-3034, 3334-3356, 3611-3633, 3614-3636, 3622-3655, 3809-3831, 3846-3868, 3847-3869, 3920-3942, 4047-4069, 4061-4083, 4156-4178, 4157-4177, 4162-4184, 4178-4200, 4226-4248, 4369-4391, 4392-4414, 4521-4543, 4522-4544, 4523-4545, 5012-5034 of SEQ ID NO: 1, such as about 85%, about 90%, about 91%, about 92%, about 93%, about 94%, about 95%, about 96%, about 97%, about 98%, or about 99% complementary.

In other embodiments, the antisense polynucleotides disclosed herein are substantially complementary to a fragment of a target complement component C3 sequence and comprise a contiguous nucleotide sequence which is at least 80% complementary over its entire length to a fragment of SEQ ID NO: 1 selected from the group of nucleotides 705-727, 809-831, or 2634-2656 of SEQ ID NO: 1, such as about 85%, about 90%, about 91%, about 92%, about 93%, about 94%, about 95%, about 96%, about 97%, about 98%, or about 99% complementary. In one embodiment, the antisense polynucleotides disclosed herein are substantially complementary to a fragment of a target complement component C3 sequence and comprise a contiguous nucleotide sequence which is at least 80% complementary over its entire length to a fragment of SEQ ID NO: 1 from nucleotides 2634-2656, such as about 85%, about 90%, about 91%, about 92%, about 93%, about 94%, about 95%, about 96%, about 97%, about 98%, or about 99% complementary.

In other embodiments, the antisense polynucleotides disclosed herein are substantially complementary to the target C3 sequence and comprise a contiguous nucleotide sequence which is at least about 80% complementary over its entire length to any one of the sense strand nucleotide sequences in any one of any one of Tables 2-7, 15, 18, 20-23, 30, and 31, or a fragment of any one of the sense strand nucleotide sequences in any one of Tables 2-7, 15, 18, 20-23, 30, and 31, such as about 85%, about 90%, about 91%, about 92%, about 93%, about 94%, about 95%, about 96%, about 97%, about 98%, about 99%, or 100% complementary.

In one embodiment, an RNAi agent of the disclosure includes a sense strand that is substantially complementary to an antisense polynucleotide which, in turn, is the same as a target C3 sequence, and wherein the sense strand polynucleotide comprises a contiguous nucleotide sequence which is at least about 80% complementary over its entire length to the equivalent region of the nucleotide sequence of SEQ ID NOs: 5-8, or a fragment of any one of SEQ ID NOs:5-8, such as about 85%, about 90%, about 91%, about 92%, about 93%, about 94%, about 95%, about 96%, about 97%, about 98%, about 99%, or 100% complementary.

In some embodiments, an iRNA of the invention includes a sense strand that is substantially complementary to an antisense polynucleotide which, in turn, is complementary to a target complement component C3 sequence, and wherein the sense strand polynucleotide comprises a contiguous nucleotide sequence which is at least about 80% complementary over its entire length to any one of the antisense strand nucleotide sequences in any one of any one of Tables 2-7, 15, 18, 20-23, 30, and 31, or a fragment of any one of the antisense strand nucleotide sequences in any one of Tables 2-7, 15, 18, 20-23, 30, and 31, such as about 85%, about 90%, about 91%, about 92%, about 93%, about 94%, about 95%, about 96%, about 97%, about 98%, about 99%, or 100% complementary In certain embodiments, the sense and antisense strands are selected from any one of duplexes AD-565541.2, AD-564742, AD-567304, AD-568978, AD-569164, AD-569272.2, AD-569765.2, AD-564730.2, AD-567315, AD-564745.2, AD-571715.2, AD-570714, AD-571826, AD-572041.2, AD-572039.2, AD-572387, AD-568586.2, AD-566837.2, AD-566444.2, AD-567700.2, AD-567814.2, AD-568003.2, AD-569164.2, AD-569763.2, AD-565281.2, AD-571539.2, AD-572389.2, AD-567315.2, AD-571752.2, AD-568026.2, AD-571298, AD-572110.2, AD-572062.2, AD-572388.2, AD-572040.2, AD-567713.2, AD-567521.2, AD-567066.2, AD-1181519, AD-569268, or AD-570714.

In some embodiments, the sense and antisense strands are selected from any one of duplexes AD-1181519, AD-569268, or AD-570714. In one embodiment, the dulex is AD-570714.

In general, an "iRNA" includes ribonucleotides with chemical modifications. Such modifications may include all types of modifications disclosed herein or known in the art. Any such modifications, as used in a dsRNA molecule, are encompassed by "iRNA" for the purposes of this specification and claims.

In an aspect of the invention, an agent for use in the methods and compositions of the invention is a single-stranded antisense oligonucleotide molecule that inhibits a target mRNA via an antisense inhibition mechanism. The single-stranded antisense oligonucleotide molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) *Mol Cancer Ther* 1:347-355. The single-stranded antisense oligonucleotide molecule may be about 14 to about 30 nucleotides in length and have a sequence that is complementary to a target sequence. For example, the single-stranded antisense oligonucleotide molecule may comprise a sequence that is at least about 14, 15, 16, 17, 18, 19, 20, or more contiguous nucleotides from any one of the antisense sequences described herein.

The phrase "contacting a cell with an iRNA," such as a dsRNA, as used herein, includes contacting a cell by any possible means. Contacting a cell with an iRNA includes contacting a cell in vitro with the iRNA or contacting a cell in vivo with the iRNA. The contacting may be done directly or indirectly. Thus, for example, the iRNA may be put into physical contact with the cell by the individual performing the method, or alternatively, the iRNA may be put into a situation that will permit or cause it to subsequently come into contact with the cell.

Contacting a cell in vitro may be done, for example, by incubating the cell with the iRNA. Contacting a cell in vivo may be done, for example, by injecting the iRNA into or near the tissue where the cell is located, or by injecting the iRNA into another area, e.g., the bloodstream or the subcutaneous space, such that the agent will subsequently reach the tissue where the cell to be contacted is located. For example, the iRNA may contain or be coupled to a ligand, e.g., GalNAc, that directs the iRNA to a site of interest, e.g., the liver. Combinations of in vitro and in vivo methods of contacting are also possible. For example, a cell may also be contacted in vitro with an iRNA and subsequently transplanted into a subject.

In certain embodiments, contacting a cell with an iRNA includes "introducing" or "delivering the iRNA into the cell" by facilitating or effecting uptake or absorption into the cell. Absorption or uptake of an iRNA can occur through unaided diffusion or active cellular processes, or by auxiliary agents or devices. Introducing an iRNA into a cell may be in vitro or in vivo. For example, for in vivo introduction, iRNA can be injected into a tissue site or administered systemically. In vitro introduction into a cell includes methods known in the art such as electroporation and lipofection. Further approaches are described herein below or are known in the art.

The term "lipid nanoparticle" or "LNP" is a vesicle comprising a lipid layer encapsulating a pharmaceutically active molecule, such as a nucleic acid molecule, e.g., an iRNA or a plasmid from which an iRNA is transcribed. LNPs are described in, for example, U.S. Pat. Nos. 6,858, 225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), a non-primate (such as a cow, a pig, a horse, a goat, a rabbit, a sheep, a hamster, a guinea pig, a cat, a dog, a rat, or a mouse), or a bird that expresses the target gene, either endogenously or heterologously. In an embodiment, the subject is a human, such as a human being treated or assessed for a disease or disorder that would benefit from reduction in complement component C3 expression; a human at risk for a disease or disorder that would benefit from reduction in C3 expression; a human having a disease or disorder that would benefit from reduction in complement component C3 expression; or human being treated for a disease or disorder that would benefit from reduction in complement component C3 expression as described herein. In some embodiments, the subject is a female human. In other embodiments, the subject is a male human. In one embodiment, the subject is an adult subject. In another embodiment, the subject is a pediatric subject.

As used herein, the terms "treating" or "treatment" refer to a beneficial or desired result, such as reducing at least one sign or symptom of a complement component C3-associated disorder, e.g., hemolysis in a subject. Treatment also includes a reduction of one or more sign or symptoms associated with unwanted complement component C3 expression, e.g., hemolysis; diminishing the extent of unwanted complement component C3 activation or stabilization; amelioration or palliation of unwanted complement component C3 activation or stabilization. "Treatment" can also mean prolonging survival as compared to expected survival in the absence of treatment.

The term "lower" in the context of the level of complement component C3 gene expression or complement component C3 protein production in a subject, or a disease marker or symptom refers to a statistically significant decrease in such level. The decrease can be, for example, at least 50%, 55%, 60%, 65%, 70%, 75%, 80%, 85%, 90%, or 95%, or below the level of detection for the detection method in a relevant cell or tissue, e.g., a liver cell, or other subject sample, e.g., blood or serum derived therefrom, urine.

As used herein, "prevention" or "preventing," when used in reference to a disease or disorder, that would benefit from a reduction in expression of a complement component C3 gene or production of complement component C3 protein, e.g., in a subject susceptible to a complement component C3-associated disorder due to, e.g., aging, genetic factors, hormone changes, diet, and a sedentary lifestyle. In certain embodiments, the disease or disorder is e.g., a symptom of unwanted C3 activation or stabilization, such as a hemolysis. The likelihood of developing, e.g., hemolysis, is reduced, for example, when an individual having one or more risk factors for hemolysis either fails to develop hemolysis or develops hemolysis with less severity relative to a population having the same risk factors and not receiving treatment as described herein. The failure to develop a complement component C3-associated disorder, e.g., hemolysis, or a delay in the time to develop hemolysis by months or years is considered effective prevention. Prevention may require administration of more than one dose if the iRNA agent.

As used herein, the term "complement component C3-associated disease" or "C3-associated disease," is a disease or disorder that would benefit from reduction in complement component C3 expression. Non-limiting examples of complement component C3-associated diseases include, cold agglutinin disease (CAD), warm autoimmune hemolytic anemia, and paroxysmal nocturnal hemoglobinuria (PNH), lupus nephritis (LN), bullous pemphigoid, *pemphigus*, e.g., *pemphigus vulgaris* (PV) and *pemphigus foliaceus* (PF), and C3 glomerulopathy.

A "therapeutically-effective amount" or "prophylactically effective amount" also includes an amount of an RNAi agent that produces some desired effect at a reasonable benefit/risk ratio applicable to any treatment. The iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition, or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Such carriers are known in the art. Pharmaceutically acceptable carriers include carriers for administration by injection.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs, or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In some embodiments, a "sample derived from a subject" refers to urine obtained from the subject. A "sample derived from a subject" can refer to blood or blood derived serum or plasma from the subject.

II. iRNAs of the Invention

The present invention provides iRNAs which inhibit the expression of a complement component C3 gene. In preferred embodiments, the iRNA includes double stranded ribonucleic acid (dsRNA) molecules for inhibiting the expression of a complement component C3 gene in a cell, such as a cell within a subject, e.g., a mammal, such as a human susceptible to developing a complement component C3-associated disorder, e.g., hemolysis. The dsRNAi agent includes an antisense strand having a region of complementarity which is complementary to at least a part of an mRNA formed in the expression of a complement component C3 gene. The region of complementarity is about 19-30 nucleotides in length (e.g., about 30, 29, 28, 27, 26, 25, 24, 23, 22, 21, 20, or 19 nucleotides in length). Upon contact with a cell expressing the complement component C3 gene, the iRNA inhibits the expression of the complement component C3 gene (e.g., a human, a primate, a non-primate, or a rat complement component C3 gene) by at least about 50% as assayed by, for example, a PCR or branched DNA (bDNA)-based method, or by a protein-based method, such as by immunofluorescence analysis, using, for example, western blotting or flow cytometric techniques. In preferred embodiments, inhibition of expression is determined by the qPCR method provided in the examples, especially in Example 2 with the siRNA at a 10 nM concentration in an appropriate organism cell line provided therein. In preferred embodiments, inhibition of expression in vivo is determined by knockdown of the human gene in a rodent expressing the human gene, e.g., a mouse or an AAV-infected mouse expressing the human target gene, e.g., when administered as single dose, e.g., at 3 mg/kg at the nadir of RNA expression. RNA expression in liver is determined using the PCR methods provided in Example 2.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of a complement component C3 gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is 19 to 30 base pairs in length. Similarly, the region of complementarity to the target sequence is 19 to 30 nucleotides in length.

In some embodiments, the dsRNA is about 19 to about 23 nucleotides in length, or about 25 to about 30 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 19 to about 30 base pairs, e.g., about 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target complement component C3 gene expression is not generated in the target cell by cleavage of a larger dsRNA.

A dsRNA as described herein can further include one or more single-stranded nucleotide overhangs e.g., 1-4, 2-4, 1-3, 2-3, 1, 2, 3, or 4 nucleotides. dsRNAs having at least one nucleotide overhang can have superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5'-end, 3'-end, or both ends of an antisense or sense strand of a dsRNA.

A dsRNA can be synthesized by standard methods known in the art. Double stranded RNAi compounds of the invention may be prepared using a two-step procedure. First, the individual strands of the double stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Similarly, single-stranded oligonucleotides of the invention can be prepared using solution-phase or solid-phase organic synthesis or both.

In an aspect, a dsRNA of the invention includes at least two nucleotide sequences, a sense sequence and an antisense sequence. The sense strand is selected from the group of sequences provided in any one of Tables 2-7, 15, 18, 20-23, 30, or 31, and the corresponding antisense strand of the sense strand is selected from the group of sequences of any one of Tables 2-7, 15, 18, 20-23, 30, or 31. In this aspect, one of the two sequences is complementary to the other of the two sequences, with one of the sequences being substantially complementary to a sequence of an mRNA generated in the expression of a complement component C3 gene. As such, in this aspect, a dsRNA will include two oligonucleotides, where one oligonucleotide is described as the sense strand in any one of Tables 2-7, 15, 18, 20-23, 30, or 31, and the second oligonucleotide is described as the corresponding antisense strand of the sense strand in any one of Tables 2-7, 15, 18, 20-23, 30, or 31. In certain embodiments, the substantially complementary sequences of the dsRNA are contained on separate oligonucleotides. In other embodiments, the substantially complementary sequences of the dsRNA are contained on a single oligonucleotide. In certain embodiments, the sense or antisense strand is selected from the sense or antisense strand of any one of duplexes AD-565541.2, AD-564742, AD-567304, AD-568978, AD-569164, AD-569272.2, AD-569765.2, AD-564730.2, AD-567315, AD-564745.2, AD-571715.2, AD-570714, AD-571826, AD-572041.2, AD-572039.2, AD-572387, AD-568586.2, AD-566837.2, AD-566444.2, AD-567700.2, AD-567814.2, AD-568003.2, AD-569164.2, AD-569763.2, AD-565281.2, AD-571539.2, AD-572389.2, AD-567315.2, AD-571752.2, AD-568026.2, AD-571298, AD-572110.2, AD-572062.2, AD-572388.2, AD-572040.2, AD-567713.2, AD-567521.2, AD-567066.2, AD-1181519, AD-569268, or AD-570714. In other embodiment, the sense or antisense strand is selected from the sense or antisense strand of any one of duplexes AD-1181519, AD-569268, or AD-570714. In one embodiment, the duplex is AD-570714.

It will be understood that, although the sequences in Tables 2, 4, 6, 20, 22, and 30 are not described as modified or conjugated sequences, the RNA of the iRNA of the invention e.g., a dsRNA of the invention, may comprise any one of the sequences set forth in any one of Tables 3, 5, 7, 15, 18, 21, 23, or 31 that is un-modified, un-conjugated, or modified or conjugated differently than described therein. In other words, the invention encompasses dsRNA of Tables 2-7, 15, 18, 20-23, 30, or 31 which are un-modified, un-conjugated, modified, or conjugated, as described herein.

The skilled person is well aware that dsRNAs having a duplex structure of about 20 to 23 base pairs, e.g., 21, base pairs have been hailed as particularly effective in inducing RNA interference (Elbashir et al., *EMBO* 2001, 20:6877-6888). However, others have found that shorter or longer RNA duplex structures can also be effective (Chu and Rana (2007) RNA 14:1714-1719; Kim et al. (2005) *Nat Biotech* 23:222-226). In the embodiments described above, by virtue of the nature of the oligonucleotide sequences provided in any one of Tables 2-7, 15, 18, 20-23, 30, or 31, dsRNAs described herein can include at least one strand of a length of minimally 21 nucleotides. It can be reasonably expected that shorter duplexes having any one of the sequences in any one of Tables 2-7, 15, 18, 20-23, 30, or 31 minus only a few nucleotides on one or both ends can be similarly effective as compared to the dsRNAs described above. Hence, dsRNAs having a sequence of at least 19, 20, or more contiguous nucleotides derived from any one of the sequences of any one of Tables 2-7, 15, 18, 20-23, 30, or 31, and differing in their ability to inhibit the expression of a complement component C3 gene by not more than about 5, 10, 15, 20, 25, or 30% inhibition from a dsRNA comprising the full sequence, are contemplated to be within the scope of the present invention.

In addition, the RNAs provided in Tables 2-7, 15, 18, 20-23, 30, or 31 identify a site(s) in a complement component C3 transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 19 contiguous nucleotides from any one of the sequences provided in any one of Tables 2-7, 15, 18, 20-23, 30, or 31 coupled to additional nucleotide sequences taken from the region contiguous to the selected sequence in a complement component C3 gene.

III. Modified iRNAs of the Invention

In certain embodiments, the RNA of the iRNA of the invention e.g., a dsRNA, is un-modified, and does not comprise, e.g., chemical modifications or conjugations known in the art and described herein. In other embodiments, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA or substantially all of the nucleotides of an iRNA are modified, i.e., not more than 5, 4, 3, 2, or 1 unmodified nucleotides are present in a strand of the iRNA.

The nucleic acids featured in the invention can be synthesized or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments of the invention, the dsRNA agents of the invention are in a free acid form. In other embodiments of the invention, the dsRNA agents of the invention are in a salt form. In one embodiment, the dsRNA agents of the invention are in a sodium salt form. In certain embodiments, when the dsRNA agents of the invention are in the sodium salt form, sodium ions are present in the agent as counterions for substantially all of the phosphodiester and/or phosphorothioate groups present in the agent. Agents in which substantially all of the phosphodiester and/or phosphorothioate linkages have a sodium counterion include not more than 5, 4, 3, 2, or 1 phosphodiester and/or phosphorothioate linkages without a sodium counterion. In some embodiments, when the dsRNA agents of the invention are in the sodium salt form, sodium ions are present in the agent as counterions for all of the phosphodiester and/or phosphorothioate groups present in the agent.

Representative U.S. Patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

Representative U.S. Patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and 5,677,439, the entire contents of each of which are hereby incorporated herein by reference.

Suitable RNA mimetics are contemplated for use in iRNAs provided herein, in which both the sugar and the internucleoside linkage, i.e., the backbone, of the nucleotide units are replaced with novel groups. The base units are maintained for hybridization with an appropriate nucleic acid target compound. One such oligomeric compound in which an RNA mimetic that has been shown to have excellent hybridization properties is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative US patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—$N(CH_3)$—O—$CH_2$— [known as a methylene (methylimino) or MMI backbone], —$CH_2$—O—$N(CH_3)$—$CH_2$—, —$CH_2$—$N(CH_3)$—$N(CH_3)$—$CH_2$— and —$N(CH_3)$—$CH_2$—$CH_2$— [wherein the native phosphodiester backbone is represented as —O—P—O—$CH_2$— ] of the above-referenced U.S. Pat. No. 5,489,677, and the amide backbones of the above-referenced U.S. Pat. No. 5,602,240.

In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)·_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_3)_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative US patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. Patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193).

In some embodiments, the RNA of an iRNA can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-$CH_2$—O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-($CH_2$)—O-2' (LNA); 4'-($CH_2$)—S-2'; 4'-($CH_2$)$_2$—O-2' (ENA); 4'-CH($CH_3$)—O-2' (also referred to as "constrained ethyl" or "cEt") and 4'-CH($CH_2OCH_3$)—O-2' (and analogs thereof; see, e.g., U.S. Pat. No. 7,399,845); 4'-C($CH_3$)($CH_3$)—O-2' (and analogs thereof; see e.g., U.S. Pat. No. 8,278,283); 4'-$CH_2$—N($OCH_3$)-2' (and analogs thereof; see e.g., U.S. Pat. No. 8,278,425); 4'-$CH_2$—O—N($CH_3$)-2' (see, e.g., U.S. Patent Publication No. 2004/0171570); 4'-$CH_2$—N(R)—O-2', wherein R is H, C1-C12 alkyl, or a protecting group (see, e.g., U.S. Pat. No. 7,427,672); 4'-$CH_2$—C(H)($CH_3$)-2' (see, e.g., Chattopadhyaya et al., *J. Org. Chem.*, 2009, 74, 118-134); and 4'-$CH_2$—C(=$CH_2$)-2' (and analogs thereof; see, e.g., U.S. Pat. No. 8,278,426). The entire contents of each of the foregoing are hereby incorporated herein by reference.

Additional representative U.S. Patents and U.S. Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH($CH_3$)—O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, U.S. Patent Publication No. 2013/0190383; and PCT publication WO 2013/036868, the entire contents of each of which are hereby incorporated herein by reference.

In some embodiments, an iRNA of the invention comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see *Nuc. Acids Symp. Series*, 52, 133-134 (2008) and Fluiter et al., *Mol. Biosyst.*, 2009, 10, 1039 hereby incorporated by reference).

Representative U.S. publications that teach the preparation of UNA include, but are not limited to, U.S. Pat. No. 8,314,227; and U.S. Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other modifications of the nucleotides of an iRNA of the invention include a 5' phosphate or 5' phosphate mimic, e.g., a 5'-terminal phosphate or phosphate mimic on the antisense strand of an iRNA. Suitable phosphate mimics are disclosed in, for example U.S. Patent Publication No. 2012/0157511, the entire contents of which are incorporated herein by reference.

A. Modified iRNAs Comprising Motifs of the Invention

In certain aspects of the invention, the double stranded RNA agents of the invention include agents with chemical modifications as disclosed, for example, in WO2013/075035, the entire contents of each of which are incorporated herein by reference. WO2013/075035 provides motifs of three identical modifications on three consecutive nucleotides into a sense strand or antisense strand of a dsRNAi agent, particularly at or near the cleavage site. In some embodiments, the sense strand and antisense strand of the dsRNAi agent may otherwise be completely modified. The introduction of these motifs interrupts the modification pattern, if present, of the sense or antisense strand. The dsRNAi agent may be optionally conjugated with a GalNAc derivative ligand, for instance on the sense strand.

More specifically, when the sense strand and antisense strand of the double stranded RNA agent are completely modified to have one or more motifs of three identical modifications on three consecutive nucleotides at or near the cleavage site of at least one strand of a dsRNAi agent, the gene silencing activity of the dsRNAi agent was observed.

Accordingly, the invention provides double stranded RNA agents capable of inhibiting the expression of a target gene (i.e., complement component C3 gene) in vivo. The RNAi agent comprises a sense strand and an antisense strand. Each strand of the RNAi agent may be, for example, 17-30 nucleotides in length, 25-30 nucleotides in length, 27-30 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as "dsRNAi agent." The duplex region of a dsRNAi agent may be, for example, the duplex region can be 27-30 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 19, 20, 21, 22, 23, 24, 25, 26, and 27 nucleotides in length.

In certain embodiments, the dsRNAi agent may contain one or more overhang regions or capping groups at the 3'-end, 5'-end, or both ends of one or both strands. The overhang can be, independently, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. In certain embodiments, the overhang regions can include extended overhang regions as provided above. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In certain embodiments, the nucleotides in the overhang region of the dsRNAi agent can each independently be a modified or unmodified nucleotide including, but no limited to 2'-sugar modified, such as, 2'-F, 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand, or both strands of the dsRNAi agent may be phosphorylated. In some embodiments, the overhang region(s) contains two nucleotides having a phosphorothioate between the two nucleotides, where the two nucleotides can be the same or different. In some embodiments, the overhang is present at the 3'-end of the sense strand, antisense strand, or both strands. In some embodiments, this 3'-overhang is present in the antisense strand. In some embodiments, this 3'-overhang is present in the sense strand.

The dsRNAi agent may contain only a single overhang, which can strengthen the interference activity of the RNAi, without affecting its overall stability. For example, the single-stranded overhang may be located at the 3'-end of the sense strand or, alternatively, at the 3-end of the antisense strand. The RNAi may also have a blunt end, located at the 5'-end of the antisense strand (or the 3'-end of the sense strand) or vice versa. Generally, the antisense strand of the dsRNAi agent has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In certain embodiments, the dsRNAi agent is a double ended bluntmer of 19 nucleotides in length, wherein the sense strand contains at least one motif of three 2'-F modifications on three consecutive nucleotides at positions 7, 8, 9 from the 5' end. The antisense strand contains at least one motif of three 2'-O-methyl modifications on three consecutive nucleotides at positions 11, 12, 13 from the 5' end.

In other embodiments, the dsRNAi agent is a double ended bluntmer of 20 nucleotides in length, wherein the sense strand contains at least one motif of three 2'-F modifications on three consecutive nucleotides at positions 8, 9, 10 from the 5' end. The antisense strand contains at least one motif of three 2'-O-methyl modifications on three consecutive nucleotides at positions 11, 12, 13 from the 5' end.

In yet other embodiments, the dsRNAi agent is a double ended bluntmer of 21 nucleotides in length, wherein the sense strand contains at least one motif of three 2'-F modifications on three consecutive nucleotides at positions 9, 10, 11 from the 5' end. The antisense strand contains at least one motif of three 2'-O-methyl modifications on three consecutive nucleotides at positions 11, 12, 13 from the 5' end.

In certain embodiments, the dsRNAi agent comprises a 21 nucleotide sense strand and a 23 nucleotide antisense strand, wherein the sense strand contains at least one motif of three 2'-F modifications on three consecutive nucleotides at positions 9, 10, 11 from the 5' end; the antisense strand contains at least one motif of three 2'-O-methyl modifications on three consecutive nucleotides at positions 11, 12, 13 from the 5' end, wherein one end of the RNAi agent is blunt, while the other end comprises a 2 nucleotide overhang. Preferably, the 2 nucleotide overhang is at the 3'-end of the antisense strand.

When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In certain embodiments, every nucleotide in the sense strand and the antisense strand of the dsRNAi agent, including the nucleotides that are part of the motifs are modified nucleotides. In certain embodiments each residue is independently modified with a 2'-O-methyl or 3'-fluoro, e.g., in an alternating motif. Optionally, the dsRNAi agent further comprises a ligand (preferably GalNAc$_3$).

In certain embodiments, the dsRNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In certain embodiments, the dsRNAi agent comprises sense and antisense strands, wherein the dsRNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein Dicer cleavage of the dsRNAi agent preferentially results in an siRNA comprising the 3'-end of the second strand, thereby reducing expression of the target gene in the mammal. Optionally, the dsRNAi agent further comprises a ligand.

In certain embodiments, the sense strand of the dsRNAi agent contains at least one motif of three identical modifications on three consecutive nucleotides, where one of the motifs occurs at the cleavage site in the sense strand.

In certain embodiments, the antisense strand of the dsRNAi agent can also contain at least one motif of three identical modifications on three consecutive nucleotides, where one of the motifs occurs at or near the cleavage site in the antisense strand.

For a dsRNAi agent having a duplex region of 19-23 nucleotides in length, the cleavage site of the antisense strand is typically around the 10, 11, and 12 positions from the 5'-end. Thus the motifs of three identical modifications may occur at the 9, 10, 11 positions; the 10, 11, 12 positions; the 11, 12, 13 positions; the 12, 13, 14 positions; or the 13, 14, 15 positions of the antisense strand, the count starting from the first nucleotide from the 5'-end of the antisense strand, or, the count starting from the first paired nucleotide within the duplex region from the 5'-end of the antisense strand. The cleavage site in the antisense strand may also change according to the length of the duplex region of the dsRNAi agent from the 5'-end.

The sense strand of the dsRNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In some embodiments, the sense strand of the dsRNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistries of the motifs are distinct from each other, and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the dsRNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In some embodiments, the wing modification on the sense strand or antisense strand of the dsRNAi agent typically does not include the first one or two terminal nucleotides at the 3'-end, 5'-end, or both ends of the strand.

In other embodiments, the wing modification on the sense strand or antisense strand of the dsRNAi agent typically does not include the first one or two paired nucleotides within the duplex region at the 3'-end, 5'-end, or both ends of the strand.

When the sense strand and the antisense strand of the dsRNAi agent each contain at least one wing modification, the wing modifications may fall on the same end of the duplex region, and have an overlap of one, two, or three nucleotides.

When the sense strand and the antisense strand of the dsRNAi agent each contain at least two wing modifications, the sense strand and the antisense strand can be so aligned that two modifications each from one strand fall on one end of the duplex region, having an overlap of one, two, or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In some embodiments, every nucleotide in the sense strand and antisense strand of the dsRNAi agent, including the nucleotides that are part of the motifs, may be modified. Each nucleotide may be modified with the same or different modification which can include one or more alteration of one or both of the non-linking phosphate oxygens or of one or more of the linking phosphate oxygens; alteration of a constituent of the ribose sugar, e.g., of the 2'-hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3'- or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5'-end or ends can be phosphorylated.

It may be possible, e.g., to enhance stability, to include particular bases in overhangs, or to include modified nucleotides or nucleotide surrogates, in single strand overhangs, e.g., in a 5'- or 3'-overhang, or in both. For example, it can be desirable to include purine nucleotides in overhangs. In some embodiments all or some of the bases in a 3'- or 5'-overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, CRN, cET, UNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In certain embodiments, the $N_a$ or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AAB-BAABBAABB . . . ," "AABAABAABAAB . . . ," "AAA-BAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABA-BAB . . . ", "ACACAC . . . " "BDBDBD . . . " or "CDCDCD . . . ," etc.

In some embodiments, the dsRNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5' to 3' of the strand and the alternating motif in the antisense strand may start with "BABABA" from 5' to 3' of the strand within the duplex region. As another example, the alternating motif in the sense strand may start with "AABBAABB" from 5' to 3' of the strand and the alternating motif in the antisense strand may start with "BBAABBAA" from 5' to 3' of the strand within the duplex region, so that there is a complete or partial shift of the modification patterns between the sense strand and the antisense strand.

In some embodiments, the dsRNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand or antisense strand interrupts the initial modification pattern present in the sense strand or antisense strand. This interruption of the modification pattern of the sense or antisense strand by introducing one or more motifs of three identical modifications on three consecutive nucleotides to the sense or antisense strand may enhance the gene silencing activity against the target gene.

In some embodiments, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYY$N_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ or $N_b$ may be present or absent when there is a wing modification present.

The iRNA may further comprise at least one phosphorothioate or methylphosphonate internucleotide linkage. The phosphorothioate or methylphosphonate internucleotide linkage modification may occur on any nucleotide of the sense strand, antisense strand, or both strands in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand. In one embodiment, a double-stranded RNAi agent comprises 6-8 phosphorothioate internucleotide linkages. In some embodiments, the antisense strand comprises two phosphorothioate internucleotide linkages at the 5'-end and two phosphorothioate internucleotide linkages at the 3'-end, and the sense strand comprises at least two phosphorothioate internucleotide linkages at either the 5'-end or the 3'-end.

In some embodiments, the dsRNAi agent comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, or the 5' end of the antisense strand.

In some embodiments, the 2-nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the dsRNAi agent may additionally have two phosphorothioate internucleotide linkages between the terminal three nucleotides at both the 5'-end of the sense strand and at the 5'-end of the antisense strand.

In one embodiment, the dsRNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In certain embodiments, the dsRNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In certain embodiments, the nucleotide at the 1 position within the duplex region from the 5'-end in the antisense strand is selected from A, dA, dU, U, and dT. Alternatively, at least one of the first 1, 2, or 3 base pair within the duplex region from the 5'-end of the antisense strand is an AU base pair. For example, the first base pair within the duplex region from the 5'-end of the antisense strand is an AU base pair.

In other embodiments, the nucleotide at the 3'-end of the sense strand is deoxy-thymine (dT) or the nucleotide at the 3'-end of the antisense strand is deoxy-thymine (dT). For example, there is a short sequence of deoxy-thymine nucleotides, for example, two dT nucleotides on the 3'-end of the sense, antisense strand, or both strands.

In certain embodiments, the sense strand sequence may be represented by formula (I):

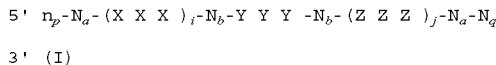

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein Nb and Y do not have the same modification; and

XXX, YYY, and ZZZ each independently represent one motif of three identical modifications on three consecutive nucleotides. Preferably YYY is all 2'-F modified nucleotides.

In some embodiments, the $N_a$ or $N_b$ comprises modifications of alternating pattern.

In some embodiments, the YYY motif occurs at or near the cleavage site of the sense strand. For example, when the dsRNAi agent has a duplex region of 17-23 nucleotides in length, the YYY motif can occur at or the vicinity of the cleavage site (e.g.: can occur at positions 6, 7, 8; 7, 8, 9; 8, 9, 10; 9, 10, 11; 10, 11,12; or 11, 12, 13) of the sense strand, the count starting from the first nucleotide, from the 5'-end; or optionally, the count starting at the first paired nucleotide within the duplex region, from the 5'-end.

In one embodiment, i is 1 and j is 0, or i is 0 and j is 1, or both i and j are 1. The sense strand can therefore be represented by the following formulas:

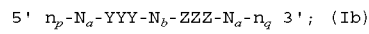

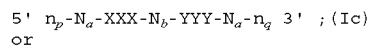

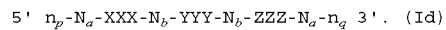

When the sense strand is represented by formula (Ib), $N_b$ represents an oligonucleotide sequence comprising 0-10, 0-7, 0-5, 0-4, 0-2, or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2, or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2, or 0 modified nucleotides. Preferably, $N_b$ is 0, 1, 2, 3, 4, 5, or 6 Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

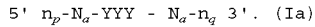

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

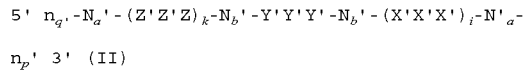

wherein:
k and l are each independently 0 or 1;
p' and q' are each independently 0-6;
each $N_a'$ independently represents an oligonucleotide sequence comprising 0-25 modified nucleotides, each sequence comprising at least two differently modified nucleotides;
each $N_b'$ independently represents an oligonucleotide sequence comprising 0-10 modified nucleotides;
each $n_p'$ and $n_q'$ independently represent an overhang nucleotide;
wherein $N_b'$ and Y' do not have the same modification; and
X'X'X', Y'Y'Y', and Z'Z'Z' each independently represent one motif of three identical modifications on three consecutive nucleotides.

In some embodiments, the $N_a'$ or $N_b'$ comprises modifications of alternating pattern.

The Y'Y'Y' motif occurs at or near the cleavage site of the antisense strand. For example, when the dsRNAi agent has a duplex region of 17-23 nucleotides in length, the Y'Y'Y' motif can occur at positions 9, 10, 11; 10, 11, 12; 11, 12, 13; 12, 13, 14; or 13, 14, 15 of the antisense strand, with the count starting from the first nucleotide, from the 5'-end; or optionally, the count starting at the first paired nucleotide within the duplex region, from the 5'-end. Preferably, the Y'Y'Y' motif occurs at positions 11, 12, 13.

In certain embodiments, Y'Y'Y' motif is all 2'-OMe modified nucleotides.

In certain embodiments, k is 1 and l is 0, or k is 0 and l is 1, or both k and l are 1.

The antisense strand can therefore be represented by the following formulas:

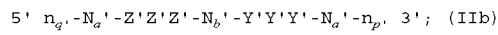
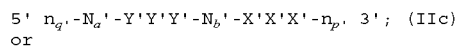
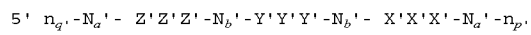

When the antisense strand is represented by formula (IIb), $N_b'$ represents an oligonucleotide sequence comprising 0-10, 0-7, 0-10, 0-7, 0-5, 0-4, 0-2, or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2, or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2, or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5, or 6.

In other embodiments, k is 0 and l is 0 and the antisense strand may be represented by the formula:

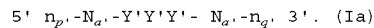

When the antisense strand is represented as formula (IIa), each $N_a'$ independently represents an oligonucleotide sequence comprising 2-20, 2-15, or 2-10 modified nucleotides. Each of X', Y' and Z' may be the same or different from each other.

Each nucleotide of the sense strand and antisense strand may be independently modified with LNA, CRN, UNA, cEt, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y', and Z', in particular, may represent a 2'-O-methyl modification or a 2'-fluoro modification.

In some embodiments, the sense strand of the dsRNAi agent may contain YYY motif occurring at 9, 10, and 11 positions of the strand when the duplex region is 21 nt, the count starting from the first nucleotide from the 5'-end, or optionally, the count starting at the first paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In some embodiments the antisense strand may contain Y'Y'Y' motif occurring at positions 11, 12, 13 of the strand, the count starting from the first nucleotide from the 5'-end, or optionally, the count starting at the first paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with an antisense strand being represented by any one of formulas (IIa), (IIb), (IIc), and (IId), respectively.

Accordingly, the dsRNAi agents for use in the methods of the invention may comprise a sense strand and an antisense strand, each strand having 14 to 30 nucleotides, the iRNA duplex represented by formula (III):

sense:
antisense:
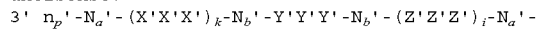

wherein:
i, j, k, and l are each independently 0 or 1;
p, p', q, and q' are each independently 0-6;

each $N_a$ and $N_a'$ independently represents an oligonucleotide sequence comprising 0-25 modified nucleotides, each sequence comprising at least two differently modified nucleotides;

each $N_b$ and $N_b'$ independently represents an oligonucleotide sequence comprising 0-10 modified nucleotides;

wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming an iRNA duplex include the formulas below:

```
5' np-Na-Y YY-Na-nq 3'

3' np'-Na' -Y'Y'Y' -Na'nq' 5'
(IIIa)

5' np -Na -Y Y Y -Nb -Z Z Z -Na-nq 3'

3' np'-Na' -Y'Y'Y'-Nb'-Z'Z'Z'-Na'nq' 5'
(IIIb)

5' np-Na- X X X -Nb -Y Y Y - Na-nq 3'

3' np'-Na'-X'X'X'-Nb'-Y'Y'Y'-Na'-nq' 5'
(IIIc)

5' np -Na -XXX -Nb-Y Y Y -Nb- Z Z Z -Na-nq 3'

3' np'-Na'-X'X'X'-Nb'-Y'Y'Y'-Nb'-Z'Z'Z'-Na-nq' 5'
(IIId)
```

When the dsRNAi agent is represented by formula (IIIa), each $N_a$ independently represents an oligonucleotide sequence comprising 2-20, 2-15, or 2-10 modified nucleotides.

When the dsRNAi agent is represented by formula (IIIb), each $N_b$ independently represents an oligonucleotide sequence comprising 1-10, 1-7, 1-5, or 1-4 modified nucleotides. Each $N_a$ independently represents an oligonucleotide sequence comprising 2-20, 2-15, or 2-10 modified nucleotides.

When the dsRNAi agent is represented as formula (IIIc), each $N_b$, $N_b'$ independently represents an oligonucleotide sequence comprising 0-10, 0-7, 0-10, 0-7, 0-5, 0-4, 0-2, or 0 modified nucleotides. Each $N_a$ independently represents an oligonucleotide sequence comprising 2-20, 2-15, or 2-10 modified nucleotides.

When the dsRNAi agent is represented as formula (IIId), each $N_b$, $N_b'$ independently represents an oligonucleotide sequence comprising 0-10, 0-7, 0-10, 0-7, 0-5, 0-4, 0-2, or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$, and $N_b'$ independently comprises modifications of alternating pattern.

Each of X, Y, and Z in formulas (III), (IIIa), (IIIb), (IIIc), and (IIId) may be the same or different from each other.

When the dsRNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the dsRNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the dsRNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In certain embodiments, the modification on the Y nucleotide is different than the modification on the Y' nucleotide, the modification on the Z nucleotide is different than the modification on the Z' nucleotide, or the modification on the X nucleotide is different than the modification on the X' nucleotide.

In certain embodiments, when the dsRNAi agent is represented by formula (IIId), the $N_a$ modifications are 2'-O-methyl or 2'-fluoro modifications. In other embodiments, when the RNAi agent is represented by formula (IIId), the $N_a$ modifications are 2'-O-methyl or 2'-fluoro modifications and $n_p'$>0 and at least one $n_p'$ is linked to a neighboring nucleotide a via phosphorothioate linkage. In yet other embodiments, when the RNAi agent is represented by formula (IIId), the $N_a$ modifications are 2'-O-methyl or 2'-fluoro modifications, $n_p'$>0 and at least one $n_p'$ is linked to a neighboring nucleotide via phosphorothioate linkage, and the sense strand is conjugated to one or more GalNAc derivatives attached through a bivalent or trivalent branched linker (described below). In other embodiments, when the RNAi agent is represented by formula (IIId), the $N_a$ modifications are 2'-O-methyl or 2'-fluoro modifications, $n_p'$>0 and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In some embodiments, when the dsRNAi agent is represented by formula (IIIa), the $N_a$ modifications are 2'-O-methyl or 2'-fluoro modifications, $n_p'$>0 and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In some embodiments, the dsRNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In some embodiments, the dsRNAi agent is a multimer containing three, four, five, six, or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two dsRNAi agents represented by at least one of formulas (III), (IIIa), (IIIb), (IIIc), and (IIId) are linked to each other at the 5' end, and one or both of the 3' ends, and are optionally conjugated to a ligand. Each of the agents can target the same gene or two different genes; or each of the agents can target same gene at two different target sites.

In certain embodiments, an RNAi agent of the invention may contain a low number of nucleotides containing a 2'-fluoro modification, e.g., 10 or fewer nucleotides with 2'-fluoro modification. For example, the RNAi agent may contain 10, 9, 8, 7, 6, 5, 4, 3, 2, 1 or 0 nucleotides with a 2'-fluoro modification. In a specific embodiment, the RNAi agent of the invention contains 10 nucleotides with a 2'-fluoro modification, e.g., 4 nucleotides with a 2'-fluoro modification in the sense strand and 6 nucleotides with a 2'-fluoro modification in the antisense strand. In another specific embodiment, the RNAi agent of the invention contains 6 nucleotides with a 2'-fluoro modification, e.g., 4 nucleotides with a 2'-fluoro modification in the sense strand and 2 nucleotides with a 2'-fluoro modification in the antisense strand.

In other embodiments, an RNAi agent of the invention may contain an ultra low number of nucleotides containing a 2'-fluoro modification, e.g., 2 or fewer nucleotides containing a 2'-fluoro modification. For example, the RNAi agent may contain 2, 1 of 0 nucleotides with a 2'-fluoro modification. In a specific embodiment, the RNAi agent may contain 2 nucleotides with a 2'-fluoro modification, e.g., 0 nucleotides with a 2-fluoro modification in the sense strand and 2 nucleotides with a 2'-fluoro modification in the antisense strand.

Various publications describe multimeric iRNAs that can be used in the methods of the invention. Such publications include WO2007/091269, U.S. Pat. No. 7,858,769, WO2010/141511, WO2007/117686, WO2009/014887, and WO2011/031520 the entire contents of each of which are hereby incorporated herein by reference.

As described in more detail below, the iRNA that contains conjugations of one or more carbohydrate moieties to an iRNA can optimize one or more properties of the iRNA. In many cases, the carbohydrate moiety will be attached to a modified subunit of the iRNA. For example, the ribose sugar of one or more ribonucleotide subunits of a iRNA can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide, or polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The iRNA may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl, and decalin; preferably, the acyclic group is a serinol backbone or diethanolamine backbone.

In another embodiment of the invention, an iRNA agent comprises a sense strand and an antisense strand, each strand having 14 to 40 nucleotides. The RNAi agent may be represented by formula (L):

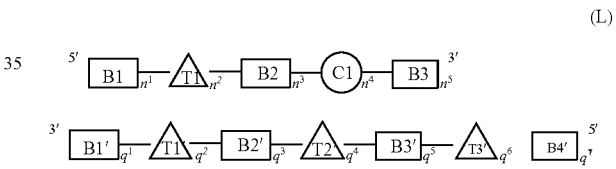

(L)

In formula (L), B1, B2, B3, B1', B2', B3', and B4' each are independently a nucleotide containing a modification selected from the group consisting of 2'-O-alkyl, 2'-substituted alkoxy, 2'-substituted alkyl, 2'-halo, ENA, and BNA/LNA. In one embodiment, B1, B2, B3, B1', B2', B3', and B4' each contain 2'-OMe modifications. In one embodiment, B1, B2, B3, B1', B2', B3', and B4' each contain 2'-OMe or 2'-F modifications. In one embodiment, at least one of B1, B2, B3, B1', B2', B3', and B4' contain 2'-O—N-methylacetamido (2'-O-NMA) modification.

C1 is a thermally destabilizing nucleotide placed at a site opposite to the seed region of the antisense strand (i.e., at positions 2-8 of the 5'-end of the antisense strand). For example, C1 is at a position of the sense strand that pairs with a nucleotide at positions 2-8 of the 5'-end of the antisense strand. In one example, C1 is at position 15 from the 5'-end of the sense strand. C1 nucleotide bears the thermally destabilizing modification which can include abasic modification; mismatch with the opposing nucleotide in the duplex; and sugar modification such as 2'-deoxy modification or acyclic nucleotide e.g., unlocked nucleic acids (UNA) or glycerol nucleic acid (GNA). In one embodiment, C1 has thermally destabilizing modification selected from the group consisting of: i) mismatch with the opposing nucleotide in the antisense strand; ii) abasic modification selected from the group consisting of:

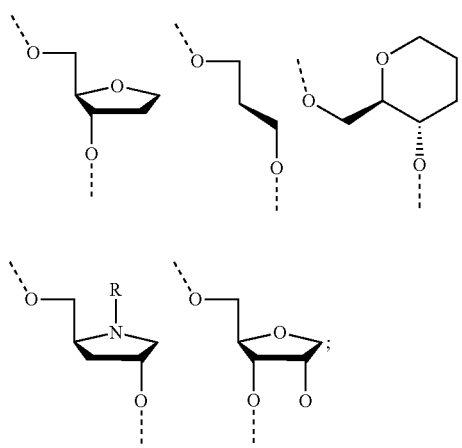

and iii) sugar modification selected from the group consisting of:

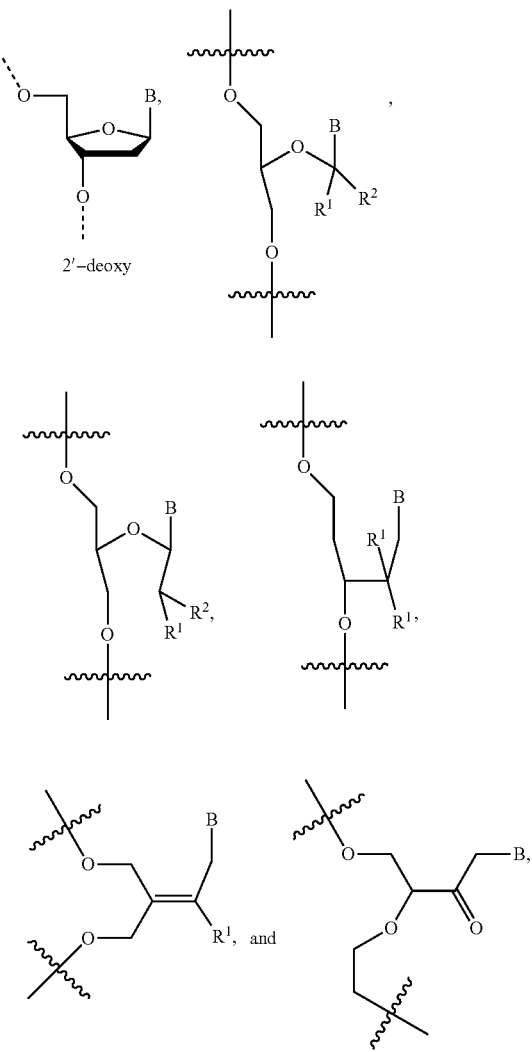

wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar. In one embodiment, the thermally destabilizing modification in C1 is a mismatch selected from the group consisting of G:G, G:A, G:U, G:T, A:A, A:C, C:C, C:U, C:T, U:U, T:T, and U:T; and optionally, at least one nucleobase in the mismatch pair is a 2'-deoxy nucleobase. In one example, the thermally destabilizing modification in C1 is GNA or

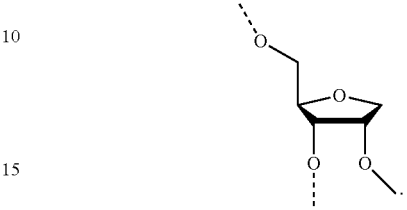

T1, T1', T2', and T3' each independently represent a nucleotide comprising a modification providing the nucleotide a steric bulk that is less or equal to the steric bulk of a 2'-OMe modification. A steric bulk refers to the sum of steric effects of a modification. Methods for determining steric effects of a modification of a nucleotide are known to one skilled in the art. The modification can be at the 2' position of a ribose sugar of the nucleotide, or a modification to a non-ribose nucleotide, acyclic nucleotide, or the backbone of the nucleotide that is similar or equivalent to the 2' position of the ribose sugar, and provides the nucleotide a steric bulk that is less than or equal to the steric bulk of a 2'-OMe modification. For example, T1, T1', T2', and T3' are each independently selected from DNA, RNA, LNA, 2'-F, and 2'-F-5'-methyl. In one embodiment, T1 is DNA. In one embodiment, T1' is DNA, RNA or LNA. In one embodiment, T2' is DNA or RNA. In one embodiment, T3' is DNA or RNA.

$n^1$, $n^3$, and $q^1$ are independently 4 to 15 nucleotides in length.

$n^5$, $q^3$, and $q^7$ are independently 1-6 nucleotide(s) in length.

$n^4$, $q^2$, and $q^6$ are independently 1-3 nucleotide(s) in length; alternatively, $n^4$ is 0.

$q^5$ is independently 0-10 nucleotide(s) in length.

$n^2$ and $q^4$ are independently 0-3 nucleotide(s) in length.

Alternatively, $n^4$ is 0-3 nucleotide(s) in length.

In one embodiment, $n^4$ can be 0. In one example, $n^4$ is 0, and $q^2$ and $q^6$ are 1. In another example, $n^4$ is 0, and $q^2$ and $q^6$ are 1, with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$, $q^2$, and $q^6$ are each 1.

In one embodiment, $n^2$, $n^4$, $q^2$, $q^4$, and $q^6$ are each 1.

In one embodiment, C1 is at position 14-17 of the 5'-end of the sense strand, when the sense strand is 19-22 nucleotides in length, and $n^4$ is 1. In one embodiment, C1 is at position 15 of the 5'-end of the sense strand In one embodiment, T3' starts at position 2 from the 5' end of the antisense strand. In one example, T3' is at position 2 from the 5' end of the antisense strand and $q^6$ is equal to 1.

In one embodiment, T1' starts at position 14 from the 5' end of the antisense strand. In one example, T1' is at position 14 from the 5' end of the antisense strand and $q^2$ is equal to 1.

In an exemplary embodiment, T3' starts from position 2 from the 5' end of the antisense strand and T1' starts from position 14 from the 5' end of the antisense strand. In one example, T3' starts from position 2 from the 5' end of the antisense strand and $q^6$ is equal to 1 and T1' starts from position 14 from the 5' end of the antisense strand and $q^2$ is equal to 1.

In one embodiment, T1' and T3' are separated by 11 nucleotides in length (i.e. not counting the T1' and T3' nucleotides).

In one embodiment, T1' is at position 14 from the 5' end of the antisense strand. In one example, T1' is at position 14 from the 5' end of the antisense strand and $q^2$ is equal to 1, and the modification at the 2' position or positions in a non-ribose, acyclic or backbone that provide less steric bulk than a 2'-OMe ribose.

In one embodiment, T3' is at position 2 from the 5' end of the antisense strand. In one example, T3' is at position 2 from the 5' end of the antisense strand and $q^6$ is equal to 1, and the modification at the 2' position or positions in a non-ribose, acyclic or backbone that provide less than or equal to steric bulk than a 2'-OMe ribose.

In one embodiment, T1 is at the cleavage site of the sense strand. In one example, T1 is at position 11 from the 5' end of the sense strand, when the sense strand is 19-22 nucleotides in length, and $n^2$ is 1. In an exemplary embodiment, T1 is at the cleavage site of the sense strand at position 11 from the 5' end of the sense strand, when the sense strand is 19-22 nucleotides in length, and $n^2$ is 1, In one embodiment, T2' starts at position 6 from the 5' end of the antisense strand. In one example, T2' is at positions 6-10 from the 5' end of the antisense strand, and $q^4$ is 1.

In an exemplary embodiment, T1 is at the cleavage site of the sense strand, for instance, at position 11 from the 5' end of the sense strand, when the sense strand is 19-22 nucleotides in length, and $n^2$ is 1; T1' is at position 14 from the 5' end of the antisense strand, and $q^2$ is equal to 1, and the modification to T1' is at the 2' position of a ribose sugar or at positions in a non-ribose, acyclic or backbone that provide less steric bulk than a 2'-OMe ribose; T2' is at positions 6-10 from the 5' end of the antisense strand, and $q^4$ is 1; and T3' is at position 2 from the 5' end of the antisense strand, and $q^6$ is equal to 1, and the modification to T3' is at the 2' position or at positions in a non-ribose, acyclic or backbone that provide less than or equal to steric bulk than a 2'-OMe ribose.

In one embodiment, T2' starts at position 8 from the 5' end of the antisense strand. In one example, T2' starts at position 8 from the 5' end of the antisense strand, and $q^4$ is 2.

In one embodiment, T2' starts at position 9 from the 5' end of the antisense strand. In one example, T2' is at position 9 from the 5' end of the antisense strand, and $q^4$ is 1.

In one embodiment, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 7, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 7, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1; optionally with at least 2 additional TT at the 3'-end of the antisense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1; optionally with at least 2 additional TT at the 3'-end of the antisense strand; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within positions 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

The RNAi agent can comprise a phosphorus-containing group at the 5'-end of the sense strand or antisense strand. The 5'-end phosphorus-containing group can be 5'-end phosphate (5'-P), 5'-end phosphorothioate (5'-PS), 5'-end phosphorodithioate (5'-PS$_2$), 5'-end vinylphosphonate (5'-VP), 5'-end methylphosphonate (MePhos), or 5'-deoxy-5'-C-malonyl

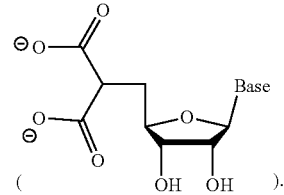

When the 5'-end phosphorus-containing group is 5'-end vinylphosphonate (5'-VP), the 5'-VP can be either 5'-E-VP isomer (i.e., trans-vinylphosphate,

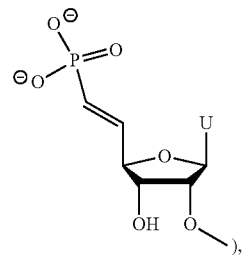

5'-Z—VP isomer (i.e., cis-vinylphosphate,

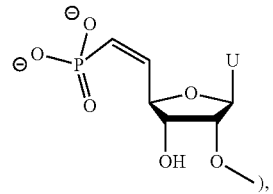

or mixtures thereof.

In one embodiment, the RNAi agent comprises a phosphorus-containing group at the 5'-end of the sense strand. In one embodiment, the RNAi agent comprises a phosphorus-containing group at the 5'-end of the antisense strand.

In one embodiment, the RNAi agent comprises a 5'-P. In one embodiment, the RNAi agent comprises a 5'-P in the antisense strand.

In one embodiment, the RNAi agent comprises a 5'-PS. In one embodiment, the RNAi agent comprises a 5'-PS in the antisense strand.

In one embodiment, the RNAi agent comprises a 5'-VP. In one embodiment, the RNAi agent comprises a 5'-VP in the antisense strand. In one embodiment, the RNAi agent comprises a 5'-E-VP in the antisense strand. In one embodiment, the RNAi agent comprises a 5'-Z—VP in the antisense strand.

In one embodiment, the RNAi agent comprises a 5'-PS$_2$. In one embodiment, the RNAi agent comprises a 5'-PS$_2$ in the antisense strand.

In one embodiment, the RNAi agent comprises a 5'-PS$_2$. In one embodiment, the RNAi agent comprises a 5'-deoxy-5'-C-malonyl in the antisense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-VP. The 5'-VP may be 5'-E-VP, 5'-Z—VP, or combination thereof. In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The dsRNAi RNA agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z—VP, or combination thereof), and a targeting ligand.

In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-VP (e.g., a 5'-E-VP, 5'-Z—VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z—VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z—VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS$_2$ and a targeting ligand. In one embodiment, the 5'-PS$_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In a particular embodiment, an RNAi agent of the present invention comprises:
 (a) a sense strand having:
  (i) a length of 21 nucleotides;
  (ii) an ASGPR ligand attached to the 3'-end, wherein said ASGPR ligand comprises three GalNAc derivatives attached through a trivalent branched linker; and
  (iii) 2'-F modifications at positions 1, 3, 5, 7, 9 to 11, 13, 17, 19, and 21, and 2'-OMe modifications at positions 2, 4, 6, 8, 12, 14 to 16, 18, and 20 (counting from the 5' end);
 and
 (b) an antisense strand having:
  (i) a length of 23 nucleotides;
  (ii) 2'-OMe modifications at positions 1, 3, 5, 9, 11 to 13, 15, 17, 19, 21, and 23, and 2'F modifications at positions 2, 4, 6 to 8, 10, 14, 16, 18, 20, and 22 (counting from the 5' end); and
  (iii) phosphorothioate internucleotide linkages between nucleotide positions 21 and 22, and between nucleotide positions 22 and 23 (counting from the 5' end);
 wherein the dsRNA agents have a two nucleotide overhang at the 3'-end of the antisense strand, and a blunt end at the 5'-end of the antisense strand.

In another particular embodiment, an RNAi agent of the present invention comprises:
 (a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 1, 3, 5, 7, 9 to 11, 13, 15, 17, 19, and 21, and 2'-OMe modifications at positions 2, 4, 6, 8, 12, 14, 16, 18, and 20 (counting from the 5' end); and
  (iv) phosphorothioate internucleotide linkages between nucleotide positions 1 and 2, and between nucleotide positions 2 and 3 (counting from the 5' end);
 and
 (b) an antisense strand having:
  (i) a length of 23 nucleotides;
  (ii) 2'-OMe modifications at positions 1, 3, 5, 7, 9, 11 to 13, 15, 17, 19, and 21 to 23, and 2'F modifications at positions 2, 4, 6, 8, 10, 14, 16, 18, and 20 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
 wherein the RNAi agents have a two nucleotide overhang at the 3'-end of the antisense strand, and a blunt end at the 5'-end of the antisense strand.

In another particular embodiment, a RNAi agent of the present invention comprises:
 (a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1 to 6, 8, 10, and 12 to 21, 2'-F modifications at positions 7, and 9, and a deoxy-nucleotide (e.g. dT) at position 11 (counting from the 5' end); and
  (iv) phosphorothioate internucleotide linkages between nucleotide positions 1 and 2, and between nucleotide positions 2 and 3 (counting from the 5' end);
 and
 (b) an antisense strand having:
  (i) a length of 23 nucleotides;
  (ii) 2'-OMe modifications at positions 1, 3, 7, 9, 11, 13, 15, 17, and 19 to 23, and 2'-F modifications at positions 2, 4 to 6, 8, 10, 12, 14, 16, and 18 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
 wherein the RNAi agents have a two nucleotide overhang at the 3'-end of the antisense strand, and a blunt end at the 5'-end of the antisense strand.

In another particular embodiment, a RNAi agent of the present invention comprises:
 (a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1 to 6, 8, 10, 12, 14, and 16 to 21, and 2'-F modifications at positions 7, 9, 11, 13, and 15; and
  (iv) phosphorothioate internucleotide linkages between nucleotide positions 1 and 2, and between nucleotide positions 2 and 3 (counting from the 5' end);
 and
 (b) an antisense strand having:
  (i) a length of 23 nucleotides;
  (ii) 2'-OMe modifications at positions 1, 5, 7, 9, 11, 13, 15, 17, 19, and 21 to 23, and 2'-F modifications at positions 2 to 4, 6, 8, 10, 12, 14, 16, 18, and 20 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1 to 9, and 12 to 21, and 2'-F modifications at positions 10, and 11; and
  (iv) phosphorothioate internucleotide linkages between nucleotide positions 1 and 2, and between nucleotide positions 2 and 3 (counting from the 5' end); and
(b) an antisense strand having:
  (i) a length of 23 nucleotides;
  (ii) 2'-OMe modifications at positions 1, 3, 5, 7, 9, 11 to 13, 15, 17, 19, and 21 to 23, and 2'-F modifications at positions 2, 4, 6, 8, 10, 14, 16, 18, and 20 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 1, 3, 5, 7, 9 to 11, and 13, and 2'-OMe modifications at positions 2, 4, 6, 8, 12, and 14 to 21; and
  (iv) phosphorothioate internucleotide linkages between nucleotide positions 1 and 2, and between nucleotide positions 2 and 3 (counting from the 5' end); and
(b) an antisense strand having:
  (i) a length of 23 nucleotides;
  (ii) 2'-OMe modifications at positions 1, 3, 5 to 7, 9, 11 to 13, 15, 17 to 19, and 21 to 23, and 2'-F modifications at positions 2, 4, 8, 10, 14, 16, and 20 (counting from the 5' end); and (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1, 2, 4, 6, 8, 12, 14, 15, 17, and 19 to 21, and 2'-F modifications at positions 3, 5, 7, 9 to 11, 13, 16, and 18; and
  (iv) phosphorothioate internucleotide linkages between nucleotide positions 1 and 2, and between nucleotide positions 2 and 3 (counting from the 5' end); and
(b) an antisense strand having:
  (i) a length of 25 nucleotides;
  (ii) 2'-OMe modifications at positions 1, 4, 6, 7, 9, 11 to 13, 15, 17, and 19 to 23, 2'-F modifications at positions 2, 3, 5, 8, 10, 14, 16, and 18, and desoxynucleotides (e.g. dT) at positions 24 and 25 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a four nucleotide overhang at the 3'-end of the antisense strand, and a blunt end at the 5'-end of the antisense strand.

In another particular embodiment, a RNAi agent of the present invention comprises:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1 to 6, 8, and 12 to 21, and 2'-F modifications at positions 7, and 9 to 11; and
  (iv) phosphorothioate internucleotide linkages between nucleotide positions 1 and 2, and between nucleotide positions 2 and 3 (counting from the 5' end); and
(b) an antisense strand having:
  (i) a length of 23 nucleotides;
  (ii) 2'-OMe modifications at positions 1, 3 to 5, 7, 8, 10 to 13, 15, and 17 to 23, and 2'-F modifications at positions 2, 6, 9, 14, and 16 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1 to 6, 8, and 12 to 21, and 2'-F modifications at positions 7, and 9 to 11; and
  (iv) phosphorothioate internucleotide linkages between nucleotide positions 1 and 2, and between nucleotide positions 2 and 3 (counting from the 5' end);

and (b) an antisense strand having:
(i) a length of 23 nucleotides;
(ii) 2'-OMe modifications at positions 1, 3 to 5, 7, 10 to 13, 15, and 17 to 23, and 2'-F modifications at positions 2, 6, 8, 9, 14, and 16 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:
(i) a length of 19 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 4, 6, and 10 to 19, and 2'-F modifications at positions 5, and 7 to 9; and
(iv) phosphorothioate internucleotide linkages between nucleotide positions 1 and 2, and between nucleotide positions 2 and 3 (counting from the 5' end);
and (b) an antisense strand having:
(i) a length of 21 nucleotides;
(ii) 2'-OMe modifications at positions 1, 3 to 5, 7, 10 to 13, 15, and 17 to 21, and 2'-F modifications at positions 2, 6, 8, 9, 14, and 16 (counting from the 5' end); and
(iii) phosphorothioate internucleotide linkages between nucleotide positions 1 and 2, between nucleotide positions 2 and 3, between nucleotide positions 19 and 20, and between nucleotide positions 20 and 21 (counting from the 5' end);

wherein the RNAi agents have a two nucleotide overhang at the 3'-end of the antisense strand, and a blunt end at the 5'-end of the antisense strand.

In certain embodiments, the iRNA for use in the methods of the invention is an agent selected from agents listed in any one of Tables 2-7, 15, 18, 20-23, 30, and 31. These agents may further comprise a ligand.

III. iRNAs Conjugated to Ligands

Another modification of the RNA of an iRNA of the invention involves chemically linking to the iRNA one or more ligands, moieties or conjugates that enhance the activity, cellular distribution, or cellular uptake of the iRNA e.g., into a cell. Such moieties include but are not limited to lipid moieties such as a cholesterol moiety (Letsinger et al., *Proc. Natl. Acid. Sci. USA*, 1989, 86: 6553-6556). In other embodiments, the ligand is cholic acid (Manoharan et al., *Biorg. Med. Chem. Let.*, 1994, 4:1053-1060), a thioether, e.g., beryl-S-tritylthiol (Manoharan et al., *Ann. N.Y. Acad. Sci.*, 1992, 660:306-309; Manoharan et al., *Biorg. Med. Chem. Let.*, 1993, 3:2765-2770), a thiocholesterol (Oberhauser et al., *Nucl. Acids Res.*, 1992, 20:533-538), an aliphatic chain, e.g., dodecandiol or undecyl residues (Saison-Behmoaras et al., *EMBO J*, 1991, 10:1111-1118; Kabanov et al., *FEBS Lett.*, 1990, 259:327-330; Svinarchuk et al., *Biochimie*, 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.*, 1995, 36:3651-3654; Shea et al., *Nucl. Acids Res.*, 1990, 18:3777-3783), a polyamine or a polyethylene glycol chain (Manoharan et al., *Nucleosides & Nucleotides*, 1995, 14:969-973), or adamantane acetic acid (Manoharan et al., *Tetrahedron Lett.*, 1995, 36:3651-3654), a palmityl moiety (Mishra et al., *Biochim. Biophys. Acta*, 1995, 1264:229-237), or an octadecylamine or hexylaminocarbonyloxycholesterol moiety (Crooke et al., *J. Pharmacol. Exp. Ther.*, 1996, 277:923-937).

In certain embodiments, a ligand alters the distribution, targeting, or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands do not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic. In certain embodiments, the ligand is a multivalent galactose, e.g., an N-acetyl-galactosamine.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, 03-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, or intermediate filaments. The drug can be, for example, taxol, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins, etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin. Oligonucleotides that comprise a number of phosphorothioate linkages are also known to bind to serum protein, thus short oligonucleotides, e.g., oligonucleotides of about 5 bases, 10 bases, 15 bases, or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated iRNAs of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems® (Foster City, Calif.). Any other methods for such synthesis known in the art may additionally or alternatively be employed. It is also known to use similar techniques to prepare other oligonucleotides, such as the phosphorothioates and alkylated derivatives.

In the ligand-conjugated iRNAs and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In certain embodiments, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In certain embodiments, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In other embodiments, the lipid based ligand binds HSA weakly or not at all, such that the conjugate will be preferably distributed to the kidney. Other moieties that target to kidney cells can also be used in place of, or in addition to, the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 9). An RFGF analogue (e.g., amino acid sequence AALLPVL-LAAP (SEQ ID NO:10) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:11) and the *Drosophila* Antennapedia protein (RQIKIWFQNRRMKWKK (SEQ ID NO:12) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA further comprises a carbohydrate. The carbohydrate conjugated iRNA is advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri-, and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In certain embodiments, a carbohydrate conjugate for use in the compositions and methods of the invention is a monosaccharide.

In one embodiment, a carbohydrate conjugate for use in the compositions and methods of the invention is selected from the group consisting of:

Formula II

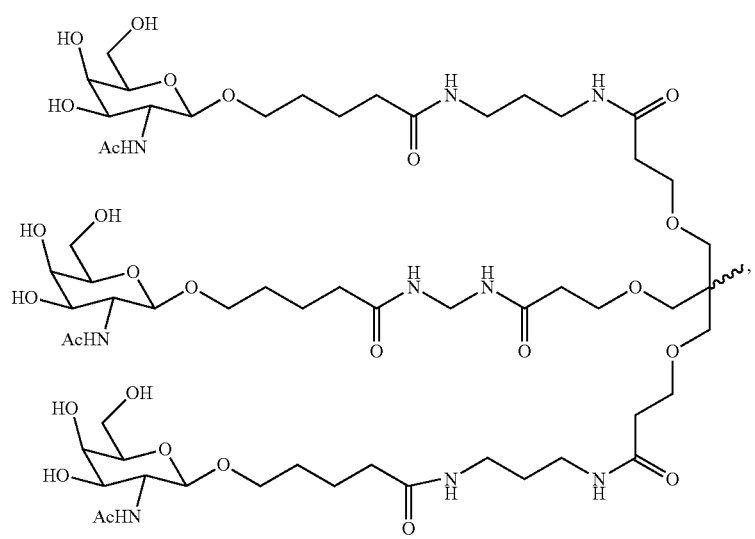

-continued
Formula III
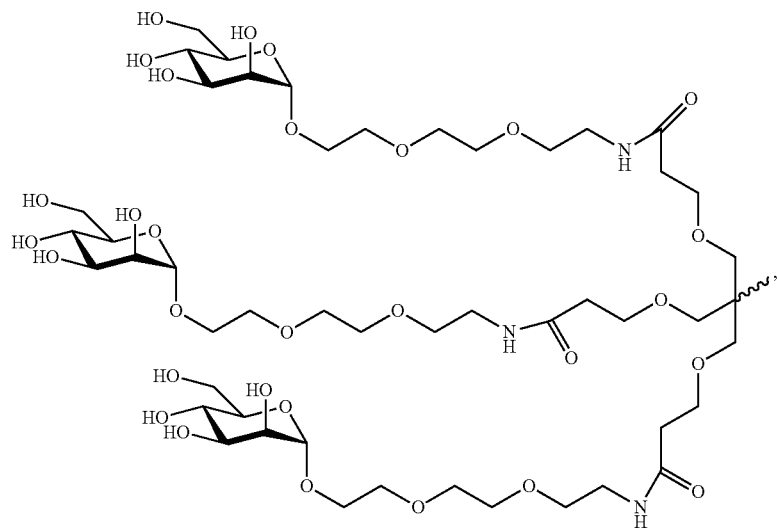
Formula IV
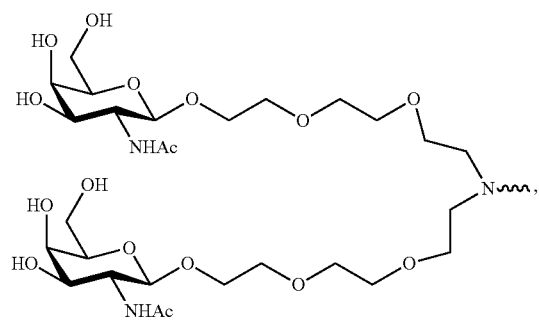
Formula V
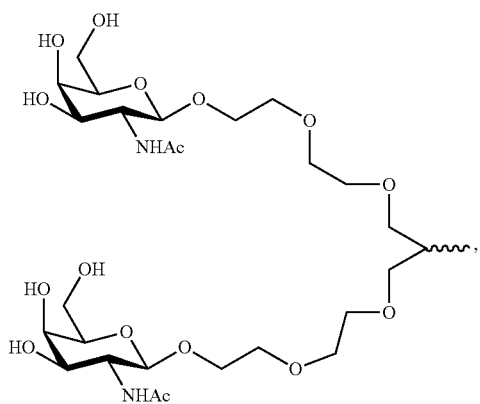
Formula VI
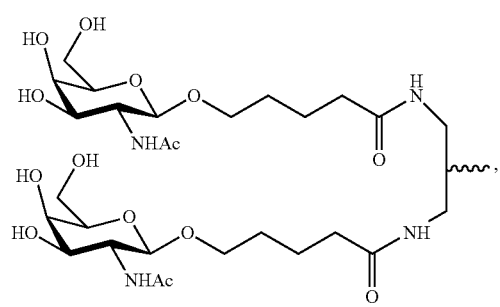
Formula VII
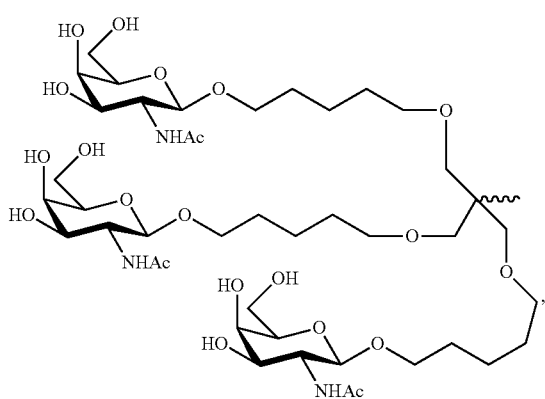
Formula VIII
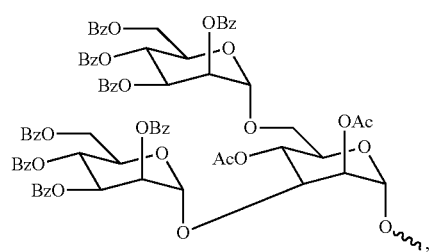

Formula IX
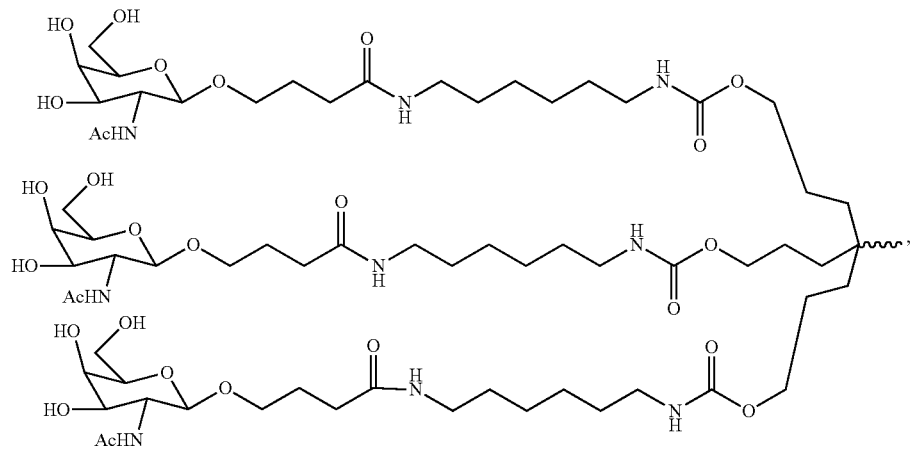
Formula X
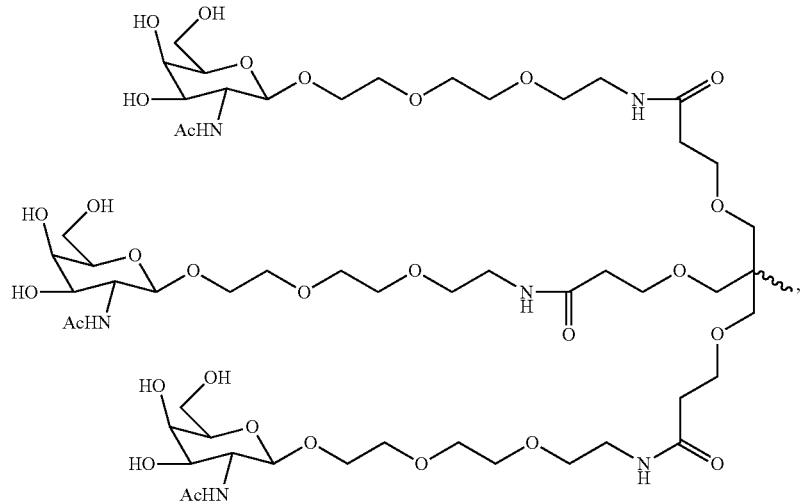
Formula XI
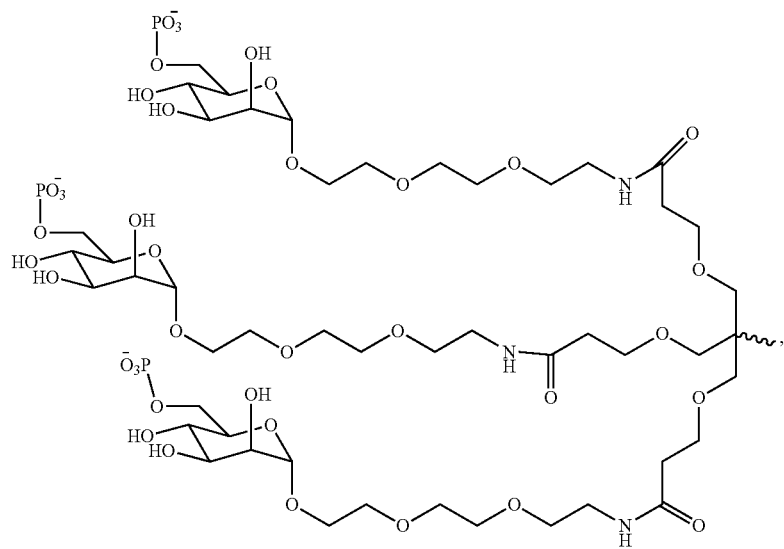

Formula XII
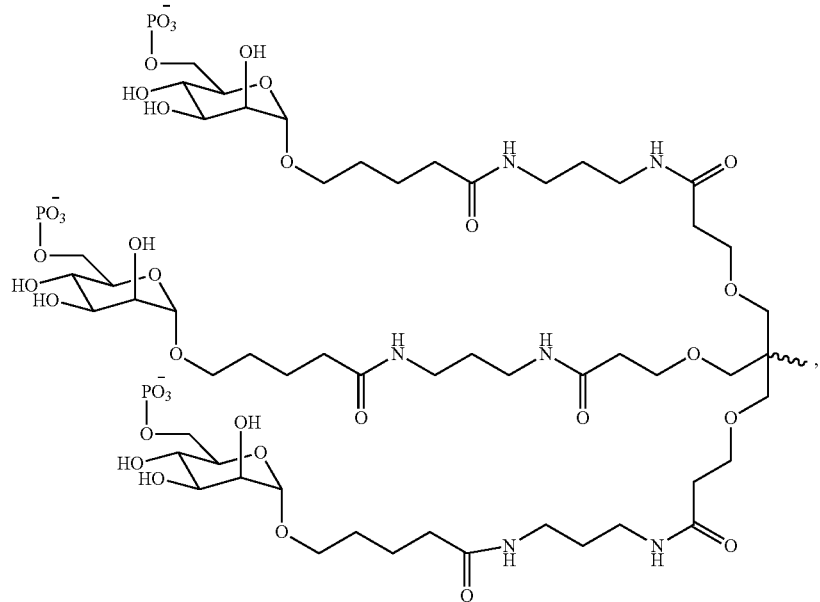
Formula XIII
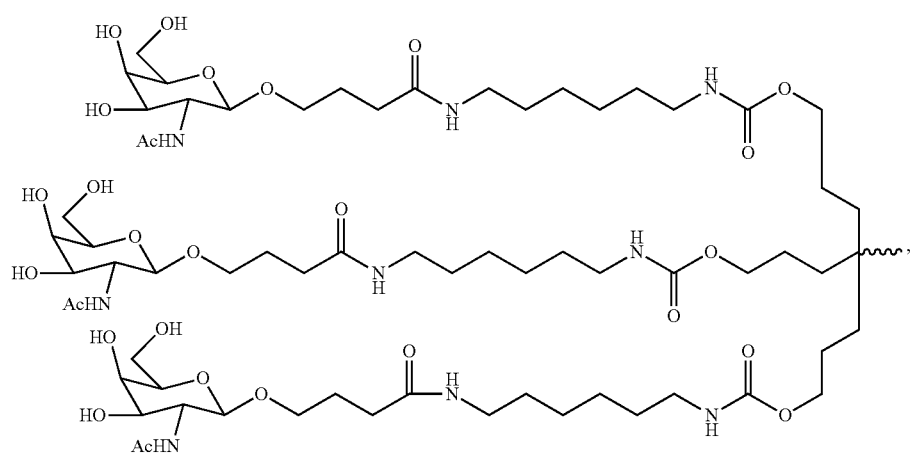
Formula XIV
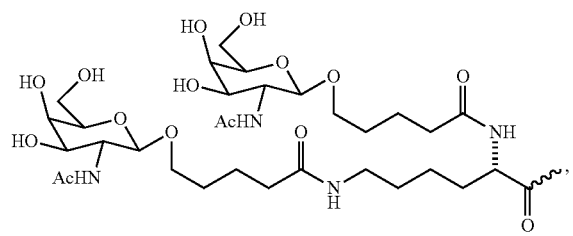
Formula XV
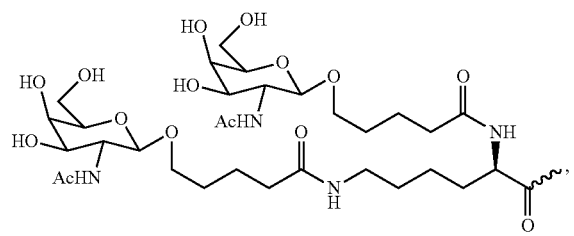
Formula XVI
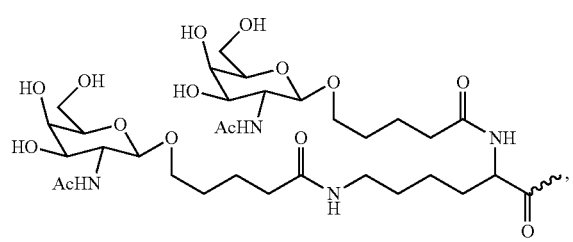
Formula XVII
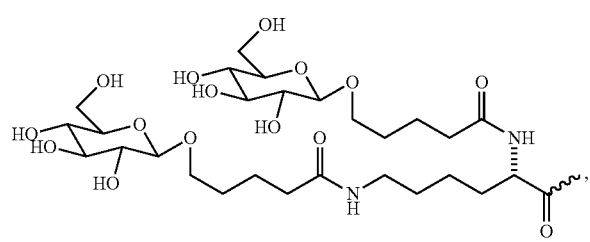

Formula XVIII
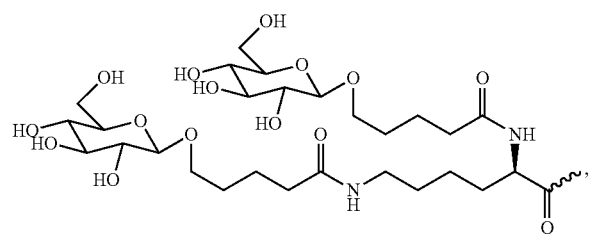
Formula XIX
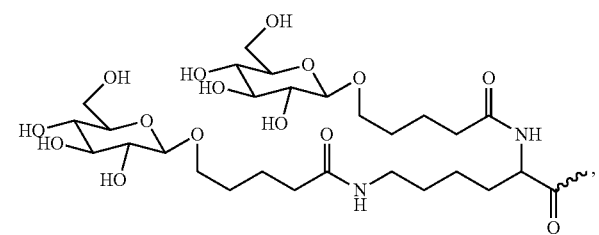
Formula XX
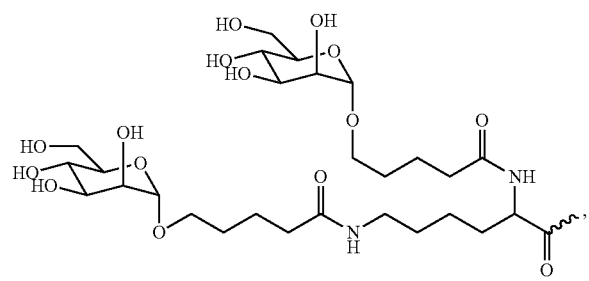
Formula XXI
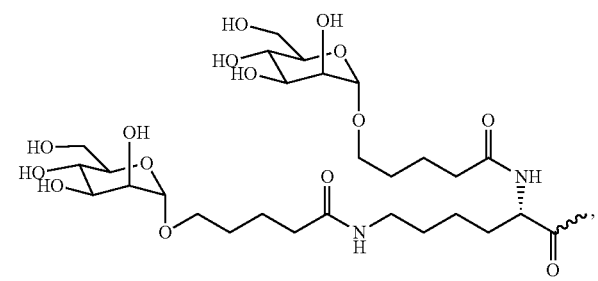
Formula XXII
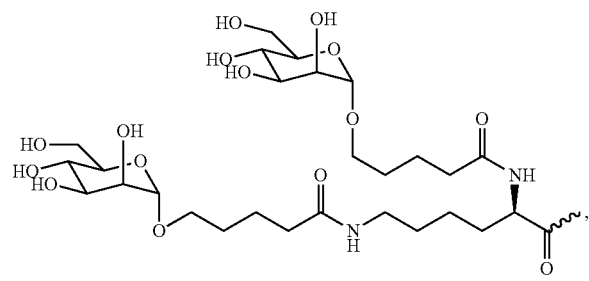
Formula XXIII
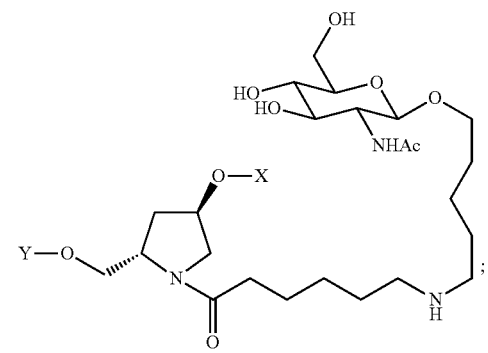
(Formula XXIV)
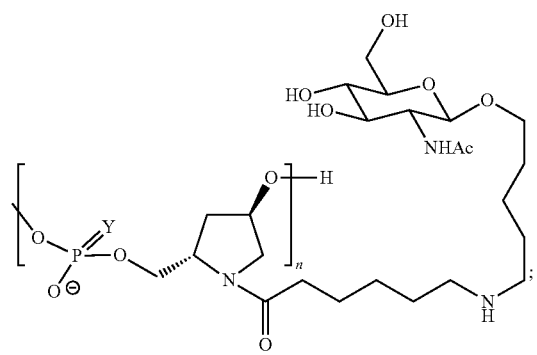
wherein Y is O or S and n is 3-6
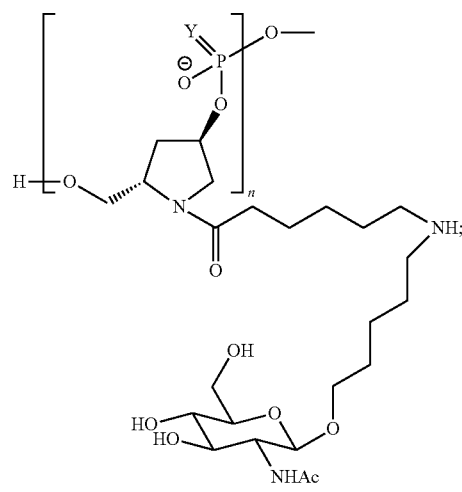
wherein Y is O or S and n is 3-6

Formula XXVI
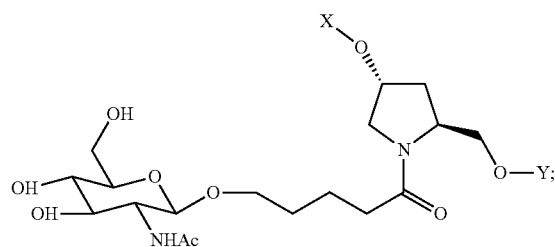
(Formula XXVII)
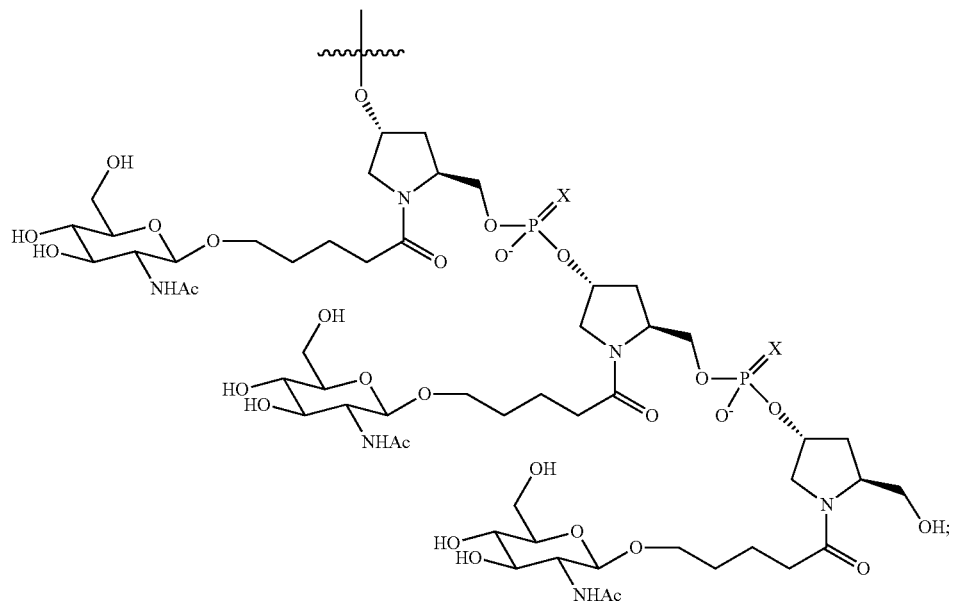
wherein X is O or S
Formula XXVII
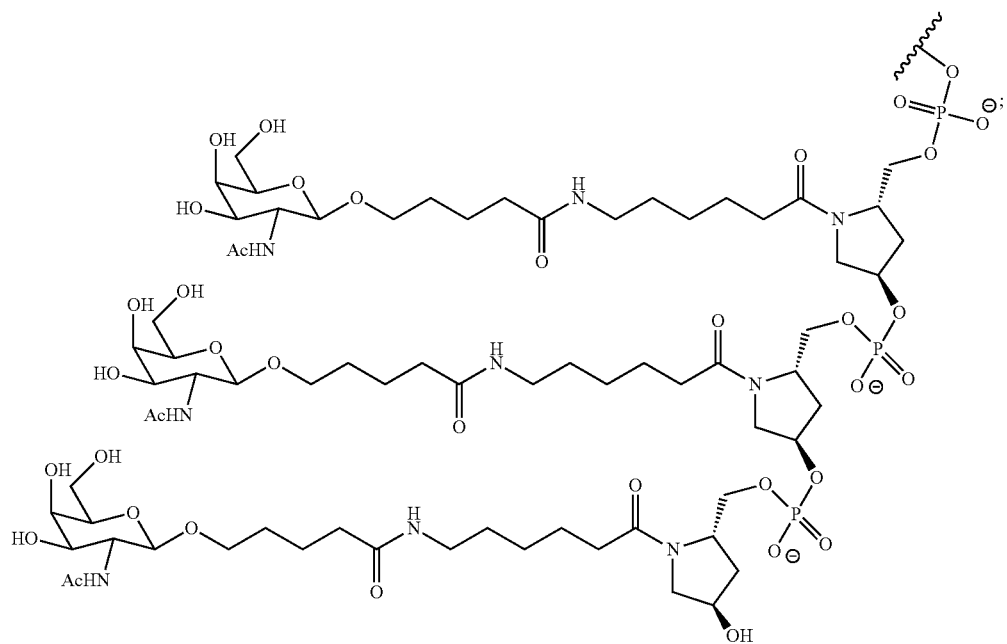

Formula XXIX
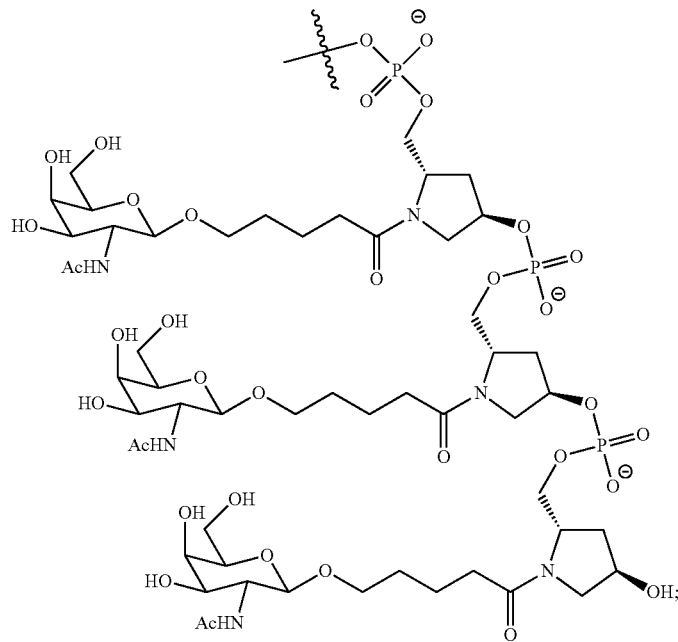
Formula XXXI
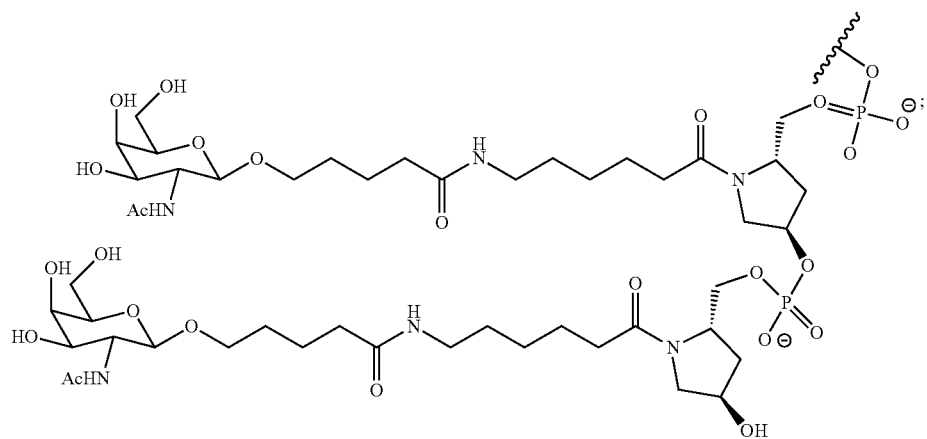
Formula XXX
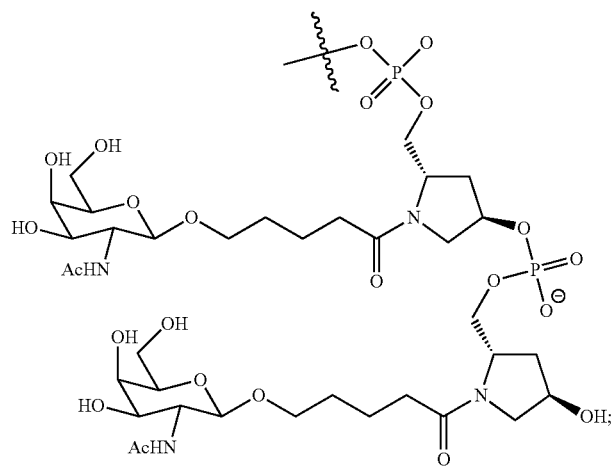

-continued
Formula XXXII
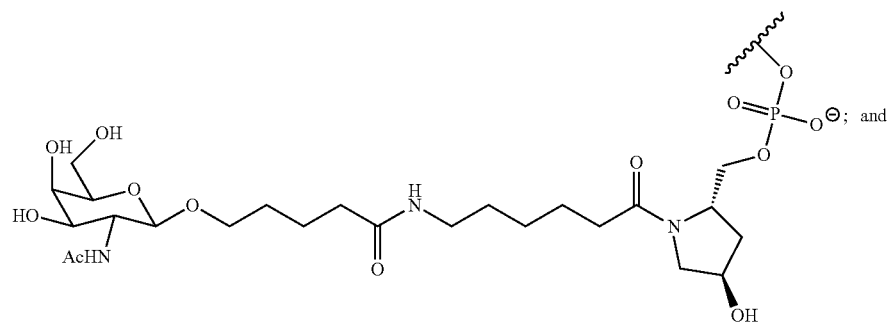
Formula XXXIII
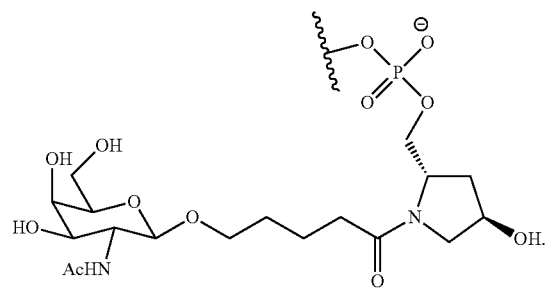
Formula XXXIV
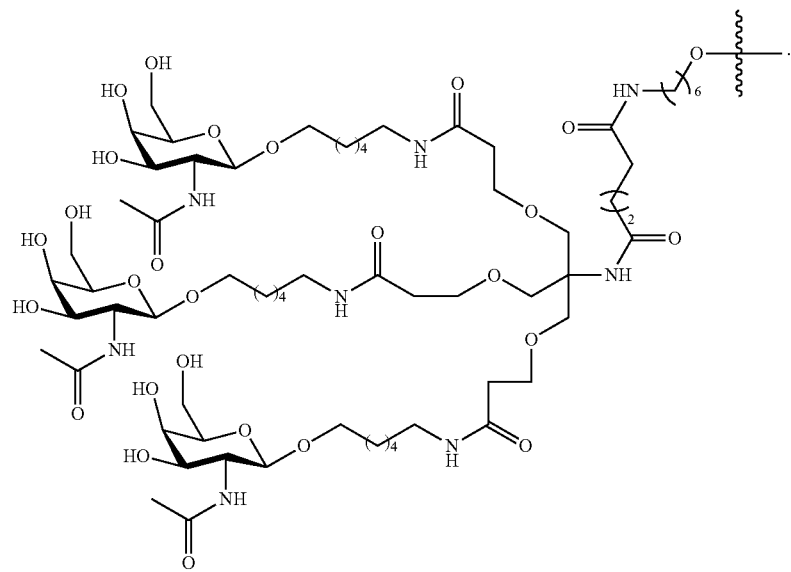

In another embodiment, a carbohydrate conjugate for use in the compositions and methods of the invention is a monosaccharide. In one embodiment, the monosaccharide is an N-acetylgalactosamine, such as
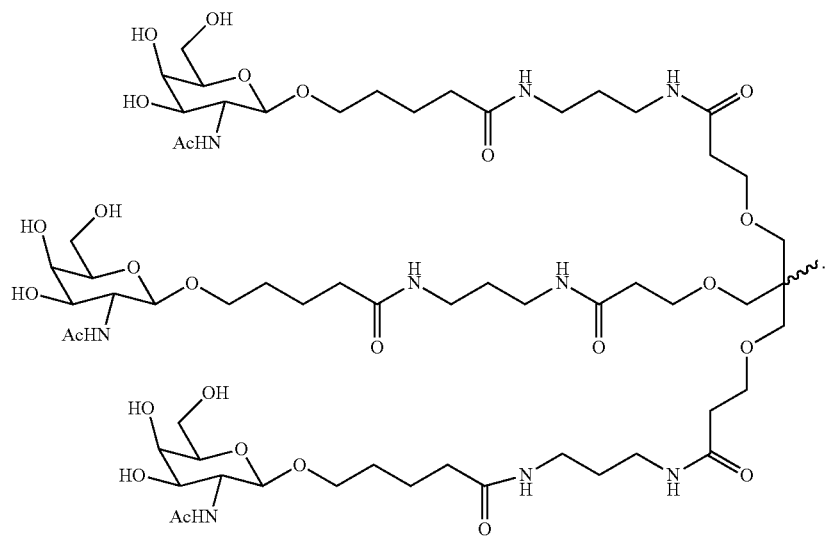
Formula II
Another representative carbohydrate conjugate for use in the embodiments described herein includes, but is not limited to,

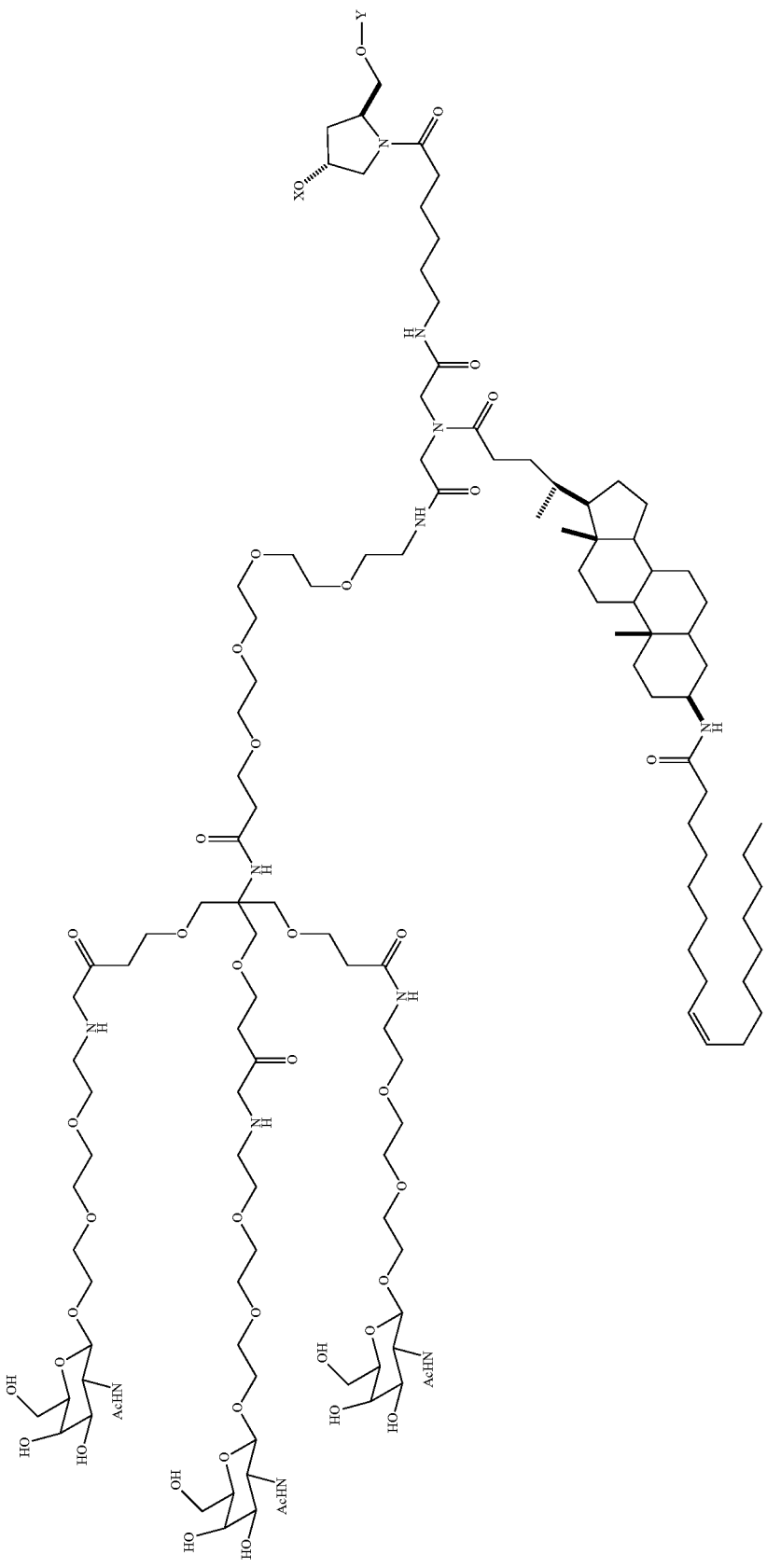

(Formula XXXVI), when one of X or Y is an oligonucleotide, the other is a hydrogen.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one or more GalNAc or GalNAc derivative attached to the iRNA agent. The GalNAc may be attached to any nucleotide via a linker on the sense strand or antsisense strand. The GalNac may be attached to the 5'-end of the sense strand, the 3' end of the sense strand, the 5'-end of the antisense strand, or the 3'-end of the antisense strand. In one embodiment, the GalNAc is attached to the 3' end of the sense strand, e.g., via a trivalent linker.

In other embodiments, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of linkers, e.g., monovalent linkers.

In some embodiments, for example, when the two strands of an iRNA agent of the invention is part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator or a cell permeation peptide.

Additional carbohydrate conjugates and linkers suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, SO$_2$, SO$_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO$_2$, N(R8), C(O), substituted or unsubstituted aryl, substituted or unsubstituted heteroaryl, or substituted or unsubstituted heterocyclic; where R8 is hydrogen, acyl, aliphatic, or substituted aliphatic. In one embodiment, the linker is about 1-24 atoms, 2-24, 3-24, 4-24, 5-24, 6-24, 6-18, 7-18, 8-18, 7-17, 8-17, 6-16, 7-17, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times, or more, or at least 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or 100 times faster in the cell (or under in vitro conditions selected to mimic intracellular conditions) as compared to blood or serum (or under in vitro conditions selected to mimic extracellular conditions).

i. Redox Cleavable Linking Groups

In certain embodiments, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In other embodiments, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, and —O—P(S)(H)—S—. A preferred embodiment is —O—P(O)(OH)—O—. These candidates can be evaluated using methods analogous to those described above.

iii. Acid Cleavable Linking Groups

In other embodiments, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In other embodiments, a cleavable linker comprises an ester-based cleavable linking group. An ester-based cleavable linking group is cleaved by enzymes such as esterases and amidases in cells. Examples of ester-based cleavable linking groups include, but are not limited to, esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet other embodiments, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In some embodiments, an iRNA of the invention is conjugated to a carbohydrate through a linker. Non-limiting examples of iRNA carbohydrate conjugates with linkers of the compositions and methods of the invention include, but are not limited to, (Formula XXXVII)
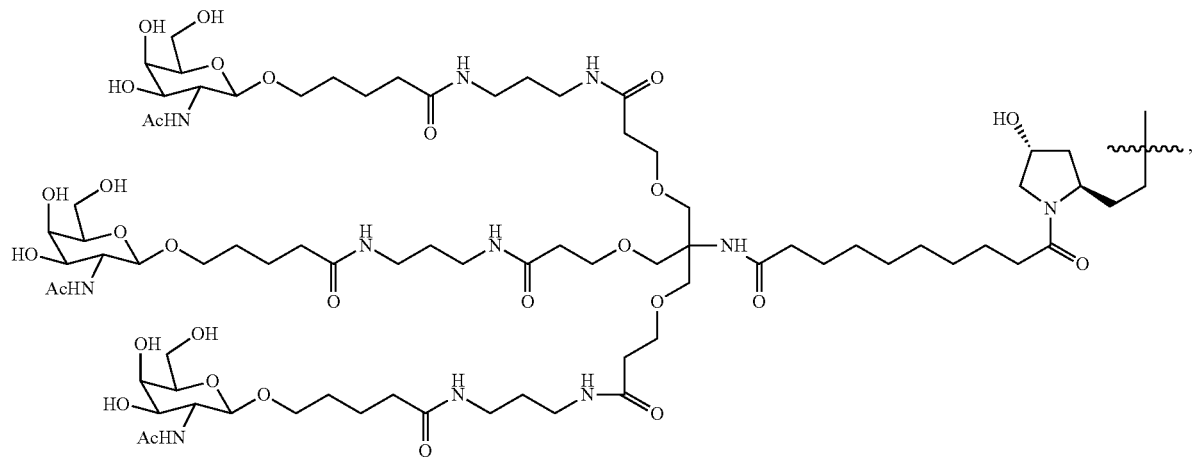
(Formula XXXVIII)
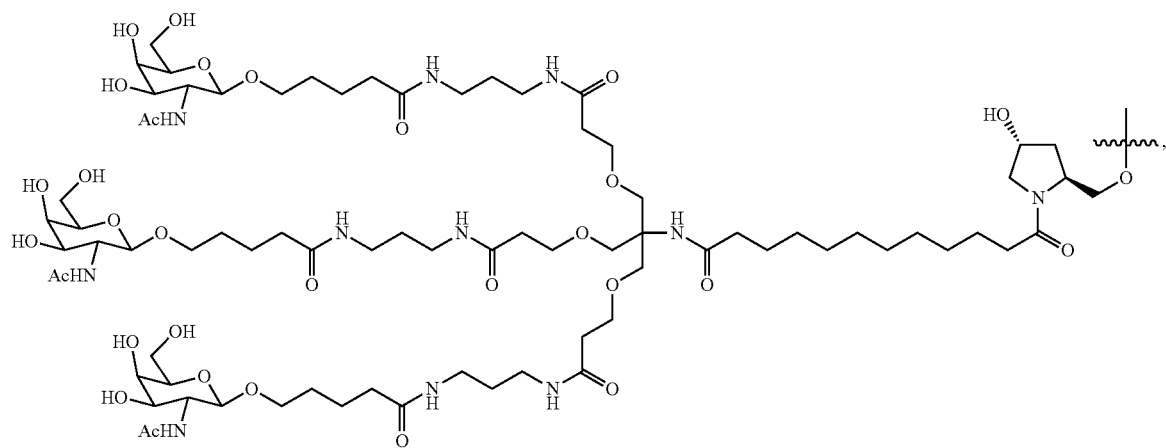
(Formula XXXIX)
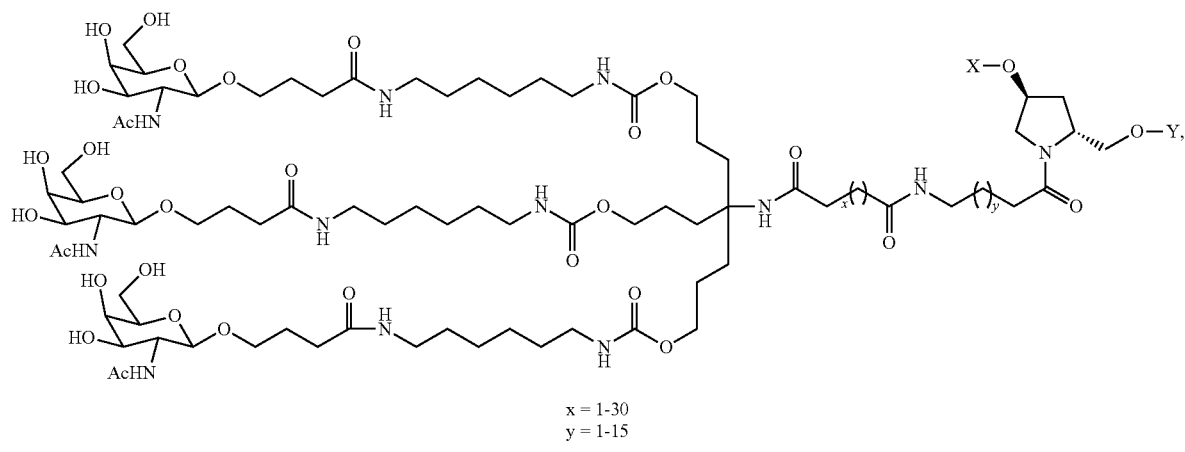
x = 1-30
y = 1-15

(Formula XL)
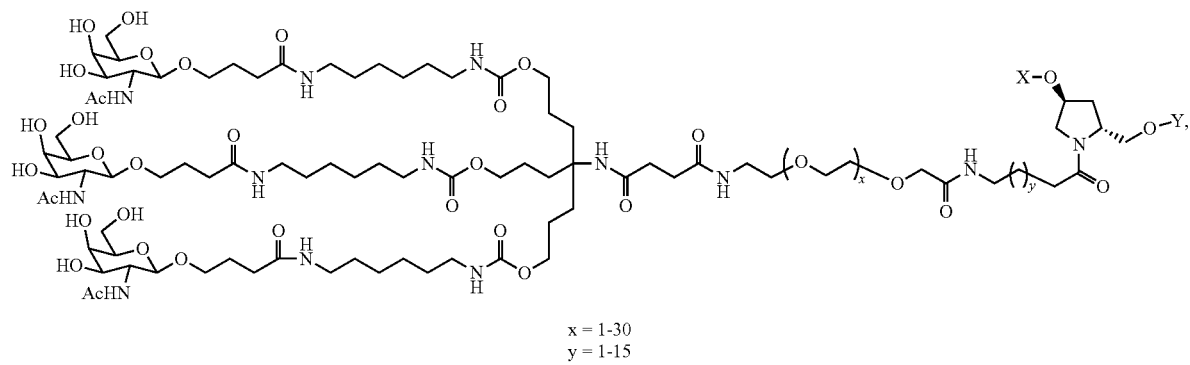
x = 1-30
y = 1-15
(Formula XLI)
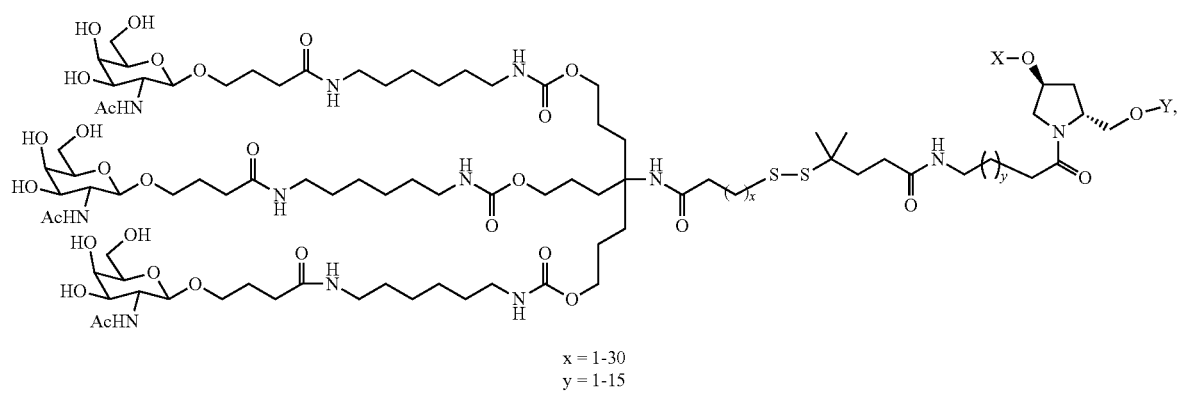
x = 1-30
y = 1-15
(Formula XLII)
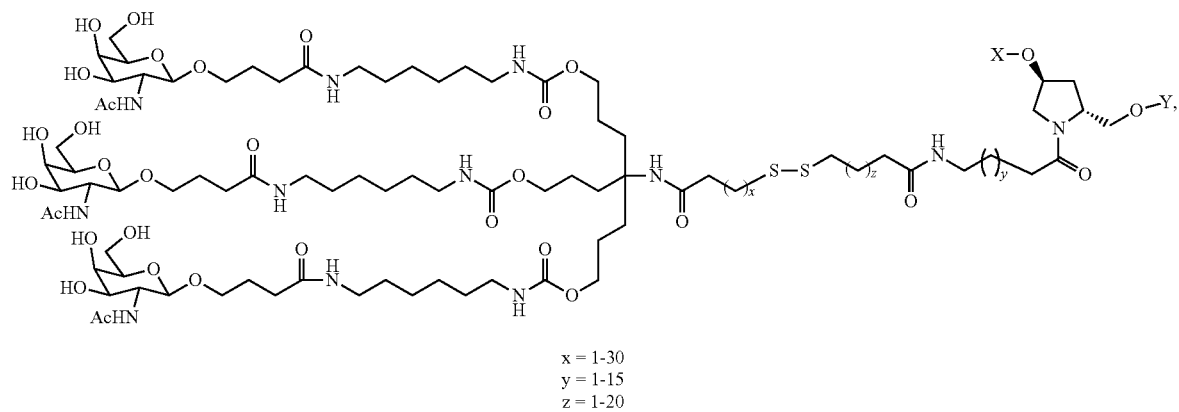
x = 1-30
y = 1-15
z = 1-20
(Formula XLIII)
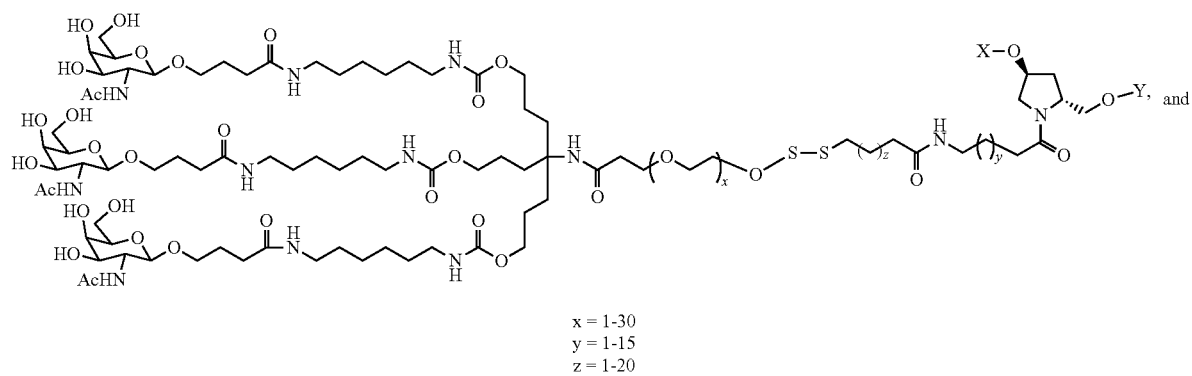
and
x = 1-30
y = 1-15
z = 1-20

(Formula XLIV)

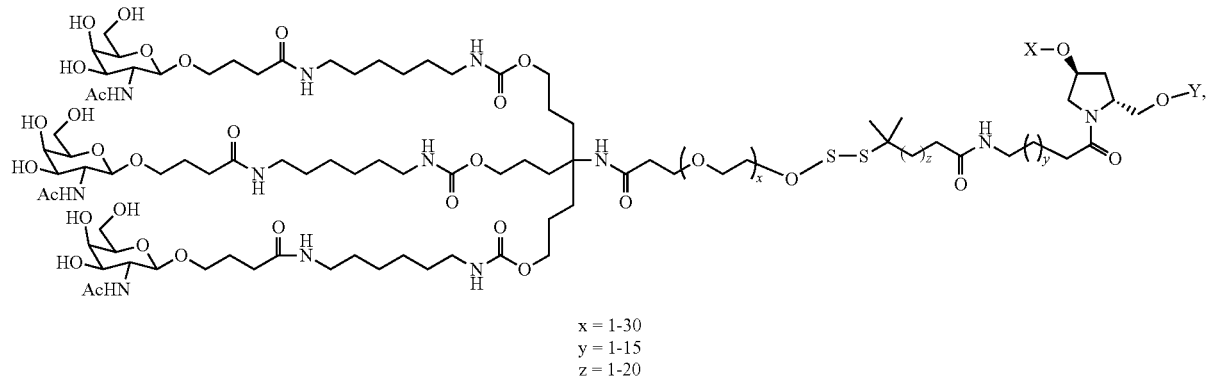

x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XLV)-(XLVI):

Formula XXXXV

Formula XLVI

Formula XLVII

Formula XLVIII

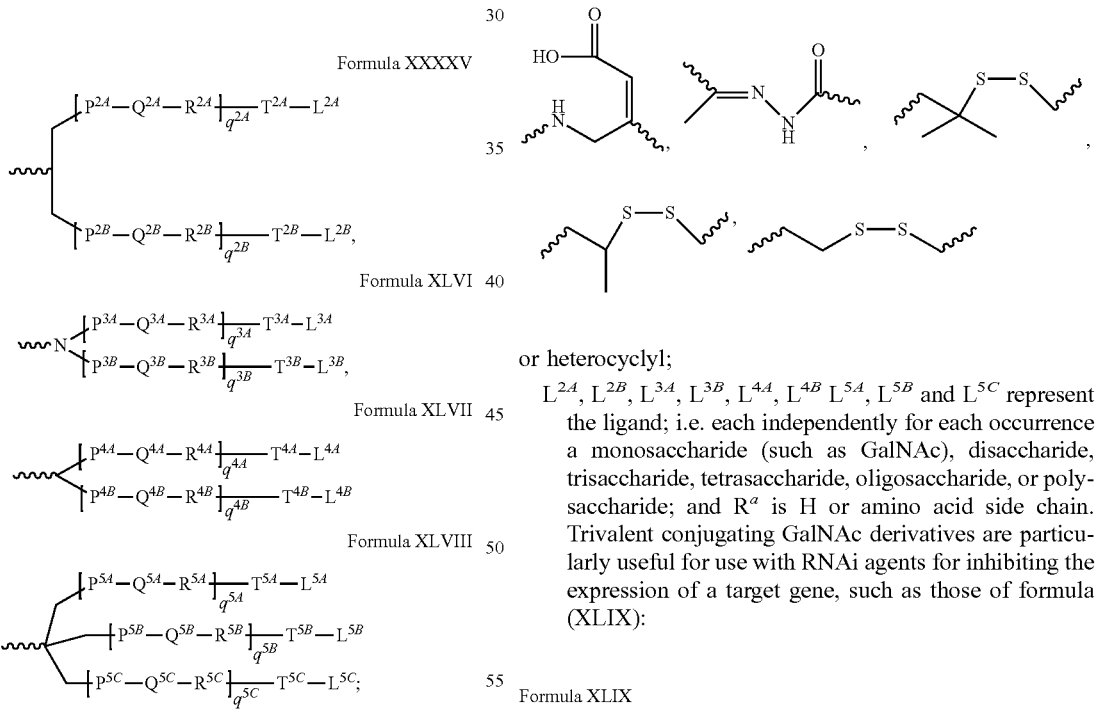

wherein:
q2A, q2B, q3A, q3B, q4A, q4B, q5A, q5B and q5C represent independently for each occurrence 0-20 and wherein the repeating unit can be the same or different;
$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{5A}$, $T^{5B}$, $T^{5C}$ are each independently for each occurrence absent, CO, NH, O, S, OC(O), NHC(O), $CH_2$, $CH_2NH$ or $CH_2O$;
$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R''), C≡C or C(O);
$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH$(R^a)$—NH—, CO, CH=N—O, N

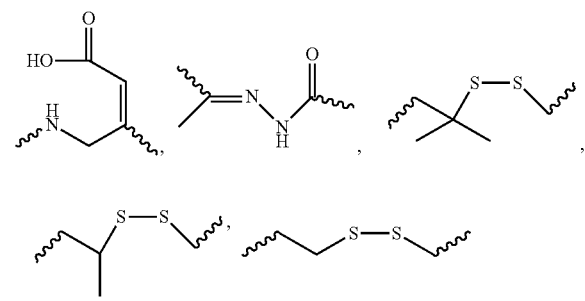

or heterocyclyl;
$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XLIX):

Formula XLIX

Formula (VII)

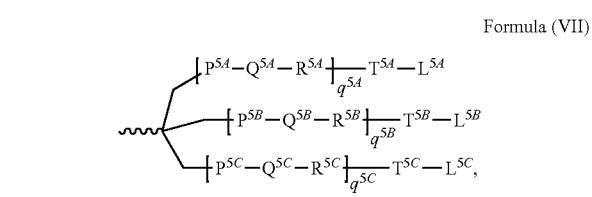

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. Patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941; 6,294,664; 6,320,017; 6,576,752; 6,783,931; 6,900,297; 7,037,646; and 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAi agents, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.*, 2007, 365(1):54-61; Letsinger et al., *Proc. Natl. Acad. Sci. USA,* 1989, 86:6553), cholic acid (Manoharan et al., *Bioorg. Med. Chem. Lett.,* 1994, 4:1053), a thioether, e.g., hexyl-S-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such RNA conjugates have been listed above. Typical conjugation protocols involve the synthesis of RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

IV. Delivery of an iRNA of the Invention

The delivery of an iRNA of the invention to a cell e.g., a cell within a subject, such as a human subject (e.g., a subject in need thereof, such as a subject susceptible to or diagnosed with a complement component C3-associated disorder, e.g., hemolysis) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602). Modification of the RNA or the pharmaceutical carrier can also permit targeting of the iRNA to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178).

In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H, et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R, et al (2003) *J. Mol. Biol* 327:761-766; Verma, U N, et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N, et al (2003), supra), "solid nucleic acid lipid particles" (Zimmermann, T S, et al (2006) *Nature* 441:111-114), cardiolipin (Chien, P Y, et al (2005) *Cancer Gene Ther.* 12:321-328; Pal, A, et al (2005) *Int J. Oncol.* 26:1087-1091), polyethyleneimine (Bonnet M E, et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A, et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the complement component C3 gene can be expressed from transcription units inserted into DNA or RNA vectors (see, e.g., Couture, A, et al., *TIG.* (1996), 12:5-10; Skillern, A, et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are known in the art.

V. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for preventing or treating a complement component C3-associated disorder, e.g., hemolysis. Such pharmaceutical compositions are formulated based on the mode of delivery. One example is compositions that are formulated for systemic administration via parenteral delivery, e.g., by subcutaneous (SC), intramuscular (IM), or intravenous (IV) delivery. The pharmaceutical compositions of the invention may be administered in dosages sufficient to inhibit expression of a complement component C3 gene.

In some embodiments, the pharmaceutical compositions of the invention are sterile. In another embodiment, the pharmaceutical compositions of the invention are pyrogen free.

The pharmaceutical compositions of the invention may be administered in dosages sufficient to inhibit expression of a complement component C3 gene. In general, a suitable dose of an iRNA of the invention will be in the range of about 0.001 to about 200.0 milligrams per kilogram body weight of the recipient per day, generally in the range of about 1 to 50 mg per kilogram body weight per day. Typically, a suitable dose of an iRNA of the invention will be in the range of about 0.1 mg/kg to about 5.0 mg/kg, preferably about 0.3 mg/kg and about 3.0 mg/kg. A repeat-dose regimen may include administration of a therapeutic amount of iRNA on a regular basis, such as every month, once every 3-6 months, or once a year. In certain embodiments, the iRNA is administered about once per month to about once per six months.

After an initial treatment regimen, the treatments can be administered on a less frequent basis. Duration of treatment can be determined based on the severity of disease.

In other embodiments, a single dose of the pharmaceutical compositions can be long lasting, such that doses are administered at not more than 1, 2, 3, or 4 month intervals. In some embodiments of the invention, a single dose of the pharmaceutical compositions of the invention is administered about once per month. In other embodiments of the invention, a single dose of the pharmaceutical compositions of the invention is administered quarterly (i.e., about every three months). In other embodiments of the invention, a single dose of the pharmaceutical compositions of the invention is administered twice per year (i.e., about once every six months).

The skilled artisan will appreciate that certain factors can influence the dosage and timing required to effectively treat a subject, including but not limited to mutations present in the subject, previous treatments, the general health or age of the subject, and other diseases present. Moreover, treatment of a subject with a prophylactically or therapeutically effective amount, as appropriate, of a composition can include a single treatment or a series of treatments.

The iRNA can be delivered in a manner to target a particular tissue (e.g., hepatocytes).

Pharmaceutical compositions of the present invention include, but are not limited to, solutions, emulsions, and liposome-containing formulations. These compositions can be generated from a variety of components that include, but are not limited to, preformed liquids, self-emulsifying solids, and self-emulsifying semisolids. Formulations include those that target the liver.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers.

A. Additional Formulations i. Emulsions

The compositions of the present invention can be prepared and formulated as emulsions. Emulsions are typically heterogeneous systems of one liquid dispersed in another in the form of droplets usually exceeding 0.1 µm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution either in the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic, and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY Rieger, in Pharmaceutical Dosage Forms, Lieberman, Rieger and Banker (Eds.), 1988, Marcel Dekker, Inc., New York, N.Y., volume 1, p. 285).

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives, and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

The application of emulsion formulations via dermatological, oral, and parenteral routes, and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199).

ii. Microemulsions

In one embodiment of the present invention, the compositions of iRNAs and nucleic acids are formulated as microemulsions. A microemulsion can be defined as a system of water, oil, and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215).

iii. Microparticles

An iRNA of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, NY, 2002; Lee et al., Critical Reviews in Therapeutic Drug Carrier Systems, 1991, p. 92). Each of the above mentioned classes of penetration enhancers and their use in manufacture of pharmaceutical compositions and delivery of pharmaceutical agents are well known in the art.

v. Excipients

In contrast to a carrier compound, a "pharmaceutical carrier" or "excipient" is a pharmaceutically acceptable solvent, suspending agent, or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Such agent are well known in the art.

vi. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings, or aromatic substances, and the like which do not deleteriously interact with the nucleic acid(s) of the formulation.

Aqueous suspensions can contain substances which increase the viscosity of the suspension including, for example, sodium carboxymethylcellulose, sorbitol, or dextran. The suspension can also contain stabilizers.

In some embodiments, pharmaceutical compositions featured in the invention include (a) one or more iRNA and (b) one or more agents which function by a non-iRNA mechanism and which are useful in treating a complement component C3-associated disorder, e.g., hemolysis.

Toxicity and prophylactic efficacy of such compounds can be determined by standard pharmaceutical procedures in cell cultures or experimental animals, e.g., for determining the LD50 (the dose lethal to 50% of the population) and the ED50 (the dose prophylactically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50, preferably an ED80 or ED90, with little or no toxicity. The dosage can vary within this range depending upon the dosage form employed and the route of administration utilized. For any compound used in the methods featured in the invention, the prophylactically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) or higher levels of inhibition as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents used for the prevention or treatment of a complement component C3-associated disorder, e.g., hemolysis. In any event, the administering physician can adjust the amount and timing of iRNA administration on the basis of results observed using standard measures of efficacy known in the art or described herein.

VI. Methods for Inhibiting Complement Component C3 Expression

The present invention also provides methods of inhibiting expression of a C3 gene in a cell. The methods include contacting a cell with an RNAi agent, e.g., double stranded RNA agent, in an amount effective to inhibit expression of complement component C3 in the cell, thereby inhibiting expression of complement component C3 in the cell.

Contacting of a cell with an iRNA, e.g., a double stranded RNA agent, may be done in vitro or in vivo. Contacting a cell in vivo with the iRNA includes contacting a cell or group of cells within a subject, e.g., a human subject, with the iRNA. Combinations of in vitro and in vivo methods of contacting a cell are also possible. Contacting a cell may be direct or indirect, as discussed above. Furthermore, contacting a cell may be accomplished via a targeting ligand, including any ligand described herein or known in the art. In preferred embodiments, the targeting ligand is a carbohydrate moiety, e.g., a GalNAc$_3$ ligand, or any other ligand that directs the RNAi agent to a site of interest.

The term "inhibiting," as used herein, is used interchangeably with "reducing," "silencing," "downregulating", "suppressing", and other similar terms, and includes any level of inhibition.

The phrase "inhibiting expression of a complement component C3" is intended to refer to inhibition of expression of any complement component C3 gene (such as, e.g., a mouse complement component C3 gene, a rat complement component C3 gene, a monkey complement component C3 gene, or a human complement component C3 gene) as well as variants or mutants of a complement component C3 gene. Thus, the complement component C3 gene may be a wild-type complement component C3 gene, a mutant complement component C3 gene, or a transgenic complement component C3 gene in the context of a genetically manipulated cell, group of cells, or organism.

"Inhibiting expression of a complement component C3 gene" includes any level of inhibition of a complement component C3 gene, e.g., at least partial suppression of the expression of a complement component C3 gene. The expression of the complement component C3 gene may be assessed based on the level, or the change in the level, of any variable associated with complement component C3 gene expression, e.g., complement component C3 mRNA level or complement component C3 protein level. This level may be assessed in an individual cell or in a group of cells, including, for example, a sample derived from a subject. It is understood that complement component C3 is expressed predominantly in the liver, but also in the brain, gall bladder, heart, and kidney, and is present in circulation.

Inhibition may be assessed by a decrease in an absolute or relative level of one or more variables that are associated with complement component C3 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a complement component C3 gene is inhibited by at least 50%, 55%, 60%, 65%, 70%, 75%, 80%, 85%, 90%, or 95%, or to below the level of detection of the assay. In preferred embodiments, expression of a complement component C3 gene is inhibited by at least 70%. It is further understood that inhibition of complement component C3 expression in certain tissues, e.g., in liver, without a significant inhibition of expression in other tissues, e.g., brain, may be desirable. In preferred embodiments, expression level is determined using the assay method provided in Example 2 with a 10 nM siRNA concentration in the appropriate species matched cell line.

In certain embodiments, inhibition of expression in vivo is determined by knockdown of the human gene in a rodent expressing the human gene, e.g., an AAV-infected mouse expressing the human target gene (i.e., complement component C3), e.g., when administered as a single dose, e.g., at 3 mg/kg at the nadir of RNA expression. Knockdown of expression of an endogenous gene in a model animal system can also be determined, e.g., after administration of a single dose at, e.g., 3 mg/kg at the nadir of RNA expression. Such systems are useful when the nucleic acid sequence of the human gene and the model animal gene are sufficiently close such that the human iRNA provides effective knockdown of the model animal gene. RNA expression in liver is determined using the PCR methods provided in Example 2.

Inhibition of the expression of a complement component C3 gene may be manifested by a reduction of the amount of mRNA expressed by a first cell or group of cells (such cells may be present, for example, in a sample derived from a subject) in which a complement component C3 gene is transcribed and which has or have been treated (e.g., by contacting the cell or cells with an iRNA of the invention, or by administering an iRNA of the invention to a subject in which the cells are or were present) such that the expression of a complement component C3 gene is inhibited, as compared to a second cell or group of cells substantially identical to the first cell or group of cells but which has not or have not been so treated (control cell(s) not treated with an iRNA or not treated with an iRNA targeted to the gene of interest). In preferred embodiments, the inhibition is assessed by the method provided in Example 2 using a 10 nM siRNA concentration in the species matched cell line and expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \cdot 100\%$$

In other embodiments, inhibition of the expression of a complement component C3 gene may be assessed in terms of a reduction of a parameter that is functionally linked to complement component C3 gene expression, e.g., complement component C3 protein level in blood or serum from a subject. Complement component C3 gene silencing may be determined in any cell expressing complement component C3, either endogenous or heterologous from an expression construct, and by any assay known in the art.

Inhibition of the expression of a complement component C3 protein may be manifested by a reduction in the level of the complement component C3 protein that is expressed by a cell or group of cells or in a subject sample (e.g., the level of protein in a blood sample derived from a subject). As explained above, for the assessment of mRNA suppression, the inhibition of protein expression levels in a treated cell or group of cells may similarly be expressed as a percentage of the level of protein in a control cell or group of cells, or the change in the level of protein in a subject sample, e.g., blood or serum derived therefrom.

A control cell, a group of cells, or subject sample that may be used to assess the inhibition of the expression of a complement component C3 gene includes a cell, group of cells, or subject sample that has not yet been contacted with an RNAi agent of the invention. For example, the control cell, group of cells, or subject sample may be derived from an individual subject (e.g., a human or animal subject) prior to treatment of the subject with an RNAi agent or an appropriately matched population control.

The level of complement component C3 mRNA that is expressed by a cell or group of cells may be determined using any method known in the art for assessing mRNA expression. In one embodiment, the level of expression of complement component C3 in a sample is determined by detecting a transcribed polynucleotide, or portion thereof, e.g., mRNA of the complement component C3 gene. RNA may be extracted from cells using RNA extraction techniques including, for example, using acid phenol/guanidine isothiocyanate extraction (RNAzol B; Biogenesis), RNeasy™ RNA preparation kits (Qiagen®) or PAXgene™ (PreAnalytix™, Switzerland). Typical assay formats utilizing ribonucleic acid hybridization include nuclear run-on assays, RT-PCR, RNase protection assays, northern blotting, in situ hybridization, and microarray analysis.

In some embodiments, the level of expression of complement component C3 is determined using a nucleic acid probe. The term "probe", as used herein, refers to any molecule that is capable of selectively binding to a specific complement component C3. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to complement component C3 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix® gene chip array. A skilled artisan can readily adapt known mRNA detection methods for use in determining the level of complement component C3 mRNA.

An alternative method for determining the level of expression of complement component C3 in a sample involves the process of nucleic acid amplification or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of C3 is determined by quantitative fluorogenic RT-PCR (i.e., the TaqMan™ System). In preferred embodiments, expression level is determined by the method provided in Example 2 using, e.g., a 10 nM siRNA concentration, in the species matched cell line.

The expression levels of complement component C3 mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of complement component C3 expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein. In preferred embodiments, expression level is determined by the method provided in Example 2 using a 10 nM siRNA concentration in the species matched cell line.

The level of C3 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like.

In some embodiments, the efficacy of the methods of the invention are assessed by a decrease in C3 mRNA or protein level (e.g., in a liver biopsy).

In some embodiments of the methods of the invention, the iRNA is administered to a subject such that the iRNA is delivered to a specific site within the subject. The inhibition of expression of complement component C3 may be assessed using measurements of the level or change in the level of complement component C3 mRNA or complement component C3 protein in a sample derived from fluid or tissue from the specific site within the subject (e.g., liver or blood).

As used herein, the terms detecting or determining a level of an analyte are understood to mean performing the steps to determine if a material, e.g., protein, RNA, is present. As used herein, methods of detecting or determining include detection or determination of an analyte level that is below the level of detection for the method used.

VII. Prophylactic and Treatment Methods of the Invention

The present invention also provides methods of using an iRNA of the invention or a composition containing an iRNA of the invention to inhibit expression of complement component C3, thereby preventing or treating a complement component C3-associated disorder, e.g., cold agglutinin disease (CAD), warm autoimmune hemolytic anemia, and paroxysmal nocturnal hemoglobinuria (PNH), lupis nephritis (LN), bullous pemphigoid, *pemphigus*, e.g., *pemphigus vulgaris* (PV) and *pemphigus foliaceus* (PF), and C3 glomerulopathy.

In the methods of the invention the cell may be contacted with the siRNA in vitro or in vivo, i.e., the cell may be within a subject.

A cell suitable for treatment using the methods of the invention may be any cell that expresses a complement component C3 gene, e.g., a liver cell, a brain cell, a gall bladder cell, a heart cell, or a kidney cell, but preferably a liver cell. A cell suitable for use in the methods of the invention may be a mammalian cell, e.g., a primate cell (such as a human cell, including human cell in a chimeric non-human animal, or a non-human primate cell, e.g., a monkey cell or a chimpanzee cell), or a non-primate cell. In certain embodiments, the cell is a human cell, e.g., a human liver cell. In the methods of the invention, complement component C3 expression is inhibited in the cell by at least 50, 55, 60, 65, 70, 75, 80, 85, 90, or 95, or to a level below the level of detection of the assay.

The in vivo methods of the invention may include administering to a subject a composition containing an iRNA, where the iRNA includes a nucleotide sequence that is complementary to at least a part of an RNA transcript of the complement component C3 gene of the mammal to which the RNAi agent is to be administered. The composition can be administered by any means known in the art including, but not limited to oral, intraperitoneal, or parenteral routes, including intracranial (e.g., intraventricular, intraparenchymal, and intrathecal), intravenous, intramuscular, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection. In certain embodiments, the compositions are administered by intramuscular injection.

In one aspect, the present invention also provides methods for inhibiting the expression of a complement component C3 gene in a mammal. The methods include administering to the mammal a composition comprising a dsRNA that targets a complement component C3 gene in a cell of the mammal and maintaining the mammal for a time sufficient to obtain degradation of the mRNA transcript of the complement component C3 gene, thereby inhibiting expression of the complement component C3 gene in the cell. Reduction in gene expression can be assessed by any methods known in the art and by methods, e.g. qRT-PCR, described herein, e.g., in Example 2. Reduction in protein production can be assessed by any methods known it the art, e.g. ELISA. In certain embodiments, a puncture liver biopsy sample serves as the tissue material for monitoring the reduction in the complement component C3 gene or protein expression. In other embodiments, a blood sample serves as the subject sample for monitoring the reduction in the complement component C3 protein expression.

The present invention further provides methods of treatment in a subject in need thereof, e.g., a subject diagnosed with a complement component C3-associated disorder, such as, cold agglutinin disease (CAD), warm autoimmune hemolytic anemia, and paroxysmal nocturnal hemoglobinuria (PNH), lupus nephritis (LN), bullous pemphigoid, *pemphigus*, e.g., *pemphigus vulgaris* (PV) and *pemphigus foliaceus* (PF), or C3 glomerulopathy.

The present invention further provides methods of prophylaxis in a subject in need thereof. The treatment methods of the invention include administering an iRNA of the invention to a subject, e.g., a subject that would benefit from a reduction of complement component C3 expression, in a prophylactically effective amount of an iRNA targeting a complement component C3 gene or a pharmaceutical composition comprising an iRNA targeting a complement component C3 gene.

In one embodiment, a complement component C3-associated disease is selected from the group consisting of cold agglutinin disease (CAD), warm autoimmune hemolytic anemia, and paroxysmal nocturnal hemoglobinuria (PNH), lupus nephritis (LN), bullous pemphigoid, *pemphigus*, e.g., *pemphigus vulgaris* (PV) and *pemphigus foliaceus* (PF), and C3 glomerulopathy.

In one embodiment, a complement component C3-associated disease is cold agglutinin disease (CAD). CAD is an autoimmune complement component C3-induced hemolytic anemia in which cold exposure causes clinical symptoms related to agglutination of red blood cells (RBCs) in cold parts of the body (e.g., livedo reticularis or acrocyanosis) and hemolytic anemia. Cold agglutinins are IgM antibodies that recognize antigens on red blood cells (RBCs) at temperatures below normal core body temperature. They can cause agglutination of the RBCs, complement activation and extravascular hemolysis, resulting in anemia, typically without hemoglobinuria. The CAD may be primary CAD (also called idiopathic CAD) or secondary CAD. In subjects having primary CAD, cold agglutinins cause RBC agglutination and extravascular hemolysis in the absence of an underlying disorder. In subjects having secondary CAD (also referred to as cold agglutinin syndrome, or CAS), cold agglutinins arise in the setting of an underlying disorder such as a viral infection, autoimmune disorder, or lymphoid malignancy (see, e.g., Berentsen (2015) *Transfus Med Hemother* 42:303-310).

In one embodiment, a complement component C3-associated disease is warm autoimmune hemolytic anemia. Warm autoimmune hemolytic anemia is an autoimmune complement component C3-induced hemolytic anemia in which red blood cells (RBCs) agglutinate in parts of the body at temperatures equal to or greater than normal body temperature and hemolytic anemia as a result of IgG antibodies directed against blood group antigens which activate the complement system. Warm autoimmune hemolytic anemia is the most common type of autoimmune hemolytic anemia, comprising ~70% to 80% of all adult cases and ~50% of the pediatric cases. About half of the warm autoimmune hemolytic anemia cases are primary because no specific etiology can be found, whereas the rest are recognized as secondary to lymphoproliferative syndromes; malignant diseases including chronic lymphoblastic leukemia (CLL), non-Hodgkin's lymphoma, and solid tumors; rheumatologic diseases, especially systemic lupus erythematosus; infections (mostly viral); drugs; frequent cephalosporins and piperacillin; or a previous transfusion or transplantation (see, e.g., Berentsen (2015) *Transfus Med Hemother* 42:303-310).

In one embodiment, a complement component C3-associated disease is paroxysmal nocturnal hemoglobinuria (PNH). The PNH may be classical PNH or PNH in the setting of another bone marrow failure syndrome and/or myelodysplastic syndromes (MDS), e.g., cytopenias. PNH is an acquired autoimmune disorder that leads to the premature death and impaired production of blood cells, characterized by complement-mediated hemolytic anemia, thrombophilia, and bone marrow failure (see, e.g., Risitano (2013) *Adv Exp Med Biol* 735:155).

In one embodiment, a complement component C3-associated disease is lupus nephritis (LN), i.e., any one of Class I-Class VI lupus nephritis). LN is a type of glomerulonephritis caused by systemic lupus erythematosus (SLE). Lupus nephritis occurs due to immune complex deposition in any or all renal compartments, including the glomeruli, tubules, and interstitium. IgG is the most prevalent antibody found but IgM, and IgA can be seen as well. These autoantibodies cause activation of both the classic and alternative complement pathways and so C1, C3 and properdin may be found on biopsy.

In one embodiment, a complement component C3-associated disease is bullous pemphigoid. Bullous pemphigoid an autoimmune blistering disease induced by autoantibodies against type XVII collagen (COL17) that activates complement and subsequently recruits inflammatory cells at the dermal/epidermal junction. Bullous pemphigoid is the most common autoimmune blistering disorder characterized by tense blisters with itchy urticarial erythema and plaques that develop on the entire body.

In one embodiment, a complement component C3-associated disease is *pemphigus*, e.g., *pemphigus vulgaris* (PV) and *pemphigus foliaceus* (PF). Pemphigus is a group of rare chronic blistering diseases characterized by IgG-autoantibodies directed against a variety of desmosomal transmembrane glycoproteins and intracellular deposition of IgG and C3c. Patients with *pemphigus vulgaris* typically present with lesions of the oral mucosa followed by skin-involvement and autoantibodies are directed against epithelial adhesion protein desmoglein 3 and/or desmoglein 1. In *pemphigus foliaceus* the lesions are localized on the skin, without involvement of the mucous membranes, and autoantibodies are directed against desmoglein 1. In one embodiment, the *pemphigus* is *pemphigus vulgaris* (PV). In another embodiment, the *pemphigus* is *pemphigus foliaceus* (PF).

In one embodiment, a complement component C3-associated disease is C3 glomerulopathy. C3 glomerulopathy is characterized by activation of the alternative complement cascade and deposition of complement component C3 without any immunoglobulin deposits in the glomeruli of the kidney.

An iRNA of the invention may be administered as a "free iRNA." A free iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from an inhibition of complement component C3 gene expression are subjects susceptible to or diagnosed with a complement component C3-associated disorder, such as cold agglutinin disease (CAD), warm autoimmune hemolytic anemia, and paroxysmal nocturnal hemoglobinuria (PNH), lupis nephritis (LN), bullous pemphigoid, *pemphigus*, e.g., *pemphigus vulgaris* (PV) and *pemphigus foliaceus* (PF), and C3 glomerulopathy.

In an embodiment, the method includes administering a composition featured herein such that expression of the target complement component C3 gene is decreased, such as for about 1, 2, 3, 4, 5, 6, 1-6, 1-3, or 3-6 months per dose. In certain embodiments, the composition is administered once every 3-6 months.

Preferably, the iRNAs useful for the methods and compositions featured herein specifically target RNAs (primary or processed) of the target complement component C3 gene. Compositions and methods for inhibiting the expression of these genes using iRNAs can be prepared and performed as described herein.

Administration of the iRNA according to the methods of the invention may result prevention or treatment of a complement component C3-associated disorder, e.g., cold agglutinin disease (CAD), warm autoimmune hemolytic anemia, and paroxysmal nocturnal hemoglobinuria (PNH), lupis nephritis (LN), bullous pemphigoid, *pemphigus*, e.g., *pemphigus vulgaris* (PV) and *pemphigus foliaceus* (PF), and C3 glomerulopathy.

Subjects can be administered a therapeutic amount of iRNA, such as about 0.01 mg/kg to about 200 mg/kg.

The iRNA is preferably administered subcutaneously, i.e., by subcutaneous injection. One or more injections may be used to deliver the desired dose of iRNA to a subject. The injections may be repeated over a period of time.

The administration may be repeated on a regular basis. In certain embodiments, after an initial treatment regimen, the treatments can be administered on a less frequent basis. A repeat-dose regimen may include administration of a therapeutic amount of iRNA on a regular basis, such as once per month to once a year. In certain embodiments, the iRNA is administered about once per month to about once every three months, or about once every three months to about once every six months.

The invention further provides methods and uses of an iRNA agent or a pharmaceutical composition thereof for treating a subject that would benefit from reduction and/or inhibition of C3 gene expression, e.g., a subject having a C3-associated disease, in combination with other pharmaceuticals and/or other therapeutic methods, e.g., with known pharmaceuticals and/or known therapeutic methods, such as, for example, those which are currently employed for treating these disorders.

Accordingly, in some aspects of the invention, the methods which include either a single iRNA agent of the invention, further include administering to the subject one or more additional therapeutic agents.

The iRNA agent and an additional therapeutic agent and/or treatment may be administered at the same time and/or in the same combination, e.g., parenterally, or the additional therapeutic agent can be administered as part of a separate composition or at separate times and/or by another method known in the art or described herein.

For example, additional therapeutics and therapeutic methods suitable for treating a subject that would benefit from reduction in C3 expression, e.g., a subject having a complement component C3-associated disease, include plasmaphoresis, thrombolytic therapy (e.g., streptokinase), antiplatelet agents, folic acid, corticosteroids; immunosuppressive agents; estrogens, methotrexate, 6-MP, azathioprine sulphasalazine, mesalazine, olsalazine, chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines, such as TNF-α or IL-1 (e.g., IRAK, NIK, IKK, p38 or MAP kinase inhibitors), IL-1β converting enzyme inhibitors, TNFαconverting enzyme (TACE) inhibitors, T-cell signalling inhibitors, such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™ and p55TNFRIgG (Lenercept)), sIL-1RI, sIL-1RII, and sIL-6R), antiinflammatory cytokines (e.g., IL-4, IL-10, IL-11, IL-13 and TGFβ), celecoxib, folic acid, hydroxychloroquine sulfate, rofecoxib, etanercept, infliximonoclonal antibody, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hydrochloride, hydrocodone bitartrate/apap, diclofenac sodium/misoprostol, fentanyl, anakinra, human recombinant, tramadol hydrochloride, salsalate, sulindac, cyanocobalamin/folic acid/pyridoxine, acetaminophen, alendronate sodium, prednisolone, morphine sulfate, lidocaine hydrochloride, indomethacin, glucosamine sulf/chondroitin, amitriptyline hydrochloride, sulfadiazine, oxycodone hydrochloride/acetaminophen, olopatadine hydrochloride, misoprostol, naproxen sodium, omeprazole, cyclophosphamide, rituximonoclonal antibody, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, Mesopram, cyclosporine, cytokine suppressive anti-inflammatory drug(s) (CSAIDs); CDP-571/BAY-10-3356 (humanized anti-TNFα antibody; Celltech/Bayer); cA2/infliximonoclonal antibody (chimeric anti-TNFα antibody; Centocor); 75 kdTNFR-IgG/etanercept (75 kD TNF receptor-IgG fusion protein; Immunex; see e.g., (1994) Arthr. Rheum. 37: S295; (1996) J. Invest. Med. 44: 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., (1995) Arthr. Rheum. 38: S185); DAB 486-IL-2 and/or DAB 389-IL-2 (IL-2 fusion proteins; Seragen; see e.g., (1993) Arthrit. Rheum. 36: 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-IRA (IL-1 receptor antagonist; Synergen/Amgen); anakinra (Kineret®/Amgen); TNF-bp/sTNF (soluble TNF binding protein; see e.g., (1996) Arthr. Rheum. 39(9 (supplement)): S284; (1995) Amer. J. Physiol. —Heart and Circ. Physiol. 268: 37-42); R973401 (phosphodiesterase Type IV inhibitor; see e.g., (1996) Arthr. Rheum. 39(9 (supplement): S282); MK-966 (COX-2 Inhibitor; see e.g., (1996) Arthr. Rheum. 39(9 (supplement): S81); Iloprost (see e.g., (1996) Arthr. Rheum. 39(9 (supplement): S82); methotrexate; thalidomide (see e.g., (1996) Arthr. Rheum. 39(9 (supplement): S282) and thalidomide-related drugs (e.g., Celgen); leflunomide (anti-inflammatory and cytokine inhibitor; see e.g., (1996) Arthr. Rheum. 39(9 (supplement): S131; (1996) Inflamm. Res. 45: 103-107); tranexamic acid (inhibitor of plasminogen activation; see e.g., (1996) Arthr. Rheum. 39(9 (supplement): S284); T-614 (cytokine inhibitor; see e.g., (1996) Arthr. Rheum. 39(9 (supplement): S282); prostaglandin E1 (see e.g., (1996) Arthr. Rheum. 39(9 (supplement): S282); Tenidap (non-steroidal anti-inflammatory drug; see e.g., (1996) Arthr. Rheum. 39(9 (supplement): S280); Naproxen (non-steroidal anti-inflammatory drug; see e.g., (1996) Neuro. Report 7: 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., (1996) Arthr. Rheum. 39(9 (supplement): S281); Azathioprine (see e.g., (1996) Arthr. Rheum. 39(9 (supplement): 5281); ICE inhibitor (inhibitor of the enzyme interleukin-1 ☐ converting enzyme); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., (1996) Arthr. Rheum. 39(9 (supplement): S296); interleukin-13 (see e.g., (1996) Arthr. Rheum. 39(9 (supplement): S308); interleukin-17 inhibitors (see e.g., (1996) Arthr. Rheum. 39(9 (supplement): S120); gold; penicillamine; chloroquine; chlorambucil; hydroxychloroquine; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) Rheum. Dis. Clin. North Am. 21: 759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; bcl-2 inhibitors (see Bruncko, M. et al. (2007) J. Med. Chem. 50(4): 641-662); antivirals and immune-modulating agents, small molecule inhibitor of KDR, small molecule inhibitor of Tie-2; methotrexate; prednisone; celecoxib; folic acid; hydroxychloroquine sulfate; rofecoxib; etanercept; infliximonoclonal antibody; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline hydrochloride; sulfadiazine; oxycodone hcl/acetaminophen; olopatadine hcl; misoprostol; naproxen sodium; omeprazole; mycophenolate mofetil; cyclophosphamide; rituximonoclonal antibody; IL-1 TRAP; MRA; CTLA4-IG; IL-18 BP; IL-12/23; anti-IL 18; anti-IL 15; BIRB-796; SCIO-469; VX-702; AMG-548; VX-740; Roflumilast; IC-485; CDC-801; mesopram, albuterol, salmeterol/fluticasone, montelukast sodium, fluticasone propionate, budesonide, prednisone, salmeterol xinafoate, levalbuterol hcl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin hcl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine hcl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, metaproterenol sulfate, aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hcl/mag carb, bumetanide, alteplase, enalaprilat, amiodarone hydrochloride, tirofiban hcl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine hcl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

In some aspects, the additional therapeutic agent is an iRNA agent targeting a C5 gene, such as described in U.S. Pat. No. 9,249,415, U.S. Provisional Patent Application Nos. 62/174,933, filed on Jun. 12, 2015, 62/263,066, filed on Dec. 4, 2015, the entire contents of each of which are hereby incorporated herein by reference.

In other aspects, the additional therapeutic agent is an anti-complement component C5 antibody, or antigen-binding fragment thereof (e.g., eculizumab). Eculizumab is a humanized monoclonal IgG2/4, kappa light chain antibody that specifically binds complement component C5 with high affinity and inhibits cleavage of C5 to C5a and C5b, thereby inhibiting the generation of the terminal complement complex C5b-9. Eculizumab is described in U.S. Pat. No. 6,355,245, the entire contents of which are incorporated herein by reference.

In yet other aspects, the additional therapeutic is a C3 peptide inhibitor, or analog thereof. In one embodiment, the C3 peptide inhibitor is compstatin. Compstatin is a cyclic tridecapeptide with potent and selective C3 inhibitory activity. Compstatin, and its analogs, are described in U.S. Pat. Nos. 7,888,323, 7,989,589, and 8,442,776, in U.S. Patent Publication No. 2012/0178694 and 2013/0053302, and in PCT Publication Nos. WO 2012/174055, WO 2012/2178083, WO 2013/036778, the entire contents of each of which are incorporated herein by reference.

VIII. Kits

The present invention also provides kits for performing any of the methods of the invention. Such kits include one or more dsRNA agent(s) and instructions for use, e.g., instructions for administering a prophylactically or therapeutically effective amount of a dsRNA agent(s). The dsRNA agent may be in a vial or a pre-filled syringe. The kits may optionally further comprise means for administering the dsRNA agent (e.g., an injection device, such as a pre-filled syringe), or means for measuring the inhibition of C3 (e.g., means for measuring the inhibition of C3 mRNA, C3 protein, and/or C3 activity). Such means for measuring the inhibition of C3 may comprise a means for obtaining a sample from a subject, such as, e.g., a plasma sample. The kits of the invention may optionally further comprise means for determining the therapeutically effective or prophylactically effective amount.

This invention is further illustrated by the following examples which should not be construed as limiting. The entire contents of all references, patents and published patent applications cited throughout this application, as well as the informal Sequence Listing and Figures, are hereby incorporated herein by reference.

EXAMPLES

Example 1. iRNA Synthesis

Source of Reagents

Where the source of a reagent is not specifically given herein, such reagent can be obtained from any supplier of reagents for molecular biology at a quality/purity standard for application in molecular biology.

siRNA Design siRNAs targeting the human complement component C3 (C3) gene (human: NCBI refseqID NM_000064.3; NCBI GeneID: 718) were designed using custom R and Python scripts. The human NM_000064.3 REFSEQ mRNA, has a length of 5148 bases.

Detailed lists of the unmodified complement component sense and antisense strand nucleotide sequences are shown in Tables 2, 4, and 6. Detailed lists of the modified complement component C3 sense and antisense strand nucleotide sequences are shown in Tables 3, 5, and 7.

It is to be understood that, throughout the application, a duplex name without a decimal is equivalent to a duplex name with a decimal which merely references the batch number of the duplex.

For example, AD-564727 is equivalent to AD-564727.1.

siRNA Synthesis siRNAs were synthesized and annealed using routine methods known in the art.

Briefly, siRNA sequences were synthesized at 1 µmol scale on a Mermade 192 synthesizer (BioAutomation) using the solid support mediated phosphoramidite chemistry. The solid support was controlled pore glass (500 A) loaded with custom GalNAc ligand or universal solid support (AM biochemical). Ancillary synthesis reagents, 2'-F and 2'-O-Methyl RNA and deoxy phosphoramidites were obtained from Thermo-Fisher (Milwaukee, WI) and Hongene (China). 2'F 2'-O-Methyl, GNA (glycol nucleic acids), 5' phosphate and other modifications were introduced using the corresponding phosphoramidites. Synthesis of 3' GalNAc conjugated single strands was performed on a GalNAc modified CPG support. Custom CPG universal solid support was used for the synthesis of antisense single strands. Coupling time for all phosphoramidites (100 mM in acetonitrile) was 5 min employing 5-Ethylthio-1H-tetrazole (ETT) as activator (0.6 M in acetonitrile). Phosphorothioate linkages were generated using a 50 mM solution of 3-((Dimethylamino-methylidene)amino)-3H-1,2,4-dithiazole-3-thione (DDTT, obtained from Chemgenes (Wilmington, MA, USA)) in anhydrous acetonitrile/pyridine (1:1 v/v). Oxidation time was 3 minutes. All sequences were synthesized with final removal of the DMT group ("DMT off").

Upon completion of the solid phase synthesis, oligoribonucleotides were cleaved from the solid support and deprotected in sealed 96 deep well plates using 200 µL Aqueous Methylamine reagents at 60° C. for 20 minutes. For sequences containing 2' ribo residues (2'-OH) that are protected with a tert-butyl dimethyl silyl (TBDMS) group, a second step deprotection was performed using TEA.3HF (triethylamine trihydro fluoride) reagent. To the methylamine deprotection solution, 200 uL of dimethyl sulfoxide (DMSO) and 300 ul TEA.3HF reagent was added and the solution was incubated for additional 20 min at 60° C. At the end of cleavage and deprotection step, the synthesis plate was allowed to come to room temperature and was precipitated by addition of 1 mL of acetontile: ethanol mixture (9:1). The plates were cooled at −80 C for 2 hrs, superanatant decanted carefully with the aid of a multi channel pipette. The oligonucleotide pellet was re-suspended in 20 mM NaOAc buffer and were desalted using a 5 mL HiTrap size exclusion column (GE Healthcare) on an AKTA Purifier System equipped with an A905 autosampler and a Frac 950 fraction collector. Desalted samples were collected in 96-well plates. Samples from each sequence were analyzed by LC-MS to confirm the identity, UV (260 nm) for quantification and a selected set of samples by IEX chromatography to determine purity.

Annealing of single strands was performed on a Tecan liquid handling robot. Equimolar mixture of sense and antisense single strands were combined and annealed in 96 well plates. After combining the complementary single strands, the 96-well plate was sealed tightly and heated in an oven at 100° C. for 10 minutes and allowed to come slowly to room temperature over a period 2-3 hours. The concentration of each duplex was normalized to 10 M in 1×PBS and then submitted for in vitro screening assays.

Example 2. In Vitro Screening Methods

Cell Culture and 384-Well Transfections

Hep3b cells (ATCC, Manassas, VA) were grown to near confluence at 37° C. in an atmosphere of 5% $CO_2$ in Eagle's Minimum Essential Medium (Gibco) supplemented with 10% FBS (ATCC) before being released from the plate by trypsinization. For mouse cross reactive duplexes, primary mouse hepatocytes (PMH) were freshly isolated less than 1 hour prior to transfections and grown in primary hepatocyte media. For both Hep3B and PMH, transfection was carried out by adding 14.8 µl of Opti-MEM plus 0.2 µl of Lipofectamine RNAiMax per well (Invitrogen, Carlsbad CA. cat #13778-150) to 5 µl of each siRNA duplex to an individual well in a 96-well plate. The mixture was then incubated at room temperature for 15 minutes. Eighty µl of complete growth media without antibiotic containing ~2×10$^4$ Hep3B cells or PMH were then added to the siRNA mixture. Cells were incubated for 24 hours prior to RNA purification. Single dose experiments were performed at 10 nM and 0.1 nM final duplex concentration and dose response experiments were done using 8× 5-fold serial dilutions over the range of 10 nM to 128 pM.

Total RNA Isolation Using DYNABEADS mRNA Isolation Kit (Invitrogen™, Part #: 610-12)

Cells were lysed in 75 µl of Lysis/Binding Buffer containing 3 µL of beads per well and mixed for 10 minutes on an electrostatic shaker. The washing steps were automated on a Biotek EL406, using a magnetic plate support. Beads were washed (in 90 µL) once in Buffer A, once in Buffer B, and twice in Buffer E, with aspiration steps in between. Following a final aspiration, complete 10 µL RT mixture was added to each well, as described below.

cDNA Synthesis Using ABI High Capacity cDNA Reverse Transcription Kit (Applied Biosystems, Foster City, CA, Cat #4368813)

A master mix of 1 µl 10× Buffer, 0.4 µl 25× dNTPs, 1 µl Random primers, 0.5 µl Reverse Transcriptase, 0.5 µl RNase inhibitor and 6.6 µl of $H_2O$ per reaction were added per well. Plates were sealed, agitated for 10 minutes on an electrostatic shaker, and then incubated at 37 degrees C. for 2 hours. Following this, the plates were agitated at 80 degrees C. for 8 minutes.

Real Time PCR

Two microlitre (µl) of cDNA were added to a master mix containing 0.5 µl of human GAPDH TaqMan Probe (4326317E), 0.5 µl human C3, 2 µl nuclease-free water and 5 µl Lightcycler 480 probe master mix (Roche Cat #04887301001) per well in a 384 well plates (Roche cat #04887301001). Real time PCR was done in a LightCycler480 Real Time PCR system (Roche).

To calculate relative fold change, data were analyzed using the ΔΔCt method and normalized to assays performed with cells transfected with 10 nM AD-1955, or mock transfected cells. $IC_{50}$s were calculated using a 4 parameter fit model using XLFit and normalized to cells transfected with AD-1955 or mock-transfected. The sense and antisense sequences of AD-1955 are: sense: cuuAcGcuGAGuAcuucGAdTsdT (SEQ ID NO: 13) and antisense UCGAAGuACUcAGCGuAAGdTsdT (SEQ ID NO:14).

The results of the screening of the dsRNA agents listed in Tables 2 and 3 in Hep3B cells are shown in Table 8. The results of the screening of the dsRNA agents listed in Tables 2 and 3 in PMH cells are shown in Table 9. The results of the screening of the dsRNA agents listed in Tables 4 and 5 in Hep3B cells are shown in Table 10. The results of the screening of the dsRNA agents listed in Tables 4 and 5 in PMH cells are shown in Table 11. The results of the screening of the dsRNA agents listed in Tables 6 and 7 in Hep3B cells are shown in Table 12. The results of the screening of the dsRNA agents listed in Tables 6 and 7 in PMH cells are shown in Table 13.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
| --- | --- |
| A | Adenosine-3'-phosphate |
| Ab | beta-L-adenosine-3'-phosphate |
| Abs | beta-L-adenosine-3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide, modified or unmodified |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L10 | N-(cholesterylcarboxamidocaproyl)-4-hydroxyprolinol (Hyp-C6-Chol) |
| L96 | N-[tris(GalNAc-alkyl)-amidodecanoyl)]-4-hydroxyprolinol (Hyp-(GalNAc-alkyl)3) |
| Y34 | 2-hydroxymethyl-tetrahydrofurane-4-methoxy-3-phosphate (abasic 2'-OMe furanose) |
| Y44 | inverted abasic DNA (2-hydroxymethyl-tetrahydrofurane-5-phosphate) |
| (Agn) | Adenosine-glycol nucleic acid (GNA) |
| (Cgn) | Cytidine-glycol nucleic acid (GNA) |
| (Ggn) | Guanosine-glycol nucleic acid (GNA) |

TABLE 1-continued

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| (Tgn) | Thymidine-glycol nucleic acid (GNA) S-Isomer |
| P | Phosphate |
| VP | Vinyl-phosphonate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine-3'-phosphate |
| dTs | 2'-deoxythymidine-3'-phosphorothioate |
| dU | 2'-deoxyuridine |
| dUs | 2'-deoxyuridine-3'-phosphorothioate |
| (C2p) | cytidine-2'-phosphate |
| (G2p) | guanosine-2'-phosphate |
| (U2p) | uridine-2'-phosphate |
| (A2p) | adenosine-2'-phosphate |
| (Ahd) | 2'-O-hexadecyl-adenosine-3'-phosphate |
| (Ahds) | 2'-O-hexadecyl-adenosine-3'-phosphorothioate |
| (Chd) | 2'-O-hexadecyl-cytidine-3'-phosphate |
| (Chds) | 2'-O-hexadecyl-cytidine-3'-phosphorothioate |
| (Ghd) | 2'-O-hexadecyl-guanosine-3'-phosphate |
| (Ghds) | 2'-O-hexadecyl-guanosine-3'-phosphorothioate |
| (Uhd) | 2'-O-hexadecyl-uiidinc-3'-phosphate |
| (Uhds) | 2'-O-hexadecyl-uridine-3'-phosphorothioate |

TABLE 2

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-564727.1 | CGGGUACCUCUUCAUCCAGAU | 15 | 474-494 | AUCUGGAUGAAGAGGUACCCGCU | 103 | 472-494 |
| AD-564730.1 | GUACCUCUUCAUCCAGACAGU | 16 | 477-497 | ACUGUCUGGAUGAAGAGGUACCC | 104 | 475-497 |
| AD-564731.1 | UACCUCUUCAUCCAGACAGAU | 17 | 478-498 | AUCUGUCUGGAUGAAGAGGUACC | 105 | 476-498 |
| AD-564739.1 | CAUCCAGACAGACAAGACCAU | 18 | 486-506 | AUGGUCUUGUCUGUCUGGAUGAA | 106 | 484-506 |
| AD-564742.1 | CCAGACAGACAAGACCAUCUU | 19 | 489-509 | AAGAUGGUCUUGUCUGUCUGGAU | 107 | 487-509 |
| AD-564744.1 | AGACAGACAAGACCAUCUACU | 20 | 491-511 | AGUAGAUGGUCUUGUCUGUCUGG | 108 | 489-511 |
| AD-564745.1 | GACAGACAAGACCAUCUACAU | 21 | 492-512 | AUGUAGAUGGUCUUGUCUGUCUG | 109 | 490-512 |
| AD-564901.1 | AUUCCGGAACUCGUCAACAUU | 22 | 676-696 | AAUGUUGACGAGUUCCGGAAUGU | 110 | 674-696 |
| AD-564975.1 | CACUGAGUUUGAGGUGAAGGU | 23 | 750-770 | ACCUUCACCUCAAACUCAGUGGA | 111 | 748-770 |
| AD-564976.1 | ACUGAGUUUGAGGUGAAGGAU | 24 | 751-771 | AUCCUUCACCUCAAACUCAGUGG | 112 | 749-771 |
| AD-565005.1 | GCCCAGUUUCGAGGUCAUAGU | 25 | 780-800 | ACUAUGACCUCGAAACUGGGCAG | 113 | 778-800 |
| AD-565040.1 | AAUUCUACUACAUCUAUAACU | 26 | 815-835 | AGUUAUAGAUGUAGUAGAAUUUC | 114 | 813-835 |
| AD-565278.1 | UCCCUACCAGAUCCACUUCAU | 27 | 1146-1166 | AUGAAGTGGAUCUGGUAGGGAGA | 115 | 1144-1166 |
| AD-565279.1 | CCCUACCAGAUCCACUUCACU | 28 | 1147-1167 | AGUGAAGUGGAUCUGGUAGGGAG | 116 | 1145-1167 |
| AD-565281.1 | CUACCAGAUCCACUUCACCAU | 29 | 1149-1169 | AUGGUGAAGUGGAUCUGGUAGGG | 117 | 1147-1169 |
| AD-565282.1 | UACCAGAUCCACUUCACCAAU | 30 | 1150-1170 | AUUGGUGAAGUGGAUCUGGUAGG | 118 | 1148-1170 |
| AD-565284.1 | CCAGAUCCACUUCACCAAGAU | 31 | 1152-1172 | AUCUUGGUGAAGUGGAUCUGGUA | 119 | 1150-1172 |
| AD-565532.1 | GGGCAACUCCAACAAUUACCU | 32 | 1440-1460 | AGGUAAUGUUGGAGUUGCCCAC | 120 | 1438-1460 |
| AD-565534.1 | GCAACUCCAACAAUUACCUGU | 33 | 1442-1462 | ACAGGUAAUUGUUGGAGUUGCCC | 121 | 1440-1462 |
| AD-565535.1 | CAACUCCAACAAUUACCUGCU | 34 | 1443-1463 | AGCAGGTAAUUGUUGGAGUUGCC | 122 | 1441-1463 |
| AD-565541.1 | CAACAAUUACCUGCAUCUCUU | 35 | 1449-1469 | AAGAGAUGCAGGUAAUUGUUGGA | 123 | 1447-1469 |
| AD-565616.1 | CAAGAUCCGCUACUACACCUU | 36 | 1548-1568 | AAGGUGUAGUAGCGGAUCUUGGC | 124 | 1546-1568 |
| AD-565904.1 | CGUGCUGAAUAAGAAGAACAU | 37 | 1902-1922 | AUGUUCUUCUUAUUCAGCACGAA | 125 | 1900-1922 |
| AD-565905.1 | GUGCUGAAUAAGAAGAACAAU | 38 | 1903-1923 | AUUGUUCUUCUUAUUCAGCACGA | 126 | 1901-1923 |
| AD-565925.1 | ACUGACGCAGAGUAAGAUCUU | 39 | 1923-1943 | AAGAUCUUACUCUGCGUCAGUUU | 127 | 1921-1943 |

TABLE 2-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-566234.1 | UGCAGAAGAGAACAUCGUUUU | 40 | 2361-2381 | AAAACGAUGUUCUCUUCUGCAAU | 128 | 2359-2381 |
| AD-566383.1 | CAUGUCGGACAAGAAAGGGAU | 41 | 2517-2537 | AUCCCUUCUUGUCCGACAUGCU | 129 | 2515-2537 |
| AD-566384.1 | AUGUCGGACAAGAAAGGGAUU | 42 | 2518-2538 | AAUCCCUUCUUGUCCGACAUGC | 130 | 2516-2538 |
| AD-566386.1 | GUCGGACAAGAAAGGGAUCUU | 43 | 2520-2540 | AAGAUCCCUUCUUGUCCGACAU | 131 | 2518-2540 |
| AD-566388.1 | CGGACAAGAAAGGGAUCUGUU | 44 | 2522-2542 | AACAGAUCCCUUUCUUGUCCGAC | 132 | 2520-2542 |
| AD-566409.1 | ACAGUAAUGCAGGACUUCUUU | 45 | 2563-2583 | AAAGAAGUCCUGCAUUACUGUA | 133 | 2561-2583 |
| AD-566411.1 | AGUAAUGCAGGACUUCUUCAU | 46 | 2565-2585 | AUGAAGAAGUCCUGCAUUACUGU | 134 | 2563-2585 |
| AD-566412.1 | GUAAUGCAGGACUUCUUCAUU | 47 | 2566-2586 | AAUGAAGAAGUCCUGCAUUACUG | 135 | 2564-2586 |
| AD-566442.1 | CUACCCUACUCUGUUGUUCGU | 48 | 2596-2616 | ACGAACAACAGAGUAGGGUAGCC | 136 | 2594-2616 |
| AD-566443.1 | UACCCUACUCUGUUGUUCGAU | 49 | 2597-2617 | AUCGAACAACAGAGUAGGGUAGC | 137 | 2595-2617 |
| AD-566444.1 | ACCCUACUCUGUUGUUCGAAU | 50 | 2598-2618 | AUUCGAACAACAGAGUAGGGUAG | 138 | 2596-2618 |
| AD-566445.1 | CCCUACUCUGUUGUUCGAAAU | 51 | 2599-2619 | AUUUCGAACAACAGAGUAGGGUA | 139 | 2597-2619 |
| AD-566446.1 | CCUACUCUGUUGUUCGAAACU | 52 | 2600-2620 | AGUUUCGAACAACAGAGUAGGGU | 140 | 2598-2620 |
| AD-566447.1 | CUACUCUGUUGUUCGAAACGU | 53 | 2601-2621 | ACGUUUCGAACAACAGAGUAGGG | 141 | 2599-2621 |
| AD-566448.1 | UACUCUGUUGUUCGAAACGAU | 54 | 2602-2622 | AUCGUUUCGAACAACAGAGUAGG | 142 | 2600-2622 |
| AD-566449.1 | ACUCUGUUGUUCGAAACGAGU | 55 | 2603-2623 | ACUCGUUCGAACAACAGAGUAG | 143 | 2601-2623 |
| AD-566485.1 | CCGUUCUCUACAAUUACCGGU | 56 | 2639-2659 | ACCGGUAAUUGUAGAGAACGCU | 144 | 2637-2659 |
| AD-566528.1 | GGUGGAACUACUCCACAAUCU | 57 | 2682-2702 | AGAUUGTGGAGUAGUUCCACCCU | 145 | 2680-2702 |
| AD-566837.1 | CCGAGUCUGAGACCAGAAUUU | 58 | 3014-3034 | AAAAUUCUGGUCUCAGACUCGGUG | 146 | 3012-3034 |
| AD-566935.1 | GUGCAUUACCUGGAUGAAACU | 59 | 3166-3186 | AGUUUCAUCCAGGUAAUGCACAG | 147 | 3164-3186 |
| AD-567063.1 | CUACGUGGUCAAGGUCUUCUU | 60 | 3333-3353 | AAGAAGACCUUGACCACGUAGGC | 148 | 3331-3353 |
| AD-567066.1 | CGUGGUCAAGGUCUUCUCUCU | 61 | 3336-3356 | AGAGAGAAGACCUUGACCACGUA | 149 | 3334-3356 |
| AD-567067.1 | GUGGUCAAGGUCUUCUCUCUU | 62 | 3337-3357 | AAGAGAGAAGACCUUGACCACGU | 150 | 3335-3357 |
| AD-567156.1 | CGUGAUACACCAAGAAAUGAU | 63 | 3462-3482 | AUCAUUUCUUGGUGUAUCACGGG | 151 | 3460-3482 |
| AD-567215.1 | CGGCCUUUGUUCUCAUCUCGU | 64 | 3524-3544 | ACGAGAUGAGAACAAAGGCCGUG | 152 | 3522-3544 |
| AD-567304.1 | GACUUCCUUGAAGCCAACUAU | 65 | 3613-3633 | AUAGUUGGCUUCAAGGAAGUCUC | 153 | 3611-3633 |
| AD-567307.1 | UUCCUUGAAGCCAACUACAUU | 66 | 3616-3636 | AAUGUAGUUGGCUUCAAGGAAGU | 154 | 3614-3636 |
| AD-567314.1 | AAGCCAACUACAUGAACCUAU | 67 | 3623-3643 | AUAGGUCAUGUAGUUGGCUUCA | 155 | 3621-3643 |
| AD-567315.1 | AGCCAACUACAUGAACCUACU | 68 | 3624-3644 | AGUAGGUCAUGUAGUUGGCUUC | 156 | 3622-3644 |
| AD-567318.1 | CAACUACAUGAACCUACAGAU | 69 | 3627-3647 | AUCUGUAGGUUCAUGUAGUUGGC | 157 | 3625-3647 |
| AD-567395.1 | UUCUGACCACAGCCAAAGAUU | 70 | 3722-3742 | AAUCUUUGGCUGUGGUCAGAAAU | 158 | 3720-3742 |
| AD-567487.1 | UGCAGCUAAAAGACUUUGACU | 71 | 3815-3835 | AGUCAAAGUCUUUUAGCUGCAGU | 159 | 3813-3835 |
| AD-567521.1 | CGUGCGUUGGCUCAAUGAACU | 72 | 3849-3869 | AGUUCAUGAGCCAACGCACGAC | 160 | 3847-3869 |
| AD-567582.1 | UUCAUGGUGUUCCAAGCCUUU | 73 | 3910-3930 | AAAGGCUGGAACACCAUGAAGG | 161 | 3908-3930 |
| AD-567699.1 | CUGCGAUCAGAAGAGACCAAU | 74 | 4048-4068 | AUUGGUCUCUUCUGAUCGCAGGA | 162 | 4046-4068 |
| AD-567700.1 | UGCGAUCAGAAGAGACCAAGU | 75 | 4049-4069 | ACUUGGUCUCUUCUGAUCGCAGG | 163 | 4047-4069 |
| AD-567713.1 | ACCAAGGAAAAUGAGGGUUUU | 76 | 4063-4083 | AAAAACCCUCAUUUUCCUUGGUCU | 164 | 4061-4083 |

TABLE 2-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-567716.1 | AAGGAAAAUGAGGGUUUCACU | 77 | 4066-4086 | AGUGAAACCCUCAUUUUCCUUGG | 165 | 4064-4086 |
| AD-567808.1 | ACUCACCUGUAAUAAAUUCGU | 78 | 4158-4178 | ACGAAUUAUUACAGGUGAGUUG | 166 | 4156-4178 |
| AD-567809.1 | CUCACCUGUAAUAAAUUCGAU | 79 | 4159-4179 | AUCGAAUUUAUUACAGGUGAGUU | 167 | 4157-4179 |
| AD-567812.1 | ACCUGUAAUAAAUUCGACCUU | 80 | 4162-4182 | AAGGUCGAAUUUAUUACAGGUGA | 168 | 4160-4182 |
| AD-567813.1 | CCUGUAAUAAAUUCGACCUCU | 81 | 4163-4183 | AGAGGUCGAAUUUAUUACAGGUG | 169 | 4161-4183 |
| AD-567814.1 | CUGUAAUAAAUUCGACCUCAU | 82 | 4164-4184 | AUGAGGUCGAAUUUAUUACAGGU | 170 | 4162-4184 |
| AD-567828.1 | ACCUCAAGGUCACCAUAAAAU | 83 | 4178-4198 | AUUUUAUGGUGACCUUGAGGUCG | 171 | 4176-4198 |
| AD-567829.1 | CCUCAAGGUCACCAUAAAACU | 84 | 4179-4199 | AGUUUUAUGGUGACCUUGAGGUC | 172 | 4177-4199 |
| AD-567831.1 | UCAAGGUCACCAUAAAACCAU | 85 | 4181-4201 | AUGGUUUAUGGUGACCUUGAGG | 173 | 4179-4201 |
| AD-568003.1 | CAGAUACAUCUCCAAGUAUGU | 86 | 4371-4391 | ACAUACUGGAGAUGUAUCUGUC | 174 | 4369-4391 |
| AD-568026.1 | UGGACAAAGCCUUCUCCGAUU | 87 | 4394-4414 | AAUCGGAGAAGGCUUUGUCCAGC | 175 | 4392-4414 |
| AD-568099.1 | UCUAGCUUUCAAAGUUCACCU | 88 | 4467-4487 | AGGUGAACUUUGAAAGCUAGACA | 176 | 4465-4487 |
| AD-568100.1 | CUAGCUUUCAAAGUUCACCAU | 89 | 4468-4488 | AUGGUGAACUUUGAAAGCUAGAC | 177 | 4466-4488 |
| AD-568153.1 | AGUCAAGGUCUACGCCUAUUU | 90 | 4521-4541 | AAAUAGGCGUAGACCUUGACUGC | 178 | 4519-4541 |
| AD-568156.1 | CAAGGUCUACGCCUAUUACAU | 91 | 4524-4544 | AUGUAAUAGGCGUAGACCUUGAC | 179 | 4522-4544 |
| AD-568157.1 | AAGGUCUACGCCUAUUACAAU | 92 | 4525-4545 | AUUGUAAUAGGCGUAGACCUUGA | 180 | 4523-4545 |
| AD-568158.1 | AGGUCUACGCCUAUUACAACU | 93 | 4526-4546 | AGUUGUAAUAGGCGUAGACCUUG | 181 | 4524-4546 |
| AD-568160.1 | GUCUACGCCUAUUACAACCUU | 94 | 4528-4548 | AAGGUUGUAAUAGGCGUAGACCU | 182 | 4526-4548 |
| AD-568161.1 | UCUACGCCUAUUACAACCUGU | 95 | 4529-4549 | ACAGGUGUAAUAGGCGUAGACC | 183 | 4527-4549 |
| AD-568341.1 | GGAGUGGACUAUGUGUACAAU | 96 | 4711-4731 | AUUGUACACAUAGUCCACUCCUG | 184 | 4709-4731 |
| AD-568343.1 | AGUGGACUAUGUGUACAAGAU | 97 | 4713-4733 | AUCUUGUACACAUAGUCCACUCC | 185 | 4711-4733 |
| AD-568344.1 | GUGGACUAUGUGUACAAGACU | 98 | 4714-4734 | AGUCUUGUACACAUAGUCCACUC | 186 | 4712-4734 |
| AD-568345.1 | UGGACUAUGUGUACAAGACCU | 99 | 4715-4735 | AGGUCTGUACACAUAGUCCACU | 187 | 4713-4735 |
| AD-568381.1 | AGCUGUCCAAUGACUUUGACU | 100 | 4751-4771 | AGUCAAAGUCAUUGGACAGCUGA | 188 | 4749-477I |
| AD-568382.1 | GCUGUCCAAUGACUUUGACGU | 101 | 4752-4772 | ACGUCAAAGUCAUUGGACAGCUG | 189 | 4750-4772 |
| AD-568586.1 | GAGAACCAGAAACAAUGCCAU | 102 | 5014-5034 | AUGGCAUUGUUUCUGGUUCUCUU | 190 | 5012-5034 |

TABLE 3

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: |
|---|---|---|---|---|
| AD-564727.1 | csgsgguaCfcUfCfUfucauccagauL96 | 191 | asUfscugg(Agn)ugaagaGfgUfacccgscsu | 279 |
| AD-564730.1 | gsusaccuCfuUfCfAfuccagacaguL96 | 192 | asCfsuguc(Tgn)ggaugaAfgAfgguacscsc | 280 |
| AD-564731.1 | usasccucUfuCfAfUfccagacagauL96 | 193 | asUfscugu(Cgn)uggaugAfaGfagguascsc | 281 |
| AD-564739.1 | csasuccaGfaCfAfGfacaagaccauL96 | 194 | asUfsgguc(Tgn)ugucugUfcUfggaugsasa | 282 |
| AD-564742.1 | cscsagacAfgAfCfAfagaccaucuuL96 | 195 | asAfsgaug(Ggn)ucuuguCfuGfucuggsasu | 283 |

TABLE 3-continued

Modified Sense and Antisense Strand Sequences of Complement Component C3 dsRNA Agents

| | | | | |
|---|---|---|---|---|
| AD-564744.1 | asgsacagAfcAfAfGfaccaucuacuL96 | 196 | asGfsuaga(Tgn)ggucuuGfuCfugucusgsg | 284 |
| AD-564745.1 | gsascagaCfaAfGfAfccaucuacauL96 | 197 | asUfsguag(Agn)uggucuUfgUfcugucsusg | 285 |
| AD-564901.1 | asusuccgGfaAfCfUfcgucaacauuL96 | 198 | asAfsuguu(Ggn)acgaguUfcCfggaausgsu | 286 |
| AD-564975.1 | csascugaGfuUfUfGfaggugaagguL96 | 199 | asCfscuuc(Agn)ccucaaAfcUfcagusgsa | 287 |
| AD-564976.1 | ascsugagUfuUfGfAfggugaaggauL96 | 200 | asUfsccuu(Cgn)accucaAfaCfucagusgsg | 288 |
| AD-565005.1 | gscsccagUfuUfCfGfaggucauaguL96 | 201 | asCfsuaug(Agn)ccucgaAfaCfugggcsasg | 289 |
| AD-565040.1 | asasuucuAfcUfAfCfaucuauaacuL96 | 202 | asGfsuuau(Agn)gauguaGfuAfgaauusuc | 290 |
| AD-565278.1 | uscsccuaCfcAfGfAfuccacuucauL96 | 203 | asUfsgaag(Tgn)ggaucuGfgUfagggasgsa | 291 |
| AD-565279.1 | cscscuacCfaGfAfUfccacuucacuL96 | 204 | asGfsugaa(Ggn)uggaucUfgGfuagggsasg | 292 |
| AD-565281.1 | csusaccaGfaUfCfCfacuucaccauL96 | 205 | asUfsggug(Agn)aguggaUfcUfgguagsgsg | 293 |
| AD-565282.1 | usasccagAfuCfCfAfcuucaccaauL96 | 206 | asUfsuggu(Ggn)aaguggAfuCfgguasgsg | 294 |
| AD-565284.1 | cscsagauCfcAfCfUfucaccaagauL96 | 207 | asUfscuug(Ggn)ugaaguGfgAfucuggsusa | 295 |
| AD-565532.1 | gsgsgcaaCfuCfCfAfacaauuaccuL96 | 208 | asGfsguaa(Tgn)uguuggAfgUfugcccsasc | 296 |
| AD-565534.1 | gscsaacuCfcAfAfCfaauuaccuguL96 | 209 | asCfsaggu(Agn)auuguuGfgAfguugcscsc | 297 |
| AD-565535.1 | csascucCfaAfCfAfauuaccugcuL96 | 210 | asGfscagg(Tgn)aauuguUfgGfaguugscsc | 298 |
| AD-565541.1 | csasacaaUfuAfCfCfugcaucucuuL96 | 211 | asAfsgaga(Tgn)gcagguAfaUfuguusgsa | 299 |
| AD-565616.1 | csasagauCfcGfCfCfUfacuacaccuuL96 | 212 | asAfsggug(Tgn)aguagCfgAfucuugsgsc | 300 |
| AD-565904.1 | csgsugcuGfaAfUfAfagaagaacauL96 | 213 | asUfsguuc(Tgn)ucuuauUfcAfgcacgsasa | 301 |
| AD-565905.1 | gsusgcugAfaUfAfAfgaagaacaauL96 | 214 | asUfsuguu(Cgn)uucuuaUfuCfagcacsgsa | 302 |
| AD-565925.1 | ascsugacGfcAfGfAfguaagaucuuL96 | 215 | asAfsgauc(Tgn)uacucuGfcGfucagususu | 303 |
| AD-566234.1 | usgscagaAfgAfGfAfacaucguuuuL96 | 216 | asAfsaacg(Agn)uguucCfuUfcugcasasu | 304 |
| AD-566383.1 | csasuguCfgAfCfAfagaaagggauL96 | 217 | asUfscccu(Tgn)ucuguCfcGfacaugscsu | 305 |
| AD-566384.1 | asusgucgGfaCfAfAfgaaagggauuL96 | 218 | asAfsuccc(Tgn)uucuugUfcCfgacausgsc | 306 |
| AD-566386.1 | gsuscggaCfaAfGfAfaagggaucuuL96 | 219 | asAfsgauc(Cgn)cuucuUfgUfccgacsasu | 307 |
| AD-566388.1 | csgsgacaAfgAfAfAfgggaucuguuL96 | 220 | asAfscaga(Tgn)cccuuuCfuUfguccgsasc | 308 |
| AD-566409.1 | ascsaguaAfuGfCfAfggacuucuuuL96 | 221 | asAfsagaa(Ggn)uccugcAfuUfacugusgsa | 309 |
| AD-566411.1 | asgsuaauGfcAfGfGfacuucuucauL96 | 222 | asUfsgaag(Agn)aguccGfcAfuuacusgsu | 310 |
| AD-566412.1 | gsusaaugCfaGfGfAfcuucuucauuL96 | 223 | asAfsugaa(Ggn)aaguccUfgCfauuacsusg | 311 |
| AD-566442.1 | csusacccUfaCfUfCfuguuguucguL96 | 224 | asCfsgaac(Agn)acagagUfaGfgguagscsc | 312 |
| AD-566443.1 | usascccuAfcUfCfUfguuguucgauL96 | 225 | asUfscgaa(Cgn)aacagaGfuAfgggusgsc | 313 |
| AD-566444.1 | ascsccuaCfuCfUfGfuuguucgaauL96 | 226 | asUfsucga(Agn)caacagAfgUfagggusasg | 314 |
| AD-566445.1 | cscscuacUfcUfGfUfuguucgaaauL96 | 227 | asUfsuucg(Agn)acaacaGfaGfuagggsusa | 315 |
| AD-566446.1 | cscsuacuCfuGfUfUfguucgaaacuL96 | 228 | asGfsuuuc(Ggn)aacaacAfgAfguaggsgsu | 316 |
| AD-566447.1 | csusacucUfgUfUfGfuucgaaacguL96 | 229 | asCfsguuu(Cgn)gaacaaCfaGfaguagsgsg | 317 |
| AD-566448.1 | usascucuGfuUfGfUfucgaaacgauL96 | 230 | asUfscguu(Tgn)cgaacaAfcAfgaguasgsg | 318 |
| AD-566449.1 | ascsucuGfuUfGfUfUfcgaaacgaguL96 | 231 | asCfsucgu(Tgn)ucgaacAfaCfagagusasg | 319 |
| AD-566485.1 | cscsguucUfcUfAfCfaauuaccguL96 | 232 | asCfscggu(Agn)auuguaGfaGfaacggscsu | 320 |
| AD-566528.1 | gsgsuggaAfcUfAfCfUfuccacaaucuL96 | 233 | asGfsauug(Tgn)ggaguaGfuUfccaccscsu | 321 |
| AD-566837.1 | cscsgaguCfuGfAfGfaccagaauuuL96 | 234 | asAfsauuc(Tgn)ggucucAfgGfAfcucggsusg | 322 |

TABLE 3-continued

Modified Sense and Antisense Strand Sequences of Complement Component C3 dsRNA Agents

| | | | | | |
|---|---|---|---|---|---|
| AD-566935.1 | gsusgcauUfaCfCfUfggaugaaacuL96 | 235 | asGfsuuuc(Agn)uccaggUfaAfugcacsasg | 323 |
| AD-567063.1 | csusacguGfgUfCfAfaggucuucuuL96 | 236 | asAfsgaag(Agn)ccuugaCfcAfcguagsgsc | 324 |
| AD-567066.1 | csgsugguCfaAfGfGfucuucucucuL96 | 237 | asGfsagag(Agn)agaccuUfgAfccacsgsusa | 325 |
| AD-567067.1 | gsusgguсAfaGfGfUfcuucucucuuL96 | 238 | asAfsgaga(Ggn)aagaccUfuGfaccacsgsu | 326 |
| AD-567156.1 | csgsugauAfcAfCfCfaagaaaugauL96 | 239 | asUfscauu(Tgn)cuugguGfuAfucacgsgsg | 327 |
| AD-567215.1 | csgsgccuUfuGfUfUfcucaucucguL96 | 240 | asCfsgaga(Tgn)gagaacAfaAfggccgsusg | 328 |
| AD-567304.1 | gsascuucCfuUfGfAfagccaacuauL96 | 241 | asUfsaguu(Ggn)gcuucaAfgGfaagucsusc | 329 |
| AD-567307.1 | ususccuuGfaAfGfCfcaacuacauuL96 | 242 | asAfsugua(Ggn)uuggcuUfcAfaggaasgsu | 330 |
| AD-567314.1 | asasgccaAfcUfAfCfaugaaccuauL96 | 243 | asUfsaggu(Tgn)cauguaGfuUfggcuuscsa | 331 |
| AD-567315.1 | asgsccaaCfuAfCfAfugaaccuacuL96 | 244 | asGfsuagg(Tgn)ucauguAfgUfuggcususc | 332 |
| AD-567318.1 | csasacuaCfaUfGfAfaccuacagauL96 | 245 | asUfscugu(Agn)gguucaUfgUfaguugsgsc | 333 |
| AD-567395.1 | ususcugaCfcAfCfAfgccaaagauuL96 | 246 | asAfsucuu(Tgn)ggcuguGfgUfcagaasasu | 334 |
| AD-567487.1 | usgscagcUfaAfAfAfgacuuugacuL96 | 247 | asGfsucaa(Agn)gucuuuUfaGfcugcasgsu | 335 |
| AD-567521.1 | csgsugcgUfuGfGfCfucaaugaacuL96 | 248 | asGfsuuca(Tgn)ugagccAfaCfgcacgsasc | 336 |
| AD-567582.1 | ususcaugGfuGfUfUfccaagccuuuL96 | 249 | asAfsaggc(Tgn)uggaacAfcCfaugaasgsg | 337 |
| AD-567699.1 | csusgcgaUfcAfGfAfagagaccaauL96 | 250 | asUfsuggu(Cgn)ucuucuGfaUfcgcagsgsa | 338 |
| AD-567700.1 | usgscgauCfaGfAfAfgagaccaaguL96 | 251 | asCfsuugg(Tgn)cucuucUfgAfucgcasgsg | 339 |
| AD-567713.1 | ascscaagGfaAfAfAfugagggguuuL96 | 252 | asAfsaacc(Cgn)ucauuuUfcCfuuggsuscsu | 340 |
| AD-567716.1 | asasggaaAfaUfGfAfggguuucacuL96 | 253 | asGfsugaa(Agn)cccucaUfuUfuccuusgsg | 341 |
| AD-567808.1 | ascsucacCfuGfUfUfAfauaaauucguL96 | 254 | asCfsgaau(Tgn)uauuacAfgGfugagususg | 342 |
| AD-567809.1 | csuscaccUfgUfAfAfuaaauucgauL96 | 255 | asUfscgaa(Tgn)uuauuaCfaGfgugagsusu | 343 |
| AD-567812.1 | ascscuguAfaUfAfAfauucgaccuuL96 | 256 | asAfsgguc(Ggn)aauuuaUfuAfcaggsusgsa | 344 |
| AD-567813.1 | cscsguaaAfuUfAfAfuucgaccucuL96 | 257 | asGfsaggu(Cgn)gaauuuAfuUfacaggsusg | 345 |
| AD-567814.1 | csusguaaUfaAfAfUfucgaccucauL96 | 258 | asUfsgagg(Tgn)cgaauuUfaUfuacagsgsu | 346 |
| AD-567828.1 | ascscucaAfgGfUfCfaccauaaaauL96 | 259 | asUfsuuua(Tgn)ggugacCfuUfgagguscsg | 347 |
| AD-567829.1 | cscsucaaGfgUfCfAfccauaaaacuL96 | 260 | asGfsuuuu(Agn)uggugaCfcUfugaggsusc | 348 |
| AD-567831.1 | uscsaaggUfcAfCfCfauaaaaccauL96 | 261 | asUfsgguu(Tgn)uaugguGfaCfcuugasgsg | 349 |
| AD-568003.1 | csasgauaCfaUfCfUfccaaguaguguL96 | 262 | asCfsauac(Tgn)uggagaUfgUfaucugsusc | 350 |
| AD-568026.1 | usgsgacaAfaGfCfCfuucuccgauuL96 | 263 | asAfsucgg(Agn)gaaggcUfuUfgucasgsc | 351 |
| AD-568099.1 | uscsuagcUfuUfCfAfaaguucaccuL96 | 264 | asGfsguga(Agn)cuuugaAfaGfcuagascsa | 352 |
| AD-568100.1 | csusagcuUfuCfAfAfaguucaccauL96 | 265 | asUfsggug(Agn)acuugAfaAfgcuagsasc | 353 |
| AD-568153.1 | asgsucaaGfuCfUfUfacgccuauuuL96 | 266 | asAfsauag(Ggn)cguagaCfcCfugacusgsc | 354 |
| AD-568156.1 | csasagguCfuAfCfCfGfccuauuacauL96 | 267 | asUfsguaa(Tgn)aggcguAfgAfccuugsasc | 355 |
| AD-568157.1 | asasgguсUfaCfGfCfcuauuacaauL96 | 268 | asUfsugua(Agn)uaggcgUfaGfaccuusgsa | 356 |
| AD-568158.1 | asgsgucuAfcGfCfCfuauuacaacuL96 | 269 | asGfsuugu(Agn)auaggcGfuAfgaccususg | 357 |
| AD-568160.1 | gsuscuacGfcCfUfAfuuacaaccuuL96 | 270 | asAfsgguu(Ggn)uaauagGfcGfuagacscsu | 358 |
| AD-568161.1 | uscsuacgCfcUfAfUfuacaaccuguL96 | 271 | asCfsaggu(Tgn)guaauaGfgCfguagascsc | 359 |
| AD-568341.1 | gsgsagugGfaCfUfUfAfuguguacaauL96 | 272 | asUfsugua(Cgn)acauagUfcCfacuccsusg | 360 |
| AD-568343.1 | asgsuggaCfuAfUfGfuguacaagauL96 | 273 | asUfscuug(Tgn)acacauAfgUfccacuscsc | 361 |

TABLE 3-continued

Modified Sense and Antisense Strand Sequences of Complement Component C3 dsRNA Agents

| | | | |
|---|---|---|---|
| AD-568344.1 gsusggacUfaUfGfUfguacaagacuL96 | 274 | asGfsucuu(Ggn)uacacaUfaGfuccacsusc | 362 |
| AD-568345.1 usgsgacuAfuGfUfGfuacaagaccuL96 | 275 | asGfsgucu(Tgn)guacacAfuAfguccascsu | 363 |
| AD-568381.1 asgscuguCfcAfAfUfgacuuugacuL96 | 276 | asGfsucaa(Agn)gucauuGfgAfcagcusgsa | 364 |
| AD-568382.1 gscsugucCfaAfUfGfacuuugacguL96 | 277 | asCfsguca(Agn)agucauUfgGfacagcsusg | 365 |
| AD-568586.1 gsasgaacCfaGfAfAfacaaugccauL96 | 278 | asUfsggca(Tgn)uguuucUfgGfuucucsusu | 366 |

| Duplex Name | mRNA target sequence | SEQ ID NO: |
|---|---|---|
| AD-564727.1 | AGCGGGUACCUCUUCAUCCAGAC | 367 |
| AD-564730.1 | GGGUACCUCUUCAUCCAGACAGA | 368 |
| AD-564731.1 | GGUACCUCUUCAUCCAGACAGAC | 369 |
| AD-564739.1 | UUCAUCCAGACAGACAAGACCAU | 370 |
| AD-564742.1 | AUCCAGACAGACAAGACCAUCUA | 371 |
| AD-564744.1 | CCAGACAGACAAGACCAUCUACA | 372 |
| AD-564745.1 | CAGACAGACAAGACCAUCUACAC | 373 |
| AD-564901.1 | ACAUUCCGGAACUCGUCAACAUG | 374 |
| AD-564975.1 | UCCACUGAGUUUGAGGUGAAGGA | 375 |
| AD-564976.1 | CCACUGAGUUUGAGGUGAAGGAG | 376 |
| AD-565005.1 | CUGCCCAGUUUCGAGGUCAUAGU | 377 |
| AD-565040.1 | GAAAUUCUACUACAUCUAUAACG | 378 |
| AD-565278.1 | UCUCCCUACCAGAUCCACUUCAC | 379 |
| AD-565279.1 | CUCCCUACCAGAUCCACUUCACC | 380 |
| AD-565281.1 | CCCUACCAGAUCCACUUCACCAA | 381 |
| AD-565282.1 | CCUACCAGAUCCACUUCACCAAG | 382 |
| AD-565284.1 | UACCAGAUCCACUUCACCAAGAC | 383 |
| AD-565532.1 | GUGGGCAACUCCAACAAUUACCU | 384 |
| AD-565534.1 | GGGCAACUCCAACAAUUACCUGC | 385 |
| AD-565535.1 | GGCAACUCCAACAAUUACCUGCA | 386 |
| AD-565541.1 | UCCAACAAUUACCUGCAUCUCUC | 387 |
| AD-565616.1 | GCCAAGAUCCGCUACUACACCUA | 388 |
| AD-565904.1 | UUCGUGCUGAAUAAGAAGAACAA | 389 |
| AD-565905.1 | UCGUGCUGAAUAAGAAGAACAAA | 390 |
| AD-565925.1 | AAACUGACGCAGAGUAAGAUCUG | 391 |
| AD-566234.1 | AUUGCAGAAGAGAACAUCGUUUC | 392 |
| AD-566383.1 | AGCAUGUCGGACAAGAAAGGGAU | 393 |
| AD-566384.1 | GCAUGUCGGACAAGAAAGGGAUC | 394 |
| AD-566386.1 | AUGUCGGACAAGAAAGGGAUCUG | 395 |
| AD-566388.1 | GUCGGACAAGAAAGGGAUCUGUG | 396 |
| AD-566409.1 | UCACAGUAAUGCAGGACUUCUUC | 397 |
| AD-566411.1 | ACAGUAAUGCAGGACUUCUUCAU | 398 |

TABLE 3-continued

Modified Sense and Antisense Strand Sequences of Complement Component C3 dsRNA Agents

| | | |
|---|---|---|
| AD-566412.1 | CAGUAAUGCAGGACUUCUUCAUC | 399 |
| AD-566442.1 | GGCUACCCUACUCUGUUGUUCGA | 400 |
| AD-566443.1 | GCUACCCUACUCUGUUGUUCGAA | 401 |
| AD-566444.1 | CUACCCUACUCUGUUGUUCGAAA | 402 |
| AD-566445.1 | UACCCUACUCUGUUGUUCGAAAC | 403 |
| AD-566446.1 | ACCCUACUCUGUUGUUCGAAACG | 404 |
| AD-566447.1 | CCCUACUCUGUUGUUCGAAACGA | 405 |
| AD-566448.1 | CCUACUCUGUUGUUCGAAACGAG | 406 |
| AD-566449.1 | CUACUCUGUUGUUCGAAACGAGC | 407 |
| AD-566485.1 | AGCCGUUCUCUACAAUUACCGGC | 408 |
| AD-566528.1 | AGGGUGGAACUACUCCACAAUCC | 409 |
| AD-566837.1 | CACCGAGUCUGAGACCAGAAUUC | 410 |
| AD-566935.1 | CUGUGCAUUACCUGGAUGAAACG | 411 |
| AD-567063.1 | GCCUACGUGGUCAAGGUCUUCUC | 412 |
| AD-567066.1 | UACGUGGUCAAGGUCUUCUCUCU | 413 |
| AD-567067.1 | ACGUGGUCAAGGUCUUCUCUCUG | 414 |
| AD-567156.1 | CCCGUGAUACACCAAGAAAUGAU | 415 |
| AD-567215.1 | CACGGCCUUUGUUCUCAUCUCGC | 416 |
| AD-567304.1 | GAGACUUCCUUGAAGCCAACUAC | 417 |
| AD-567307.1 | ACUUCCUUGAAGCCAACUACAUG | 418 |
| AD-567314.1 | UGAAGCCAACUACAUGAACCUAC | 419 |
| AD-567315.1 | GAAGCCAACUACAUGAACCUACA | 420 |
| AD-567318.1 | GCCAACUACAUGAACCUACAGAG | 421 |
| AD-567395.1 | AUUUCUGACCACAGCCAAAGAUA | 422 |
| AD-567487.1 | ACUGCAGCUAAAAGACUUUGACU | 423 |
| AD-567521.1 | GUCGUGCGUUGGCUCAAUGAACA | 424 |
| AD-567582.1 | CCUUCAUGGUGUUCCAAGCCUUG | 425 |
| AD-567699.1 | UCCUGCGAUCAGAAGAGACCAAG | 426 |
| AD-567700.1 | CCUGCGAUCAGAAGAGACCAAGG | 427 |
| AD-567713.1 | AGACCAAGGAAAAUGAGGGUUUC | 428 |
| AD-567716.1 | CCAAGGAAAAUGAGGGUUUCACA | 429 |
| AD-567808.1 | CAACUCACCUGUAAUAAAUUCGA | 430 |
| AD-567809.1 | AACUCACCUGUAAUAAAUUCGAC | 431 |
| AD-567812.1 | UCACCUGUAAUAAAUUCGACCUC | 432 |
| AD-567813.1 | CACCUGUAAUAAAUUCGACCUCA | 433 |
| AD-567814.1 | ACCUGUAAUAAAUUCGACCUCAA | 434 |
| AD-567828.1 | CGACCUCAAGGUCACCAUAAAAC | 435 |
| AD-567829.1 | GACCUCAAGGUCACCAUAAAACC | 436 |
| AD-567831.1 | CCUCAAGGUCACCAUAAAACCAG | 437 |

TABLE 3-continued

Modified Sense and Antisense Strand Sequences of Complement Component C3 dsRNA Agents

| | | |
|---|---|---|
| | AD-568003.1 GACAGAUACAUCUCCAAGUAUGA | 438 |
| | AD-568026.1 GCUGGACAAAGCCUUCUCCGAUA | 439 |
| | AD-568099.1 UGUCUAGCUUUCAAAGUUCACCA | 440 |
| | AD-568100.1 GUCUAGCUUUCAAAGUUCACCAA | 441 |
| | AD-568153.1 GCAGUCAAGGUCUACGCCUAUUA | 442 |
| | AD-568156.1 GUCAAGGUCUACGCCUAUUACAA | 443 |
| | AD-568157.1 UCAAGGUCUACGCCUAUUACAAC | 444 |
| | AD-568158.1 CAAGGUCUACGCCUAUUACAACC | 445 |
| | AD-568160.1 AGGUCUACGCCUAUUACAACCUG | 446 |
| | AD-568161.1 GGUCUACGCCUAUUACAACCUGG | 447 |
| | AD-568341.1 CAGGAGUGGACUAUGUGUACAAG | 448 |
| | AD-568343.1 GGAGUGGACUAUGUGUACAAGAC | 449 |
| | AD-568344.1 GAGUGGACUAUGUGUACAAGACC | 450 |
| | AD-568345.1 AGUGGACUAUGUGUACAAGACCC | 451 |
| | AD-568381.1 UCAGCUGUCCAAUGACUUUGACG | 452 |
| | AD-568382.1 CAGCUGUCCAAUGACUUUGACGA | 453 |
| | AD-568586.1 AAGAGAACCAGAAACAAUGCCAG | 454 |

TABLE 4

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-569034.1 | ACGGUCAUGGUCAACAUUGAU | 455 | 577-597 | AUCAAUGUUGACCAUGACCGUCC | 489 | 575-597 |
| AD-569164.1 | AGAUCCGAGCCUACUAUGAAU | 456 | 707-727 | AUUCAUAGUAGGCUCGGAUCUUC | 490 | 705-727 |
| AD-569165.1 | GAUCCGAGCCUACUAUGAAAU | 457 | 708-728 | AUUUCAUAGUAGGCUCGGAUCUU | 491 | 706-728 |
| AD-569272.1 | AAUUCUACUACAUCUAUAACU | 458 | 815-835 | AGUUAUAGAUGUAGUAGAAUUUC | 492 | 813-835 |
| AD-569763.1 | UGGGCAACUCCAACAAUUACU | 459 | 1439-1459 | AGUAAUUGUUGGAGUUGCCCACG | 493 | 1437-1459 |
| AD-569765.1 | GGCAACUCCAACAAUUACCUU | 460 | 1441-1461 | AAGGUAAUUGUUGGAGUUGCCCA | 494 | 1439-1461 |
| AD-570130.1 | CGUGUUCGUGCUGAAUAAGAU | 461 | 1896-1916 | AUCUUAUUCAGCACGAACACGCC | 495 | 1894-1916 |
| AD-570132.1 | UGUUCGUGCUGAAUAAGAAGU | 462 | 1898-1918 | ACUUCUUAUUCAGCACGAACACG | 496 | 1896-1918 |
| AD-570133.1 | GUUCGUGCUGAAUAAGAAGAU | 463 | 1899-1919 | AUCUUCUUAUUCAGCACGAACAC | 497 | 1897-1919 |
| AD-570134.1 | UUCGUGCUGAAUAAGAAGAAU | 464 | 1900-1920 | AUUCUUCUUAUUCAGCACGAACA | 498 | 1898-1920 |
| AD-570157.1 | ACUGACGCAGAGUAAGAUCUU | 465 | 1923-1943 | AAGAUCUUACUCUGCGUCAGUUU | 499 | 1921-1943 |
| AD-570711.1 | UCCGAGCCGUUCUCUACAAUU | 466 | 2633-2653 | AAUUGUAGAGAACGGCUCGGAUU | 500 | 2631-2653 |
| AD-570712.1 | CCGAGCCGUUCUCUACAAUUU | 467 | 2634-2654 | AAAUUGUAGAGAACGGCUCGGAU | 501 | 2632-2654 |
| AD-570713.1 | CGAGCCGUUCUCUACAAUUAU | 468 | 2635-2655 | AUAAUUGUAGAGAACGGCUCGGA | 502 | 2633-2655 |
| AD-570714.1 | GAGCCGUUCUCUACAAUUACU | 469 | 2636-2656 | AGUAAUUGUAGAGAACGGCUCGG | 503 | 2634-2656 |
| AD-571539.1 | UUCCUUGAAGCCAACUACAUU | 470 | 3616-3636 | AAUGUAGUUGGCUUCAAGGAAGU | 504 | 3614-3636 |
| AD-571610.1 | GCCUCUUCUUAACAAAUUUCU | 471 | 3705-3725 | AGAAAUUUGUUAAGAAGAGGCCC | 505 | 3703-3725 |

TABLE 4-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-571633.1 | CCACAGCCAAAGAUAAGAACU | 472 | 3728-3748 | AGUUCUUAUCUUUGGCUGUGGUC | 506 | 3726-3748 |
| AD-571715.1 | CUACUGCAGCUAAAAGACUUU | 473 | 3811-3831 | AAAGUCUUUUAGCUGCAGUAGGG | 507 | 3809-3831 |
| AD-571752.1 | UCGUGCGUUGGCUCAAUGAAU | 474 | 3848-3868 | AUUCAUUGAGCCAACGCACGACG | 508 | 3846-3868 |
| AD-571754.1 | GUGCGUUGGCUCAAUGAACAU | 475 | 3850-3870 | AUGUUCAUUGAGCCAACGCACGA | 509 | 3848-3870 |
| AD-571828.1 | AGCCUUGGCUCAAUACCAAAU | 476 | 3924-3944 | AUUUGGUAUUGAGCCAAGGCUUG | 510 | 3922-3944 |
| AD-572039.1 | AACUCACCUGUAAUAAAUUCU | 477 | 4157-4177 | AGAAUUUAUUACAGGUGAGUUGA | 511 | 4155-4177 |
| AD-572040.1 | ACUCACCUGUAAUAAAUUCGU | 478 | 4158-4178 | ACGAAUUUAUUACAGGUGAGUUG | 512 | 4156-4178 |
| AD-572041.1 | CUCACCUGUAAUAAAUUCGAU | 479 | 4159-4179 | AUCGAAUUUAUUACAGGUGAGUU | 513 | 4157-4179 |
| AD-572059.1 | GACCUCAAGGUCACCAUAAAU | 480 | 4177-4197 | AUUUAUGGUGACCUUGAGGUCGA | 514 | 4175-4197 |
| AD-572061.1 | CCUCAAGGUCACCAUAAAACU | 481 | 4179-4199 | AGUUUUAUGGUGACCUUGAGGUC | 515 | 4177-4199 |
| AD-572062.1 | CUCAAGGUCACCAUAAAACCU | 482 | 4180-4200 | AGGUUUUAUGGUGACCUUGAGGU | 516 | 4178-4200 |
| AD-572063.1 | UCAAGGUCACCAUAAAACCAU | 483 | 4181-4201 | AUGGUUUUAUGGUGACCUUGAGG | 517 | 4179-4201 |
| AD-572110.1 | GAUGCCAAGAACACUAUGAUU | 484 | 4228-4248 | AAUCAUAGUGUUCUUGGCAUCCU | 518 | 4226-4248 |
| AD-572144.1 | AGGAUGCCACUAUGUCUAUAU | 485 | 4280-4300 | AUAUAGACAUAGUGGCAUCCUGG | 519 | 4278-4300 |
| AD-572388.1 | CAAGGUCUACGCCUAUUACAU | 486 | 4524-4544 | AUGUAAUAGGCGUAGACCUUGAC | 520 | 4522-4544 |
| AD-572389.1 | AAGGUCUACGCCUAUUACAAU | 487 | 4525-4545 | AUUGUAAUAGGCGUAGACCUUGA | 521 | 4523-4545 |
| AD-572390.1 | AGGUCUACGCCUAUUACAACU | 488 | 4526-4546 | AGUUGUAAUAGGCGUAGACCUUG | 522 | 4524-4546 |

TABLE 5

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-569034.1 | ascsgg ucAfuG fGfUfc aacauu gauL96 | 523 | asUfsc aaUfgU fUfgac cAfuGf accgus csc | 557 | GGACGG UCAUGG UCAACA UUGAG | 591 |
| AD-569164.1 | asgsau ccGfaG fCfCfu acuaug aauL96 | 524 | asUfsu caUfaG fUfagg cUfcGf gaucus usc | 558 | GAAGAU CCGAGC CUACUA UGAAA | 592 |
| AD-569165.1 | gsasuc cgAfgC fCfUfa cuauga aauL96 | 525 | asUfsu ucAfuA fGfuag gCfuCf ggaucs usu | 559 | AAGAUC CGAGCC UACUAU GAAAA | 593 |
| AD-569272.1 | asasuu cuAfcU fAfCfa ucuaua acuL96 | 526 | asGfsu uaUfaG fAfugu aGfuAf gaauus usc | 560 | GAAAUU CUACUA CAUCUA UAACG | 594 |
| AD-569763.1 | usgsgg caAfcU fCfCfa acaauu acuL96 | 527 | asGfsu aaUfuG fUfugg aGfuUf gcccas csg | 561 | CGUGGG CAACUC CAACAA UUACC | 595 |
| AD-569765.1 | gsgsca acUfcC fAfAfc aauuac cuuL96 | 528 | asAfsg guAfaU fUfguu gGfaGf uugccs csa | 562 | UGGGCA ACUCCA ACAAUU ACCUG | 596 |
| AD-570130.1 | csgsug uuCfgU fGfCfu gaauaa gauL96 | 529 | asUfsc uuAfuU fCfagc aCfgAf acacgs csc | 563 | GGCGUG UUCGUG CUGAAU AAGAA | 597 |
| AD-570132.1 | usgsuu cgUfgC fUfGfa | 530 | asCfsu ucUfuA fUfuca | 564 | CGUGUU CGUGCU GAAUAA | 598 |

TABLE 5-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| | auaaga aguL96 | | gCfaCf gaacas csg | | GAAGA | |
| AD-570133.1 | gsusuc guGfcU fGfAfa uaagaa gauL96 | 531 | asUfsc uuCfuU fAfuuc aGfcAf cgaacs asc | 565 | GUGUUC GUGCUG AAUAAG AAGAA | 599 |
| AD-570134.1 | ususcg ugCfuG fAfAfu aagaag aauL96 | 532 | asUfsu cuUfcU fUfauu cAfgCf acgaas csa | 566 | UGUUCG UGCUGA AUAAGA AGAAC | 600 |
| AD-570157.1 | ascsug acGfcA fGfAfg uaagau cuuL96 | 533 | asAfsg auCfuU fAfcuc uGfcGf ucagus usu | 567 | AAACUG ACGCAG AGUAAG AUCUG | 601 |
| AD-570711.1 | uscscg agCfcG fUfUfc ucuaca auuL96 | 534 | asAfsu ugUfaG fAfgaa cGfgCf ucggas usu | 568 | AAUCCG AGCCGU UCUCUA CAAUU | 602 |
| AD-570712.1 | cscsga gcCfgU fUfCfu cuacaa uuuL96 | 535 | asGfsa uuGfuA fGfaga aCfgGf cucggs asu | 569 | AUCCGA GCCGUU CUCUAC AAUUA | 603 |
| AD-570713.1 | csgsag ccGfuU fCfUfc uacaau uauL96 | 536 | asUfsa auUfgU fAfgag aAfgGf gcucgs gsa | 570 | UCCGAG CCGUUC UCUACA AUUAC | 604 |
| Ftable1.1 | gsasgc cgUfuC fUfCfu acaauu acuL96 | 537 | asGfsu aaUfuG fUfaga gAfaCf ggcucs gsg | 571 | CCGAGC CGUUCU CUACAA UUACC | 605 |
| AD-571539.1 | ususcc uuGfaA fGfGfc aacuac auuL96 | 538 | asAfsu guAfgU fUfggc uUfcAf aggaas gsu | 572 | ACUUCC UUGAAG CCAACU ACAUG | 606 |
| AD-571610.1 | gscscu cuUfcU fUfAfa caaauu ucuL96 | 539 | asGfsa aaUfuU fGfuua aGfaAf gaggcs csc | 573 | GGGCCU CUUCUU AACAAA UUUCU | 607 |
| AD-571633.1 | cscsac agCfcA fUfAfg auaaga acuL96 | 540 | asGfsu ucUfuA fUfcuu uGfgCf uguggs usc | 574 | GACCAC AGCCAA AGAUAA GAACC | 608 |
| AD-571715.1 | csusac ugCfaG fCfUfa aaagac uuuL96 | 541 | asAfsa guCfuU fUfuag cUfgCf aguags gsg | 575 | CCCUAC UGCAGC UAAAAG ACUUU | 609 |
| AD-571752.1 | uscsgu gcGfuU fGfGfc ucaaug aauL96 | 542 | asUfsu caUfuG fAfgcc aAfcGf cacgas csg | 576 | CGUCGU GCGUUG GCUCAA UGAAC | 610 |
| AD-571754.1 | gsusgc guUfgG fCfUfc aaugaa cauL96 | 543 | asUfsg uuCfaU fUfgag cCfaAf cgcacs gsa | 577 | UCGUGC GUUGGC UCAAUG AACAG | 611 |
| AD-571828.1 | asgscc uuGfgC fUfUfa auacca aauL96 | 544 | asUfsu ugGfuA fUfuga gCfcAf aggcus usg | 578 | CAAGCC UUGGCU CAAUAC CAAAA | 612 |
| AD-572039.1 | asascu caCfcU fGfUfa auaaau ucuL96 | 545 | asGfsa auUfaA fUfuac aGfgUf gaguus gsa | 579 | UCAACU CACCUG UAAUAA AUUCG | 613 |
| AD-572040.1 | ascsuc acCfuG fUfAfa uaaauu cguL96 | 546 | asCfsg aaUfuU fAfuua cAfgGf ugagus usg | 580 | CAACUC ACCUGU AAUAAA UUCGA | 614 |
| AD-572041.1 | csusca ccUfgU fAfAfu aaauuc gauL96 | 547 | asUfsc gaAfuU fUfauu aCfaGf gugags usu | 581 | AACUCA CCUGUA AUAAAU UCGAC | 615 |
| AD-572059.1 | gsascc ucAfaG fGfUfc accaua aauL96 | 548 | asUfsu uaUfgG fUfgac cUfuGf aggucs gsa | 582 | UCGACC UCAAGG UCACCA UAAAA | 616 |
| AD-572061.1 | cscsuc aaGfgU fCfAfc cauaaa acuL96 | 549 | asGfsu uuUfaU fGfgug aCfcUf ugaggs usc | 583 | GACCUC AAGGUC ACCAUA AAACC | 617 |
| AD-572062.1 | csusca agGfuC fAfCfc auaaaa ccuL96 | 550 | asGfsg uuUfuA fUfggu gAfcCf uugags gsu | 584 | ACCUCA AGGUCA CCAUAA AACCA | 618 |
| AD-572063.1 | uscsaa ggUfcA fCfCfa | 551 | asFsg guUfuU fAfugg | 585 | CCUCAA GGUCAC CAUAAA | 619 |

TABLE 5-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| | uaaaac cauL96 | | uGfaCf cuugas gsg | | ACCAG | |
| AD-572110.1 | gsasug ccAfaG fAfAfc acuaug auuL96 | 552 | asAfsu caUfaG fUfguu cUfuGf gcaucs csu | 586 | AGGAUG CCAAGA ACACUA UGAUC | 620 |
| AD-572144.1 | asgsga ugCfcA fCfUfa ugucua uauL96 | 553 | asUfsa uaGfaC fAfuag uGfgCf auccus gsg | 587 | CCAGGA UGCCAC UAUGUC UAUAU | 621 |
| AD-572388.1 | csasag guCfuA fCfGfc cuauua cauL96 | 554 | asUfsg uaAfuA fGfgcg uAfgAf ccuugs asc | 588 | GUCAAG GUCUAC GCCUAU UACAA | 622 |
| AD-572389.1 | asasgg ucUfaC fGfCfc uauuac aauL96 | 555 | asUfsu guAfaU fAfggc gUfaGf accuus gsa | 589 | UCAAGG UCUACG CCUAUU ACAAC | 623 |
| AD-572390.1 | asgsgu cuAfcG fCfCfu auuaca acuL96 | 556 | asGfsu ugUfaA fUfagg cGfuAf gaccus usg | 590 | CAAGGU CUACGC CUAUUA CAACC | 624 |

TABLE 6

Unmodified Sense and Antisense Strand Sequences of Complement Component C3 dsRNA Agents

| Duplex Name | Sense Sequence 5' to 3' | SEQ ID NO: | Range in NM_00 0064.3 | Antisense Sequence 5' to 3' | SEQ ID NO: | Range in NM_00 0064.3 |
|---|---|---|---|---|---|---|
| AD-568976.1 | AGACAG ACAAGA CCAUCU ACU | 625 | 491-511 | AGUAGA UGGUCU UGUCUG UCUGG | 714 | 489-511 |
| AD-568978.1 | ACAGAC AAGACC AUCUAC ACU | 626 | 493-513 | AGUGUA GAUGGU CUUGUC UGUCU | 715 | 491-513 |
| AD-569127.1 | UGGGAC AUUCCG GAACUC GUU | 627 | 670-690 | AACGAG UUCCGG AAUGUC CCAAG | 716 | 668-690 |
| AD-569133.1 | AUUCCG GAACUC GUCAAC AUU | 628 | 676-696 | AAUGUU GACGAG UUCCGG AAUGU | 717 | 674-696 |
| AD-569164.1 | AGAUCC GAGCCU ACUAUG AAU | 629 | 707-727 | AUUCAU AGUAGG CUCGGA UCUUC | 718 | 705-727 |
| AD-569195.1 | GCAGGU CUUCUC CACUGA GUU | 630 | 738-758 | AACUCA GUGGAG AAGACC UGCUG | 719 | 736-758 |
| AD-569237.1 | GCCCAG UUUCGA GGUCAU AGU | 631 | 780-800 | ACUAUG ACCUCG AAACUG GGCAG | 720 | 778-800 |
| AD-569239.1 | CCAGUU UCGAGG UCAUAG UGU | 632 | 782-802 | ACACUA UGACCU CGAAAC UGGGC | 721 | 780-802 |
| AD-569272.1 | AAUUCU ACUACA UCUAUA ACU | 633 | 815-835 | AGUUAU AGAUGU AGUAGA AUUUC | 722 | 813-835 |
| AD-569350.1 | ACUGCC UUUGUC AUCUUC GGU | 634 | 895-915 | ACCGAA GAUGAC AAAGGC AGUUC | 723 | 893-915 |
| AD-569571.1 | CUCAUG GUGUUC GUGACG AAU | 635 | 1207-1227 | AUUCGU CACGAA CACCAU GAGGU | 724 | 1205-1227 |
| AD-569763.1 | UGGGCA ACUCCA ACAAUU ACU | 636 | 1439-1459 | AGUAAU UGUUGG AGUUGC CCACG | 725 | 1437-1459 |
| AD-569764.1 | GGGCAA CUCCAA CAAUUA CCU | 637 | 1440-1460 | AGGUAA UUGUUG GAGUUG CCCAC | 726 | 1438-1460 |
| AD-569766.1 | GCAACU CCAACA AUUACC UGU | 638 | 1442-1462 | ACAGGU AAUUGU UGGAGU UGCCC | 727 | 1440-1462 |
| AD-569816.1 | GUCAAC UUCCUC CUGCGA AUU | 639 | 1510-1530 | AAUUCG CAGGAG GAAGUU GACGU | 728 | 1508-1530 |
| AD-570156.1 | AACUGA CGCAGA GUAAGA UCU | 640 | 1922-1942 | AGAUCU UACUCU GCGUCA GUUUG | 729 | 1920-1942 |

TABLE 6-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-570466.1 | UGCAGAAGAGAACAUCGUUUU | 641 | 2361-2381 | AAAACGAUGUUCUCUUCUGCAAU | 730 | 2359-2381 |
| AD-570470.1 | GAAGAGAACAUCGUUUCCCGU | 642 | 2365-2385 | ACGGGAAACGAUGUUCUCUUCUG | 731 | 2363-2385 |
| AD-570471.1 | AAGAGAACAUCGUUUCCCGAU | 643 | 2366-2386 | AUCGGGAAACGAUGUUCUCUUCU | 732 | 2364-2386 |
| AD-570474.1 | AGAACAUCGUUUCCCGAAGUU | 644 | 2369-2389 | AACUUCGGGAAACGAUGUUCUCU | 733 | 2367-2389 |
| AD-570475.1 | GAACAUCGUUUCCCGAAGUGU | 645 | 2370-2390 | ACACUUCGGGAAACGAUGUUCUC | 734 | 2368-2390 |
| AD-570476.1 | AACAUCGUUUCCCGAAGUGAU | 646 | 2371-2391 | AUCACUUCGGGAAACGAUGUUCU | 735 | 2369-2391 |
| AD-570620.1 | CGGACAAGAAAGGGAUCUGUU | 647 | 2522-2542 | AACAGAUCCCUUUCUUGUCCGAC | 736 | 2520-2542 |
| AD-570621.1 | GGACAAGAAAGGGAUCUGUGU | 648 | 2523-2543 | ACACAGAUCCCUUUCUUGUCCGA | 737 | 2521-2543 |
| AD-570622.1 | GACAAGAAAGGGAUCUGUGGU | 649 | 2524-2544 | AACACAGAUCCCUUUCUUGUCCG | 738 | 2522-2544 |
| AD-570623.1 | ACAAGAAAGGGAUCUGUGUGU | 650 | 2525-2545 | ACACACAGAUCCCUUUCUUGUCC | 739 | 2523-2545 |
| AD-570624.1 | CAAGAAAGGGAUCUGUGUGGU | 651 | 2526-2546 | ACCACACAGAUCCCUUUCUUGUC | 740 | 2524-2546 |
| AD-570625.1 | AAGAAAGGGAUCUGUGUGGCU | 652 | 2527-2547 | AGCCACACAGAUCCCUUUCUUGU | 741 | 2525-2547 |
| AD-570627.1 | GAAAGGGAUCUGUGUGGCAGU | 653 | 2529-2549 | ACUGCCACACAGAUCCCUUUCUU | 742 | 2527-2549 |
| AD-570631.1 | CUUCGAGGUCACAGUAAUGCU | 654 | 2553-2573 | AGCAUUACUGUGACCUCGAAGGG | 743 | 2551-2573 |
| AD-570632.1 | UUCGAGGUCACAGUAAUGCAU | 655 | 2554-2574 | AUGCAUUACUGUGACCUCGAAGG | 744 | 2552-2574 |
| AD-570672.1 | GGCUACCCUACUCUGUUGUUU | 656 | 2594-2614 | AAACAACAGAGUAGGGUAGCCGC | 745 | 2592-2614 |
| AD-570674.1 | CUACCCUACUCUGUUGUUCGU | 657 | 2596-2616 | ACGAACAACAGAGUAGGGUAGCC | 746 | 2594-2616 |
| AD-570675.1 | UACCCUACUCUGUUGUUCGAU | 658 | 2597-2617 | AUCGAACAACAGAGUAGGGUAGC | 747 | 2595-2617 |
| AD-570676.1 | ACCCUACUCUGUUGUUCGAAU | 659 | 2598-2618 | AUUCGAACAACAGAGUAGGGUAG | 748 | 2596-2618 |
| AD-570677.1 | CCCUACUCUGUUGUUCGAAAU | 660 | 2599-2619 | AUUUCGAACAACAGAGUAGGGUA | 749 | 2597-2619 |
| AD-570678.1 | CCUACUCUGUUGUUCGAAACU | 661 | 2600-2620 | AGUUUCGAACAACAGAGUAGGGU | 750 | 2598-2620 |
| AD-570679.1 | CUACUCUGUUGUUCGAAACGU | 662 | 2601-2621 | ACGUUUCGAACAACAGAGUAGGG | 751 | 2599-2621 |
| AD-570680.1 | UACUCUGUUGUUCGAAACGAU | 663 | 2602-2622 | AUCGUUUCGAACAACAGAGUAGG | 752 | 2600-2622 |
| AD-570681.1 | ACUCUGUUGUUCGAAACGAGU | 664 | 2603-2623 | ACUCGUUUCGAACAACAGAGUAG | 753 | 2601-2623 |
| AD-570682.1 | CUCUGUUGUUCGAAACGAGCU | 665 | 2604-2624 | AGCUCGUUUCGAACAACAGAGUA | 754 | 2602-2624 |
| AD-570717.1 | CCGUUCUCUACAAUUACCGGU | 666 | 2639-2659 | ACCGGUAAUUGUAGAGAACGGCU | 755 | 2637-2659 |

TABLE 6-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-570963.1 | AACAAACUGUGGCUGUUCGU | 667 | 2908-2928 | ACGAACAGCCACAGUUUUGUUCA | 756 | 2906-2928 |
| AD-571157.1 | GGUCAUCGCUGUGCAUUACCU | 668 | 3156-3176 | AGGUAAUGCACAGCGAUGACCGU | 757 | 3154-3176 |
| AD-571158.1 | GUCAUCGCUGUGCAUUACCUU | 669 | 3157-3177 | AAGGUAAUGCACAGCGAUGACCG | 758 | 3155-3177 |
| AD-571168.1 | UGCAUUACCUGGAUGAAACGU | 670 | 3167-3187 | ACGUUUCAUCCAGGUAAUGCACA | 759 | 3165-3187 |
| AD-571298.1 | CGUGGUCAAGGUCUUCUCUCU | 671 | 3336-3356 | AGAGAGAAGACCUUGACCACGUA | 760 | 3334-3356 |
| AD-571447.1 | CGGCCUUUGUUCUCAUCUCGU | 672 | 3524-3544 | ACGAGAUGAGAACAAAGGCCGUG | 761 | 3522-3544 |
| AD-571448.1 | GGCCUUUGUUUCUCAUCUCGCU | 673 | 3525-3545 | AGCGAGAUGAGAACAAAGGCCGU | 762 | 3523-3545 |
| AD-571449.1 | GCCUUUGUUCUCAUCUCGCUU | 674 | 3526-3546 | AAGCGAGAUGAGAACAAAGGCCG | 763 | 3524-3546 |
| AD-571539.1 | UUCCUUGAAGCCAACUACAUU | 675 | 3616-3636 | AAUGUAGUUGGCUUCAAGGAAGU | 764 | 3614-3636 |
| AD-571719.1 | UGCAGCUAAAAGACUUUGACU | 676 | 3815-3835 | AGUCAAAGUCUUUUAGCUGCAGU | 765 | 3813-3835 |
| AD-571752.1 | UCGUGCGUUGGCUCAAUGAAU | 677 | 3848-3868 | AUUCAUUGAGCCAACGCACGACG | 766 | 3846-3868 |
| AD-571753.1 | CGUGCGUUGGCUCAAUGAACU | 678 | 3849-3869 | AGUUCAUUGAGCCAACGCACGAC | 767 | 3847-3869 |
| AD-571765.1 | CAAUGAACAGAGAUACUACGU | 679 | 3861-3881 | ACGUAGUAUCUCUGUUCAUUGAG | 768 | 3859-3881 |
| AD-571766.1 | AAUGAACAGAGAUACUACGGU | 680 | 3862-3882 | ACCGUAGUAUCUCUGUUCAUUGA | 769 | 3860-3882 |
| AD-571767.1 | AUGAACAGAGAUACUACGGUU | 681 | 3863-3883 | AACCGUAGUAUCUCUGUUCAUUG | 770 | 3861-3883 |
| AD-571825.1 | CCAAGCCUUGGCUCAAUACCU | 682 | 3921-3941 | AGGUAUUGAGCCAAGGCUUGGAA | 771 | 3919-3941 |
| AD-571826.1 | CAAGCCUUGGCUCAAUACCAU | 683 | 3922-3942 | AUGGUAUUGAGCCAAGGCUUGGA | 772 | 3920-3942 |
| AD-571900.1 | CCACCGUAUCCACUGGGAAUU | 684 | 4017-4037 | AAUUCCCAGUGGAUACGGUGGGU | 773 | 4015-4037 |
| AD-571945.1 | ACCAAGGAAAAUGAGGGUUUU | 685 | 4063-4083 | AAAACCCUCAUUUUCCUUGGUCU | 774 | 4061-4083 |
| AD-571948.1 | AAGGAAAAUGAGGGUUUCACU | 686 | 4066-4086 | AGUGAAACCCUCAUUUUCCUUGG | 775 | 4064-4086 |
| AD-572039.1 | AACUCACCUGUAAUAAAUUCU | 687 | 4157-4177 | AGAAUUUAUUACAGGUGAGUUGA | 776 | 4155-4177 |
| AD-572040.1 | ACUCACCUGUAAUAAAUUCGU | 688 | 4158-4178 | ACGAAUUUAUUACAGGUGAGUUG | 777 | 4156-4178 |
| AD-572041.1 | CUCACCUGUAAUAAAUUCGAU | 689 | 4159-4179 | AUCGAAUUUAUUACAGGUGAGUU | 778 | 4157-4179 |
| AD-572044.1 | ACCUGUAAUAAAUUCGACCUU | 690 | 4162-4182 | AAGGUCGAAUUUAUUACAGGUGA | 779 | 4160-4182 |
| AD-572049.1 | UAAUAAAUUCGACCUCAAGGU | 691 | 4167-4187 | ACCUUGAGGUCGAAUUUAUUACA | 780 | 4165-4187 |
| AD-572060.1 | ACCUCAAGGUCACCAUAAAAU | 692 | 4178-4198 | AUUUUAUGGUGACCUUGAGGUCG | 781 | 4176-4198 |

TABLE 6-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-572061.1 | CCUCAAGGUCACCAUAAAACU | 693 | 4179-4199 | AGUUUUAUGGUGACCUUGAGGUC | 782 | 4177-4199 |
| AD-572062.1 | CUCAAGGUCACCAUAAAACCU | 694 | 4180-4200 | AGUUUUAUGGUGACCUUGAGGU | 783 | 4178-4200 |
| AD-572108.1 | AGGAUGCCAAGAACACUAUGU | 695 | 4226-4246 | ACAUAGUGUUCUUGGCAUCCUGA | 784 | 4224-4246 |
| AD-572235.1 | CAGAUACAUCUCCAAGUAUGU | 696 | 4371-4391 | ACAUACUUGGAGAUGUAUCUGUC | 785 | 4369-4391 |
| AD-572258.1 | UGGACAAAGCCUUCUCCGAUU | 697 | 4394-4414 | AAUCGGAGAAGGCUUUGUCCAGC | 786 | 4392-4414 |
| AD-572278.1 | AGGAACACCCUCAUCAUCUAU | 698 | 4414-4434 | AUAGAUGAUGAGGGUGUUCCUAU | 787 | 4412-4434 |
| AD-572279.1 | GGAACACCCUCAUCAUCUACU | 699 | 4415-4435 | AGUAGAUGAUGAGGGUGUUCCUA | 788 | 4413-4435 |
| AD-572281.1 | AACACCCUCAUCAUCUACCUU | 700 | 4417-4437 | AAGGUAGAUGAUGAGGGUGUUCC | 789 | 4415-4437 |
| AD-572355.1 | CUUUAAUGUAGAGCUUAUCCU | 701 | 4491-4511 | AGGAUAAGCUCUACAUUAAAGUA | 790 | 4489-4511 |
| AD-572356.1 | UUUAAUGUAGAGCUUAUCCAU | 702 | 4492-4512 | AUGGAUAAGCUCUACAUUAAAGU | 791 | 4490-4512 |
| AD-572387.1 | UCAAGGUCUACGCCUAUUACU | 703 | 4523-4543 | AGUAAUAGGCGUAGACCUUGACU | 792 | 4521-4543 |
| AD-572388.1 | CAAGGUCUACGCCUAUUACAU | 704 | 4524-4544 | AUGUAAUAGGCGUAGACCUUGAC | 793 | 4522-4544 |
| AD-572389.1 | AAGGUCUACGCCUAUUACAAU | 705 | 4525-4545 | AUUGUAAUAGGCGUAGACCUUGA | 794 | 4523-4545 |

TABLE 6-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-572390.1 | AGGUCUACGCCUAUUACACU | 706 | 4526-4546 | AGUUGUAAUAGGCGUAGACCUUG | 795 | 4524-4546 |
| AD-572393.1 | UCUACGCCUAUUACAACCUGU | 707 | 4529-4549 | ACAGGUUGUAAUAGGCGUAGACC | 796 | 4527-4549 |
| AD-572613.1 | AGCUGUCCAAUGACUUUGACU | 708 | 4751-4771 | AGUCAAAGUCAUUGGACAGCUGA | 797 | 4749-4771 |
| AD-572614.1 | GCUGUCCAAUGACUUUGACGU | 709 | 4752-4772 | ACGUCAAAGUCAUUGGACAGCUG | 798 | 4750-4772 |
| AD-572858.1 | AGCAUGGUUGUCUUUGGGUGU | 710 | 5056-5076 | ACACCCAAAGACAACCAUGCUCU | 799 | 5054-5076 |
| AD-890084.1 | AAUAAGAAGAACAAACUGACA | 711 | 1909-1928 | UGUCAGUUUGUUCUUCUUAUUCA | 800 | 1907-1928 |
| AD-890085.1 | AAUAAGAAGAACAAGCUGACA | 712 | 1909-1928 | UGUCAGCUUGUUCUUCUUAUUCA | 801 | 1907-1928 |
| AD-572281 | AACACCCUCAUCAUCUACCUU | 713 | 4417-4436 | AAGGUAGAUGAUGAGGGUGUUCC | 802 | 4415-4436 |

TABLE 7

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-568976.1 | asgsacagAfcAfAfGfaccaucuacuL96 | 803 | asGfsuagAfuGfGfucuuGfucUfugucusgsg | 892 | CCAGACAGACAAGACCAUCUACA | 981 |
| AD-568978.1 | ascsagacAfaGfAfCfcaucuacaccL96 | 804 | asGfsuguAfgAfUfgguCfuUfgUfucugsusgsu | 893 | AGACAGACAAGACCAUCUACACC | 982 |

TABLE 7-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-569127.1 | usgsggacAfuUfCfCfggaacucguuL96 | 805 | asAfscgaGfuUfCfcggaAfuGfucccasasg | 894 | CUUGGGACAUUCCGGAACUCGUC | 983 |
| AD-569133.1 | asusuccgGfaAfCfCfUfcgucaacauuL96 | 806 | asAfsuguUfgAguCfgagUfcCfggaausgsu | 895 | ACAUUCCGGAACUCGUCACAUG | 984 |
| AD-569164.1 | asgsauccGfaGfCfCfuacuaugaauL96 | 807 | asUfsucaUfaGuAfaggCfUfcGfgaucususc | 896 | GAAGAUCCGAGCUACUAUGAAA | 985 |
| AD-569195.1 | gscsagguCfuUfCfCfUfcacugaguuL96 | 808 | asAfscucAfgUgGfagaAfgAfaccugcusg | 897 | CAGCAGGUCUUCUCCACUGAGUU | 986 |
| AD-569237.1 | gscsccagUfuUfCfCfGfaggucauaguL96 | 809 | asCfsuauGfaCcUfucgAfaAfacugggcsasg | 898 | CUGCCCAGUUUCGAGGUCAUAGU | 987 |
| AD-569239.1 | cscsaguuUfcGfAfGfgucauagusguL96 | 810 | asCfsacuAfuGgAfccuCfGfaAfacuggsgsc | 899 | GCCCAGUUUCGAGGUCAUAGUGG | 988 |
| AD-569272.1 | asasuuccuAfcUfAfCfuaucuaauacuL96 | 811 | asGfsuauAfaGfAfuguAfgUfaAfgaauusuc | 900 | GAAAUUCUACUACAUCUAACG | 989 |
| AD-569350.1 | ascsugccUfuUfCfGfUfaucuucggguL96 | 812 | asCfscgaAfgAfCfUfgacAfaAfgcagusc | 901 | GAACUGCCUUUGUCAUCUCGGG | 990 |
| AD-569571.1 | csusscaugGfuGfUfUfUfcgugacgaauL96 | 813 | asUfsucgUfcAcGfaaaCfAfcCfaugagsgsu | 902 | ACCUCAUGGUGUUCGUGA CGAAC | 991 |
| AD-569763.1 | usgsgggcaAfcUfUfCfCfaacaauuacuL96 | 814 | asGfsuaaUfuGfUfuggAfgUfuGfcccascsg | 903 | CGUGGGCAACUCCAACAAUUACC | 992 |
| AD-569764.1 | gsgscaaCfuUfCfCfAfaacaauuaccuL96 | 815 | asGfsguaAfuUfGfuugGfaAfgUfugcccsasc | 904 | GUGGGCAACUCCAACAAUUACCU | 993 |
| AD-569766.1 | gscsaaaCfuCfCfAfAfcaauuaccugsu | 816 | asCfsaggUfaAfuUfacCffUfugugguugcscsc | 905 | GGGCAACUCCAACAAUUACCUGC | 994 |
| AD-569816.1 | gsuscaacUfuCfCfUfUfcugcgaauuL96 | 817 | asAfsuucGfcAguCfgagGfAfaGfuugacsgsu | 906 | ACGUCAACUUCCUCUGCGAAUG | 995 |
| AD-570156.1 | asasucugaCfgCfCfAfFfGfaguaaagaucuL96 | 818 | asGfsaucUfuAcUfcucGfCfgUfcaguusg | 907 | CAAACUGACGCAGAGUAAGAUCU | 996 |
| AD-570466.1 | usgscagaAfgAfFfGfAfAfcaucguuuL96 | 819 | asAfsaacGfaUgGfuucUfCfuUfcugcasasu | 908 | AUUGCAGAAGAGAACAUCGUUUC | 997 |
| AD-570470.1 | gsasagagAfCfFfAfAfCfgUfuCfcccgau | 820 | asCfsgggAfaAcGfUfuCfuUfcuucusg | 909 | CAGAAGAGAACAUCGUUUCCCGA | 998 |
| AD-570471.1 | asasgaaAfcAfUfCfFfGfuuucccgauL96 | 821 | asUfsgggGfaAacGfUfuCfgaucucuuscsu | 910 | AGAAGAACAUCGUUUCCGAA | 999 |
| AD-570474.1 | asgsgaaCfaUfCfGfUfFfucccgaaguL96 | 822 | asAfsccuUfCfgGfaaacCfCfaUfguucususc | 911 | AGAGAACAUCGUUUCCCGAAGUG | 1000 |
| AD-570475.1 | gsasacauCfgUfUfUfCfccgaaguguL96 | 823 | asCfscCfaCfuUfCfgGfaaaCfgAfguuscsu | 912 | GAGAACAUCGUUUCCCGAAGUGA | 1001 |
| AD-570476.1 | asasacaUfcGfUfUfUfcccgaaguauL96 | 824 | asUfscgAfaCfuUfCfcggaaGfGfaAfcgfscsu | 913 | AGAACAUCGUUUCCCGAAGUGAG | 1002 |

TABLE 7-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-570620.1 | csgsgacaAfgAfAfAfgggaucuguccgsguuL96 | 825 | asAfscagAfuCfCfcuuuCfuUfguccgsasc | 914 | GUCGGACAAGAAAGGGAUCUGUG | 1003 |
| AD-570621.1 | gsgsacaaGfaAfAfGfggaucuguguuL96 | 826 | asCfsacaGfaUfCfccuuUfcUfuguccsgsa | 915 | UCGGACAAGAAAGGGAUCUGUGU | 1004 |
| AD-570622.1 | gsascaagAfaAfAfGfGfgaucugu guuL96 | 827 | asAfscacAfgAfUfcccuUfuCfuuugucscsg | 916 | CGGACAAGAAAGGGAUCUGUGUG | 1005 |
| AD-570623.1 | ascsaagaAfaAfGfGfGfaucugug uuguL96 | 828 | asCfsacaCfaGfAfuccuUfuCfuugucsscsc | 917 | GGACAAGAAAGGGAUCUGUGG | 1006 |
| AD-570624.1 | csasagaaAfaGfGfGfAfucugugu gguL96 | 829 | asCfscacAfcAfGfauccCfuUfucuugscsc | 918 | GACAAGAAAGGGAUCUGUGGGC | 1007 |
| AD-570625.1 | asasgaaaGfaGfGfAfUfcugugug cuL96 | 830 | asGfscacCfaCfAfgauUfcCfcuuuucuusgsu | 919 | ACAAGAAAGGGAUCUGUGUGGCA | 1008 |
| AD-570627.1 | gsasaaggFfaUfCfUfUfgugggc aguL96 | 831 | asCfsugcCfaCfAfcagAfuCfcuusu | 920 | AAGAAAGGGAUCUGUGUGGCAGA | 1009 |
| AD-570631.1 | csususcgaGfgUfCfAfcaguaauL96 | 832 | asGfscauUfaCfUfgugAfcCfucgasagsg | 921 | CCCUUCGAGGUCACAGUAAUGCA | 1010 |
| AD-570632.1 | usususcgagGfuCfAfCfaguaaug cauL96 | 833 | asUfsgcaUfuAfCfuguGfaAfccucgasasg | 922 | CCUUCGAGGUCACAGUAAUGCAG | 1011 |
| AD-570672.1 | gsgscuacCfcUfAfCfuguuguuuL96 | 834 | asAfscaaCfaAfcAfguAfgGfguasgccsc | 923 | GCGGCUACCCUACUCUGUGUUC | 1012 |
| AD-570674.1 | ccUfaCfUfCfUfguuguucgu uL96 | 835 | asCfsgaaCfaAfcAfgagUfaGfgguasgscsc | 924 | GGCUACCCUACUCUGUUGUUCGA | 1013 |
| AD-570675.1 | usasccUfaCfUfCfUfguuguucgauL96 | 836 | asUfscgaAfcAfAfcagUfaGfgguasgsc | 925 | GCUACCCUACUCUGUUGUUCGAA | 1014 |
| AD-570676.1 | ascsccuaCfuCfUfguuguucgaauL96 | 837 | asUfsucgAfaCfAfacaGfaGfugguasgg | 926 | CUACCCUACUCUGUUGUUCGAAA | 1015 |
| AD-570677.1 | cscscuacUfcUfUfguucgaauL96 | 838 | asUfsucgAfaCfaCfaacAfgAfgugsuasgsu | 927 | UACCCUACUCUGUUGUUCGAAAC | 1016 |
| AD-570678.1 | cscscuaucCfuGfUfUfguucgaaaacuL96 | 839 | asGfscauUfaCfaAfcagUfaGfggsgsu | 928 | ACCCUACUCUGUUGUUCGAAACG | 1017 |
| AD-570679.1 | csususacucUfgUfUfGfucgaaacguL96 | 840 | asCfsgucGfaAfcaAfcAfgagUfaAfggsu | 929 | CCCUACUCUGUUGUUCGAAACGA | 1018 |
| AD-570680.1 | usasccucCfgUfUfUfcgaaacgauL96 | 841 | asUfscgaAfcAfAfcagUfgGfaacAfagsgsu | 930 | CCUACUCUGUUGUUCGAAACGAG | 1019 |
| AD-570681.1 | ascscucUfgUfUfUfgaacgagagsu | 842 | asCfsugaCfgUfUfcgaCfaAfcAfagasgsu | 931 | CUACUCUGUUGUUCGAAACGAGC | 1020 |
| AD-570682.1 | csususcuguUfcFgUfaaacgaagcuL96 | 843 | asGfscauCfuCfgaAfacAfguAfcagasgsu | 932 | UACUCUGUUGUUCGAAACGAGCA | 1021 |
| AD-570717.1 | cscscguUfcUfUfUfaauuaccgguL96 | 844 | asCfscgaAfcAfuAfucgcCfgCfsuCfasasgscsu | 933 | AGCCGUUCUCUACAAUUACCGGC | 1022 |

TABLE 7-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-570963.1 | asasca aaAfcU fGfUfg gcuguu cguL96 | 845 | asCfsg aaCfaG fCfcac aGfuUf uuguus csa | 934 | UGAACA AAACUG UGGCUG UUCGC | 1023 |
| AD-571157.1 | gsgsuc auCfgC fUfGfu gcauua ccuL96 | 846 | asGfsg uaAfuG fCfaca gCfgAf ugaccs gsu | 935 | ACGGUC AUCGCU GUGCAU UACCU | 1024 |
| AD-571158.1 | gsusca ucGfcU fGfUfg cauuac cuuL96 | 847 | asAfsg guAfaU fGfcac aGfcGf augacs csg | 936 | CGGUCA UCGCUG UGCAUU ACCUG | 1025 |
| AD-571168.1 | usgsca uuAfcC fUfGfg augaaa cguL96 | 848 | asCfsg uuUfcA fUfcca gGfuAf augcas csa | 937 | UGUGCA UUACCU GGAUGA AACGG | 1026 |
| AD-571298.1 | csgsug guCfaA fGfGfu cuucuc ucuL96 | 849 | asGfsa gaGfaA fGfacc uUfgAf ccacgs usa | 938 | UACGUG GUCAAG GUCUUC UCUCU | 1027 |
| AD-571447.1 | csgsgc cuUfuG fUfUfc ucaucu cguL96 | 850 | asCfsg agAfuG fAfgaa cAfaAf ggccgs usg | 939 | CACGGC CUUUGU UCUCAU CUCGC | 1028 |
| AD-571448.1 | gsgscc uuUfgU fUfCfu caucuc gcuL96 | 851 | asGfsc gaGfaU fGfaga aCfaAf aggccs gsu | 940 | ACGGCC UUUGUU CUCAUC UCGCU | 1029 |
| AD-571449.1 | gscscu uuGfuU fCfUfc aucucg cuuL96 | 852 | asAfsg cgAfgA fUfgag aAfcAf aaggcs csg | 941 | CGGCCU UUGUUC UCAUCU CGCUG | 1030 |
| AD-571539.1 | ususcc uuGfaA fGfCfc aacuac auuL96 | 853 | asAfsu guAfgU fUfggc uUfcAf aggaas gsu | 942 | ACUUCC UUGAAG CCAACU ACAUG | 1031 |
| AD-571719.1 | usgsca gcUfaA fAfAfg acuuug acuL96 | 854 | asGfsu caAfaG fUfcuu uUfaGf cugcas gsu | 943 | ACUGCA GCUAAA AGACUU UGACU | 1032 |
| AD-571752.1 | uscsgu gcGfuU fGfGfc ucaaug aauL96 | 855 | asUfsu caUfuG fAfgcc aAfcGf cacgas csg | 944 | CGUCGU GCGUUG GCUCAA UGAAC | 1033 |
| AD-571753.1 | csgsug cgUfuG fGfCfu caauga acuL96 | 856 | asGfsu ucAfuU fGfagc cAfacf gcacgs asc | 945 | GUCGUG CGUUGG CUCAAU GAACA | 1034 |
| AD-571765.1 | csasau gaAfcA fGfAfg auacua cguL96 | 857 | asCfsg uaGfuA fUfcuc uGfuUf cauugs asg | 946 | CUCAAU GAACAG AGAUAC UACGG | 1035 |
| AD-571766.1 | asasug aaCfaG fAfGfa uacuac gguL96 | 858 | asCfsc guAfgU fAfucu cUfgUf ucauus gsa | 947 | UCAAUG AACAGA GAUACU ACGGU | 1036 |
| AD-571767.1 | asusga acAfgA fGfAfu acuacg guuL96 | 859 | asAfsc cgUfaG fUfauc uCfuGf uucaus usg | 948 | CAAUGA ACAGAG AUACUA CGGUG | 1037 |
| AD-571825.1 | cscsaa gcCfuU fGfGfc ucaaua ccuL96 | 860 | asGfsg uaUfuG fAfgcc aAfgGf cuuggs asa | 949 | UUCCAA GCCUUG GCUCAA UACCA | 1038 |
| AD-571826.1 | csasag ccUfuG fGfCfu caauac cauL96 | 861 | asUfsg guAfuU fGfagc cAfaGf gcuugs gsa | 950 | UCCAAG CCUUGG CUCAAU ACCAA | 1039 |
| AD-571900.1 | cscsac cgUfaU fCfCfa cuggga auuL96 | 862 | asAfsu ucCfcA fGfugg aUfaCf gguggs gsu | 951 | ACCCAC CGUAUC CACUGG GAAUC | 1040 |
| AD-571945.1 | ascsca agGfaA fAfAfu gagggu uuuL96 | 863 | asAfsa acCfcU fCfauu uUfcCf uuggus csu | 952 | AGACCA AGGAAA AUGAGG GUUUC | 1041 |
| AD-571948.1 | asasgg aaAfaU fGfAfg gguuuc acuL96 | 864 | asGfsu gaAfaC fCfcuc aUfuUf uccuus gsg | 953 | CCAAGG AAAAUG AGGGUU UCACA | 1042 |

TABLE 7-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-572039.1 | asascucaCfcUfGfUfaauaaaucuL96 | 865 | asGfsaauUfuAfUfuacaGfgUfgaguusgsa | 954 | UCAACUCACCUGUAAUAAAUUCG | 1043 |
| AD-572040.1 | ascsucacCfuGfUfAfauaaauucguL96 | 866 | asCfsgaaUfuUfAfuuacAfgGfugagususg | 955 | CAACUCACCUGUAAUAAAUUCGA | 1044 |
| AD-572041.1 | csuscaccCfgUfAfAfuaaauucgauL96 | 867 | asUfscgaAfuUfUfauuaCfaGfgugagsusu | 956 | AACUCACCUGUAAUAAAUUCGAC | 1045 |
| AD-572044.1 | ascscuguAfaUfAfAfauuucgaccuuL96 | 868 | asAfsgguCfgAfAfuuuaUfuAfcaggusgsa | 957 | UCACCUGUAAUAAAUUCGACCUC | 1046 |
| AD-572049.1 | usasauaaAfuUfCfGfaccucaagguL96 | 869 | asCfscuuGfaGfGfucgaAfuUfuauuascsa | 958 | UGUAAUAAAUUCGACCUCAAGGU | 1047 |
| AD-572060.1 | ascscucaAfgGfUfCffaccauaaaauL96 | 870 | asUfsuuAfuGfGfugaccCfuUfgaggguscsg | 959 | CGACCUCAAGGUCACCAUAAAAC | 1048 |
| AD-572061.1 | cscsucaaGfgUfCfAfccauaaaacuL96 | 871 | asGfsuuUfaUfGfgugaCfcUfugaggsusc | 960 | GACCUCAAGGUCACCAUAAAACC | 1049 |
| AD-572062.1 | csuscaagGfuCfAfCfcauaaaaccuL96 | 872 | asGfsguuUfuAfUfgguAfcCfuugagsgsu | 961 | ACCUCAAGGUCACCAUAAAACCA | 1050 |
| AD-572108.1 | asgsgauugCfcAfUfuCfuGfgGfaacacuaguL96 | 873 | asCfsaaUfaGfuUfucuGfcCfauccusgsa | 962 | UCAGGAUGCCAUGGAACACUAUGA | 1051 |
| AD-572235.1 | csasgauaCfaUfCfUfUfccaaguauguL96 | 874 | asCfsaaUfaCfuUfgGfaGffaUfgUfaucugsusc | 963 | GACAGAUACAUCUCCAAGUAUGA | 1052 |
| AD-572258.1 | usgsgacaAfaGfCfCfuucuccgauuL96 | 875 | asAfsucgGfaGffAfaggcUfuUfguccasgsc | 964 | GCUGGACAAAGCCUUCUCCGAUA | 1053 |
| AD-572278.1 | asgsgacAfcAfcCfCfUfcaucaucauuL96 | 876 | asUfsagaUfgAfUfgagGfgUfguuccsasu | 965 | AUAGGACACCCUCAUCUCUAC | 1054 |
| AD-572279.1 | gsgsaacaCfcCfUfCfaucuacuL96 | 877 | asGfsuagAfuGfAfugaGfgGfguuccsusa | 966 | UAGGAACACCCUCAUCAUCUACC | 1055 |
| AD-572281.1 | asasascaccCfuCfAfUfcuacaucuauccuuL96 | 878 | asAfsgguAfgAfuGfugauGfAfgGfguussscsc | 967 | GGAACACCCUCAUCUACCUG | 1056 |
| AD-572355.1 | csusuuaaUfgUfAfAfGfGfagcuuauccuL96 | 879 | asGfsauAfaGfCfucuAfaCfuuaasgsa | 968 | UACUUUAAUGUAGAGCUUAUCCA | 1057 |
| AD-572356.1 | ususuuaAfuGfUfAfAfgaGfGfcucuauccauL96 | 880 | asUfsugAfgAfaUfgAfgAfgCfuUfuaaasgsu | 969 | ACUUUAAUGUAGAGCUUAUCCAG | 1058 |
| AD-572387.1 | usscsaaggUfcUfCfAfCfCfgccuauuacuL96 | 881 | asGfsusUfuAfGfcgtAfcUfcuugasscsu | 970 | AGUCAAGGUCUACGCCUAUUACA | 1059 |
| AD-572388.1 | csasagguCfuAfCfGfCfcuauucauL96 | 882 | asUfsuaAfuAfGfggcguAfgAfccuugassc | 971 | GUCAAGGUCUACGCCUAUUACAA | 1060 |
| AD-572389.1 | asasgguCfuAfCfGfcUfauuacauL96 | 883 | asUfsguAfaUfAfggcgUfaGfaccuusgsa | 972 | UCAAGGUCUACGCCUAUUACAAC | 1061 |
| AD-572390.1 | asgsguCfuAfCfGfCfuauuacacuL96 | 884 | asUfsugUfaAfuAfggcGfuAfgaccusg | 973 | CAAGGUCUACGCCUAUUACAACC | 1062 |

TABLE 7-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-572393.1 | uscsua cgCfcU fAfUfu acaacc uguL96 | 885 | asCfsa ggUfuG fUfaau aGfgCf guagas csc | 974 | GGUCUA CGCCUA UUACAA CCUGG | 1063 |
| AD-572613.1 | asgscu guCfcA fAfUfg acuuug acuL96 | 886 | asGfsu caAfaG fUfcau uGfgAf cagcus gsa | 975 | UCAGCU GUCCAA UGACUU UGACG | 1064 |
| AD-572614.1 | gscsug ucCfaA fUfGfa cuuuga cguL96 | 887 | asCfsg ucAfaA fGfuca uUfgGf acagcs usg | 976 | CAGCUG UCCAAU GACUUU GACGA | 1065 |
| AD-572858.1 | asgsca ugGfuU fGfUfc uuuggg uguL96 | 888 | asCfsa ccCfaA fAfgac aAfcCf augcus csu | 977 | AGAGCA UGGUUG UCUUUG GGUGC | 1066 |
| AD-890084.1 | asasua agAfaG fAfAfc aaacug acaL96 | 889 | usGfsu caGfuu uguucU fuCfuu auuscs a | 978 | AAUAAG AAGAAC AAACUG ACA | 1067 |
| AD-890085.1 | asasua agAfaG fAfAfc aagcug acaL96 | 890 | usGfsu caGfcu uguucU fuCfuu auuscs a | 979 | AAUAAG AAGAAC AAGCUG ACA | 1068 |
| AD-572281.1 | asasca ccCfuC fAfUfc aucuac cuuL96 | 891 | asAfsg guAfgA fUfgau gAfgGf guguus csc | 980 | AACACC CUCAUC AUCUAC CUU | 1069 |

TABLE 8

C3 Single Dose Screens in Hep3B cells

| | 10 nM Dose | | 1.0 nM Dose | | 0.1 nM Dose | |
|---|---|---|---|---|---|---|
| Duplex | Avg % C3 mRNA Remaining | SD | Avg % C3 mRNA Remaining | SD | Avg % C3 mRNA Remaining | SD |
| AD-565279.1 | 17.6 | 6.0 | 54.0 | 11.4 | 99.8 | 17.7 |
| AD-565541.1 | 7.7 | 2.3 | 23.4 | 2.0 | 72.7 | 10.0 |
| AD-566234.1 | 32.9 | 4.8 | 66.9 | 7.3 | 98.1 | 21.5 |
| AD-566383.1 | 36.8 | 7.3 | 66.7 | 2.6 | 105.4 | 21.7 |
| AD-566412.1 | 15.9 | 5.1 | 43.0 | 2.8 | 94.9 | 27.3 |
| AD-566444.1 | 12.6 | 0.9 | 50.3 | 5.1 | 88.9 | 13.5 |
| AD-566448.1 | 25.4 | 9.3 | 43.0 | 6.7 | 107.7 | 18.3 |
| AD-567066.1 | 10.0 | 2.4 | 44.9 | 3.5 | 91.0 | 28.2 |
| AD-567307.1 | 21.5 | 2.9 | 48.6 | 8.7 | 94.2 | 10.7 |
| AD-567487.1 | 21.0 | 6.6 | 49.0 | 5.6 | 67.6 | 23.5 |
| AD-567700.1 | 12.9 | 1.8 | 39.5 | 4.4 | 95.0 | 18.1 |
| AD-567716.1 | 27.5 | 6.9 | 59.0 | 8.0 | 110.5 | 30.4 |
| AD-568003.1 | 18.5 | 3.7 | 73.3 | 4.6 | 113.3 | 13.5 |
| AD-568026.1 | 11.8 | 1.4 | 32.5 | 7.5 | 51.7 | 10.5 |
| AD-568157.1 | 22.5 | 6.4 | 40.0 | 5.7 | 80.6 | 15.0 |
| AD-568586.1 | 9.9 | 1.2 | 28.0 | 5.1 | 91.5 | 9.8 |
| AD-566445.1 | 22.4 | 8.4 | 60.0 | 1.8 | 108.5 | 15.0 |
| AD-567812.1 | 35.2 | 8.2 | 60.2 | 8.6 | 100.7 | 16.7 |
| AD-564901.1 | 57.2 | 9.3 | 95.2 | 7.4 | 100.3 | 29.6 |
| AD-566446.1 | 55.5 | 3.2 | 96.6 | 8.4 | 114.1 | 8.2 |
| AD-566409.1 | 80.5 | 30.3 | 63.1 | 36.1 | 95.5 | 12.2 |
| AD-567067.1 | 21.5 | 15.5 | 44.3 | 5.7 | 101.3 | 12.9 |
| AD-568160.1 | 18.5 | 1.5 | 49.1 | 9.3 | 72.5 | 16.8 |
| AD-565282.1 | 27.3 | 1.6 | 51.0 | 7.1 | 102.9 | 20.4 |
| AD-568344.1 | 33.7 | 6.9 | 85.5 | 4.1 | 121.9 | 23.9 |
| AD-567304.1 | 9.9 | 2.3 | 22.2 | 3.8 | 64.8 | 6.1 |
| AD-568153.1 | 24.3 | 3.5 | 53.8 | 7.0 | 100.9 | 12.3 |
| AD-564742.1 | 8.7 | 1.4 | 20.6 | 7.9 | 63.6 | 21.3 |
| AD-565284.1 | 13.6 | 3.5 | 45.4 | 6.4 | 102.5 | 16.7 |
| AD-566485.1 | 96.5 | 15.4 | 112.4 | 7.6 | 110.9 | 13.7 |
| AD-567808.1 | 65.1 | 14.3 | 94.5 | 6.0 | 118.2 | 14.7 |
| AD-566449.1 | 89.3 | 5.8 | 117.1 | 7.1 | 114.3 | 17.4 |
| AD-568382.1 | 50.5 | 10.8 | 98.3 | 2.5 | 125.4 | 13.6 |
| AD-566442.1 | 36.4 | 5.2 | 94.3 | 9.5 | 116.4 | 16.5 |
| AD-567809.1 | 81.5 | 23.1 | 93.8 | 8.1 | 121.5 | 19.1 |
| AD-565534.1 | 106.1 | 24.3 | 109.6 | 7.0 | 113.5 | 8.7 |
| AD-567215.1 | 55.0 | 6.0 | 95.8 | 3.1 | 94.2 | 13.4 |
| AD-566443.1 | 79.9 | 7.3 | 117.1 | 7.8 | 126.2 | 9.8 |
| AD-568156.1 | 54.1 | 6.9 | 76.5 | 5.9 | 72.0 | 8.4 |
| AD-565532.1 | 65.0 | 13.4 | 101.8 | 3.6 | 105.2 | 22.1 |
| AD-566447.1 | 50.4 | 5.4 | 98.9 | 5.4 | 125.3 | 9.0 |
| AD-565040.1 | 99.7 | 12.0 | 111.2 | 7.0 | 124.6 | 11.5 |
| AD-568161.1 | 59.7 | 8.4 | 86.9 | 12.5 | 82.7 | 8.9 |
| AD-567829.1 | 57.9 | 10.9 | 96.9 | 12.3 | 102.6 | 22.1 |
| AD-564975.1 | 106.6 | 9.3 | 102.3 | 25.2 | 126.7 | 10.1 |
| AD-567713.1 | 10.8 | 3.5 | 23.4 | 1.6 | 70.1 | 21.0 |
| AD-566411.1 | 32.5 | 3.8 | 65.2 | 8.7 | 112.7 | 41.1 |
| AD-565005.1 | 42.2 | 5.8 | 84.7 | 12.3 | 99.7 | 15.5 |
| AD-567156.1 | 44.6 | 21.2 | 75.5 | 20.7 | 94.1 | 21.1 |
| AD-566388.1 | 66.6 | 8.2 | 105.7 | 6.4 | 99.6 | 10.6 |
| AD-566384.1 | 32.2 | 5.9 | 75.8 | 7.0 | 115.8 | 19.0 |
| AD-564744.1 | 65.3 | 14.4 | 96.4 | 5.8 | 122.2 | 34.5 |
| AD-567828.1 | 99.9 | 6.9 | 108.7 | 7.4 | 113.4 | 14.1 |
| AD-567063.1 | 33.0 | 11.0 | 67.4 | 6.6 | 92.1 | 20.3 |
| AD-568158.1 | 74.1 | 8.0 | 85.4 | 9.6 | 87.1 | 10.8 |
| AD-567521.1 | 12.7 | 5.8 | 24.5 | 5.6 | 70.6 | 9.1 |
| AD-567395.1 | 78.7 | 14.6 | 101.5 | 8.5 | 106.0 | 18.7 |
| AD-567582.1 | 65.5 | 9.4 | 82.3 | 4.5 | 112.3 | 17.2 |
| AD-564745.1 | 20.0 | 5.7 | 61.2 | 7.6 | 105.8 | 21.7 |
| AD-567831.1 | 68.7 | 11.4 | 100.1 | 7.2 | 123.3 | 16.4 |
| AD-565535.1 | 60.1 | 9.4 | 86.7 | 11.8 | 103.8 | 20.5 |
| AD-564730.1 | 14.3 | 6.9 | 41.4 | 3.4 | 95.1 | 6.2 |
| AD-567318.1 | 25.4 | 2.1 | 69.7 | 6.3 | 107.0 | 17.4 |
| AD-567314.1 | 101.9 | 4.2 | 115.5 | 8.4 | 103.6 | 22.1 |
| AD-568341.1 | 67.0 | 18.2 | 92.7 | 11.0 | 104.7 | 20.5 |
| AD-568099.1 | 14.5 | 3.6 | 60.6 | 7.4 | 113.5 | 13.5 |
| AD-566837.1 | 7.1 | 1.5 | 31.7 | 4.8 | 88.3 | 22.0 |
| AD-565616.1 | 95.7 | 9.4 | 95.0 | 20.1 | 122.7 | 14.1 |
| AD-568345.1 | 40.4 | 5.4 | 83.9 | 8.7 | 114.5 | 14.7 |
| AD-565925.1 | 27.8 | 6.2 | 70.1 | 3.5 | 103.8 | 13.3 |
| AD-564727.1 | 25.2 | 5.1 | 78.1 | 9.4 | 103.6 | 19.1 |
| AD-565281.1 | 24.9 | 3.8 | 54.3 | 13.4 | 88.2 | 15.4 |
| AD-565278.1 | 20.5 | 2.6 | 66.5 | 15.7 | 106.0 | 27.8 |
| AD-564976.1 | 80.3 | 4.1 | 96.9 | 8.9 | 90.8 | 13.7 |
| AD-568343.1 | 20.4 | 5.5 | 35.1 | 20.5 | 79.8 | 7.7 |
| AD-568100.1 | 11.5 | 2.6 | 35.5 | 4.5 | 81.4 | 12.5 |
| AD-566935.1 | 42.0 | 8.9 | 80.6 | 7.9 | 116.6 | 12.1 |
| AD-567315.1 | 7.5 | 0.9 | 11.0 | 1.7 | 43.7 | 12.0 |
| AD-566386.1 | 25.0 | 2.8 | 62.7 | 13.1 | 94.7 | 18.4 |
| AD-567813.1 | 27.6 | 2.6 | 61.8 | 5.8 | 118.2 | 20.3 |
| AD-564739.1 | 46.7 | 11.9 | 66.3 | 3.8 | 117.7 | 28.3 |
| AD-564731.1 | 56.7 | 15.0 | 95.2 | 3.8 | 117.1 | 21.3 |

TABLE 8-continued

C3 Single Dose Screens in Hep3B cells

| Duplex | 10 nM Dose | | 1.0 nM Dose | | 0.1 nM Dose | |
|---|---|---|---|---|---|---|
| | Avg % C3 mRNA Remaining | SD | Avg % C3 mRNA Remaining | SD | Avg % C3 mRNA Remaining | SD |
| AD-565904.1 | 7.8 | 4.4 | 23.6 | 4.3 | 64.5 | 16.1 |
| AD-566528.1 | 32.0 | 7.8 | 64.3 | 12.3 | 102.7 | 27.8 |
| AD-567699.1 | 86.1 | 8.4 | 104.8 | 6.3 | 116.5 | 16.2 |
| AD-565905.1 | 33.3 | 19.4 | 58.9 | 5.2 | 96.9 | 12.4 |
| AD-567814.1 | 11.3 | 2.0 | 30.8 | 5.1 | 95.8 | 20.8 |
| AD-568381.1 | 87.3 | 15.7 | 92.7 | 8.5 | 117.0 | 10.6 |

TABLE 9

C3 Single Dose Screens in PMH cells

| Duplex | 10 nM Dose | | 1.0 nM Dose | | 0.1 nM Dose | |
|---|---|---|---|---|---|---|
| | Avg % C3 mRNA Remaining | SD | Avg % C3 mRNA Remaining | SD | Avg % C3 mRNA Remaining | SD |
| AD-565279.1 | 31.0 | 8.3 | 57.8 | 10.4 | 123.1 | 8.8 |
| AD-565541.1 | 110.9 | 7.6 | 108.5 | 2.9 | 97.3 | 23.7 |
| AD-566234.1 | 94.2 | 8.9 | 77.0 | 35.4 | 105.4 | 9.0 |
| AD-566383.1 | 89.7 | 24.3 | 54.8 | 31.0 | 68.6 | 39.1 |
| AD-566412.1 | 30.0 | 4.1 | 38.3 | 14.5 | 88.1 | 17.0 |
| AD-566444.1 | 110.6 | 12.5 | 102.6 | 6.7 | 105.7 | 48.0 |
| AD-566448.1 | 127.1 | 8.0 | 84.0 | 14.7 | 120.8 | 9.1 |
| AD-567066.1 | 21.4 | 5.9 | 33.1 | 8.0 | 100.5 | 24.8 |
| AD-567307.1 | 110.7 | 9.0 | 111.3 | 5.7 | 84.8 | 43.9 |
| AD-567487.1 | 105.8 | 12.4 | 77.2 | 7.4 | 100.9 | 15.5 |
| AD-567700.1 | 22.6 | 4.5 | 44.4 | 3.7 | 68.7 | 25.3 |
| AD-567716.1 | 122.0 | 6.3 | 102.5 | 4.2 | 93.1 | 15.6 |
| AD-568003.1 | 110.4 | 22.4 | 104.7 | 4.6 | 115.9 | 20.6 |
| AD-568026.1 | 55.1 | 16.9 | 81.5 | 7.8 | 94.4 | 7.1 |
| AD-568157.1 | 60.9 | 8.8 | 83.2 | 9.9 | 102.2 | 36.7 |
| AD-568586.1 | 106.4 | 11.9 | 105.0 | 8.4 | 103.7 | 24.9 |
| AD-566445.1 | 110.3 | 4.8 | 90.3 | 9.2 | 104.2 | 12.0 |
| AD-567812.1 | 111.8 | 7.1 | 91.8 | 8.4 | 127.5 | 11.1 |
| AD-564901.1 | 120.0 | 8.1 | 109.3 | 8.0 | 104.2 | 20.7 |
| AD-566446.1 | 112.7 | 16.7 | 92.6 | 10.3 | 100.9 | 19.3 |
| AD-566409.1 | 109.1 | 18.7 | 52.0 | 17.7 | 90.7 | 21.6 |
| AD-567067.1 | 15.7 | 3.2 | 22.5 | 8.9 | 80.9 | 30.8 |
| AD-568160.1 | 87.2 | 8.0 | 97.5 | 7.6 | 92.3 | 19.4 |
| AD-565282.1 | 30.4 | 8.7 | 63.1 | 3.0 | 99.9 | 9.2 |
| AD-568344.1 | 36.7 | 4.9 | 77.8 | 13.7 | 104.8 | 8.8 |
| AD-567304.1 | 88.4 | 16.6 | 100.0 | 15.1 | 81.0 | 48.3 |
| AD-568153.1 | 87.3 | 3.7 | 100.4 | 8.2 | 97.9 | 34.6 |
| AD-564742.1 | 20.2 | 1.6 | 34.7 | 8.4 | 67.3 | 14.8 |
| AD-565284.1 | 25.1 | 4.2 | 48.7 | 3.9 | 103.5 | 29.2 |
| AD-566485.1 | 93.8 | 28.0 | 113.5 | 8.5 | 96.8 | 23.3 |
| AD-567808.1 | 112.5 | 18.1 | 86.2 | 6.1 | 98.7 | 10.8 |
| AD-566449.1 | 123.5 | 9.0 | 81.7 | 27.6 | 96.6 | 40.4 |
| AD-568382.1 | 111.9 | 17.7 | 107.5 | 9.6 | 107.5 | 13.9 |
| AD-566442.1 | 109.7 | 9.7 | 100.0 | 6.9 | 105.7 | 20.8 |
| AD-567809.1 | 97.6 | 13.6 | 54.0 | 29.7 | 117.1 | 5.6 |
| AD-565534.1 | 114.9 | 6.8 | 113.2 | 5.9 | 110.6 | 8.6 |
| AD-567215.1 | 105.5 | 19.2 | 85.6 | 12.3 | 111.1 | 3.6 |
| AD-566443.1 | 119.7 | 12.3 | 109.3 | 5.2 | 109.5 | 24.2 |
| AD-568156.1 | 72.9 | 9.7 | 91.2 | 4.7 | 97.7 | 9.5 |
| AD-565532.1 | 102.4 | 10.2 | 103.5 | 6.8 | 98.0 | 36.3 |
| AD-566447.1 | 114.2 | 4.4 | 102.7 | 4.5 | 88.7 | 37.2 |
| AD-565040.1 | 127.8 | 15.7 | 98.6 | 11.2 | 104.0 | 7.1 |
| AD-568161.1 | 88.2 | 10.4 | 93.5 | 9.8 | 98.4 | 9.7 |
| AD-567829.1 | 108.9 | 9.4 | 76.7 | 10.5 | 132.9 | 16.7 |
| AD-564975.1 | 118.7 | 12.2 | 97.5 | 7.0 | 110.0 | 23.1 |
| AD-567713.1 | 111.7 | 11.6 | 97.8 | 12.0 | 64.6 | 36.6 |
| AD-566411.1 | 76.4 | 10.7 | 63.1 | 18.3 | 98.9 | 20.4 |
| AD-565005.1 | 113.6 | 7.4 | 112.2 | 8.5 | 76.2 | 23.4 |
| AD-567156.1 | 78.3 | 16.8 | 63.4 | 6.6 | 73.5 | 22.2 |
| AD-566388.1 | 80.3 | 12.0 | 83.6 | 14.1 | 109.9 | 12.6 |
| AD-566384.1 | 76.2 | 10.0 | 79.3 | 12.7 | 120.1 | 15.7 |
| AD-564744.1 | 38.1 | 10.0 | 63.6 | 24.1 | 91.0 | 39.1 |

TABLE 9-continued

C3 Single Dose Screens in PMH cells

| Duplex | 10 nM Dose | | 1.0 nM Dose | | 0.1 nM Dose | |
|---|---|---|---|---|---|---|
| | Avg % C3 mRNA Remaining | SD | Avg % C3 mRNA Remaining | SD | Avg % C3 mRNA Remaining | SD |
| AD-567828.1 | 100.8 | 23.0 | 91.7 | 13.7 | 108.9 | 24.8 |
| AD-567063.1 | 27.0 | 7.4 | 33.6 | 14.4 | 97.3 | 18.1 |
| AD-568158.1 | 87.9 | 13.0 | 116.6 | 9.6 | 108.7 | 18.3 |
| AD-567521.1 | 74.5 | 12.0 | 93.9 | 5.5 | 95.0 | 32.1 |
| AD-567395.1 | 87.6 | 6.2 | 78.3 | 12.1 | 118.8 | 7.3 |
| AD-567582.1 | 85.3 | 11.3 | 83.0 | 7.8 | 105.4 | 20.4 |
| AD-564745.1 | 24.6 | 1.7 | 45.6 | 3.0 | 101.2 | 22.3 |
| AD-567831.1 | 112.4 | 7.6 | 106.1 | 12.3 | 93.4 | 32.9 |
| AD-565535.1 | 85.8 | 13.2 | 97.5 | 12.1 | 96.6 | 39.6 |
| AD-564730.1 | 21.1 | 3.0 | 29.7 | 14.9 | 98.8 | 9.6 |
| AD-567318.1 | 56.0 | 11.2 | 93.9 | 4.2 | 125.9 | 12.0 |
| AD-567314.1 | 119.1 | 12.5 | 105.2 | 7.7 | 99.9 | 34.0 |
| AD-568341.1 | 126.3 | 18.8 | 82.3 | 26.2 | 97.9 | 28.5 |
| AD-568099.1 | 133.5 | 18.4 | 102.6 | 1.3 | 110.5 | 7.7 |
| AD-566837.1 | 42.1 | 11.7 | 55.3 | 7.2 | 108.7 | 18.8 |
| AD-565616.1 | 38.7 | 7.6 | 59.5 | 5.7 | 99.1 | 13.6 |
| AD-568345.1 | 38.7 | 8.2 | 66.4 | 7.6 | 101.7 | 5.9 |
| AD-565925.1 | 117.3 | 12.9 | 106.3 | 3.0 | 92.6 | 41.3 |
| AD-564727.1 | 37.2 | 7.4 | 59.3 | 4.3 | 95.8 | 11.0 |
| AD-565281.1 | 18.8 | 3.6 | 25.2 | 13.0 | 47.7 | 30.8 |
| AD-565278.1 | 61.2 | 11.1 | 77.2 | 8.0 | 91.3 | 44.1 |
| AD-564976.1 | 76.0 | 25.2 | 29.2 | 6.5 | 71.5 | 27.3 |
| AD-568343.1 | 29.3 | 3.3 | 30.2 | 8.5 | 83.6 | 19.4 |
| AD-568100.1 | 109.2 | 23.2 | 86.6 | 14.7 | 117.8 | 12.8 |
| AD-566935.1 | 128.7 | 12.5 | 98.3 | 9.8 | 85.2 | 37.1 |
| AD-567315.1 | 47.0 | 3.5 | 78.1 | 11.0 | 110.6 | 9.0 |
| AD-566386.1 | 65.3 | 17.0 | 64.6 | 11.3 | 132.8 | 17.4 |
| AD-567813.1 | 111.8 | 19.7 | 99.0 | 9.8 | 79.9 | 24.2 |
| AD-564739.1 | 21.0 | 2.2 | 46.8 | 3.1 | 112.7 | 8.6 |
| AD-564731.1 | 71.0 | 11.9 | 67.2 | 26.6 | 83.0 | 41.0 |
| AD-565904.1 | 65.5 | 14.7 | 60.6 | 23.4 | 92.2 | 17.5 |
| AD-566528.1 | 97.2 | 16.5 | 114.1 | 10.6 | 103.9 | 19.7 |
| AD-567699.1 | 117.3 | 17.7 | 74.6 | 17.0 | 76.0 | 38.7 |
| AD-565905.1 | 89.0 | 13.7 | 74.0 | 15.0 | 92.0 | 11.1 |
| AD-567814.1 | 106.6 | 24.8 | 103.0 | 3.8 | 123.8 | 4.9 |
| AD-568381.1 | 112.1 | 5.9 | 104.6 | 7.4 | 84.8 | 25.0 |

TABLE 10

C3 Single Dose Screens in Hep3B cells

| Duplex | 10 nM Dose | | 1.0 nM Dose | | 0.1 nM Dose | |
|---|---|---|---|---|---|---|
| | Avg % C3 mRNA Remaining | SD | Avg % C3 mRNA Remaining | SD | Avg % C3 mRNA Remaining | SD |
| AD-569034.1 | 17.5 | 3.2 | 50.3 | 12.4 | 81.5 | 20.9 |
| AD-569164.1 | 9.7 | 1.6 | 22.3 | 2.7 | 43.9 | 7.0 |
| AD-569165.1 | 20.8 | 1.8 | 51.1 | 9.3 | 80.0 | 15.2 |
| AD-569272.1 | 14.2 | 0.3 | 44.0 | 9.9 | 78.5 | 9.2 |
| AD-569763.1 | 9.6 | 1.2 | 41.8 | 4.9 | 74.9 | 5.6 |
| AD-569765.1 | 13.4 | 2.2 | 41.7 | 9.5 | 83.1 | 29.8 |
| AD-570130.1 | 10.8 | 0.9 | 27.6 | 9.0 | 49.1 | 6.3 |
| AD-570132.1 | 18.0 | 3.3 | 57.7 | 2.8 | 59.3 | 5.8 |
| AD-570133.1 | 23.9 | 4.8 | 70.8 | 13.0 | 114.2 | 19.8 |
| AD-570134.1 | 9.3 | 4.3 | 18.1 | 4.6 | 31.1 | 5.5 |
| AD-570157.1 | 14.7 | 1.2 | 50.1 | 13.8 | 92.4 | 13.6 |
| AD-570711.1 | 11.3 | 1.1 | 33.5 | 5.1 | 70.8 | 9.0 |
| AD-570712.1 | 7.6 | 1.0 | 20.2 | 2.2 | 51.0 | 11.2 |
| AD-570713.1 | 8.5 | 2.5 | 13.5 | 2.4 | 37.6 | 11.3 |
| AD-570714.1 | 7.5 | 2.2 | 16.2 | 5.2 | 35.3 | 7.4 |
| AD-571539.1 | 4.6 | 0.1 | 18.5 | 2.9 | 28.4 | 4.7 |
| AD-571610.1 | 12.5 | 2.3 | 41.2 | 6.8 | 77.5 | 11.3 |
| AD-571633.1 | 20.2 | 2.5 | 65.1 | 12.8 | 73.6 | 5.0 |
| AD-571715.1 | 6.1 | 1.0 | 18.2 | 5.8 | 46.0 | 7.8 |
| AD-571752.1 | 8.7 | 1.8 | 20.2 | 3.3 | 51.7 | 12.8 |
| AD-571754.1 | 23.1 | 2.4 | 67.0 | 12.4 | 97.1 | 28.4 |
| AD-571828.1 | 28.9 | 2.9 | 61.6 | 11.2 | 84.0 | 8.4 |

TABLE 10-continued

C3 Single Dose Screens in Hep3B cells

| Duplex | 10 nM Dose Avg % C3 mRNA Remaining | SD | 1.0 nM Dose Avg % C3 mRNA Remaining | SD | 0.1 nM Dose Avg % C3 mRNA Remaining | SD |
|---|---|---|---|---|---|---|
| AD-572039.1 | 16.6 | 3.1 | 46.0 | 13.7 | 83.5 | 12.2 |
| AD-572040.1 | 10.3 | 2.6 | 28.4 | 4.8 | 67.1 | 21.6 |
| AD-572041.1 | 16.0 | 1.8 | 42.3 | 14.6 | 76.0 | 21.7 |
| AD-572059.1 | 12.9 | 2.8 | 36.9 | 7.1 | 77.2 | 14.1 |
| AD-572061.1 | 17.2 | 5.1 | 39.2 | 6.0 | 74.3 | 19.6 |
| AD-572062.1 | 11.6 | 2.2 | 31.0 | 1.7 | 63.4 | 10.0 |
| AD-572063.1 | 14.5 | 1.2 | 41.7 | 5.8 | 81.0 | 15.5 |
| AD-572110.1 | 10.4 | 1.1 | 25.5 | 6.6 | 63.3 | 18.8 |
| AD-572144.1 | 13.3 | 1.6 | 41.7 | 3.4 | 94.6 | 10.9 |
| AD-572388.1 | 12.8 | 2.1 | 33.3 | 4.1 | 63.8 | 19.8 |
| AD-572389.1 | 9.8 | 1.5 | 13.6 | 1.8 | 32.1 | 7.5 |
| AD-572390.1 | 14.2 | 1.6 | 38.7 | 6.8 | 74.2 | 7.7 |

TABLE 11

C3 Single Dose Screens in PMH cells

| Duplex | 10 nM Dose Avg % C3 mRNA Remaining | SD | 1.0 nM Dose Avg % C3 mRNA Remaining | SD | 0.1 nM Dose Avg % C3 mRNA Remaining | SD |
|---|---|---|---|---|---|---|
| AD-569034.1 | 87.3 | 9.8 | 94.4 | 8.2 | 83.5 | 8.5 |
| AD-569164.1 | 66.6 | 3.9 | 85.1 | 21.3 | 77.2 | 4.3 |
| AD-569165.1 | 86.3 | 12.7 | 106.1 | 12.8 | 101.9 | 9.8 |
| AD-569272.1 | 92.1 | 13.5 | 89.2 | 21.7 | 91.8 | 7.6 |
| AD-569763.1 | 42.3 | 10.4 | 93.0 | 16.4 | 100.8 | 13.7 |
| AD-569765.1 | 28.7 | 2.9 | 64.2 | 4.6 | 97.3 | 7.6 |
| AD-570130.1 | 23.8 | 3.5 | 68.5 | 14.7 | 81.8 | 11.3 |
| AD-570132.1 | 72.5 | 11.6 | 86.6 | 9.6 | 76.3 | 9.4 |
| AD-570133.1 | 76.6 | 15.4 | 86.6 | 22.3 | 80.1 | 10.7 |
| AD-570134.1 | 9.6 | 1.4 | 24.8 | 5.4 | 66.3 | 7.5 |
| AD-570157.1 | 92.0 | 12.3 | 108.1 | 7.4 | 95.7 | 5.4 |
| AD-570711.1 | 90.0 | 25.1 | 84.6 | 14.0 | 104.5 | 21.7 |
| AD-570712.1 | 102.1 | 7.5 | 95.6 | 12.2 | 97.8 | 12.7 |
| AD-570713.1 | 99.4 | 4.9 | 110.2 | 8.0 | 94.0 | 18.2 |
| AD-570714.1 | 87.7 | 2.9 | 113.2 | 9.6 | 87.0 | 11.6 |
| AD-571539.1 | 60.2 | 14.0 | 84.8 | 18.0 | 78.9 | 11.1 |
| AD-571610.1 | 83.0 | 16.3 | 96.7 | 4.4 | 88.4 | 8.4 |
| AD-571633.1 | 66.6 | 15.3 | 70.6 | 17.2 | 87.1 | 14.4 |
| AD-571715.1 | 16.0 | 2.9 | 50.2 | 4.4 | 90.6 | 8.1 |
| AD-571752.1 | 94.9 | 5.4 | 99.5 | 10.1 | 111.4 | 12.4 |
| AD-571754.1 | 96.0 | 5.4 | 90.2 | 18.5 | 103.7 | 9.1 |
| AD-571828.1 | 61.1 | 8.9 | 98.2 | 4.9 | 100.1 | 5.6 |
| AD-572039.1 | 99.8 | 5.3 | 110.7 | 22.2 | 91.1 | 13.8 |
| AD-572040.1 | 97.2 | 10.0 | 104.4 | 22.2 | 81.8 | 20.1 |
| AD-572041.1 | 93.3 | 15.6 | 81.2 | 19.7 | 90.5 | 11.0 |
| AD-572059.1 | 101.3 | 15.9 | 88.7 | 14.1 | 105.2 | 15.1 |
| AD-572061.1 | 101.0 | 6.6 | 74.1 | 18.2 | 113.5 | 11.3 |
| AD-572062.1 | 80.4 | 14.4 | 102.8 | 18.6 | 101.3 | 10.4 |
| AD-572063.1 | 100.9 | 7.7 | 90.7 | 22.2 | 113.7 | 15.3 |
| AD-572110.1 | 91.4 | 10.4 | 98.0 | 14.6 | 108.1 | 9.9 |
| AD-572144.1 | 102.7 | 7.4 | 90.0 | 32.4 | 108.5 | 10.8 |
| AD-572388.1 | 17.9 | 2.8 | 48.6 | 3.7 | 85.3 | 6.9 |
| AD-572389.1 | 8.7 | 2.9 | 27.6 | 7.1 | 73.7 | 8.1 |
| AD-572390.1 | 26.8 | 6.0 | 60.1 | 13.2 | 102.5 | 4.4 |

TABLE 12

C3 Single Dose Screens in Hep3B cells

| Duplex | Avg % C3 mRNA Remaining | SD | Dose nM |
|---|---|---|---|
| AD-568976.1 | 14.7 | 0.2 | 50 |
| AD-568978.1 | 14.2 | 4.1 | 50 |
| AD-569127.1 | 16.7 | 1.8 | 50 |
| AD-569133.1 | 21.6 | 1.3 | 50 |
| AD-569164.3 | 21.4 | 5.8 | 50 |
| AD-569164.4 | 22.1 | 3.3 | 50 |
| AD-569195.1 | 22.7 | 6.8 | 50 |
| AD-569237.1 | 103.6 | 5.6 | 50 |
| AD-569239.1 | 76.5 | 2.8 | 50 |
| AD-569272.3 | 26.3 | 2.2 | 50 |
| AD-569350.1 | 63.8 | 6.4 | 50 |
| AD-569571.1 | 19.1 | 7.6 | 50 |
| AD-569763.3 | 20.9 | 3.5 | 50 |
| AD-569764.1 | 18.7 | 2.1 | 50 |
| AD-569766.1 | 74.4 | 21.6 | 50 |
| AD-569816.1 | 21.0 | 5.5 | 50 |
| AD-570156.1 | 19.2 | 2.5 | 50 |
| AD-570466.1 | 23.1 | 1.4 | 50 |
| AD-570470.1 | 59.1 | 10.2 | 50 |
| AD-570471.1 | 36.8 | 8.3 | 50 |
| AD-570474.1 | 54.0 | 8.4 | 50 |
| AD-570475.1 | 35.7 | 4.9 | 50 |
| AD-570476.1 | 22.4 | 6.3 | 50 |
| AD-570620.1 | 16.1 | 2.5 | 50 |
| AD-570621.1 | 20.8 | 3.7 | 50 |
| AD-570622.1 | 16.1 | 5.7 | 50 |
| AD-570623.1 | 16.7 | 2.8 | 50 |
| AD-570624.1 | 20.6 | 1.5 | 50 |
| AD-570625.1 | 19.5 | 5.5 | 50 |
| AD-570627.1 | 20.5 | 4.1 | 50 |
| AD-570631.1 | 26.5 | 3.0 | 50 |
| AD-570632.1 | 24.7 | 5.2 | 50 |
| AD-570672.1 | 21.2 | 4.7 | 50 |
| AD-570674.1 | 33.5 | 15.3 | 50 |
| AD-570675.1 | 107.8 | 1.7 | 50 |
| AD-570676.1 | 64.7 | 13.8 | 50 |
| AD-570677.1 | 29.9 | 3.0 | 50 |
| AD-570678.1 | 102.7 | 3.7 | 50 |
| AD-570679.1 | 49.1 | 6.4 | 50 |
| AD-570680.1 | 50.0 | 8.0 | 50 |
| AD-570681.1 | 23.6 | 4.2 | 50 |
| AD-570682.1 | 27.5 | 3.8 | 50 |
| AD-570717.1 | 83.2 | 11.9 | 50 |
| AD-570963.1 | 28.9 | 6.5 | 50 |
| AD-571157.1 | 61.5 | 5.2 | 50 |
| AD-571158.1 | 96.6 | 6.2 | 50 |
| AD-571168.1 | 62.8 | 7.7 | 50 |
| AD-571298.1 | 12.9 | 2.7 | 50 |
| AD-571298.2 | 9.0 | 1.6 | 50 |
| AD-571447.1 | 49.9 | 2.1 | 50 |
| AD-571448.1 | 28.3 | 7.7 | 50 |
| AD-571449.1 | 78.7 | 11.7 | 50 |
| AD-571539.4 | 21.9 | 4.8 | 50 |
| AD-571719.1 | 14.9 | 2.7 | 50 |
| AD-571752.3 | 29.0 | 2.4 | 50 |
| AD-571753.1 | 19.0 | 3.9 | 50 |
| AD-571765.1 | 41.6 | 11.4 | 50 |
| AD-571766.1 | 25.1 | 4.4 | 50 |
| AD-571767.1 | 23.8 | 1.0 | 50 |
| AD-571825.1 | 15.1 | 0.9 | 50 |
| AD-571826.1 | 17.3 | 1.3 | 50 |
| AD-571900.1 | 25.1 | 2.6 | 50 |
| AD-571945.1 | 23.6 | 8.1 | 50 |
| AD-571948.1 | 89.7 | 19.3 | 50 |
| AD-572039.3 | 34.2 | 13.5 | 50 |
| AD-572040.3 | 26.6 | 3.7 | 50 |
| AD-572041.3 | 25.6 | 0.6 | 50 |
| AD-572044.1 | 25.4 | 5.4 | 50 |
| AD-572049.1 | 31.9 | 4.3 | 50 |
| AD-572060.1 | 25.5 | 4.8 | 50 |
| AD-572061.2 | 24.8 | 8.1 | 50 |
| AD-572062.3 | 23.3 | 4.5 | 50 |
| AD-572108.1 | 61.8 | 0.9 | 50 |
| AD-572235.1 | 17.7 | 3.1 | 50 |
| AD-572258.1 | 14.9 | 3.3 | 50 |

TABLE 12-continued

C3 Single Dose Screens in Hep3B cells

| Duplex | Avg % C3 mRNA Remaining | SD | Dose nM |
|---|---|---|---|
| AD-572278.1 | 14.7 | 5.5 | 50 |
| AD-572279.1 | 14.6 | 2.1 | 50 |
| AD-572281.1 | 13.9 | 1.3 | 50 |
| AD-572355.1 | 70.2 | 6.2 | 50 |
| AD-572356.1 | 22.5 | 5.7 | 50 |
| AD-57238.2 | 15.7 | 5.3 | 50 |
| AD-572387.1 | 15.3 | 0.5 | 50 |
| AD-572388.4 | 14.8 | 2.3 | 50 |
| AD-572389.3 | 12.1 | 1.1 | 50 |
| AD-572390.2 | 15.0 | 4.1 | 50 |
| AD-572393.1 | 19.6 | 2.3 | 50 |
| AD-572613.1 | 125.8 | 13.8 | 50 |
| AD-572614.1 | 30.9 | 4.9 | 50 |
| AD-572858.1 | 26.7 | 4.0 | 50 |
| AD-80806.9 | 11.9 | 2.4 | 50 |
| AD-890084.1 | 15.9 | 2.2 | 50 |
| AD-890085.1 | 43.1 | 2.4 | 50 |
| AD-568976.1 | 25.2 | 4.3 | 10 |
| AD-568978.1 | 18.0 | 0.5 | 10 |
| AD-569127.1 | 22.6 | 8.6 | 10 |
| AD-569133.1 | 33.5 | 10.9 | 10 |
| AD-569164.3 | 10.7 | 0.6 | 10 |
| AD-569164.4 | 37.7 | 15.6 | 10 |
| AD-569195.1 | 18.3 | 2.3 | 10 |
| AD-569237.1 | 106.9 | 2.2 | 10 |
| AD-569239.1 | 123.8 | 22.4 | 10 |
| AD-569272.3 | 63.0 | 8.3 | 10 |
| AD-569350.1 | 106.7 | 8.7 | 10 |
| AD-569571.1 | 21.3 | 0.8 | 10 |
| AD-569763.3 | 34.1 | 5.6 | 10 |
| AD-569764.1 | 37.9 | 4.5 | 10 |
| AD-569766.1 | 94.8 | 14.9 | 10 |
| AD-569816.1 | 13.7 | 0.9 | 10 |
| AD-570156.1 | 27.0 | 2.4 | 10 |
| AD-570466.1 | 14.7 | 2.7 | 10 |
| AD-570470.1 | 95.6 | 16.6 | 10 |
| AD-570471.1 | 48.4 | 5.1 | 10 |
| AD-570474.1 | 25.6 | 2.9 | 10 |
| AD-570475.1 | 84.4 | 20.6 | 10 |
| AD-570476.1 | 26.7 | 5.9 | 10 |
| AD-570620.1 | 22.3 | 0.5 | 10 |
| AD-570621.1 | 31.7 | 9.8 | 10 |
| AD-570622.1 | 10.9 | 2.1 | 10 |
| AD-570623.1 | 22.5 | 3.4 | 10 |
| AD-570624.1 | 25.2 | 2.6 | 10 |
| AD-570625.1 | 14.8 | 0.3 | 10 |
| AD-570627.1 | 29.9 | 3.2 | 10 |
| AD-570631.1 | 35.9 | 4.2 | 10 |
| AD-570632.1 | 38.5 | 2.2 | 10 |
| AD-570672.1 | 39.4 | 6.6 | 10 |
| AD-570674.1 | 34.3 | 4.0 | 10 |
| AD-570675.1 | 97.7 | 8.2 | 10 |
| AD-570676.1 | 86.9 | 3.8 | 10 |
| AD-570677.1 | 60.3 | 1.4 | 10 |
| AD-570678.1 | 56.5 | 13.4 | 10 |
| AD-570679.1 | 98.0 | 15.0 | 10 |
| AD-570680.1 | 62.4 | 17.6 | 10 |
| AD-570681.1 | 44.9 | 2.0 | 10 |
| AD-570682.1 | 23.9 | 7.9 | 10 |
| AD-570717.1 | 112.1 | 3.8 | 10 |
| AD-570963.1 | 54.1 | 14.8 | 10 |
| AD-571157.1 | 70.6 | 5.8 | 10 |
| AD-571158.1 | 60.8 | 9.7 | 10 |
| AD-571168.1 | 112.1 | 27.3 | 10 |
| AD-571298.1 | 18.4 | 3.4 | 10 |
| AD-571298.2 | 16.1 | 0.7 | 10 |
| AD-571447.1 | 24.4 | 1.2 | 10 |
| AD-571448.1 | 30.6 | 0.3 | 10 |
| AD-571449.1 | 106.0 | 22.3 | 10 |
| AD-571539.4 | 27.8 | 4.7 | 10 |
| AD-571719.1 | 22.6 | 1.5 | 10 |
| AD-571752.3 | 27.6 | 7.7 | 10 |
| AD-571753.1 | 16.1 | 1.6 | 10 |
| AD-571765.1 | 64.1 | 15.8 | 10 |
| AD-571766.1 | 55.0 | 5.8 | 10 |
| AD-571767.1 | 32.1 | 5.8 | 10 |
| AD-571825.1 | 17.6 | 3.5 | 10 |
| AD-571826.1 | 19.8 | 3.3 | 10 |
| AD-571900.1 | 44.3 | 5.2 | 10 |
| AD-571945.1 | 29.3 | 3.3 | 10 |
| AD-571948.1 | 58.6 | 14.3 | 10 |
| AD-572039.3 | 60.4 | 0.9 | 10 |
| AD-572040.3 | 27.6 | 8.2 | 10 |
| AD-572041.3 | 34.5 | 1.6 | 10 |
| AD-572044.1 | 46.2 | 3.5 | 10 |
| AD-572049.1 | 45.8 | 4.6 | 10 |
| AD-572060.1 | 55.6 | 6.5 | 10 |
| AD-572061.2 | 33.3 | 3.7 | 10 |
| AD-572062.3 | 27.7 | 0.3 | 10 |
| AD-572108.1 | 116.7 | 22.8 | 10 |
| AD-572235.1 | 13.6 | 3.8 | 10 |
| AD-572258.1 | 21.1 | 6.0 | 10 |
| AD-572278.1 | 26.8 | 10.1 | 10 |
| AD-572279.1 | 23.4 | 5.7 | 10 |
| AD-572281.1 | 16.1 | 3.0 | 10 |
| AD-572355.1 | 126.5 | 3.3 | 10 |
| AD-572356.1 | 15.0 | 3.9 | 10 |
| AD-57238.2 | 18.4 | 3.6 | 10 |
| AD-572387.1 | 26.8 | 1.2 | 10 |
| AD-572388.4 | 32.0 | 8.3 | 10 |
| AD-572389.3 | 23.9 | 3.5 | 10 |
| AD-572390.2 | 27.7 | 1.0 | 10 |
| AD-572393.1 | 33.8 | 3.3 | 10 |
| AD-572613.1 | 59.1 | 12.2 | 10 |
| AD-572614.1 | 45.4 | 12.3 | 10 |
| AD-572858.1 | 34.6 | 0.7 | 10 |
| AD-80806.9 | 18.8 | 2.1 | 10 |
| AD-890084.1 | 10.0 | 2.2 | 10 |
| AD-890085.1 | 73.2 | 12.5 | 10 |
| AD-568976.1 | 43.6 | 6.6 | 1 |
| AD-568978.1 | 37.1 | 4.4 | 1 |
| AD-569127.1 | 57.8 | 6.9 | 1 |
| AD-569133.1 | 28.9 | 2.8 | 1 |
| AD-569164.3 | 36.1 | 8.2 | 1 |
| AD-569164.4 | 66.7 | 7.7 | 1 |
| AD-569195.1 | 47.7 | 2.3 | 1 |
| AD-569237.1 | 104.2 | 16.9 | 1 |
| AD-569239.1 | 97.9 | 0.6 | 1 |
| AD-569272.3 | 83.3 | 2.5 | 1 |
| AD-569350.1 | 96.0 | 8.6 | 1 |
| AD-569571.1 | 45.3 | 1.7 | 1 |
| AD-569763.3 | 30.4 | 10.2 | 1 |
| AD-569764.1 | 60.6 | 10.0 | 1 |
| AD-569766.1 | 97.0 | 10.7 | 1 |
| AD-569816.1 | 35.8 | 2.7 | 1 |
| AD-570156.1 | 50.7 | 7.8 | 1 |
| AD-570466.1 | 47.2 | 10.5 | 1 |
| AD-570470.1 | 104.5 | 9.3 | 1 |
| AD-570471.1 | 79.8 | 8.0 | 1 |
| AD-570474.1 | 71.1 | 13.3 | 1 |
| AD-570475.1 | 96.1 | 5.0 | 1 |
| AD-570476.1 | 47.1 | 4.0 | 1 |
| AD-570620.1 | 33.8 | 5.0 | 1 |
| AD-570621.1 | 50.0 | 5.5 | 1 |
| AD-570622.1 | 23.0 | 1.3 | 1 |
| AD-570623.1 | 25.8 | 2.6 | 1 |
| AD-570624.1 | 24.5 | 4.1 | 1 |
| AD-570625.1 | 42.3 | 7.6 | 1 |
| AD-570627.1 | 46.6 | 1.6 | 1 |
| AD-570631.1 | 71.3 | 6.1 | 1 |
| AD-570632.1 | 51.7 | 4.1 | 1 |
| AD-570672.1 | 55.4 | 3.5 | 1 |
| AD-570674.1 | 49.1 | 7.1 | 1 |
| AD-570675.1 | 79.1 | 5.3 | 1 |
| AD-570676.1 | 104.9 | 3.3 | 1 |
| AD-570677.1 | 81.2 | 3.2 | 1 |
| AD-570678.1 | 88.9 | 15.3 | 1 |
| AD-570679.1 | 47.1 | 8.1 | 1 |

TABLE 12-continued

C3 Single Dose Screens in Hep3B cells

| Duplex | Avg % C3 mRNA Remaining | SD | Dose nM |
|---|---|---|---|
| AD-570680.1 | 65.2 | 2.9 | 1 |
| AD-570681.1 | 68.2 | 4.0 | 1 |
| AD-570682.1 | 59.1 | 8.0 | 1 |
| AD-570717.1 | 67.5 | 7.9 | 1 |
| AD-570963.1 | 83.7 | 1.0 | 1 |
| AD-571157.1 | 103.6 | 15.4 | 1 |
| AD-571158.1 | 83.5 | 11.5 | 1 |
| AD-571168.1 | 95.5 | 5.4 | 1 |
| AD-571298.1 | 29.0 | 9.5 | 1 |
| AD-571298.2 | 26.7 | 2.1 | 1 |
| AD-571447.1 | 83.8 | 7.0 | 1 |
| AD-571448.1 | 72.5 | 5.6 | 1 |
| AD-571449.1 | 85.6 | 8.0 | 1 |
| AD-571539.4 | 47.7 | 4.8 | 1 |
| AD-571719.1 | 23.6 | 4.3 | 1 |
| AD-571752.3 | 69.3 | 9.5 | 1 |
| AD-571753.1 | 37.9 | 6.5 | 1 |
| AD-571765.1 | 65.3 | 3.2 | 1 |
| AD-571766.1 | 56.3 | 9.7 | 1 |
| AD-571767.1 | 30.4 | 9.6 | 1 |
| AD-571825.1 | 19.5 | 4.7 | 1 |
| AD-571826.1 | 24.2 | 3.6 | 1 |
| AD-571900.1 | 55.9 | 4.3 | 1 |
| AD-571945.1 | 31.2 | 1.6 | 1 |
| AD-571948.1 | 91.5 | 19.5 | 1 |
| AD-572039.3 | 86.5 | 8.4 | 1 |
| AD-572040.3 | 65.8 | 2.2 | 1 |
| AD-572041.3 | 41.5 | 4.4 | 1 |
| AD-572044.1 | 60.9 | 0.8 | 1 |
| AD-572049.1 | 60.4 | 0.9 | 1 |
| AD-572060.1 | 68.9 | 6.1 | 1 |
| AD-572061.2 | 42.7 | 4.7 | 1 |
| AD-572062.3 | 27.5 | 6.5 | 1 |
| AD-572108.1 | 82.1 | 10.1 | 1 |
| AD-572235.1 | 21.6 | 2.5 | 1 |
| AD-572258.1 | 30.4 | 5.4 | 1 |
| AD-572278.1 | 22.1 | 3.9 | 1 |
| AD-572279.1 | 37.0 | 6.4 | 1 |
| AD-572281.1 | 26.6 | 1.5 | 1 |
| AD-572355.1 | 88.8 | 17.7 | 1 |
| AD-572356.1 | 57.4 | 16.2 | 1 |
| AD-57238.2 | 47.0 | 7.0 | 1 |
| AD-572387.1 | 37.9 | 2.5 | 1 |
| AD-572388.4 | 25.7 | 3.3 | 1 |
| AD-572389.3 | 28.1 | 4.4 | 1 |
| AD-572390.2 | 36.4 | 1.6 | 1 |
| AD-572393.1 | 52.1 | 2.7 | 1 |
| AD-572613.1 | 95.0 | 6.4 | 1 |
| AD-572614.1 | 60.8 | 1.1 | 1 |
| AD-572858.1 | 46.6 | 0.3 | 1 |
| AD-80806.9 | 27.0 | 3.4 | 1 |
| AD-890084.1 | 23.3 | 6.5 | 1 |
| AD-890085.1 | 109.4 | 8.4 | 1 |
| AD-568976.1 | 61.6 | 17.4 | 0.1 |
| AD-568978.1 | 81.5 | 7.4 | 0.1 |
| AD-569127.1 | 93.9 | 18.4 | 0.1 |
| AD-569133.1 | 55.0 | 7.4 | 0.1 |
| AD-569164.3 | 77.5 | 20.5 | 0.1 |
| AD-569164.4 | 93.7 | 3.2 | 0.1 |
| AD-569195.1 | 89.6 | 2.7 | 0.1 |
| AD-569237.1 | 110.5 | 13.2 | 0.1 |
| AD-569239.1 | 108.4 | 2.2 | 0.1 |
| AD-569272.3 | 89.2 | 13.7 | 0.1 |
| AD-569350.1 | 96.1 | 10.9 | 0.1 |
| AD-569571.1 | 91.2 | 11.2 | 0.1 |
| AD-569763.3 | 87.3 | 9.1 | 0.1 |
| AD-569764.1 | 88.7 | 7.7 | 0.1 |
| AD-569766.1 | 103.3 | 10.3 | 0.1 |
| AD-569816.1 | 81.0 | 8.2 | 0.1 |
| AD-570156.1 | 81.4 | 9.9 | 0.1 |
| AD-570466.1 | 87.4 | 1.5 | 0.1 |
| AD-570470.1 | 100.2 | 12.6 | 0.1 |
| AD-570471.1 | 96.4 | 4.0 | 0.1 |
| AD-570474.1 | 95.0 | 6.4 | 0.1 |
| AD-570475.1 | 104.7 | 2.8 | 0.1 |
| AD-570476.1 | 88.1 | 13.9 | 0.1 |
| AD-570620.1 | 56.3 | 8.1 | 0.1 |
| AD-570621.1 | 93.7 | 24.7 | 0.1 |
| AD-570622.1 | 61.7 | 13.5 | 0.1 |
| AD-570623.1 | 75.4 | 4.9 | 0.1 |
| AD-570624.1 | 80.8 | 6.3 | 0.1 |
| AD-570625.1 | 90.4 | 6.4 | 0.1 |
| AD-570627.1 | 89.3 | 6.8 | 0.1 |
| AD-570631.1 | 91.6 | 8.4 | 0.1 |
| AD-570632.1 | 86.5 | 7.7 | 0.1 |
| AD-570672.1 | 78.1 | 12.7 | 0.1 |
| AD-570674.1 | 90.8 | 7.5 | 0.1 |
| AD-570675.1 | 94.8 | 6.1 | 0.1 |
| AD-570676.1 | 101.1 | 0.7 | 0.1 |
| AD-570677.1 | 88.5 | 15.2 | 0.1 |
| AD-570678.1 | 95.4 | 4.1 | 0.1 |
| AD-570679.1 | 100.5 | 8.2 | 0.1 |
| AD-570680.1 | 100.0 | 3.6 | 0.1 |
| AD-570681.1 | 70.3 | 14.5 | 0.1 |
| AD-570682.1 | 94.8 | 9.0 | 0.1 |
| AD-570717.1 | 98.8 | 8.1 | 0.1 |
| AD-570963.1 | 97.1 | 8.0 | 0.1 |
| AD-571157.1 | 94.0 | 10.5 | 0.1 |
| AD-571158.1 | 98.6 | 7.3 | 0.1 |
| AD-571168.1 | 103.7 | 8.9 | 0.1 |
| AD-571298.1 | 56.5 | 9.3 | 0.1 |
| AD-571298.2 | 46.2 | 12.6 | 0.1 |
| AD-571447.1 | 111.3 | 8.3 | 0.1 |
| AD-571448.1 | 98.9 | 6.9 | 0.1 |
| AD-571449.1 | 101.0 | 4.6 | 0.1 |
| AD-571539.4 | 86.3 | 9.2 | 0.1 |
| AD-571719.1 | 69.1 | 5.8 | 0.1 |
| AD-571752.3 | 93.8 | 25.2 | 0.1 |
| AD-571753.1 | 86.2 | 12.6 | 0.1 |
| AD-571765.1 | 100.3 | 9.3 | 0.1 |
| AD-571766.1 | 92.0 | 16.7 | 0.1 |
| AD-571767.1 | 87.6 | 3.3 | 0.1 |
| AD-571825.1 | 36.2 | 7.2 | 0.1 |
| AD-571826.1 | 64.0 | 8.1 | 0.1 |
| AD-571900.1 | 94.0 | 8.3 | 0.1 |
| AD-571945.1 | 85.9 | 5.5 | 0.1 |
| AD-571948.1 | 91.7 | 8.5 | 0.1 |
| AD-572039.3 | 118.3 | 9.9 | 0.1 |
| AD-572040.3 | 90.6 | 9.6 | 0.1 |
| AD-572041.3 | 81.0 | 7.3 | 0.1 |
| AD-572044.1 | 94.0 | 0.3 | 0.1 |
| AD-572049.1 | 100.1 | 11.7 | 0.1 |
| AD-572060.1 | 94.7 | 6.8 | 0.1 |
| AD-572061.2 | 78.4 | 3.2 | 0.1 |
| AD-572062.3 | 91.7 | 14.2 | 0.1 |
| AD-572108.1 | 93.7 | 10.4 | 0.1 |
| AD-572235.1 | 70.4 | 10.5 | 0.1 |
| AD-572258.1 | 68.0 | 3.6 | 0.1 |
| AD-572278.1 | 80.0 | 9.0 | 0.1 |
| AD-572279.1 | 78.6 | 4.9 | 0.1 |
| AD-572281.1 | 66.7 | 3.6 | 0.1 |
| AD-572355.1 | 101.9 | 7.5 | 0.1 |
| AD-572356.1 | 85.5 | 8.2 | 0.1 |
| AD-57238.2 | 81.2 | 13.9 | 0.1 |
| AD-572387.1 | 90.3 | 1.0 | 0.1 |
| AD-572388.4 | 76.1 | 12.0 | 0.1 |
| AD-572389.3 | 81.1 | 13.6 | 0.1 |
| AD-572390.2 | 88.8 | 1.2 | 0.1 |
| AD-572393.1 | 86.4 | 1.5 | 0.1 |
| AD-572613.1 | 101.3 | 16.5 | 0.1 |
| AD-572614.1 | 95.5 | 3.1 | 0.1 |
| AD-572858.1 | 78.1 | 19.1 | 0.1 |
| AD-80806.9 | 61.6 | 1.7 | 0.1 |
| AD-890084.1 | 73.7 | 9.0 | 0.1 |
| AD-890085.1 | 109.0 | 13.9 | 0.1 |

TABLE 13

C3 Single Dose Screens in PMH cells

| Duplex | Avg % C3 mRNA Remaining | SD | Dose nM |
|---|---|---|---|
| AD-568976.1 | 3.0 | 0.7 | 50 |
| AD-568978.1 | 2.1 | 0.2 | 50 |
| AD-569127.1 | 15.8 | 1.0 | 50 |
| AD-569133.1 | 70.4 | 29.5 | 50 |
| AD-569164.3 | 69.0 | 20.9 | 50 |
| AD-569164.4 | 75.4 | 22.3 | 50 |
| AD-569195.1 | 81.9 | 25.8 | 50 |
| AD-569237.1 | 207.6 | 49.5 | 50 |
| AD-569239.1 | 161.6 | 51.4 | 50 |
| AD-569272.3 | 101.8 | 23.8 | 50 |
| AD-569350.1 | 146.4 | 53.4 | 50 |
| AD-569571.1 | 23.8 | 6.6 | 50 |
| AD-569763.3 | 57.4 | 28.9 | 50 |
| AD-569764.1 | 22.3 | 6.5 | 50 |
| AD-569766.1 | 159.6 | 28.7 | 50 |
| AD-569816.1 | 59.9 | 19.5 | 50 |
| AD-570156.1 | 26.6 | 11.5 | 50 |
| AD-570466.1 | 81.9 | 3.3 | 50 |
| AD-570470.1 | 140.3 | 51.7 | 50 |
| AD-570471.1 | 121.3 | 43.9 | 50 |
| AD-570474.1 | 139.2 | 57.9 | 50 |
| AD-570475.1 | 119.7 | 54.3 | 50 |
| AD-570476.1 | 77.5 | 1.6 | 50 |
| AD-570620.1 | 13.3 | 0.1 | 50 |
| AD-570621.1 | 52.4 | 16.5 | 50 |
| AD-570622.1 | 13.9 | 1.8 | 50 |
| AD-570623.1 | 15.3 | 1.2 | 50 |
| AD-570624.1 | 50.7 | 5.1 | 50 |
| AD-570625.1 | 27.6 | 2.1 | 50 |
| AD-570627.1 | 36.8 | 1.7 | 50 |
| AD-570631.1 | 103.0 | 5.0 | 50 |
| AD-570632.1 | 89.5 | 19.1 | 50 |
| AD-570672.1 | 66.0 | 13.2 | 50 |
| AD-570674.1 | 118.1 | 35.4 | 50 |
| AD-570675.1 | 210.6 | 49.7 | 50 |
| AD-570676.1 | 151.5 | 34.6 | 50 |
| AD-570677.1 | 116.2 | 32.0 | 50 |
| AD-570678.1 | 194.9 | 9.9 | 50 |
| AD-570679.1 | 128.4 | 56.7 | 50 |
| AD-570680.1 | 135.9 | 47.7 | 50 |
| AD-570681.1 | 84.0 | 7.4 | 50 |
| AD-570682.1 | 107.7 | 37.1 | 50 |
| AD-570717.1 | 165.7 | 61.6 | 50 |
| AD-570963.1 | 113.2 | 32.5 | 50 |
| AD-571157.1 | 140.6 | 8.0 | 50 |
| AD-571158.1 | 179.6 | 62.3 | 50 |
| AD-571168.1 | 144.1 | 56.1 | 50 |
| AD-571298.1 | 2.0 | 0.2 | 50 |
| AD-571298.2 | 1.0 | 0.2 | 50 |
| AD-571447.1 | 133.2 | 53.5 | 50 |
| AD-571448.1 | 109.2 | 34.9 | 50 |
| AD-571449.1 | 164.6 | 61.6 | 50 |
| AD-571539.4 | 73.3 | 1.1 | 50 |
| AD-571719.1 | 5.2 | 1.4 | 50 |
| AD-571752.3 | 115.0 | 23.3 | 50 |
| AD-571753.1 | 23.1 | 3.4 | 50 |
| AD-571765.1 | 121.3 | 19.5 | 50 |
| AD-571766.1 | 94.8 | 30.2 | 50 |
| AD-571767.1 | 88.0 | 32.8 | 50 |
| AD-571825.1 | 7.7 | 1.7 | 50 |
| AD-571826.1 | 18.2 | 5.0 | 50 |
| AD-571900.1 | 92.7 | 28.1 | 50 |
| AD-571945.1 | 85.7 | 10.8 | 50 |
| AD-571948.1 | 169.3 | 87.5 | 50 |
| AD-572039.3 | 118.5 | 58.9 | 50 |
| AD-572040.3 | 105.6 | 4.1 | 50 |
| AD-572041.3 | 101.1 | 1.8 | 50 |
| AD-572044.1 | 97.4 | 11.5 | 50 |
| AD-572049.1 | 116.5 | 18.6 | 50 |
| AD-572060.1 | 99.7 | 3.2 | 50 |
| AD-572061.2 | 90.6 | 2.4 | 50 |
| AD-572062.3 | 83.1 | 31.2 | 50 |
| AD-572108.1 | 141.0 | 12.3 | 50 |
| AD-572235.1 | 21.0 | 1.1 | 50 |
| AD-572258.1 | 4.5 | 1.3 | 50 |
| AD-572278.1 | 2.6 | 0.1 | 50 |
| AD-572279.1 | 2.5 | 0.6 | 50 |
| AD-572281.1 | 2.0 | 0.5 | 50 |
| AD-572355.1 | 159.0 | 48.4 | 50 |
| AD-572356.1 | 78.3 | 12.7 | 50 |
| AD-57238.2 | 9.9 | 0.8 | 50 |
| AD-572387.1 | 9.0 | 1.9 | 50 |
| AD-572388.4 | 4.3 | 1.2 | 50 |
| AD-572389.3 | 1.8 | 0.7 | 50 |
| AD-572390.2 | 5.8 | 2.3 | 50 |
| AD-572393.1 | 31.9 | 6.1 | 50 |
| AD-572613.1 | 217.6 | 101.2 | 50 |
| AD-572614.1 | 116.3 | 22.1 | 50 |
| AD-572858.1 | 107.6 | 42.0 | 50 |
| AD-80806.9 | 1.1 | 0.2 | 50 |
| AD-890084.1 | 13.1 | 5.5 | 50 |
| AD-890085.1 | 121.6 | 20.3 | 50 |
| AD-568976.1 | 10.5 | 1.8 | 10 |
| AD-568978.1 | 9.8 | 5.4 | 10 |
| AD-569127.1 | 52.8 | 11.1 | 10 |
| AD-569133.1 | 116.3 | 31.4 | 10 |
| AD-569164.3 | 99.7 | 7.5 | 10 |
| AD-569164.4 | 42.7 | 3.8 | 10 |
| AD-569195.1 | 117.9 | 47.1 | 10 |
| AD-569237.1 | 177.3 | 6.2 | 10 |
| AD-569239.1 | 154.2 | 30.6 | 10 |
| AD-569272.3 | 122.8 | 24.2 | 10 |
| AD-569350.1 | 71.4 | 11.6 | 10 |
| AD-569571.1 | 20.8 | 5.4 | 10 |
| AD-569763.3 | 31.1 | 9.9 | 10 |
| AD-569764.1 | 62.8 | 26.7 | 10 |
| AD-569766.1 | 158.6 | 21.9 | 10 |
| AD-569816.1 | 61.8 | 22.2 | 10 |
| AD-570156.1 | 35.0 | 6.6 | 10 |
| AD-570466.1 | 149.7 | 29.3 | 10 |
| AD-570470.1 | 138.8 | 45.5 | 10 |
| AD-570471.1 | 59.6 | 5.4 | 10 |
| AD-570474.1 | 61.0 | 0.4 | 10 |
| AD-570475.1 | 68.6 | 12.7 | 10 |
| AD-570476.1 | 93.3 | 11.6 | 10 |
| AD-570620.1 | 50.2 | 13.3 | 10 |
| AD-570621.1 | 102.6 | 12.3 | 10 |
| AD-570622.1 | 78.7 | 22.3 | 10 |
| AD-570623.1 | 45.0 | 13.8 | 10 |
| AD-570624.1 | 115.2 | 43.3 | 10 |
| AD-570625.1 | 85.5 | 10.7 | 10 |
| AD-570627.1 | 111.1 | 16.7 | 10 |
| AD-570631.1 | 69.7 | 22.4 | 10 |
| AD-570632.1 | 96.7 | 21.6 | 10 |
| AD-570672.1 | 68.9 | 14.1 | 10 |
| AD-570674.1 | 150.8 | 33.1 | 10 |
| AD-570675.1 | 170.0 | 28.6 | 10 |
| AD-570676.1 | 152.1 | 4.7 | 10 |
| AD-570677.1 | 203.3 | 10.3 | 10 |
| AD-570678.1 | 190.5 | 30.9 | 10 |
| AD-570679.1 | 209.3 | 45.6 | 10 |
| AD-570680.1 | 169.1 | 17.7 | 10 |
| AD-570681.1 | 116.0 | 26.5 | 10 |
| AD-570682.1 | 118.6 | 33.8 | 10 |
| AD-570717.1 | 198.1 | 4.5 | 10 |
| AD-570963.1 | 97.4 | 31.4 | 10 |
| AD-571157.1 | 72.7 | 8.0 | 10 |
| AD-571158.1 | 57.4 | 4.9 | 10 |
| AD-571168.1 | 57.9 | 6.1 | 10 |
| AD-571298.1 | 5.7 | 1.7 | 10 |
| AD-571298.2 | 2.7 | 1.0 | 10 |
| AD-571447.1 | 187.9 | 30.2 | 10 |
| AD-571448.1 | 55.4 | 7.1 | 10 |
| AD-571449.1 | 174.5 | 53.4 | 10 |
| AD-571539.4 | 124.8 | 50.3 | 10 |
| AD-571719.1 | 22.7 | 5.7 | 10 |
| AD-571752.3 | 54.4 | 5.9 | 10 |
| AD-571753.1 | 91.4 | 12.2 | 10 |

TABLE 13-continued

C3 Single Dose Screens in PMH cells

| Duplex | Avg % C3 mRNA Remaining | SD | Dose nM |
|---|---|---|---|
| AD-571765.1 | 92.9 | 33.3 | 10 |
| AD-571766.1 | 57.0 | 3.6 | 10 |
| AD-571767.1 | 50.5 | 5.8 | 10 |
| AD-571825.1 | 27.0 | 7.4 | 10 |
| AD-571826.1 | 18.1 | 3.0 | 10 |
| AD-571900.1 | 71.4 | 11.9 | 10 |
| AD-571945.1 | 96.8 | 7.3 | 10 |
| AD-571948.1 | 119.7 | 27.4 | 10 |
| AD-572039.3 | 117.5 | 18.2 | 10 |
| AD-572040.3 | 169.3 | 47.8 | 10 |
| AD-572041.3 | 134.4 | 44.7 | 10 |
| AD-572044.1 | 159.2 | 22.4 | 10 |
| AD-572049.1 | 57.7 | 6.2 | 10 |
| AD-572060.1 | 170.5 | 7.1 | 10 |
| AD-572061.2 | 144.3 | 31.5 | 10 |
| AD-572062.3 | 96.8 | 37.4 | 10 |
| AD-572108.1 | 54.9 | 5.8 | 10 |
| AD-572235.1 | 77.9 | 44.2 | 10 |
| AD-572258.1 | 18.0 | 4.6 | 10 |
| AD-572278.1 | 10.7 | 3.2 | 10 |
| AD-572279.1 | 11.3 | 5.8 | 10 |
| AD-572281.1 | 7.2 | 0.6 | 10 |
| AD-572355.1 | 57.0 | 6.3 | 10 |
| AD-572356.1 | 56.4 | 6.0 | 10 |
| AD-57238.2 | 39.9 | 3.8 | 10 |
| AD-572387.1 | 25.3 | 10.0 | 10 |
| AD-572388.4 | 25.3 | 7.5 | 10 |
| AD-572389.3 | 4.0 | 0.6 | 10 |
| AD-572390.2 | 25.0 | 4.1 | 10 |
| AD-572393.1 | 102.7 | 20.6 | 10 |
| AD-572613.1 | 150.3 | 34.6 | 10 |
| AD-572614.1 | 139.9 | 44.5 | 10 |
| AD-572858.1 | 54.4 | 5.3 | 10 |
| AD-80806.9 | 1.4 | 0.5 | 10 |
| AD-890084.1 | 42.3 | 7.2 | 10 |
| AD-890085.1 | 151.9 | 21.0 | 10 |
| AD-568976.1 | 56.6 | 32.8 | 1 |
| AD-568978.1 | 46.8 | 16.6 | 1 |
| AD-569127.1 | 46.2 | 2.3 | 1 |
| AD-569133.1 | 109.6 | 22.6 | 1 |
| AD-569164.3 | 99.8 | 16.0 | 1 |
| AD-569164.4 | 39.9 | 1.3 | 1 |
| AD-569195.1 | 73.1 | 28.2 | 1 |
| AD-569237.1 | 86.5 | 26.9 | 1 |
| AD-569239.1 | 115.6 | 17.9 | 1 |
| AD-569272.3 | 117.3 | 13.3 | 1 |
| AD-569350.1 | 123.4 | 21.0 | 1 |
| AD-569571.1 | 77.2 | 28.3 | 1 |
| AD-569763.3 | 96.4 | 22.9 | 1 |
| AD-569764.1 | 107.4 | 7.7 | 1 |
| AD-569766.1 | 72.0 | 37.4 | 1 |
| AD-569816.1 | 84.3 | 29.9 | 1 |
| AD-570156.1 | 77.2 | 11.3 | 1 |
| AD-570466.1 | 112.4 | 31.4 | 1 |
| AD-570470.1 | 87.9 | 18.5 | 1 |
| AD-570471.1 | 95.2 | 8.7 | 1 |
| AD-570474.1 | 100.2 | 21.4 | 1 |
| AD-570475.1 | 100.1 | 17.1 | 1 |
| AD-570476.1 | 65.5 | 4.2 | 1 |
| AD-570620.1 | 88.9 | 22.3 | 1 |
| AD-570621.1 | 114.1 | 57.6 | 1 |
| AD-570622.1 | 118.7 | 26.7 | 1 |
| AD-570623.1 | 107.4 | 25.7 | 1 |
| AD-570624.1 | 100.8 | 23.8 | 1 |
| AD-570625.1 | 134.9 | 17.5 | 1 |
| AD-570627.1 | 117.1 | 19.9 | 1 |
| AD-570631.1 | 67.0 | 1.7 | 1 |
| AD-570632.1 | 78.9 | 17.5 | 1 |
| AD-570672.1 | 85.0 | 25.5 | 1 |
| AD-570674.1 | 92.1 | 28.0 | 1 |
| AD-570675.1 | 127.1 | 18.9 | 1 |
| AD-570676.1 | 111.7 | 28.9 | 1 |
| AD-570677.1 | 139.7 | 35.4 | 1 |
| AD-570678.1 | 150.4 | 15.1 | 1 |
| AD-570679.1 | 76.8 | 12.4 | 1 |
| AD-570680.1 | 98.3 | 14.7 | 1 |
| AD-570681.1 | 110.4 | 10.0 | 1 |
| AD-570682.1 | 66.0 | 15.0 | 1 |
| AD-570717.1 | 99.7 | 8.4 | 1 |
| AD-570963.1 | 132.6 | 25.3 | 1 |
| AD-571157.1 | 116.5 | 18.5 | 1 |
| AD-571158.1 | 117.7 | 23.5 | 1 |
| AD-571168.1 | 97.9 | 10.8 | 1 |
| AD-571298.1 | 22.6 | 12.7 | 1 |
| AD-571298.2 | 13.0 | 3.1 | 1 |
| AD-571447.1 | 100.3 | 4.7 | 1 |
| AD-571448.1 | 83.5 | 12.5 | 1 |
| AD-571449.1 | 64.9 | 9.1 | 1 |
| AD-571539.4 | 94.1 | 20.2 | 1 |
| AD-571719.1 | 81.1 | 35.0 | 1 |
| AD-571752.3 | 93.9 | 17.5 | 1 |
| AD-571753.1 | 59.7 | 12.0 | 1 |
| AD-571765.1 | 114.5 | 18.7 | 1 |
| AD-571766.1 | 105.2 | 10.6 | 1 |
| AD-571767.1 | 111.3 | 22.5 | 1 |
| AD-571825.1 | 95.5 | 6.9 | 1 |
| AD-571826.1 | 94.3 | 20.3 | 1 |
| AD-571900.1 | 105.4 | 22.4 | 1 |
| AD-571945.1 | 104.8 | 17.4 | 1 |
| AD-571948.1 | 104.1 | 21.3 | 1 |
| AD-572039.3 | 135.4 | 11.0 | 1 |
| AD-572040.3 | 128.9 | 26.4 | 1 |
| AD-572041.3 | 115.9 | 43.0 | 1 |
| AD-572044.1 | 112.3 | 6.8 | 1 |
| AD-572049.1 | 86.1 | 12.8 | 1 |
| AD-572060.1 | 133.9 | 13.8 | 1 |
| AD-572061.2 | 137.5 | 3.0 | 1 |
| AD-572062.3 | 86.9 | 5.7 | 1 |
| AD-572108.1 | 109.8 | 25.8 | 1 |
| AD-572235.1 | 75.6 | 17.8 | 1 |
| AD-572258.1 | 36.8 | 7.4 | 1 |
| AD-572278.1 | 49.8 | 16.2 | 1 |
| AD-572279.1 | 73.8 | 28.3 | 1 |
| AD-572281.1 | 56.8 | 13.9 | 1 |
| AD-572355.1 | 96.9 | 13.9 | 1 |
| AD-572356.1 | 95.9 | 11.2 | 1 |
| AD-57238.2 | 132.4 | 20.9 | 1 |
| AD-572387.1 | 60.5 | 21.8 | 1 |
| AD-572388.4 | 39.8 | 10.3 | 1 |
| AD-572389.3 | 26.0 | 7.1 | 1 |
| AD-572390.2 | 88.5 | 25.7 | 1 |
| AD-572393.1 | 114.8 | 25.2 | 1 |
| AD-572613.1 | 82.7 | 16.4 | 1 |
| AD-572614.1 | 121.5 | 9.4 | 1 |
| AD-572858.1 | 90.8 | 9.7 | 1 |
| AD-80806.9 | 6.1 | 2.3 | 1 |
| AD-890084.1 | 90.9 | 24.6 | 1 |
| AD-890085.1 | 108.3 | 63.0 | 1 |
| AD-568976.1 | 108.7 | 10.5 | 0.1 |
| AD-568978.1 | 89.4 | 17.2 | 0.1 |
| AD-569127.1 | 113.6 | 35.6 | 0.1 |
| AD-569133.1 | 83.3 | 16.5 | 0.1 |
| AD-569164.3 | 103.9 | 28.8 | 0.1 |
| AD-569164.4 | 112.7 | 28.0 | 0.1 |
| AD-569195.1 | 148.7 | 14.3 | 0.1 |
| AD-569237.1 | 123.3 | 25.7 | 0.1 |
| AD-569239.1 | 108.0 | 13.5 | 0.1 |
| AD-569272.3 | 107.5 | 14.8 | 0.1 |
| AD-569350.1 | 117.1 | 27.8 | 0.1 |
| AD-569571.1 | 107.2 | 30.7 | 0.1 |
| AD-569763.3 | 163.9 | 11.1 | 0.1 |
| AD-569764.1 | 73.1 | 10.8 | 0.1 |
| AD-569766.1 | 152.3 | 13.3 | 0.1 |
| AD-569816.1 | 118.5 | 24.7 | 0.1 |
| AD-570156.1 | 124.5 | 32.6 | 0.1 |
| AD-570466.1 | 103.6 | 25.5 | 0.1 |
| AD-570470.1 | 140.4 | 34.3 | 0.1 |
| AD-570471.1 | 124.0 | 35.8 | 0.1 |

TABLE 13-continued

C3 Single Dose Screens in PMH cells

| Duplex | Avg % C3 mRNA Remaining | SD | Dose nM |
|---|---|---|---|
| AD-570474.1 | 103.0 | 24.7 | 0.1 |
| AD-570475.1 | 90.4 | 10.1 | 0.1 |
| AD-570476.1 | 132.6 | 22.6 | 0.1 |
| AD-570620.1 | 129.3 | 46.6 | 0.1 |
| AD-570621.1 | 116.8 | 5.5 | 0.1 |
| AD-570622.1 | 109.1 | 17.6 | 0.1 |
| AD-570623.1 | 130.5 | 15.8 | 0.1 |
| AD-570624.1 | 92.6 | 14.7 | 0.1 |
| AD-570625.1 | 103.8 | 3.9 | 0.1 |
| AD-570627.1 | 99.9 | 0.5 | 0.1 |
| AD-570631.1 | 120.9 | 21.2 | 0.1 |
| AD-570632.1 | 124.5 | 21.6 | 0.1 |
| AD-570672.1 | 116.3 | 15.7 | 0.1 |
| AD-570674.1 | 80.7 | 13.7 | 0.1 |
| AD-570675.1 | 106.4 | 38.0 | 0.1 |
| AD-570676.1 | 83.4 | 16.8 | 0.1 |
| AD-570677.1 | 138.1 | 5.4 | 0.1 |
| AD-570678.1 | 103.1 | 16.3 | 0.1 |
| AD-570679.1 | 81.6 | 11.9 | 0.1 |
| AD-570680.1 | 121.7 | 20.3 | 0.1 |
| AD-570681.1 | 111.4 | 18.4 | 0.1 |
| AD-570682.1 | 128.5 | 22.4 | 0.1 |
| AD-570717.1 | 129.3 | 36.1 | 0.1 |
| AD-570963.1 | 129.7 | 28.9 | 0.1 |
| AD-571157.1 | 115.1 | 2.3 | 0.1 |
| AD-571158.1 | 131.7 | 29.6 | 0.1 |
| AD-571168.1 | 132.0 | 42.0 | 0.1 |
| AD-571298.1 | 81.0 | 15.3 | 0.1 |
| AD-571298.2 | 116.1 | 18.1 | 0.1 |
| AD-571447.1 | 142.9 | 60.2 | 0.1 |
| AD-571448.1 | 94.5 | 28.3 | 0.1 |
| AD-571449.1 | 137.8 | 18.9 | 0.1 |
| AD-571539.4 | 126.8 | 43.6 | 0.1 |
| AD-571719.1 | 95.0 | 22.0 | 0.1 |
| AD-571752.3 | 127.5 | 28.5 | 0.1 |
| AD-571753.1 | 142.2 | 39.1 | 0.1 |
| AD-571765.1 | 127.6 | 31.8 | 0.1 |
| AD-571766.1 | 161.2 | 16.9 | 0.1 |
| AD-571767.1 | 191.4 | 8.6 | 0.1 |
| AD-571825.1 | 132.2 | 37.6 | 0.1 |
| AD-571826.1 | 156.2 | 52.6 | 0.1 |
| AD-571900.1 | 135.3 | 24.6 | 0.1 |
| AD-571945.1 | 99.6 | 8.3 | 0.1 |
| AD-571948.1 | 80.1 | 14.9 | 0.1 |
| AD-572039.3 | 138.5 | 13.3 | 0.1 |
| AD-572040.3 | 140.2 | 7.2 | 0.1 |
| AD-572041.3 | 110.9 | 27.0 | 0.1 |
| AD-572044.1 | 111.8 | 14.5 | 0.1 |
| AD-572049.1 | 160.6 | 39.0 | 0.1 |
| AD-572060.1 | 113.3 | 18.8 | 0.1 |
| AD-572061.2 | 114.8 | 21.0 | 0.1 |
| AD-572062.3 | 131.5 | 32.8 | 0.1 |
| AD-572108.1 | 150.8 | 23.6 | 0.1 |
| AD-572235.1 | 80.3 | 11.2 | 0.1 |
| AD-572258.1 | 88.5 | 1.9 | 0.1 |
| AD-572278.1 | 99.5 | 19.6 | 0.1 |
| AD-572279.1 | 99.8 | 32.6 | 0.1 |
| AD-572281.1 | 108.0 | 7.9 | 0.1 |
| AD-572355.1 | 130.0 | 19.3 | 0.1 |
| AD-572356.1 | 131.8 | 29.0 | 0.1 |
| AD-57238.2 | 89.6 | 32.9 | 0.1 |
| AD-572387.1 | 136.2 | 34.6 | 0.1 |
| AD-572388.4 | 100.6 | 10.7 | 0.1 |
| AD-572389.3 | 98.0 | 21.8 | 0.1 |
| AD-572390.2 | 123.9 | 37.7 | 0.1 |
| AD-572393.1 | 132.4 | 45.2 | 0.1 |
| AD-572613.1 | 126.0 | 25.0 | 0.1 |
| AD-572614.1 | 78.8 | 11.9 | 0.1 |
| AD-572858.1 | 103.7 | 19.5 | 0.1 |
| AD-80806.9 | 27.8 | 3.0 | 0.1 |
| AD-890084.1 | 152.2 | 33.6 | 0.1 |
| AD-890085.1 | 112.9 | 8.8 | 0.1 |

Example 3. In Vivo Screening of dsRNA Duplexes in Mice

Duplexes of interest, identified from the above in vitro studies and shown in Table 15, were evaluated in vivo. In particular, at pre-dose day −14 wild-type mice (C57BL/6) were transduced by intravenous administration of $2 \times 10^{11}$ viral particles of an adeno-associated virus 8 (AAV8) vector encoding human complement component C3. In particular, mice were administered an AAV8 encoding a portion of human complement component C3 mRNA spanning nucleotides 93-2893 of NM_000064.3, which includes a portion proximal to the 5' UTR (referred to herein as AAV8.HsC3_p1), or an AAV8 encoding a portion of human complement component C3 mRNA spanning nucleotides 2293-4531 of NM_000064.3, which includes a portion of the 3' UTR (referred to herein as AAV8.HsC3_p2).

At day 0, groups of three mice were subcutaneously administered a single 2 mg/kg dose of the agents of interest or PBS control. Table 14 provides the treatment groups and Table 15 provides the modified nucleotide sequences of the sense and antisense strands of the duplexes of interest. At day 14 post-dose animals were sacrificed, liver samples were collected and snap-frozen in liquid nitrogen. Tissue mRNA was extracted and analyzed by the RT-QPCR method.

Figure 2:
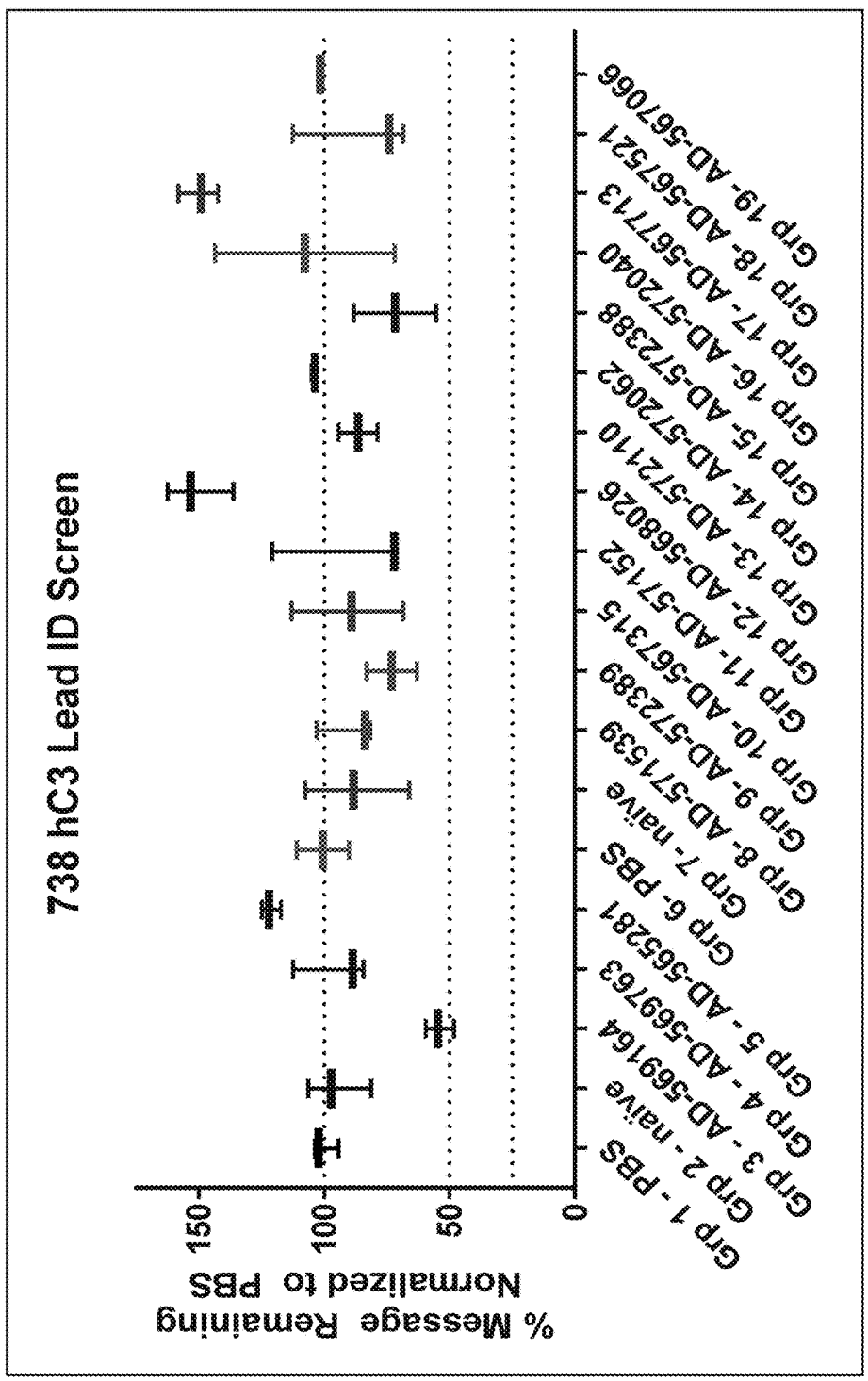
FIG. 2 is a graph showing C3 mRNA levels in mice (n=3 per group) subcutaneously administered a single 2 mg/kg dose of the indicated dsRNA duplexes, on day 14 post-dose. C3 mRNA levels are shown relative to control levels detected with PBS treatment.

Human C3 mRNA levels were compared to housekeeping gene GAPDH. The values were then normalized to the average of PBS vehicle control group. The data were expressed as percent of baseline value, and presented as mean plus standard deviation. The results, listed in Table 16 and shown in FIG. 2, demonstrate that the exemplary duplex agents tested effectively reduce the level of the human C3 messenger RNA in vivo.

TABLE 14

| Group # | Animal # | Treatment | AAV | Dose |
|---|---|---|---|---|
| 1 | 1 | PBS | AAV8.HsC3_p1 | 2 mpk |
|  | 2 |  |  |  |
|  | 3 |  |  |  |
| 2 | 4 | Naïve |  |  |
|  | 5 |  |  |  |
|  | 6 |  |  |  |
| 3 | 7 | AD-569164.2 |  |  |
|  | 8 |  |  |  |
|  | 9 |  |  |  |
| 4 | 10 | AD-569763.2 |  |  |
|  | 11 |  |  |  |
|  | 12 |  |  |  |
| 5 | 13 | AD-565281.2 |  |  |
|  | 14 |  |  |  |
|  | 15 |  |  |  |
| 6 | 16 | PBS | AAV8.HsC3_p2 | 2 mpk |
|  | 17 |  |  |  |
|  | 18 |  |  |  |
| 7 | 19 | Naïve |  |  |
|  | 20 |  |  |  |
|  | 21 |  |  |  |
| 8 | 22 | AD-571539.2 |  |  |
|  | 23 |  |  |  |
|  | 24 |  |  |  |
| 9 | 25 | AD-572389.2 |  |  |
|  | 26 |  |  |  |
|  | 27 |  |  |  |
| 10 | 28 | AD-567315.2 |  |  |
|  | 29 |  |  |  |
|  | 30 |  |  |  |
| 11 | 31 | AD-571752.2 |  |  |
|  | 32 |  |  |  |
|  | 33 |  |  |  |

TABLE 14-continued

| Group # | Animal # | Treatment | AAV | Dose |
|---|---|---|---|---|
| 12 | 34 | AD-568026.2 | | |
|  | 35 | | | |
|  | 36 | | | |
| 13 | 37 | AD-572110.2 | | |
|  | 38 | | | |
|  | 39 | | | |
| 14 | 40 | AD-572062.2 | | |
|  | 41 | | | |
|  | 42 | | | |
| 15 | 43 | AD-572388.2 | | |
|  | 44 | | | |
|  | 45 | | | |
| 16 | 46 | AD-572040.2 | | |
|  | 47 | | | |
|  | 48 | | | |
| 17 | 49 | AD-567713.2 | | |
|  | 50 | | | |
|  | 51 | | | |
| 18 | 52 | AD-567521.2 | | |
|  | 53 | | | |
|  | 54 | | | |
| 19 | 55 | AD-567066.2 | | |
|  | 56 | | | |
|  | 57 | | | |

TABLE 15

| Duplex ID | Oligo ID | Strand | Nucleotide Sequence 5' to 3' | SEQ ID NO: |
|---|---|---|---|---|
| AD-569164.2 | A-1085246.1 | sense | asgsauccG faGfCfCfu acuaugaau L96 | 1070 |
|  | A-1093171.1 | antis | asUfsucaU faGfUfagg cUfcGfgau cususc | 1071 |
| AD-569763.2 | A-1086444.1 | sense | usgsggcaA fcUfCfCfa acaauuacu L96 | 1072 |
|  | A-1093754.1 | antis | asGfsuaaU fuGfUfugg aGfuUfgcc cascsg | 1073 |
| AD-565281.2 | A-1085944.1 | sense | csusaccaG faUfCfCfa cuucaccau L96 | 1074 |
|  | A-1085945.1 | antis | asUfsggug (Agn)agug gaUfcUfgg uagsgsg | 1075 |
| AD-571539.2 | A-1089996.2 | sense | ususccuuG faAfGfCfc aacuacauu L96 | 1076 |
|  | A-1095513.1 | antis | asAfsuguA fgUfUfggc uUfcAfagg aasgsu | 1077 |
| AD-572389.2 | A-1091696.2 | sense | asasggucU faCfGfCfc uauuacauu L96 | 1078 |
|  | A-1096354.1 | antis | asUfsuguA faUfAfggc gUfaGfacc uusgsa | 1079 |
| AD-567315.2 | A-1090012.1 | sense | asgsccaaC fuAfCfAfu gaaccuacu L96 | 1080 |
|  | A-1090013.1 | antis | asGfsuagg (Tgn)ucau guAfgUfug gcususc | 1081 |
| AD-571752.2 | A-1090422.1 | sense | uscsgugcG fuUfGfGfc ucaaugaau L96 | 1082 |
|  | A-1095726.1 | antis | asUfsucaU fuGfAfgcc aAfcGfcac gascsg | 1083 |
| AD-568026.2 | A-1091434.1 | sense | usgsgacaA faGfCfCfu ucuccgauu L96 | 1084 |
|  | A-1091435.1 | antis | asAfsucgg (Agn)gaag gcUfuUfgu ccasgsc | 1085 |
| AD-572110.2 | A-1091138.1 | sense | gsasugccA faGfAfAfc acaugauu L96 | 1086 |
|  | A-1096084.1 | antis | asAfsucaU faGfUfguu cUfuGfgca ucscsu | 1087 |
| AD-572062.2 | A-1091042.1 | sense | csuscaagG fuCfAfCfc auaaaaccu L96 | 1088 |
|  | A-1096036.1 | antis | asGfsguuU fuAfUfggu gAfcCfuug agsgsu | 1089 |
| AD-572388.2 | A-1091694.2 | sense | csasagguC fuAfCfGfc cuauuacau L96 | 1090 |
|  | A-1096353.1 | antis | asUfsguaA fuAfGfgcg uAfgAfccu ugsasc | 1091 |
| AD-572040.2 | A-1090998.2 | sense | ascsucacC fuGfUfAfa uaaauucgu L96 | 1092 |
|  | A-1096014.1 | antis | asCfsgaaU fuUfAfuua cAfgGfuga gususg | 1093 |
| AD-567713.2 | A-1090808.1 | sense | ascscaagG faAfAfAfu gagguuuu L96 | 1094 |

TABLE 15-continued

| Duplex ID | Oligo ID | Strand | Nucleotide Sequence 5' to 3' | SEQ ID NO: |
|---|---|---|---|---|
| | A-1090809.1 | antis | asAfsaacc(Cgn)ucauuuUfcCfuugguscsu | 1095 |
| AD-567521.2 | A-1090424.1 | sense | csgsugcgUfuGfGfCfucaaugaacuL96 | 1096 |
| | A-1090425.1 | antis | asGfsuuca(Tgn)ugagccAfaCfgcacgsasc | 1097 |
| AD-567066.2 | A-1089514.1 | sense | csgsugguCfaAfGfGfucuucucucuL96 | 1098 |
| | A-1089515.1 | antis | asGfsagag(Agn)agacuUfgAfccacgsusa | 1099 |

TABLE 16

| Duplex | Avg | SD |
|---|---|---|
| PBS | 100.10 | 5.09 |
| Naïve | 95.00 | 12.77 |
| AD-569164.2 | 54.14 | 5.78 |
| AD-569763.2 | 95.20 | 15.06 |
| AD-565281.2 | 121.24 | 3.82 |
| PBS | 100.57 | 14.71 |
| Naïve | 87.32 | 20.75 |
| AD-571539.2 | 89.52 | 11.77 |
| AD-572389.2 | 73.16 | 14.10 |
| AD-567315.2 | 90.15 | 22.27 |
| AD-571752.2 | 87.97 | 28.36 |
| AD-568026.2 | 150.52 | 13.23 |
| AD-572110.2 | 86.55 | 10.98 |
| AD-572062.2 | 104.01 | 0.90 |
| AD-572388.2 | 71.83 | 23.25 |
| AD-572040.2 | 107.74 | 50.53 |
| AD-567713.2 | 149.76 | 7.94 |
| AD-567521.2 | 85.10 | 23.93 |
| AD-567066.2 | 101.62 | 0.28 |

Additional duplexes of interest, identified from the above in vitro studies and shown in Table 18, were also evaluated in vivo. In particular, at pre-dose day −14 wild-type mice (C57BL/6) were transduced by intravenous administration of $2 \times 10^{11}$ viral particles of an adeno-associated virus 8 (AAV8) vector encoding human complement component C3.

At day 0, groups of three mice were subcutaneously administered a single 2 mg/kg dose of the agents of interest or PBS control. Table 17 provides the treatment groups and Table 18 provides the modified nucleotide sequences of the sense and antisense strands of the duplexes of interest. At day 14 post-dose animals were sacrificed, liver samples were collected and snap-frozen in liquid nitrogen. Tissue mRNA was extracted and analyzed by the RT-QPCR method.

Figure 3:
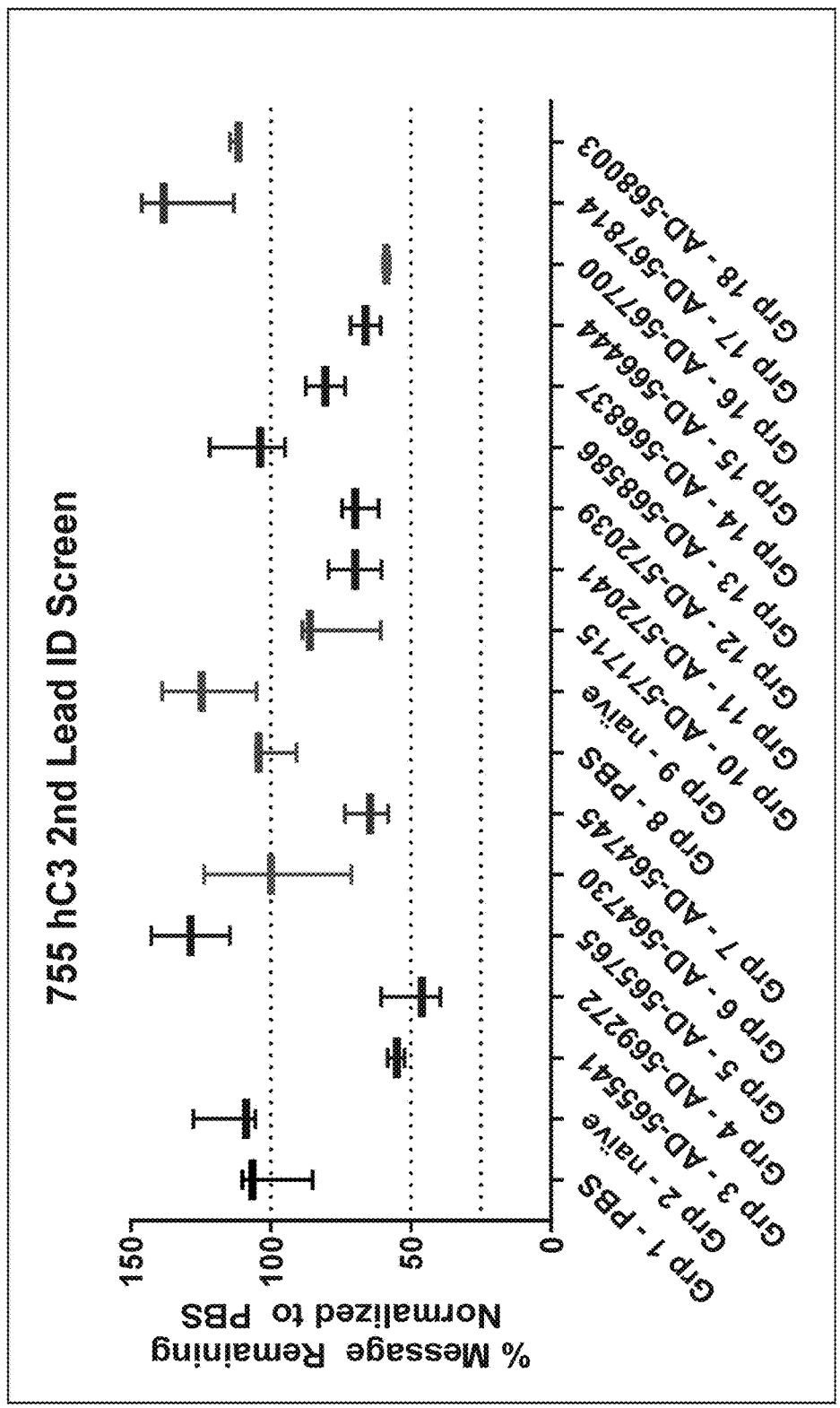
FIG. 3 is a graph showing C3 mRNA levels in mice (n=3 per group) subcutaneously administered a single 2 mg/kg dose of the indicated dsRNA duplexes, on day 14 post-dose. C3 mRNA levels are shown relative to control levels detected with PBS treatment.

Human C3 mRNA levels were compared to housekeeping gene GAPDH. The values were then normalized to the average of PBS vehicle control group. The data were expressed as percent of baseline value, and presented as mean plus standard deviation. The results, listed in Table 19 and shown in FIG. 3, demonstrate that the exemplary duplex agents tested effectively reduce the level of the human C3 messenger RNA in vivo.

TABLE 17

| Group # | Animal # | Treatment | AAV | Dose |
|---|---|---|---|---|
| 1 | 1 | PBS | AAV8.HsC3_p1 | 2 mpk |
| | 2 | | | |
| | 3 | | | |
| 2 | 4 | Naïve | | |
| | 5 | | | |
| | 6 | | | |
| 3 | 7 | AD-565541.2 | | |
| | 8 | | | |
| | 9 | | | |
| 4 | 10 | AD-569272.2 | | |
| | 11 | | | |
| | 12 | | | |
| 5 | 13 | AD-569765.2 | | |
| | 14 | | | |
| | 15 | | | |
| 6 | 16 | AD-564730.2 | | |
| | 17 | | | |
| | 18 | | | |
| 7 | 19 | AD-564745.2 | | |
| | 20 | | | |
| | 21 | | | |
| 8 | 22 | PBS | AAV8.HsC3_p2 | 2 mpk |
| | 23 | | | |
| | 24 | | | |
| 9 | 25 | Naïve | | |
| | 26 | | | |
| | 27 | | | |
| 10 | 28 | AD-571715.2 | | |
| | 29 | | | |
| | 30 | | | |
| 11 | 31 | AD-572041.2 | | |
| | 32 | | | |
| | 33 | | | |
| 12 | 34 | AD-572039.2 | | |
| | 35 | | | |
| | 36 | | | |
| 13 | 37 | AD-568586.2 | | |
| | 38 | | | |
| | 39 | | | |
| 14 | 40 | AD-566837.2 | | |
| | 41 | | | |
| | 42 | | | |
| 15 | 43 | AD-566444.2 | | |
| | 44 | | | |
| | 45 | | | |
| 16 | 46 | AD-567700.2 | | |
| | 47 | | | |
| | 48 | | | |
| 17 | 49 | AD-567814.2 | | |
| | 50 | | | |
| | 51 | | | |
| 18 | 52 | AD-568003.2 | | |
| | 53 | | | |
| | 54 | | | |

TABLE 18

| Duplex ID | Oligo ID | Strand | Nucleotide Sequence 5' to 3' | SEQ ID NO: |
|---|---|---|---|---|
| AD-565541.2 | A-1086464.1 | sense | csasacaaUfuAfCfCfugcaucucuuL96 | 1100 |
| | A-1086465.1 | antis | asAfsgaga(Tgn)gcagguAfaUfuguugsgsa | 1101 |
| AD-569272.2 | A-1085462.2 | sense | asasuucuAfcUfAfCfaucuauaacuL96 | 1102 |

TABLE 18-continued

| Duplex ID | Oligo ID | Strand | Nucleotide Sequence 5' to 3' | SEQ ID NO: |
|---|---|---|---|---|
| | A-1093279.1 | antis | asGfsuuaU faGfAfugu aGfuAfgaa uususc | 1103 |
| AD-569765.2 | A-1086448.1 | sense | gsgscaacU fcCfAfAfc aauuaccuu L96 | 1104 |
| | A-1093756.1 | antis | asAfsgguA faUfUfguu gGfaGfuug ccscsa | 1105 |
| AD-564730.2 | A-1084842.1 | sense | gsusaccuC fuUfCfAfu ccagacagu L96 | 1106 |
| | A-1084843.1 | antis | asCfsuguc (Tgn)ggau gaAfgAfgg uacscsc | 1107 |
| AD-564745.2 | A-1084872.1 | sense | gsascagaC faAfGfAfc caucuacau L96 | 1108 |
| | A-1084873.1 | antis | asUfsguag (Agn)uggu cuUfgUfcu gucsusg | 1109 |
| AD-571715.2 | A-1090348.1 | sense | csusacugC faGfCfUfa aaagacuuu L96 | 1110 |
| | A-1095689.1 | antis | asAfsaguC fuUfUfuag cUfgCfagu agsgsg | 1111 |
| AD-572041.2 | A-1091000.2 | sense | csuscaccU fgUfAfAfu aaauucgau L96 | 1112 |
| | A-1096015.1 | antis | asUfscgaA fuUfUfauu aCfaGfgug agsusu | 1113 |
| AD-572039.2 | A-1090996.1 | sense | asascucaC fcUfGfUfa auaaauucu L96 | 1114 |
| | A-1096013.1 | antis | asGfsaauU fuAfUfuac aGfgUfgag uusgsa | 1115 |
| AD-568586.2 | A-1092554.1 | sense | gsasgaacC faGfAfAfa caaugccau L96 | 1116 |
| | A-1092555.1 | antis | asUfsggca (Tgn)uguu ucUfgGfuu cucsusu | 1117 |
| AD-566837.2 | A-1089056.1 | sense | cscsgaguC fuGfAfGfa ccagaauuu L96 | 1118 |
| | A-1089057.1 | antis | asAfsauuc (Tgn)gguc ucAfgAfcu cggsusg | 1119 |
| AD-566444.2 | A-1088270.1 | sense | ascsccuaC fuCfUfGfu uguucgaau L96 | 1120 |
| | A-1088271.1 | antis | asUfsucga (Agn)caac agAfgUfag ggusasg | 1121 |
| AD-567700.2 | A-1090782.1 | sense | usgscgauC faGfAfAfg agaccaagu L96 | 1122 |
| | A-1090783.1 | antis | asCfsuugg (Tgn)cucu ucUfgAfuc gcasgsg | 1123 |
| AD-567814.2 | A-1091010.1 | sense | csusguaaU faAfAfUfu cgaccucau L96 | 1124 |
| | A-1091011.1 | antis | asUfsgagg (Tgn)cgaa uuUfaUfua cagsgsu | 1125 |
| AD-568003.2 | A-1091388.1 | sense | csasgauaC faUfCfUfc caaguaugu L96 | 1126 |
| | A-1091389.1 | antis | asCfsauac (Tgn)ugga gaUfgUfau cugsusc | 1127 |

TABLE 19

| Duplex | Avg | SD |
|---|---|---|
| AD-565541.2 | 55.32 | 3.02 |
| AD-569272.2 | 48.80 | 10.91 |
| AD-569765.2 | 128.71 | 20.00 |
| AD-564730.2 | 98.43 | 26.22 |
| AD-564745.2 | 65.56 | 7.73 |
| AD-571715.2 | 78.62 | 15.38 |
| AD-572041.2 | 70.13 | 9.43 |
| AD-572039.2 | 68.83 | 6.56 |
| AD-568586.2 | 106.88 | 13.68 |
| AD-566837.2 | 80.63 | 9.98 |
| AD-566444.2 | 66.32 | 7.57 |
| AD-567700.2 | 58.92 | 1.17 |
| AD-567814.2 | 132.61 | 17.19 |
| AD-568003.2 | 112.42 | 1.84 |

Example 4. Additional Duplexes Targeting Human C3

Additional agents targeting the human complement component C3 (C3) gene (human: NCBI refseqID NM_000064.3; NCBI GeneID: 718) were designed using custom R and Python scripts and synthesized as described above.

Detailed lists of the unmodified complement component C3 sense and antisense strand nucleotide sequences are shown in Tables 20 and 22. Detailed lists of the modified complement component C3 sense and antisense strand nucleotide sequences are shown in Tables 21 and 23.

Single dose screens of the additional agents were performed by free uptake and transfection.

For free uptake, experiments were performed by adding 2.5 µl of siRNA duplexes in PBS per well into a 96 well plate. Complete growth media (47.5 µl) containing about 1.5×10⁴ primary *cynomolgus* hepatocytes (PCH) were then added to the siRNA. Cells were incubated for 48 hours prior to RNA purification and RT-qPCR. Single dose experiments were performed at 500 nM, 100 nM, and 10 nM final duplex concentration.

For transfections, 7.5 µl of Opti-MEM plus 0.1 µl of Lipofectamine RNAiMax per well (Invitrogen, Carlsbad CA. cat #13778-150) was added to 2.5 µl of each siRNA duplex to an individual well in a 384-well plate. The mixture was then incubated at room temperature for 15 minutes. Forty µl of complete growth media without antibiotic containing ~1.5×10⁴ primary *cynomolgus* hepatocytes (PCH) were then added to the siRNA mixture. Cells were incubated for 24 hours prior to RNA purification. Single dose experiments were performed at 50, nM, 10 nM, 1 nM, and 0.1 nM final duplex concentration.

Total RNA isolation was performed using DYNABEADS. Briefly, cells are lysed in 10 µl of Lysis/Binding Buffer containing 3 µL of beads per well are mixed for 10 minutes on an electrostatic shaker. The washing steps are automated on a Biotek EL406, using a magnetic plate support. Beads are washed (in 3 L) once in Buffer A, once in Buffer B, and twice in Buffer E, with aspiration steps in between. Following a final aspiration, complete 12 µL RT mixture is added to each well, as described below.

For cDNA synthesis, a master mix of 1.5 µl 10× Buffer, 0.6 µl 10× dNTPs, 1.5 µl Random primers, 0.75 µl Reverse Transcriptase, 0.75 µl RNase inhibitor and 9.9 µl of H₂O per reaction were added per well. Plates were sealed, agitated for 10 minutes on an electrostatic shaker, and then incubated at 37 degrees C. for 2 hours. Following this, the plates were agitated at 80 degrees C. for 8 minutes.

RT-qPCR was performed as described above and relative fold change was calculated as described above.

The results of the free uptake experiments (FU) and the transfection experiments (TX) of the dsRNA agents in Tables 20 and 21 in PCH are shown in Tables 24-26. The results of the free uptake experiments (FU) and the transfection experiments (TX) of the dsRNA agents in Tables 22 and 23 in PCH are shown in Tables 27-29.

TABLE 20

Unmodified Sense and Antisense Strand Sequences of Complement Component C3 dsRNA Agents

| Duplex Name | Sense Sequence 5' to 3' | SEQ ID NO: | Range in NM_000 064.3 | Antisense Sequence 5' to 3' | SEQ ID NO: | Range in NM_000 064.3 |
|---|---|---|---|---|---|---|
| AD-570137.1 | GUGCUGAAUAAGAAGAACAAU | 1128 | 1903-1923 | AUUGUUCUUCUUAUUCAGCACGA | 1393 | 1901-1923 |
| AD-570138.1 | UGCUGAAUAAGAAGAACAAAU | 1129 | 1904-1924 | AUUUGUUCUUCUUAUUCAGCACG | 1394 | 1902-1924 |
| AD-570139.1 | GCUGAAUAAGAAGAACAAACU | 1130 | 1905-1925 | AGUUUGUUCUUCUUAUUCAGCAC | 1395 | 1903-1925 |
| AD-570140.1 | CUGAAUAAGAAGAACAAACUU | 1131 | 1906-1926 | AAGUUUGUUCUUCUUAUUCAGCA | 1396 | 1904-1926 |
| AD-570141.1 | UGAAUAAGAAGAACAAACUGU | 1132 | 1907-1927 | ACAGUUUGUUCUUCUUAUUCAGC | 1397 | 1905-1927 |
| AD-570142.1 | GAAUAAGAAGAACAAACUGAU | 1133 | 1908-1928 | AUCAGUUUGUUCUUCUUAUUCAG | 1398 | 1906-1928 |
| AD-570143.1 | AAUAAGAAGAACAAACUGACU | 1134 | 1909-1929 | AGUCAGUUUGUUCUUCUUAUUCA | 1399 | 1907-1929 |
| AD-570144.1 | AUAAGAAGAACAAACUGACGU | 1135 | 1910-1930 | ACGUCAGUUUGUUCUUCUUAUUC | 1400 | 1908-1930 |
| AD-570145.1 | UAAGAAGAACAAACUGACGCU | 1136 | 1911-1931 | AGCGUCAGUUUGUUCUUCUUAUU | 1401 | 1909-1931 |
| AD-570146.1 | AAGAAGAACAAACUGACGCAU | 1137 | 1912-1932 | AUGCGUCAGUUUGUUCUUCUUAU | 1402 | 1910-1932 |
| AD-570147.1 | AGAAGAACAAACUGACGCAGU | 1138 | 1913-1933 | ACUGCGUCAGUUUGUUCUUCUUA | 1403 | 1911-1933 |
| AD-570148.1 | GAAGAACAAACUGACGCAGAU | 1139 | 1914-1934 | AUCUGCGUCAGUUUGUUCUUCUU | 1404 | 1912-1934 |
| AD-570149.1 | AAGAACAAACUGACGCAGAGU | 1140 | 1915-1935 | ACUCUGCGUCAGUUUGUUCUUCU | 1405 | 1913-1935 |
| AD-570150.1 | AGAACAAACUGACGCAGAGUU | 1141 | 1916-1936 | AACUCUGCGUCAGUUUGUUCUUC | 1406 | 1914-1936 |
| AD-570151.1 | GAACAAACUGACGCAGAGUAU | 1142 | 1917-1937 | AUACUCUGCGUCAGUUUGUUCUU | 1407 | 1915-1937 |
| AD-570152.1 | AACAAACUGACGCAGAGUAAU | 1143 | 1918-1938 | AUUACUCUGCGUCAGUUUGUUCU | 1408 | 1916-1938 |
| AD-570153.1 | ACAAACUGACGCAGAGUAAGU | 1144 | 1919-1939 | ACUUACUCUGCGUCAGUUUGUUC | 1409 | 1917-1939 |
| AD-570154.1 | CAAACUGACGCAGAGUAAGAU | 1145 | 1920-1940 | AUCUUACUCUGCGUCAGUUUGUU | 1410 | 1918-1940 |
| AD-570155.1 | AAACUGACGCAGAGUAAGAUU | 1146 | 1921-1941 | AAUCUUACUCUGCGUCAGUUUGU | 1411 | 1919-1941 |
| AD-570156.2 | AACUGACGCAGAGUAAGAUCU | 1147 | 1922-1942 | AGAUCUUACUCUGCGUCAGUUUG | 1412 | 1920-1942 |
| AD-570158.1 | CUGACGCAGAGUAAGAUCUGU | 1148 | 1924-1944 | ACAGAUCUUACUCUGCGUCAGUU | 1413 | 1922-1944 |
| AD-570159.1 | UGACGCAGAGUAAGAUCUGGU | 1149 | 1925-1945 | ACCAGAUCUUACUCUGCGUCAGU | 1414 | 1923-1945 |
| AD-570160.1 | GACGCAGAGUAAGAUCUGGGU | 1150 | 1926-1946 | ACCCAGAUCUUACUCUGCGUCAG | 1415 | 1924-1946 |

TABLE 20-continued

Unmodified Sense and Antisense Strand Sequences of Complement Component C3 dsRNA Agents

| Duplex Name | Sense Sequence 5' to 3' | SEQ ID NO: | Range in NM_000 064.3 | Antisense Sequence 5' to 3' | SEQ ID NO: | Range in NM_000 064.3 |
|---|---|---|---|---|---|---|
| AD-570161.1 | ACGCAGAGUAAGAUCUGGGAU | 1151 | 1927-1947 | AUCCCAGAUCUUACUCUGCGUCA | 1416 | 1925-1947 |
| AD-570611.1 | UGAGCAUGUCGGACAAGAAAU | 1152 | 2513-2533 | AUUUCUUGUCCGACAUGCUCACA | 1417 | 2511-2533 |
| AD-570612.1 | GAGCAUGUCGGACAAGAAAGU | 1153 | 2514-2534 | ACUUUCUUGUCCGACAUGCUCAC | 1418 | 2512-2534 |
| AD-570613.1 | AGCAUGUCGGACAAGAAAGGU | 1154 | 2515-2535 | ACCUUUCUUGUCCGACAUGCUCA | 1419 | 2513-2535 |
| AD-570614.1 | GCAUGUCGGACAAGAAAGGGU | 1155 | 2516-2536 | ACCCUUUCUUGUCCGACAUGCUC | 1420 | 2514-2536 |
| AD-570615.1 | CAUGUCGGACAAGAAAGGGAU | 1156 | 2517-2537 | AUCCCUUUCUUGUCCGACAUGCU | 1421 | 2515-2537 |
| AD-570616.1 | AUGUCGGACAAGAAAGGGAUU | 1157 | 2518-2538 | AAUCCCUUUCUUGUCCGACAUGC | 1422 | 2516-2538 |
| AD-570617.1 | UGUCGGACAAGAAAGGGAUCU | 1158 | 2519-2539 | AGAUCCCUUUCUUGUCCGACAUG | 1423 | 2517-2539 |
| AD-570618.1 | GUCGGACAAGAAAGGGAUCUU | 1159 | 2520-2540 | AAGAUCCCUUUCUUGUCCGACAU | 1424 | 2518-2540 |
| AD-570619.1 | UCGGACAAGAAAGGGAUCUGU | 1160 | 2521-2541 | ACAGAUCCCUUUCUUGUCCGACA | 1425 | 2519-2541 |
| AD-570620.3 | CGGACAAGAAAGGGAUCUGUU | 1161 | 2522-2542 | AACAGAUCCCUUUCUUGUCCGAC | 1426 | 2520-2542 |
| AD-570621.2 | GGACAAGAAAGGGAUCUGUGU | 1162 | 2523-2543 | ACACAGAUCCCUUUCUUGUCCGA | 1427 | 2521-2543 |
| AD-570622.2 | GACAAGAAAGGGAUCUGUGUU | 1163 | 2524-2544 | AACACAGAUCCCUUUCUUGUCCG | 1428 | 2522-2544 |
| AD-570623.4 | ACAAGAAAGGGAUCUGUGUGU | 1164 | 2525-2545 | ACACACAGAUCCCUUUCUUGUCC | 1429 | 2523-2545 |
| AD-570624.2 | CAAGAAAGGGAUCUGUGUGGU | 1165 | 2526-2546 | ACCACACAGAUCCCUUUCUUGUC | 1430 | 2524-2546 |
| AD-570625.2 | AAGAAAGGGAUCUGUGUGGCU | 1166 | 2527-2547 | AGCCACACAGAUCCCUUUCUUGU | 1431 | 2525-2547 |
| AD-570626.1 | AGAAAGGGAUCUGUGUGGCAU | 1167 | 2528-2548 | AUGCCACACAGAUCCCUUUCUUG | 1432 | 2526-2548 |
| AD-570627.2 | GAAAGGGAUCUGUGUGGCAGU | 1168 | 2529-2549 | ACUGCCACACAGAUCCCUUUCUU | 1433 | 2527-2549 |
| AD-570628.1 | AAAGGGAUCUGUGUGGCAGAU | 1169 | 2530-2550 | AUCUGCCACACAGAUCCCUUUCU | 1434 | 2528-2550 |
| AD-570629.1 | AAGGGAUCUGUGUGGCAGACU | 1170 | 2531-2551 | AGUCUGCCACACAGAUCCCUUUC | 1435 | 2529-2551 |
| AD-570630.1 | AGGGAUCUGUGUGGCAGACCU | 1171 | 2532-2552 | AGGUCUGCCACACAGAUCCCUUU | 1436 | 2530-2552 |
| AD-1069837.1 | GGGAUCUGUGUGGCAGACCCU | 1172 | 2500-2520 | AGGGUCUGCCACACAGAUCCCUU | 1437 | 2498-2520 |
| AD-570707.1 | GAAAUCCGAGCCGUUCUCUAU | 1173 | 2629-2649 | AUAGAGAACGGCUCGGAUUUCCA | 1438 | 2627-2649 |
| AD-570708.1 | AAAUCCGAGCCGUUCUCUACU | 1174 | 2630-2650 | AGUAGAGAACGGCUCGGAUUUCC | 1439 | 2628-2650 |
| AD-570709.1 | AAUCCGAGCCGUUCUCUACAU | 1175 | 2631-2651 | AUGUAGAGAACGGCUCGGAUUUC | 1440 | 2629-2651 |
| AD-570710.1 | AUCCGAGCCGUUCUCUACAAU | 1176 | 2632-2652 | AUUGUAGAGAACGGCUCGGAUUU | 1441 | 2630-2652 |
| AD-570715.1 | AGCCGUUCUCUACAAUUACCU | 1177 | 2637-2657 | AGGUAAUUGUAGAGAACGGCUCG | 1442 | 2635-2657 |
| AD-570716.1 | GCCGUUCUCUACAAUUACCGU | 1178 | 2638-2658 | ACGGUAAUUGUAGAGAACGGCUC | 1443 | 2636-2658 |
| AD-570717.2 | CCGUUCUCUACAAUUACCGGU | 1179 | 2639-2659 | ACCGGUAAUUGUAGAGAACGGCU | 1444 | 2637-2659 |
| AD-570718.1 | CGUUCUCUACAAUUACCGGCU | 1180 | 2640-2660 | AGCCGGUAAUUGUAGAGAACGGC | 1445 | 2638-2660 |
| AD-570719.1 | GUUCUCUACAAUUACCGGCAU | 1181 | 2641-2661 | AUGCCGGUAAUUGUAGAGAACGG | 1446 | 2639-2661 |
| AD-570720.1 | UUCUCUACAAUUACCGGCAGU | 1182 | 2642-2662 | ACUGCCGGUAAUUGUAGAGAACG | 1447 | 2640-2662 |
| AD-570721.1 | UCUCUACAAUUACCGGCAGAU | 1183 | 2643-2663 | AUCUGCCGGUAAUUGUAGAGAAC | 1448 | 2641-2663 |
| AD-571285.1 | GGCUGACCGCUACGUGGUCU | 1184 | 3323-3343 | AGACCACGUAGGCGGUCAGCCAG | 1449 | 3321-3343 |
| AD-571286.1 | GCUGACCGCUACGUGGUCAU | 1185 | 3324-3344 | AUGACCACGUAGGCGGUCAGCCA | 1450 | 3322-3344 |
| AD-571287.1 | CUGACCGCUACGUGGUCAAU | 1186 | 3325-3345 | AUUGACCACGUAGGCGGUCAGCC | 1451 | 3323-3345 |
| AD-571288.1 | UGACCGCCUACGUGGUCAAGU | 1187 | 3326-3346 | ACUUGACCACGUAGGCGGUCAGC | 1452 | 3324-3346 |

TABLE 20-continued

Unmodified Sense and Antisense Strand Sequences of Complement Component C3 dsRNA Agents

| Duplex Name | Sense Sequence 5' to 3' | SEQ ID NO: | Range in NM_000 064.3 | Antisense Sequence 5' to 3' | SEQ ID NO: | Range in NM_000 064.3 |
|---|---|---|---|---|---|---|
| AD-571289.1 | GACCGCCUACGUGGUCAAGGU | 1188 | 3327-3347 | ACCUUGACCACGUAGGCGGUCAG | 1453 | 3325-3347 |
| AD-571290.1 | ACCGCCUACGUGGUCAAGGUU | 1189 | 3328-3348 | AACCUUGACCACGUAGGCGGUCA | 1454 | 3326-3348 |
| AD-571291.1 | CCGCCUACGUGGUCAAGGUCU | 1190 | 3329-3349 | AGACCUUGACCACGUAGGCGGUC | 1455 | 3327-3349 |
| AD-571292.1 | CGCCUACGUGGUCAAGGUCUU | 1191 | 3330-3350 | AAGACCUUGACCACGUAGGCGGU | 1456 | 3328-3350 |
| AD-571293.1 | GCCUACGUGGUCAAGGUCUUU | 1192 | 3331-3351 | AAAGACCUUGACCACGUAGGCGG | 1457 | 3329-3351 |
| AD-571294.1 | CCUACGUGGUCAAGGUCUUCU | 1193 | 3332-3352 | AGAAGACCUUGACCACGUAGGCG | 1458 | 3330-3352 |
| AD-571295.1 | CUACGUGGUCAAGGUCUUCUU | 1194 | 3333-3353 | AAGAAGACCUUGACCACGUAGGC | 1459 | 3331-3353 |
| AD-571296.1 | UACGUGGUCAAGGUCUUCUCU | 1195 | 3334-3354 | AGAGAAGACCUUGACCACGUAGG | 1460 | 3332-3354 |
| AD-571297.1 | ACGUGGUCAAGGUCUUCUCUU | 1196 | 3335-3355 | AAGAGAAGACCUUGACCACGUAG | 1461 | 3333-3355 |
| AD-571298.6 | CGUGGUCAAGGUCUUCUCUCU | 1197 | 3336-3356 | AGAGAGAAGACCUUGACCACGUA | 1462 | 3334-3356 |
| AD-571299.1 | GUGGUCAAGGUCUUCUCUCUU | 1198 | 3337-3357 | AAGAGAGAAGACCUUGACCACGU | 1463 | 3335-3357 |
| AD-571300.1 | UGGUCAAGGUCUUCUCUCUGU | 1199 | 3338-3358 | ACAGAGAGAAGACCUUGACCACG | 1464 | 3336-3358 |
| AD-571301.1 | GGUCAAGGUCUUCUCUCUGGU | 1200 | 3339-3359 | ACCAGAGAGAAGACCUUGACCAC | 1465 | 3337-3359 |
| AD-571302.1 | GUCAAGGUCUUCUCUCUGGCU | 1201 | 3340-3360 | AGCCAGAGAGAAGACCUUGACCA | 1466 | 3338-3360 |
| AD-571303.1 | UCAAGGUCUUCUCUCUGGCUU | 1202 | 3341-3361 | AAGCCAGAGAGAAGACCUUGACC | 1467 | 3339-3361 |
| AD-571304.1 | CAAGGUCUUCUCUCUGGCUGU | 1203 | 3342-3362 | ACAGCCAGAGAGAAGACCUUGAC | 1468 | 3340-3362 |
| AD-571305.1 | AAGGUCUUCUCUCUGGCUGUU | 1204 | 3343-3363 | AACAGCCAGAGAGAAGACCUUGA | 1469 | 3341-3363 |
| AD-571306.1 | AGGUCUUCUCUCUGGCUGUCU | 1205 | 3344-3364 | AGACAGCCAGAGAGAAGACCUUG | 1470 | 3342-3364 |
| AD-571307.1 | GGUCUUCUCUCUGGCUGUCAU | 1206 | 3345-3365 | AUGACAGCCAGAGAGAAGACCUU | 1471 | 3343-3365 |
| AD-571308.1 | GUCUUCUCUCUGGCUGUCAAU | 1207 | 3346-3366 | AUUGACAGCCAGAGAGAAGACCU | 1472 | 3344-3366 |
| AD-571309.1 | UCUUCUCUCUGGCUGUCAACU | 1208 | 3347-3367 | AGUUGACAGCCAGAGAGAAGACC | 1473 | 3345-3367 |
| AD-571526.1 | UAAAGCAGGAGACUUCCUUGU | 1209 | 3603-3623 | ACAAGGAAGUCUCCUGCUUUAGU | 1474 | 3601-3623 |
| AD-571527.1 | AAAGCAGGAGACUUCCUUGAU | 1210 | 3604-3624 | AUCAAGGAAGUCUCCUGCUUUAG | 1475 | 3602-3624 |
| AD-571528.1 | AAGCAGGAGACUUCCUUGAAU | 1211 | 3605-3625 | AUUCAAGGAAGUCUCCUGCUUUA | 1476 | 3603-3625 |
| AD-571529.1 | AGCAGGAGACUUCCUUGAAGU | 1212 | 3606-3626 | ACUUCAAGGAAGUCUCCUGCUUU | 1477 | 3604-3626 |
| AD-571530.1 | GCAGGAGACUUCCUUGAAGCU | 1213 | 3607-3627 | AGCUUCAAGGAAGUCUCCUGCUU | 1478 | 3605-3627 |
| AD-571531.1 | CAGGAGACUUCCUUGAAGCCU | 1214 | 3608-3628 | AGGCUUCAAGGAAGUCUCCUGCU | 1479 | 3606-3628 |
| AD-571532.1 | AGGAGACUUCCUUGAAGCCAU | 1215 | 3609-3629 | AUGGCUUCAAGGAAGUCUCCUGC | 1480 | 3607-3629 |
| AD-571533.1 | GGAGACUUCCUUGAAGCCAAU | 1216 | 3610-3630 | AUUGGCUUCAAGGAAGUCUCCUG | 1481 | 3608-3630 |
| AD-571534.1 | GAGACUUCCUUGAAGCCAACU | 1217 | 3611-3631 | AGUUGGCUUCAAGGAAGUCUCCU | 1482 | 3609-3631 |
| AD-568955.1 | AGAGCGGGUACCUCUUCAUCU | 1218 | 470-490 | AGAUGAAGAGGUACCCGCUCUGC | 1483 | 468-490 |
| AD-568956.1 | GAGCGGGUACCUCUUCAUCCU | 1219 | 471-491 | AGGAUGAAGAGGUACCCGCUCUG | 1484 | 469-491 |
| AD-568957.1 | AGCGGGUACCUCUUCAUCCAU | 1220 | 472-492 | AUGGAUGAAGAGGUACCCGCUCU | 1485 | 470-492 |
| AD-568958.1 | GCGGGUACCUCUUCAUCCAGU | 1221 | 473-493 | ACUGGAUGAAGAGGUACCCGCUC | 1486 | 471-493 |
| AD-568959.1 | CGGGUACCUCUUCAUCCAGAU | 1222 | 474-494 | AUCUGGAUGAAGAGGUACCCGCU | 1487 | 472-494 |
| AD-568960.1 | GGGUACCUCUUCAUCCAGACU | 1223 | 475-495 | AGUCUGGAUGAAGAGGUACCCGC | 1488 | 473-495 |
| AD-568961.1 | GGUACCUCUUCAUCCAGACAU | 1224 | 476-496 | AUGUCUGGAUGAAGAGGUACCCG | 1489 | 474-496 |

TABLE 20-continued

Unmodified Sense and Antisense Strand Sequences of Complement Component C3 dsRNA Agents

| Duplex Name | Sense Sequence 5' to 3' | SEQ ID NO: | Range in NM_000 064.3 | Antisense Sequence 5' to 3' | SEQ ID NO: | Range in NM_000 064.3 |
| --- | --- | --- | --- | --- | --- | --- |
| AD-568962.1 | GUACCUCUUCAUCCAGACAGU | 1225 | 477-497 | ACUGUCUGGAUGAAGAGGUACCC | 1490 | 475-497 |
| AD-568963.2 | UACCUCUUCAUCCAGACAGAU | 1226 | 478-498 | AUCUGUCUGGAUGAAGAGGUACC | 1491 | 476-498 |
| AD-568964.1 | ACCUCUUCAUCCAGACAGACU | 1227 | 479-499 | AGUCUGUCUGGAUGAAGAGGUAC | 1492 | 477-499 |
| AD-568965.1 | CCUCUUCAUCCAGACAGACAU | 1228 | 480-500 | AUGUCUGUCUGGAUGAAGAGGUA | 1493 | 478-500 |
| AD-568966.1 | CUCUUCAUCCAGACAGACAAU | 1229 | 481-501 | AUUGUCUGUCUGGAUGAAGAGGU | 1494 | 479-501 |
| AD-568967.1 | UCUUCAUCCAGACAGACAAGU | 1230 | 482-502 | ACUUGUCUGUCUGGAUGAAGAGG | 1495 | 480-502 |
| AD-568968.1 | CUUCAUCCAGACAGACAAGAU | 1231 | 483-503 | AUCUUGUCUGUCUGGAUGAAGAG | 1496 | 481-503 |
| AD-568969.1 | UUCAUCCAGACAGACAAGACU | 1232 | 484-504 | AGUCUUGUCUGUCUGGAUGAAGA | 1497 | 482-504 |
| AD-568970.1 | UCAUCCAGACAGACAAGACCU | 1233 | 485-505 | AGGUCUUGUCUGUCUGGAUGAAG | 1498 | 483-505 |
| AD-568971.1 | CAUCCAGACAGACAAGACCAU | 1234 | 486-506 | AUGGUCUUGUCUGUCUGGAUGAA | 1499 | 484-506 |
| AD-568972.1 | AUCCAGACAGACAAGACCAUU | 1235 | 487-507 | AAUGGUCUUGUCUGUCUGGAUGA | 1500 | 485-507 |
| AD-568973.1 | UCCAGACAGACAAGACCAUCU | 1236 | 488-508 | AGAUGGUCUUGUCUGUCUGGAUG | 1501 | 486-508 |
| AD-568974.1 | CCAGACAGACAAGACCAUCUU | 1237 | 489-509 | AAGAUGGUCUUGUCUGUCUGGAU | 1502 | 487-509 |
| AD-568975.1 | CAGACAGACAAGACCAUCUAU | 1238 | 490-510 | AUAGAUGGUCUUGUCUGUCUGGA | 1503 | 488-510 |
| AD-568977.1 | GACAGACAAGACCAUCUACAU | 1239 | 492-512 | AUGUAGAUGGUCUUGUCUGUCUG | 1504 | 490-512 |
| AD-568979.1 | CAGACAAGACCAUCUACACCU | 1240 | 494-514 | AGGUGUAGAUGGUCUUGUCUGUC | 1505 | 492-514 |
| AD-1069834.1 | AGACAAGACCAUCUACACCCU | 1241 | 495-515 | AGGGUGUAGAUGGUCUUGUCUGU | 1506 | 493-515 |
| AD-1069835.1 | GACAAGACCAUCUACACCCCU | 1242 | 496-516 | AGGGGUGUAGAUGGUCUUGUCUG | 1507 | 494-516 |
| AD-1069836.1 | ACAAGACCAUCUACACCCCUU | 1243 | 497-517 | AAGGGGUGUAGAUGGUCUUGUCU | 1508 | 495-517 |
| AD-569154.1 | GGCCAGUGGAAGAUCCGAGCU | 1244 | 697-717 | AGCUCGGAUCUUCCACUGGCCCA | 1509 | 695-717 |
| AD-569155.1 | GCCAGUGGAAGAUCCGAGCCU | 1245 | 698-718 | AGGCUCGGAUCUUCCACUGGCCC | 1510 | 696-718 |
| AD-569156.1 | CCAGUGGAAGAUCCGAGCCUU | 1246 | 699-719 | AAGGCUCGGAUCUUCCACUGGCC | 1511 | 697-719 |
| AD-569157.1 | CAGUGGAAGAUCCGAGCCUAU | 1247 | 700-720 | AUAGGCUCGGAUCUUCCACUGGC | 1512 | 698-720 |
| AD-569158.1 | AGUGGAAGAUCCGAGCCUACU | 1248 | 701-721 | AGUAGGCUCGGAUCUUCCACUGG | 1513 | 699-721 |
| AD-569159.1 | GUGGAAGAUCCGAGCCUACUU | 1249 | 702-722 | AAGUAGGCUCGGAUCUUCCACUG | 1514 | 700-722 |
| AD-569160.1 | UGGAAGAUCCGAGCCUACUAU | 1250 | 703-723 | AUAGUAGGCUCGGAUCUUCCACU | 1515 | 701-723 |
| AD-569161.1 | GGAAGAUCCGAGCCUACUAUU | 1251 | 704-724 | AAUAGUAGGCUCGGAUCUUCCAC | 1516 | 702-724 |
| AD-569162.1 | GAAGAUCCGAGCCUACUAUGU | 1252 | 705-725 | ACAUAGUAGGCUCGGAUCUUCCA | 1517 | 703-725 |
| AD-569163.1 | AAGAUCCGAGCCUACUAUGAU | 1253 | 706-726 | AUCAUAGUAGGCUCGGAUCUUCC | 1518 | 704-726 |
| AD-569166.1 | AUCCGAGCCUACUAUGAAAAU | 1254 | 709-729 | AUUUUCAUAGUAGGCUCGGAUCU | 1519 | 707-729 |
| AD-569167.1 | UCCGAGCCUACUAUGAAAACU | 1255 | 710-730 | AGUUUUCAUAGUAGGCUCGGAUC | 1520 | 708-730 |
| AD-569168.1 | CCGAGCCUACUAUGAAAACUU | 1256 | 711-731 | AAGUUUUCAUAGUAGGCUCGGAU | 1521 | 709-731 |
| AD-569169.1 | CGAGCCUACUAUGAAAACUCU | 1257 | 712-732 | AGAGUUUUCAUAGUAGGCUCGGA | 1522 | 710-732 |
| AD-569170.1 | GAGCCUACUAUGAAAACUCAU | 1258 | 713-733 | AUGAGUUUUCAUAGUAGGCUCGG | 1523 | 711-733 |
| AD-569171.1 | AGCCUACUAUGAAAACUCACU | 1259 | 714-734 | AGUGAGUUUUCAUAGUAGGCUCG | 1524 | 712-734 |
| AD-569172.1 | GCCUACUAUGAAAACUCACCU | 1260 | 715-735 | AGGUGAGUUUUCAUAGUAGGCUC | 1525 | 713-735 |
| AD-569173.1 | CCUACUAUGAAAACUCACCAU | 1261 | 716-736 | AUGGUGAGUUUUCAUAGUAGGCU | 1526 | 714-736 |

TABLE 20-continued

Unmodified Sense and Antisense Strand Sequences of Complement Component C3 dsRNA Agents

| Duplex Name | Sense Sequence 5' to 3' | SEQ ID NO: | Range in NM_000 064.3 | Antisense Sequence 5' to 3' | SEQ ID NO: | Range in NM_000 064.3 |
|---|---|---|---|---|---|---|
| AD-569174.1 | CUACUAUGAAAACUCACCACU | 1262 | 717-737 | AGUGGUGAGUUUUCAUAGUAGGC | 1527 | 715-737 |
| AD-569175.1 | UACUAUGAAAACUCACCACAU | 1263 | 718-738 | AUGUGGUGAGUUUUCAUAGUAGG | 1528 | 716-738 |
| AD-569262.1 | CCUACAGAGAAAUUCUACUAU | 1264 | 805-825 | AUAGUAGAAUUUCUCUGUAGGCU | 1529 | 803-825 |
| AD-569263.1 | CUACAGAGAAAUUCUACUACU | 1265 | 806-826 | AGUAGUAGAAUUUCUCUGUAGGC | 1530 | 804-826 |
| AD-569264.1 | UACAGAGAAAUUCUACUACAU | 1266 | 807-827 | AUGUAGUAGAAUUUCUCUGUAGG | 1531 | 805-827 |
| AD-569265.1 | ACAGAGAAAUUCUACUACAUU | 1267 | 808-828 | AAUGUAGUAGAAUUUCUCUGUAG | 1532 | 806-828 |
| AD-569266.1 | CAGAGAAAUUCUACUACAUCU | 1268 | 809-829 | AGAUGUAGUAGAAUUUCUCUGUA | 1533 | 807-829 |
| AD-569267.1 | AGAGAAAUUCUACUACAUCUU | 1269 | 810-830 | AAGAUGUAGUAGAAUUUCUCUGU | 1534 | 808-830 |
| AD-569268.1 | GAGAAAUUCUACUACAUCUAU | 1270 | 811-831 | AUAGAUGUAGUAGAAUUUCUCUG | 1535 | 809-831 |
| AD-569269.1 | AGAAAUUCUACUACAUCUAUU | 1271 | 812-832 | AAUAGAUGUAGUAGAAUUUCUCU | 1536 | 810-832 |
| AD-569270.1 | GAAAUUCUACUACAUCUAUAU | 1272 | 813-833 | AUAUAGAUGUAGUAGAAUUUCUC | 1537 | 811-833 |
| AD-569271.1 | AAAUUCUACUACAUCUAUAAU | 1273 | 814-834 | AUUAUAGAUGUAGUAGAAUUUCU | 1538 | 812-834 |
| AD-569273.1 | AUUCUACUACAUCUAUAACGU | 1274 | 816-836 | ACGUUAUAGAUGUAGUAGAAUUU | 1539 | 814-836 |
| AD-569274.1 | UUCUACUACAUCUAUAACGAU | 1275 | 817-837 | AUCGUUAUAGAUGUAGUAGAAUU | 1540 | 815-837 |
| AD-569275.1 | UCUACUACAUCUAUAACGAGU | 1276 | 818-838 | ACUCGUUAUAGAUGUAGUAGAAU | 1541 | 816-838 |
| AD-569276.1 | CUACUACAUCUAUAACGAGAU | 1277 | 819-839 | AUCUCGUUAUAGAUGUAGUAGAA | 1542 | 817-839 |
| AD-569277.1 | UACUACAUCUAUAACGAGAAU | 1278 | 820-840 | AUUCUCGUUAUAGAUGUAGUAGA | 1543 | 818-840 |
| AD-569278.1 | ACUACAUCUAUAACGAGAAGU | 1279 | 821-841 | ACUUCUCGUUAUAGAUGUAGUAG | 1544 | 819-841 |
| AD-569279.1 | CUACAUCUAUAACGAGAAGGU | 1280 | 822-842 | ACCUUCUCGUUAUAGAUGUAGUA | 1545 | 820-842 |
| AD-569280.1 | UACAUCUAUAACGAGAAGGGU | 1281 | 823-843 | ACCCUUCUCGUUAUAGAUGUAGU | 1546 | 821-843 |
| AD-569281.1 | ACAUCUAUAACGAGAAGGGCU | 1282 | 824-844 | AGCCCUUCUCGUUAUAGAUGUAG | 1547 | 822-844 |
| AD-569282.1 | CAUCUAUAACGAGAAGGGCCU | 1283 | 825-845 | AGGCCCUUCUCGUUAUAGAUGUA | 1548 | 823-845 |
| AD-569506.1 | CCUCUCCCUACCAGAUCCACU | 1284 | 1142-1162 | AGUGGAUCUGGUAGGGAGAGGUC | 1549 | 1140-1162 |
| AD-569507.1 | CUCUCCCUACCAGAUCCACUU | 1285 | 1143-1163 | AAGUGGAUCUGGUAGGGAGAGGU | 1550 | 1141-1163 |
| AD-569508.1 | UCUCCCUACCAGAUCCACUUU | 1286 | 1144-1164 | AAAGUGGAUCUGGUAGGGAGAGG | 1551 | 1142-1164 |
| AD-569509.1 | CUCCCUACCAGAUCCACUUCU | 1287 | 1145-1165 | AGAAGUGGAUCUGGUAGGGAGAG | 1552 | 1143-1165 |
| AD-569510.1 | UCCCUACCAGAUCCACUUCAU | 1288 | 1146-1166 | AUGAAGUGGAUCUGGUAGGGAGA | 1553 | 1144-1166 |
| AD-569511.1 | CCCUACCAGAUCCACUUCACU | 1289 | 1147-1167 | AGUGAAGUGGAUCUGGUAGGGAG | 1554 | 1145-1167 |
| AD-569512.1 | CCUACCAGAUCCACUUCACCU | 1290 | 1148-1168 | AGGUGAAGUGGAUCUGGUAGGGA | 1555 | 1146-1168 |
| AD-569513.1 | CUACCAGAUCCACUUCACCAU | 1291 | 1149-1169 | AUGGUGAAGUGGAUCUGGUAGGG | 1556 | 1147-1169 |
| AD-569514.1 | UACCAGAUCCACUUCACCAAU | 1292 | 1150-1170 | AUUGGUGAAGUGGAUCUGGUAGG | 1557 | 1148-1170 |
| AD-569515.1 | ACCAGAUCCACUUCACCAAGU | 1293 | 1151-1171 | ACUUGGUGAAGUGGAUCUGGUAG | 1558 | 1149-1171 |
| AD-569516.1 | CCAGAUCCACUUCACCAAGAU | 1294 | 1152-1172 | AUCUUGGUGAAGUGGAUCUGGUA | 1559 | 1150-1172 |
| AD-569517.1 | CAGAUCCACUUCACCAAGACU | 1295 | 1153-1173 | AGUCUUGGUGAAGUGGAUCUGGU | 1560 | 1151-1173 |
| AD-569518.1 | AGAUCCACUUCACCAAGACAU | 1296 | 1154-1174 | AUGUCUUGGUGAAGUGGAUCUGG | 1561 | 1152-1174 |
| AD-569519.1 | GAUCCACUUCACCAAGACACU | 1297 | 1155-1175 | AGUGUCUUGGUGAAGUGGAUCUG | 1562 | 1153-1175 |
| AD-569520.1 | AUCCACUUCACCAAGACACCU | 1298 | 1156-1176 | AGGUGUCUUGGUGAAGUGGAUCU | 1563 | 1154-1176 |

TABLE 20-continued

Unmodified Sense and Antisense Strand Sequences of Complement Component C3 dsRNA Agents

| Duplex Name | Sense Sequence 5' to 3' | SEQ ID NO: | Range in NM_000 064.3 | Antisense Sequence 5' to 3' | SEQ ID NO: | Range in NM_000 064.3 |
|---|---|---|---|---|---|---|
| AD-569565.1 | UUUGACCUCAUGGUGUUCGUU | 1299 | 1201-1221 | AACGAACACCAUGAGGUCAAAGG | 1564 | 1199-1221 |
| AD-569567.1 | UGACCUCAUGGUGUUCGUGAU | 1300 | 1203-1223 | AUCACGAACACCAUGAGGUCAAA | 1565 | 1201-1223 |
| AD-570126.1 | AGGGCGUGUUCGUGCUGAAUU | 1301 | 1892-1912 | AAUUCAGCACGAACACGCCCUUG | 1566 | 1890-1912 |
| AD-570127.1 | GGGCGUGUUCGUGCUGAAUAU | 1302 | 1893-1913 | AUAUUCAGCACGAACACGCCCUU | 1567 | 1891-1913 |
| AD-570128.1 | GGCGUGUUCGUGCUGAAUAAU | 1303 | 1894-1914 | AUUAUUCAGCACGAACACGCCCU | 1568 | 1892-1914 |
| AD-570129.1 | GCGUGUUCGUGCUGAAUAAGU | 1304 | 1895-1915 | ACUUAUUCAGCACGAACACGCCC | 1569 | 1893-1915 |
| AD-570131.1 | GUGUUCGUGCUGAAUAAGAAU | 1305 | 1897-1917 | AUUCUUAUUCAGCACGAACACGC | 1570 | 1895-1917 |
| AD-570135.1 | UCGUGCUGAAUAAGAAGAACU | 1306 | 1901-1921 | AGUUCUUCUUAUUCAGCACGAAC | 1571 | 1899-1921 |
| AD-570136.1 | CGUGCUGAAUAAGAAGAACAU | 1307 | 1902-1922 | AUGUUCUUCUUAUUCAGCACGAA | 1572 | 1900-1922 |
| AD-571535.1 | AGACUUCCUUGAAGCCAACUU | 1308 | 3612-3632 | AAGUUGGCUUCAAGGAAGUCUCC | 1573 | 3610-3632 |
| AD-571536.1 | GACUUCCUUGAAGCCAACUAU | 1309 | 3613-3633 | AUAGUUGGCUUCAAGGAAGUCUC | 1574 | 3611-3633 |
| AD-571537.1 | ACUUCCUUGAAGCCAACUACU | 1310 | 3614-3634 | AGUAGUUGGCUUCAAGGAAGUCU | 1575 | 3612-3634 |
| AD-571538.1 | CUUCCUUGAAGCCAACUACAU | 1311 | 3615-3635 | AUGUAGUUGGCUUCAAGGAAGUC | 1576 | 3613-3635 |
| AD-571540.1 | UCCUUGAAGCCAACUACAUGU | 1312 | 3617-3637 | ACAUGUAGUUGGCUUCAAGGAAG | 1577 | 3615-3637 |
| AD-571541.1 | CCUUGAAGCCAACUACAUGAU | 1313 | 3618-3638 | AUCAUGUAGUUGGCUUCAAGGAA | 1578 | 3616-3638 |
| AD-571542.1 | CUUGAAGCCAACUACAUGAAU | 1314 | 3619-3639 | AUUCAUGUAGUUGGCUUCAAGGA | 1579 | 3617-3639 |
| AD-571543.1 | UUGAAGCCAACUACAUGAACU | 1315 | 3620-3640 | AGUUCAUGUAGUUGGCUUCAAGG | 1580 | 3618-3640 |
| AD-571544.1 | UGAAGCCAACUACAUGAACCU | 1316 | 3621-3641 | AGGUUCAUGUAGUUGGCUUCAAG | 1581 | 3619-3641 |
| AD-571545.1 | GAAGCCAACUACAUGAACCUU | 1317 | 3622-3642 | AAGGUUCAUGUAGUUGGCUUCAA | 1582 | 3620-3642 |
| AD-571546.1 | AAGCCAACUACAUGAACCUAU | 1318 | 3623-3643 | AUAGGUUCAUGUAGUUGGCUUCA | 1583 | 3621-3643 |
| AD-571547.1 | AGCCAACUACAUGAACCUACU | 1319 | 3624-3644 | AGUAGGUUCAUGUAGUUGGCUUC | 1584 | 3622-3644 |
| AD-571548.1 | GCCAACUACAUGAACCUACAU | 1320 | 3625-3645 | AUGUAGGUUCAUGUAGUUGGCUU | 1585 | 3623-3645 |
| AD-571549.1 | CCAACUACAUGAACCUACAGU | 1321 | 3626-3646 | ACUGUAGGUUCAUGUAGUUGGCU | 1586 | 3624-3646 |
| AD-571550.1 | CAACUACAUGAACCUACAGAU | 1322 | 3627-3647 | AUCUGUAGGUUCAUGUAGUUGGC | 1587 | 3625-3647 |
| AD-571551.1 | AACUACAUGAACCUACAGAGU | 1323 | 3628-3648 | ACUCUGUAGGUUCAUGUAGUUGG | 1588 | 3626-3648 |
| AD-571552.1 | ACUACAUGAACCUACAGAGAU | 1324 | 3629-3649 | AUCUCUGUAGGUUCAUGUAGUUG | 1589 | 3627-3649 |
| AD-571553.1 | CUACAUGAACCUACAGAGAUU | 1325 | 3630-3650 | AAUCUCUGUAGGUUCAUGUAGUU | 1590 | 3628-3650 |
| AD-571554.1 | UACAUGAACCUACAGAGAUCU | 1326 | 3631-3651 | AGAUCUCUGUAGGUUCAUGUAGU | 1591 | 3629-3651 |
| AD-571555.1 | ACAUGAACCUACAGAGAUCCU | 1327 | 3632-3652 | AGGAUCUCUGUAGGUUCAUGUAG | 1592 | 3630-3652 |
| AD-571556.1 | CAUGAACCUACAGAGAUCCUU | 1328 | 3633-3653 | AAGGAUCUCUGUAGGUUCAUGUA | 1593 | 3631-3653 |
| AD-571557.1 | AUGAACCUACAGAGAUCCUAU | 1329 | 3634-3654 | AUAGGAUCUCUGUAGGUUCAUGU | 1594 | 3632-3654 |
| AD-571558.1 | UGAACCUACAGAGAUCCUACU | 1330 | 3635-3655 | AGUAGGAUCUCUGUAGGUUCAUG | 1595 | 3633-3655 |
| AD-571559.1 | GAACCUACAGAGAUCCUACAU | 1331 | 3636-3656 | AUGUAGGAUCUCUGUAGGUUCAU | 1596 | 3634-3656 |
| AD-571560.1 | AACCUACAGAGAUCCUACACU | 1332 | 3637-3657 | AGUGUAGGAUCUCUGUAGGUUCA | 1597 | 3635-3657 |
| AD-571711.1 | GGCCCUACUGCAGCUAAAAGU | 1333 | 3807-3827 | ACUUUUAGCUGCAGUAGGGCCAA | 1598 | 3805-3827 |
| AD-571712.1 | GCCCUACUGCAGCUAAAAGAU | 1334 | 3808-3828 | AUCUUUUAGCUGCAGUAGGGCCA | 1599 | 3806-3828 |
| AD-571713.1 | CCCUACUGCAGCUAAAAGACU | 1335 | 3809-3829 | AGUCUUUUAGCUGCAGUAGGGCC | 1600 | 3807-3829 |

TABLE 20-continued

Unmodified Sense and Antisense Strand Sequences of Complement Component C3 dsRNA Agents

| Duplex Name | Sense Sequence 5' to 3' | SEQ ID NO: | Range in NM_000 064.3 | Antisense Sequence 5' to 3' | SEQ ID NO: | Range in NM_000 064.3 |
|---|---|---|---|---|---|---|
| AD-571714.1 | CCUACUGCAGCUAAAAGACUU | 1336 | 3810-3830 | AAGUCUUUUAGCUGCAGUAGGGC | 1601 | 3808-3830 |
| AD-571716.1 | UACUGCAGCUAAAAGACUUUU | 1337 | 3812-3832 | AAAAGUCUUUUAGCUGCAGUAGG | 1602 | 3810-3832 |
| AD-571717.1 | ACUGCAGCUAAAAGACUUUGU | 1338 | 3813-3833 | ACAAAGUCUUUUAGCUGCAGUAG | 1603 | 3811-3833 |
| AD-571718.1 | CUGCAGCUAAAAGACUUUGAU | 1339 | 3814-3834 | AUCAAAGUCUUUUAGCUGCAGUA | 1604 | 3812-3834 |
| AD-571719.2 | UGCAGCUAAAAGACUUUGACU | 1340 | 3815-3835 | AGUCAAAGUCUUUUAGCUGCAGU | 1605 | 3813-3835 |
| AD-571720.1 | GCAGCUAAAAGACUUUGACUU | 1341 | 3816-3836 | AAGUCAAAGUCUUUUAGCUGCAG | 1606 | 3814-3836 |
| AD-571721.1 | CAGCUAAAAGACUUUGACUUU | 1342 | 3817-3837 | AAAGUCAAAGUCUUUUAGCUGCA | 1607 | 3815-3837 |
| AD-571722.1 | AGCUAAAAGACUUUGACUUUU | 1343 | 3818-3838 | AAAAGUCAAAGUCUUUUAGCUGC | 1608 | 3816-3838 |
| AD-571723.1 | GCUAAAAGACUUUGACUUUGU | 1344 | 3819-3839 | ACAAAGUCAAAGUCUUUUAGCUG | 1609 | 3817-3839 |
| AD-571742.1 | GUGCCUCCCGUCGUGCGUUGU | 1345 | 3838-3858 | ACAACGCACGACGGGAGGCACAA | 1610 | 3836-3858 |
| AD-571743.1 | UGCCUCCCGUCGUGCGUUGGU | 1346 | 3839-3859 | ACCAACGCACGACGGGAGGCACA | 1611 | 3837-3859 |
| AD-571744.1 | GCCUCCCGUCGUGCGUUGGCU | 1347 | 3840-3860 | AGCCAACGCACGACGGGAGGCAC | 1612 | 3838-3860 |
| AD-571745.1 | CCUCCCGUCGUGCGUUGGCUU | 1348 | 3841-3861 | AAGCCAACGCACGACGGGAGGCA | 1613 | 3839-3861 |
| AD-571746.1 | CUCCCGUCGUGCGUUGGCUCU | 1349 | 3842-3862 | AGAGCCAACGCACGACGGGAGGC | 1614 | 3840-3862 |
| AD-571747.1 | UCCCGUCGUGCGUUGGCUCAU | 1350 | 3843-3863 | AUGAGCCAACGCACGACGGGAGG | 1615 | 3841-3863 |
| AD-571748.1 | CCCGUCGUGCGUUGGCUCAAU | 1351 | 3844-3864 | AUUGAGCCAACGCACGACGGGAG | 1616 | 3842-3864 |
| AD-571749.1 | CCGUCGUGCGUUGGCUCAAUU | 1352 | 3845-3865 | AAUUGAGCCAACGCACGACGGGA | 1617 | 3843-3865 |
| AD-571750.1 | CGUCGUGCGUUGGCUCAAUGU | 1353 | 3846-3866 | ACAUUGAGCCAACGCACGACGGG | 1618 | 3844-3866 |
| AD-571751.1 | GUCGUGCGUUGGCUCAAUGAU | 1354 | 3847-3867 | AUCAUUGAGCCAACGCACGACGG | 1619 | 3845-3867 |
| AD-571753.2 | CGUGCGUUGGCUCAAUGAACU | 1355 | 3849-3869 | AGUUCAUUGAGCCAACGCACGAC | 1620 | 3847-3869 |
| AD-571755.1 | UGCGUUGGCUCAAUGAACAGU | 1356 | 3851-3871 | ACUGUUCAUUGAGCCAACGCACG | 1621 | 3849-3871 |
| AD-571756.1 | GCGUUGGCUCAAUGAACAGAU | 1357 | 3852-3872 | AUCUGUUCAUUGAGCCAACGCAC | 1622 | 3850-3872 |
| AD-571757.1 | CGUUGGCUCAAUGAACAGAGU | 1358 | 3853-3873 | ACUCUGUUCAUUGAGCCAACGCA | 1623 | 3851-3873 |
| AD-571758.1 | GUUGGCUCAAUGAACAGAGAU | 1359 | 3854-3874 | AUCUCUGUUCAUUGAGCCAACGC | 1624 | 3852-3874 |
| AD-571759.1 | UUGGCUCAAUGAACAGAGAUU | 1360 | 3855-3875 | AAUCUCUGUUCAUUGAGCCAACG | 1625 | 3853-3875 |
| AD-571760.1 | UGGCUCAAUGAACAGAGAUAU | 1361 | 3856-3876 | AUAUCUCUGUUCAUUGAGCCAAC | 1626 | 3854-3876 |
| AD-571761.1 | GGCUCAAUGAACAGAGAUACU | 1362 | 3857-3877 | AGUAUCUCUGUUCAUUGAGCCAA | 1627 | 3855-3877 |
| AD-571762.1 | GCUCAAUGAACAGAGAUACUU | 1363 | 3858-3878 | AAGUAUCUCUGUUCAUUGAGCCA | 1628 | 3856-3878 |
| AD-571763.1 | CUCAAUGAACAGAGAUACUAU | 1364 | 3859-3879 | AUAGUAUCUCUGUUCAUUGAGCC | 1629 | 3857-3879 |
| AD-571764.1 | UCAAUGAACAGAGAUACUACU | 1365 | 3860-3880 | AGUAGUAUCUCUGUUCAUUGAGC | 1630 | 3858-3880 |
| AD-571765.2 | CAAUGAACAGAGAUACUACGU | 1366 | 3861-3881 | ACGUAGUAUCUCUGUUCAUUGAG | 1631 | 3859-3881 |
| AD-571766.2 | AAUGAACAGAGAUACUACGGU | 1367 | 3862-3882 | ACCGUAGUAUCUCUGUUCAUUGA | 1632 | 3860-3882 |
| AD-571767.2 | AUGAACAGAGAUACUACGGUU | 1368 | 3863-3883 | AACCGUAGUAUCUCUGUUCAUUG | 1633 | 3861-3883 |
| AD-572383.1 | GCAGUCAAGGUCUACGCCUAU | 1369 | 4519-4539 | AUAGGCGUAGACCUUGACUGCUC | 1634 | 4517-4539 |
| AD-572384.1 | CAGUCAAGGUCUACGCCUAUU | 1370 | 4520-4540 | AAUAGGCGUAGACCUUGACUGCU | 1635 | 4518-4540 |
| AD-572385.1 | AGUCAAGGUCUACGCCUAUUU | 1371 | 4521-4541 | AAAUAGGCGUAGACCUUGACUGC | 1636 | 4519-4541 |
| AD-572386.1 | GUCAAGGUCUACGCCUAUUAU | 1372 | 4522-4542 | AUAAUAGGCGUAGACCUUGACUG | 1637 | 4520-4542 |

TABLE 20-continued

Unmodified Sense and Antisense Strand Sequences of Complement Component C3 dsRNA Agents

| Duplex Name | Sense Sequence 5' to 3' | SEQ ID NO: | Range in NM_000 064.3 | Antisense Sequence 5' to 3' | SEQ ID NO: | Range in NM_000 064.3 |
|---|---|---|---|---|---|---|
| AD-572387.4 | UCAAGGUCUACGCCUAUUACU | 1373 | 4523-4543 | AGUAAUAGGCGUAGACCUUGACU | 1638 | 4521-4543 |
| AD-572391.1 | GGUCUACGCCUAUUACAACCU | 1374 | 4527-4547 | AGGUUGUAAUAGGCGUAGACCUU | 1639 | 4525-4547 |
| AD-572392.1 | GUCUACGCCUAUUACAACCUU | 1375 | 4528-4548 | AAGGUUGUAAUAGGCGUAGACCU | 1640 | 4526-4548 |
| AD-572393.2 | UCUACGCCUAUUACAACCUGU | 1376 | 4529-4549 | ACAGGUUGUAAUAGGCGUAGACC | 1641 | 4527-4549 |
| AD-572394.1 | CUACGCCUAUUACAACCUGGU | 1377 | 4530-4550 | ACCAGGUUGUAAUAGGCGUAGAC | 1642 | 4528-4550 |
| AD-572395.1 | UACGCCUAUUACAACCUGGAU | 1378 | 4531-4551 | AUCCAGGUUGUAAUAGGCGUAGA | 1643 | 4529-4551 |
| AD-572396.1 | ACGCCUAUUACAACCUGGAGU | 1379 | 4532-4552 | ACUCCAGGUUGUAAUAGGCGUAG | 1644 | 4530-4552 |
| AD-572397.1 | CGCCUAUUACAACCUGGAGGU | 1380 | 4533-4553 | ACCUCCAGGUUGUAAUAGGCGUA | 1645 | 4531-4553 |
| AD-572495.1 | GCUGAGGAGAAUUGCUUCAUU | 1381 | 4633-4653 | AAUGAAGCAAUUCUCCUCAGCAC | 1646 | 4631-4653 |
| AD-572569.1 | GCCAGGAGUGGACUAUGUGUU | 1382 | 4707-4727 | AACACAUAGUCCACUCCUGGCUC | 1647 | 4705-4727 |
| AD-572570.1 | CCAGGAGUGGACUAUGUGUAU | 1383 | 4708-4728 | AUACACAUAGUCCACUCCUGGCU | 1648 | 4706-4728 |
| AD-572571.1 | CAGGAGUGGACUAUGUGUACU | 1384 | 4709-4729 | AGUACACAUAGUCCACUCCUGGC | 1649 | 4707-4729 |
| AD-572572.1 | AGGAGUGGACUAUGUGUACAU | 1385 | 4710-4730 | AUGUACACAUAGUCCACUCCUGG | 1650 | 4708-4730 |
| AD-572573.1 | GGAGUGGACUAUGUGUACAAU | 1386 | 4711-4731 | AUUGUACACAUAGUCCACUCCUG | 1651 | 4709-4731 |
| AD-572574.1 | GAGUGGACUAUGUGUACAAGU | 1387 | 4712-4732 | ACUUGUACACAUAGUCCACUCCU | 1652 | 4710-4732 |
| AD-572575.1 | AGUGGACUAUGUGUACAAGAU | 1388 | 4713-4733 | AUCUUGUACACAUAGUCCACUCC | 1653 | 4711-4733 |
| AD-572576.1 | GUGGACUAUGUGUACAAGACU | 1389 | 4714-4734 | AGUCUUGUACACAUAGUCCACUC | 1654 | 4712-4734 |
| AD-572577.1 | UGGACUAUGUGUACAAGACCU | 1390 | 4715-4735 | AGGUCUUGUACACAUAGUCCACU | 1655 | 4713-4735 |
| AD-572580.1 | ACUAUGUGUACAAGACCCGAU | 1391 | 4718-4738 | AUCGGGUCUUGUACACAUAGUCC | 1656 | 4716-4738 |
| AD-572581.1 | CUAUGUGUACAAGACCCGACU | 1392 | 4719-4739 | AGUCGGGUCUUGUACACAUAGUC | 1657 | 4717-4739 |

TABLE 21

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-570137.1 | gsusgcugAfaUfAfAfgaagaacaauL96 | 1658 | asUfsuguUfcUfUfucuuaUfuCfagcacsgsa | 1923 | UCGUGCUGAAUAAGAAGAACACAAA | 2188 |
| AD-570138.1 | usgscugaAfuAfAfGfgaagaacaauL96 | 1659 | asUfsuugUfucUfCfucuuuAfuUfcagcascsg | 1924 | CGUGCUGAAUAAGAAGAACACAAAC | 2189 |
| AD-570139.1 | gscsugaaUfaAfAfGfAfagaacaaacuL96 | 1660 | asGfsuuguuGfuUfCfucuuUfaUfucagcsasc | 1925 | GUGCUGAAUAAGAAGAACAAACU | 2190 |
| AD-570140.1 | csusgaauAfaGfAfAfgaacaaacuuL96 | 1661 | asAfsguuUfugUfUfcuucUfuAfuucagscsa | 1926 | UGCUGAAUAAGAAGAACAAACUG | 2191 |
| AD-570141.1 | usgsaauaAfgAfAfGfAfacaaacuguL96 | 1662 | asCfsaguUfugUfUfcuuCfuUfauucasgsc | 1927 | GCUGAAUAAGAAGAACAAACUGA | 2192 |
| AD-570142.1 | gsasauaaGfaAfGfAfAfcaaacug... | 1663 | asUfscagUfuuGfUfucuu... | 1928 | CUGAAUAAGAAGAACAAA | 2193 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| | caaacu gauL96 | | uUfcUf uauucs asg | | CUGAC | |
| AD-570143.1 | asasua agAfaG fAfAfc aaacug acuL96 | 1664 | asGfsu caGfuU fUfguu cUfuCf uuauus csa | 1929 | UGAAUA AGAAGA ACAAAC UGACG | 2194 |
| AD-570144.1 | asusaa gaAfgA fAfCfa aacuga cguL96 | 1665 | asCfsg ucAfgU fUfugu uCfuUf cuuaus usc | 1930 | GAAUAA GAAGAA CAAACU GACGC | 2195 |
| AD-570145.1 | usasag aaGfaA fCfAfa acugac gcuL96 | 1666 | asGfsc guCfaG fUfuug uUfcUf ucuuas usu | 1931 | AAUAAG AAGAAC AAACUG ACGCA | 2196 |
| AD-570146.1 | asasga agAfaC fAfAfa cugacg cauL96 | 1667 | asUfsg cgUfcA fGfuuu gUfuCf uuccus asu | 1932 | AUAAGA AGAACA AACUGA CGCAG | 2197 |
| AD-570147.1 | asgsaa gaAfcA fAfAfc ugacgc aguL96 | 1668 | asCfsu gcGfuC fAfguu uGfuUf cuucus usa | 1933 | UAAGAA GAACAA ACUGAC GCAGA | 2198 |
| AD-570148.1 | gsasag aaCfaA fAfCfu gacgca gauL96 | 1669 | asUfsc ugCfgU fCfagu uUfgUf ucuucs usu | 1934 | AAGAAG AACAAA CUGACG CAGAG | 2199 |
| AD-570149.1 | asasga acAfaA fCfUfg acgcag aguL96 | 1670 | asCfsu cuGfcG fUfcag uUfuGf uuccus csu | 1935 | AGAAGA ACAAAC UGACGC AGAGU | 2200 |
| AD-570150.1 | asgsaa caAfaC fUfUfa cgcaga guuL96 | 1671 | asAfsc ucUfgC fGfuca gUfuUf guucus usc | 1936 | GAAGAA CAAACU GACGCA GAGUA | 2201 |
| AD-570151.1 | gsasac aaAfcU fGfAfg cagagu auL96 | 1672 | asUfsa cuCfuG fCfguc aGfuUf uguucs usu | 1937 | AAGAAC AAACUG ACGCAG AGUAA | 2202 |
| AD-570152.1 | asasca aaCfuG fAfCfg cagagu aauL96 | 1673 | asUfsu acUfcU fGfcgu cAfgUf uuguus csu | 1938 | AGAACA AACUGA CGCAGA GUAAG | 2203 |
| AD-570153.1 | ascsaa acUfgA fCfGfc agagua aguL96 | 1674 | asCfsu uaCfuC fUfgcg uCfaGf uuugus usc | 1939 | GAACAA ACUGAC GCAGAG UAAGA | 2204 |
| AD-570154.1 | csasaa cuGfaC fGfCfa gaguaa gauL96 | 1675 | asUfsc uuAfcU fCfugc gUfcAf guuugs usu | 1940 | AACAAA CUGACG CAGAGU AAGAU | 2205 |
| AD-570155.1 | asasac ugAfcG fCfAfg aguaag auuL96 | 1676 | asAfsu cuUfaC fUfcug cGfuCf aguuus gsu | 1941 | ACAAAC UGACGC AGAGUA AGAUC | 2206 |
| AD-570156.2 | asascu gaCfgC fAfAfa guaaga ucuL96 | 1677 | asGfsa ucUfuA fCfucu gCfgUf caguus usg | 1942 | CAAACU GACGCA GAGUAA GAUCU | 2207 |
| AD-570158.1 | csusga cgCfaG fAfAfu aagauc uguL96 | 1678 | asCfsa gaUfcU fUfacu cUfgCf gucags usu | 1943 | AACUGA CGCAGA GUAAGA UCUGG | 2208 |
| AD-570159.1 | usgsac gcAfgA fGfUfa agaucu gguL96 | 1679 | asCfsc agAfgA fUfuac uCfuGf cgucas gsu | 1944 | ACUGAC GCAGAG UAAGAU CUGGG | 2209 |
| AD-570160.1 | gsascg caGfaG fUfAfa gaucug gguL96 | 1680 | asCfsc caGfaU fCfuua cUfcUf gcgucs asg | 1945 | CUGACG CAGAGU AAGAUC UGGGA | 2210 |
| AD-570161.1 | ascsgc agAfgU fAfAfg aucugg gauL96 | 1681 | asUfsc ccAfgA fUfcuu aCfuCf ugcgus csa | 1946 | UGACGC AGAGUA AGAUCU GGGAC | 2211 |
| AD-570611.1 | usgsag caUfgU fCfGfg acaaga aauL96 | 1682 | asUfsu ucUfuG fUfccg aCfaUf gcucas csa | 1947 | UGUGAG CAUGUC GGACAA GAAAG | 2212 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-570612.1 | gsasgc auGfuC fGfGfa caagaa aguL96 | 1683 | asCfsu uuCfuU fGfucc gAfcAf ugcucs asc | 1948 | GUGAGC AUGUCG GACAAG AAAGG | 2213 |
| AD-570613.1 | asgsca ugUfcG fGfAfc aagaaa gguL96 | 1684 | asCfsc uuUfcU fUfguc cGfaCf augcus csa | 1949 | UGAGCA UGUCGG ACAAGA AAGGG | 2214 |
| AD-570614.1 | gscsau guCfgG fAfCfa agaaag gguL96 | 1685 | asCfsc cuUfuC fUfugu cCfgAf caugcs usc | 1950 | GAGCAU GUCGGA CAAGAA AGGGA | 2215 |
| AD-570615.1 | csasug ucGfgA fCfAfa gaaagg gauL96 | 1686 | asUfsc ccUfuU fCfuug uCfcGf acaugs csu | 1951 | AGCAUG UCGGAC AAGAAA GGGAU | 2216 |
| AD-570616.1 | asusgu cgGfaC fAfAfg aaaggg auuL96 | 1687 | asAfsu ccCfuU fUfcuu gUfcCf gacaus gsc | 1952 | GCAUGU CGGACA AGAAAG GGAUC | 2217 |
| AD-570617.1 | usgsuc ggAfcA fAfAfga aaggga ucuL96 | 1688 | asGfsa ucCfcU fUfucu uGfuCf egacas usg | 1953 | CAUGUC GGACAA GAAAGG GAUCU | 2218 |
| AD-570618.1 | gsuscg gaCfaA fGfAfa agggau cuuL96 | 1689 | asAfsg auCfcC fUfuuc uUfgUf ccgacs asu | 1954 | AUGUCG GACAAG AAAGGG AUCUG | 2219 |
| AD-570619.1 | uscsgg acAfaG fAfAfa gggauc uguL96 | 1690 | asCfsa gaUfcC fCfuuu cUfuGf uccgas csa | 1955 | UGUCGG ACAAGA AAGGGA UCUGU | 2220 |
| AD-570620.3 | csgsga caAfgA fAfAfg ggaucu guuL96 | 1691 | asAfsc agUfuC fCfcuu uCfuUf guccgs asc | 1956 | GUCGGA CAAGAA AGGGAU CUGUG | 2221 |
| AD-570621.2 | gsgsac aaGfaA fAfGfg gaucug uguL96 | 1692 | asCfsa caGfaU fCfccu uUfcUf ugucos gsa | 1957 | UCGGAC AAGAAA GGGAUC UGUGU | 2222 |
| AD-570622.2 | gsasca agAfaA fGfGfg aucugu guuL96 | 1693 | asAfsc acAfgA fUfccc uUfuCf uugucs csg | 1958 | CGGACA AGAAAG GGAUCU GUGUG | 2223 |
| AD-570623.4 | ascsaa gaAfaG fGfGfa ucugug uguL96 | 1694 | asCfsa caCfaG fAfucc cUfuUf cuugus csc | 1959 | GGACAA GAAAGG GAUCUG UGUGG | 2224 |
| AD-570624.2 | csasag aaAfgG fGfGfAfu cugugu gguL96 | 1695 | asCfsc acAfcA fGfauc cCfuUf ucuugs usc | 1960 | GACAAG AAAGGG AUCUGU GUGGC | 2225 |
| AD-570625.2 | asasga aaGfgG fAfAfUf ugugug gcuL96 | 1696 | asGfsc caCfaC fAfgau cCfcUf uucuus gsu | 1961 | ACAAGA AAGGGA UCUGUG UGGCA | 2226 |
| AD-570626.1 | asgsaa agGfgA fUfCfu gugugg cauL96 | 1697 | asUfsg ccAfcA fCfaga uCfcCf uuucus usg | 1962 | CAAGAA AGGGAU CUGUGU GGCAG | 2227 |
| AD-570627.2 | gsasaa ggGfaU fCfUfg uguggc aguL96 | 1698 | asCfsu gcCfaC fAfcag aUfcCf cuuucs usu | 1963 | AAGAAA GGGAUC UGUGUG GCAGA | 2228 |
| AD-570628.1 | asasag ggAfuC fUfGfu guggca gauL96 | 1699 | asUfsc ugCfcA fCfaca gAfuCf ccuuus csu | 1964 | AGAAAG GGAUCU GUGUGG CAGAC | 2229 |
| AD-570629.1 | asasgg gaUfcU fGfUfg uggcag acuL96 | 1700 | asGfsu cuGfcC fAfcac aGfaUf cccuus usc | 1965 | GAAAGG GAUCUG UGUGGC AGACC | 2230 |
| AD-570630.1 | asgsgg auCfuG fUfGfu ggcaga ccuL96 | 1701 | asGfsg ucUfgC fCfaca cAfgAf ucccus usu | 1966 | AAAGGG AUCUGU GUGGCA GACCC | 2231 |
| AD-1069837.1 | gsgsga ucUfgU fGfUfg cagacc ccuL96 | 1702 | asGfsg guCfuG fCfcac aCfaGf aucccs usu | 1967 | AAGGGA UCUGUG UGGCAG ACCCC | 2232 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-570707.1 | gsasaa ucCfgA fGfCfc guucuc uauL96 | 1703 | asUfsa gaGfaA fCfggc uCfgGf auuucs csa | 1968 | UGGAAA UCCGAG CCGUUC UCUAC | 2233 |
| AD-570708.1 | asasau ccGfaG fCfCfg uucucu acuL96 | 1704 | asGfsu agAfgA fAfcgg cUfcGf gauuus csc | 1969 | GGAAAU CCGAGC CGUUCU CUACA | 2234 |
| AD-570709.1 | asasuc cgAfgC fCfGfu ucucua cauL96 | 1705 | asUfsg uaGfaG fAfacg gCfuCf ggauus usc | 1970 | GAAAUC CGAGCC GUUCUC UACAA | 2235 |
| AD-570710.1 | asuscc gaGfcC fGfUfu cucuac aauL96 | 1706 | asUfsu guAfgA fGfaac gGfcUf cggaus usu | 1971 | AAAUCC GAGCCG UUCUCU ACAAU | 2236 |
| AD-570715.1 | asgscc guUfcU fCfUfa caauua ccuL96 | 1707 | asGfsg uaAfuU fGfuag aGfaAf cggcus csg | 1972 | CGAGCC GUUCUC UACAAU UACCG | 2237 |
| AD-570716.1 | gscscg uuCfuC fUfAfc aauuac cguL96 | 1708 | asCfsg guAfaU fUfgua gAfgAf acggcs usc | 1973 | GAGCCG UUCUCU ACAAUU ACCGG | 2238 |
| AD-570717.2 | cscsgu ucUfcU fAfCfa auuacc gguL96 | 1709 | asCfsc ggUfaA fUfugu aGfaGf aacggs csu | 1974 | AGCCGU UCUCUA CAAUUA CCGGC | 2239 |
| AD-570718.1 | csgsuu cuCfuA fCfAfa uuaccg gcuL96 | 1710 | asGfsc cgGfuA fAfuug uAfgAf gaacgs gsc | 1975 | GCCGUU CUCUAC AAUUAC CGGCA | 2240 |
| AD-570719.1 | gsusuc ucUfaC fAfAfu uaccgg cauL96 | 1711 | asUfsg ccGfgU fAfauu gUfaGf agaacs gsg | 1976 | CCGUUC UCUACA AUUACC GGCAG | 2241 |
| AD-570720.1 | ususcu cuAfcA fAfUfu accggc aguL96 | 1712 | asCfsu gcCfgG fUfaau uGfuAf gagaas csg | 1977 | CGUUCU CUACAA UUACCG GCAGA | 2242 |
| AD-570721.1 | uscsuc uaCfaA fUfUfa ccggca gauL96 | 1713 | asUfsc ugCfcG fGfuaa uUfgUf agagas asc | 1978 | GUUCUC UACAAU UACCGG CAGAA | 2243 |
| AD-571285.1 | gsgscu gaCfcG fCfCfu acgugg ucuL96 | 1714 | asGfsa ccAfcG fUfagg cGfgUf cagccs asg | 1979 | CUGGCU GACCGC CUACGU GGUCA | 2244 |
| AD-571286.1 | gscsug acCfgC fCfUfa cguggu cauL96 | 1715 | asUfsg acCfaC fGfuag gCfgGf ucagcs csa | 1980 | UGGCUG ACCGCC UACGUG GUCAA | 2245 |
| AD-571287.1 | csusga ccGfcC fUfAfc guaguc aauL96 | 1716 | asUfsu gaCfcA fCfgua gGfcGf gucags csc | 1981 | GGCUGA CCGCCU ACGUGG UCAAG | 2246 |
| AD-571288.1 | usgsac cgCfcU fAfCfg ugguca aguL96 | 1717 | asCfsu ugAfcC fAfcgu aGfgCf ggucas gsc | 1982 | GCUGAC CGCCUA CGUGGU CAAGG | 2247 |
| AD-571289.1 | gsascc gcCfuA fCfGfu gucaag gguL96 | 1718 | asCfsc uuGfaC fCfacg uAfgGf cggucs asg | 1983 | CUGACC GCCUAC GUGGUC AAGGU | 2248 |
| AD-571290.1 | ascscg ccUfaC fGfUfg gucaag guuL96 | 1719 | asAfsc cuUfgA fCfcac gUfaGf gcggus csa | 1984 | UGACCG CCUACG UGGUCA AGGUC | 2249 |
| AD-571291.1 | cscsgc cuAfcG fUfGfg ucaagg ucuL96 | 1720 | asGfsa ccUfuG fAfcca cGfuAf ggcggs usc | 1985 | GACCGC CUACGU GGUCAA GGUCU | 2250 |
| AD-571292.1 | csgscc uaCfgU fGfGfu caaggu cuuL96 | 1721 | asAfsg acCfuU fGfacc aCfgUf aggcgs gsu | 1986 | ACCGCC UACGUG GUCAAG GUCUU | 2251 |
| AD-571293.1 | gscscu acGfuG fGfUfc aaggcu uuuL96 | 1722 | asAfsa gaCfcU fUfgac cAfcGf uaggcs gsg | 1987 | CCGCCU ACGUGG UCAAGG UCUUC | 2252 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-571294.1 | cscsuacgUfgGfUfCfaaggucuucuL96 | 1723 | asGfsaagAfcCfUfugacCfaCfguaggscsg | 1988 | CGCCUACGUGGUCAAGGUCUUCU | 2253 |
| AD-571295.1 | csusacguGfgUfCfAfafaggucuucuuL96 | 1724 | asAfsgaaGfaCfCfuugaCfcAfcguagsgsc | 1989 | GCCUACGUGGUCAAGGUCUUCUC | 2254 |
| AD-571296.1 | usascguggGfuCfAfAfAfgucuucucuL96 | 1725 | asGfsaagAfaCfCfcuuacCfuUfacguasgsg | 1990 | CCUACGUGGUCAAGGUCUCUCU | 2255 |
| AD-571297.1 | ascsguggGfuCfAfAfGfgucuucucuuL96 | 1726 | asAfsgagAfaGfAfccuuGfaCfcacgusasg | 1991 | CUACGUGGUCAAGGUCUCUCUC | 2256 |
| AD-571298.6 | csgsugguCfAfAfGfGfucuucucucuL96 | 1727 | asGfsfagAfaGfAfaccGfacuUfgAfccacgsusa | 1992 | UACGUGGUCAAGGUCUUCUCUCU | 2257 |
| AD-571299.1 | gsusgguCfAfAfGfGfuucucucucuuL96 | 1728 | asAfsgaagAfaGfAfacCfuUfGfaccaccsgsu | 1993 | ACGUGGUCAAGGUCUCUCUCUG | 2258 |
| AD-571300.1 | usgsgucCfAfAfGfCfucucucucugsuL96 | 1729 | asCfsaagGfaAfAfacCfCfuUfgaccascsg | 1994 | CGUGGUCAAGGUCUCUCUCUGG | 2259 |
| AD-571301.1 | gsgsucCfaAfGfGfUfcucucucugsgsuL96 | 1730 | asCfscsaAfgAfAfAfcCfuUfgasccsasc | 1995 | GUGGUCAAGGUCUCUCUCUGGC | 2260 |
| AD-571302.1 | gsusscaCfAgGfuCfUUfCfcucucuggscuL96 | 1731 | asGfscaCfaGfAfaGfcCfuUfGfacsusa | 1996 | UGGUCAAGGUCUCUCUGGCU | 2261 |
| AD-571303.1 | uscsaagGfUfCfUfUfcucuggcsuuL96 | 1732 | asAfsccAfcAfGfaAgagGfaCfcuugsascsc | 1997 | GGUCAAGGUCUCUCUGGCUG | 2262 |
| AD-571304.1 | csasagguCfUfUfCfCfucuggcuguL96 | 1733 | asCfsagCffCfaGfafAfgAfccuusgascss | 1998 | GUCAAGGUCUCUCUGCUGU | 2263 |
| AD-571305.1 | asasgguCfUfUfCfCfuggcuguuL96 | 1734 | asAfscAgCfAGfaGfAfafaccusugsssa | 1999 | UCAAGGUCUUCUCUGGCUGUC | 2264 |
| AD-571306.1 | asgsgucCuUfCfUfcfuggcuguccusg | 1735 | asGfsacAfaGfCfcAfGfaGfaAfggaccsusg | 2000 | CAAGGUCUCUCUGGCUGUCA | 2265 |
| AD-571307.1 | gsgsucuUCfUfCfuGfggcuguccuL96 | 1736 | asUfscAfgCCfAfaGfaGfAfagaccsusu | 2001 | AAGGUCUCUCUGGCUGUCAA | 2266 |
| AD-571308.1 | gsuscuUCfUfUfCfCfgcugucaauL96 | 1737 | asUfscaGfcCfaGfagaAfaGfaagscss | 2002 | AGGUCUCUCUGGCUGUCAAC | 2267 |
| AD-571309.1 | uscsuucUCfUfCfgGfcugucacuL96 | 1738 | asGfugAfuCfaGfcfGfgAfgaagscs | 2003 | GGUCUCUCUGGCUGUCAACC |
| AD-571526.1 | usasaaGfcAfgGfAfFafcuuccuL96 | 1739 | asCfsaagAfgCfaGfucufCfuuassu | 2004 | ACUAAAGCAGGAGACUUCCUUGA | 2269 |
| AD-571527.1 | asasagcaGfgAfcuuccuuugL96 | 1740 | asUfscagGfaAfgAfucCfuUgcuussg | 2005 | CUAAAGCAGGAGACUUCCUUGAA | 2270 |
| AD-571528.1 | asasagcagGfAfcuugcuauL96 | 1741 | asUfsuacAfgGfuCfucCfuCfccussa | 2006 | UAAAGCAGGAGACUUCCUUGAAG | 2271 |
| AD-571529.1 | asgscagGfAfccuugasguL96 | 1742 | asCfsucAfaGfaAfgcCfuuugscs | 2007 | AAAGCAGGAGACUUCCUUGAAGC | 2272 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-571530.1 | gscsag gaGfaC fUfUfc cuugaa gcuL96 | 1743 | asGfsc uuCfaA fGfgaa gUfcUf ccugcs usu | 2008 | AAGCAG GAGACU UCCUUG AAGCC | 2273 |
| AD-571531.1 | csasgg agAfcU fUfCfc uugaag ccuL96 | 1744 | asGfsg cuUfcA fAfgga aGfuCf uccugs csu | 2009 | AGCAGG AGACUU CCUUGA AGCCA | 2274 |
| AD-571532.1 | asgsga gaCfuU fCfCfu ugaagc cauL96 | 1745 | asUfsg gcUfuC fAfagg aAfgUf cuccus gsc | 2010 | GCAGGA GACUUC CUUGAA GCCAA | 2275 |
| AD-571533.1 | gsgsag acUfuC fCfUfu gaagcc aauL96 | 1746 | asUfsu ggCfuU fCfaag gAfaGf ucuccs usg | 2011 | CAGGAG ACUUCC UUGAAG CCAAC | 2276 |
| AD-571534.1 | gsasga cuUfcC fUfUfg aagcca acuL96 | 1747 | asGfsu ugGfcU fUfcaa gGfaAf gucucs csu | 2012 | AGGAGA CUUCCU UGAAGC CAACU | 2277 |
| AD-568955.1 | asgsag cgGfgU fAfAfC ucuuca ucuL96 | 1748 | asGfsa ugAfaG fAfggu aCfcCf gcucus gsc | 2013 | GCAGAG CGGGUA CCUCUU CAUCC | 2278 |
| AD-568956.1 | gsasgc ggGfuA fCfCfu cuucau ccuL96 | 1749 | asGfsg auGfaA fGfagg uAfcCf cgcucs usg | 2014 | CAGAGC GGGUAC CUCUUC AUCCA | 2279 |
| AD-568957.1 | asgscg ggUfaC fCfUfc uucauc cauL96 | 1750 | asUfsg gaUfgA fAfgag gUfaCf ccgcus csu | 2015 | AGAGCG GGUACC UCUUCA UCCAG | 2280 |
| AD-568958.1 | gscsgg guAfcC fUfCfu ucaucc aguL96 | 1751 | asCfsu ggAfuG fAfaga gGfuAf cccgcs usc | 2016 | GAGCGG GUACCU CUUCAU CCAGA | 2281 |
| AD-568959.1 | csgsgg uaCfcU fCfUfu caucca gauL96 | 1752 | asUfsc ugGfaU fGfaag aGfgUf acccgs csu | 2017 | AGCGGG UACCUC UUCAUC CAGAC | 2282 |
| AD-568960.1 | gsgsgu acCfuC fUfUfc auccag acuL96 | 1753 | asGfsu cuGfgA fUfgaa gAfgGf uacccs gsc | 2018 | GCGGGU ACCUCU UCAUCC AGACA | 2283 |
| AD-568961.1 | gsgsua ccUfcU fUfCfa uccaga cauL96 | 1754 | asUfsg ucUfgG fAfuga aGfaGf guaccs csg | 2019 | CGGGUA CCUCUU CAUCCA GACAG | 2284 |
| AD-568962.1 | gsusac cuCfuU fCfAfu ccagac aguL96 | 1755 | asCfsu guCfuG fGfaug aAfgAf gguacs csc | 2020 | GGGUAC CUCUUC AUCCAG ACAGA | 2285 |
| AD-568963.2 | usascc ucCfuU fAfUfc cagaca gauL96 | 1756 | asUfsc ugUfcU fGfgau gAfaGf agguas csc | 2021 | GGUACC UCUUCA UCCAGA CAGAC | 2286 |
| AD-568964.1 | ascscu cuUfcA fUfCfc agaca g acuL96 | 1757 | asGfsu cuGfuC fUfgga uGfaAf gaggus asc | 2022 | GUACCU CUUCAU CCAGAC AGACA | 2287 |
| AD-568965.1 | cscsuc uuCfaU fCfCfa gacaga cauL96 | 1758 | asUfsg ucUfgU fCfugg aUfgAf agaggs usa | 2023 | UACCUC UUCAUC CAGACA GACAA | 2288 |
| AD-568966.1 | csuscu ucAfuC fCfAfg acagac aauL96 | 1759 | asUfsu guCfuG fUfcug gAfuGf aagags gsu | 2024 | ACCUCU UCAUCC AGACAG ACAAG | 2289 |
| AD-568967.1 | uscsuu caUfcC fAfGfa cagaca aguL96 | 1760 | asCfsu ugUfcU fGfucu gGfaUf gaagas gsg | 2025 | CCUCUU CAUCCA GACAGA CAAGA | 2290 |
| AD-568968.1 | csusuc auCfcA fGfGfa ccagac agacaa gauL96 | 1761 | asUfsc uuGfuC fUfguc uGfgAf ugaags asg | 2026 | CUCUUC AUCCAG ACAGAC AAGAC | 2291 |
| AD-568969.1 | ususca ucCfaG fAfCfa gacaag acuL96 | 1762 | asGfsu cuUfgU fCfugu cUfgGf augaas gsa | 2027 | UCUUCA UCCAGA CAGACA AGACC | 2292 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-568970.1 | uscsau ccAfgA fCfAfg acaaga ccuL96 | 1763 | asGfsg ucUfuG fUfcug uCfuGf gaugas asg | 2028 | CUUCAU CCAGAC AGACAA GACCA | 2293 |
| AD-568971.1 | csasuc caGfaC fAfGfa caagac cauL96 | 1764 | asUfsg guCfuU fGfucu gUfcUf ggaugs asa | 2029 | UUCAUC CAGACA GACAAG ACCAU | 2294 |
| AD-568972.1 | asuscc agAfcA fGfAfc aagacc auuL96 | 1765 | asAfsu ggUfcU fUfguc uGfuCf uggaus gsa | 2030 | UCAUCC AGACA ACAAGA CCAUC | 2295 |
| AD-568973.1 | uscsca gaCfaG fAfCfa agacca ucuL96 | 1766 | asGfsa ugGfuC fUfugu cUfgUf cuggas usg | 2031 | CAUCCA GACAGA CAAGAC CAUCU | 2296 |
| AD-568974.1 | cscsag acAfgA fCfAfa gaccau cuuL96 | 1767 | asAfsg auGfgU fCfuug uCfuGf ucuggs asu | 2032 | AUCCAG ACAGAC AAGACC AUCUA | 2297 |
| AD-568975.1 | csasga caGfaC fAfAfg accauc uauL96 | 1768 | asUfsa gaUfgG fUfcuu gUfcUf gucugs gsa | 2033 | UCCAGA CAGACA AGACCA UCUAC | 2298 |
| AD-568977.1 | gsasca gaCfaA fGfAfc caucua cauL96 | 1769 | asUfsg uaGfaU fGfguc uUfgUf cugucs usg | 2034 | CAGACA GACAAG ACCAUC UACAC | 2299 |
| AD-568979.1 | csasga caAfgA fCfCfa ucuaca ccuL96 | 1770 | asGfsg ugUfaG fAfugg uCfuUf gucugs usc | 2035 | GACAGA CAAGAC CAUCUA CACCC | 2300 |
| AD-1069834.1 | asgsac aaGfaC fCfAfu cuacac ccuL96 | 1771 | asGfsg guUfuA fGfaug gUfcUf ugucus gsu | 2036 | ACAGAC AAGACC AUCUAC ACCCC | 2301 |
| AD-1069835.1 | gsasca agAfcC fAfUfc uacacc ccuL96 | 1772 | asGfsg ggUfgU fAfgau gGfuCf uugucs usg | 2037 | CAGACA AGACCA UCUACA CCCCU | 2302 |
| AD-1069836.1 | ascsaa gaCfcA fUfCfu acaccc cuuL96 | 1773 | asAfsg ggGfuG fUfaga uGfgUf cuugus csu | 2038 | AGACAA GACCAU CUACAC CCCUG | 2303 |
| AD-569154.1 | gsgscc agUfgG fAfAfg auccga gcuL96 | 1774 | asGfsc ucGfgA fUfcuu cCfaCf uggccs csa | 2039 | UGGGCC AGUGGA AGAUCC GAGCC | 2304 |
| AD-569155.1 | gscsca guGfgA fAfGfa uccgag ccuL96 | 1775 | asGfsg cuCfgG fAfucu uCfcAf cuggcs csc | 2040 | GGGCCA GUGGAA GAUCCG AGCCU | 2305 |
| AD-569156.1 | cscsag ugGfaA fGfAfu ccgagc cuuL96 | 1776 | asGfsg gcUfcG fGfauc uUfcCf acuggs csc | 2041 | GGCCAG UGGAAG AUCCGA GCCUA | 2306 |
| AD-569157.1 | csasgu ggAfaG fAfUfc cgagcc uauL96 | 1777 | asUfsa ggCfuC fGfgau cUfuCf cacugs gsc | 2042 | GCCAGU GGAAGA UCCGAG CCUAC | 2307 |
| AD-569158.1 | asgsug gaAfgA fUfCfc gagccu acuL96 | 1778 | asGfsu agGfcU fCfgga uCfuUf ccacus gsg | 2043 | CCAGUG GAAGAU CCGAGC CUACU | 2308 |
| AD-569159.1 | gsusgg aaGfaU fCfCfg agccua cuuL96 | 1779 | asAfsg uaGfgC fUfcgg aUfcUf uccacs usg | 2044 | CAGUGG AAGAUC CGAGCC UACUA | 2309 |
| AD-569160.1 | usgsga agAfuC fCfGfa gccuac uauL96 | 1780 | asUfsa guAfgG fCfucg gAfuCf uuccas csu | 2045 | AGUGGA AGAUCC GAGCCU ACUAU | 2310 |
| AD-569161.1 | gsgsaa gaUfcC fGfAfg ccuacu auuL96 | 1781 | asAfsu agUfaG fGfcuc gGfaUf cuuccs asc | 2046 | GUGGAA GAUCCG AGCCUA CUAUG | 2311 |
| AD-569162.1 | gsasag auCfcG fAfGfc cuacua uguL96 | 1782 | asCfsa uaGfuA fGfgcu cGfgAf ucuucs csa | 2047 | UGGAAG AUCCGA GCCUAC UAUGA | 2312 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-569163.1 | asasgaucCfgAfGfCfcuacuaugauL96 | 1783 | asUfscauAfgUfAfggcuCfgGfaucuuscsc | 2048 | GGAAGACCGAGCCUACUAUGAA | 2313 |
| AD-569166.1 | asusccgaGfcCfFfUfAfcuaugaaaauL96 | 1784 | asUfsuuuCfaUfAfguagGfcUfcggauscsu | 2049 | AGAUCCGAGCCUACUAUGAAAAC | 2314 |
| AD-569167.1 | usescgagCfcUfAfAfCfuaugaaaacuL96 | 1785 | asGfsuuuUfcAfAfaguaGfgCfucggasusc | 2050 | GAUCCGAGCCUACUAUGAAACU | 2315 |
| AD-569168.1 | cscsgagcCfUfAfCfCfUfauugaaaacuuL96 | 1786 | asAfsguuUfuCfAfuagGfcUfaggGfcucggsasu | 2051 | AUCCGAGCCUACUAUGAACUC | 2316 |
| AD-569169.1 | csgsagccCfUfAfCfFfAfugaaaacucuL96 | 1787 | asGfsfaGfsfauaGfgCfcCfauaGfgCfucgsgsa | 2052 | UCCGAGCCUACUAUGAAACUCA | 2317 |
| AD-569170.1 | gsasgccuAfcCfUfAfUfgaaacucasauL96 | 1788 | asUfsguAfgUfuUfcaAfuAfgAfgGfucgggcsgsg | 2053 | CCGAGCCUACUAUGAAACUCAC | 2318 |
| AD-569171.1 | asgsccuaCfuUfAfUfGfaaacucacauL96 | 1789 | asGfsuUfsuUfcAfaUfaGfgAfcUfaUfgAfgFsg | 2054 | CGAGCCUACUAUGAAACUCACC | 2319 |
| AD-569172.1 | gscscsuaCfUfAfUfgaaacucaccuL96 | 1790 | asGfsugAfGfuuAfuUfaGfaGffuaggsgcsusc | 2055 | GAGCCUACUAUGAAAACUCACCA | 2320 |
| AD-569173.1 | cscsuauCfCfAfUfgaaaacucacucauL96 | 1791 | asGfsuGfaGfUfuuuCfaFuAfAfguagggsscu | 2056 | AGCCUACUAUGAAACUCACCAC | 2321 |
| AD-569174.1 | csusacuAfuGfAfAfacucaccccauL96 | 1792 | asGfsfuGfgAfUfuuCfaFuAfuagagsgsc | 2057 | GCCUACUAUGAAACUCACCCCA | 2322 |
| AD-569175.1 | usascuaUfGfAfAfacucaccacauL96 | 1793 | asUfsuggGfuGfFfagguuUfcAfuaguasgsg | 2058 | CCUACUAUGAAACUCACCACAG | 2323 |
| AD-569262.1 | cscsuacaGfaGfAfFfAfuucuacuacauL96 | 1794 | asUfsaGfaGfFfuuuUfcUfcFufgagaggsscsu | 2059 | AGCCUACAGAGAAAUUCUACUAC | 2324 |
| AD-569263.1 | csusacagAfgAfAfFfAfuucuaacuacuL96 | 1795 | asGfsuaGfsfauuUfcUfcFuCfgagagsgsc | 2060 | GCCUACAGAGAAAUUCUACUACA | 2325 |
| AD-569264.1 | usascagaGfaGfFfaAfuucuacucaucauL96 | 1796 | asUfsfgaUfaGfFfaauUfcUfcFuFfgagggsc | 2061 | CCUACAGAGAAAUUCUACAU | 2326 |
| AD-569265.1 | ascsagagAfaAfFfFfcuacucuaucuauL96 | 1797 | asAfsfuGfsfagGfuUfuFfaGfgFfagagscsg | 2062 | CUACAGAGAAAUUCUACUACAUC | 2327 |
| AD-569266.1 | csasagaAfaUfFfCfFufacuaacuaucuL96 | 1798 | asGfsfuGfaGfFfaaGfaFuFfcucuguscsa | 2063 | UACAGAGAAAUUCUACUACAUCU | 2328 |
| AD-569267.1 | asgsagaAfAfFfFfcuacuaucucuaucuL96 | 1799 | asAfsfsgAfuGfFfuaGfaAfFfcucussgsu | 2064 | ACAGAGAAAUUCUACUACAUCUA | 2329 |
| AD-569268.1 | gsasgaAfaUfFfCfFfuacaucuauL96 | 1800 | asUfsfagaUfgUfFfguaGfafAfuuuscsug | 2065 | CAGAGAAAUUCUACUACUAU | 2330 |
| AD-569269.1 | asgsaaAfuUfCfFfacaucuauauL96 | 1801 | asAfsuuAfgUfFfaguFfaAfguuscsu | 2066 | AGAGAAAUUCUACUACUAUA | 2331 |
| AD-569270.1 | gsasaaUfuCfFfaAfcaucuauaauL96 | 1802 | asUfsaAfuGfFfaGfFfAfauuscus | 2067 | GAGAAAUUCUACUACUAUAA | 2332 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-569271.1 | asasau cUfaC fUfAfc aucuau aauL96 | 1803 | asUfsu auAfgA fUfgua gUfaGf aauuus csu | 2068 | AGAAAU UCUACU ACAUCU AUAAC | 2333 |
| AD-569273.1 | asusuc uaCfuA fCfAfu cuauaa cguL96 | 1804 | asCfsg uuAfuA fGfaug uAfgUf agaaus usu | 2069 | AAAUUC UACUAC AUCUAU AACGA | 2334 |
| AD-569274.1 | ususcu acUfaC fAfUfc uauaac gauL96 | 1805 | asUfsc guUfaU fAfgau gUfaGf uagaas usu | 2070 | AAUUCU ACUACA UCUAUA ACGAG | 2335 |
| AD-569275.1 | uscsua cuAfcA fUfCfu auaacg aguL96 | 1806 | asCfsu cgUfuA fUfaga uGfuAf guagas asu | 2071 | AUUCUA CUACAU CUAUAA CGAGA | 2336 |
| AD-569276.1 | csusac uaCfaU fCfUfa uaacga gauL96 | 1807 | asUfsc ucGfuU fAfuag aUfgUf aguags asa | 2072 | UUCUAC UACAUC UAUAAC GAGAA | 2337 |
| AD-569277.1 | usascu acAfuC fUfAfu aacgag aauL96 | 1808 | asUfsu cuCfgU fUfaua gAfuGf uaguas gsa | 2073 | UCUACU ACAUCU AUAACG AGAAG | 2338 |
| AD-569278.1 | ascsua caUfcU fAfUfa acgaga aguL96 | 1809 | asCfsu ucUfcG fUfuau aGfaUf guagus asg | 2074 | CUACUA CAUCUA UAACGA GAAGG | 2339 |
| AD-569279.1 | csusac auCfuA fUfAfa cgagaa gguL96 | 1810 | asCfsc uuCfuC fGfuua uAfgAf uguags usa | 2075 | UACUAC AUCUAU AACGAG AAGGG | 2340 |
| AD-569280.1 | usasca ucUfaU fAfAfc gagaag gguL96 | 1811 | asCfsc cuUfcU fCfguu aUfaGf auguas gsu | 2076 | ACUACA UCUAUA ACGAGA AGGGC | 2341 |
| AD-569281.1 | ascsau cuAfuA fAfCfg agaagg gcuL96 | 1812 | asGfsf ccUfuC fUfcgu uAfuAf gaugus asg | 2077 | CUACAU CUAUAA CGAGAA GGGCC | 2342 |
| AD-569282.1 | csasuc uaUfaA fCfGfa gaaggg ccuL96 | 1813 | asGfsg ccCfuU fCfucg uUfaUf agaugs usa | 2078 | UACAUC UAUAAC GAGAAG GGCCU | 2343 |
| AD-569506.1 | cscsuc ucCfcU fAfCfc agaucc acuL96 | 1814 | asGfsu ggAfuC fUfggu aGfgGf agaggs usc | 2079 | GACCUC UCCCUA CCAGAU CCACU | 2344 |
| AD-569507.1 | csuscu ccCfuA fCfCfa gaucca cuuL96 | 1815 | asAfsg ugGfaU fCfugg uAfgGf gagags gsu | 2080 | ACCUCU CCCUAC CAGAUC CACUU | 2345 |
| AD-569508.1 | uscsuc ccCfuA fCfCfg auccac uuuL96 | 1816 | asAfsa guGfgA fUfcug gUfaGf ggagas gsg | 2081 | CCUCUC CCUACC AGAUCC ACUUC | 2346 |
| AD-569509.1 | cscscc cuAfcC fAfGfa uccacu ucuL96 | 1817 | asGfsa agUfgG fAfucu gGfuAf gggags asg | 2082 | CUCUCC CUACCA GAUCCA CUUCA | 2347 |
| AD-569510.1 | uscscc uaCfcA fGfAfu ccacuu cauL96 | 1818 | asUfsg aaGfuG fGfauc uGfgUf agggas gsa | 2083 | UCUCCC UACCAG AUCCAC UUCAC | 2348 |
| AD-569511.1 | cscscu acCfaG fAfUfc cacuuc acuL96 | 1819 | asGfsu gaAfgU fGfgau cUfgGf uagggs asg | 2084 | CUCCCU ACCAGA UCCACU UCACC | 2349 |
| AD-569512.1 | cscsua ccAfgA fUfCfc acuuca ccuL96 | 1820 | asGfsg ugAfaG fUfgga uCfuGf guaggs gsa | 2085 | UCCCUA CCAGAU CCACUU CACCA | 2350 |
| AD-569513.1 | csusac caGfaU fCfCfa cuucac cauL96 | 1821 | asUfsg guGfaA fGfugg aUfcUf gguags gsg | 2086 | CCCUAC CAGAUC CACUUC ACCAA | 2351 |
| AD-569514.1 | usascc agAfuC fCfAfc uucacc aauL96 | 1822 | asUfsu ggUfgA fAfgug gAfuCf ugguas gsg | 2087 | CCUACC AGAUCC ACUUCA CCAAG | 2352 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-569515.1 | ascscagaUfcCfAfCfuucaccaguL96 | 1823 | asCfsuugGfuGfAfagugGfaUfcuggusasg | 2088 | CUACCAGAUCCACUUCACCAAGA | 2353 |
| AD-569516.1 | cscsagauCfcAfCfUfUfucaccaagauL96 | 1824 | asUfscuuGfgUfGfaaguGfgAfucuggsusa | 2089 | UACCAGAUCCACUUCACCAAGAC | 2354 |
| AD-569517.1 | csasgaucCfaCfUfUfUfcaccaagacuL96 | 1825 | asGfsucuUfgGfUfgaagUfgGfaucugsgsu | 2090 | ACCAGAUCCACUUCACCAAGACA | 2355 |
| AD-569518.1 | asgsauccAfcUfUfCfUfcaccaagacauL96 | 1826 | asUfsguCfUfuGfgUfugaaGfuGfgaucusgsg | 2091 | CCAGAUCCACUUCACCAAGACAC | 2356 |
| AD-569519.1 | gsasuccaCfuUfCfCfAfcaagacacuL96 | 1827 | asGfsuguCfuUfUfgGfgugGfgAfucusgsg | 2092 | CAGAUCCACUUCACCAAGACACC | 2357 |
| AD-569520.1 | asusccacUfuCfCfAfCfaagacaccuL96 | 1828 | asGfsguUfgCfUfuGfgGfuGfgAfAfGfuggauscsu | 2093 | AGAUCCACUUCACCAAGACACCC | 2358 |
| AD-569565.1 | ususugacCfuCfCfAfcfUfuguucguuL96 | 1829 | asFfscgaAfcAfUfCfcauGfgGfucaaasgsg | 2094 | CCUUUGACCUCAUGGUGUUCGUG | 2359 |
| AD-569567.1 | usgsaccuCfaUfGfGfuguucgugauL96 | 1830 | asUfscAfcGfAfafAfCfaccAfUfgAfAfgGfgucasasa | 2095 | UUUGACCUCAUGGUGUUCGUGAC | 2360 |
| AD-570126.1 | asgsggcgUfgUfUfCfCfgugcugaauuL96 | 1831 | asAfsuucAfCfAfgCfgaAfCfaCfacCfgcccsusg | 2096 | CAAGGGCGUGUUCGUGCUGAAUA | 2361 |
| AD-570127.1 | gsgsgcguGfuUfUfcgugcugaauauL96 | 1832 | asUfsauUfcAfGfcfAfcgAfAfcAfAfcgcccsusu | 2097 | AAGGGCGUGUUCGUGCUGAAUAA | 2362 |
| AD-570128.1 | gsgscguguUfCfGfUfgcugaauacgccsu | 1833 | asUfsuaAfaUfcAfgCfacGfaAfacgccscsu | 2098 | AGGGCGUGUUCGUGCUGAAUAAG | 2363 |
| AD-570129.1 | gscsguguUfcGfugaauacgcsc | 1834 | asCfsuauUfcAfgCfafAfcaCfgcacgscsc | 2099 | GGGCGUGUUCGUGCUGAAUAAGA | 2364 |
| AD-570131.1 | gsusguucGfuGfCfUfgaauaagcacacsgsc | 1835 | asUfsuucUfaUfUfcaGfcAfcGfaacacscs | 2100 | GCGUGUUCGUGCUGAAUAAGAAG | 2365 |
| AD-570135.1 | usGsuGfAagaagacacgasc | 1836 | asCfsuuCfUfufafuuCfaGfcacgsasc | 2101 | GUUCGUGCUGAAUAAGAACA | 2366 |
| AD-570136.1 | csgsugCfuGfaAfgaagaacaugcacgsasa | 1837 | asFfsguuCfuUfaUfUfcAfgcacgsasa | 2102 | UUCGUGCUGAAUAAGAAGAACAA | 2367 |
| AD-571535.1 | asgsacuUfCfCfuUfGfagccaaacuuL96 | 1838 | asAfsguuGfCfuUfcAfaGfAfagucuscsc | 2103 | GGAGACUUCCUUGAAGCCAACUA | 2368 |
| AD-571536.1 | gsascuUfCfCfuufGfGfCfuUfAfagucsusc | 1839 | asUfsaguGfgGfCfuUfcAfAfgGfaagucusc | 2104 | GAGACUUCCUUGAAGCCAACUAC | 2369 |
| AD-571537.1 | ascsuucCfuUfGfccaacauL96 | 1840 | asUfsaGfuUfGfGfcUfuCfAfaGfaagusc | 2105 | AGACUUCCUUGAAGCCAACUACA | 2370 |
| AD-571538.1 | csuscCfuUfgAfacaacuacauL96 | 1841 | asUfsfuGfGfCfcUfcAfAfgGfaagsusc | 2106 | GACUUCCUUGAAGCCAACUACAU | 2371 |
| AD-571540.1 | uscscuuGfaUfGfCfCfaUfuCfuacacagusuL96 | 1842 | asFfsuagGfuUfGfGfcUfcAfaggsasg | 2107 | CUUCCUUGAAGCCAACUACAUGA | 2372 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-571541.1 | cscsuugaAfgCfCfAfacuacaugauL96 | 1843 | asUfscauGfuAfGfuugcCfuUfcaaggsasa | 2108 | UUCCUUGAAGCCAACUACAUGAA | 2373 |
| AD-571542.1 | csusugaaGfcCfFfAfAfcuacaugaauL96 | 1844 | asUfsucaUfgUfAfguuggGfcUfucaaggsa | 2109 | UCCUUGAAGCCAACUACAUGAAC | 2374 |
| AD-571543.1 | ususgaagCfcAfFfAfCfuacaugaacuL96 | 1845 | asGfsuucAfuGfFfagutGfgCfuucaasgsg | 2110 | CCUUGAAGCCAACUACAUGAACC | 2375 |
| AD-571544.1 | usgsaagcCfaAfFfCfUfacaugaaccuL96 | 1846 | asGfsguuCfaUfFfguagtUfgGfcuucasasg | 2111 | CUUGAAGCCAACUACAUGAACCU | 2376 |
| AD-571545.1 | gsasagccAfaCfFfUfAfcaugaacccuuL96 | 1847 | asAfsguuCfaUfFfguatgGfuUfgGfgcuucsasa | 2112 | UUGAAGCCAACUACAUGAACCUA | 2377 |
| AD-571546.1 | asasagccaCfaAfCfUfAfCfcfaugaacccuauL96 | 1848 | asUfsaggUfuCfAfugutAfGfuUfggcuuscsa | 2113 | UGAAGCCAACUACAUGAACCUAC | 2378 |
| AD-571547.1 | asgscccaAfcUfAfCfUfCfAfugaaccuacuL96 | 1849 | asGfsuagGfuUfCfaugAfUfgfuAfgfuUfuggcususc | 2114 | GAAGCCAACUACAUGAACCUACA | 2379 |
| AD-571548.1 | gsscscaaCfuAfcAfFfAfUfgaaccuacauL96 | 1850 | asUfsfsguagGfuUfcauFfuGfuAfGfuuggcsusu | 2115 | AAGCCAACUACAUGAACCUACAG | 2380 |
| AD-571549.1 | cscssaacUfAfCfAfCfUfgaaccuacaguL96 | 1851 | asCfsuguAfgGfUfucaFfuGfuAfFfguuggsc | 2116 | AGCCAACUACAUGAACCUACAGA | 2381 |
| AD-571550.1 | cssasacuAfCfAfUfGfaaccuacagauL96 | 1852 | asUfscugUfaGfGfuucaUfgUfaGfuuugsc | 2117 | GCCAACUACAUGAACCUACAGAG | 2382 |
| AD-571551.1 | asascuacAfuGfAfAfCfcuacagagauL96 | 1853 | asCfsucuCfuGfFfgguuCfAfuGfuaguusgsg | 2118 | CCAACUACAUGAACCUACAGAGA | 2383 |
| AD-571552.1 | asccsuacaUfgAfAfFfCfuacagaguuL96 | 1854 | asUfscuCfuGfFfgguFfgUfCfaUfguaguusg | 2119 | CAACUACAUGAACCUACAGAGAU | 2384 |
| AD-571553.1 | csussacauGfaAfFfCfCfuacagagauuL96 | 1855 | asAfsfsuAfuGfFfaggFfaUfcAfguagusu | 2120 | AACUACAUGAACCUACAGAGAUC | 2385 |
| AD-571554.1 | usasacaugAfaCfFfUfAfcagagaucuL96 | 1856 | asGfssaucUfcUfFfuagFfgUfcAfuguagsu | 2121 | ACUACAUGAACCUACAGAGAUCC | 2386 |
| AD-571555.1 | asscssaugaAfcCfFfUfAfcagagauccuL96 | 1857 | asGfsfsgaucUfcUfFfguaFfgUfuAfCfauguscs | 2122 | CUACAUGAACCUACAGAGAUCCU | 2387 |
| AD-571556.1 | csasugaaCfcUfAfCfAfgagauccucuL96 | 1858 | asAfsfsggaucUfcUfFfguaFfgUfuCfaugusa | 2123 | UACAUGAACCUACAGAGAUCCUA | 2388 |
| AD-571557.1 | asususgaacCfuAfCfFfAfgauccuacuL96 | 1859 | asUfsaggAfuCfUfcugFfaUfGfFfuucasgsu | 2124 | ACAUGAACCUACAGAGAUCCUAC | 2389 |
| AD-571558.1 | usgsgsaaccUfaCfAfGfAfgauccuacuL96 | 1860 | asGfsuagGfaUfcucugGfFfaUfguucsussg | 2125 | CAUGAACCUACAGAGAUCCUACA | 2390 |
| AD-571559.1 | gsasaccuAfCfAfGfAfgauccuacauL96 | 1861 | asUfsguaGfgAfucUfcUfGfuAfgguucsasu | 2126 | AUGAACCUACAGAGAUCCUACAC | 2391 |
| AD-571560.1 | asassccaAfGfAfGfauccuacacuL96 | 1862 | asGfsguagGfaUfcucUfgUfaGfgguucscsa | 2127 | UGAACCUACAGAGAUCCUACACU | 2392 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-571711.1 | gsgscccuAfcUfGfCfagcuaaaaguL96 | 1863 | asCfsuuuUfaGfCfugcaGfuAfgggccsasa | 2128 | UUGGCCCUACUGCAGCUAAAAGA | 2393 |
| AD-571712.1 | gscsccuaCfuGfCfCfAfgcuaaaaagauL96 | 1864 | asUfscuuUfuAfGfCfcugcAfgGfUfagggcscsa | 2129 | UGGCCCUACUGCAGCUAAAAGAC | 2394 |
| AD-571713.1 | cscscuacUfgCfAfAfGfcuaaaaagacuL96 | 1865 | asGfsucuUfuUfLfAfgcugCfaGfuagggscscsc | 2130 | GGCCCUACUGCAGCUAAAGACU | 2395 |
| AD-571714.1 | cscsuacuGfcAfGfCfCfuaaaaagacuuL96 | 1866 | asAfsguUfcUfuLfuAfgcugCfaGffguaggsgscsc | 2131 | GCCCUACUGCAGCUAAAAGACUU | 2396 |
| AD-571716.1 | usascugcAfgCfUfAfAfaaagacuuuuL96 | 1867 | asAfsfaaGfuCfuUfuuuaGfcUfuGfcaguasgsg | 2132 | CCUACUGCAGCUAAAAGACUUUG | 2397 |
| AD-571717.1 | ascsugcAfGfcUfAfAfAfaagacuuuguL96 | 1868 | asCfsaaaGfuCfuUfuuuaGfcUfgcaguasasg | 2133 | CUACUGCAGCUAAAAGACUUUGA | 2398 |
| AD-571718.1 | csusgcagCfuAfAfFfAfacuuugauL96 | 1869 | asUfscaaaAfgUfcUfuuuAfgCfugcagsusa | 2134 | UACUGCAGCUAAAAGACUUUGAC | 2399 |
| AD-571719.2 | usgscagcUfaAfAfAfFfgcuuugacuL96 | 1870 | asGfsucaAfaGfUfcUfcuuUfaGfgcugcasgsu | 2135 | ACUGCAGCUAAAGACUUUGACU | 2400 |
| AD-571720.1 | gscsagcuAfaAfAfGfFfcuuugacuuL96 | 1871 | asAfsguUfcAfaAfuUfcuUfuUfAfgcugcsasg | 2136 | CUGCAGCUAAAAGACUUUGACUU | 2401 |
| AD-571721.1 | csasagcuaAfAfAfGfcuuugauuuuL96 | 1872 | asAfsaguCfaAfAfgucuUfuUfaggcugscsa | 2137 | UGCAGCUAAAAGACUUUGACUUU | 2402 |
| AD-571722.1 | asgscuaaAfaGfAfCfAfuugacuuuL96 | 1873 | asAfsfaagUfcAfAfagucUfuUfuagcusgsc | 2138 | GCAGCUAAAAGACUUUGACUUUG | 2403 |
| AD-571723.1 | gscsuaaAfgAfAfCfFfUfugacuuguL96 | 1874 | asCfsaaGfuCfAfAfaaagUfcUfuuagscusg | 2139 | CAGCUAAAAGACUUUGACUUUGU | 2404 |
| AD-571742.1 | gsusgccuCfcCfFfGfUfcgugcguguL96 | 1875 | asCfsaAfcGfcAfAfCfgacgGfgAfggcacsasa | 2140 | UUGUGCCUCCCGUCGUGCGUUGG | 2405 |
| AD-571743.1 | usgsccucCfcGfUfFfcguugguL96 | 1876 | asCfscaaAfcCfgcacCfAfacgcGfgGfaggscsa | 2141 | UGUGCCUCCCGUCGUGCGUUGGC | 2406 |
| AD-571744.1 | gscscucCfgUfFfCfGfuggcuuuL96 | 1877 | asGfsfCfaAfcGfFfcacgAfcGfgaggscsasc | 2142 | GUGCCUCCCGUCGUGCGUUGGCU | 2407 |
| AD-571745.1 | cscsucGfuCfCfGfUfgcguuggcuuL96 | 1878 | asAfsfcgCfcAfcAfcGfcacGfAfcGfggaggscsa | 2143 | UGCCUCCCGUCGUGCGUUGGCUC | 2408 |
| AD-571746.1 | csuscucCfgUfCfGfuuggcucuL96 | 1879 | asAfsfsaGfcCfaAfCfgcaCfgAfcfgggagsgsc | 2144 | GCCUCCCGUCGUGCGUUGGCUCA | 2409 |
| AD-571747.1 | uscscCfgUfCfGfUfFfuggcucaasuL96 | 1880 | asUfsfsuGfaGfCfAfFfcgcaCffgAfcggasgsg | 2145 | CCUCCCGUCGUGCGUUGGCUCAA | 2410 |
| AD-571748.1 | csescgucGfuCfFfCfGfuuggcucaasuL96 | 1881 | asUfsgaGfcCfAfAfacgCfaCffAfcgggsasg | 2146 | CUCCCGUCGUGCGUUGGCUCAAU | 2411 |
| AD-571749.1 | cscscuGfuFfGfCfFfggcucauuuL96 | 1882 | asUfsguUfGfAfgccaCfaFfaacgCfaCffdacgggsa | 2147 | UCCCGUCGUGCGUUGGCUCAAUG | 2412 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-571750.1 | csgsucguGfcGfUfUfgcucaauguuL96 | 1883 | asCfsauuGfaGfCfcaacGfcAfcgacgsg | 2148 | CCCGUCGUGCGUUGGCUCAAUGA | 2413 |
| AD-571751.1 | gsuscgugCfgUfUfUfGfgcucaaugauL96 | 1884 | asUfsfcauUfgAfGfccaaCfgCfacgacgsg | 2149 | CCGUCGUGCGUUGGCUCAUGAA | 2414 |
| AD-571753.2 | csgsugegUfuGfFfGfCfucaaugaacuL96 | 1885 | asGfsuucAfuUfGfagccAfaCfgcacgsasc | 2150 | GUCGUGCGUUGGCUCAAUGAACA | 2415 |
| AD-571755.1 | usgscguuGfgCfFfUfCfaaugaacaguL96 | 1886 | asCfsuguUfcAfFfugaGfcCfaCfacgcascsg | 2151 | CGUGCGUUGGCUCAAUGAACAGA | 2416 |
| AD-571756.1 | gscsguugGfcUfFfCfAfaugaacagauL96 | 1887 | asCfsucugUfuCfFfAfuugAfgCfcCfaacgcsasc | 2152 | GUGCGUUGGCUCAAUGAACAGAG | 2417 |
| AD-571757.1 | csgsuuggCfuCfFfAfAfugaacagaguL96 | 1888 | asCfsuucuGfuUfFfcauuGfAfgCfcaacgscsa | 2153 | UGCGUUGGCUCAAUGAACAGAGA | 2418 |
| AD-571758.1 | gsusugggCfuCfAfFfAfUfgaacagaaugauL96 | 1889 | asCfsuucuUfcUfGfUfcauuGfaGfccaacsgsc | 2154 | GCGUUGGCUCAAUGAACAGAGAU | 2419 |
| AD-571759.1 | ususggcuCffAfFfUfGfacagagauuL96 | 1890 | asAfsuucuCfuGfFfucauUfgAfgccaascsg | 2155 | CGUUGGCUCAAUGAACAGAGAUA | 2420 |
| AD-571760.1 | usgsgcucAfaUfFfCfFfaAfcagagauauL96 | 1891 | asUfsauucUfcUfFfuuuCfaUfuGfaagccasasc | 2156 | GUUGGCUCAAUGAACAGAGAUAC | 2421 |
| AD-571761.1 | gsgscucaAfuGfAfFfAfcagagauacuL96 | 1892 | asGfsusuauCfuCfUfguuCfAfuUfgagccsasa | 2157 | UUGGCUCAAUGAACAGAGAUACU | 2422 |
| AD-571762.1 | gscsucaaUfgAfAfFfCfagagauacuuL96 | 1893 | asAfsfsguAfAfuCfFfugucCfaAfUfugagcscsa | 2158 | UGGCUCAAUGAACAGAGAUACUA | 2423 |
| AD-571763.1 | csusucaaUfgAfFfCfAfgagauauacuauL96 | 1894 | asUfsfaguAfuCfFfuuCfgUfuUcAfuugagscsc | 2159 | GGCUCAAUGAACAGAGAUACUAC | 2424 |
| AD-571764.1 | uscsaaugAfaCfAfFfGfAfgauacuacuL96 | 1895 | asGfsuagUfAfuCfFfuCfucgUfuUfcauugsasc | 2160 | GCUCAAUGAACAGAGAUACUACG | 2425 |
| AD-571765.2 | csasauugAfaCfAfFfGfAfgauacuacguL96 | 1896 | asCfsguaUfUfcUfFfGfucUfcfuUfcauugsasg | 2161 | CUCAAUGAACAGAGAUACUACGG | 2426 |
| AD-571766.2 | asasauugAfaCfFfAfGfFfaGfafuacuacgguL96 | 1897 | asCfsfccguAfFfGfUfAfucUfcUfgUfucauusgsa | 2162 | UCAAUGAACAGAGAUACUACGGU | 2427 |
| AD-571767.2 | asusugaaCfAfGfAfFfgauacuacgguuL96 | 1898 | asAfsccgUfaGfFfauuCfFfcUfGfuuuCfausug | 2163 | CAAUGAACAGAGAUACUACGGUG | 2428 |
| AD-572383.1 | gscsagucAfaGfFfGfFfcaaugcuacgccuauL96 | 1899 | asUfsfauagGfCfFfgCfuFfAfgacCfUfGfuGfCfacugcsusc | 2164 | GAGCAGUCAAGGUCUACGCCUAU | 2429 |
| AD-572384.1 | csasagugcaAfgGfFfFfUfcFfacgccuauuL96 | 1900 | asAfsfauaGfGfCfGfFfagaCfcUfuUfgacugscsu | 2165 | AGCAGUCAAGGUCUACGCCUAUU | 2430 |
| AD-572385.1 | asgsuscAfaGfGfFfUfcacgccuauuuL96 | 1901 | asAfsfsauaUfaGfFfCfFfgtagAfcCfuUfugacugsc | 2166 | GCAGUCAAGGUCUACGCCUAUUA | 2431 |
| AD-572386.1 | gsusucaaGfgFfUfCfAfcAfcfgccuauuauL96 | 1902 | asUfsfauaAfuAfFfgGfCfguaGfAfcCfuuugacsusg | 2167 | CAGUCAAGGUCUACGCCUAUUAC | 2432 |

TABLE 21-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-572387.4 | uscsaa ggUfcU fAfCfg ccuauu acuL96 | 1903 | asGfsu aaUfaG fGfcgu aGfaCf cuugas csu | 2168 | AGUCAA GGUCUA CGCCUA UUACA | 2433 |
| AD-572391.1 | gsgsuc uaCfgC fCfUfa uuacaa ccuL96 | 1904 | asGfsg uuGfuA fAfuag gCfgUf agaccs usu | 2169 | AAGGUC UACGCC UAUUAC AACCU | 2434 |
| AD-572392.1 | gsuscu acGfcC fUfAfu uacaac cuuL96 | 1905 | asAfsg guUfgU fAfaua gGfcGf uagacs csu | 2170 | AGGUCU ACGCCU AUUACA ACCUG | 2435 |
| AD-572393.2 | uscsua cgCfcU fAfUfu acaacc uguL96 | 1906 | asCfsa ggUfuG fUfaau aGfgCf guagas csc | 2171 | GGUCUA CGCCUA UUACAA CCUGG | 2436 |
| AD-572394.1 | csusac gcCfuA fUfUfa caaccu gguL96 | 1907 | asCfsc agGfuU fGfuaa uAfgGf cguags asc | 2172 | GUCUAC GCCUAU UACAAC CUGGA | 2437 |
| AD-572395.1 | usascg ccUfaU fUfAfc aaccug gauL96 | 1908 | asUfsc caGfgU fUfgua aUfaGf gcguas gsa | 2173 | UCUACG CCUAUU ACAACC UGGAG | 2438 |
| AD-572396.1 | ascsgc cuAfuU fAfCfa accugg aguL96 | 1909 | asCfsu ccAfgG fUfugu aAfuAf ggcgus asg | 2174 | CUACGC CUAUUA CAACCU GGAGG | 2439 |
| AD-572397.1 | csgscc uaUfuA fCfAfa ccugga gguL96 | 1910 | asCfsc ucCfaG fGfuug uAfaUf aggcgs usa | 2175 | UACGCC UAUUAC AACCUG GAGGA | 2440 |
| AD-572495.1 | gscsug agGfaG fAfAfu ugcuuc auuL96 | 1911 | asAfsu gaAfgC fAfauu cUfcCf ucagcs asc | 2176 | GUGCUG AGGAGA AUUGCU UCAUA | 2441 |
| AD-572569.1 | gscsca ggAfgU fGfGfa cuaugu guuL96 | 1912 | asAfsc acAfuA fGfucc aCfuCf cuggcs usc | 2177 | GAGCCA GGAGUG GACUAU GUGUA | 2442 |
| AD-572570.1 | cscsag gaGfuG fGfAfc uaugug uauL96 | 1913 | asUfsa caCfaU fAfguc cAfcUf ccuggs csu | 2178 | AGCCAG GAGUGG ACUAUG UGUAC | 2443 |
| AD-572571.1 | csasgg agUfgG fAfCfu augugu acuL96 | 1914 | asGfsu acAfcA fUfagu cCfaCf uccugs gsc | 2179 | GCCAGG AGUGGA CUAUGU GUACA | 2444 |
| AD-572572.1 | asgsga guGfgA fCfUfa ugugua cauL96 | 1915 | asUfsg uaCfaC fAfuag uCfcAf cuccus gsg | 2180 | CCAGGA GUGGAC UAUGUG UACAA | 2445 |
| AD-572573.1 | gsgsag ugGfaC fUfAfu guguac aauL96 | 1916 | asUfsu guAfcA fCfaua gUfcCf acuccs usg | 2181 | CAGGAG UGGACU AUGUGU ACAAG | 2446 |
| AD-572574.1 | gsasgu ggAfcU fAfUfg uguaca aguL96 | 1917 | asCfsu ugUfaC fAfcau aGfuCf cacucs csu | 2182 | AGGAGU GGACUA UGUGUA CAAGA | 2447 |
| AD-572575.1 | asgsug gaCfuA fUfGfu guacaa gauL96 | 1918 | asUfsc uuGfuA fCfaca uAfgUf ccacus csc | 2183 | GGAGUG GACUAU GUGUAC AAGAC | 2448 |
| AD-572576.1 | gsusgg acUfaU fGfUfg uacaag acuL96 | 1919 | asGfsu cuUfgU fAfcac aUfaGf uccacs usc | 2184 | GAGUGG ACUAUG UGUACA AGACC | 2449 |
| AD-572577.1 | usgsga cuAfuG fUfGfu acaaga ccuL96 | 1920 | asGfsg ucUfuG fUfaca cAfuAf guccas csu | 2185 | AGUGGA CUAUGU GUACAA GACCC | 2450 |
| AD-572580.1 | ascsua ugUfgU fAfCfa agaccc gauL96 | 1921 | asUfsc ggGfuC fUfugu aCfaCf auagus esc | 2186 | GGACUA UGUGUA CAAGAC CCGAC | 2451 |
| AD-572581.1 | csusau guGfuA fCfAfa gacccg acuL96 | 1922 | asGfsu cgGfgU fCfuug uAfcAf cauags usc | 2187 | GACUAU GUGUAC AAGACC CGACU | 2452 |

TABLE 22

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-564723.1 | AGAGCGGGUACCUCUUCAUCU | 2453 | 470-490 | AGAUGAAGAGGUACCCGCUCUGC | 2714 | 468-490 |
| AD-564724.1 | GAGCGGGUACCUCUUCAUCCU | 2454 | 471-491 | AGGAUGAAGAGGUACCCGCUCUG | 2715 | 469-491 |
| AD-1069838.1 | AGCGGGUACCUCUUCAUCCAU | 2455 | 472-492 | AUGGAUGAAGAGGUACCCGCUCU | 2716 | 470-492 |
| AD-564726.1 | GCGGGUACCUCUUCAUCCAGU | 2456 | 473-493 | ACUGGAUGAAGAGGUACCCGCUC | 2717 | 471-493 |
| AD-564727.3 | CGGGUACCUCUUCAUCCAGAU | 2457 | 474-494 | AUCUGGAUGAAGAGGUACCCGCU | 2718 | 472-494 |
| AD-1069839.1 | GGGUACCUCUUCAUCCAGACU | 2458 | 475-495 | AGUCUGGAUGAAGAGGUACCCGC | 2719 | 473-495 |
| AD-1069840.1 | GGUACCUCUUCAUCCAGACAU | 2459 | 476-496 | AUGUCUGGAUGAAGAGGUACCCG | 2720 | 474-496 |
| AD-564730.3 | GUACCUCUUCAUCCAGACAGU | 2460 | 477-497 | ACUGUCUGGAUGAAGAGGUACCC | 2721 | 475-497 |
| AD-1069841.1 | UACCUCUUCAUCCAGACAGAU | 2461 | 478-498 | AUCUGUCUGGAUGAAGAGGUACC | 2722 | 476-498 |
| AD-564732.1 | ACCUCUUCAUCCAGACAGACU | 2462 | 479-499 | AGUCUGUCUGGAUGAAGAGGUAC | 2723 | 477-499 |
| AD-1069842.1 | CCUCUUCAUCCAGACAGACAU | 2463 | 480-500 | AUGUCUGUCUGGAUGAAGAGGUA | 2724 | 478-500 |
| AD-564734.1 | CUCUUCAUCCAGACAGACAAU | 2464 | 481-501 | AUUGUCUGUCUGGAUGAAGAGGU | 2725 | 479-501 |
| AD-1069843.1 | UCUUCAUCCAGACAGACAAGU | 2465 | 482-502 | ACUUGUCUGUCUGGAUGAAGAGG | 2726 | 480-502 |
| AD-564736.1 | CUUCAUCCAGACAGACAAGAU | 2466 | 483-503 | AUCUUGUCUGUCUGGAUGAAGAG | 2727 | 481-503 |
| AD-1069844.1 | UUCAUCCAGACAGACAAGACU | 2467 | 484-504 | AGUCUUGUCUGUCUGGAUGAAGA | 2728 | 482-504 |
| AD-564738.1 | UCAUCCAGACAGACAAGACCU | 2468 | 485-505 | AGGUCUUGUCUGUCUGGAUGAAG | 2729 | 483-505 |
| AD-564739.2 | CAUCCAGACAGACAAGACCAU | 2469 | 486-506 | AUGGUCUUGUCUGUCUGGAUGAA | 2730 | 484-506 |
| AD-1069845.1 | AUCCAGACAGACAAGACCAUU | 2470 | 487-507 | AAUGGUCUUGUCUGUCUGGAUGA | 2731 | 485-507 |
| AD-564741.1 | UCCAGACAGACAAGACCAUCU | 2471 | 488-508 | AGAUGGUCUUGUCUGUCUGGAUG | 2732 | 486-508 |
| AD-1069846.1 | CCAGACAGACAAGACCAUCUU | 2472 | 489-509 | AAGAUGGUCUUGUCUGUCUGGAU | 2733 | 487-509 |
| AD-1069847.1 | CAGACAGACAAGACCAUCUAU | 2473 | 490-510 | AUAGAUGGUCUUGUCUGUCUGGA | 2734 | 488-510 |
| AD-564745.3 | GACAGACAAGACCAUCUACAU | 2474 | 492-512 | AUGUAGAUGGUCUUGUCUGUCUG | 2735 | 490-512 |
| AD-564747.1 | CAGACAAGACCAUCUACACCU | 2475 | 494-514 | AGGUGUAGAUGGUCUUGUCUGUC | 2736 | 492-514 |
| AD-1069850.1 | ACAAGACCAUCUACACCCUU | 2476 | 497-517 | AAGGGGUGUAGAUGGUCUUGUCU | 2737 | 495-517 |
| AD-1069851.1 | GGCCAGUGGAAGAUCCGAGCU | 2477 | 697-717 | AGCUCGGAUCUUCCACUGGCCCA | 2738 | 695-717 |
| AD-1069852.1 | GCCAGUGGAAGAUCCGAGCCU | 2478 | 698-718 | AGGCUCGGAUCUUCCACUGGCCC | 2739 | 696-718 |
| AD-1069853.1 | CCAGUGGAAGAUCCGAGCCUU | 2479 | 699-719 | AAGGCUCGGAUCUUCCACUGGCC | 2740 | 697-719 |
| AD-564925.1 | CAGUGGAAGAUCCGAGCCUAU | 2480 | 700-720 | AUAGGCUCGGAUCUUCCACUGGC | 2741 | 698-720 |
| AD-1069854.1 | AGUGGAAGAUCCGAGCCUACU | 2481 | 701-721 | AGUAGGCUCGGAUCUUCCACUGG | 2742 | 699-721 |
| AD-1069855.1 | GUGGAAGAUCCGAGCCUACUU | 2482 | 702-722 | AAGUAGGCUCGGAUCUUCCACUG | 2743 | 700-722 |
| AD-1069856.1 | UGGAAGAUCCGAGCCUACUAU | 2483 | 703-723 | AUAGUAGGCUCGGAUCUUCCACU | 2744 | 701-723 |
| AD-564929.1 | GGAAGAUCCGAGCCUACUAUU | 2484 | 704-724 | AAUAGUAGGCUCGGAUCUUCCAC | 2745 | 702-724 |
| AD-564930.1 | GAAGAUCCGAGCCUACUAUGU | 2485 | 705-725 | ACAUAGUAGGCUCGGAUCUUCCA | 2746 | 703-725 |
| AD-1069857.1 | AAGAUCCGAGCCUACUAUGAU | 2486 | 706-726 | AUCAUAGUAGGCUCGGAUCUUCC | 2747 | 704-726 |
| AD-564934.1 | AUCCGAGCCUACUAUGAAAAU | 2487 | 709-729 | AUUUUCAUAGUAGGCUCGGAUCU | 2748 | 707-729 |
| AD-1069858.1 | UCCGAGCCUACUAUGAAAACU | 2488 | 710-730 | AGUUUUCAUAGUAGGCUCGGAUC | 2749 | 708-730 |
| AD-564936.1 | CCGAGCCUACUAUGAAAACUU | 2489 | 711-731 | AAGUUUUCAUAGUAGGCUCGGAU | 2750 | 709-731 |

TABLE 22-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-564937.1 | CGAGCCUACUAUGAAAACUCU | 2490 | 712-732 | AGAGUUUCAUAGUAGGCUCGGA | 2751 | 710-732 |
| AD-564938.1 | GAGCCUACUAUGAAAACUCAU | 2491 | 713-733 | AUGAGUUUCAUAGUAGGCUCGG | 2752 | 711-733 |
| AD-1069859.1 | GCCUACUAUGAAAACUCACCU | 2492 | 715-735 | AGGUGAGUUUUCAUAGUAGGCUC | 2753 | 713-735 |
| AD-564941.1 | CCUACUAUGAAAACUCACCAU | 2493 | 716-736 | AUGGUGAGUUUUCAUAGUAGGCU | 2754 | 714-736 |
| AD-1069860.1 | CUACUAUGAAAACUCACCACU | 2494 | 717-737 | AGUGGUGAGUUUUCAUAGUAGGC | 2755 | 715-737 |
| AD-564943.1 | UACUAUGAAAACUCACCACAU | 2495 | 718-738 | AUGUGGUGAGUUUUCAUAGUAGG | 2756 | 716-738 |
| AD-1069861.1 | CCUACAGAGAAAUUCUACUAU | 2496 | 805-825 | AUAGUAGAAUUUCUCUGUAGGCU | 2757 | 803-825 |
| AD-565031.1 | CUACAGAGAAAUUCUACUACU | 2497 | 806-826 | AGUAGUAGAAUUUCUCUGUAGGC | 2758 | 804-826 |
| AD-565032.1 | UACAGAGAAAUUCUACUACAU | 2498 | 807-827 | AUGUAGUAGAAUUUCUCUGUAGG | 2759 | 805-827 |
| AD-1069862.1 | ACAGAGAAAUUCUACUACAUU | 2499 | 808-828 | AAUGUAGUAGAAUUUCUCUGUAG | 2760 | 806-828 |
| AD-565034.1 | CAGAGAAAUUCUACUACAUCU | 2500 | 809-829 | AGAUGUAGUAGAAUUUCUCUGUA | 2761 | 807-829 |
| AD-565035.1 | AGAGAAAUUCUACUACAUCUU | 2501 | 810-830 | AAGAUGUAGUAGAAUUUCUCUGU | 2762 | 808-830 |
| AD-1069863.1 | GAGAAAUUCUACUACAUCUAU | 2502 | 811-831 | AUAGAUGUAGUAGAAUUUCUCUG | 2763 | 809-831 |
| AD-565037.1 | AGAAAUUCUACUACAUCUAUU | 2503 | 812-832 | AAUAGAUGUAGUAGAAUUUCUCU | 2764 | 810-832 |
| AD-565038.1 | GAAAUUCUACUACAUCUAUAU | 2504 | 813-833 | AUAUAGAUGUAGUAGAAUUUCUC | 2765 | 811-833 |
| AD-1069864.1 | AAAUUCUACUACAUCUAUAAU | 2505 | 814-834 | AUUAUAGAUGUAGUAGAAUUUCU | 2766 | 812-834 |
| AD-565041.1 | AUUCUACUACAUCUAUAACGU | 2506 | 816-836 | ACGUUAUAGAUGUAGUAGAAUUU | 2767 | 814-836 |
| AD-565042.1 | UUCUACUACAUCUAUAACGAU | 2507 | 817-837 | AUCGUUAUAGAUGUAGUAGAAUU | 2768 | 815-837 |
| AD-565043.1 | UCUACUACAUCUAUAACGAGU | 2508 | 818-838 | ACUCGUUAUAGAUGUAGUAGAAU | 2769 | 816-838 |
| AD-565044.1 | CUACUACAUCUAUAACGAGAU | 2509 | 819-839 | AUCUCGUAUAGAUGUAGUAGAA | 2770 | 817-839 |
| AD-1069865.1 | UACUACAUCUAUAACGAGAAU | 2510 | 820-840 | AUUCUCGUUAUAGAUGUAGUAGA | 2771 | 818-840 |
| AD-1069866.1 | ACUACAUCUAUAACGAGAAGU | 2511 | 821-841 | ACUUCUCGUUAUAGAUGUAGUAG | 2772 | 819-841 |
| AD-565047.1 | CUACAUCUAUAACGAGAAGGU | 2512 | 822-842 | ACCUUCUCGUUAUAGAUGUAGUA | 2773 | 820-842 |
| AD-1069867.1 | UACAUCUAUAACGAGAAGGGU | 2513 | 823-843 | ACCCUUCUCGUUAUAGAUGUAGU | 2774 | 821-843 |
| AD-565049.1 | ACAUCUAUAACGAGAAGGGCU | 2514 | 824-844 | AGCCCUUCUCGUUAUAGAUGUAG | 2775 | 822-844 |
| AD-565050.1 | CAUCUAUAACGAGAAGGGCCU | 2515 | 825-845 | AGGCCCUUCUCGUUAUAGAUGUA | 2776 | 823-845 |
| AD-565274.1 | CCUCUCCCUACCAGAUCCACU | 2516 | 1142-1162 | AGUGGAUCUGGUAGGGAGAGGUC | 2777 | 1140-1162 |
| AD-565275.1 | CUCUCCCUACCAGAUCCACUU | 2517 | 1143-1163 | AAGUGGAUCUGGUAGGGAGAGGU | 2778 | 1141-1163 |
| AD-1069868.1 | UCUCCCUACCAGAUCCACUUU | 2518 | 1144-1164 | AAAGUGGAUCUGGUAGGGAGAGG | 2779 | 1142-1164 |
| AD-1069869.1 | CUCCCUACCAGAUCCACUUCU | 2519 | 1145-1165 | AGAAGUGGAUCUGGUAGGGAGAG | 2780 | 1143-1165 |
| AD-565278.2 | UCCCUACCAGAUCCACUUCAU | 2520 | 1146-1166 | AUGAAGUGGAUCUGGUAGGGAGA | 2781 | 1144-1166 |
| AD-1069870.1 | CCCUACCAGAUCCACUUCACU | 2521 | 1147-1167 | AGUGAAGUGGAUCUGGUAGGGAG | 2782 | 1145-1167 |
| AD-565280.1 | CCUACCAGAUCCACUUCACCU | 2522 | 1148-1168 | AGGUGAAGUGGAUCUGGUAGGGA | 2783 | 1146-1168 |
| AD-565281.3 | CUACCAGAUCCACUUCACCAU | 2523 | 1149-1169 | AUGGUGAAGUGGAUCUGGUAGGG | 2784 | 1147-1169 |
| AD-1069871.1 | UACCAGAUCCACUUCACCAAU | 2524 | 1150-1170 | AUUGGUGAAGUGGAUCUGGUAGG | 2785 | 1148-1170 |
| AD-565283.1 | ACCAGAUCCACUUCACCAAGU | 2525 | 1151-1171 | ACUUGGUGAAGUGGAUCUGGUAG | 2786 | 1149-1171 |
| AD-1069872.1 | CCAGAUCCACUUCACCAAGAU | 2526 | 1152-1172 | AUCUUGGUGAAGUGGAUCUGGUA | 2787 | 1150-1172 |

TABLE 22-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-1069873.1 | CAGAUCCACUUCACCAAGACU | 2527 | 1153-1173 | AGUCUUGGUGAAGUGGAUCUGGU | 2788 | 1151-1173 |
| AD-565286.1 | AGAUCCACUUCACCAAGACAU | 2528 | 1154-1174 | AUGUCUUGGUGAAGUGGAUCUGG | 2789 | 1152-1174 |
| AD-565287.1 | GAUCCACUUCACCAAGACACU | 2529 | 1155-1175 | AGUGCUUGGUGAAGUGGAUCUG | 2790 | 1153-1175 |
| AD-1069874.1 | AUCCACUUCACCAAGACACCU | 2530 | 1156-1176 | AGGUGUCUUGGUGAAGUGGAUCU | 2791 | 1154-1176 |
| AD-1069875.1 | UUUGACCUCAUGGUGUUCGUU | 2531 | 1201-1221 | AACGAACACCAUGAGGUCAAAGG | 2792 | 1199-1221 |
| AD-565335.1 | UGACCUCAUGGUGUUCGUGAU | 2532 | 1203-1223 | AUCACGAACACCAUGAGGUCAAA | 2793 | 1201-1223 |
| AD-1069876.1 | AGGGCGUGUUCGUGCUGAAUU | 2533 | 1892-1912 | AAUUCAGCACGAACACGCCCUUG | 2794 | 1890-1912 |
| AD-565895.1 | GGGCGUGUUCGUGCUGAAUAU | 2534 | 1893-1913 | AUAUUCAGCACGAACACGCCCUU | 2795 | 1891-1913 |
| AD-1069877.1 | GGCGUGUUCGUGCUGAAUAAU | 2535 | 1894-1914 | AUUAUUCAGCACGAACACGCCCU | 2796 | 1892-1914 |
| AD-565897.1 | GCGUGUUCGUGCUGAAUAAGU | 2536 | 1895-1915 | ACUUAUCAGCACGAACACGCCC | 2797 | 1893-1915 |
| AD-565899.1 | GUGUUCGUGCUGAAUAAGAAU | 2537 | 1897-1917 | AUUCUUAUUCAGCACGAACACGC | 2798 | 1895-1917 |
| AD-565903.1 | UCGUGCUGAAUAAGAAGAACU | 2538 | 1901-1921 | AGUUCUCUUAUUCAGCACGAAC | 2799 | 1899-1921 |
| AD-565904.3 | CGUGCUGAAUAAGAAGAACAU | 2539 | 1902-1922 | AUGUUCUCUUAUUCAGCACGAA | 2800 | 1900-1922 |
| AD-1069878.1 | GUGCUGAAUAAGAAGAACAAU | 2540 | 1903-1923 | AUUGUUCUUCUUAUUCAGCACGA | 2801 | 1901-1923 |
| AD-565906.1 | UGCUGAAUAAGAAGAACAAAU | 2541 | 1904-1924 | AUUUGUCUUCUUAUUCAGCACG | 2802 | 1902-1924 |
| AD-565907.1 | GCUGAAUAAGAAGAACAAACU | 2542 | 1905-1925 | AGUUUGUCUUCUUAUUCAGCAC | 2803 | 1903-1925 |
| AD-1069879.1 | CUGAAUAAGAAGAACAAACUU | 2543 | 1906-1926 | AAGUUUGUUCUUCUUAUUCAGCA | 2804 | 1904-1926 |
| AD-565909.1 | UGAAUAAGAAGAACAAACUGU | 2544 | 1907-1927 | ACAGUUUGUUCUUCUUAUUCAGC | 2805 | 1905-1927 |
| AD-565910.1 | GAAUAAGAAGAACAAACUGAU | 2545 | 1908-1928 | AUCAGUUGUUCUUCUUAUUCAG | 2806 | 1906-1928 |
| AD-565911.1 | AAUAAGAAGAACAAACUGACU | 2546 | 1909-1929 | AGUCAGTUUGUUCUUCUUAUUCA | 2807 | 1907-1929 |
| AD-1069880.1 | AUAAGAAGAACAAACUGACGU | 2547 | 1910-1930 | ACGUCAGUUUGUUCUUCUUAUUC | 2808 | 1908-1930 |
| AD-565913.1 | UAAGAAGAACAAACUGACGCU | 2548 | 1911-1931 | AGCGUCAGUUUGUUCUUCUUAUU | 2809 | 1909-1931 |
| AD-1069881.1 | AAGAAGAACAAACUGACGCAU | 2549 | 1912-1932 | AUGCGUCAGUUUGUUCUUCUUAU | 2810 | 1910-1932 |
| AD-565915.1 | AGAAGAACAAACUGACGCAGU | 2550 | 1913-1933 | ACUGCGUCAGUUUGUUCUUCUUA | 2811 | 1911-1933 |
| AD-1069882.1 | GAAGAACAAACUGACGCAGAU | 2551 | 1914-1934 | AUCUGCGUCAGUUUGUUCUUCUU | 2812 | 1912-1934 |
| AD-1069883.1 | AAGAACAAACUGACGCAGAGU | 2552 | 1915-1935 | ACUCUGCGUCAGUUUGUUCUUCU | 2813 | 1913-1935 |
| AD-1069884.1 | AGAACAAACUGACGCAGAGUU | 2553 | 1916-1936 | AACUCUGCGUCAGUUUGUUCUUC | 2814 | 1914-1936 |
| AD-565919.1 | GAACAAACUGACGCAGAGUAU | 2554 | 1917-1937 | AUACUCUGCGUCAGUUUGUUCUU | 2815 | 1915-1937 |
| AD-1069885.1 | AACAAACUGACGCAGAGUAAU | 2555 | 1918-1938 | AUUACUCUGCGUCAGUUUGUUCU | 2816 | 1916-1938 |
| AD-565921.1 | ACAAACUGACGCAGAGUAAGU | 2556 | 1919-1939 | ACUUACUCUGCGUCAGUUUGUUC | 2817 | 1917-1939 |
| AD-1069886.1 | CAAACUGACGCAGAGUAAGAU | 2557 | 1920-1940 | AUCUUACUCUGCGUCAGUUUGUU | 2818 | 1918-1940 |
| AD-565923.1 | AAACUGACGCAGAGUAAGAUU | 2558 | 1921-1941 | AAUCUUACUCUGCGUCAGUUUGU | 2819 | 1919-1941 |
| AD-565924.1 | AACUGACGCAGAGUAAGAUCU | 2559 | 1922-1942 | AGAUCUUACUCUGCGUCAGUUUG | 2820 | 1920-1942 |
| AD-1069887.1 | CUGACGCAGAGUAAGAUCUGU | 2560 | 1924-1944 | ACAGAUCUUACUCUGCGUCAGUU | 2821 | 1922-1944 |
| AD-565927.1 | UGACGCAGAGUAAGAUCUGGU | 2561 | 1925-1945 | ACCAGATCUUACUCUGCGUCAGU | 2822 | 1923-1945 |
| AD-565928.1 | GACGCAGAGUAAGAUCUGGGU | 2562 | 1926-1946 | ACCCAGAUCUUACUCUGCGUCAG | 2823 | 1924-1946 |
| AD-1069888.1 | ACGCAGAGUAAGAUCUGGGAU | 2563 | 1927-1947 | AUCCCAGAUCUUACUCUGCGUCA | 2824 | 1925-1947 |

TABLE 22-continued

Unmodified Sense and Antisense Strand Sequences of Complement Component C3 dsRNA Agents

| Duplex Name | Sense Sequence 5' to 3' | SEQ ID NO: | Range in NM_ 000064.3 | Antisense Sequence 5' to 3' | SEQ ID NO: | Range in NM_ 000064.3 |
|---|---|---|---|---|---|---|
| AD-566379.1 | UGAGCAUGUCGGACAAGAAAU | 2564 | 2513-2533 | AUUUCUTGUCCGACAUGCUCACA | 2825 | 2511-2533 |
| AD-566380.1 | GAGCAUGUCGGACAAGAAAGU | 2565 | 2514-2534 | ACUUUCUGUCCGACAUGCUCAC | 2826 | 2512-2534 |
| AD-1069889.1 | AGCAUGUCGGACAAGAAAGGU | 2566 | 2515-2535 | ACCUUUCUUGUCCGACAUGCUCA | 2827 | 2513-2535 |
| AD-566382.1 | GCAUGUCGGACAAGAAAGGGU | 2567 | 2516-2536 | ACCCUUCUUGUCCGACAUGCUC | 2828 | 2514-2536 |
| AD-566383.2 | CAUGUCGGACAAGAAAGGGAU | 2568 | 2517-2537 | AUCCCUUCUUGUCCGACAUGCU | 2829 | 2515-2537 |
| AD-566384.2 | AUGUCGGACAAGAAAGGGAUU | 2569 | 2518-2538 | AAUCCCUUCUUGUCCGACAUGC | 2830 | 2516-2538 |
| AD-1069890.1 | UGUCGGACAAGAAAGGGAUCU | 2570 | 2519-2539 | AGAUCCCUUUCUUGUCCGACAUG | 2831 | 2517-2539 |
| AD-1069891.1 | GUCGGACAAGAAAGGGAUCUU | 2571 | 2520-2540 | AAGAUCCCUUUCUUGUCCGACAU | 2832 | 2518-2540 |
| AD-1069892.1 | UCGGACAAGAAAGGGAUCUGU | 2572 | 2521-2541 | ACAGAUCCCUUUCUUGUCCGACA | 2833 | 2519-2541 |
| AD-566388.2 | CGGACAAGAAAGGGAUCUGUU | 2573 | 2522-2542 | AACAGATCCCUUUCUUGUCCGAC | 2834 | 2520-2542 |
| AD-566389.1 | GGACAAGAAAGGGAUCUGUGU | 2574 | 2523-2543 | ACACAGAUCCCUUUCUUGUCCGA | 2835 | 2521-2543 |
| AD-1069893.1 | GACAAGAAAGGGAUCUGUGUU | 2575 | 2524-2544 | AACACAGAUCCCUUUCUUGUCCG | 2836 | 2522-2544 |
| AD-566391.1 | ACAAGAAAGGGAUCUGUGUGU | 2576 | 2525-2545 | ACACACAGAUCCCUUUCUUGUCC | 2837 | 2523-2545 |
| AD-1069894.1 | CAAGAAAGGGAUCUGUGUGGU | 2577 | 2526-2546 | ACCACACAGAUCCCUUUCUUGUC | 2838 | 2524-2546 |
| AD-566393.1 | AAGAAAGGGAUCUGUGUGGCU | 2578 | 2527-2547 | AGCCACACAGAUCCCUUUCUUGU | 2839 | 2525-2547 |
| AD-566395.1 | GAAAGGGAUCUGUGUGGCAGU | 2579 | 2529-2549 | ACUGCCACACAGAUCCCUUUCUU | 2840 | 2527-2549 |
| AD-1069896.1 | AAAGGGAUCUGUGUGGCAGAU | 2580 | 2530-2550 | AUCUGCCACACAGAUCCCUUUCU | 2841 | 2528-2550 |
| AD-1069897.1 | AAGGGAUCUGUGUGGCAGACU | 2581 | 2531-2551 | AGUCUGCCACACAGAUCCCUUUC | 2842 | 2529-2551 |
| AD-1069898.1 | AGGGAUCUGUGUGGCAGACCU | 2582 | 2532-2552 | AGGUCUGCCACACAGAUCCCUUU | 2843 | 2530-2552 |
| AD-1069899.1 | GGGAUCUGUGUGGCAGACCCU | 2583 | 2533-2553 | AGGGUCTGCCACACAGAUCCCUU | 2844 | 2531-2553 |
| AD-566475.1 | GAAAUCCGAGCCGUUCUCUAU | 2584 | 2629-2649 | AUAGAGAACGGCUCGGAUUUCCA | 2845 | 2627-2649 |
| AD-1069900.1 | AAAUCCGAGCCGUUCUCUACU | 2585 | 2630-2650 | AGUAGAGAACGGCUCGGAUUUCC | 2846 | 2628-2650 |
| AD-566477.1 | AAUCCGAGCCGUUCUCUACAU | 2586 | 2631-2651 | AUGUAGAGAACGGCUCGGAUUUC | 2847 | 2629-2651 |
| AD-1069901.1 | AUCCGAGCCGUUCUCUACAAU | 2587 | 2632-2652 | AUUGUAGAGAACGGCUCGGAUUU | 2848 | 2630-2652 |
| AD-566483.1 | AGCCGUUCUCUACAAUUACCU | 2588 | 2637-2657 | AGGUAAUGUAGAGAACGGCUCG | 2849 | 2635-2657 |
| AD-566484.1 | GCCGUUCUCUACAAUUACCGU | 2589 | 2638-2658 | ACGGUAAUUGUAGAGAACGGCUC | 2850 | 2636-2658 |
| AD-566485.2 | CCGUUCUCUACAAUUACCGGU | 2590 | 2639-2659 | ACCGGUAAUUGUAGAGAACGGCU | 2851 | 2637-2659 |
| AD-566486.1 | CGUUCUCUACAAUUACCGGCU | 2591 | 2640-2660 | AGCCGGUAAUUGUAGAGAACGGC | 2852 | 2638-2660 |
| AD-1069902.1 | GUUCUCUACAAUUACCGGCAU | 2592 | 2641-2661 | AUGCCGGUAAUUGUAGAGAACGG | 2853 | 2639-2661 |
| AD-1069903.1 | UUCUCUACAAUUACCGGCAGU | 2593 | 2642-2662 | ACUGCCGGUAAUUGUAGAGAACG | 2854 | 2640-2662 |
| AD-1069904.1 | UCUCUACAAUUACCGGCAGAU | 2594 | 2643-2663 | AUCUGCCGGUAAUUGUAGAGAAC | 2855 | 2641-2663 |
| AD-1069905.1 | GGCUGACCGCCUACGUGGUCU | 2595 | 3323-3343 | AGACCACGUAGGCGGUCAGCCAG | 2856 | 3321-3343 |
| AD-567054.1 | GCUGACCGCCUACGUGGUCAU | 2596 | 3324-3344 | AUGACCACGUAGGCGGUCAGCCA | 2857 | 3322-3344 |
| AD-1069906.1 | CUGACCGCCUACGUGGUCAAU | 2597 | 3325-3345 | AUUGACCACGUAGGCGGUCAGCC | 2858 | 3323-3345 |
| AD-1069907.1 | UGACCGCCUACGUGGUCAAGU | 2598 | 3326-3346 | ACUUGACCACGUAGGCGGUCAGC | 2859 | 3324-3346 |
| AD-567057.1 | GACCGCCUACGUGGUCAAGGU | 2599 | 3327-3347 | ACCUUGACCACGUAGGCGGUCAG | 2860 | 3325-3347 |
| AD-1069908.1 | ACCGCCUACGUGGUCAAGGUU | 2600 | 3328-3348 | AACCUUGACCACGUAGGCGGUCA | 2861 | 3326-3348 |

TABLE 22-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-567059.1 | CCGCCUACGUGGUCAAGGUCU | 2601 | 3329-3349 | AGACCUUGACCACGUAGGCGGUC | 2862 | 3327-3349 |
| AD-567060.1 | CGCCUACGUGGUCAAGGUCUU | 2602 | 3330-3350 | AAGACCUUGACCACGUAGGCGGU | 2863 | 3328-3350 |
| AD-1069909.1 | GCCUACGUGGUCAAGGUCUUU | 2603 | 3331-3351 | AAAGACCUUGACCACGUAGGCGG | 2864 | 3329-3351 |
| AD-1069910.1 | CCUACGUGGUCAAGGUCUUCU | 2604 | 3332-3352 | AGAAGACCUUGACCACGUAGGCG | 2865 | 3330-3352 |
| AD-567063.4 | CUACGUGGUCAAGGUCUUCUU | 2605 | 3333-3353 | AAGAAGACCUUGACCACGUAGGC | 2866 | 3331-3353 |
| AD-1069911.1 | UACGUGGUCAAGGUCUUCUCU | 2606 | 3334-3354 | AGAGAAGACCUUGACCACGUAGG | 2867 | 3332-3354 |
| AD-567065.1 | ACGUGGUCAAGGUCUUCUCUU | 2607 | 3335-3355 | AAGAGAAGACCUUGACCACGUAG | 2868 | 3333-3355 |
| AD-567066.4 | CGUGGUCAAGGUCUUCUCUCU | 2608 | 3336-3356 | AGAGAGAAGACCUUGACCACGUA | 2869 | 3334-3356 |
| AD-1069912.1 | GUGGUCAAGGUCUUCUCUCUU | 2609 | 3337-3357 | AAGAGAGAAGACCUUGACCACGU | 2870 | 3335-3357 |
| AD-567068.1 | UGGUCAAGGUCUUCUCUCUGU | 2610 | 3338-3358 | ACAGAGAGAAGACCUUGACCACG | 2871 | 3336-3358 |
| AD-1069913.1 | GGUCAAGGUCUUCUCUCUGGU | 2611 | 3339-3359 | ACCAGAGAGAAGACCUUGACCAC | 2872 | 3337-3359 |
| AD-567070.1 | GUCAAGGUCUUCUCUCUGGCU | 2612 | 3340-3360 | AGCCAGAGAGAAGACCUUGACCA | 2873 | 3338-3360 |
| AD-1069914.1 | UCAAGGUCUUCUCUCUGGCUU | 2613 | 3341-3361 | AAGCCAGAGAGAAGACCUUGACC | 2874 | 3339-3361 |
| AD-567072.1 | CAAGGUCUUCUCUCUGGCUGU | 2614 | 3342-3362 | ACAGCCAGAGAGAAGACCUUGAC | 2875 | 3340-3362 |
| AD-1069915.1 | AAGGUCUUCUCUCUGGCUGUU | 2615 | 3343-3363 | AACAGCCAGAGAGAAGACCUUGA | 2876 | 3341-3363 |
| AD-1069916.1 | AGGUCUUCUCUCUGGCUGUCU | 2616 | 3344-3364 | AGACAGCCAGAGAGAAGACCUUG | 2877 | 3342-3364 |
| AD-1069917.1 | GGUCUUCUCUCUGGCUGUCAU | 2617 | 3345-3365 | AUGACAGCCAGAGAGAAGACCUU | 2878 | 3343-3365 |
| AD-567076.1 | GUCUUCUCUCUGGCUGUCAAU | 2618 | 3346-3366 | AUUGACAGCCAGAGAGAAGACCU | 2879 | 3344-3366 |
| AD-1069918.1 | UCUUCUCUCUGGCUGUCAACU | 2619 | 3347-3367 | AGUUGACAGCCAGAGAGAAGACC | 2880 | 3345-3367 |
| AD-567294.1 | UAAAGCAGGAGACUUCCUUGU | 2620 | 3603-3623 | ACAAGGAAGUCUCCUGCUUUAGU | 2881 | 3601-3623 |
| AD-1069919.1 | AAAGCAGGAGACUUCCUUGAU | 2621 | 3604-3624 | AUCAAGGAAGUCUCCUGCUUUAG | 2882 | 3602-3624 |
| AD-1069920.1 | AAGCAGGAGACUUCCUUGAAU | 2622 | 3605-3625 | AUUCAAGGAAGUCUCCUGCUUUA | 2883 | 3603-3625 |
| AD-567297.1 | AGCAGGAGACUUCCUUGAAGU | 2623 | 3606-3626 | ACUUCAAGGAAGUCUCCUGCUUU | 2884 | 3604-3626 |
| AD-567300.1 | AGGAGACUUCCUUGAAGCCAU | 2624 | 3609-3629 | AUGGCUUCAAGGAAGUCUCCUGC | 2885 | 3607-3629 |
| AD-567301.1 | GGAGACUUCCUUGAAGCCAAU | 2625 | 3610-3630 | AUUGGCUUCAAGGAAGUCUCCUG | 2886 | 3608-3630 |
| AD-1069922.1 | GAGACUUCCUUGAAGCCAACU | 2626 | 3611-3631 | AGUUGGCUUCAAGGAAGUCUCCU | 2887 | 3609-3631 |
| AD-1069923.1 | AGACUUCCUUGAAGCCAACUU | 2627 | 3612-3632 | AAGUUGGCUUCAAGGAAGUCUCC | 2888 | 3610-3632 |
| AD-1069924.1 | GACUUCCUUGAAGCCAACUAU | 2628 | 3613-3633 | AUAGUUGGCUUCAAGGAAGUCUC | 2889 | 3611-3633 |
| AD-567305.1 | ACUUCCUUGAAGCCAACUACU | 2629 | 3614-3634 | AGUAGUUGGCUUCAAGGAAGUCU | 2890 | 3612-3634 |
| AD-567306.1 | CUUCCUUGAAGCCAACUACAU | 2630 | 3615-3635 | AUGUAGUUGGCUUCAAGGAAGUC | 2891 | 3613-3635 |
| AD-567308.1 | UCCUUGAAGCCAACUACAUGU | 2631 | 3617-3637 | ACAUGUAGUUGGCUUCAAGGAAG | 2892 | 3615-3637 |
| AD-567309.1 | CCUUGAAGCCAACUACAUGAU | 2632 | 3618-3638 | AUCAUGUAGUUGGCUUCAAGGAA | 2893 | 3616-3638 |
| AD-1069925.1 | CUUGAAGCCAACUACAUGAAU | 2633 | 3619-3639 | AUUCAUGUAGUUGGCUUCAAGGA | 2894 | 3617-3639 |
| AD-567311.1 | UUGAAGCCAACUACAUGAACU | 2634 | 3620-3640 | AGUUCAUGUAGUUGGCUUCAAGG | 2895 | 3618-3640 |
| AD-567312.1 | UGAAGCCAACUACAUGAACCU | 2635 | 3621-3641 | AGGUUCAUGUAGUUGGCUUCAAG | 2896 | 3619-3641 |
| AD-1069926.1 | GAAGCCAACUACAUGAACCUU | 2636 | 3622-3642 | AAGGUUCAUGUAGUUGGCUUCAA | 2897 | 3620-3642 |
| AD-567314.2 | AAGCCAACUACAUGAACCUAU | 2637 | 3623-3643 | AUAGGUUCAUGUAGUUGGCUUCA | 2898 | 3621-3643 |

TABLE 22-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-567315.6 | AGCCAACUACAUGAACCUACU | 2638 | 3624-3644 | AGUAGGUUCAUGUAGUUGGCUUC | 2899 | 3622-3644 |
| AD-1069927.1 | GCCAACUACAUGAACCUACAU | 2639 | 3625-3645 | AUGUAGGUUCAUGUAGUUGGCUU | 2900 | 3623-3645 |
| AD-1069928.1 | CCAACUACAUGAACCUACAGU | 2640 | 3626-3646 | ACUGUAGGUUCAUGUAGUUGGCU | 2901 | 3624-3646 |
| AD-567318.2 | CAACUACAUGAACCUACAGAU | 2641 | 3627-3647 | AUCUGUAGGUUCAUGUAGUUGGC | 2902 | 3625-3647 |
| AD-567319.1 | AACUACAUGAACCUACAGAGU | 2642 | 3628-3648 | ACUCUGUAGGUUCAUGUAGUUGG | 2903 | 3626-3648 |
| AD-1069929.1 | ACUACAUGAACCUACAGAGAU | 2643 | 3629-3649 | AUCUCUGUAGGUUCAUGUAGUUG | 2904 | 3627-3649 |
| AD-567321.1 | CUACAUGAACCUACAGAGAUU | 2644 | 3630-3650 | AAUCUCUGUAGGUUCAUGUAGUU | 2905 | 3628-3650 |
| AD-1069930.1 | UACAUGAACCUACAGAGAUCU | 2645 | 3631-3651 | AGAUCUCUGUAGGUUCAUGUAGU | 2906 | 3629-3651 |
| AD-567323.1 | ACAUGAACCUACAGAGAUCCU | 2646 | 3632-3652 | AGGAUCUCUGUAGGUUCAUGUAG | 2907 | 3630-3652 |
| AD-1069931.1 | CAUGAACCUACAGAGAUCCUU | 2647 | 3633-3653 | AAGGAUCUCUGUAGGUUCAUGUA | 2908 | 3631-3653 |
| AD-567325.1 | AUGAACCUACAGAGAUCCUAU | 2648 | 3634-3654 | AUAGGAUCUCUGUAGGUUCAUGU | 2909 | 3632-3654 |
| AD-567326.1 | UGAACCUACAGAGAUCCUACU | 2649 | 3635-3655 | AGUAGGAUCUCUGUAGGUUCAUG | 2910 | 3633-3655 |
| AD-1069932.1 | GAACCUACAGAGAUCCUACAU | 2650 | 3636-3656 | AUGUAGGAUCUCUGUAGGUUCAU | 2911 | 3634-3656 |
| AD-1069933.1 | AACCUACAGAGAUCCUACACU | 2651 | 3637-3657 | AGUGUAGGAUCUCUGUAGGUUCA | 2912 | 3635-3657 |
| AD-567479.1 | GGCCCUACUGCAGCUAAAAGU | 2652 | 3807-3827 | ACUUUUAGCUGCAGUAGGGCCAA | 2913 | 3805-3827 |
| AD-567480.1 | GCCCUACUGCAGCUAAAAGAU | 2653 | 3808-3828 | AUCUUUUAGCUGCAGUAGGGCCA | 2914 | 3806-3828 |
| AD-567481.1 | CCCUACUGCAGCUAAAAGACU | 2654 | 3809-3829 | AGUCUUUUAGCUGCAGUAGGGCC | 2915 | 3807-3829 |
| AD-567482.1 | CCUACUGCAGCUAAAAGACUU | 2655 | 3810-3830 | AAGUCUUUUAGCUGCAGUAGGGC | 2916 | 3808-3830 |
| AD-1069934.1 | UACUGCAGCUAAAAGACUUUU | 2656 | 3812-3832 | AAAAGUCUUUUAGCUGCAGUAGG | 2917 | 3810-3832 |
| AD-567485.1 | ACUGCAGCUAAAAGACUUUGU | 2657 | 3813-3833 | ACAAAGUCUUUUAGCUGCAGUAG | 2918 | 3811-3833 |
| AD-1069935.1 | CUGCAGCUAAAAGACUUUGAU | 2658 | 3814-3834 | AUCAAAGUCUUUUAGCUGCAGUA | 2919 | 3812-3834 |
| AD-567487.2 | UGCAGCUAAAAGACUUUGACU | 2659 | 3815-3835 | AGUCAAAGUCUUUUAGCUGCAGU | 2920 | 3813-3835 |
| AD-567488.1 | GCAGCUAAAAGACUUUGACUU | 2660 | 3816-3836 | AAGUCAAAGUCUUUUAGCUGCAG | 2921 | 3814-3836 |
| AD-567489.1 | CAGCUAAAAGACUUUGACUUU | 2661 | 3817-3837 | AAAGUCAAAGUCUUUUAGCUGCA | 2922 | 3815-3837 |
| AD-1069936.1 | AGCUAAAAGACUUUGACUUUU | 2662 | 3818-3838 | AAAAGUCAAAGUCUUUUAGCUGC | 2923 | 3816-3838 |
| AD-567491.1 | GCUAAAAGACUUUGACUUUGU | 2663 | 3819-3839 | ACAAAGUCAAAGUCUUUUAGCUG | 2924 | 3817-3839 |
| AD-1069937.1 | GUGCCUCCCGUCGUGCGUUGU | 2664 | 3838-3858 | ACAACGCACGACGGGAGGCACAA | 2925 | 3836-3858 |
| AD-1069938.1 | UGCCUCCCGUCGUGCGUUGGU | 2665 | 3839-3859 | ACCAACGCACGACGGGAGGCACA | 2926 | 3837-3859 |
| AD-1069939.1 | GCCUCCCGUCGUGCGUUGGCU | 2666 | 3840-3860 | AGCCAACGCACGACGGGAGGCAC | 2927 | 3838-3860 |
| AD-567513.1 | CCUCCCGUCGUGCGUUGGCUU | 2667 | 3841-3861 | AAGCCAACGCACGACGGGAGGCA | 2928 | 3839-3861 |
| AD-567514.1 | CUCCCGUCGUGCGUUGGCUCU | 2668 | 3842-3862 | AGAGCCAACGCACGACGGGAGGC | 2929 | 3840-3862 |
| AD-1069940.1 | UCCCGUCGUGCGUUGGCUCAU | 2669 | 3843-3863 | AUGAGCCAACGCACGACGGGAGG | 2930 | 3841-3863 |
| AD-1069941.1 | CCCGUCGUGCGUUGGCUCAAU | 2670 | 3844-3864 | AUUGAGCCAACGCACGACGGGAG | 2931 | 3842-3864 |
| AD-1069942.1 | CCGUCGUGCGUUGGCUCAAUU | 2671 | 3845-3865 | AAUUGAGCCAACGCACGACGGGA | 2932 | 3843-3865 |
| AD-567518.1 | CGUCGUGCGUUGGCUCAAUGU | 2672 | 3846-3866 | ACAUUGAGCCAACGCACGACGGG | 2933 | 3844-3866 |
| AD-1069943.1 | GUCGUGCGUUGGCUCAAUGAU | 2673 | 3847-3867 | AUCAUUGAGCCAACGCACGACGG | 2934 | 3845-3867 |
| AD-567521.4 | CGUGCGUUGGCUCAAUGAACU | 2674 | 3849-3869 | AGUUCAUGAGCCAACGCACGAC | 2935 | 3847-3869 |

TABLE 22-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-1069944.1 | UGCGUUGGCUCAAUGAACAGU | 2675 | 3851-3871 | ACUGUUCAUUGAGCCAACGCACG | 2936 | 3849-3871 |
| AD-567524.1 | GCGUUGGCUCAAUGAACAGAU | 2676 | 3852-3872 | AUCUGUCAUUGAGCCAACGCAC | 2937 | 3850-3872 |
| AD-567525.1 | CGUUGGCUCAAUGAACAGAGU | 2677 | 3853-3873 | ACUCUGUCAUUGAGCCAACGCA | 2938 | 3851-3873 |
| AD-1069945.1 | GUUGGCUCAAUGAACAGAGAU | 2678 | 3854-3874 | AUCUCUGUUCAUUGAGCCAACGC | 2939 | 3852-3874 |
| AD-567527.1 | UUGGCUCAAUGAACAGAGAUU | 2679 | 3855-3875 | AAUCUCUGUUCAUUGAGCCAACG | 2940 | 3853-3875 |
| AD-1069946.1 | UGGCUCAAUGAACAGAGAUAU | 2680 | 3856-3876 | AUAUCUCUGUUCAUUGAGCCAAC | 2941 | 3854-3876 |
| AD-567529.1 | GGCUCAAUGAACAGAGAUACU | 2681 | 3857-3877 | AGUAUCUCUGUUCAUUGAGCCAA | 2942 | 3855-3877 |
| AD-1069947.1 | GCUCAAUGAACAGAGAUACUU | 2682 | 3858-3878 | AAGUAUCUCUGUUCAUUGAGCCA | 2943 | 3856-3878 |
| AD-567531.1 | CUCAAUGAACAGAGAUACUAU | 2683 | 3859-3879 | AUAGUAUCUCUGUUCAUUGAGCC | 2944 | 3857-3879 |
| AD-567532.1 | UCAAUGAACAGAGAUACUACU | 2684 | 3860-3880 | AGUAGUAUCUCUGUUCAUUGAGC | 2945 | 3858-3880 |
| AD-567533.1 | CAAUGAACAGAGAUACUACGU | 2685 | 3861-3881 | ACGUAGUAUCUCUGUUCAUUGAG | 2946 | 3859-3881 |
| AD-1069948.1 | AAUGAACAGAGAUACUACGGU | 2686 | 3862-3882 | ACCGUAGUAUCUCUGUUCAUUGA | 2947 | 3860-3882 |
| AD-567535.1 | AUGAACAGAGAUACUACGGUU | 2687 | 3863-3883 | AACCGUAGUAUCUCUGUUCAUUG | 2948 | 3861-3883 |
| AD-568149.1 | GAGCAGUCAAGGUCUACGCCU | 2688 | 4517-4537 | AGGCGUAGACCUUGACUGCUCCA | 2949 | 4515-4537 |
| AD-568150.1 | AGCAGUCAAGGUCUACGCCUU | 2689 | 4518-4538 | AAGGCGUAGACCUUGACUGCUCC | 2950 | 4516-4538 |
| AD-1069949.1 | GCAGUCAAGGUCUACGCCUAU | 2690 | 4519-4539 | AUAGGCGUAGACCUUGACUGCUC | 2951 | 4517-4539 |
| AD-1069950.1 | CAGUCAAGGUCUACGCCUAUU | 2691 | 4520-4540 | AAUAGGCGUAGACCUUGACUGCU | 2952 | 4518-4540 |
| AD-1069951.1 | AGUCAAGGUCUACGCCUAUUU | 2692 | 4521-4541 | AAAUAGGCGUAGACCUUGACUGC | 2953 | 4519-4541 |
| AD-1069952.1 | GUCAAGGUCUACGCCUAUUAU | 2693 | 4522-4542 | AUAAUAGGCGUAGACCUUGACUG | 2954 | 4520-4542 |
| AD-568155.1 | UCAAGGUCUACGCCUAUUACU | 2694 | 4523-4543 | AGUAAUAGGCGUAGACCUUGACU | 2955 | 4521-4543 |
| AD-568159.1 | GGUCUACGCCUAUUACAACCU | 2695 | 4527-4547 | AGGUUGUAAUAGGCGUAGACCUU | 2956 | 4525-4547 |
| AD-1069953.1 | GUCUACGCCUAUUACAACCUU | 2696 | 4528-4548 | AAGGUUGUAAUAGGCGUAGACCU | 2957 | 4526-4548 |
| AD-568161.2 | UCUACGCCUAUUACAACCUGU | 2697 | 4529-4549 | ACAGGUUGUAAUAGGCGUAGACC | 2958 | 4527-4549 |
| AD-568162.1 | CUACGCCUAUUACAACCUGGU | 2698 | 4530-4550 | ACCAGGUUGUAAUAGGCGUAGAC | 2959 | 4528-4550 |
| AD-1069954.1 | UACGCCUAUUACAACCUGGAU | 2699 | 4531-4551 | AUCCAGGUUGUAAUAGGCGUAGA | 2960 | 4529-4551 |
| AD-1069955.1 | ACGCCUAUUACAACCUGGAGU | 2700 | 4532-4552 | ACUCCAGGUUGUAAUAGGCGUAG | 2961 | 4530-4552 |
| AD-568165.1 | CGCCUAUUACAACCUGGAGGU | 2701 | 4533-4553 | ACCUCCAGGUUGUAAUAGGCGUA | 2962 | 4531-4553 |
| AD-1069956.1 | GCUGAGGAGAAUUGCUUCAUU | 2702 | 4633-4653 | AAUGAAGCAAUUCUCCUCAGCAC | 2963 | 4631-4653 |
| AD-568337.1 | GCCAGGAGUGGACUAUGUGUU | 2703 | 4707-4727 | AACACAUAGUCCACUCCUGGCUC | 2964 | 4705-4727 |
| AD-568338.1 | CCAGGAGUGGACUAUGUGUAU | 2704 | 4708-4728 | AUACACAUAGUCCACUCCUGGCU | 2965 | 4706-4728 |
| AD-1069957.1 | CAGGAGUGGACUAUGUGUACU | 2705 | 4709-4729 | AGUACACAUAGUCCACUCCUGGC | 2966 | 4707-4729 |
| AD-568340.1 | AGGAGUGGACUAUGUGUACAU | 2706 | 4710-4730 | AUGUACACAUAGUCCACUCCUGG | 2967 | 4708-4730 |
| AD-1069958.1 | GGAGUGGACUAUGUGUACAAU | 2707 | 4711-4731 | AUUGUACACAUAGUCCACUCCUG | 2968 | 4709-4731 |
| AD-568342.1 | GAGUGGACUAUGUGUACAAGU | 2708 | 4712-4732 | ACUUGUACACAUAGUCCACUCCU | 2969 | 4710-4732 |
| AD-568343.4 | AGUGGACUAUGUGUACAAGAU | 2709 | 4713-4733 | AUCUUGUACACAUAGUCCACUCC | 2970 | 4711-4733 |
| AD-1069959.1 | GUGGACUAUGUGUACAAGACU | 2710 | 4714-4734 | AGUCUUGUACACAUAGUCCACUC | 2971 | 4712-4734 |
| AD-568345.2 | UGGACUAUGUGUACAAGACCU | 2711 | 4715-4735 | AGGUCUGUACACAUAGUCCACU | 2972 | 4713-4735 |

TABLE 22-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-568348.1 | ACUAUGUGUACAAGACCCGAU | 2712 | 4718-4738 | AUCGGGTCUUGUACACAUAGUCC | 2973 | 4716-4738 |
| AD-1069961.1 | CUAUGUGUACAAGACCCGACU | 2713 | 4719-4739 | AGUCGGGUCUUGUACACAUAGUC | 2974 | 4717-4739 |

TABLE 23

Modified Sense and Antisense Strand Sequences of Complement Component C3 dsRNA Agents

| Duplex Name | Sense Sequene 5' to 3' | SEQ ID NO: | Antisense Sequence 5' to 3' | SEQ ID NO: | mRNA Target Sequence | SEQ ID NO: |
|---|---|---|---|---|---|---|
| AD-564723.1 | asgsagcggGfgUfAfCfcucuucaucuL96 | 2975 | asGfsauga(Agn)gaguaCfcCfgcucusgsc | 3236 | GCAGAGCGGGUACCUCUUCAUCC | 3497 |
| AD-564724.1 | gsasgcggGfuAfCfCfcuucaucuucauL96 | 2976 | asGfsgaug(Agn)agaguaAfcCfegcucsusg | 3237 | CAGAGCGGGUACCUCUUCAUCCA | 3498 |
| AD-1069838.1 | asgscggUfaCfCfUfCfuucaucaucauL96 | 2977 | asUfsggau(G2p)aagaggUfaCfecgcucscu | 3238 | AGAGCGGGUACCUCUUCAUCCAG | 3499 |
| AD-564726.1 | gscsgguAfcCfCfUfCfuucauccaguL96 | 2978 | asCfsugga(Tgn)gaagagGfuAfeccgcsusc | 3239 | GAGCGGGUACCUCUUCAUCCAGA | 3500 |
| AD-564727.3 | csgsggguaCfcUfCfUfcuucauccagaUL96 | 2979 | asUfscugg(Agn)ugaagaGfgUfacccgscsu | 3240 | AGCGGGUACCUCUUCAUCCAGAC | 3501 |
| AD-1069839.1 | gsgsguacCfuCfUfUfCfauccagacauL96 | 2980 | asGfsucug(G2p)augaagAfgGfuaccesgsc | 3241 | GCGGGUACCUCUUCAUCCAGACA | 3502 |
| AD-1069840.1 | gsgsuaccUfcUfUfCfauccagacagL96 | 2981 | asUfsgucu(G2p)gaugaaGfaGfuaccscsg | 3242 | CGGGUACCUCUUCAUCCAGACAG | 3503 |
| AD-564730.3 | gsusaccuUfcUfUfCfauccagacaguL96 | 2982 | asCfsuguc(Tgn)ggaugaAfgGfuaccscsc | 3243 | GGGUACCUCUUCAUCCAGACAGA | 3504 |
| AD-1069841.1 | usasccucUfuCfAfUfCfcagacagacauL96 | 2983 | asGfscugu(C2p)uggaugAfaGfagguascsc | 3244 | GGUACCUCUUCAUCCAGACAGAC | 3505 |
| AD-1069732.1 | ascscucuCfaUfCfCfAfGfcagacagacauL96 | 2984 | asCfscucu(Tgn)cuggauGfaAfgaggusasc | 3245 | GUACCUCUUCAUCCAGACAGACA | 3506 |
| AD-1069842.1 | cscsucucUfaUfCfCfagacagacauL96 | 2985 | asGfsucu(G2p)ucuggaUfgAfagagguga | 3246 | UACCUCUUCAUCCAGACAGACAA | 3507 |
| AD-1069734.1 | csusucuuCfaUfCfCfAfGfacagacaauL96 | 2986 | asUfsgucu(Tgn)gucuggAfuGfaagagsgsu | 3247 | ACCUCUUCAUCCAGACAGACAAG | 3508 |
| AD-1069843.1 | uscsuucaUfcCfAfGfacagacaaguL96 | 2987 | asCfsuugu(C2p)ugucugGfaUfgaagasgsg | 3248 | CCUCUUCAUCCAGACAGACAAGA | 3509 |
| AD-564736.1 | csusuucauCfcAfGfAfGfacagacaauL96 | 2988 | asUfscuug(Tgn)cugucuGfgAfugaagsasg | 3249 | CUCUUCAUCCAGACAGACAAGAC | 3510 |
| AD-1069844.1 | ususcauCfcAfgAfCfAfGfacaagacuL96 | 2989 | asGfsucu(G2p)ucuguCfgGfaugaasgsa | 3250 | UCUUCAUCCAGACAGACAAGACC | 3511 |
| AD-1069738.1 | uscsaucaGfaCfAfgAfCfaagagaccuL96 | 2990 | asCfsuucu(Tgn)gucuguGfgAfugasasg | 3251 | CUUCAUCCAGACAGACAAGACCA | 3512 |
| AD-564739.2 | csasuccaGfaCfAfGfAfCfaagacaccuL96 | 2991 | asUfsugcu(Tgn)ugucugUfcUfggaugsasa | 3252 | UUCAUCCAGACAGACAAGACCAU | 3513 |
| AD-1069845.1 | asuscagGfacAfGfAfCfaagaccaauL96 | 2992 | asAfsuggu(C2p)uugucuGfuCfuggausgsa | 3253 | UCAUCCAGACAGACAAGACCAUC | 3514 |
| AD-564741.1 | uscscagaCfaGfAfCfAfagaccaucuL96 | 2993 | asGfsaugg(Tgn)cuugucUfguCfuggasusg | 3254 | CAUCCAGACAGACAAGACCAUCU | 3515 |
| AD-1069846.1 | cscsagacAfgAfCfAfAfagaccaucuuL96 | 2994 | asAfsgaug(G2p)ucuuguCfucuggsasu | 3255 | AUCCAGACAGACAAGACCAUCUA | 3516 |
| AD-1069847.1 | csasgacaGfaCfAfAfGfaccaucuauL96 | 2995 | asUfsagau(Gzp)gucuuuGfucuggsasa | 3256 | UCCAGACAGACAAGACCAUCUAC | 3517 |
| AD-564745.3 | gsascagaCfaAfGfAfccaucuacuL96 | 2996 | asUfsaguag(Agn)uggucuUfgUfcucususg | 3257 | CAGACAGACAAGACCAUCUACAC | 3518 |
| AD-564747.1 | csasagacaAfgAfCfCfAfucacacccuL96 | 2997 | asGfsgugu(Agn)gauggUfuUfgucugsusc | 3258 | GACAGACAAGACCAUCUACACCC | 3519 |

TABLE 23-continued

Modified Sense and Antisense Strand Sequences of Complement Component C3 dsRNA Agents

| Duplex Name | Sense Sequene 5' to 3' | SEQ ID NO: | Antisense Sequence 5' to 3' | SEQ ID NO: | mRNA Target Sequence | SEQ ID NO: |
|---|---|---|---|---|---|---|
| AD-1069850.1 | ascsaagaCfcAfUfCfuacacccccuuL96 | 2998 | asAfsgggg(Tgn)guagauGfgUfcuuguscsu | 3259 | AGACAAGACCAUCUACCCCUG | 3520 |
| AD-1069851.1 | gsgsccagUfgGfAfAfgauccgagccuL96 | 2999 | asGfscucg(G2p)aucuucCfaCfuggcsscsa | 3260 | UGGGCCAGUGGAAGAUCCGAGCC | 3521 |
| AD-1069852.1 | gscscaguGfgAfAfGfauccgagccuL96 | 3000 | asGfsgcuc(G2p)gaucucCfcAfcuggcscsc | 3261 | GGGCCAGUGGAAGAUCCGAGCCU | 3522 |
| AD-1069853.1 | cscsagugGfaAfGfAfuccgagccuuL96 | 3001 | asAfsggcu(C2p)ggaucuUfcCfacuggscsc | 3262 | GGCCAGUGGAAGAUCCGAGCCUA | 3523 |
| AD-564925.1 | csasguggAfaGfAfUfccgagccuauL96 | 3002 | asUfsagc(Tgn)cggaucUfuCfcacugsgsc | 3263 | GCCAGUGGAAGAUCCGAGCCUAC | 3524 |
| AD-1069854.1 | asgsuggaAfgAfUfCfccgagccuacuL96 | 3003 | asGfsuagg(C2p)ucggauCfuUfccacusgsg | 3264 | CCAGUGGAAGAUCCGAGCCUACU | 3525 |
| AD-1069855.1 | gsusggaaGfaUfCfCfgagccuacuauL96 | 3004 | asAfsguag(G2p)cucggaUfcCfufccacsusg | 3265 | CAGUGGAAGAUCCGAGCCUACUA | 3526 |
| AD-1069856.1 | usgsgaagAfuCfCfgAfgccuacuauuL96 | 3005 | asAfsagua(G2p)gcucggAfucUfccuuccsascu | 3266 | AGUGGAAGAUCCGAGCCUACUAU | 3527 |
| AD-564929.1 | gsgsaagauCfcGfAfgccuacuauguL96 | 3006 | asAfsuagu(Agn)ggcucgGfaUfcuuccsasc | 3267 | GUGGAAGAUCCGAGCCUACUAUG | 3528 |
| AD-564930.1 | gsasagauCfcGfAfGfccuacuaugaL96 | 3007 | asCfsauag(Tgn)agcucgGfAfucuuccscsa | 3268 | UGGAAGAUCCGAGCCUACUAUGA | 3529 |
| AD-1069857.1 | asasgaucCfgAfGfCfcuacuaugauL96 | 3008 | asUfscaua(G2p)uaggcuCfgGfaucuuscsc | 3269 | GGAAGAUCCGAGCCUACUAUGAA | 3530 |
| AD-1069858.1 | asusccgaGfcCfUfAfCfuaugaaaacuL96 | 3009 | asUfsuuuc(Agn)uaguagGfcUfcggauscsu | 3270 | AGAUCCGAGCCUACUAUGAAAAC | 3531 |
| AD-1069858.1 | uscscgagCfuAfCfUfAfuaugaaacuL96 | 3010 | asGfsuuuu(C2p)auaguaGfgCfucggasusc | 3271 | GAUCCGAGCCUACUAUGAAAAACU | 3532 |
| AD-564936.1 | cscsgagCfuAfCfUfAfUfgaugaaacucuL96 | 3011 | asAfsguuu(Tgn)cauaguAfgGfcucggsasu | 3272 | AUCCGAGCCUACUAUGAAAAACUC | 3533 |
| AD-564937.1 | csgsagccUfaCfUfAfUfgaaaacucuL96 | 3012 | asGfsaguu(Tgn)ucauagUfaGfgcucgsgsa | 3273 | UCCGAGCCUACUAUGAAAAACUCA | 3534 |
| AD-564938.1 | gsasgccuAfcUfAfUfgAfaaacucacL96 | 3013 | asGfsgagu(Tgn)uucauaGfuAfgcucsgsg | 3274 | CCGAGCCUACUAUGAAAAACUCAC | 3535 |
| AD-564941.1 | gscscuacUfaUfGfAfAfaaacuccacL96 | 3014 | asUfsgagu(G2p)uuucaUfaGfuaggcsusc | 3275 | GAGCCUACUAUGAAAAACUCACC | 3536 |
| AD-1069859.1 | cscsuacuaUfaUfGfAfAfaaacuccacuL96 | 3015 | asUfsgguu(G2p)uuucaUfaGfuaggcsusc | 3276 | AGCCUACUAUGAAAAACUCACCA | 3537 |
| AD-1069860.1 | csusuacuaUfgAfAfAfAfcuccaccauL96 | 3016 | asUfsgguug(G2p)aguuuUfaGfuagsgsg | 3277 | GCCUACUAUGAAAAACUCACCAC | 3538 |
| AD-564943.1 | usascauUfgAfAfAfAfcuccaccauL96 | 3017 | asUfsguug(Agn)guuuUfCfAfuaguasgsg | 3278 | CCUACUAUGAAAAACUCACCACA | 3539 |
| AD-1069861.1 | cscsuacaGfaAfAfAfAfauucuacuacuL96 | 3018 | asUfsagua(G2p)aauuuCfUfguaggscsu | 3279 | AGCCUACAGAGAAAUUCUACUAC | 3540 |
| AD-565031.1 | csusacagAfgAfAfAfuucuacuacuL96 | 3019 | asGfsuagu(Agn)gaauuuCfuCfuguagsgsc | 3280 | GCCUACAGAGAAAUUCUACUACA | 3541 |
| AD-565032.1 | usascagaGfaAfAfAfuUfucuacuacauL96 | 3020 | asUfsguag(Tgn)agaauuUfCfcuguasgsg | 3281 | CCUACAGAGAAAUUCUACUACAU | 3542 |

TABLE 23-continued

Modified Sense and Antisense Strand Sequences of Complement Component C3 dsRNA Agents

| Duplex Name | Sense Sequene 5' to 3' | SEQ ID NO: | Antisense Sequence 5' to 3' | SEQ ID NO: | mRNA Target Sequence | SEQ ID NO: |
|---|---|---|---|---|---|---|
| AD-1069862.1 | ascsagagAfaAfUfUfcuacuacauuL96 | 3021 | asAfsugua(G2p)uagaauUfcfucugusasg | 3282 | CUACAGAGAAAUUCUACUACAUC | 3543 |
| AD-565034.1 | csasgagaAfaUfUfCfuacuacaucuL96 | 3022 | asGfsaugu(Agn)guagaaUfuUfcucugusa | 3283 | UACAGAGAAAUUCUACUACAUCU | 3544 |
| AD-565035.1 | asgsgagaAfiuUfCfUfacuacaucuuL96 | 3023 | asAfsgaug(Tgn)aguagaAfiuUfucucusgsu | 3284 | ACAGAGAAAUUCUACUACAUCUA | 3545 |
| AD-1069863.1 | gsasgagaAfuCfUfAfcuacaucuauL96 | 3024 | asUfsagau(G2p)uaguagAfaUfuucucsusg | 3285 | CAGAGAAAUUCUACUACAUCUAU | 3546 |
| AD-565037.1 | asgsaaauUfcUfAfCfuacaucuauuL96 | 3025 | asAfsuaga(Tgn)guaguaGfaAfuuucscsu | 3286 | AGAGAAAUUCUACUACAUCUAUA | 3547 |
| AD-565038.1 | gsasaaauuCfuAfCfUfacaucuauauL96 | 3026 | asUfsauag(Agn)uguaguAfgAfauuucsusc | 3287 | GAGAAAUUCUACUACAUCUAUAA | 3548 |
| AD-1069864.1 | asasauuuCfuAfCfAfcaucuauauaL96 | 3027 | asUfsuaua(G2p)auguagUfaGfaauuuscsu | 3288 | AGAAAUUCUACUACAUCUAUAAC | 3549 |
| AD-565041.1 | asusucuaCfuAfCfAfucuauaaacguL96 | 3028 | asCfsguua(Tgn)agaugaAfgUfagaaususu | 3289 | AAAUUCUACUACAUCUAUAACGA | 3550 |
| AD-565042.1 | ususucuaCfCfAfUfcuauaaacgauL96 | 3029 | asUfscguu(Agn)uagaugUfaGfuagaasasu | 3290 | AAUUCUACUACAUCUAUAACGAG | 3551 |
| AD-565043.1 | uscsucuaCfaUfCfUfauaaacgagaL96 | 3030 | asCfsucgu(Tgn)auagaaUfgUfaguagsasu | 3291 | AUUCUACUACAUCUAUAACGAGA | 3552 |
| AD-565044.1 | csusucuaCfaUfCfUfAfuaacgagaaL96 | 3031 | asUfscucg(Tgn)uauagaAfgUfuaguasgsa | 3292 | UUCUACUACAUCUAUAACGAGAA | 3553 |
| AD-1069865.1 | usasucuaCfuCfUfAfuaacgagaauL96 | 3032 | asUfsucuc(G2p)uuauagAfgUfuagusgsa | 3293 | UCUACUACAUCUAUAACGAGAAG | 3554 |
| AD-565047.1 | ascsucuaUfcUfAfUfaacgagaaguL96 | 3033 | asCfsuucu(C2p)guuauaAfgAfguagsasg | 3294 | CUACUACAUCUAUAACGAGAAGA | 3555 |
| AD-1069866.1 | csusacauCfuAfUfAfacgagaagguL96 | 3034 | asCfscuuc(Tgn)cguuauAfgAfuguagsusa | 3295 | UACUACAUCUAUAACGAGAAGAG | 3556 |
| AD-565049.1 | usasacauCfuAfUfAfAfcgagaaggguL96 | 3035 | asCfscuuc(Tgn)ucgguuAfafguagusasg | 3296 | ACUACAUCUAUAACGAGAAGGGG | 3557 |
| AD-565050.1 | ascsauuaCfuAfUfAfCfgagaagggcuL96 | 3036 | asGfsgccu(Tgn)cucguuAfaUfaguasag | 3297 | CUACAUCUAUAACGAGAAGGGGCC | 3558 |
| AD-565274.1 | csasucuaUfaAfCfGfagaagggccuL96 | 3037 | asGfsgccc(Tgn)ucucguUfaAfagausasa | 3298 | UACAUCUAUAACGAGAAGGGCCU | 3559 |
| AD-565275.1 | csusucucCfcUfAfCfcagaucccacuL96 | 3038 | asGfsugga(Tgn)cugguaGfgGfagaggsusc | 3299 | GACCUCCCCUACCAGAUCCCACUC | 3560 |
| AD-1069868.1 | cscsucucCfcUfAfCfCfagaucccacuL96 | 3039 | asGfsgugg(Agn)ucggugAfgGfgagasgsu | 3300 | ACCUCCCCUACCAGAUCCCACUU | 3561 |
| AD-1069869.1 | uscsucuCfuAfCfCfAfgauccaccuuL96 | 3040 | asAfsagug(G2p)aucuggGfuAfgggasgsg | 3301 | CCUCCCCUACCAGAUCCACCUUC | 3562 |
| AD-1069869.1 | csusucccUfaCfCfAfgauccaccuuL96 | 3041 | asGfsaagu(G2p)gaucugGfuAfagggasg | 3302 | CUCCCCUACCAGAUCCACCUUCA | 3563 |
| AD-565278.2 | uscsccuaCfcAfGfAfuccacuucauL96 | 3042 | asUfsgaag(Tgn)ggaucuGfgUfagggasgs | 3303 | UCUCCCCUACCAGAUCCACUUCAC | 3564 |
| AD-1069870.1 | cscscuaCfaGfAfUfccacuucacuL96 | 3043 | asGfsugaa(G2p)uggaucUfgGfuaggsgsa | 3304 | CUCCCCUACCAGAUCCACCUUCAC | 3565 |
| AD-565280.1 | cscsuaccAfgAfUfCfcacuucaccuL96 | 3044 | asGfsguga(Agn)gguaucUfgGfuaggsgsa | 3305 | UCCCUACCAGAUCCACCUUCACCA | 3566 |

TABLE 23-continued

Modified Sense and Antisense Strand Sequences of Complement Component C3 dsRNA Agents

| Duplex Name | Sense Sequene 5' to 3' | SEQ ID NO: | Antisense Sequence 5' to 3' | SEQ ID NO: | mRNA Target Sequence | SEQ ID NO: |
|---|---|---|---|---|---|---|
| AD-565281.3 | csusaccagUfaGfCfCfcacuucaccauL96 | 3045 | asUfsgguq(Agn)aguggaUfcUfgguagsgsg | 3306 | CCCUACCAGAUCCACUUCACCAA | 3567 |
| AD-1069871.1 | usasccagAfuCfCfAfcuucaccaauL96 | 3046 | asUfsuugu(G2p)aaguggAfuCfugguasgsg | 3307 | CCUACCAGAUCCACUUCACCAAG | 3568 |
| AD-565283.1 | ascscagaUfcCfAfCfuuccaccaaguL96 | 3047 | asCfsuugg(Tgn)gaagugGfaUfcuggusasg | 3308 | CUACCAGAUCCACUUCACCAAGA | 3569 |
| AD-1069872.1 | cscsagauCfcAfCfUfucaccaagauL96 | 3048 | asUfscuug(G2p)ugaaguGfgAfucuggsusa | 3309 | UACCAGAUCCACUUCACCAAGAC | 3570 |
| AD-565285.1 | csasgauCfaCfUfUfCfcaccaagacuL96 | 3049 | asGfsucuu(G2p)gugaagUfgGfaucugsgsu | 3310 | ACCAGAUCCACUUCACCAAGACA | 3571 |
| AD-565286.1 | asgsauccAfcUfUfCfaccagacacuL96 | 3050 | asGfsgucu(Tgn)gggugaGfuGfgaucusgsg | 3311 | CCAGAUCCACUUCACCAAGACAC | 3572 |
| AD-565287.1 | gsasuccaCfuUfCfAfccaagacaccL96 | 3051 | asGfsuguc(Tgn)uggugaAfgUfggaucsusg | 3312 | CAGAUCCACUUCACCAAGACACC | 3573 |
| AD-1069874.1 | asusccacUfuCfAfCfcaagacaccuL96 | 3052 | asGfsgugu(C2p)uuggugAfaGfuggauscsu | 3313 | AGAUCCACUUCACCAAGACACCC | 3574 |
| AD-1069875.1 | ususugacCfuCfAfUfggugugucguuL96 | 3053 | asAfscgaa(C2p)accaugAfgGfucaaasgsg | 3314 | CCUUUGACCUCAUGGUGUUCGUG | 3575 |
| AD-565335.1 | usgsaccuCfaUfGfGfuguucgugauL96 | 3054 | asAfscacg(Agn)acaccaUfgAfggucasasa | 3315 | UUUUGACCUCAUGGUGUUCGUGAC | 3576 |
| AD-1069876.1 | asgsggcgUfgUfUfCfgugcugaauuL96 | 3055 | asAfsuuca(G2p)cacgaaCfaCfgcccusug | 3316 | CAAGGGCGUGUUCGUGCUGAAUA | 3577 |
| AD-565895.1 | gsgsgcguUfgUfUfCfgugcugaauaL96 | 3056 | asUfsauuc(Agn)gcacgaAfcAfcgcccusu | 3317 | AAGGGCGUGUUCGUGCUGAAUAA | 3578 |
| AD-1069877.1 | gsgscgugUfuCfGfUfgcugaauauL96 | 3057 | asUfsuauu(C2p)agcacgAfaCfacgcccsu | 3318 | AGGGCGUGUUCGUGCUGAAUAAG | 3579 |
| AD-565897.1 | gscsgugUfcGfUfGfcugaauaagauL96 | 3058 | asCfsuuau(Tgn)cagcacGfaAfcacgcscsc | 3319 | GGGCGUGUUCGUGCUGAAUAAGA | 3580 |
| AD-565899.1 | gsgsuguUfcGfUfGfcugaauaagauL96 | 3059 | asUfsucuu(Agn)uucagcAfcGfaacacsgsc | 3320 | GCGUGUUCGUGCUGAAUAAGAAG | 3581 |
| AD-1069878.1 | uscsgugCfuGfAfAfUfaagagaacauL96 | 3060 | asGfsuucu(Tgn)cuuauuCfaGfcacgasasc | 3321 | GUUCGUGCUGAAUAAGAAGAACA | 3582 |
| AD-565904.3 | csgsugCfuGfAfAfUfAfagaagaacauL96 | 3061 | asUfsgguc(Tgn)ucuuauUfcAfgcacgsaa | 3322 | UUCGUGCUGAAUAAGAAGAACAA | 3583 |
| AD-1069878.1 | gsusgcugAfaUfAfAfGfaagaacaauL96 | 3062 | asUfsuguu(C2p)uucuuaUfuCfagcacsgsa | 3323 | UCGUGCUGAAUAAGAAGAACAAA | 3584 |
| AD-565906.1 | usgscugaAfuAfAfGfAfaagaacaaauL96 | 3063 | asUfsuugu(Tgn)cuucuuAfuUfcagcascsg | 3324 | CGUGCUGAAUAAGAAGAACAAAC | 3585 |
| AD-565907.1 | gscsugaaUfaAfGfAfAfagaacaaacuL96 | 3064 | asGfsuuug(Tgn)ucuucuUfuAfuucagcsasc | 3325 | GUGCUGAAUAAGAAGAACAAACU | 3586 |
| AD-1069879.1 | csusugaaUfaAfGfAfAfgaacaaacuL96 | 3065 | asAfsguuu(G2p)uucuucUfuAfuucagscsa | 3326 | UGCUGAAUAAGAAGAACAAACUG | 3587 |
| AD-565909.1 | usgsaauaAfgAfAfGfAfaacaaacuguL96 | 3066 | asCfsaguu(Tgn)guucuuCfuUfauucasgsc | 3327 | GCUGAAUAAGAAGAACAAACUGA | 3588 |
| AD-565910.1 | gsasauaaGfaAfGfAfacaaacuguL96 | 3067 | asUfscagu(Tgn)uguucuUfcUfuauucsasg | 3328 | CUGAAUAAGAAGAACAAACUGAC | 3589 |

TABLE 23-continued

Modified Sense and Antisense Strand Sequences of Complement Component C3 dsRNA Agents

| Duplex Name | Sense Sequene 5' to 3' | SEQ ID NO: | Antisense Sequence 5' to 3' | SEQ ID NO: | mRNA Target Sequence | SEQ ID NO: |
|---|---|---|---|---|---|---|
| AD-565911.1 | asasuaagAfaGfAfAfcaaacugacuL96 | 3068 | asGfsucag(Tgn)uuguucUfuCfuuauuscsa | 3329 | UGAAUAAGAAGAACAAACUGACG | 3590 |
| AD-1069880.1 | asusaagaAfaAfAfcfaaacugacguL96 | 3069 | asCfsguca(G2p)uuuguuCfuUfcuuaususc | 3330 | GAAUAAGAAGAACAAACUGACGC | 3591 |
| AD-565913.1 | usasagaaGfaAfCfAfAfaacugacgcuL96 | 3070 | asGfscguc(Agn)guuuguUfcUfucuuasasu | 3331 | AAUAAGAAGAACAAACUGACGCA | 3592 |
| AD-1069881.1 | asasgaagAfaCfAfAfAfcugacgcauL96 | 3071 | asUfsggcu(C2p)aguuugUfiUfcuucusasu | 3332 | AUAAGAAGAACAAACUGACGCAG | 3593 |
| AD-565915.1 | asgsaagaAfcAfAfAfcfugacgcaguL96 | 3072 | asCfsugcg(Tgn)caguuuGfiUfcuucususa | 3333 | UAAGAAGAACAAACUGACGCAGA | 3594 |
| AD-1069882.1 | gsasagaaCfaAfAfCfugacgcagauL96 | 3073 | asUfscugc(G2p)ucaguuUfgUfucuucsusu | 3334 | AAGAAGAACAAACUGACGCAGAG | 3595 |
| AD-1069883.1 | asasgacaCfaAfCfUfgacgcagaguL96 | 3074 | asCfsucug(C2p)gucaguUfiuGfucuuuscsu | 3335 | AGAAGAACAAACUGACGCAGAGU | 3596 |
| AD-1069884.1 | asgsaacaAfaCfUfGfacgcagaguuL96 | 3075 | asAfscucu(G2p)cgucagUfiuUfguucususc | 3336 | GAAGAACAAACUGACGCAGAGUA | 3597 |
| AD-565919.1 | gsasacaaAfcUfGfAfCfgcgcagaguauL96 | 3076 | asUfsuacu(Tgn)gcgucaGfiuUfuguucusus | 3337 | AAGAACAAACUGACGCAGAGUAA | 3598 |
| AD-1069885.1 | asasacaaAfcUfGfAfCfgcagaguaaL96 | 3077 | asUfsuacu(C2p)ugcgucAfgfuuugususu | 3338 | AGAACAAACUGACGCAGAGUAAG | 3599 |
| AD-565921.1 | ascsaaacUfgAfCfGfCfagaguaauL96 | 3078 | asCfsuuac(Tgn)cugcguCfaGfuuugusus | 3339 | GAACAAACUGACGCAGAGUAAGA | 3600 |
| AD-1069886.1 | csasaacuGfaCfGfCfagaguaagauL96 | 3079 | asUfscuua(C2p)ucugcGfucCfagusususu | 3340 | AACAAACUGACGCAGAGUAAGAU | 3601 |
| AD-565923.1 | asasacugAfcGfCfAfGfaguaagauuL96 | 3080 | asAfsucuu(Agn)cucugcGfuCfagvuusgsu | 3341 | ACAAACUGACGCAGAGUAAGAUC | 3602 |
| AD-1069887.1 | asascugaCfgCfAfGfaGfuaagaucuL96 | 3081 | asGfsaucu(Tgn)acucugCfgUfcagususug | 3342 | CAAACUGACGCAGAGUAAGAUCU | 3603 |
| AD-565924.1 | csusgacgCfaGfAfGfuaagaucuguL96 | 3082 | asCfsagau(C2p)uuacucUfgCfgucasgsu | 3343 | AACUGACGCAGAGUAAGAUCUGG | 3604 |
| AD-1069888.1 | usgsacgcAfgAfGfUfuaagaucugguL96 | 3083 | asCfscaga(Tgn)cuuacuCfuGfcgucasgsu | 3344 | ACUGACGCAGAGUAAGAUCUGGG | 3605 |
| AD-565927.1 | gsascgcaGfaGfUfAfGfuaagaucuggguL96 | 3084 | asCfsccag(Agn)ucuuacUfcUfgcgcusca | 3345 | CUGACGCAGAGUAAGAUCUGGGA | 3606 |
| AD-565928.1 | gsasascgaGfuGfUfAfAfgaucugggauL96 | 3085 | asUfsccca(G2p)aucuuaCfuCfugcgcusca | 3346 | UGACGCAGAGUAAGAUCUGGGAC | 3607 |
| AD-1069888.1 | ascsgcagAfgUfAfAfAfgaucuggacuL96 | 3086 | asUfsuccu(Tgn)guccgaCfaUfcaugcsusc | 3347 | UGUGAGCAUGUCGGACAAGAAAG | 3608 |
| AD-566379.1 | usgsagcaUfgUfCfGfGfacaagaaauL96 | 3087 | asCfsuuuc(Tgn)uguccgAfcAfugcucsasc | 3348 | GUGAGCAUGUCGGACAAGAAAGG | 3609 |
| AD-566380.1 | gsasgcauGfucGfGfAfCfaagaaagguL96 | 3088 | asUfscuuu(C2p)uuguccGfaCfaugcuscsa | 3349 | UGAGCAUGUCGGACAAGAAAGGG | 3610 |
| AD-1069889.1 | asgscaugUfcGfGfAfCfaagaaagggauL96 | 3089 | asCfsccuu(Tgn)cuuugucCfgAfcaugcsusc | 3350 | GAGCAUGUCGGACAAGAAAGGGA | 3611 |
| AD-566382.1 | gscsaugUfcGfAfCfAfAfgaaaggguuL96 | 3090 | asUfscccuu(Tgn)ucuuguCfcGfacaugscsu | 3351 | AGCAUGUCGGACAAGAAAGGGAU | 3612 |
| AD-566383.2 | csasuguCfGfaCfAfAfgaaagggauuL96 | 3091 | asAfsuccc(Tgn)uccuugUfcCfgacausgsc | 3352 | GCAUGUCGGACAAGAAAGGGAUC | 3613 |
| AD-566384.2 | asusugucGfaCfAfAfgaaagggauuL96 | | | | | |

TABLE 23-continued

Modified Sense and Antisense Strand Sequences of Complement Component C3 dsRNA Agents

| Duplex Name | Sense Sequene 5' to 3' | SEQ ID NO: | Antisense Sequence 5' to 3' | SEQ ID NO: | mRNA Target Sequence | SEQ ID NO: |
|---|---|---|---|---|---|---|
| AD-1069890.1 | usgsucggAfcAfAfGfaaagggaucuuL96 | 3092 | asGfsaucc(C2p)uuucuuGfuCfcgacasusg | 3353 | CAUGUCGACAAGAAAGGGAUCU | 3614 |
| AD-1069891.1 | gsuscggaCfaAfGfAfaaggaucuuL96 | 3093 | asAfsgauc(C2p)cuuucuUfgUfccgacsasu | 3354 | AUGUCGACAAGAAAGGGAUCUG | 3615 |
| AD-1069892.1 | uscsggacAfaGfAfAfagggaucuguL96 | 3094 | asCfsagau(C2p)ccuuucUfuGfuccgascsa | 3355 | UGUCGACAAGAAAGGGAUCUGU | 3616 |
| AD-566388.2 | csgsgacaAfgAfAfAfgggaucuguuL96 | 3095 | asAfscaga(Tgn)cccuuuCfuUfguccgasac | 3356 | GUCGACAAGAAAGGGAUCUGUG | 3617 |
| AD-566389.1 | gsgsacaaGfaAfAfGfgg aucuguguuL96 | 3096 | asCfsacag(Agn)ucccuuUfcUfuguccsgsa | 3357 | UCGACAAGAAAGGGAUCUGUGU | 3618 |
| AD-566391.1 | gsascaagAfaAfGfGfgaucuguguguL96 | 3097 | asAfscaca(G2p)auccccuUfcUfuugucscsg | 3358 | CGACAAGAAAGGGAUCUGUGUG | 3619 |
| AD-566391.1 | ascsaagaAfaGfGfGfaucuguguggL96 | 3098 | asCfsacac(Agn)gauccccUfuUfcuuguscsc | 3359 | GGACAAGAAAGGGAUCUGUGUGG | 3620 |
| AD-1069894.1 | csasagaaAfgGfGfAfucuguguggguL96 | 3099 | asCfscaca(C2p)agauccCfuUfucuugsusc | 3360 | GACAAGAAAGGGAUCUGUGUGGC | 3621 |
| AD-1069895.1 | asasgaaaGfgGfAfUfcuguguggcuL96 | 3100 | asGfsccac(Agn)cagaucCfcUfuucuusgsu | 3361 | ACAAGAAAGGGAUCUGUGUGGCA | 3622 |
| AD-1069895.1 | gsasaaggGfaUfCfUfguguggcagL96 | 3101 | asCfstugcc(Agn)cacagaUfcCfuuucsusu | 3362 | AAGAAAGGGAUCUGUGUGGCAGA | 3623 |
| AD-1069896.1 | asasaggGfaUfCfUfGfguguggcagauL96 | 3102 | asUfscugc(C2p)acacagAfuCfccuuuscsu | 3363 | AGAAAGGGAUCUGUGUGGCAGAC | 3624 |
| AD-1069897.1 | asasgggaUfcUfGfUfguggcagaccuL96 | 3103 | asGfsucug(C2p)cacacaGfaUfcccuusuc | 3364 | GAAAGGGAUCUGUGUGGCAGACC | 3625 |
| AD-1069898.1 | asgsggauCfugUfGfUfguggcagaccuL96 | 3104 | asGfsgucu(G2p)ccacacAfgUfcccusus | 3365 | AAAGGGAUCUGUGUGGCAGACCC | 3626 |
| AD-1069899.1 | gsgsgaucUfgUfGfUfGfggcagaccccuL96 | 3105 | asGfsgguc(Tgn)gccacaCfaGfucccsusu | 3366 | AAGGGAUCUGUGUGGCAGACCCC | 3627 |
| AD-566475.1 | gsasaauCfgAfGfCfcguucucuauL96 | 3106 | asUfsagag(Agn)acggcuCfgGfauuucscsa | 3367 | UGGAAAUCCGAGCCGUUCUCUAC | 3628 |
| AD-1069900.1 | asasauccGfaGfCfCfguucucuacuL96 | 3107 | asGfsuaga(G2p)aacggCfuCfgauuuscsc | 3368 | GGAAAUCCGAGCCGUUCUCUACA | 3629 |
| AD-566477.1 | asasuccgAfgCfCfGfuucucuacauL96 | 3108 | asUfsguag(Agn)gaacggCfuCfggauusus | 3369 | GAAAUCCGAGCCGUUCUCUACAA | 3630 |
| AD-1069901.1 | asuscgGfcCfGfUfucucuacaauL96 | 3109 | asUfsugua(G2p)agaacgGfcCfcggausus | 3370 | AAAUCCGAGCCGUUCUCUACAAU | 3631 |
| AD-566483.1 | asgsccguUfcUfCfUfacaauuaccuL96 | 3110 | asGfsguaa(Tgn)uguagaGfaAfcggcuscsg | 3371 | CGAGCCGUUCUCUACAAUUACCG | 3632 |
| AD-566484.1 | gscscguuCfuCfUfAfcaauuaccguL96 | 3111 | asCfsggua(Agn)uuguagAfgAfacggcsusc | 3372 | GAGCCGUUCUCUACAAUUACCGG | 3633 |
| AD-566485.2 | cscsguuCfuCfUfAfcaauuaccgcuL96 | 3112 | asCfsccgu(Agn)auuguaGfaGfaacggscsu | 3373 | AGCCGUUCUCUACAAUUACCGGC | 3634 |
| AD-566486.1 | csgsuucUfuAfcCfAfauuaccggcuL96 | 3113 | asGfsccgg(Tgn)aauuguAfgAfgaacgsgsc | 3374 | GCCGUUCUCUACAAUUACCGGCA | 3635 |
| AD-1069902.1 | gsusucuCfuAfCfAfuuaccggcauL96 | 3114 | asUfsgccg(G2p)uaauugUfaGfagaacsgsg | 3375 | CCGUUCUCUACAAUUACCGGCAG | 3636 |

TABLE 23-continued

Modified Sense and Antisense Strand Sequences of Complement Component C3 dsRNA Agents

| Duplex Name | Sense Sequene 5' to 3' | SEQ ID NO: | Antisense Sequence 5' to 3' | SEQ ID NO: | mRNA Target Sequence | SEQ ID NO: |
|---|---|---|---|---|---|---|
| AD-1069903.1 | ususcucuAfcAfAfUfuaccggcaguL96 | 3115 | ascFsugcc(G2p)guaauuGfuAfgagaascsg | 3376 | CGUUCCUUACAAUUACCGGCAGA | 3637 |
| AD-1069904.1 | uscsucuaCfaAfUfUfaccggcagauL96 | 3116 | asUfscugc(C2p)gguaauUfgUfagagasasc | 3377 | GUUCCUUACAAUUACCGGCAGAA | 3638 |
| AD-1069905.1 | gsgscugaCfcgCfcfCfuacguggcuL96 | 3117 | asGfsacca(C2p)guaggcGfgUfcagccsasg | 3378 | CUGGCUGACCGCCUACGUGGUCA | 3639 |
| AD-1069906.1 | gscsugacCfgCfCfUfacguggucauL96 | 3118 | asUfsgacc(Agn)cguaggCfgGfucagcscsa | 3379 | UGGCUGACCGCCUACGUGGUCAA | 3640 |
| AD-1069906.1 | csusgaccGfcCfUfAfcguggucaauL96 | 3119 | asUfsugac(C2p)acguagGfcGfucagscsc | 3380 | GGCUGACCGCCUACGUGGUCAAG | 3641 |
| AD-1069907.1 | usgsaccgCfcUfAfCfguggucaaguL96 | 3120 | ascFsuuga(C2p)cacguaGfgCfgucasgsc | 3381 | GCUGACCGCCUACGUGGUCAAGG | 3642 |
| AD-567057.1 | gsasccgCfuAfCfGfuggucaagguL96 | 3121 | ascFscuug(Agn)ccacguAfgGfcggucsasg | 3382 | CUGACCGCCUACGUGGUCAAGGU | 3643 |
| AD-1069908.1 | ascsgccUfaCfgUfGfgucaagguuL96 | 3122 | asAfsccuu(G2p)accacgUfaGfcgguscsa | 3383 | UGACCGCCUACGUGGUCAAGGUC | 3644 |
| AD-567059.1 | cscsgccuAfcGfUfGfgucaagguucL96 | 3123 | asGfsaccu(Tgn)gaccacGfuAfggcggsusc | 3384 | GACCGCCUACGUGGUCAAGGUCU | 3645 |
| AD-567060.1 | csgsccuaCfgUfGfGfucaagguucuL96 | 3124 | asAfsgacc(Tgn)ugaccaCfgUfaggcgsgsu | 3385 | ACCGCCUACGUGGUCAAGGUCUU | 3646 |
| AD-567060.1 | gscsucaCfgUfgGfUfcaagguucucL96 | 3125 | asAfsagac(C2p)uugaccAfcGfuaggcsgsg | 3386 | CCGCCUACGUGGUCAAGGUCUUC | 3647 |
| AD-1069909.1 | cscsuacgUfgGfuCfAfaggucuucucL96 | 3126 | asGfsaaga(C2p)ccuugaAfcCfacguasgsc | 3387 | CGCCUACGUGGUCAAGGUCUUCU | 3648 |
| AD-1069910.1 | usascgugGfuCfAfAfggucuucucuL96 | 3127 | asGfsagaa(G2p)accuugAfcCfacguasgg | 3388 | GCCUACGUGGUCAAGGUCUUCUC | 3649 |
| AD-1069911.1 | ascsguggUfcAfAfGfgucuucucuL96 | 3128 | asGfsagag(Agn)gaccuuGfaCfcacusasg | 3389 | CCUACGUGGUCAAGGUCUUCUCU | 3650 |
| AD-567065.1 | csgsugguCfaAfGfGfucuucucucuL96 | 3129 | asGfsagag(Agn)agaccuUfgAfccacgsusa | 3390 | CUACGUGGUCAAGGUCUUCUCUC | 3651 |
| AD-567066.4 | gsusuggucAfaGfGfUfcuucucucuL96 | 3130 | asAfsgaga(Agn)agaccuUfgAfccacgsu | 3391 | UACGUGGUCAAGGUCUUCUCUCU | 3652 |
| AD-567068.1 | usgsgucaAfgGfUfCfuucucucucuL96 | 3131 | asAfsgaga(Agn)aagacCfuUfgaccascsg | 3392 | ACGUGGUCAAGGUCUUCUCUCUG | 3653 |
| AD-567068.1 | gsgsucaaGfgUfCfUfucucucucugL96 | 3132 | asCfsagag(Agn)gaagacCfuUfgaccascg | 3393 | CGUGGUCAAGGUCUUCUCUCUGG | 3654 |
| AD-1069913.1 | gsgsucaaGfgUfcUfCfucucucuggL96 | 3133 | asCfscaga(G2p)agagaaCfcUfugaccsa | 3394 | GUGGUCAAGGUCUUCUCUCUGGC | 3655 |
| AD-567070.1 | gsuscaagGfuCfUfUfcucucuggcuL96 | 3134 | asGfsccag(Agn)gagaagAfcCfuugacscsa | 3395 | UGGUCAAGGUCUUCUCUCUGGCU | 3656 |
| AD-1069914.1 | uscsaagGfuCfUfCfucucuggcuL96 | 3135 | asAfsgcca(G2p)agagaaGfcCfuugasscc | 3396 | GGUCAAGGUCUUCUCUCUGGCUG | 3657 |
| AD-567072.1 | csaasggUfcUfCfuCfcucugguguL96 | 3136 | ascFsagcc(Agn)gagagaAfcCfuugasasc | 3397 | GUCAAGGUCUUCUCUCUGGCUGU | 3658 |
| AD-1069915.1 | asasasgguCfuuCfUfcFucFucuggucuL96 | 3137 | asAfscagc(C2p)agagaAfaGfaccuusgsa | 3398 | UCAAGGUCUUCUCUCUGGCUGUC | 3659 |
| AD-1069916.1 | asgsgucUfcUfCfucFucFucuggucuL96 | 3138 | asGfsacag(C2p)cagagaGfaAfgaccususg | 3399 | CAAGGUCUUCUCUCUGGCUGUCA | 3660 |

TABLE 23-continued

Modified Sense and Antisense Strand Sequences of Complement Component C3 dsRNA Agents

| Duplex Name | Sense Sequene 5' to 3' | SEQ ID NO: | Antisense Sequence 5' to 3' | SEQ ID NO: | mRNA Target Sequence | SEQ ID NO: |
|---|---|---|---|---|---|---|
| AD-1069917.1 | gsgsucuuCfuCfCfuggcugucauL96 | 3139 | asUfsgaca(G2p)ccagagAfgAfagaccsusu | 3400 | AAGGUCUUCUCUGGCUGUCAA | 3661 |
| AD-567076.1 | gsuscuuCfuCfCfUfUfggcugucaauL96 | 3140 | asUfsugac(Agn)gccagaGfaGfaagacsscu | 3401 | AGGUCUUCUCUCUGGCUGUCAC | 3662 |
| AD-1069918.1 | uscsuucuCfuCfUfGfgcugucaacuL96 | 3141 | asGfsuuga(C2p)agccagAfgAfagaascsc | 3402 | GGUCUUCUCUCUGGCUGUCAACC | 3663 |
| AD-567294.1 | usasaagcAfgGfAfGfacuuccuuguL96 | 3142 | asCfsaagg(Agn)agucucCfuGfcuuuasgsu | 3403 | ACUAAAGCAGGAGACUUCCUUGA | 3664 |
| AD-1069919.1 | asasagcaGfgAfGfAfCfcuuccuugaaL96 | 3143 | asUfscaag(G2p)aagucuCfCfugcuuusasg | 3404 | CUAAAGCAGGAGACUUCCUUGAA | 3665 |
| AD-1069920.1 | asasgcagGfaGfAfCfuuccuugaauuL96 | 3144 | asUfsucaa(Agn)ggaaguCfcCfugcuuusa | 3405 | UAAAGCAGGAGACUUCCUUGAAG | 3666 |
| AD-567297.1 | asgscaggAfgAfCfUfucccuugaaguL96 | 3145 | asCfsuuca(Agn)ggaaguCfuCfcugcuusu | 3406 | AAAGCAGGAGACUUCCUUGAAGC | 3667 |
| AD-567300.1 | asgsgagaCfuuCfCfCfuugaagccauL96 | 3146 | asUfsggcu(Tgn)caaggaAfguUfcccusgsc | 3407 | GCAGGAGACUUCCUUGAAGCCAA | 3668 |
| AD-567301.1 | gsgsagacUfuCfCfCfUfugaagccacuL96 | 3147 | asUfsuggc(Tgn)ucaaggAfaGfucccsusg | 3408 | CAGGAGACUUCCUUGAAGCCAAC | 3669 |
| AD-1069922.1 | gsasgacuUfcCfUfUfGfgaagccaacuL96 | 3148 | asGfsuugg(C2p)uucaagGfaAfgucuscscu | 3409 | AGGAGACUUCCUUGAAGCCAACU | 3670 |
| AD-1069923.1 | asgsgacuuCfCfUfUfGfGfaagccaacuuL96 | 3149 | asAfsguug(G2p)cuucaaGfgAfaguscuscsc | 3410 | GGAGACUUCCUUGAAGCCAACUA | 3671 |
| AD-1069924.1 | gsaacuuCfuUfGfAfAfgccaacuacuuL96 | 3150 | asUfsagau(G2p)gcuucaAfgGfaaguscsuc | 3411 | GAGACUUCCUUGAAGCCAACUAC | 3672 |
| AD-567305.1 | ascsuuccUfuGfAfAfGfccaacuacuuL96 | 3151 | asGfsuagu(Tgn)ggcuucAfaGfgaagusuc | 3412 | AGACUUCCUUGAAGCCAACUACA | 3673 |
| AD-567306.1 | csusuccuUfgAfAfGfCfCfaacuacauuL96 | 3152 | asCfsaugu(Tgn)uggcuuCfaAfggaasasg | 3413 | GACUUCCUUGAAGCCAACUACAU | 3674 |
| AD-1069925.1 | uscsuccugAfaGfCfCfaacuacaugaaL96 | 3153 | asUfscaug(Tgn)aguugGfcUfucaaggsga | 3414 | CUUCCUUGAAGCCAACUACAUGA | 3675 |
| AD-567308.1 | cscsuugaAfaGfCfCfAfacuacaugauL96 | 3154 | asCfsaugu(Agn)guuggCfuUfcaaggasa | 3415 | UUCCUUGAAGCCAACUACAUGAA | 3676 |
| AD-567309.1 | csesuugaaGfcCfAfAfCfuacaugaauL96 | 3155 | asUfsucau(G2p)uaguugGfcUfucaagsga | 3416 | UCCUUGAAGCCAACUACAUGAAC | 3677 |
| AD-1069925.1 | ususgaagCfCfAfAfCfuacaugaaccuL96 | 3156 | asGfsuuca(Tgn)guaguuGfcUfuaagsgg | 3417 | CCUUGAAGCCAACUACAUGAACC | 3678 |
| AD-567311.1 | ususgaagCfCfAfAfCfuacaugaaccuL96 | 3157 | asGfsguuc(Agn)uguaguUfgGfcuucasag | 3418 | CUUGAAGCCAACUACAUGAACCU | 3679 |
| AD-567312.1 | usgsaagcCfaAfCfuAfCfaugaaccuuL96 | 3158 | asAfsgguu(C2p)auguagUfuGfgcuusasa | 3419 | UGAAGCCAACUACAUGAACCUA | 3680 |
| AD-1069926.1 | gsasagccAfaCfuAfCfaugaaccuacuL96 | 3159 | asUfsaggu(Tgn)cauguaGfuUfggcuuscsa | 3420 | UGAAGCCAACUACAUGAACCUAC | 3681 |
| AD-567314.2 | asasagccCfuAfCfAfCfaugaaccuacuL96 | 3160 | asGfsuagg(Tgn)ucauguAfgUfuggcuscusc | 3421 | GAAGCCAACUACAUGAACCUACA | 3682 |
| AD-567315.6 | asgsgccaaCfuAfCfAfufugaaccuacaL96 | 3161 | asGfsuagg(G2p)uucauguAfgUfuggcususc | 3421 | GAAGCCAACUACAUGAACCUACA | 3682 |
| AD-1069927.1 | gscscaaCfuAfCfAfUfgaaccuacagL96 | 3161 | asGfsuag(G2p)uucauGfuAfgUfuggcsusu | 3422 | AAGCCAACUACAUGAACCUACAG | 3683 |

TABLE 23-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence | SEQ ID NO: |
|---|---|---|---|---|---|---|
| AD-1069928.1 | cscsaacuAfcAfUfGfaaccuacaguL96 | 3162 | asCfsugua(G2p)guucauGfuAfguuggscsu | 3423 | AGCCAACUACAUGAACCUACAGA | 3684 |
| AD-567318.2 | csasacuaCfaUfGfAfAfaccuacagauL96 | 3163 | asUfscugu(Agn)gguucaUfgUfaguugsgsc | 3424 | GCCAACUACAUGAACCUACAGAG | 3685 |
| AD-567319.1 | asascuacAfuGfAfAfCfccuacagaguL96 | 3164 | asCfsucug(Tgn)agguucAfuGfuaguusgsg | 3425 | CAACUACAUGAACCUACAGAGA | 3686 |
| AD-1069929.1 | ascsuacaUfgAfAfCfcuacagagauL96 | 3165 | asUfscucu(G2p)uagguuCfaUfguagusug | 3426 | CAACUACAUGAACCUACAGAGAU | 3687 |
| AD-567321.1 | csusacauGfaAfCfCfuacagagauuL96 | 3166 | asAfsucuc(Tgn)guaggUfuCfauguagsusu | 3427 | AACUACAUGAACCUACAGAGAUC | 3688 |
| AD-1069930.1 | usascaugAfaCfCfUfacagagaucuL96 | 3167 | asGfsaucu(C2p)uguaggUfuCfauguasgsu | 3428 | ACUACAUGAACCUACAGAGAUCC | 3689 |
| AD-567323.1 | ascsaugaAfcCfUfAfcagagauccuL96 | 3168 | asGfsgauc(Tgn)cuguagGfuUfcauguasag | 3429 | CUACAUGAACCUACAGAGAUCCU | 3690 |
| AD-1069931.1 | csasugaaCfcUfAfCfagagauccuuL96 | 3169 | asAfsggau(C2p)ucuguaGfgUfucauguasa | 3430 | UACAUGAACCUACAGAGAUCCUA | 3691 |
| AD-567325.1 | asusgaacCfuAfCfAfgagauccuuaL96 | 3170 | asUfsagga(Tgn)cucuguAfgGfuucausgsu | 3431 | ACAUGAACCUACAGAGAUCCUAC | 3692 |
| AD-1069932.1 | usgsaaccUfaCfAfGfagauccuacuL96 | 3171 | asGfsuagg(Agn)ucucugUfaGfguucasusg | 3432 | CAUGAACCUACAGAGAUCCUACA | 3693 |
| AD-1069932.1 | gsasaccUfaCfAfGfAfgauccuacaL96 | 3172 | asUfsguag(G2p)gaucucUfgGfuagguscsa | 3433 | AUGAACCUACAGAGAUCCUACAC | 3694 |
| AD-1069933.1 | asasaccuaCfaGfAfGfAfuccuacacuL96 | 3173 | asGfsugua(G2p)gaucucUfgGfuaggususc | 3434 | UGAACCUACAGAGAUCCUACACU | 3695 |
| AD-567479.1 | gsgsccuAfcUfGfCfAfgcuaaaagauL96 | 3174 | asCfsuuuu(Agn)gcucagGfuAfgggccsasa | 3435 | UUGGCCCUACUGCAGCUAAAAGA | 3696 |
| AD-567480.1 | gscsccuaCfuGfCfAfGfcuaaaagauL96 | 3175 | asUfscuuu(Tgn)agcugcUfaGfaggcscsa | 3436 | UGGCCCUACUGCAGCUAAAAGAC | 3697 |
| AD-567481.1 | cscsuacuGfcAfGfCfuaaaagacuL96 | 3176 | asGfsucuu(Tgn)uagcugCfaGfuagggscsc | 3437 | GGCCCUACUGCAGCUAAAAGACU | 3698 |
| AD-567482.1 | cscsuacuGfcAfGfCfuaaaagacuL96 | 3177 | asAfsgucu(Tgn)uuagcuGfCfAfguagsgsc | 3438 | GCCCUACUGCAGCUAAAAGACUU | 3699 |
| AD-1069934.1 | usascugCfAfgCfUfAfAfAfaagacuuuguL96 | 3178 | asAfsaagu(C2p)uuuuagCfuGfcaguasgsg | 3439 | CCUACUGCAGCUAAAAGACUUUG | 3700 |
| AD-567485.1 | ascsugcaGfcUfAfAfAfagacuuugaL96 | 3179 | asCfsaaag(Tgn)cuuuuaGfcUfgcagusaa | 3440 | CUACUGCAGCUAAAAGACUUUGA | 3701 |
| AD-1069935.1 | csusgcagCfuAfAfAfAfagacuuugacL96 | 3180 | asUfscaaa(G2p)ucuuuuAfgCfugcasgsu | 3441 | UACUGCAGCUAAAAGACUUUGAC | 3702 |
| AD-567487.2 | usgscagcUfaAfAfAfAfgacuuugacuL96 | 3181 | asGfsucaa(Agn)gucuuuUfaGfcugcasgsu | 3442 | ACUGCAGCUAAAAGACUUUGACU | 3703 |
| AD-567488.1 | gscsagcuAfaAfAfGfacuuugacuuL96 | 3182 | asAfsguca(Agn)agucuuUfuAfgcugscsa | 3443 | CUGCAGCUAAAAGACUUUGACUU | 3704 |
| AD-567489.1 | csasgcuaAfaAfGfAfCfuuugacuuuL96 | 3183 | asAfsaguc(Agn)aagucuUfuUfagcugscsa | 3444 | UGCAGCUAAAAGACUUUGACUUU | 3705 |
| AD-1069936.1 | asgscuaaAfaGfAfCfuuugacuuugL96 | 3184 | asAfsaagu(C2p)aaagucUfuUfuagcsusgc | 3445 | GCAGCUAAAAGACUUUGACUUUG | 3706 |
| AD-567491.1 | gscsuaaaAfgAfCfUfUfugacuuugUL96 | 3185 | asCfsaaag(Tgn)caaaguCfuUfuuagcsusg | 3446 | CAGCUAAAAGACUUUGACUUUGU | 3707 |

TABLE 23-continued

Modified Sense and Antisense Strand Sequences of Complement Component C3 dsRNA Agents

| Duplex Name | Sense Sequene 5' to 3' | SEQ ID NO: | Antisense Sequence 5' to 3' | SEQ ID NO: | mRNA Target Sequence | SEQ ID NO: |
|---|---|---|---|---|---|---|
| AD-1069937.1 | gsusgccuCfccCfGfUfcgugcguugguL96 | 3186 | asCfsaacg(C2p)acgacGfgAfggcacsasa | 3447 | UUGUGCCUCCCGUCGUGCGUUGG | 3708 |
| AD-1069938.1 | usgsccucCfcGfUfCfcgugcguuggcuL96 | 3187 | asCfscaac(G2p)cacgacGfgGfaggcaascsa | 3448 | UGUGCCUCCCGUCGUGCGUUGGC | 3709 |
| AD-1069939.1 | gscsuccCfgUfCfGfufcgcguuggcuL96 | 3188 | asGfsccaa(C2p)gcacgaCfgGfgaggcsasc | 3449 | GUGCCUCCCGUCGUGCGUUGGCU | 3710 |
| AD-567513.1 | csusucccGfuCfGfUfGfcguuggcuuL96 | 3189 | asAfsgcca(Agn)cgcacgAfcGfggagscsa | 3450 | UGCCUCCCGUCGUGCGUUGGCUC | 3711 |
| AD-567514.1 | csusuccgUfcGfUfGfcguuggcucuL96 | 3190 | asGfsagcc(Agn)acgcacGfacGfgggagsgsc | 3451 | GCCUCCCGUCGUGCGUUGGCUCA | 3712 |
| AD-1069940.1 | uscsccgucCfgUfGfCfguuggcucaaL96 | 3191 | asUfsggac(C2p)aacgcaCfgAfcggasgsg | 3452 | CCUCCCGUCGUGCGUUGGCUCAA | 3713 |
| AD-1069941.1 | cscscgucGfuGfCfGfufuggcucaauL96 | 3192 | asGfsugag(C2p)caacgcAfcGfacggasag | 3453 | CUCCCGUCGUGCGUUGGCUCAAU | 3714 |
| AD-1069942.1 | cscscgucGfuGfCfGfufuggcucaauuL96 | 3193 | asAfsuuga(G2p)ccaacgCfacGfacggssga | 3454 | UCCCGUCGUGCGUUGGCUCAAUG | 3715 |
| AD-567518.1 | csgsuccGfucGfCfGfufuggcucaauguL96 | 3194 | asCfsauug(Agn)gccaacGfcAfcgacgsgg | 3455 | CCCGUCGUGCGUUGGCUCAAUGA | 3716 |
| AD-1069943.1 | gsuscugUfcGfUfGfGfCfucaaugaacaL96 | 3195 | asCfscauu(G2p)agcaacCfgCfacgacsgg | 3456 | CCGUCGUGCGUUGGCUCAAUGAA | 3717 |
| AD-567521.4 | csgsucgUfuGfCfGfCfUfucaaugaacacL96 | 3196 | asGfsauuca(Tgn)ugagccAfaCfgcacgasc | 3457 | GUCGUGCGUUGGCUCAAUGAACA | 3718 |
| AD-1069944.1 | usgsccguUfgGfCfGfuCfaaugaacagaL96 | 3197 | asCfsuguu(C2p)auugagCfcAfacgcascsg | 3458 | CGUGCGUUGGCUCAAUGAACAGA | 3719 |
| AD-567524.1 | gscsguugGfcUfCfAfaugaacagagauL96 | 3198 | asCfscugu(Tgn)cauugaGfcCfaacgcsca | 3459 | GUGCGUUGGCUCAAUGAACAGAG | 3720 |
| AD-567525.1 | csgsuuggCfuCfAfaufugaacagagauL96 | 3199 | asCfsucug(Tgn)ucauugAfgCfcaacgsca | 3460 | UGCGUUGGCUCAAUGAACAGAGA | 3721 |
| AD-1069945.1 | gsuusggCfUfcAfAfUfgaacagagauuL96 | 3200 | asUfscucu(G2p)ucauuGfaGfccaacgsc | 3461 | GCGUUGGCUCAAUGAACAGAGAU | 3722 |
| AD-567527.1 | ususggcuCfaAfUfGfAfacagagauuL96 | 3201 | asAfsucuc(Tgn)guucauUfgAfgccaascg | 3462 | CGUUGGCUCAAUGAACAGAGAUA | 3723 |
| AD-1069946.1 | usgsgcucAfaUfGfAfAfcagagauauL96 | 3202 | asUfsaucu(C2p)uguucaUfuGfagccaasac | 3463 | GUUGGCUCAAUGAACAGAGAUAU | 3724 |
| AD-567529.1 | gsgscucaAfuGfAfAfCfagagauacuL96 | 3203 | asGfsuauc(Tgn)cuguucAfuUfgagccsasa | 3464 | UUGGCUCAAUGAACAGAGAUACU | 3725 |
| AD-1069947.1 | gscsucaaUfgAfAfCfAfgagauacuuL96 | 3204 | asAfsguau(C2p)ucuguuCfaUfugagcscsa | 3465 | UGGCUCAAUGAACAGAGAUACUA | 3726 |
| AD-567531.1 | csuscaauGfaAfCfAfgagauacuauL96 | 3205 | asUfsagua(Tgn)cucuguUfcAfuugagscsc | 3466 | GGCUCAAUGAACAGAGAUACUAC | 3727 |
| AD-567532.1 | uscsaaugAfaCfAfGfAfgauacuacgL96 | 3206 | asGfsuagu(Tgn)ucucugUfuCfauugasgsc | 3467 | GCUCAAUGAACAGAGAUACUACG | 3728 |
| AD-567533.1 | csasaugaAfcAfGfAfGfauacuacggL96 | 3207 | asCfsguag(Tgn)aucucuGfuUfcauugaasg | 3468 | CUCAAUGAACAGAGAUACUACGG | 3729 |
| AD-1069948.1 | asasugaaCfaGfAfGfAfuauacuacgguL96 | 3208 | asCfscgua(G2p)uaucucUfgUfucauusgsa | 3469 | UCAAUGAACAGAGAUACUACGGU | 3730 |

TABLE 23-continued

Modified Sense and Antisense Strand Sequences of Complement Component C3 dsRNA Agents

| Duplex Name | Sense Sequene 5' to 3' | SEQ ID NO: | Antisense Sequence 5' to 3' | SEQ ID NO: | mRNA Target Sequence | SEQ ID NO: |
|---|---|---|---|---|---|---|
| AD-567535.1 | asusgaacAfgAfGfAfuacuacgguuL96 | 3209 | asAfsccgu(Agn)guaucuCfuGfuucaususg | 3470 | CAAUGAACAGAGAUACUACGGUG | 3731 |
| AD-568149.1 | gsasgcagUfcAfAfGfgucuacgccuuL96 | 3210 | asGfsggcgu(Agn)gaccuuGfaCfugcucscsa | 3471 | UGGAGCAGUCAAGGUCUACGCCU | 3732 |
| AD-568150.1 | asgscaguCfaAfGfGfucuacgccuuL96 | 3211 | asAfsggcg(Tgn)agaccuUfgAfcugcuscsc | 3472 | GGAGCAGUCAAGGUCUACGCCUA | 3733 |
| AD-1069949.1 | gscsaguCfaAfGfGfucacgccuauL96 | 3212 | asUfsaggc(G2p)uagaccUfuGfacugcsusc | 3473 | GAGCAGUCAAGGUCUACGCCUAU | 3734 |
| AD-1069950.1 | csasgucaAfgGfUfCfuacgccuauuL96 | 3213 | asAfsuagg(C2p)guagacCfuUfgacugscsu | 3474 | AGCAGUCAAGGUCUACGCCUAUU | 3735 |
| AD-1069951.1 | asgsucaaGfgUfCfUfacgccuauuuL96 | 3214 | asAfsauag(G2p)cguagaCfcUfugacusgsc | 3475 | GCAGUCAAGGUCUACGCCUAUUA | 3736 |
| AD-1069952.1 | gsuscaagGfucUfCfUfAfcgccuauuauL96 | 3215 | asUfsaaua(G2p)gcguagAfcCfuugacsusg | 3476 | CAGUCAAGGUCUACGCCUAUUAC | 3737 |
| AD-568155.1 | uscsaaggUfcUfAfCfgccuauuacuL96 | 3216 | asGfsuaau(Agn)ggcguaGfaCfcuugascsu | 3477 | AGUCAAGGUCUACGCCUAUUACA | 3738 |
| AD-568159.1 | gsgsucuaCfgCfCfUfauuacaaccuL96 | 3217 | asGfsguug(Tgn)aauaggCfgUfagaccsusu | 3478 | AAGGUCUACGCCUAUUACAACCU | 3739 |
| AD-1069953.1 | gsuscuacGfcCfUfAfuuacaaccugL96 | 3218 | asAfsgguu(G2p)uaauagGfcGfuagascsu | 3479 | AGGUCUACGCCUAUUACAACCUG | 3740 |
| AD-568161.2 | uscsuacgCfcCfUfAfUfuacaaccuguL96 | 3219 | asCfsaggu(Tgn)guaauaGfgCfguagascc | 3480 | GGUCUACGCCUAUUACAACCUGG | 3741 |
| AD-568162.1 | csusuacgCfcUfAfUfUfacaaccuggL96 | 3220 | asCfscagg(Tgn)uguaauAfgGfcguagasc | 3481 | GUCUACGCCUAUUACAACCUGGA | 3742 |
| AD-1069954.1 | usasgccUfaUfUfAfcaaccuggauL96 | 3221 | asUfsccag(G2p)uuguaaUfaGfcguasgsa | 3482 | UCUACGCCUAUUACAACCUGGAG | 3743 |
| AD-1069955.1 | ascsgccuAfuUfAfCfaaccuggagL96 | 3222 | asCfsucca(G2p)guuguaAfaUfaggcgusasg | 3483 | CUACGCCUAUUACAACCUGGAGG | 3744 |
| AD-568165.1 | csgsccuaUfuAfCfAfaccuggaggL96 | 3223 | asCfscucc(Agn)gguuguAfaUfaggcgsusa | 3484 | UACGCCUAUUACAACCUGGAGGA | 3745 |
| AD-1069956.1 | gscsuguagAfaGfAfAfuugcuucauL96 | 3224 | asAfsugaa(G2p)caauucUfcCfucagcsasc | 3485 | GUGCUGGAGGAGAAUUGCUUCAUA | 3746 |
| AD-568337.1 | gscsaggAfgUfGfGfAfcuaugugauL96 | 3225 | asAfscaca(Tgn)aguccaCfcUfcuggcsusc | 3486 | GAGCCAGGAGUGGACUAUGUGUA | 3747 |
| AD-568338.1 | cscsaggaUfgGfGfAfcuauguguacL96 | 3226 | asUfsacac(Agn)uagccaCfUfccuggscsu | 3487 | AGCCAGGAGUGGACUAUGUGUAC | 3748 |
| AD-1069957.1 | csasgagUfgGfAfCfuauguguacaL96 | 3227 | asGfsuaca(C2p)auaguGfcCfuccugsgsc | 3488 | GCCAGGAGUGGACUAUGUGUACA | 3749 |
| AD-568340.1 | asgsgagGfuGfGfAfCfuauguguacauL96 | 3228 | asUfsguac(Agn)cauaguCfcAfccugsgg | 3489 | CCAGGAGUGGACUAUGUGUACAA | 3750 |
| AD-1069958.1 | gsgsagUfgGfAfCfUfaugugcaauL96 | 3229 | asUfsugua(C2p)acauagUfcCfaccusg | 3490 | CAGGAGUGGACUAUGUGUACAAG | 3751 |

TABLE 23-continued

Modified Sense and Antisense Strand Sequences of Complement Component C3 dsRNA Agents

| Duplex Name | Sense Sequene 5' to 3' | SEQ ID NO: | Antisense Sequence 5' to 3' | SEQ ID NO: | mRNA Target Sequence | SEQ ID NO: |
| --- | --- | --- | --- | --- | --- | --- |
| AD-568342.1 | gsasguggAfCfUfAfUfguguacaaguL96 | 3230 | asCfsuugu(Agn)cacauaGfuCfcacucscsu | 3491 | AGGAGUGGACUAUGUGUACAAGA | 3752 |
| AD-568343.4 | asgsuggaCfuAfUfGfuguacaagauL96 | 3231 | asUfscuug(Tgn)acacauAfguCfccacuscsc | 3492 | GGAGUGGACUAUGUGUACAAGAC | 3753 |
| AD-1069959.1 | gsusggacUfaUfGfUfguacaagacuL96 | 3232 | asGfsucuu(G2p)uacacaUfaGfuccacsusc | 3493 | GAGUGGACUAUGUGUACAAGACC | 3754 |
| AD-568345.2 | usgsgacuAfuGfUfGfuacaagaccuL96 | 3233 | asGfsgucu(Tgn)guacacAfuAfguccascsu | 3494 | AGUGGACUAUGUGUACAAGACCC | 3755 |
| AD-568348.1 | ascsuaugUfgUfAfCfaagacccgauL96 | 3234 | asUfscggg(Tgn)cuuguaCfaCfauaguscsc | 3495 | GGACUAUGUGUACAAGACCCGAC | 3756 |
| AD-1069961.1 | csusauguGfuAfCfAfagacccgacuL96 | 3235 | asGfsucgg(G2p)ucuuguAfcAfcauagsusc | 3496 | GACUAUGUGUACAAGACCCGACU | 3757 |

TABLE 24

C3 Single Dose Screens in PCH cells (% C3 mRNA Remaining)

| Duplex | FU* 500 nM | SD | FU* 100 nM | SD | FU* 10 nM | SD | TX# 10 nM | SD | TX# 1 nM | SD | TX# 0.1 nM | SD |
|---|---|---|---|---|---|---|---|---|---|---|---|---|
| AD-570137.1 | 60.5 | 19.0 | 73.6 | 24.1 | 71.8 | 43.2 | 1.8 | 0.4 | 9.8 | 4.1 | 31.8 | 4.2 |
| AD-570138.1 | 71.5 | 7.9 | 127.1 | 40.6 | 67.4 | 49.1 | 6.1 | 1.2 | 15.4 | 4.5 | 50.4 | 6.0 |
| AD-570139.1 | 84.2 | 40.6 | 111.1 | 42.9 | 90.7 | 14.7 | 2.1 | 0.8 | 28.6 | 6.1 | 67.7 | 21.1 |
| AD-570140.1 | 166.3 | 20.6 | 91.3 | 22.5 | 79.0 | 42.1 | 1.6 | 0.6 | 18.1 | 4.4 | 87.8 | 22.5 |
| AD-570141.1 | 118.0 | 10.4 | 130.1 | 48.1 | 66.0 | 26.4 | 2.1 | 0.2 | 29.3 | 13.9 | 111.3 | 30.1 |
| AD-570142.1 | 112.0 | 14.8 | 115.6 | 49.1 | 74.7 | 27.4 | 2.9 | 0.5 | 31.8 | 9.4 | 99.5 | 25.8 |
| AD-570143.1 | 69.9 | 32.7 | 85.0 | 28.8 | 73.5 | 7.2 | 2.1 | 1.3 | 6.2 | 2.4 | 34.8 | 11.0 |
| AD-570144.1 | 49.6 | 14.8 | 123.7 | 29.1 | 103.3 | 78.1 | 5.2 | 1.0 | 39.9 | 11.8 | 139.4 | 34.9 |
| AD-570145.1 | 65.9 | 25.8 | 102.9 | 50.0 | 106.6 | 54.4 | 2.9 | 1.3 | 30.7 | 16.0 | 58.1 | 5.3 |
| AD-570146.1 | 132.3 | 36.8 | 129.1 | 30.7 | 90.9 | 19.4 | 1.2 | 0.6 | 11.3 | 3.2 | 22.1 | 5.4 |
| AD-570147.1 | 82.8 | 18.5 | 118.5 | 6.4 | 92.5 | 20.4 | 38.4 | 3.6 | 75.5 | 22.9 | 66.1 | 19.5 |
| AD-570148.1 | 54.2 | 13.6 | 139.0 | 8.0 | 95.3 | 36.3 | 1.6 | 0.4 | 19.0 | 8.1 | 107.8 | 53.3 |
| AD-570149.1 | 70.4 | 13.4 | 157.7 | 38.0 | 112.1 | 20.8 | 15.0 | 6.3 | 64.0 | 5.2 | 143.8 | 35.2 |
| AD-570150.1 | 125.5 | 29.6 | 110.1 | 4.3 | 146.3 | 35.4 | 10.7 | 2.0 | 80.2 | 12.2 | 118.3 | 18.1 |
| AD-570151.1 | 86.9 | 15.4 | 141.7 | 12.1 | 99.0 | 15.0 | 5.4 | 0.5 | 61.6 | 11.1 | 128.3 | 29.8 |
| AD-570152.1 | 61.1 | 15.8 | 110.4 | 52.4 | 88.7 | 22.4 | 3.7 | 2.0 | 30.4 | 5.0 | 120.7 | 33.3 |
| AD-570153.1 | 44.1 | 1.1 | 106.0 | 62.0 | 74.7 | 45.3 | 24.4 | 3.3 | 75.8 | 41.7 | 78.3 | 11.0 |
| AD-570154.1 | 58.9 | 10.0 | 168.1 | 5.8 | 87.3 | 15.6 | 1.6 | 0.5 | 21.5 | 15.3 | 50.2 | 6.3 |
| AD-570155.1 | 93.9 | 13.0 | 112.4 | 13.3 | 76.5 | 31.1 | 2.7 | 0.5 | 33.5 | 7.5 | 98.1 | 33.0 |
| AD-570156.2 | 88.6 | 16.8 | 123.8 | 12.0 | 73.0 | 19.0 | 2.6 | 1.5 | 22.4 | 7.4 | 58.4 | 14.5 |
| AD-570158.1 | 81.0 | 21.1 | 93.8 | 18.5 | 116.6 | 37.7 | 1.1 | 0.2 | 20.6 | 9.3 | 73.6 | 46.3 |
| AD-570159.1 | 79.9 | 13.8 | 93.8 | 8.7 | 100.4 | 33.7 | 23.4 | 4.9 | 77.5 | 6.6 | 165.8 | 22.2 |
| AD-570160.1 | 48.5 | 25.0 | 92.4 | 44.8 | 99.9 | 37.6 | 10.0 | 4.5 | 100.1 | 8.0 | 182.5 | 57.7 |
| AD-570161.1 | 37.2 | 2.2 | 95.6 | 72.1 | 76.6 | 52.9 | 8.6 | 2.5 | 51.4 | 44.7 | 56.1 | 5.4 |
| AD-570611.1 | 56.2 | 8.4 | N/A | N/A | 81.5 | 11.2 | 30.8 | 8.0 | 52.3 | 27.7 | 79.7 | 8.0 |
| AD-570612.1 | 81.2 | 20.4 | 153.7 | 37.5 | 125.4 | 73.3 | 96.6 | 19.3 | 126.3 | 48.5 | 111.1 | 27.8 |
| AD-570613.1 | 113.4 | 19.6 | 142.9 | 15.7 | 116.8 | 41.2 | 136.3 | 29.1 | 112.9 | 29.0 | 145.2 | 73.4 |
| AD-570614.1 | 60.7 | 14.4 | 145.3 | 35.2 | 148.5 | 15.5 | 98.4 | 27.0 | 110.5 | 6.1 | 181.3 | 61.8 |
| AD-570615.1 | 67.6 | 13.1 | 124.5 | 25.9 | 136.2 | 29.4 | 36.0 | 28.6 | 149.9 | 105.5 | 153.5 | 53.7 |
| AD-570616.1 | 56.0 | 32.5 | 101.8 | 47.2 | 105.6 | 19.4 | 14.5 | 7.1 | 69.7 | 14.8 | 112.2 | 24.5 |
| AD-570617.1 | 52.2 | 25.3 | 121.4 | 64.7 | 59.8 | 15.0 | 79.2 | 29.0 | 54.9 | 22.2 | 84.3 | 33.5 |
| AD-570618.1 | 26.6 | 6.0 | 126.6 | 41.5 | 73.8 | 19.2 | 3.6 | 0.3 | 42.0 | 32.6 | 59.6 | 10.1 |
| AD-570619.1 | 41.3 | 7.8 | 108.4 | 18.4 | 82.0 | 5.1 | 3.6 | 2.8 | 36.7 | 27.2 | 62.0 | 20.1 |
| AD-570620.3 | 67.8 | 16.3 | 142.3 | 32.1 | 99.0 | 23.2 | 8.6 | 0.8 | 81.7 | 45.6 | 78.5 | 8.1 |
| AD-570621.2 | 39.1 | 3.8 | 123.1 | 19.3 | 116.1 | 31.4 | 61.3 | 19.4 | 86.5 | 9.3 | 144.6 | 46.4 |
| AD-570622.2 | 25.5 | 8.2 | 131.5 | 29.2 | 151.2 | 51.7 | 5.7 | 0.9 | 78.3 | 39.9 | 88.9 | 8.6 |
| AD-570623.4 | 51.0 | 9.1 | 99.7 | 24.2 | 111.6 | 53.1 | 6.1 | 1.3 | 81.9 | 41.1 | 143.9 | 27.5 |
| AD-570624.2 | 80.6 | 20.6 | 100.6 | 46.7 | 97.1 | 31.4 | 43.2 | 13.0 | 111.9 | 54.8 | 170.3 | 41.9 |
| AD-570625.2 | 44.4 | 13.1 | 96.8 | 57.1 | 59.2 | 25.8 | 14.0 | 5.4 | 49.0 | 25.6 | 73.9 | 17.4 |
| AD-570626.1 | 71.6 | 20.1 | 108.2 | 24.0 | 94.2 | 72.7 | 6.7 | 4.5 | 58.7 | 26.7 | 55.3 | 4.1 |
| AD-570627.2 | 56.7 | 17.0 | 98.3 | 6.5 | 99.1 | 12.6 | 18.0 | 7.4 | 90.7 | 40.7 | 67.0 | 14.0 |
| AD-570628.1 | 79.4 | 8.8 | 134.5 | 11.0 | 118.7 | 61.1 | 18.9 | 3.1 | 82.4 | 36.4 | 91.8 | 21.1 |
| AD-570629.1 | 68.2 | 22.0 | 128.7 | 29.6 | 114.8 | 7.1 | 68.2 | 26.9 | 108.8 | 40.0 | 129.3 | 35.5 |
| AD-570630.1 | 37.5 | 11.2 | 107.3 | 5.6 | 125.3 | 38.8 | 67.7 | 13.5 | 121.8 | 52.2 | 127.2 | 22.5 |
| AD-1069837.1 | 28.4 | 3.9 | 81.3 | 9.7 | 165.3 | 36.1 | 129.7 | 47.9 | 104.3 | 28.4 | 113.7 | 11.9 |
| AD-570707.1 | 81.8 | 43.9 | 80.3 | 46.8 | 48.2 | 16.5 | 1.0 | 0.2 | 8.1 | 2.7 | 27.7 | 2.4 |
| AD-570708.1 | 65.2 | 18.9 | 141.0 | 18.7 | 66.1 | 40.2 | 9.3 | 1.3 | 53.2 | 30.9 | 47.7 | 19.1 |
| AD-570709.1 | 34.8 | 14.1 | 128.6 | 32.0 | 72.7 | 15.4 | 23.4 | 4.1 | 88.9 | 50.0 | 40.9 | 8.7 |
| AD-570710.1 | 73.8 | 10.7 | 157.4 | 19.7 | 108.1 | 16.8 | 31.8 | 9.8 | 113.8 | 52.8 | 52.9 | 10.9 |
| AD-570715.1 | 65.6 | 7.5 | 119.5 | 31.9 | 109.4 | 12.7 | 3.3 | 1.4 | 22.4 | 5.6 | 47.2 | 7.2 |
| AD-570716.1 | 72.6 | 27.0 | 113.2 | 18.7 | 111.8 | 26.5 | 3.5 | 2.3 | 41.0 | 7.8 | 48.8 | 16.7 |
| AD-570717.2 | 69.6 | 12.6 | 89.4 | 28.8 | 119.1 | 32.5 | 16.2 | 2.8 | 99.0 | 20.6 | 71.2 | 29.7 |
| AD-570718.1 | 29.5 | 10.9 | 82.9 | 36.8 | 132.7 | 18.8 | 3.4 | 0.9 | 78.7 | 30.1 | 27.0 | 10.6 |
| AD-570719.1 | 65.9 | 43.7 | 66.0 | 33.7 | 60.2 | 26.8 | 1.8 | 1.0 | 9.7 | 3.9 | 21.4 | 3.9 |
| AD-570720.1 | 62.6 | 37.2 | 132.0 | 26.0 | 75.9 | 20.9 | 33.1 | 4.9 | 67.2 | 45.6 | 66.8 | 14.8 |
| AD-570721.1 | 38.2 | 22.5 | 111.5 | 20.3 | 91.5 | 20.4 | 8.0 | 4.2 | 63.5 | 23.1 | 57.1 | 18.2 |
| AD-571285.1 | 39.5 | 15.1 | 120.7 | 25.8 | 90.5 | 13.6 | 115.2 | 36.2 | 125.4 | 60.7 | 94.3 | 17.6 |
| AD-571286.1 | 62.7 | 2.4 | 126.1 | 13.5 | 79.6 | 32.2 | 26.4 | 3.1 | 79.4 | 43.2 | 92.5 | 49.0 |
| AD-571287.1 | 64.9 | 9.9 | 114.4 | 9.1 | 105.4 | 16.4 | 171.9 | 56.1 | 88.1 | 39.8 | 94.4 | 18.9 |
| AD-571288.1 | 37.9 | 12.1 | 86.4 | 22.2 | 112.9 | 41.2 | 153.0 | 27.6 | 81.0 | 11.7 | 106.9 | 29.8 |
| AD-571289.1 | 41.8 | 10.2 | 82.0 | 37.5 | 117.3 | 45.1 | 34.6 | 9.5 | 83.8 | 17.9 | 99.4 | 5.5 |
| AD-571290.1 | 65.8 | 30.0 | 98.5 | 40.2 | 54.1 | 22.5 | 74.8 | 29.1 | 74.7 | 50.1 | 79.5 | 12.5 |
| AD-571291.1 | 114.1 | 14.4 | 142.5 | 31.4 | 104.0 | 24.3 | 76.6 | 14.0 | 98.7 | 36.8 | 64.6 | 10.3 |
| AD-571292.1 | 70.6 | 13.9 | 93.3 | 4.8 | 123.4 | 34.8 | 1.4 | 0.6 | 28.9 | 10.1 | 62.2 | 17.7 |
| AD-571293.1 | 70.7 | 28.1 | 96.6 | 21.1 | 114.4 | 21.1 | 1.6 | 0.7 | 36.5 | 20.7 | 73.7 | 8.1 |
| AD-571294.1 | 63.6 | 8.8 | 126.3 | 50.3 | 94.7 | 18.7 | 6.7 | 2.8 | 69.2 | 37.0 | 84.9 | 9.6 |
| AD-571295.1 | 31.5 | 8.7 | 79.5 | 20.0 | 125.2 | 45.9 | 1.9 | 1.0 | 25.9 | 15.6 | 52.1 | 13.9 |
| AD-571296.1 | 68.1 | 29.7 | 66.6 | 30.0 | 87.3 | 24.8 | 1.1 | 0.6 | 14.3 | 2.2 | 36.5 | 6.9 |
| AD-571297.1 | 62.1 | 15.9 | 83.5 | 25.5 | 55.2 | 9.2 | 3.1 | 1.4 | 37.3 | 16.2 | 65.6 | 29.0 |
| AD-571298.6 | 82.7 | 18.1 | 125.1 | 20.1 | 94.5 | 25.7 | 2.6 | 0.4 | 19.9 | 9.9 | 36.8 | 6.8 |
| AD-571299.1 | 94.6 | 19.6 | 73.2 | 14.4 | 79.3 | 33.8 | 0.9 | 0.6 | 13.7 | 3.4 | 20.4 | 3.4 |
| AD-571300.1 | 64.3 | 8.3 | 92.0 | 12.2 | 97.8 | 43.9 | 2.1 | 1.2 | 29.8 | 19.5 | 47.1 | 7.2 |
| AD-571301.1 | 81.4 | 15.7 | 92.2 | 14.8 | 77.6 | 17.4 | 19.1 | 5.5 | 104.5 | 35.4 | 85.8 | 16.8 |
| AD-571302.1 | 80.2 | 23.4 | 69.5 | 10.4 | 76.3 | 35.1 | 3.4 | 0.3 | 43.2 | 14.9 | 57.4 | 13.1 |
| AD-571303.1 | 67.2 | 25.9 | 72.7 | 42.9 | 62.2 | 6.4 | 3.2 | 0.8 | 51.3 | 6.9 | 65.1 | 27.4 |

TABLE 24-continued

C3 Single Dose Screens in PCH cells (% C3 mRNA Remaining)

| Duplex | FU* 500 nM | SD | FU* 100 nM | SD | FU* 10 nM | SD | TX# 10 nM | SD | TX# 1 nM | SD | TX# 0.1 nM | SD |
|---|---|---|---|---|---|---|---|---|---|---|---|---|
| AD-571304.1 | 18.6 | 4.4 | 78.4 | 29.7 | 56.3 | 21.8 | 3.0 | 0.7 | 39.7 | 10.4 | 62.4 | 10.1 |
| AD-571305.1 | 74.6 | 30.3 | 103.8 | 6.7 | 82.1 | 23.9 | 3.2 | 2.2 | 16.8 | 4.7 | 38.6 | 4.1 |
| AD-571306.1 | 42.0 | 11.8 | 90.3 | 31.1 | 78.5 | 35.7 | 4.6 | 1.7 | 22.4 | 12.4 | 56.7 | 13.3 |
| AD-571307.1 | 56.0 | 20.3 | 61.1 | 13.5 | 67.1 | 9.0 | 1.1 | 0.3 | 13.1 | 5.3 | 24.9 | 6.6 |
| AD-571308.1 | 64.3 | 21.8 | 80.2 | 15.9 | 104.8 | 32.7 | 3.1 | 1.0 | 25.9 | 9.6 | 50.6 | 5.6 |
| AD-571309.1 | 51.6 | 9.0 | 96.8 | 41.1 | 113.7 | 18.4 | 4.8 | 1.9 | 39.8 | 25.3 | 67.5 | 8.0 |
| AD-571526.1 | 43.3 | 8.6 | 88.2 | 29.2 | 137.1 | 29.5 | 10.8 | 1.5 | 67.2 | 27.8 | 57.5 | 7.1 |
| AD-571527.1 | 36.8 | 6.5 | 60.2 | 14.1 | 72.1 | 27.8 | 2.1 | 0.5 | 16.3 | 7.9 | 42.0 | 8.0 |
| AD-571528.1 | 64.0 | 9.5 | 50.3 | 11.4 | 63.8 | 19.3 | 1.4 | 0.4 | 3.7 | 1.4 | 15.7 | 5.7 |
| AD-571529.1 | 60.6 | 15.6 | 88.0 | 20.9 | 97.1 | 36.5 | 6.3 | 1.4 | 46.0 | 20.7 | 49.0 | 15.3 |
| AD-571530.1 | 92.8 | 16.5 | 98.1 | 27.6 | 76.9 | 47.0 | 18.7 | 8.9 | 57.0 | 18.6 | 56.4 | 10.8 |
| AD-571531.1 | 92.5 | 11.1 | 87.3 | 2.1 | 58.0 | 26.4 | 5.2 | 1.8 | 31.3 | 16.7 | 54.2 | 7.0 |
| AD-571532.1 | 71.6 | 27.8 | 70.9 | 9.6 | 61.7 | 16.6 | 2.3 | 0.6 | 8.5 | 4.0 | 28.6 | 2.6 |
| AD-571533.1 | 41.5 | 12.5 | 46.4 | 7.6 | 65.6 | 28.5 | 1.3 | 0.4 | 4.0 | 5.1 | 10.3 | 2.3 |
| AD-571534.1 | 46.7 | 5.6 | 79.7 | 20.5 | 66.7 | 25.1 | 2.5 | 0.8 | 15.1 | 2.4 | 42.8 | 13.6 |

Transfection (TX)

*Free Uptake (FU)

TABLE 25

C3 Single Dose Screens in PCH cells (% C3 mRNA Remaining)

| Duplex | FU* 500 nM | SD | FU* 100 nM | SD | FU* 10 nM | SD | TX# 10 nM | SD | TX# 1 nM | SD | TX# 0.1 nM | SD |
|---|---|---|---|---|---|---|---|---|---|---|---|---|
| AD-568955.1 | 63.2 | 9.9 | 61.5 | 17.9 | 97.0 | 34.4 | 1.8 | 0.8 | 15.3 | 3.7 | 28.0 | 4.4 |
| AD-568956.1 | 65.4 | 2.0 | 93.0 | 23.7 | 123.9 | 26.8 | 3.1 | 0.3 | 59.5 | 22.9 | 53.7 | 11.9 |
| AD-568957.1 | 55.5 | 7.3 | 78.3 | 15.0 | 88.8 | 6.3 | 3.2 | 1.5 | 25.3 | 12.7 | 37.8 | 15.6 |
| AD-568958.1 | 96.8 | 14.2 | 85.5 | 20.8 | N/A | N/A | 4.8 | 1.5 | 82.1 | 23.7 | 72.7 | 13.4 |
| AD-568959.1 | 87.4 | 12.1 | 84.2 | 42.0 | 126.8 | 22.7 | 3.8 | 0.4 | 80.4 | 26.4 | 64.3 | 20.6 |
| AD-568960.1 | 100.2 | 5.5 | 70.3 | 3.1 | 117.6 | 11.3 | 14.9 | 5.6 | 141.7 | 22.9 | 79.0 | 23.6 |
| AD-568961.1 | 92.0 | 7.2 | 91.9 | 23.2 | 114.3 | 34.7 | 5.6 | 0.8 | 88.2 | 36.9 | 59.1 | 19.9 |
| AD-568962.1 | 83.1 | 20.6 | 91.5 | 15.2 | 98.0 | 14.8 | 4.4 | 1.4 | 36.7 | 9.1 | 57.0 | 34.0 |
| AD-568963.2 | 53.6 | 11.2 | 73.8 | 36.3 | 107.6 | 28.6 | 1.6 | 0.8 | 20.3 | 7.0 | 35.5 | 9.5 |
| AD-568964.1 | 72.4 | 3.6 | 89.2 | 24.9 | 106.7 | 1.6 | 8.5 | 4.6 | 85.6 | 20.1 | 52.1 | 16.5 |
| AD-568965.1 | 42.7 | 1.7 | 76.6 | 22.0 | 66.5 | 11.0 | 1.2 | 0.1 | 56.3 | 50.2 | 24.8 | 8.0 |
| AD-568966.1 | 58.2 | 7.2 | 79.8 | 13.4 | 83.0 | 16.5 | 2.0 | 1.7 | 82.4 | 34.2 | 42.5 | 25.0 |
| AD-568967.1 | 96.5 | 3.9 | 87.6 | 11.0 | 88.9 | 13.3 | 4.8 | 2.4 | 99.8 | 28.1 | 40.5 | 17.8 |
| AD-568968.1 | 88.0 | 8.0 | 94.6 | 18.8 | 85.3 | 10.1 | 3.1 | 1.0 | 129.0 | 60.6 | 54.4 | 15.0 |
| AD-568969.1 | 53.2 | 5.7 | 73.9 | 23.4 | 88.9 | 26.4 | 2.7 | 1.0 | 22.0 | 8.6 | 37.0 | 12.5 |
| AD-568970.1 | 85.9 | 12.8 | 80.1 | 22.5 | 111.1 | 6.6 | 4.0 | 0.7 | 60.9 | 20.3 | 54.2 | 14.8 |
| AD-568971.1 | 58.4 | 12.8 | 73.4 | 31.0 | 105.1 | 27.8 | 2.8 | 3.1 | 10.5 | 2.3 | 34.4 | 11.8 |
| AD-568972.1 | 48.7 | 8.3 | 70.6 | 14.8 | 99.9 | 26.1 | 1.9 | 1.6 | 9.6 | 2.2 | 22.4 | 4.3 |
| AD-568973.1 | 59.5 | 3.7 | 72.9 | 4.4 | 72.7 | 3.8 | 1.9 | 1.3 | 18.4 | 5.7 | 58.9 | 38.2 |
| AD-568974.1 | 67.4 | 2.4 | 84.0 | 9.9 | 78.8 | 6.2 | 1.7 | 0.5 | 23.3 | 14.2 | 44.7 | 20.3 |
| AD-568975.1 | 42.8 | 7.8 | 54.5 | 7.0 | 65.1 | 12.3 | 1.1 | 0.3 | 9.6 | 2.5 | 8.6 | 1.9 |
| AD-568977.1 | 67.2 | 11.2 | 78.7 | 26.8 | 92.3 | 24.4 | 2.3 | 0.7 | 13.3 | 3.7 | 19.8 | 5.8 |
| AD-568979.1 | 92.6 | 9.5 | 135.6 | 46.5 | 91.1 | 4.8 | 5.1 | 2.6 | 92.7 | 9.9 | 40.3 | 17.1 |
| AD-1069834.1 | 99.1 | 17.1 | 39.6 | 10.7 | 90.5 | 41.0 | 1.9 | 0.4 | 37.4 | 13.6 | 41.3 | 31.1 |
| AD-1069835.1 | 94.1 | 11.7 | 74.3 | 9.5 | 94.5 | 15.5 | 3.7 | 0.8 | 44.7 | 4.0 | 50.0 | 3.3 |
| AD-1069836.1 | 78.1 | 8.3 | 84.3 | 11.7 | 92.9 | 15.6 | 3.7 | 0.9 | 45.0 | 16.4 | 75.6 | 16.6 |
| AD-569154.1 | 115.3 | 28.0 | 108.7 | 17.5 | 101.9 | 19.2 | 36.3 | 5.0 | 120.2 | 19.0 | 65.5 | 12.1 |
| AD-569155.1 | 93.0 | 7.7 | 82.7 | 8.9 | 85.3 | 8.4 | 6.4 | 1.6 | 92.2 | 24.5 | 49.3 | 14.1 |
| AD-569156.1 | 63.8 | 6.5 | 79.8 | 8.3 | 96.3 | 30.2 | 3.1 | 1.3 | 22.2 | 4.1 | 38.8 | 17.1 |
| AD-569157.1 | 58.5 | 13.6 | 75.3 | 11.6 | 80.7 | 11.8 | 1.5 | 0.2 | 8.8 | 2.4 | 15.5 | 1.8 |
| AD-569158.1 | 67.8 | 3.1 | 78.5 | 42.2 | 83.5 | 23.5 | 1.8 | 0.3 | 11.5 | 5.7 | 27.4 | 12.6 |
| AD-569159.1 | 50.1 | 9.4 | 66.5 | 14.7 | 89.9 | 21.2 | 1.5 | 0.3 | 9.2 | 1.8 | 24.6 | 11.5 |
| AD-569160.1 | 61.7 | 8.6 | 86.8 | 16.6 | 89.4 | 9.9 | 2.0 | 1.6 | 7.7 | 1.9 | 19.6 | 1.9 |
| AD-569161.1 | 64.9 | 11.6 | 79.6 | 8.9 | 90.4 | 3.6 | 2.2 | 1.3 | 13.6 | 2.7 | 38.6 | 14.7 |
| AD-569162.1 | 105.3 | 6.1 | 117.7 | 9.9 | 96.8 | 17.9 | 41.7 | 6.4 | 73.4 | 23.9 | 35.6 | 5.8 |
| AD-569163.1 | 59.6 | 5.1 | 88.4 | 19.4 | 74.3 | 17.0 | 1.5 | 0.3 | 13.3 | 3.4 | 36.7 | 24.0 |
| AD-569166.1 | 114.2 | 32.3 | 100.1 | 16.5 | 84.0 | 11.8 | 6.6 | 0.7 | 59.2 | 11.5 | 53.7 | 16.0 |
| AD-569167.1 | 106.8 | 21.9 | 85.8 | 30.9 | 98.8 | 13.3 | 7.3 | 1.1 | 98.6 | 15.9 | 46.7 | 26.0 |
| AD-569168.1 | 78.5 | 8.3 | 51.7 | 17.4 | 103.3 | 26.6 | 7.8 | 0.4 | 66.8 | 34.2 | 25.6 | 3.2 |
| AD-569169.1 | 90.2 | 8.5 | 84.5 | 17.3 | 122.3 | 16.7 | 2.6 | 0.1 | 41.0 | 25.0 | 19.5 | 10.9 |
| AD-569170.1 | 101.9 | 9.1 | 98.3 | 16.2 | 112.4 | 14.8 | 45.9 | 11.1 | 57.9 | 8.3 | 57.4 | 23.2 |
| AD-569171.1 | 117.3 | 5.8 | 106.7 | 18.1 | 107.1 | 11.1 | 62.2 | 4.9 | 93.8 | 43.6 | 56.8 | 12.8 |
| AD-569172.1 | 94.1 | 7.1 | 107.3 | 17.3 | 91.5 | 13.4 | 34.2 | 9.8 | 80.8 | 15.1 | 59.2 | 27.5 |
| AD-569173.1 | 94.3 | 9.1 | 102.1 | 17.9 | 98.5 | 14.7 | 20.5 | 2.4 | 79.7 | 12.3 | 50.7 | 31.9 |
| AD-569174.1 | 90.4 | 11.8 | 107.0 | 13.9 | 93.3 | 10.2 | 52.9 | 6.8 | 121.6 | 30.3 | 63.7 | 22.8 |
| AD-569175.1 | 93.6 | 7.1 | 68.2 | 8.1 | 86.6 | 20.7 | 9.8 | 3.4 | 34.1 | 7.0 | 41.5 | 22.6 |
| AD-569262.1 | 14.8 | 6.0 | 38.5 | 6.4 | 68.7 | 11.9 | 0.8 | 0.3 | 5.5 | 1.8 | 6.7 | 6.2 |

TABLE 25-continued

C3 Single Dose Screens in PCH cells (% C3 mRNA Remaining)

| Duplex | FU* 500 nM | SD | FU* 100 nM | SD | FU* 10 nM | SD | TX# 10 nM | SD | TX# 1 nM | SD | TX# 0.1 nM | SD |
|---|---|---|---|---|---|---|---|---|---|---|---|---|
| AD-569263.1 | 24.6 | 3.1 | 47.2 | 1.8 | 82.3 | 18.0 | 1.3 | 0.5 | 14.2 | 14.4 | 9.4 | 7.0 |
| AD-569264.1 | 28.1 | 4.9 | 47.5 | 5.8 | 72.4 | 2.7 | 1.3 | 0.1 | 5.5 | 1.3 | 8.8 | 1.9 |
| AD-569265.1 | 31.5 | 0.9 | 48.5 | 5.4 | 65.2 | 9.3 | 1.7 | 1.6 | 4.5 | 1.0 | 8.2 | 5.8 |
| AD-569266.1 | 27.1 | 4.2 | 51.3 | 8.2 | 61.9 | 13.2 | 0.9 | 0.4 | 10.4 | 10.5 | 15.0 | 8.7 |
| AD-569267.1 | 31.0 | 2.1 | 47.8 | 4.5 | 68.9 | 11.0 | 2.7 | 2.8 | 5.6 | 0.5 | 15.6 | 10.3 |
| AD-569268.1 | 13.2 | 2.1 | 31.6 | 6.6 | 57.7 | 22.4 | 1.0 | 0.5 | 4.0 | 0.5 | 1.1 | 0.4 |
| AD-569269.1 | 17.1 | 2.8 | 30.0 | 15.2 | 46.8 | 10.4 | 1.2 | 0.5 | 3.2 | 1.3 | 4.7 | 4.4 |
| AD-569270.1 | 31.3 | 4.8 | 42.9 | 8.3 | 80.9 | 20.1 | 0.9 | 0.1 | 5.0 | 2.7 | 7.6 | 1.2 |
| AD-569271.1 | 36.2 | 19.9 | 59.3 | 5.9 | 76.5 | 12.6 | 1.0 | 0.2 | 9.0 | 5.3 | 9.1 | 4.6 |
| AD-569273.1 | 72.4 | 18.1 | 106.7 | 26.2 | 113.3 | 22.6 | 2.5 | 0.3 | 31.5 | 10.4 | 25.7 | 11.2 |
| AD-569274.1 | 51.7 | 2.4 | 76.1 | 14.4 | 82.5 | 13.3 | 1.6 | 0.3 | 10.7 | 2.3 | 31.9 | 8.2 |
| AD-569275.1 | 108.1 | 16.0 | 105.2 | 6.0 | 102.9 | 9.8 | 28.4 | 7.8 | 82.5 | 23.1 | 52.3 | 37.7 |
| AD-569276.1 | 83.6 | 10.6 | 86.9 | 9.6 | 112.3 | 14.5 | 4.4 | 1.2 | 48.4 | 12.9 | 38.1 | 10.6 |
| AD-569277.1 | 69.0 | 6.0 | 85.1 | 16.2 | 102.3 | 40.6 | 2.4 | 1.0 | 19.5 | 4.3 | 49.3 | 47.4 |
| AD-569278.1 | 102.5 | 19.7 | 62.3 | 1.8 | 80.2 | 19.9 | 24.7 | 3.7 | 51.6 | 10.5 | 48.3 | 33.1 |
| AD-569279.1 | 113.3 | 28.3 | 105.6 | 7.2 | 108.8 | 24.7 | 78.8 | 7.4 | 73.3 | 20.9 | 47.6 | 15.9 |
| AD-569280.1 | 103.2 | 12.0 | 121.9 | 22.0 | 96.4 | 12.3 | 62.7 | 4.6 | 74.6 | 7.1 | 56.5 | 11.8 |
| AD-569281.1 | 98.3 | 8.6 | 109.2 | 15.7 | 96.2 | 16.0 | 84.4 | 26.7 | 87.4 | 33.8 | 48.6 | 17.7 |
| AD-569282.1 | 106.1 | 5.7 | 92.0 | 1.5 | 98.5 | 11.3 | 113.7 | 20.7 | 86.2 | 28.3 | 30.2 | 2.6 |
| AD-569506.1 | 85.5 | 3.6 | 114.8 | 23.0 | 93.7 | 11.4 | 5.9 | 1.3 | 43.0 | 18.6 | 42.6 | 8.8 |
| AD-569507.1 | 76.8 | 6.5 | 105.7 | 35.9 | 87.6 | 20.7 | 2.1 | 0.6 | 19.9 | 4.8 | 28.4 | 9.1 |
| AD-569508.1 | 73.6 | 5.9 | 75.0 | 32.4 | 67.4 | 19.5 | 3.4 | 1.7 | 18.4 | 8.3 | 29.8 | 7.2 |
| AD-569509.1 | 79.2 | 15.0 | 82.9 | 8.6 | 94.8 | 13.2 | 3.5 | 1.8 | 25.8 | 5.2 | 46.5 | 10.2 |
| AD-569510.1 | 45.4 | 7.4 | 71.9 | 2.9 | 81.1 | 11.8 | 2.7 | 2.0 | 8.7 | 2.4 | 18.0 | 9.9 |
| AD-569511.1 | 34.1 | 5.6 | 57.9 | 14.2 | 68.6 | 5.4 | 1.5 | 0.5 | 7.0 | 1.1 | 17.7 | 10.2 |
| AD-569512.1 | 70.5 | 7.9 | 111.5 | 7.4 | 76.4 | 16.4 | 5.0 | 3.8 | 28.3 | 9.7 | 41.2 | 14.0 |
| AD-569513.1 | 80.0 | 16.1 | 107.8 | 19.0 | 91.3 | 20.3 | 2.5 | 1.2 | 19.0 | 2.1 | 26.7 | 6.5 |
| AD-569514.1 | 28.4 | 2.5 | 62.9 | 23.9 | 70.8 | 11.9 | 1.2 | 0.3 | 4.6 | 0.6 | 11.3 | 4.7 |
| AD-569515.1 | 58.7 | 6.4 | 61.8 | 22.7 | 55.2 | 12.0 | 3.2 | 0.5 | 19.8 | 5.7 | 20.3 | 12.6 |
| AD-569516.1 | 71.0 | 5.5 | 111.5 | 19.0 | 91.1 | 1.4 | 3.8 | 0.7 | 37.2 | 7.1 | 51.3 | 26.2 |
| AD-569517.1 | 95.4 | 12.9 | 78.1 | 11.7 | 96.7 | 11.1 | 2.2 | 0.7 | 13.2 | 4.5 | 27.1 | 11.8 |
| AD-569518.1 | 97.2 | 6.6 | 97.2 | 9.3 | 116.1 | 12.5 | 12.6 | 2.4 | 61.1 | 33.7 | 76.4 | 34.0 |
| AD-569519.1 | 87.1 | 8.9 | 103.7 | 29.5 | 80.8 | 10.0 | 6.5 | 0.6 | 58.8 | 20.8 | 40.1 | 16.2 |
| AD-569520.1 | 75.5 | 4.0 | 100.6 | 15.9 | 99.5 | 26.2 | 2.5 | 0.3 | 32.0 | 5.6 | 33.2 | 1.1 |
| AD-569565.1 | 67.9 | 9.9 | 79.4 | 11.1 | 97.4 | 6.2 | 2.1 | 0.4 | 13.8 | 1.1 | 21.7 | 6.1 |
| AD-569567.1 | 61.8 | 9.3 | 83.3 | 25.9 | 84.9 | 10.5 | 1.7 | 0.6 | 11.6 | 2.3 | 18.1 | 4.8 |
| AD-570126.1 | 107.5 | 16.9 | 63.4 | 12.9 | 98.8 | 30.6 | 32.2 | 16.0 | 50.1 | 8.7 | 34.6 | 6.2 |
| AD-570127.1 | 52.2 | 1.4 | 69.2 | 15.8 | 69.8 | 10.8 | 3.9 | 1.2 | 6.1 | 2.1 | 19.5 | 1.8 |
| AD-570128.1 | 104.2 | 17.0 | 78.4 | 4.4 | 92.9 | 27.3 | 6.8 | 1.4 | 38.1 | 12.8 | 44.3 | 20.2 |
| AD-570129.1 | 113.3 | 18.9 | 71.3 | 15.9 | 96.7 | 15.0 | 23.1 | 8.1 | 50.8 | 18.9 | 36.5 | 7.8 |
| AD-570131.1 | 75.6 | 14.5 | 81.3 | 14.8 | 101.2 | 16.5 | 2.7 | 1.1 | 15.0 | 4.7 | 35.5 | 10.0 |
| AD-570135.1 | 69.5 | 9.8 | 64.6 | 22.3 | 78.9 | 7.7 | 1.6 | 0.7 | 12.1 | 2.2 | 20.1 | 3.1 |
| AD-570136.1 | 52.8 | 8.4 | 66.2 | 16.4 | 73.4 | 4.9 | 1.3 | 0.3 | 6.5 | 0.9 | 9.0 | 2.8 |

Transfection (TX)
*Free Uptake (FU)

TABLE 26

C3 Single Dose Screens in PCH cells (% C3 mRNA Remaining)

| Duplex | FU* 500 nM | SD | FU* 100 nM | SD | FU* 10 nM | SD | TX# 10 nM | SD | TX# 1 nM | SD | TX# 0.1 nM | SD |
|---|---|---|---|---|---|---|---|---|---|---|---|---|
| AD-571535.1 | 79.2 | 8.9 | 83.4 | 10.0 | 87.7 | 29.6 | 75.7 | 29.2 | N/A | N/A | 93.9 | 19.1 |
| AD-571536.1 | 50.2 | 6.5 | 45.0 | 7.5 | 102.8 | 25.6 | 93.4 | 16.8 | 54.5 | 29.7 | 51.2 | 12.9 |
| AD-571537.1 | 46.4 | 4.9 | 42.1 | 6.8 | 93.3 | 14.1 | 96.6 | 21.5 | 85.3 | 7.5 | 44.9 | 5.7 |
| AD-571538.1 | 80.6 | 7.4 | 74.1 | 8.0 | 173.4 | 51.1 | 108.2 | 24.0 | 73.1 | 84.9 | 153.3 | 19.0 |
| AD-571540.1 | 68.4 | 12.7 | 64.3 | 13.5 | 132.7 | 35.0 | 150.0 | 51.9 | 54.2 | 26.0 | 100.2 | 7.2 |
| AD-571541.1 | 108.6 | 25.7 | 80.9 | 5.1 | 165.1 | 38.3 | 147.7 | 16.4 | 84.8 | 12.8 | 147.1 | 47.6 |
| AD-571542.1 | 49.1 | 6.4 | 48.0 | 4.8 | 144.1 | 46.2 | 193.0 | 127.6 | 36.5 | 14.3 | 35.0 | 10.0 |
| AD-571543.1 | 55.7 | 10.2 | 52.3 | 7.0 | 127.5 | 43.5 | 126.3 | 46.9 | 47.3 | 39.6 | 69.1 | 24.3 |
| AD-571544.1 | 74.3 | 14.1 | 49.0 | 8.7 | 82.0 | 36.5 | 76.2 | 16.3 | 9.3 | 8.5 | 78.5 | 21.1 |
| AD-571545.1 | 82.3 | 4.9 | 77.4 | 7.5 | 104.5 | 24.5 | 96.7 | 8.3 | 96.3 | 7.1 | 105.6 | 15.8 |
| AD-571546.1 | 64.4 | 25.3 | 53.0 | 3.0 | 72.0 | 11.8 | 100.3 | 14.5 | 88.4 | 9.5 | 46.3 | 5.5 |
| AD-571547.1 | 36.9 | 7.7 | 39.6 | 3.8 | 72.4 | 18.0 | 131.2 | 32.1 | 124.1 | 75.5 | 20.5 | 4.3 |
| AD-571548.1 | 56.8 | 17.3 | 64.6 | 8.3 | 80.8 | 16.9 | 125.7 | 6.9 | 131.3 | 154.6 | 40.6 | 7.3 |
| AD-571549.1 | 114.2 | 26.2 | 99.2 | 19.1 | 110.3 | 33.9 | 119.0 | 16.3 | 211.2 | 74.0 | 127.6 | 34.8 |
| AD-571550.1 | 69.9 | 4.8 | 68.2 | 16.3 | 92.9 | 23.8 | 142.0 | 32.5 | 43.0 | 8.2 | 90.4 | 22.0 |
| AD-571551.1 | 89.0 | 32.8 | 71.7 | 7.7 | 130.0 | 30.4 | 150.4 | 30.2 | 49.6 | 45.5 | 148.0 | 5.7 |
| AD-571552.1 | 82.3 | 18.6 | 75.0 | 13.8 | 109.0 | 32.1 | 82.3 | 14.4 | 29.8 | 18.3 | 68.9 | 17.2 |
| AD-571553.1 | 41.5 | 4.2 | 55.0 | 1.2 | 72.9 | 18.3 | 96.2 | 9.5 | 42.3 | 13.3 | 18.2 | 6.4 |
| AD-571554.1 | 74.0 | 12.6 | 64.1 | 7.6 | 98.7 | 9.4 | 111.4 | 7.3 | 92.2 | 42.0 | 58.1 | 12.7 |

TABLE 26-continued

C3 Single Dose Screens in PCH cells (% C3 mRNA Remaining)

| Duplex | FU* 500 nM | SD | FU* 100 nM | SD | FU* 10 nM | SD | TX# 10 nM | SD | TX# 1 nM | SD | TX# 0.1 nM | SD |
|---|---|---|---|---|---|---|---|---|---|---|---|---|
| AD-571555.1 | 86.5 | 16.5 | 96.8 | 12.5 | 108.8 | 14.1 | 107.4 | 6.5 | 67.0 | 38.0 | 135.9 | 16.3 |
| AD-571556.1 | 75.4 | 19.7 | 88.5 | 4.4 | 106.0 | 18.6 | 119.6 | 14.9 | 58.4 | 35.2 | 111.8 | 9.0 |
| AD-571557.1 | 59.8 | 12.1 | 66.8 | 4.9 | 80.8 | 4.1 | 148.8 | 44.8 | 68.7 | 20.8 | 19.0 | 3.5 |
| AD-571558.1 | 73.3 | 24.1 | 62.1 | 6.0 | 107.7 | 33.0 | 111.8 | 11.6 | 125.1 | 33.4 | 59.4 | 12.2 |
| AD-571559.1 | 91.2 | 14.0 | 80.5 | 21.3 | 104.5 | 22.1 | 87.6 | 13.4 | 28.2 | 11.4 | 44.8 | 4.7 |
| AD-571560.1 | 48.0 | 12.4 | 66.6 | 4.4 | 86.5 | 11.9 | 122.6 | 4.1 | 39.6 | 30.5 | 27.0 | 8.6 |
| AD-571711.1 | 102.2 | 11.3 | 112.9 | 16.7 | 112.1 | 9.8 | 108.7 | 6.3 | 125.7 | 93.2 | 117.4 | 21.6 |
| AD-571712.1 | 96.4 | 11.0 | 89.8 | 9.8 | 105.2 | 11.4 | 97.5 | 21.2 | 87.5 | 46.2 | 113.7 | 28.1 |
| AD-571713.1 | 55.7 | 7.5 | 69.0 | 5.1 | 104.6 | 28.1 | 128.9 | 18.2 | 109.0 | 25.8 | 89.4 | 14.2 |
| AD-571714.1 | 68.3 | 9.5 | 68.2 | 8.8 | 94.1 | 5.6 | 123.6 | 24.1 | 84.7 | 57.5 | 105.8 | 14.3 |
| AD-571716.1 | 96.0 | 11.1 | 60.0 | 11.5 | 87.8 | 14.7 | 101.3 | 21.8 | 55.5 | 12.2 | 113.2 | 8.7 |
| AD-571717.1 | 74.9 | 15.5 | 62.8 | 6.9 | 103.5 | 32.1 | 95.4 | 22.2 | 43.8 | 19.7 | 33.6 | 5.2 |
| AD-571718.1 | 27.4 | 4.1 | 45.5 | 6.3 | 71.8 | 15.2 | 204.5 | 82.6 | 84.7 | 133.8 | 19.8 | 4.5 |
| AD-571719.2 | 31.9 | 3.6 | 57.1 | 6.2 | 98.9 | 29.4 | 171.1 | 37.0 | 109.2 | 130.1 | 32.1 | 3.8 |
| AD-571720.1 | 67.0 | 4.8 | 77.0 | 11.4 | 95.1 | 11.1 | 193.3 | 61.4 | 19.7 | 8.0 | 40.3 | 11.4 |
| AD-571721.1 | 35.8 | 6.7 | 48.2 | 5.6 | 79.0 | 10.6 | 130.7 | 34.1 | 32.2 | 17.1 | 21.2 | 9.6 |
| AD-571722.1 | 22.2 | 4.7 | 35.1 | 5.5 | 84.9 | 15.3 | 150.9 | 72.0 | 125.1 | 103.5 | 24.1 | 13.8 |
| AD-571723.1 | 49.0 | 12.1 | 64.9 | 8.0 | 97.4 | 16.1 | 234.7 | 140.7 | 124.5 | 47.1 | 67.2 | 16.2 |
| AD-571742.1 | 106.4 | 2.6 | 87.8 | 17.6 | 113.3 | 31.5 | 168.2 | 79.2 | 42.5 | 13.9 | 209.9 | 24.0 |
| AD-571743.1 | 89.9 | 17.3 | 104.8 | 27.6 | 112.3 | 54.1 | 81.0 | 20.6 | 64.9 | 17.6 | 40.0 | 11.7 |
| AD-571744.1 | 88.1 | 18.2 | 106.7 | 9.7 | 133.8 | 56.9 | 121.1 | 19.3 | 61.0 | 20.5 | 46.8 | 15.5 |
| AD-571745.1 | 66.1 | 15.6 | 96.2 | 14.4 | 99.6 | 5.0 | 100.0 | 12.8 | N/A | N/A | 64.5 | 14.6 |
| AD-571746.1 | 114.5 | 25.5 | 120.1 | 14.6 | 136.5 | 31.4 | 91.8 | 3.7 | 83.6 | 48.4 | 82.3 | 7.2 |
| AD-571747.1 | 82.6 | 11.3 | 89.6 | 8.3 | 109.5 | 13.0 | 76.7 | 37.8 | 40.0 | 23.5 | 75.0 | 19.0 |
| AD-571748.1 | 30.2 | 5.5 | 57.5 | 7.4 | 87.7 | 11.5 | 108.5 | 19.3 | 48.0 | 14.2 | 31.3 | 6.0 |
| AD-571749.1 | 29.6 | 3.2 | 55.3 | 5.8 | 79.1 | 8.4 | 106.2 | 8.9 | 22.3 | 18.9 | 28.5 | 3.3 |
| AD-571750.1 | 107.4 | 11.5 | 95.7 | 21.2 | 115.5 | 52.4 | 86.1 | 22.2 | N/A | N/A | 39.6 | 10.7 |
| AD-571751.1 | 81.4 | 12.8 | 101.6 | 13.1 | 101.4 | 11.0 | 102.5 | 17.3 | 25.4 | 24.7 | 44.0 | 4.7 |
| AD-571753.2 | 36.4 | 9.3 | 52.6 | 6.3 | 85.8 | 7.0 | 102.8 | 18.4 | 85.5 | 34.7 | 31.5 | 7.0 |
| AD-571755.1 | 81.5 | 21.0 | 91.3 | 8.0 | 111.7 | 18.1 | 103.3 | 15.1 | 43.2 | 30.7 | 73.7 | 8.6 |
| AD-571756.1 | 98.2 | 14.2 | 106.6 | 37.5 | 116.4 | 17.5 | 101.3 | 13.4 | 126.1 | 55.2 | 78.7 | 24.4 |
| AD-571757.1 | 64.3 | 5.7 | 75.7 | 10.9 | 105.9 | 17.9 | 115.5 | 29.6 | 39.9 | 25.2 | 63.0 | 11.8 |
| AD-571758.1 | 90.3 | 11.1 | 93.6 | 11.9 | 114.7 | 44.8 | 108.9 | 23.8 | 34.5 | 18.4 | 109.3 | 16.6 |
| AD-571759.1 | 49.6 | 9.8 | 42.9 | 5.8 | 69.8 | 7.8 | 89.0 | 14.9 | 67.4 | 23.9 | 52.3 | 20.2 |
| AD-571760.1 | 63.3 | 4.7 | 72.5 | 7.0 | 91.4 | 37.3 | 82.2 | 22.6 | 33.7 | 15.1 | 18.5 | 8.6 |
| AD-571761.1 | 54.1 | 3.5 | 70.9 | 8.7 | 82.3 | 14.6 | 126.3 | 20.6 | 15.2 | 4.0 | 25.6 | 4.9 |
| AD-571762.1 | 37.2 | 3.9 | 63.6 | 7.8 | 74.1 | 6.0 | 116.4 | 18.3 | 98.1 | 34.9 | 28.3 | 4.3 |
| AD-571763.1 | 33.8 | 8.0 | 50.1 | 6.5 | 78.7 | 8.3 | 121.9 | 21.4 | 80.6 | 62.4 | 24.4 | 7.6 |
| AD-571764.1 | 62.0 | 20.4 | 71.3 | 3.2 | 105.0 | 36.9 | 117.6 | 8.9 | 67.5 | 36.9 | 30.3 | 5.8 |
| AD-571765.2 | 84.7 | 10.7 | 92.0 | 14.3 | 110.0 | 7.1 | 122.2 | 6.2 | 146.0 | 113.7 | 97.8 | 21.9 |
| AD-571766.2 | 65.4 | 11.3 | 73.5 | 22.0 | 101.6 | 13.3 | 116.5 | 12.8 | 71.3 | 81.4 | 78.4 | 22.0 |
| AD-571767.2 | 80.6 | 19.5 | 58.1 | 5.9 | 91.0 | 20.8 | 97.1 | 17.0 | 143.9 | 83.0 | 88.8 | 7.8 |
| AD-572383.1 | 69.2 | 18.0 | 79.1 | 2.6 | 80.9 | 5.6 | 102.5 | 11.1 | 109.1 | 34.7 | 53.3 | 11.5 |
| AD-572384.1 | 78.1 | 11.3 | 97.5 | 10.8 | 121.5 | 8.4 | 107.2 | 6.5 | 115.5 | 3.4 | 64.8 | 15.5 |
| AD-572385.1 | 79.2 | 9.2 | 94.8 | 12.5 | 92.7 | 10.4 | 104.3 | 14.6 | 79.5 | 27.8 | 64.5 | 5.6 |
| AD-572386.1 | 41.7 | 3.6 | 66.6 | 4.8 | 92.1 | 27.8 | 99.9 | 22.9 | 68.5 | 1.7 | 35.4 | 14.3 |
| AD-572387.4 | 86.4 | 3.0 | 70.1 | 8.1 | 77.8 | 10.0 | 80.3 | 10.7 | 66.2 | 82.6 | 119.9 | 17.8 |
| AD-572391.1 | 90.7 | 19.3 | 91.9 | 10.5 | 125.7 | 28.0 | 86.0 | 29.4 | 44.2 | 19.6 | 113.0 | 11.7 |
| AD-572392.1 | 66.1 | 13.5 | 72.3 | 8.9 | 88.7 | 7.6 | 134.5 | 36.2 | N/A | N/A | 46.4 | 8.8 |
| AD-572393.2 | 99.8 | 13.6 | 97.1 | 20.3 | 100.0 | 19.3 | 116.0 | 19.1 | 152.6 | 108.7 | 56.7 | 8.0 |
| AD-572394.1 | 102.9 | 8.9 | 111.1 | 22.1 | 108.6 | 22.1 | 125.6 | 14.9 | 48.1 | 26.4 | 61.8 | 17.7 |
| AD-572395.1 | 109.6 | 18.9 | 102.9 | 11.9 | 115.5 | 19.1 | 118.0 | 18.8 | 47.0 | 21.9 | 82.3 | 14.6 |
| AD-572396.1 | 98.1 | 14.9 | 104.2 | 7.7 | 118.3 | 27.5 | 166.3 | 106.9 | 23.7 | 10.1 | 82.7 | 32.0 |
| AD-572397.1 | 109.3 | 5.7 | 80.3 | 8.7 | 123.0 | 28.6 | 108.7 | 10.6 | 51.6 | 22.6 | 125.3 | 27.3 |
| AD-572495.1 | 25.9 | 4.5 | 28.9 | 4.6 | 97.7 | 48.0 | 87.7 | 39.7 | 39.4 | 17.6 | 10.0 | 3.9 |
| AD-572569.1 | 117.7 | 31.0 | 100.9 | 13.4 | 110.9 | 26.1 | 124.2 | 16.5 | N/A | N/A | 85.4 | 24.5 |
| AD-572570.1 | 43.8 | 6.6 | 58.0 | 6.6 | 95.9 | 24.3 | 100.3 | 10.5 | 34.6 | 9.2 | 37.7 | 6.1 |
| AD-572571.1 | 60.3 | 8.7 | 74.0 | 15.7 | 98.9 | 28.9 | 116.1 | 17.2 | 119.1 | 100.7 | 42.0 | 5.8 |
| AD-572572.1 | 81.3 | 15.5 | 83.3 | 11.3 | 96.8 | 22.9 | 95.5 | 3.1 | 76.9 | 37.2 | 36.2 | 10.7 |
| AD-572573.1 | 70.2 | 22.3 | 72.2 | 23.1 | 66.0 | 17.5 | 127.1 | 29.9 | 315.6 | 73.6 | 26.9 | 4.7 |
| AD-572574.1 | 93.8 | 13.6 | 90.6 | 15.0 | 129.2 | 56.9 | 100.7 | 9.3 | 10.8 | 13.7 | 86.0 | 20.5 |
| AD-572575.1 | 66.5 | 17.4 | 64.7 | 14.9 | 105.6 | 30.1 | 88.4 | 9.8 | 34.1 | 7.8 | 68.3 | 20.7 |
| AD-572576.1 | 88.0 | 5.2 | 103.4 | 33.5 | 100.7 | 41.7 | 94.6 | 65.2 | 70.8 | 25.4 | 112.6 | 46.5 |
| AD-572577.1 | 118.6 | 27.9 | 111.9 | 17.0 | 176.5 | 84.7 | 140.6 | 28.6 | 36.2 | 12.9 | 114.4 | 15.3 |
| AD-572580.1 | 90.9 | 61.5 | 97.7 | 16.0 | 127.3 | 36.4 | 123.8 | 16.6 | N/A | N/A | 121.6 | 46.9 |
| AD-572581.1 | 77.3 | 11.5 | 80.4 | 14.9 | 143.2 | 51.4 | 109.6 | 21.3 | 150.2 | 107.7 | 87.8 | 19.7 |

Transfection (TX)
*Free Uptake (FU)

TABLE 27

C3 Single Dose Screens in PCH cells (% C3 mRNA Remaining)

| Duplex | FU* 500 nM | ST DEV | FU* 100 nM | ST DEV | FU* 10 nM | ST DEV | TX# 50 nM | ST DEV | TX# 10 nM | ST DEV | TX# 1 nM | ST DEV | TX# 0.1 nM | ST DEV |
|---|---|---|---|---|---|---|---|---|---|---|---|---|---|---|
| AD-564723.1 | 51.6 | 21.2 | 52.2 | 24.7 | 82.7 | 58.9 | 19.8 | 3.8 | 13.3 | 6.8 | 55.8 | 24.0 | 145.8 | 88.9 |
| AD-564724.1 | 64.3 | 13.1 | 102.9 | 30.8 | 106.6 | 31.7 | 4.7 | 1.6 | 3.8 | 0.8 | 37.8 | 14.9 | 101.9 | 13.1 |
| AD-1069838.1 | 110.5 | 19.4 | 94.8 | 13.3 | 139.4 | 65.9 | 36.0 | 6.5 | 16.8 | 5.9 | 87.5 | 3.5 | 106.5 | 9.7 |
| AD-564726.1 | 140.5 | 42.4 | 129.4 | 77.4 | 127.2 | 10.8 | 14.9 | 1.8 | 13.6 | 3.9 | 84.2 | 6.7 | 75.9 | 12.4 |
| AD-564727.3 | 120.7 | 43.2 | 149.1 | 107.3 | 158.0 | 46.3 | 8.1 | 1.2 | 7.1 | 2.4 | 65.8 | 20.3 | 79.0 | 14.1 |
| AD-1069839.1 | 180.1 | 78.3 | 132.6 | 50.8 | 184.9 | 59.0 | 4.9 | 0.5 | 3.3 | 0.9 | 58.6 | 20.4 | 80.6 | 19.7 |
| AD-1069840.1 | 122.7 | 26.8 | 164.0 | 78.4 | 181.7 | 52.7 | 23.8 | 6.3 | 13.6 | 6.7 | 65.0 | 20.5 | 77.4 | 17.2 |
| AD-564730.3 | 64.5 | 14.5 | 151.1 | 55.1 | 214.4 | 86.6 | 0.7 | 0.1 | 1.0 | 0.4 | 7.5 | 4.5 | 32.0 | 12.6 |
| AD-1069841.1 | 42.9 | 16.9 | 69.8 | 8.1 | 88.1 | 15.0 | 13.3 | 2.6 | 11.0 | 3.3 | 51.6 | 7.1 | 106.5 | 40.2 |
| AD-564732.1 | 78.1 | 14.9 | 95.4 | 37.1 | 62.7 | 17.3 | 65.1 | 30.7 | 20.7 | 4.4 | 66.3 | 15.5 | 97.0 | 11.7 |
| AD-1069842.1 | 63.4 | 21.5 | 91.6 | 20.6 | 81.5 | 16.9 | 0.7 | 0.1 | 0.4 | 0.1 | 1.5 | 0.2 | 44.1 | 9.6 |
| AD-564734.1 | 49.7 | 12.5 | 97.1 | 38.6 | 91.8 | 31.4 | 1.1 | 0.1 | 0.5 | 0.1 | 1.2 | 0.4 | 21.5 | 5.8 |
| AD-1069843.1 | 82.1 | 28.8 | 127.2 | 41.0 | 107.0 | 27.5 | 34.9 | 0.7 | 20.3 | 8.2 | 85.7 | 3.7 | 73.9 | 3.3 |
| AD-564736.1 | 87.0 | 16.4 | 129.9 | 37.8 | 148.5 | 23.6 | 11.5 | 2.8 | 6.0 | 1.0 | 39.5 | 3.0 | 77.0 | 14.0 |
| AD-1069844.1 | 97.3 | 70.9 | 156.6 | 63.5 | 143.4 | 46.3 | 1.1 | 0.1 | 0.6 | 0.1 | 2.1 | 0.6 | 36.8 | 5.5 |
| AD-564738.1 | 79.8 | 49.6 | 189.2 | 57.4 | 212.1 | 52.0 | 1.1 | 0.2 | 0.8 | 0.2 | 8.9 | 2.9 | 70.8 | 60.8 |
| AD-564739.2 | 62.4 | 27.8 | 67.3 | 11.7 | 67.1 | 20.4 | 3.5 | 0.6 | 1.9 | 0.2 | 3.2 | 0.9 | 77.4 | 13.2 |
| AD-1069845.1 | 70.0 | 20.9 | 64.7 | 26.4 | 64.1 | 7.2 | 21.2 | 3.8 | 5.8 | 0.8 | 7.3 | 4.0 | 51.0 | 18.4 |
| AD-564741.1 | 85.4 | 11.3 | 89.6 | 43.6 | 86.3 | 8.4 | 0.9 | 0.1 | 0.8 | 0.1 | 1.8 | 0.7 | 23.8 | 4.6 |
| AD-1069846.1 | 70.5 | 6.6 | 85.3 | 12.3 | 92.7 | 16.2 | 0.9 | 0.2 | 1.6 | 2.0 | 1.3 | 0.4 | 16.7 | 3.5 |
| AD-1069847.1 | 84.0 | 44.2 | 111.8 | 39.6 | 144.2 | 32.3 | 1.2 | 0.1 | 0.7 | 0.1 | 1.8 | 0.4 | 25.7 | 7.4 |
| AD-564745.3 | 71.6 | 22.1 | 149.7 | 16.0 | 156.5 | 39.8 | 1.2 | 0.3 | 0.6 | 0.1 | 4.5 | 1.2 | 44.0 | 50.1 |
| AD-564747.1 | 77.1 | 23.0 | 124.9 | 26.7 | 206.1 | 63.9 | 3.1 | 1.3 | 4.0 | 4.1 | 45.7 | 7.9 | 89.9 | 90.8 |
| AD-1069850.1 | 116.0 | 12.9 | 117.3 | 51.4 | 88.8 | 18.0 | 77.9 | 32.4 | 65.4 | 15.5 | 82.9 | 7.4 | 116.3 | 11.0 |
| AD-1069851.1 | 175.9 | 87.7 | 110.6 | 28.8 | 90.1 | 14.4 | 46.4 | 8.7 | 41.5 | 2.1 | 84.6 | 10.7 | 91.5 | 6.8 |
| AD-1069852.1 | 83.9 | 29.4 | 142.7 | 54.9 | 114.9 | 23.9 | 6.1 | 1.4 | 6.3 | 1.5 | 58.8 | 7.1 | 96.5 | 11.4 |
| AD-1069853.1 | 65.5 | 34.3 | 212.8 | 66.4 | 154.0 | 24.8 | 1.0 | 0.2 | 0.6 | 0.1 | 4.5 | 1.1 | 99.0 | 73.4 |
| AD-564925.1 | 67.1 | 31.9 | 182.9 | 26.2 | 233.5 | 65.7 | 1.6 | 0.2 | 1.2 | 0.2 | 8.9 | 2.6 | 18.6 | 20.2 |
| AD-1069854.1 | 55.6 | 27.1 | 57.9 | 35.7 | 53.7 | 38.2 | 1.7 | 0.2 | 1.6 | 0.5 | 3.7 | 0.8 | 53.5 | 21.8 |
| AD-1069855.1 | 90.1 | 28.9 | 50.4 | 25.9 | 43.8 | 20.2 | 1.7 | 0.6 | 0.8 | 0.4 | 2.4 | 1.2 | 48.6 | 9.8 |
| AD-1069856.1 | 119.0 | 43.7 | 63.1 | 15.4 | 56.3 | 8.3 | 3.9 | 0.7 | 2.3 | 1.2 | 4.9 | 0.2 | 83.1 | 13.8 |
| AD-564929.1 | 133.2 | 31.0 | 94.5 | 48.8 | 68.6 | 12.6 | 54.0 | 5.6 | 45.9 | 13.3 | 60.8 | 5.7 | 95.0 | 15.0 |
| AD-564930.1 | 137.8 | 39.7 | 112.8 | 11.8 | 80.8 | 10.0 | 94.4 | 46.1 | 43.2 | 9.3 | 72.4 | 7.3 | 105.3 | 19.5 |
| AD-1069857.1 | 121.1 | 54.4 | 95.7 | 11.2 | 105.7 | 19.4 | 1.5 | 0.5 | 1.0 | 0.2 | 10.2 | 0.7 | 83.6 | 14.4 |
| AD-564934.1 | 80.9 | 25.7 | 201.1 | 71.7 | 125.8 | 11.0 | 131.0 | 76.5 | 84.2 | 30.5 | 89.7 | 9.5 | 118.2 | 8.5 |
| AD-1069858.1 | 110.6 | 55.7 | 138.5 | 63.5 | 166.6 | 26.4 | 30.6 | 5.0 | 44.7 | 21.2 | 102.6 | 13.1 | 81.0 | 21.4 |
| AD-564936.1 | 109.6 | 55.7 | 53.8 | 16.1 | 47.5 | 8.5 | 34.0 | 7.1 | 72.7 | 35.1 | 67.1 | 18.7 | 95.8 | 17.7 |
| AD-564937.1 | 89.3 | 54.3 | 78.9 | 23.9 | 44.1 | 9.4 | 23.4 | 6.2 | 24.8 | 6.1 | 29.4 | 10.4 | 87.0 | 50.7 |
| AD-564938.1 | 114.2 | 28.9 | 119.7 | 94.1 | 77.4 | 15.3 | 116.8 | 48.7 | 117.9 | 12.2 | 88.9 | 11.7 | 105.9 | 12.7 |
| AD-1069859.1 | 97.0 | 22.5 | 88.1 | 39.6 | 106.7 | 55.0 | 31.3 | 5.8 | 36.9 | 7.4 | 70.7 | 2.9 | 99.2 | 18.2 |
| AD-564941.1 | 138.1 | 75.5 | 126.7 | 72.8 | 145.6 | 50.3 | 195.8 | 40.5 | 140.9 | 3.1 | 93.0 | 18.7 | 109.2 | 13.3 |
| AD-1069860.1 | 143.9 | 45.8 | 146.3 | 62.2 | 141.7 | 35.7 | 128.5 | 73.3 | 118.5 | 12.8 | 110.3 | 13.5 | 112.8 | 36.5 |
| AD-564943.1 | 107.4 | 92.7 | 50.2 | 20.1 | 47.1 | 14.3 | 15.1 | 1.0 | 19.9 | 9.7 | 21.4 | 7.6 | 85.5 | 7.1 |
| AD-1069861.1 | 64.0 | 39.2 | 53.1 | 17.6 | 54.1 | 14.5 | 0.6 | 0.1 | 0.5 | 0.3 | 0.4 | 0.0 | 3.6 | 1.1 |
| AD-565031.1 | 60.7 | 8.6 | 105.7 | 48.3 | 46.9 | 10.6 | 0.8 | 0.1 | 0.5 | 0.1 | 1.0 | 0.1 | 5.3 | 0.4 |
| AD-565032.1 | 75.1 | 14.1 | 82.6 | 21.7 | 81.2 | 9.9 | 0.9 | 0.2 | 0.7 | 0.0 | 0.6 | 0.1 | 4.7 | 0.8 |
| AD-1069862.1 | 59.8 | 15.1 | 93.2 | 15.2 | 84.4 | 9.4 | 0.8 | 0.1 | 0.9 | 0.1 | 0.9 | 0.1 | 7.6 | 0.9 |
| AD-565034.1 | 38.2 | 10.1 | 65.7 | 22.4 | 76.9 | 7.8 | 0.7 | 0.1 | 0.6 | 0.2 | 0.8 | 0.2 | 5.2 | 0.6 |
| AD-565035.1 | 30.8 | 5.7 | 88.6 | 16.3 | 96.5 | 23.9 | 0.7 | 0.1 | 0.7 | 0.3 | 0.6 | 0.1 | 3.2 | 0.6 |
| AD-1069863.1 | 52.4 | 25.9 | 123.5 | 69.8 | 186.4 | 61.0 | 0.8 | 0.1 | 0.5 | 0.1 | 0.8 | 0.1 | 4.0 | 1.0 |
| AD-565037.1 | 59.2 | 54.4 | 43.7 | 13.3 | 43.0 | 14.5 | 0.6 | 0.2 | 0.4 | 0.1 | 0.6 | 0.1 | 3.7 | 0.5 |
| AD-565038.1 | 153.3 | 95.6 | 77.3 | 27.8 | 44.4 | 28.3 | 0.8 | 0.3 | 1.0 | 0.4 | 0.7 | 0.1 | 16.7 | 3.5 |
| AD-1069864.1 | 78.0 | 26.5 | 64.1 | 38.5 | 44.9 | 8.1 | 2.5 | 0.3 | 1.2 | 0.2 | 1.6 | 0.3 | 34.8 | 14.1 |
| AD-565041.1 | 147.5 | 44.2 | 89.8 | 25.9 | 67.7 | 20.2 | 7.5 | 2.2 | 10.5 | 2.5 | 29.8 | 9.7 | 80.3 | 10.7 |
| AD-565042.1 | 119.3 | 51.9 | 106.0 | 40.0 | 81.9 | 31.9 | 26.3 | 7.5 | 31.8 | 6.1 | 54.7 | 9.5 | 93.3 | 20.9 |
| AD-565043.1 | 118.8 | 19.8 | 96.4 | 24.0 | 131.5 | 60.2 | 78.8 | 26.5 | 92.7 | 13.0 | 102.3 | 6.5 | 106.2 | 15.4 |
| AD-565044.1 | 138.1 | 65.0 | 120.5 | 55.1 | 94.7 | 29.2 | 140.6 | 35.1 | 106.6 | 7.4 | 113.1 | 16.4 | 119.9 | 37.6 |
| AD-1069865.1 | 87.9 | 34.7 | 113.0 | 52.7 | 131.1 | 51.4 | 12.3 | 2.4 | 5.2 | 1.0 | 13.0 | 3.3 | 64.8 | 12.8 |
| AD-1069866.1 | 100.3 | 23.2 | 51.0 | 11.4 | 69.9 | 25.1 | 95.0 | 58.7 | 150.1 | 16.7 | 105.2 | 7.5 | 100.4 | 27.0 |
| AD-565047.1 | 89.4 | 30.3 | 75.5 | 13.4 | 92.8 | 29.8 | 146.5 | 50.0 | 165.3 | 20.7 | 96.5 | 10.3 | 119.5 | 19.8 |
| AD-1069867.1 | 126.4 | 38.6 | 110.7 | 9.7 | 171.0 | 14.9 | 160.8 | 60.1 | 169.2 | 14.9 | 98.3 | 17.6 | 113.7 | 14.8 |
| AD-565049.1 | 111.7 | 35.4 | 105.5 | 27.0 | 111.3 | 37.3 | 138.2 | 50.8 | 171.1 | 6.9 | 108.4 | 3.8 | 118.0 | 20.3 |
| AD-565050.1 | 96.4 | 61.5 | 125.6 | 39.4 | 116.9 | 30.8 | 180.9 | 55.9 | 175.6 | 27.4 | 119.2 | 11.4 | 118.1 | 22.6 |
| AD-565274.1 | 137.1 | 70.3 | 152.5 | 59.8 | 109.4 | 23.5 | 69.4 | 11.7 | 127.5 | 16.0 | 119.2 | 8.1 | 99.4 | 30.3 |
| AD-565275.1 | 75.7 | 54.5 | 120.0 | 28.2 | 130.7 | 33.6 | 3.5 | 1.2 | 5.4 | 0.4 | 57.3 | 16.0 | 65.7 | 16.7 |
| AD-1069868.1 | 105.4 | 79.2 | 77.0 | 29.7 | 50.2 | 19.7 | 3.5 | 1.2 | 2.5 | 0.1 | 12.0 | 3.7 | 103.7 | 9.2 |
| AD-1069869.1 | 89.0 | 37.8 | 75.5 | 25.4 | 65.4 | 11.9 | 14.4 | 2.9 | 19.2 | 6.0 | 53.6 | 16.1 | 106.2 | 24.4 |
| AD-565278.2 | 94.1 | 35.2 | 67.6 | 13.4 | 68.7 | 19.4 | 1.9 | 0.4 | 2.4 | 0.8 | 11.6 | 2.5 | 94.1 | 23.0 |
| AD-1069870.1 | 66.1 | 37.2 | 61.6 | 1.6 | 70.4 | 9.1 | 0.8 | 0.2 | 0.8 | 0.4 | 1.8 | 0.4 | 28.6 | 4.3 |
| AD-565280.1 | 71.8 | 21.2 | 88.2 | 40.0 | 165.3 | 112.7 | 56.9 | 25.4 | 54.1 | 15.8 | 80.2 | 7.7 | 114.3 | 18.0 |
| AD-565281.3 | 49.5 | 22.2 | 79.9 | 24.8 | 79.9 | 16.7 | 5.9 | 2.0 | 3.6 | 0.5 | 9.9 | 2.7 | 74.0 | 8.1 |
| AD-1069871.1 | 52.4 | 11.2 | 83.9 | 36.5 | 108.4 | 22.2 | 2.1 | 0.3 | 1.1 | 0.3 | 2.4 | 0.3 | 18.3 | 1.0 |
| AD-565283.1 | 37.3 | 16.7 | 131.6 | 39.1 | 173.4 | 121.6 | 1.2 | 0.2 | 1.8 | 0.2 | 7.5 | 2.2 | 70.8 | 30.9 |
| AD-1069872.1 | 80.4 | 25.9 | 84.2 | 44.3 | 71.8 | 42.0 | 1.8 | 0.4 | 1.5 | 0.5 | 7.9 | 3.9 | 81.9 | 29.0 |
| AD-1069873.1 | 57.7 | 31.1 | 82.4 | 10.0 | 59.2 | 13.7 | 1.4 | 0.2 | 1.8 | 0.6 | 5.1 | 1.3 | 81.8 | 30.3 |

TABLE 27-continued

C3 Single Dose Screens in PCH cells (% C3 mRNA Remaining)

| Duplex | FU* 500 nM | ST DEV | FU* 100 nM | ST DEV | FU* 10 nM | ST DEV | TX# 50 nM | ST DEV | TX# 10 nM | ST DEV | TX# 1 nM | ST DEV | TX# 0.1 nM | ST DEV |
|---|---|---|---|---|---|---|---|---|---|---|---|---|---|---|
| AD-565286.1 | 91.7 | 38.5 | 114.8 | 56.6 | 66.1 | 16.9 | 84.5 | 24.1 | 111.0 | 25.3 | 113.5 | 16.4 | 118.5 | 13.2 |
| AD-565287.1 | 57.7 | 10.6 | 115.5 | 44.9 | 73.9 | 23.0 | 29.7 | 12.3 | 23.1 | 9.7 | 73.5 | 11.3 | 131.4 | 12.8 |
| AD-1069874.1 | 49.9 | 10.3 | 72.7 | 13.1 | 87.0 | 36.6 | 32.5 | 6.6 | 71.2 | 64.3 | 109.3 | 56.2 | 160.1 | 64.6 |
| AD-1069875.1 | 103.4 | 31.7 | 117.0 | 37.5 | 97.3 | 26.8 | 75.8 | 21.8 | 128.7 | 94.9 | 78.3 | 14.0 | 114.8 | 12.1 |
| AD-565335.1 | 52.9 | 16.8 | 100.5 | 16.6 | 200.3 | 91.6 | 2.5 | 0.5 | 2.5 | 0.4 | 14.7 | 4.2 | 38.3 | 6.7 |
| AD-1069876.1 | 46.4 | 18.4 | 46.7 | 25.1 | 70.2 | 21.6 | 29.2 | 12.9 | 74.9 | 13.1 | 93.8 | 8.9 | 35.5 | 12.4 |
| AD-565895.1 | 77.5 | 56.1 | 69.7 | 22.4 | 93.6 | 44.3 | 1.7 | 0.7 | 1.7 | 0.1 | 5.5 | 0.6 | 62.9 | 14.8 |
| AD-1069877.1 | 55.6 | 21.0 | 90.8 | 20.6 | 113.8 | 38.3 | 111.5 | 61.6 | 142.5 | 28.7 | 112.1 | 9.0 | 111.5 | 14.2 |
| AD-565897.1 | 91.6 | 15.2 | 80.3 | 9.7 | 78.3 | 29.1 | 111.4 | 74.4 | 150.6 | 13.8 | 110.0 | 6.7 | 79.7 | 10.0 |
| AD-565899.1 | 51.9 | 7.7 | 73.4 | 12.8 | 90.3 | 10.4 | 35.9 | 19.7 | 34.0 | 12.8 | 80.6 | 16.3 | 105.7 | 19.9 |
| AD-565903.1 | 71.9 | 20.4 | 80.6 | 21.1 | 102.8 | 42.6 | 10.3 | 2.9 | 7.9 | 3.2 | 14.4 | 6.6 | 59.0 | 13.8 |
| AD-565904.3 | 77.0 | 8.0 | 62.9 | 29.1 | 90.2 | 18.5 | 2.3 | 0.7 | 3.9 | 2.7 | 2.6 | 0.9 | 21.9 | 3.6 |

Transfection (TX)
*Free Uptake (FU)

TABLE 28

C3 Single Dose Screens in PCH cells (% C3 mRNA Remaining)

| Duplex ID | FU* 500 nM | STDEV | FU* 100 nM | STDEV | FU* 10 nM | STDEV | TX# 50 nM | STDEV | TX# 10 nM | STDEV | TX# 1 nM | STDEV | TX# 0.1 nM | STDEV |
|---|---|---|---|---|---|---|---|---|---|---|---|---|---|---|
| AD-1069878.1 | 51.3 | 5.7 | 62.2 | 36.8 | 214.9 | 37.4 | 4.2 | 0.6 | 1.8 | 0.3 | 3.8 | 2.0 | 254.9 | 63.1 |
| AD-565906.1 | 59.0 | 2.5 | 60.6 | 38.4 | 202.5 | 44.2 | 120.6 | 10.1 | 103.4 | 30.2 | 95.3 | 14.1 | 242.6 | 53.0 |
| AD-565907.1 | 62.6 | 10.5 | 39.9 | 18.9 | 232.0 | 103.1 | 0.7 | 0.3 | 1.3 | 0.3 | 9.6 | 2.0 | 278.0 | 123.5 |
| AD-1069879.1 | 82.6 | 12.0 | 43.4 | 16.7 | 165.9 | 70.0 | 7.1 | 2.3 | 7.9 | 1.0 | 30.3 | 4.5 | 198.8 | 83.9 |
| AD-565909.1 | 93.3 | 15.5 | 49.4 | 23.0 | 245.8 | 78.8 | 4.2 | 0.1 | 8.5 | 1.3 | 47.3 | 12.2 | 264.8 | 112.0 |
| AD-565910.1 | 96.8 | 10.9 | 70.3 | 38.6 | 154.2 | 70.6 | 0.7 | 0.2 | 2.9 | 2.1 | 25.1 | 4.9 | 184.8 | 84.5 |
| AD-565911.1 | 82.9 | 6.1 | 54.1 | 33.7 | 207.4 | 25.3 | 0.5 | 0.1 | 0.9 | 0.1 | 3.4 | 1.4 | N/A | N/A |
| AD-1069880.1 | 98.1 | 26.1 | 64.0 | 32.2 | N/A | N/A | 11.6 | 6.0 | 36.3 | 3.5 | 101.2 | 16.7 | N/A | N/A |
| AD-565913.1 | 67.5 | 17.9 | 32.8 | 4.3 | 141.2 | 69.8 | 2.9 | 0.4 | 4.4 | 1.1 | 71.0 | 25.0 | 169.2 | 83.6 |
| AD-1069881.1 | 57.3 | 7.4 | 51.1 | 25.9 | 125.4 | 61.1 | 0.4 | 0.1 | 0.7 | 0.1 | 3.9 | 1.3 | 150.2 | 73.2 |
| AD-565915.1 | 72.8 | 4.4 | 83.2 | 45.4 | 170.7 | 81.6 | 121.8 | 3.6 | 103.0 | 36.0 | 104.3 | 3.5 | 204.5 | 97.8 |
| AD-1069882.1 | 65.1 | 10.5 | 58.2 | 42.0 | 151.4 | 60.5 | 0.4 | 0.1 | 1.0 | 0.5 | 8.4 | 1.3 | 181.3 | 72.5 |
| AD-1069883.1 | 89.1 | 6.7 | 72.3 | 41.9 | 146.3 | 29.9 | 27.3 | 5.8 | 73.3 | 12.7 | 105.3 | 5.4 | 175.3 | 35.9 |
| AD-1069884.1 | 104.0 | 10.5 | 44.0 | 15.7 | 198.2 | 32.0 | 51.0 | 10.7 | 72.9 | 23.9 | 112.5 | 7.6 | 237.5 | 38.3 |
| AD-565919.1 | 126.6 | 29.1 | 34.6 | 12.2 | 225.4 | 54.6 | 81.9 | 9.2 | 126.6 | 14.3 | 112.5 | 7.9 | 275.8 | 54.7 |
| AD-1069885.1 | 92.2 | 13.8 | 55.4 | 4.5 | 214.4 | 120.2 | 49.6 | 17.2 | 51.4 | 18.8 | 70.5 | 13.8 | 209.7 | 77.3 |
| AD-565921.1 | 82.7 | 10.0 | 83.9 | 91.9 | 96.4 | 39.7 | 75.2 | 4.7 | 55.9 | 23.1 | 105.6 | 14.3 | 115.5 | 47.6 |
| AD-1069886.1 | 70.1 | 13.8 | 89.6 | 100.6 | 117.8 | 49.1 | 1.1 | 0.5 | 2.4 | 0.6 | 30.9 | 8.4 | 141.1 | 58.8 |
| AD-565923.1 | 85.8 | 3.8 | 59.6 | 26.2 | 134.9 | 18.9 | 93.9 | 6.2 | 90.2 | 21.5 | 91.9 | 2.4 | 161.7 | 22.6 |
| AD-565924.1 | 84.2 | 12.1 | 80.5 | 31.1 | 151.3 | 72.1 | 1.2 | 0.3 | 1.9 | 0.2 | 12.7 | 1.1 | 181.2 | 86.4 |
| AD-1069887.1 | 93.0 | 6.7 | 89.5 | 48.8 | 145.5 | 29.4 | 1.5 | 0.7 | 1.9 | 0.1 | 42.4 | 8.8 | 174.3 | 35.2 |
| AD-565927.1 | 99.1 | 17.4 | 48.8 | 9.0 | 155.6 | 22.0 | 120.4 | 17.1 | 124.3 | 43.6 | 121.4 | 16.2 | 186.5 | 26.3 |
| AD-565928.1 | 81.9 | 8.4 | 35.2 | 7.3 | N/A | N/A | 49.1 | 3.5 | 109.2 | 33.7 | 112.6 | 9.1 | N/A | N/A |
| AD-1069888.1 | 74.5 | 15.4 | 44.3 | 21.0 | 101.9 | 48.2 | 2.8 | 0.6 | 10.6 | 5.8 | 71.0 | 5.5 | 122.1 | 57.8 |
| AD-566379.1 | 83.0 | 7.7 | 109.1 | 77.5 | 100.6 | 44.5 | 122.3 | 27.4 | 104.5 | 49.0 | 85.6 | 6.6 | 120.5 | 53.3 |
| AD-566380.1 | 91.9 | 8.7 | 128.7 | 35.6 | 122.5 | 10.5 | 109.5 | 6.1 | 124.9 | 7.0 | 113.4 | 12.1 | 146.8 | 12.6 |
| AD-1069889.1 | 102.2 | 10.9 | 126.8 | 41.6 | 147.3 | 28.4 | 109.2 | 12.4 | 126.8 | 18.2 | 104.8 | 13.8 | 176.5 | 34.0 |
| AD-566382.1 | 97.8 | 24.0 | 45.4 | 4.4 | 151.2 | 15.0 | 112.7 | 4.7 | 130.0 | 12.0 | 109.0 | 9.1 | 181.2 | 18.0 |
| AD-566383.2 | 105.2 | 18.5 | 133.5 | 93.9 | 136.9 | 39.0 | 115.4 | 13.0 | 129.5 | 11.3 | 112.4 | 9.3 | 164.0 | 46.7 |
| AD-566384.2 | 102.6 | 32.5 | 56.4 | 23.3 | 152.3 | 24.9 | 106.6 | 8.2 | 117.1 | 47.3 | 106.2 | 5.8 | 165.7 | 8.9 |
| AD-1069890.1 | 90.0 | 63.7 | 39.5 | 10.3 | 87.7 | 45.3 | 106.1 | 4.2 | 93.1 | 52.3 | 95.1 | 8.7 | 105.1 | 54.2 |
| AD-1069891.1 | 90.9 | 8.3 | 171.8 | 27.6 | 76.4 | 30.6 | 1.0 | 0.1 | 2.3 | 0.6 | 16.1 | 4.7 | 91.6 | 36.7 |
| AD-1069892.1 | 87.7 | 4.3 | 103.5 | 6.9 | 53.3 | 18.4 | 10.9 | 1.2 | 16.3 | 4.9 | 76.7 | 10.6 | 63.9 | 22.0 |
| AD-566388.2 | 89.3 | 9.3 | 81.8 | 44.2 | 66.4 | 8.8 | 83.9 | 2.8 | 104.1 | 12.5 | 106.4 | 14.7 | 79.5 | 10.5 |
| AD-566389.1 | 96.8 | 9.7 | 133.1 | 83.6 | 100.5 | 41.9 | 100.0 | 2.6 | 118.4 | 17.9 | 107.1 | 9.6 | 120.4 | 50.2 |
| AD-1069893.1 | 115.3 | 17.1 | 134.5 | 63.5 | 83.7 | 22.4 | 7.9 | 1.3 | 20.2 | 4.9 | 86.1 | 4.8 | 100.3 | 26.8 |
| AD-566391.1 | 100.5 | 19.3 | 83.1 | 26.3 | 123.2 | 11.8 | 8.6 | 1.8 | 29.4 | 15.5 | 90.0 | 2.9 | 147.7 | 14.1 |
| AD-1069894.1 | 111.0 | 9.5 | 59.6 | 20.7 | 192.8 | 78.0 | 106.5 | 4.6 | 122.2 | 24.5 | 118.5 | 11.2 | 156.3 | 12.2 |
| AD-566393.1 | 71.5 | 41.2 | 71.8 | 14.8 | 63.8 | 27.2 | 86.1 | 13.1 | 87.3 | 38.2 | 106.8 | 14.7 | 76.4 | 32.5 |
| AD-566395.1 | 129.1 | 44.8 | 144.5 | 35.2 | 63.7 | 19.1 | 21.6 | 4.9 | 48.8 | 6.6 | 96.4 | 11.9 | 76.4 | 22.8 |
| AD-1069896.1 | 111.7 | 16.2 | 163.6 | 31.1 | 59.1 | 11.9 | 90.8 | 5.7 | 98.9 | 9.8 | 96.4 | 14.4 | 70.8 | 14.3 |
| AD-1069897.1 | 117.2 | 27.4 | 165.7 | 34.2 | 56.6 | 27.0 | 66.1 | 7.2 | 83.6 | 11.4 | 106.0 | 5.2 | 67.8 | 32.4 |
| AD-1069898.1 | 113.9 | 33.1 | 149.8 | 6.0 | 74.2 | 29.1 | 62.8 | 5.7 | 89.4 | 15.6 | 117.9 | 13.6 | 88.9 | 34.9 |
| AD-1069899.1 | 110.5 | 23.1 | 140.1 | 17.7 | 130.9 | 46.9 | 121.6 | 12.5 | 139.5 | 29.2 | 114.8 | 14.1 | 156.8 | 56.2 |
| AD-566475.1 | 113.8 | 39.3 | 84.2 | 68.5 | 38.1 | 4.0 | 28.3 | 6.6 | 18.5 | 5.7 | 48.2 | 5.8 | 45.6 | 4.8 |
| AD-1069900.1 | 138.2 | 41.4 | 139.2 | 111.8 | 38.0 | 6.4 | 14.9 | 1.4 | 23.1 | 5.8 | 61.6 | 12.6 | 45.5 | 7.7 |
| AD-566477.1 | 143.3 | 15.3 | 109.6 | 36.4 | 45.1 | 3.5 | 61.2 | 7.5 | 63.5 | 3.8 | 84.9 | 3.7 | 54.0 | 4.2 |
| AD-1069901.1 | 119.6 | 12.0 | 146.5 | 66.0 | 81.6 | 32.7 | 102.3 | 7.2 | 94.4 | 6.6 | 102.2 | 8.9 | 97.8 | 39.2 |
| AD-566483.1 | 93.8 | 37.5 | 128.6 | 19.1 | 71.1 | 3.8 | 10.7 | 0.8 | 14.7 | 1.1 | 85.8 | 1.9 | 85.2 | 4.6 |
| AD-566484.1 | 113.5 | 27.1 | 146.1 | 26.1 | 68.7 | 24.4 | 32.3 | 13.4 | 51.8 | 10.0 | 99.5 | 6.7 | 82.3 | 29.3 |

TABLE 28-continued

C3 Single Dose Screens in PCH cells (% C3 mRNA Remaining)

| Duplex ID | FU* 500 nM | STDEV | FU* 100 nM | STDEV | FU* 10 nM | STDEV | TX# 50 nM | STDEV | TX# 10 nM | STDEV | TX# 1 nM | STDEV | TX# 0.1 nM | STDEV |
|---|---|---|---|---|---|---|---|---|---|---|---|---|---|---|
| AD-566485.2 | 127.7 | 22.8 | 173.0 | 16.5 | 85.3 | 37.7 | 106.1 | 13.3 | 115.6 | 11.4 | 119.0 | 14.5 | 102.2 | 45.2 |
| AD-566486.1 | 60.4 | 20.1 | 107.2 | 56.5 | 142.2 | 73.2 | 50.8 | 9.3 | 58.7 | 21.8 | 117.6 | 5.2 | 170.3 | 87.7 |
| AD-1069902.1 | 53.3 | 36.3 | 40.6 | 19.3 | 95.8 | 75.0 | 0.2 | 0.1 | 0.6 | 0.2 | 0.8 | 0.1 | 114.8 | 89.9 |
| AD-1069903.1 | 88.0 | 13.3 | 148.8 | 55.5 | 104.6 | 55.8 | 35.7 | 7.6 | 40.5 | 14.3 | 76.5 | 9.7 | 125.3 | 66.8 |
| AD-1069904.1 | 130.4 | 21.0 | 99.7 | 41.0 | 87.1 | 16.1 | 15.7 | 3.4 | 21.0 | 8.0 | 73.2 | 11.8 | 104.4 | 19.3 |
| AD-1069905.1 | 109.9 | 4.2 | 117.9 | 52.4 | 85.6 | 18.6 | 91.2 | 3.4 | 88.3 | 13.6 | 97.5 | 10.5 | 102.6 | 22.3 |
| AD-567054.1 | 152.7 | 15.6 | 163.6 | 99.0 | 89.5 | 20.5 | 71.2 | 12.9 | 74.5 | 12.7 | 92.6 | 8.3 | 107.3 | 24.5 |
| AD-1069906.1 | 123.5 | 13.0 | 129.7 | 18.6 | 83.1 | 33.4 | 107.6 | 12.1 | 97.8 | 7.9 | 99.0 | 8.2 | 99.6 | 40.0 |
| AD-1069907.1 | 126.7 | 33.5 | 132.0 | 74.4 | 89.0 | 55.4 | 114.9 | 4.0 | 109.7 | 10.3 | 99.4 | 8.5 | 106.6 | 66.4 |
| AD-567057.1 | 95.7 | 30.3 | 81.3 | 36.2 | 132.1 | 53.1 | 36.1 | 15.0 | 59.5 | 12.2 | 96.4 | 10.8 | 201.8 | 101.3 |
| AD-1069908.1 | 100.1 | 37.9 | 61.6 | 42.8 | 70.9 | 33.2 | 110.1 | 22.4 | 95.6 | 20.3 | 97.2 | 8.1 | 85.0 | 39.8 |
| AD-567059.1 | 107.3 | 7.7 | 79.7 | 43.1 | 51.4 | 19.8 | 115.4 | 9.9 | 123.4 | 16.4 | 119.3 | 19.4 | 61.6 | 23.7 |
| AD-567060.1 | 87.9 | 23.1 | 78.4 | 19.8 | 51.0 | 19.9 | 1.0 | 0.3 | 2.3 | 0.6 | 26.4 | 14.1 | 61.1 | 23.8 |
| AD-1069909.1 | 134.1 | 20.5 | 84.9 | 47.6 | 83.2 | 32.7 | 10.0 | 1.8 | 11.0 | 2.3 | 61.0 | 11.8 | 99.7 | 39.2 |
| AD-1069910.1 | 124.2 | 30.7 | 147.1 | 56.9 | 42.3 | 8.2 | 67.7 | 12.3 | 69.6 | 12.2 | 102.1 | 20.2 | 50.7 | 9.8 |
| AD-567063.4 | 90.6 | 13.4 | 48.6 | 19.4 | 62.0 | 15.1 | 1.4 | 0.2 | 2.2 | 0.3 | 35.0 | 17.6 | 74.3 | 18.1 |
| AD-1069911.1 | 47.8 | 13.8 | 86.7 | 84.5 | 85.3 | 19.5 | 1.2 | 0.1 | 2.7 | 1.0 | 21.4 | 5.4 | 102.2 | 23.3 |
| AD-567065.1 | 37.1 | 5.3 | 90.8 | 70.5 | 54.6 | 30.8 | 131.2 | 8.1 | 125.6 | 29.8 | 124.4 | 21.7 | 65.4 | 36.9 |
| AD-567066.4 | 103.1 | 16.9 | 34.6 | 21.0 | 53.5 | 13.2 | 0.3 | 0.0 | 0.7 | 0.3 | 7.1 | 2.2 | 64.1 | 15.8 |
| AD-1069912.1 | 108.4 | 37.9 | 112.5 | 34.5 | 48.0 | 10.4 | 0.5 | 0.2 | 0.8 | 0.2 | 9.1 | 4.1 | 57.5 | 12.4 |
| AD-567068.1 | 112.7 | 20.5 | 112.5 | 13.4 | 52.1 | 17.9 | 39.8 | 11.2 | 23.4 | 2.9 | 85.7 | 7.7 | 62.5 | 21.5 |
| AD-1069913.1 | 120.3 | 31.4 | 110.3 | 24.4 | 40.2 | 6.5 | 9.9 | 2.2 | 36.0 | 8.4 | 111.0 | 26.6 | 48.2 | 7.8 |
| AD-567070.1 | 120.6 | 26.5 | 125.7 | 68.0 | 46.4 | 6.9 | 1.6 | 0.5 | 5.8 | 2.1 | 93.4 | 31.1 | 55.6 | 8.3 |
| AD-1069914.1 | 71.6 | 31.3 | 44.7 | 17.3 | 130.9 | 65.4 | 1.4 | 0.1 | 3.2 | 0.4 | 65.4 | 6.3 | 156.8 | 78.4 |
| AD-567072.1 | 55.9 | 3.0 | 24.4 | 12.5 | 49.3 | 36.6 | 1.3 | 0.3 | 2.1 | 0.4 | 45.3 | 14.0 | 59.1 | 43.9 |
| AD-1069915.1 | 93.1 | 25.8 | 44.0 | 6.5 | 60.3 | 24.8 | 0.8 | 0.1 | 1.2 | 0.2 | 10.5 | 1.6 | 72.3 | 29.8 |
| AD-1069916.1 | 109.8 | 18.2 | 99.2 | 61.3 | 52.2 | 6.3 | 0.5 | 0.1 | 1.7 | 0.6 | 24.8 | 10.7 | 62.6 | 7.5 |
| AD-1069917.1 | 118.8 | 32.2 | 99.0 | 27.5 | 45.1 | 9.0 | 0.3 | 0.2 | 0.5 | 0.1 | 2.5 | 0.8 | 54.0 | 10.8 |
| AD-567076.1 | 99.5 | 4.2 | 115.5 | 92.3 | 38.2 | 9.8 | 90.9 | 6.3 | 59.2 | 4.7 | 105.0 | 8.1 | 45.7 | 11.8 |
| AD-1069918.1 | 112.6 | 32.1 | 64.0 | 28.4 | 59.4 | 17.1 | 92.3 | 21.7 | 88.7 | 22.5 | 141.0 | 6.0 | 71.2 | 20.5 |
| AD-567294.1 | 134.9 | 38.6 | 115.6 | 63.1 | 64.7 | 50.6 | 111.9 | 15.5 | 71.9 | 23.0 | 117.9 | 29.5 | 77.6 | 60.7 |
| AD-1069919.1 | 111.9 | 46.9 | 54.8 | 32.3 | 118.7 | 25.9 | 2.0 | 0.2 | 2.3 | 0.4 | 34.4 | 18.1 | 142.3 | 31.0 |
| AD-1069920.1 | 53.1 | 13.4 | 31.1 | 20.3 | 115.6 | 34.6 | 0.4 | 0.2 | 0.7 | 0.1 | 2.0 | 0.5 | 138.5 | 41.5 |
| AD-567297.1 | 87.3 | 54.6 | 81.8 | 52.4 | 100.8 | 56.5 | 4.0 | 0.3 | 7.9 | 1.7 | 86.4 | 21.6 | 120.7 | 67.7 |
| AD-567300.1 | 78.0 | 51.8 | 22.7 | 10.4 | 54.6 | 27.1 | 0.5 | 0.3 | 0.4 | 0.3 | 1.5 | 0.3 | 65.5 | 32.5 |
| AD-567301.1 | 47.1 | 29.1 | 43.7 | 34.7 | 65.6 | 20.4 | 0.4 | 0.3 | 0.4 | 0.2 | 0.8 | 0.1 | 78.6 | 24.5 |
| AD-1069922.1 | 57.0 | 44.0 | 36.7 | 17.3 | 131.5 | 51.5 | 0.7 | 0.3 | 0.7 | 0.2 | 10.3 | 5.8 | 157.5 | 61.7 |

Transfection (TX)
*Free Uptake (FU)

TABLE 29

C3 Single Dose Screens in PCH cells (% C3 mRNA Remaining)

| Duplex ID | FU* 500 nM | STDEV | FU* 100 nM | STDEV | FU* 10 nM | STDEV | TX# 50 nM | STDEV | TX# 10 nM | STDEV | TX# 1 nM | STDEV | TX# 0.1 nM | STDEV |
|---|---|---|---|---|---|---|---|---|---|---|---|---|---|---|
| AD-1069923.1 | 116.2 | 27.1 | 81.4 | 38.3 | 179.0 | 108.7 | 2.6 | 0.6 | 1.3 | 0.2 | 47.0 | 14.8 | 119.9 | 20.1 |
| AD-1069924.1 | 102.9 | 34.6 | 33.8 | 13.8 | 168.2 | 33.6 | 1.8 | 0.6 | 0.4 | 0.1 | 39.7 | 33.6 | 64.8 | 21.9 |
| AD-567305.1 | 130.3 | 31.6 | 72.2 | 8.2 | 291.8 | 126.6 | 7.8 | 1.5 | 1.7 | 0.6 | 36.2 | 23.0 | 127.1 | 21.7 |
| AD-567306.1 | 134.9 | 46.0 | 137.7 | 42.7 | 257.1 | 17.6 | 84.2 | 46.0 | 39.0 | 21.4 | 136.0 | 15.9 | 226.3 | 31.8 |
| AD-567308.1 | 93.4 | 38.5 | 146.2 | 55.5 | 278.5 | 63.2 | 1.0 | 0.6 | 0.8 | 0.1 | 48.7 | 20.7 | 112.7 | 23.6 |
| AD-567309.1 | 162.5 | 19.0 | 295.9 | 146.1 | 276.8 | 114.1 | 2.0 | 0.7 | 1.2 | 0.2 | 56.0 | 9.4 | 126.8 | 26.0 |
| AD-1069925.1 | 99.8 | 18.2 | 444.7 | 194.1 | N/A | N/A | 1.4 | 0.2 | 0.9 | 0.2 | 68.8 | 30.9 | 128.0 | 33.1 |
| AD-567311.1 | 96.5 | 11.9 | 118.8 | 62.2 | N/A | N/A | 0.7 | 0.2 | 0.4 | 0.1 | 12.6 | 12.0 | 123.3 | 55.4 |
| AD-567312.1 | 102.6 | 33.6 | 90.9 | 62.9 | N/A | N/A | 1.8 | 0.5 | 1.2 | 0.4 | 35.0 | 7.7 | 79.9 | 39.9 |
| AD-1069926.1 | 116.0 | 29.4 | 97.5 | 22.9 | 209.7 | 100.9 | 70.8 | 37.0 | 25.9 | 0.7 | 96.2 | 30.6 | 155.8 | 60.7 |
| AD-567314.2 | 150.3 | 39.8 | 138.4 | 74.7 | 201.6 | 86.9 | 45.4 | 33.7 | 36.8 | 4.5 | 126.3 | 52.9 | 182.0 | 9.8 |
| AD-567315.6 | 52.5 | 11.9 | 48.1 | 9.6 | 162.4 | 136.5 | 4.0 | 3.5 | 0.3 | 0.1 | 81.0 | 36.4 | 20.0 | 5.2 |
| AD-1069927.1 | 83.4 | 13.0 | 92.8 | 33.3 | 200.9 | 85.4 | 1.7 | 1.2 | 0.3 | 0.0 | 100.8 | 74.2 | 33.0 | 11.0 |
| AD-1069928.1 | 209.2 | 48.7 | 167.8 | 79.2 | 176.4 | 74.2 | 30.5 | 6.1 | 13.1 | 3.3 | N/A | N/A | 159.7 | 26.3 |
| AD-567318.2 | 201.4 | 24.6 | 206.8 | 55.7 | 173.8 | 78.7 | 1.2 | 0.3 | 1.3 | 0.3 | 49.2 | 4.6 | 162.1 | 40.8 |
| AD-567319.1 | 218.4 | 46.8 | 173.7 | 12.9 | 281.0 | 91.9 | 5.3 | 0.5 | 5.4 | 1.5 | 144.3 | 55.0 | 190.7 | 24.4 |
| AD-1069929.1 | 94.1 | 20.6 | 47.2 | 16.8 | 192.4 | 134.2 | 5.0 | 0.4 | 4.9 | 1.0 | 65.1 | 7.7 | 96.6 | 14.2 |
| AD-567321.1 | 59.5 | 14.9 | 40.7 | 7.4 | 79.3 | 28.8 | 0.8 | 0.4 | 0.2 | 0.0 | 118.7 | 24.8 | 25.9 | 9.4 |
| AD-1069930.1 | 95.1 | 15.5 | 100.1 | 17.5 | 161.3 | 37.9 | 1.7 | 0.5 | 0.4 | 0.1 | 50.8 | 27.2 | 68.7 | 18.7 |
| AD-567323.1 | 204.7 | 17.6 | 165.4 | 35.3 | 203.3 | 62.1 | 24.8 | 4.1 | 14.0 | 0.8 | 126.1 | 26.8 | 273.1 | 54.0 |
| AD-1069931.1 | 187.8 | 63.2 | 110.9 | 15.3 | 205.8 | 39.3 | 147.6 | 30.3 | 52.6 | 11.1 | 144.3 | 19.4 | 223.7 | 57.8 |
| AD-567325.1 | 205.1 | 62.3 | 148.1 | 50.0 | 185.1 | 131.7 | 0.5 | 0.1 | 0.3 | 0.0 | 99.9 | 88.7 | 61.0 | 10.9 |
| AD-567326.1 | 207.1 | 17.8 | 144.3 | 25.6 | 295.7 | 95.1 | 1.0 | 0.2 | 0.8 | 0.1 | 38.3 | 15.3 | 163.1 | 48.5 |
| AD-1069932.1 | 80.4 | 19.5 | 128.3 | 145.9 | 147.4 | 119.4 | 34.0 | 9.0 | 19.3 | 3.2 | 63.0 | 21.7 | 56.2 | 6.0 |
| AD-1069933.1 | 52.4 | 11.3 | 57.7 | 30.2 | 130.5 | 80.5 | 0.7 | 0.3 | 0.7 | 0.2 | 69.1 | 55.9 | 41.7 | 15.8 |

TABLE 29-continued

C3 Single Dose Screens in PCH cells (% C3 mRNA Remaining)

| Duplex ID | FU* 500 nM | STDEV | FU* 100 nM | STDEV | FU* 10 nM | STDEV | TX# 50 nM | STDEV | TX# 10 nM | STDEV | TX# 1 nM | STDEV | TX# 0.1 nM | STDEV |
|---|---|---|---|---|---|---|---|---|---|---|---|---|---|---|
| AD-567479.1 | 108.0 | 16.6 | 118.1 | 78.7 | 181.8 | 40.0 | 172.2 | 28.4 | 75.2 | 9.7 | 141.3 | 23.7 | 157.2 | 17.8 |
| AD-567480.1 | 152.0 | 52.8 | 92.5 | 32.3 | 194.7 | 150.3 | 6.1 | 0.4 | 4.7 | 1.1 | 143.6 | 77.6 | 194.7 | 65.9 |
| AD-567481.1 | 161.6 | 33.7 | 94.1 | 32.1 | 107.2 | 26.9 | 0.8 | 0.1 | 0.7 | 0.1 | 52.6 | 33.1 | 188.8 | 16.8 |
| AD-567482.1 | 209.4 | 24.5 | 150.6 | 45.5 | 152.3 | 49.1 | 1.2 | 0.2 | 1.5 | 0.3 | 99.2 | 101.0 | 211.0 | 53.0 |
| AD-1069934.1 | 272.6 | 45.2 | 154.1 | 47.2 | 246.4 | 98.2 | 188.8 | 17.8 | 22.8 | 1.9 | 149.2 | 64.6 | 226.5 | 25.9 |
| AD-567485.1 | 55.6 | 16.2 | 84.6 | 5.0 | 190.1 | 49.6 | 8.5 | 1.7 | 8.7 | 2.4 | 68.3 | 4.3 | 51.4 | 12.9 |
| AD-1069935.1 | 29.7 | 10.2 | 76.8 | 31.4 | 146.3 | 81.9 | 2.2 | 2.9 | 0.6 | 0.3 | 107.9 | 54.2 | 42.6 | 2.8 |
| AD-567487.2 | 61.0 | 21.7 | 66.7 | 21.8 | 67.7 | 12.1 | 3.0 | 2.6 | 1.3 | 0.5 | 64.8 | 37.5 | 66.9 | 17.4 |
| AD-567488.1 | 73.9 | 16.2 | 70.9 | 19.5 | 118.8 | 20.7 | 4.1 | 2.8 | 1.5 | 0.4 | 49.5 | 5.8 | 94.5 | 13.3 |
| AD-567489.1 | 78.5 | 30.2 | 97.2 | 43.8 | 140.2 | 60.7 | 1.8 | 0.1 | 1.2 | 0.3 | 45.1 | 28.9 | 138.1 | 14.4 |
| AD-1069936.1 | 104.9 | 39.1 | 75.3 | 24.7 | 158.3 | 53.1 | 0.4 | 0.1 | 0.3 | 0.0 | 155.1 | 111.3 | 48.3 | 9.0 |
| AD-567491.1 | 154.0 | 28.5 | 101.3 | 61.1 | 166.5 | 98.7 | 0.7 | 0.1 | 0.8 | 0.2 | 56.9 | 9.5 | 143.5 | 42.2 |
| AD-1069937.1 | 231.3 | 16.6 | 142.1 | 68.6 | 222.8 | 142.7 | 218.9 | 18.1 | 113.8 | 33.9 | 212.4 | 20.9 | 204.5 | 19.0 |
| AD-1069938.1 | 46.5 | 13.8 | 55.3 | 4.6 | 150.7 | 116.5 | 129.1 | 46.8 | 51.9 | 10.0 | 96.3 | 50.3 | 69.1 | 17.4 |
| AD-1069939.1 | 50.0 | 28.4 | 107.4 | 98.8 | 123.4 | 46.8 | 47.8 | 16.1 | 38.4 | 8.7 | 88.2 | 33.0 | 61.4 | 8.6 |
| AD-567513.1 | 53.5 | 11.7 | 114.5 | 58.8 | 77.7 | 18.3 | 28.3 | 5.4 | 29.5 | 7.6 | 81.6 | 10.8 | 84.9 | 10.4 |
| AD-567514.1 | 110.4 | 17.7 | 84.9 | 27.5 | 101.1 | 18.2 | 121.5 | 31.7 | 84.7 | 35.5 | 128.7 | 41.6 | 116.6 | 25.6 |
| AD-1069940.1 | 70.4 | 12.5 | 73.1 | 21.7 | 169.2 | 31.9 | 22.2 | 3.1 | 13.9 | 1.6 | 83.3 | 7.0 | 132.4 | 20.2 |
| AD-1069941.1 | 72.5 | 21.3 | 53.9 | 23.9 | 144.0 | 86.9 | 0.7 | 0.1 | 0.5 | 0.1 | 56.0 | 28.1 | 73.8 | 4.9 |
| AD-1069942.1 | 69.5 | 27.5 | 43.0 | 11.4 | 119.8 | 15.8 | 0.5 | 0.1 | 0.6 | 0.1 | 92.6 | 61.0 | 77.9 | 28.3 |
| AD-567518.1 | 38.6 | 23.2 | 80.0 | 4.3 | 112.2 | 111.5 | 89.7 | 27.7 | 31.9 | 6.7 | 83.5 | 25.1 | 58.4 | 10.1 |
| AD-1069943.1 | 53.2 | 27.4 | 84.1 | 61.3 | 124.4 | 65.2 | 36.5 | 7.1 | 17.1 | 1.6 | 86.1 | 8.6 | 124.5 | 29.2 |
| AD-567521.4 | 35.0 | 26.6 | 37.9 | 16.1 | 69.5 | 34.0 | 1.2 | 0.7 | 0.7 | 0.2 | 86.7 | 81.2 | 63.5 | 20.0 |
| AD-1069944.1 | 44.8 | 19.9 | 52.6 | 33.8 | 81.9 | 24.9 | 7.0 | 0.6 | 6.6 | 0.5 | 60.9 | 23.9 | 120.0 | 18.3 |
| AD-567524.1 | 89.2 | 59.0 | 53.1 | 27.4 | 99.6 | 99.2 | 5.4 | 1.3 | 6.5 | 2.2 | 113.1 | 80.0 | 165.8 | 19.3 |
| AD-567525.1 | 62.6 | 11.3 | 53.3 | 18.8 | 109.7 | 43.2 | 1.2 | 0.2 | 1.9 | 0.3 | 59.6 | 11.6 | 124.2 | 27.2 |
| AD-1069945.1 | 133.9 | 32.5 | 82.1 | 25.0 | 177.8 | 59.9 | 21.4 | 2.5 | 58.8 | 17.4 | 94.2 | 23.7 | 146.4 | 13.4 |
| AD-567527.1 | 93.2 | 34.2 | 35.1 | 33.7 | 145.0 | 49.3 | 0.7 | 0.1 | 0.9 | 0.1 | 49.6 | 46.8 | 73.4 | 4.6 |
| AD-1069946.1 | 44.2 | 10.6 | 40.8 | 9.0 | 134.5 | 123.5 | 0.6 | 0.1 | 0.5 | 0.1 | 51.1 | 18.8 | 27.7 | 6.4 |
| AD-567529.1 | 48.1 | 6.9 | N/A | N/A | 74.9 | 25.7 | 1.9 | 1.2 | 1.2 | 0.1 | 48.1 | 33.4 | 67.6 | 28.4 |
| AD-1069947.1 | 68.7 | 18.7 | 50.0 | 12.6 | 67.1 | 16.7 | 10.4 | 3.0 | 10.0 | 1.0 | 59.1 | 13.6 | 116.6 | 22.7 |
| AD-567531.1 | 56.7 | 6.7 | 38.2 | 6.9 | 57.9 | 25.5 | 2.2 | 2.9 | 0.5 | 0.1 | 100.1 | 109.3 | 23.0 | 3.6 |
| AD-567532.1 | 94.8 | 8.0 | 65.5 | 25.1 | 201.4 | 115.2 | 0.7 | 0.1 | 0.5 | 0.1 | 133.0 | 2.0 | 71.5 | 19.5 |
| AD-567533.1 | 109.5 | 23.7 | 57.4 | 19.2 | 105.8 | 12.8 | 25.8 | 6.1 | 31.9 | 18.2 | 140.0 | 65.8 | 148.8 | 50.5 |
| AD-1069948.1 | 87.7 | 33.7 | 63.2 | 22.2 | 122.7 | 50.7 | 1.1 | 0.4 | 1.9 | 0.4 | 105.1 | 73.0 | 111.1 | 29.9 |
| AD-567535.1 | 107.4 | 24.7 | 55.2 | 4.1 | 154.2 | 65.1 | 0.8 | 0.2 | 0.8 | 0.1 | 63.5 | 67.6 | 109.8 | 21.8 |
| AD-568149.1 | 76.7 | 29.9 | 57.9 | 20.3 | 58.0 | 40.3 | 96.3 | 23.9 | 89.6 | 58.4 | 86.2 | 29.6 | 62.2 | 5.9 |
| AD-568150.1 | 55.6 | 4.1 | 65.0 | 30.0 | 88.8 | 44.6 | 1.0 | 0.2 | 1.2 | 0.2 | N/A | N/A | 56.9 | 12.1 |
| AD-1069949.1 | 65.9 | 11.6 | 57.3 | 8.4 | 83.2 | 61.3 | 1.2 | 0.2 | 4.2 | 5.5 | 61.2 | 22.8 | 67.1 | 2.7 |
| AD-1069950.1 | 89.1 | 22.9 | 52.0 | 10.2 | 102.4 | 23.6 | 8.5 | 0.8 | 10.8 | 3.1 | 101.9 | 29.2 | 120.3 | 32.2 |
| AD-1069951.1 | 110.2 | 10.9 | 57.9 | 15.5 | 104.6 | 12.0 | 2.1 | 0.9 | 1.5 | 0.2 | 61.0 | 50.5 | 107.2 | 29.0 |
| AD-1069952.1 | 104.0 | 36.7 | 60.5 | 31.8 | 132.8 | 45.4 | 1.4 | 0.4 | 2.1 | 1.1 | 99.1 | 34.4 | 72.6 | 14.3 |
| AD-568155.1 | 78.2 | 29.3 | 92.1 | 48.5 | 143.8 | 40.2 | 102.3 | 46.2 | 163.3 | 39.9 | 97.2 | 30.8 | 124.1 | 18.2 |
| AD-568159.1 | 52.2 | 13.2 | 33.4 | 10.4 | 119.0 | 39.7 | 99.5 | 39.5 | 95.0 | 26.4 | 99.9 | 26.8 | 86.1 | 12.5 |
| AD-1069953.1 | 52.8 | 21.1 | 53.5 | 13.3 | 76.2 | 47.0 | 15.3 | 4.1 | 10.1 | 1.5 | 54.4 | 10.0 | 85.9 | 19.7 |
| AD-568161.2 | 80.6 | 24.1 | 44.8 | 16.1 | 78.0 | 48.1 | 59.1 | 7.8 | 101.1 | 37.5 | 74.2 | 17.8 | 101.8 | 28.4 |
| AD-568162.1 | 45.8 | 9.2 | 60.5 | 18.7 | 57.0 | 18.2 | 37.6 | 10.6 | 120.4 | 23.8 | 83.0 | 4.6 | 118.8 | 15.4 |
| AD-1069954.1 | 64.2 | 20.8 | 32.8 | 8.3 | 71.4 | 20.9 | 106.8 | 36.7 | 116.0 | 7.8 | 98.4 | 27.9 | 108.5 | 35.8 |
| AD-1069955.1 | 83.2 | 12.8 | 81.3 | 25.1 | 84.9 | 90.5 | 179.5 | 57.7 | 161.9 | 17.3 | 83.4 | 32.4 | 95.5 | 30.8 |
| AD-568165.1 | 106.8 | 58.7 | 65.1 | 4.4 | 76.1 | 53.1 | 156.5 | 45.0 | 178.2 | 19.8 | 124.1 | 13.8 | 75.4 | 9.6 |
| AD-1069956.1 | 29.1 | 6.4 | 31.0 | 15.9 | 58.9 | 48.9 | 2.2 | 1.1 | 0.5 | 0.1 | 8.7 | 12.1 | 24.7 | 6.0 |
| AD-568337.1 | 60.8 | 22.7 | 38.8 | 16.8 | 59.7 | 26.6 | 123.3 | 24.8 | 120.7 | 24.2 | 100.5 | 21.7 | 71.4 | 18.6 |
| AD-568338.1 | 86.4 | 7.9 | 38.1 | 14.8 | 60.2 | 35.7 | 6.9 | 1.4 | 7.5 | 3.6 | 78.3 | 76.1 | 77.8 | 18.7 |
| AD-1069957.1 | 59.9 | 32.6 | 40.9 | 18.8 | 53.5 | 16.2 | 2.4 | 1.0 | 2.2 | 0.2 | 21.2 | 23.7 | 67.8 | 6.1 |
| AD-568340.1 | 56.9 | 24.4 | 39.4 | 10.5 | 99.2 | 53.1 | 1.9 | 0.4 | 3.1 | 1.5 | 130.6 | 49.3 | 90.6 | 11.3 |
| AD-1069958.1 | 40.3 | 14.3 | 55.5 | 10.7 | 55.6 | 5.5 | 0.9 | 0.3 | 0.8 | 0.1 | N/A | N/A | 40.4 | 2.2 |
| AD-568342.1 | 121.1 | 27.0 | 65.7 | 14.4 | 144.7 | 49.6 | 71.1 | 33.5 | 140.9 | 19.0 | 87.9 | 23.1 | 101.0 | 38.5 |
| AD-568343.4 | 81.1 | 15.2 | 43.1 | 9.6 | 75.7 | 40.2 | 2.6 | 0.4 | 3.3 | 0.8 | 67.7 | 69.3 | 71.4 | 9.8 |
| AD-1069959.1 | 54.5 | 14.6 | 45.4 | 41.0 | 85.8 | 65.3 | 2.0 | 0.7 | 4.8 | 0.2 | 50.9 | 16.4 | 73.3 | 29.2 |
| AD-568345.2 | 70.6 | 13.7 | 33.2 | 9.7 | 98.8 | 48.3 | 2.1 | 0.8 | 2.0 | 0.2 | 61.2 | 29.8 | 74.6 | 25.6 |
| AD-568348.1 | 59.8 | 10.6 | 52.4 | 19.7 | 76.7 | 61.3 | 23.5 | 15.5 | 67.3 | 15.4 | 82.0 | 32.7 | 57.9 | 13.2 |
| AD-1069961.1 | 38.0 | 11.4 | 71.2 | 21.8 | 98.5 | 32.0 | 0.8 | 0.3 | 0.9 | 0.1 | 122.3 | 50.1 | 44.5 | 12.5 |

Transfection (TX)
*Free Uptake (FU)

Example 5. Structure-Activity Relationship Analyses

Based on the in vitro analyses in Example 4, structure-active relationship (SAR) analyses were performed. In particular, additional duplexes were designed, synthesized, and assayed in vitro.

siRNAs were synthesized and annealed using routine methods known in the art and described above.

Detailed lists of the unmodified complement component C3 sense and antisense strand nucleotide sequences are shown in Table 30. Detailed lists of the modified complement component C3 sense and antisense strand nucleotide sequences are shown in Table 31.

Free uptake experiments and transfection experiments in primary *cynomolgus* hepatocytes (PCH) were performed as described above.

Single dose free uptake experiments were performed at 500 nM, 100 nM, 10 nM, and 1 nM final duplex concentration.

Single dose transfection experiments were performed at 50 nM, 10 nM, 1 nM, and 0.1 nM final duplex concentration.

The results of the free uptake experiments are shown in Table 32 and the results of the transfection assays are shown in Table 33.

TABLE 30

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-564742.5 | CCAGACAGACAAGACCAUCUU | 3758 | 489-509 | AAGAUGGUCUUGUCUGUCUGGAU | 3937 | 487-509 |
| AD-1181478.1 | CCAGACAGACAAGACCAUCUU | 3759 | 489-509 | AAGAUGGUCUUGUCUGUCUGGAU | 3938 | 487-509 |
| AD-1181479.1 | CCAGACAGACAAGACCAUCUU | 3760 | 489-509 | AAGAUGGUCUUGUCUGUCUGGAU | 3939 | 487-509 |
| AD-1181480.1 | CCAGACAGACAAGACCAUCUU | 3761 | 489-509 | AAGAUGGUCUUGUCUGUCUGGCU | 3940 | 487-509 |
| AD-1181481.1 | CCAGACAGACAAGACCAUCUU | 3762 | 489-509 | AAGAUGGUCUUGUCUGUCUGCC | 3941 | 487-509 |
| AD-1181482.1 | AGACAGACAAGACCAUCUU | 3763 | 491-509 | AAGAUGGUCUUGUCUGUCUGG | 3942 | 489-509 |
| AD-1181483.1 | CCAGACAGACAAGACCAUCUU | 3764 | 489-509 | AAGAUGGUCUUGUCUGUCUGGCU | 3943 | 487-509 |
| AD-1181484.1 | CCAGACAGACAAGACCAUCUU | 3765 | 489-509 | AAGAUGGUCUUGUCUGUCUGGCU | 3944 | 487-509 |
| AD-1567304.4 | GACUUCCUUGAAGCCAACUAU | 3766 | 3613-3633 | AUAGUUGGCUUCAAGGAAGUCC | 3945 | 3611-3633 |
| AD-1181485.1 | GACUUCCUUGAAGCCAACUAU | 3767 | 3613-3633 | AUAGUUGGCUUCAAGGAAGUCC | 3946 | 3611-3633 |
| AD-1181486.1 | GACUUCCUUGAAGCCAACUAU | 3768 | 3613-3633 | AUAGUUGGCUUCAAGGAAGUCC | 3947 | 3611-3633 |
| AD-1181487.1 | GACUUCCUUGAAGCCAACUAU | 3769 | 3613-3633 | AUAGUUGGCUUCAAGGAAGUCCC | 3948 | 3611-3633 |
| AD-1181488.1 | CUUCCUUGAAGCCAACUAU | 3770 | 3615-3633 | AUAGUUGGCUUCAAGGAAGUC | 3949 | 3613-3633 |
| AD-1181489.1 | GACUUCCUUGAAGCCAACUAU | 3771 | 3613-3633 | AUAGUUGGCUUCAAGGAAGUCCC | 3950 | 3611-3633 |
| AD-1181490.1 | GACUUCCUUGAAGCCAACUAU | 3772 | 3613-3633 | AUAGUUGGCUUCAAGGAAGUCCC | 3951 | 3611-3633 |
| AD-1181491.1 | GACUUCCUUGAAGCCAACUAU | 3773 | 3613-3633 | AUAGUUGGCUUCAAGGAAGUCCC | 3952 | 3611-3633 |
| AD-1181492.1 | GACUUCCUUGAAGCCAACUAU | 3774 | 3613-3633 | AUAGUUGGCUUCAAGGAAGUCCC | 3953 | 3611-3633 |
| AD-567315.8 | AGCCAACUACAUGAACCUACU | 3775 | 3624-3644 | AGUAGGUUCAUGUAGUUGGCUUC | 3954 | 3622-3644 |
| AD-1181493.1 | AGCCAACUACAUGAACCUACU | 3776 | 3624-3644 | AGUAGGUUCAUGUAGUUGGCUUC | 3955 | 3622-3644 |
| AD-1181494.1 | AGCCAACUACAUGAACCUACU | 3777 | 3624-3644 | AGUAGGUUCAUGUAGUUGGCUUC | 3956 | 3622-3644 |
| AD-1181495.1 | AGCCAACUACAUGAACCUACU | 3778 | 3624-3644 | AGUAGGUUCAUGUAGUUGGCUUC | 3957 | 3622-3644 |
| AD-1181496.1 | AGCCAACUACAUGAACCUACU | 3779 | 3624-3644 | AGUAGGUUCAUGUAGUUGGCUCC | 3958 | 3622-3644 |
| AD-1181497.1 | CCAACUACAUGAACCUACU | 3780 | 3626-3644 | AGUAGGUUCAUGUAGUUGGCU | 3959 | 3624-3644 |

TABLE 30-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-1181498.1 | AGCCAACUACAUGAACCUACU | 3781 | 3624-3644 | AGUAGGUUCAUGUAGUUGGCUCC | 3960 | 3622-3644 |
| AD-1181499.1 | AGCCAACUACAUGAACCUACU | 3782 | 3624-3644 | AGUAGGUUCAUGUAGUUGGCUCC | 3961 | 3622-3644 |
| AD-1181500.1 | AGCCAACUACAUGAACCUACU | 3783 | 3624-3644 | AGUAGGUUCAUGUAGUUGGCUCC | 3962 | 3622-3644 |
| AD-1181501.1 | AGCCAACUACAUGAACCUACU | 3784 | 3624-3644 | AGUAGGUUCAUGUAGUUGGCUCC | 3963 | 3622-3644 |
| AD-1181502.1 | AGCCAACUACAUGAACCUACU | 3785 | 3624-3644 | AGUAGGUUCAUGUAGUUGGCUUC | 3964 | 3622-3644 |
| AD-568586.5 | GAGAACCAGAAACAAUGCCAU | 3786 | 5014-5034 | AUGGCAUUGUUUCUGGUUCUCUU | 3965 | 5012-5034 |
| AD-1181503.1 | GAGAACCAGAAACAAUGCCAU | 3787 | 5014-5034 | AUGGCAUUGUUUCUGGUUCUCUU | 3966 | 5012-5034 |
| AD-1181504.1 | GAGAACCAGAAACAAUGCCAU | 3788 | 5014-5034 | AUGGCAUUGUUUCUGGUUCUCUU | 3967 | 5012-5034 |
| AD-1181505.1 | GAGAACCAGAAACAAUGCCAU | 3789 | 5014-5034 | AUGGCAUUGUUUCUGGUUCUCCU | 3968 | 5012-5034 |
| AD-1181506.1 | GAACCAGAAACAAUGCCAU | 3790 | 5016-5034 | AUGGCAUUGUUUCUGGUUCUC | 3969 | 5012-5034 |
| AD-1181507.1 | GAGAACCAGAAACAAUGCCAU | 3791 | 5014-5034 | ATGGCAUUGUUUCUGGUUCUCCU | 3970 | 5012-5034 |
| AD-1181508.1 | GAGAACCAGAAACAAUGCCAU | 3792 | 5014-5034 | AUGGCAUUGUUUCUGGUUCUCCU | 3971 | 5012-5034 |
| AD-1181509.1 | GAGAACCAGAAACAAUGCCAU | 3793 | 5014-5034 | AUGGCAUUGUUUCUGGUUCUCCU | 3972 | 5012-5034 |
| AD-1181510.1 | GAGAACCAGAAACAAUGCCAU | 3794 | 5014-5034 | AUGGCAUUGUUUCUGGUUCUCCU | 3973 | 5012-5034 |
| AD-568978.5 | ACAGACAAGACCAUCUACACU | 3795 | 493-513 | AGUGUAGAUGGUCUUGUCUGUCU | 3974 | 491-513 |
| AD-1181511.1 | ACAGACAAGACCAUCUACACU | 3796 | 493-513 | AGUGUAGAUGGUCUUGUCUGUCU | 3975 | 491-513 |
| AD-1181513.1 | ACAGACAAGACCAUCUACACU | 3797 | 493-513 | AGUGUAGAUGGUCUUGUCUGUGC | 3976 | 491-513 |
| AD-1181514.1 | AGACAAGACCAUCUACACU | 3798 | 495-513 | AGUGUAGAUGGUCUUGUCUGU | 3977 | 493-513 |
| AD-1181515.1 | ACAGACAAGACCAUCUACACU | 3799 | 493-513 | AGUGUAGAUGGUCUUGUCUGUCU | 3978 | 491-513 |
| AD-1181516.1 | ACAGACAAGACCAUCUACACU | 3800 | 493-513 | AGUGUAGAUGGUCUUGUCUGUCU | 3979 | 491-513 |
| AD-1181517.1 | ACAGACAAGACCAUCUACACU | 3801 | 493-513 | AGUGUAGAUGGUCUUGUCUGUCU | 3980 | 491-513 |
| AD-569164.9 | AGAUCCGAGCCUACUAUGAAU | 3802 | 707-727 | AUUCAUAGUAGGCUCGGAUCUUC | 3981 | 705-727 |
| AD-1181518.1 | AGAUCCGAGCCUACUAUGAAU | 3803 | 707-727 | AUUCAUAGUAGGCUCGGAUCUUC | 3982 | 705-727 |

TABLE 30-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-1181519.1 | AGAUCCGAGCCUACUAUGAAU | 3804 | 707-727 | AUUCAUAGUAGGCUCGGAUCUCC | 3983 | 705-727 |
| AD-1181520.1 | AUCCGAGCCUACUAUGAAU | 3805 | 709-727 | AUUCAUAGUAGGCUCGGAUCU | 3984 | 707-727 |
| AD-1181521.1 | AGAUCCGAGCCUACUAUGAAU | 3806 | 707-727 | AUUCAUAGUAGGCUCGGAUCUUC | 3985 | 705-727 |
| AD-1181522.1 | AGAUCCGAGCCUACUAUGAAU | 3807 | 707-727 | AUUCAUAGUAGGCUCGGAUCUUC | 3986 | 705-727 |
| AD-1181523.1 | AGAUCCGAGCCUACUAUGAAU | 3808 | 707-727 | AUUCAUAGUAGGCUCGGAUCUUC | 3987 | 705-727 |
| AD-1181524.1 | AGAUCCGAGCCUACUAUGAAU | 3809 | 707-727 | AUUCAUAGUAGGCUCGGAUCUUC | 3988 | 705-727 |
| AD-570712.3 | CCGAGCCGUUCUCUACAAUUU | 3810 | 2634-2654 | AAAUUGUAGAGAACGGCUCGGAU | 3989 | 2632-2654 |
| AD-1181525.1 | CCGAGCCGUUCUCUACAAUUU | 3811 | 2634-2654 | AAAUUGUAGAGAACGGCUCGGAU | 3990 | 2632-2654 |
| AD-1181526.1 | CCGAGCCGUUCUCUACAAUUU | 3812 | 2634-2654 | AAAUUGUAGAGAACGGCUCGGAU | 3991 | 2632-2654 |
| AD-1181527.1 | CCGAGCCGUUCUCUACAAUUU | 3813 | 2634-2654 | AAAUTGTAGAGAACGGCUCGGAU | 3992 | 2632-2654 |
| AD-1181528.1 | CCGAGCCGUUCUCUACAAUUU | 3814 | 2634-2654 | AAAUTGTAGAGAACGGCUCGGAU | 3993 | 2632-2654 |
| AD-1181529.1 | CCGAGCCGUUCUCUACAAUUU | 3815 | 2634-2654 | AAAUTGTAGAGAACGGCUCGGAU | 3994 | 2632-2654 |
| AD-1181530.1 | GAGCCGUUCUCUACAAUUU | 3816 | 2636-2654 | AAAUTGTAGAGAACGGCUCGG | 3995 | 2632-2654 |
| AD-1181531.1 | CCGAGCCGUUCUCUACAAUUU | 3817 | 2634-2654 | AAAUTGTAGAGAACGGCUCGGGC | 3996 | 2632-2654 |
| AD-1181532.1 | CCGAGCCGUUCUCUACAAUUU | 3818 | 2634-2654 | AAAUTGTAGAGAACGGCUCGGGC | 3997 | 2632-2654 |
| AD-1181533.1 | CCGAGCCGUUCUCUACAAUUU | 3819 | 2634-2654 | AAAUTGTAGAGAACGGCUCGGGC | 3998 | 2632-2654 |
| AD-570713.3 | CGAGCCGUUCUCUACAAUUAU | 3820 | 2635-2655 | AUAAUUGUAGAGAACGGCUCGGA | 3999 | 2633-2655 |
| AD-1181534.1 | CGAGCCGUUCUCUACAAUUAU | 3821 | 2635-2655 | AUAAUUGUAGAGAACGGCUCGGA | 4000 | 2633-2655 |
| AD-1181535.1 | CGAGCCGUUCUCUACAAUUAU | 3822 | 2635-2655 | AUAAUUGUAGAGAACGGCUCGGA | 4001 | 2633-2655 |
| AD-1181536.1 | CGAGCCGUUCUCUACAAUUAU | 3823 | 2635-2655 | AUAAUUGUAGAGAACGGCUCGGC | 4002 | 2633-2655 |
| AD-1181537.1 | CGAGCCGUUCUCUACAAUUAU | 3824 | 2635-2655 | AUAATUGUAGAGAACGGCUCGGC | 4003 | 2633-2655 |
| AD-1181538.1 | AGCCGUUCUCUACAAUUAU | 3825 | 2637-2655 | AUAATUGUAGAGAACGGCUCG | 4004 | 2635-2655 |
| AD-1181539.1 | CGAGCCGUUCUCUACAAUUAU | 3826 | 2635-2655 | AUAAUUGUAGAGAACGGCUCGGC | 4005 | 2633-2655 |
| AD-1181540.1 | CGAGCCGUUCUCUACAAUUAU | 3827 | 2635-2655 | AUAAUUGUAGAGAACGGCUCGGC | 4006 | 2633-2655 |

TABLE 30-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-1181541.1 | CGAGCCGUTCUCUACAAUUAU | 3828 | 2635-2655 | AUAAUUGUAGAGAACGGCUCGGC | 4007 | 2633-2655 |
| AD-1181542.1 | CGAGCCGUTCUCUACAAUUAU | 3829 | 2635-2655 | AUAAUUGUAGAGAACGGCUCGGC | 4008 | 2633-2655 |
| AD-570714.4 | GAGCCGUUCUCUACAAUUACU | 3830 | 2636-2656 | AGUAAUUGUAGAGAACGGCUCGG | 4009 | 2634-2656 |
| AD-1181543.1 | GAGCCGUUCUCUACAAUUACU | 3831 | 2636-2656 | AGUAAUUGUAGAGAACGGCUCGG | 4010 | 2634-2656 |
| AD-1181544.1 | GAGCCGUUCUCUACAAUUACU | 3832 | 2636-2656 | AGUAAUUGUAGAGAACGGCUCGG | 4011 | 2634-2656 |
| AD-1181545.1 | GAGCCGUUCUCUACAAUUACU | 3833 | 2636-2656 | AGUAAUUGUAGAGAACGGCUCCU | 4012 | 2634-2656 |
| AD-1181546.1 | GCCGUUCUCUACAAUUACU | 3834 | 2638-2656 | AGUAAUUGUAGAGAACGGCUC | 4013 | 2636-2656 |
| AD-1181547.1 | GAGCCGUUCUCUACAAUUACU | 3835 | 2636-2656 | AGUAAUUGUAGAGAACGGCUCGG | 4014 | 2634-2656 |
| AD-1181548.1 | GAGCCGUUCUCUACAAUUACU | 3836 | 2636-2656 | AGUAAUUGUAGAGAACGGCUCGG | 4015 | 2634-2656 |
| AD-1181549.1 | GAGCCGUCUCUCUACAAUUACU | 3837 | 2636-2656 | AGUAAUUGUAGAGAACGGCUCGG | 4016 | 2634-2656 |
| AD-571826.5 | CAAGCCUUGGCUCAAUACCAU | 3838 | 3922-3942 | AUGGUAUUGAGCCAAGGCUUGA | 4017 | 3920-3942 |
| AD-1181550.1 | CAAGCCUUGGCUCAAUACCAU | 3839 | 3922-3942 | AUGGUAUUGAGCCAAGGCUUGA | 4018 | 3920-3942 |
| AD-1181551.1 | CAAGCCUUGGCUCAAUACCAU | 3840 | 3922-3942 | AUGGUAUUGAGCCAAGGCUUGC | 4019 | 3920-3942 |
| AD-1181552.1 | CAAGCCUUGGCUCAAUACCAU | 3841 | 3922-3942 | AUGGUAUUGAGCCAAGGCUUGC | 4020 | 3920-3942 |
| AD-1181553.1 | AGCCUUGGCUCAUACCAU | 3842 | 3924-3942 | AUGGUAUGAGCCAAGGCUUG | 4021 | 3922-3942 |
| AD-1181554.1 | CAAGCCUUGGCUCAAUACCAU | 3843 | 3922-3942 | AUGGUAUGAGCCAAGGCUUGC | 4022 | 3920-3942 |
| AD-1181555.1 | CAAGCCUUGGCUCAAUACCAU | 3844 | 3922-3942 | AUGGUAUGAGCCAAGGCUUGC | 4023 | 3920-3942 |
| AD-572040.6 | ACUCACCUGUAAUAAAUUCGU | 3845 | 4158-4178 | ACGAAUUUAUUACAGGUGAGUUG | 4024 | 4156-4178 |
| AD-1181556.1 | ACUCACCUGUAAUAAAUUCGU | 3846 | 4158-4178 | ACGAAUUUAUUACAGGUGAGUUG | 4025 | 4156-4178 |
| AD-1181557.1 | ACUCACCUGUAAUAAAUUCGU | 3847 | 4158-4178 | ACGAAUUAUUACAGGUGAGUUG | 4026 | 4156-4178 |
| AD-1181558.1 | ACUCACCUGUAAUAAAUUCGU | 3848 | 4158-4178 | ACGAAUUUAUUACAGGUGAGUCC | 4027 | 4156-4178 |
| AD-1181559.1 | UCACCUGUAAUAAAUUCGU | 3849 | 4160-4178 | ACGAAUUUAUUACAGGUGAGU | 4028 | 4158-4178 |
| AD-1181560.1 | ACUCACCUGUAAUAAAUUCGU | 3850 | 4158-4178 | ACGAAUUUAUUACAGGUGAGUUG | 4029 | 4156-4178 |

TABLE 30-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-1181561.1 | ACUCACCUGUAAUAAAUUCGU | 3851 | 4158-4178 | ACGAAUUUAUUACAGGUGAGUUG | 4030 | 4156-4178 |
| AD-1181562.1 | ACUCACCUGUAAUAAAUUCGU | 3852 | 4158-4178 | ACGAAUUUAUUACAGGUGAGUUG | 4031 | 4156-4178 |
| AD-1181560.2 | ACUCACCUGUAAUAAAUUCGU | 3853 | 4158-4178 | ACGAAUUUAUUACAGGUGAGUUG | 4032 | 4156-4178 |
| AD-572110.5 | GAUGCCAAGAACACUAUGAUU | 3854 | 4228-4248 | AAUCAUAGUGUUCUUGGCAUCCU | 4033 | 4226-4248 |
| AD-1181563.1 | GAUGCCAAGAACACUAUGAUU | 3855 | 4228-4248 | AAUCAUAGUGUUCUUGGCAUCCU | 4034 | 4226-4248 |
| AD-1181564.1 | GAUGCCAAGAACACUAUGAUU | 3856 | 4228-4248 | AAUCAUAGUGUUCUUGGCAUCCU | 4035 | 4226-4248 |
| AD-1181565.1 | GAUGCCAAGAACACUAUGAUU | 3857 | 4228-4248 | AAUCAUAGUGUUCUUGGCAUCCU | 4036 | 4226-4248 |
| AD-1181566.1 | GAUGCCAAGAACACUAUGAUU | 3858 | 4228-4248 | AAUCAUAGUGUUCUUGGCAUCCU | 4037 | 4226-4248 |
| AD-1181567.1 | UGCCAAGAACACUAUGAUU | 3859 | 4230-4248 | AAUCAUAGUGUUCUUGGCAUC | 4038 | 4226-4248 |
| AD-1181568.1 | GAUGCCAAGAACACUAUGAUU | 3860 | 4228-4248 | AAUCAUAGUGUUCUUGGCAUCCU | 4039 | 4226-4248 |
| AD-1181569.1 | GAUGCCAAGAACACUAUGAUU | 3861 | 4228-4248 | AAUCAUAGUGUUCUUGGCAUCCU | 4040 | 4226-4248 |
| AD-1181570.1 | GAUGCCAAGAACACUAUGAUU | 3862 | 4228-4248 | AAUCAUAGUGUUCUUGGCAUCCU | 4041 | 4226-4248 |
| AD-1181571.1 | GAUGCCAAGAACACUAUGAUU | 3863 | 4228-4248 | AAUCAUAGUGUUCUUGGCAUCCU | 4042 | 4226-4248 |
| AD-1181572.1 | GAUGCCAAGAACACUAUGAUU | 3864 | 4228-4248 | AAUCAUAGUGUUCUUGGCAUCCU | 4043 | 4226-4248 |
| AD-1181572.1 | UCAAGGUCUACGCCUAUUACU | 3865 | 4523-4543 | AGUAAUAGGCGUAGACCUUGACU | 4044 | 4521-4543 |
| AD-572387.6 | UCAAGGUCUACGCCUAUUACU | 3866 | 4523-4543 | AGUAAUAGGCGUAGACCUUGACU | 4045 | 4521-4543 |
| AD-1181573.1 | UCAAGGUCUACGCCUAUUACU | 3867 | 4523-4543 | AGUAAUAGGCGUAGACCUUGACU | 4046 | 4521-4543 |
| AD-1181574.1 | UCAAGGUCUACGCCUAUUACU | 3868 | 4525-4543 | AGUAAUAGGCGUAGACCUUGACC | 4047 | 4521-4543 |
| AD-1181575.1 | AAGGUCUACGCCUAUUACU | 3869 | 4523-4543 | AGUAAUAGGCGUAGACCUUGA | 4048 | 4523-4543 |
| AD-1181576.1 | UCAAGGUCUACGCCUAUUACU | 3870 | 4523-4543 | AGUAAUAGGCGUAGACCUUGACU | 4049 | 4521-4543 |
| AD-1181577.1 | UCAAGGUCUACGCCUAUUACU | 3871 | 4523-4543 | AGUAAUAGGCGUAGACCUUGACU | 4050 | 4521-4543 |
| AD-1181578.1 | UCAAGGUCUACGCCUAUUACU | 3872 | 4523-4543 | AGUAAUAGGCGUAGACCUUGACU | 4051 | 4521-4543 |
| AD-1181579.1 | UCAAGGUCUACGCCUAUUACU | 3873 | 4523-4543 | AGUAAUAGGCGUAGACCUUGACU | 4052 | 4521-4543 |
| AD-1181580.1 | UCAAGGUCUACGCCUAUUACU | 3874 | 4523-4543 | AGUAAUAGGCGUAGACCUUGACU | 4053 | 4521-4543 |

TABLE 30-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-569272.6 | AAUUCUACUACAUCUAUAACU | 3875 | 815-835 | AGUUAUAGAUGUAGUAGAAUUC | 4054 | 813-835 |
| AD-1181582.1 | AAUUCUACUACAUCUAUAACU | 3876 | 815-835 | AGUUAUAGAUGUAGUAGAAUUC | 4055 | 813-835 |
| AD-1181583.1 | AAUUCUACUACAUCUAUAACU | 3877 | 815-835 | AGUUAUAGAUGUAGUAGAAUUC | 4056 | 813-835 |
| AD-1181584.1 | AAUUCUACUACAUCUAUAACU | 3878 | 815-835 | AGUUAUAGAUGUAGUAGAAUUC | 4057 | 813-835 |
| AD-1181585.1 | AAUUCUACUACAUCUAUAACU | 3879 | 815-835 | AGUUAUAGAUGUAGUAGAAUUGG | 4058 | 813-835 |
| AD-1181586.1 | AAUUCUACUACAUCUAUAACU | 3880 | 815-835 | AGUUAUAGAUGUAGUAGAAUUGG | 4059 | 813-835 |
| AD-1181587.1 | AAUUCUACUACAUCUAUAACU | 3881 | 815-835 | AGUUAUAGAUGUAGUAGAAU | 4060 | 815-833 |
| AD-1181588.1 | AAUUCUACUACAUCUAUAACU | 3882 | 815-835 | AGUUAUAGAUGUAGUAGAAUU | 4061 | 815-833 |
| AD-1181589.1 | AAUUCUACUACAUCUAUAACU | 3883 | 815-835 | AGUUAUAGAUGUAGUAGAAUUC | 4062 | 815-835 |
| AD-1181590.1 | AAUUCUACUACAUCUAUAACU | 3884 | 815-835 | AGUUAUAGAUGUAGUAGAAUUGG | 4063 | 815-835 |
| AD-1181591.1 | AAUUCUACUACAUCUAUAACU | 3885 | 815-835 | AGUUAUAGAUGUAGUAGAAUUGG | 4064 | 815-835 |
| AD-1181592.1 | AAUUCUACUACAUCUAUAACU | 3886 | 815-835 | AGUUAUAGAUGUAGUAGAAAUU | 4065 | 815-833 |
| AD-1181593.1 | AAUUCUACUACAUCUAUAACU | 3887 | 815-835 | AGUUAUAGAUGUAGUAGAAAU | 4066 | 815-833 |
| AD-565034.2 | CAGAGAAAUUCUACUACAUCU | 3888 | 809-829 | AGAUGUAGUAGAAUUUCUCUGUA | 4067 | 807-829 |
| AD-1181594.1 | CAGAGAAAUUCUACUACAUCU | 3889 | 809-829 | AGAUGUAGUAGAAUUUCUCUGUC | 4068 | 807-829 |
| AD-1181595.1 | CAGAGAAAUUCUACUACAUCU | 3890 | 809-829 | AGAUGUAGUAGAAUUUCUCUGUC | 4069 | 807-829 |
| AD-565035.2 | AGAGAAAUUCUACUACAUCUU | 3891 | 810-830 | AAGAUGUAGUAGAAUUUCUCUGU | 4070 | 808-830 |
| AD-1181596.1 | AGAGAAAUUCUACUACAUCUU | 3892 | 810-830 | AAGAUGUAGUAGAAUUUCUCUGU | 4071 | 808-830 |
| AD-1181597.1 | AGAGAAAUUCUACUACAUCUU | 3893 | 810-830 | AAGAUGUAGUAGAAUUUCUCUGU | 4072 | 808-830 |
| AD-1181598.1 | AGAGAAAUUCUACUACAUCUU | 3894 | 810-830 | AAGAUAUAGUAGAAUUUCUCUGU | 4073 | 808-830 |
| AD-565037.2 | AGAAAUUCUACUACAUCUAUU | 3895 | 812-832 | AAGAUGUAGUAGAAUUUCUCU | 4074 | 810-832 |
| AD-1181599.1 | AGAAAUUCUACUACAUCUAUU | 3896 | 812-832 | AAUAGAUGUAGUAGAAUUUCUCU | 4075 | 810-832 |
| AD-1181600.1 | AGAAAUUCUACUACAUCUAUU | 3897 | 812-832 | AAUAGAUGUAGUAGAAUUUCUCU | 4076 | 810-832 |

TABLE 30-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-1181601.1 | AGAAAUUCUACUACAUCUAUU | 3898 | 812-832 | AAUAGAUGUAGUAGAAUUUCUCU | 4077 | 810-832 |
| AD-567072.2 | CAAGGUCUUCUCUCUCUGGCUGU | 3899 | 3342-3362 | ACAGCCAGAGAGAAGACCUUGAC | 4078 | 3340-3362 |
| AD-1181602.1 | CAAGGUCUUCUCUCUCUGGCUGU | 3900 | 3342-3362 | ACAGCCAGAGAGAAGACCUUGGC | 4079 | 3340-3362 |
| AD-1181603.1 | CAAGGUCUUCUCUCUCUGGCUGU | 3901 | 3342-3362 | ACAGCCAGAGAGAAGACCUUGGC | 4080 | 3340-3362 |
| AD-1181604.1 | CAAGGUCUUCUCUCUCUGGCUGU | 3902 | 3342-3362 | ACAGCCAGAGAGAAGACCUUGGC | 4081 | 3340-3362 |
| AD-567300.2 | AGGAGACUUCCUUGAAGCCAAU | 3903 | 3609-3629 | AUGGCUUCAAGGAAGUCUCCUGC | 4082 | 3607-3629 |
| AD-1181605.1 | AGGAGACUUCCUUGAAGCCAAU | 3904 | 3609-3629 | AUGGCUUCAAGGAAGUCUCCUGC | 4083 | 3607-3629 |
| AD-1181606.1 | AGGAGACUUCCUUGAAGCCAAU | 3905 | 3609-3629 | AUGGCCUUCAAGGAAGUCUCCUGC | 4084 | 3607-3629 |
| AD-567301.2 | GGAGACUUCCUUGAAGCCAAU | 3906 | 3610-3630 | AUUGGCUUCAAGGAAGUCUCCUG | 4085 | 3608-3630 |
| AD-1181607.1 | GGAGACUUCCUUGAAGCCAAU | 3907 | 3610-3630 | AUUGGCUUCAAGGAAGUCUCCUG | 4086 | 3608-3630 |
| AD-1181608.1 | GGAGACUUCCUUGAAGCCAAU | 3908 | 3610-3630 | AUUGGCUUCAAGGAAGUCUCCUG | 4087 | 3608-3630 |
| AD-569262.2 | CCUACAGAGAAAUUCUACUAU | 3909 | 805-825 | AUAGUAGAAUUUCUCUGUAGGCU | 4088 | 803-825 |
| AD-1181609.1 | CCUACAGAGAAAUUCUACUAU | 3910 | 805-825 | AUAGUAGAAUUUCUCUGUAGGCU | 4089 | 803-825 |
| AD-1181610.1 | CCUACAGAGAAAUUCUACUAU | 3911 | 805-825 | AUAGUAGAAUUUCUCUGUAGGCU | 4090 | 803-825 |
| AD-569265.2 | ACAGAGAAAUUCUACUACAUU | 3912 | 808-828 | AAUGUAGUAGAAUUUCUCUGUAG | 4091 | 806-828 |
| AD-1181611.1 | ACAGAGAAAUUCUACUACAUU | 3913 | 808-828 | AAUGUAGUAGAAUUUCUCUGUGG | 4092 | 806-828 |
| AD-1181612.1 | ACAGAGAAAUUCUACUACAUU | 3914 | 808-828 | AAUGUAGUAGAAUUUCUCUGUGG | 4093 | 806-828 |
| AD-569268.2 | GAGAAAUUCUACUACAUCUAU | 3915 | 811-831 | AUAGAUGUAGUAGAAUUUCUCUG | 4094 | 809-831 |
| AD-1181613.1 | GAGAAAUUCUACUACAUCUAU | 3916 | 811-831 | AUAGAUGUAGUAGAAUUUCUCUG | 4095 | 809-831 |
| AD-1181614.1 | GAGAAAUUCUACUACAUCUAU | 3917 | 811-831 | AUAGAUGUAGUAGAAUUUCUCUG | 4096 | 809-831 |
| AD-569269.2 | AGAAAUUCUACUACAUCUAUU | 3918 | 812-832 | AAUAGAUGUAGUAGAAUUUCUCU | 4097 | 810-832 |
| AD-1181615.1 | AGAAAUUCUACUACAUCUAUU | 3919 | 812-832 | AAUAGAUGUAGUAGAAUUUCUCU | 4098 | 810-832 |
| AD-1181616.1 | AGAAAUUCUACUACAUCUAUU | 3920 | 812-832 | AAUAGAUGUAGUAGAAUUUCUCU | 4099 | 810-832 |
| AD-569270.2 | GAAAUUCUACUACAUCUAUAU | 3921 | 813-833 | AUAUAGAUGUAGUAGAAUUUCUC | 4100 | 811-833 |

TABLE 30-continued

Unmodified Sense and Antisense Strand Sequences of Complement Component C3 dsRNA Agents

| Duplex Name | Sense Sequence 5' to 3' | SEQ ID NO: | Range in NM_000064.3 | Antisense Sequence 5' to 3' | SEQ ID NO: | Range in NM_000064.3 |
|---|---|---|---|---|---|---|
| AD-1181617.1 | GAAAUUCUACUACCAUCUAUAU | 3922 | 813-833 | AUAUAGAUGUAGUAGAAUUCUC | 4101 | 811-833 |
| AD-1181618.1 | GAAAUUCUACUACCAUCUAUAU | 3923 | 813-833 | AUAUAGAUGUAGUAGAAUUCUC | 4102 | 811-833 |
| AD-570676.2 | ACCCUACUCUGUUGUUCGAAU | 3924 | 2598-2618 | AUUCGAACAACAGAGAGUAGGUAG | 4103 | 2596-2618 |
| AD-1181619.1 | ACCCUACUCUGUUGUUCGAAU | 3925 | 2598-2618 | AUUCGAACAACAGAGAGUAGGUGG | 4104 | 2596-2618 |
| AD-1181620.1 | ACCCUACUCUGUUGUUCGAAU | 3926 | 2598-2618 | AUUCGAACAACAGAGAGUAGGUGG | 4105 | 2596-2618 |
| AD-571304.2 | CAAGGUCUUCUCUCUCGGCUGU | 3927 | 3342-3362 | ACAGCCAGAGAGAGAAGACCUUGAC | 4106 | 3340-3362 |
| AD-1181604.2 | CAAGGUCUUCUCUCUCGGCUGU | 3928 | 3342-3362 | ACAGCCAGAGAGAGAAGACCUUGGC | 4107 | 3340-3362 |
| AD-1181621.1 | CAAGGUCUUCUCUCUCGGCUGU | 3929 | 3342-3362 | ACAGCCAGAGAGAGAAGACCUUGGC | 4108 | 3340-3362 |
| AD-1069946.2 | UGGCUCAAUGAACAGAGAUAU | 3930 | 3856-3876 | AUAUCUCUGUUCAUUGAGCCAAC | 4109 | 3854-3876 |
| AD-1181622.1 | UGGCUCAAUGAACAGAGAUAU | 3931 | 3856-3876 | AUAUCUCUGUUCAUUGAGCCAGC | 4110 | 3854-3876 |
| AD-1181623.1 | UGGCUCAAUGAACAGAGAUAU | 3932 | 3856-3876 | AUAUCUCUGUUCAUUGAGCCAGC | 4111 | 3854-3876 |
| AD-1181624.1 | UGGCUCAAUGAACAGAGAUAU | 3933 | 3856-3876 | AUAUCUCUGUUCAUUGAGCCAGC | 4112 | 3854-3876 |
| AD-1069956.2 | GCUGAGGAGAAUUGCUUCAUU | 3934 | 4633-4653 | AAUGAAGCAAUUCUCCUCAGCAC | 4113 | 4631-4653 |
| AD-1181625.1 | GCUGAGGAGAAUUGCUUCAUU | 3935 | 4633-4653 | AAUGAAGCAAUUCUCCUCAGCGC | 4114 | 4631-4653 |
| AD-1181626.1 | GCUGAGGAGAAUUGCUUCAUU | 3936 | 4633-4653 | AAUGAAGCAAUUCUCCUCAGCGC | 4115 | 4631-4653 |

TABLE 31

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: | SEQ ID NO: |
|---|---|---|---|---|---|---|---|
| AD-564742.5 | cscsagacAfgAfCfCfAfagaccaucuuL96 | 4116 | asAfsgaug(Ggn)ucuuguCfuGfucuggsasu | 4295 | AUCCAGACAGACAAGACCAUCUA | 4474 | |
| AD-1181478.1 | cscsagacAfgAfCfCfAfagaccaucuuL96 | 4117 | asAfsgadTg(G2p)ucuuguCfuGfucuggsasu | 4296 | AUCCAGACAGACAAGACCAUCUA | 4475 | |
| AD-1181479.1 | cscsagacAfgAfCfCfAfagaccaucuuL96 | 4118 | asAfsgadTg(G2p)ucuuguCfudGucuggsasu | 4297 | AUCCAGACAGACAAGACCAUCUA | 4476 | |
| AD-1181480.1 | cscsagacAfgAfCfCfAfagaccaucuuL96 | 4119 | asAfsgadTg(G2p)ucuuguCfudGucuggscsu | 4298 | AUCCAGACAGACAAGACCAUCUA | 4477 | |
| AD-1181481.1 | cscsagacAfgAfCfCfAfagaccaucuuL96 | 4120 | asAfsgadTg(G2p)ucuuguCfudGucuggscsc | 4299 | AUCCAGACAGACAAGACCAUCUA | 4478 | |
| AD-1181482.1 | asgsagacAfgAfCfCfAfagaccaucuuL96 | 4121 | asAfsgadTg(G2p)ucuuguCfudGucugsg | 4300 | AUCCAGACAGACAAGACCAUCUA | 4479 | |
| AD-1181483.1 | cscsagacagdAcdAagaccaucuuL96 | 4122 | asdAsgadTg(G2p)ucuuguCfudGucuggscsu | 4301 | AUCCAGACAGACAAGACCAUCUA | 4480 | |
| AD-1181484.1 | cscsagacAfgdAfdAagaccaucuuL96 | 4123 | asdAsgadTg(G2p)ucuuguCfudGucuggscsu | 4302 | AUCCAGACAGACAAGACCAUCUA | 4481 | |
| AD-5667304.4 | gsascuucCfuUfGfAfCfAfagccaacuauL96 | 4124 | asUfsaguu(Ggn)gcuucaAfgGfaagucsusc | 4303 | GAGACUUCCCUGAAGCCAACUAC | 4482 | |
| AD-1181485.1 | gsascuucCfuUfGfAfCfAfagccaacuauL96 | 4125 | asUfsagdTu(G2p)gcuucaAfgGfaagucsusc | 4304 | GAGACUUCCCUGAAGCCAACUAC | 4483 | |
| AD-1181486.1 | gsascuucCfuUfGfAfCfAfagccaacuauL96 | 4126 | asUfsagdTu(G2p)gcuucaAfgGfaagucscsc | 4305 | GAGACUUCCCUGAAGCCAACUAC | 4484 | |
| AD-1181487.1 | gsascuucCfuUfGfAfCfAfagccaacuauL96 | 4127 | asUfsagdTu(G2p)gcuucadAgdGaagucscsc | 4306 | GAGACUUCCCUGAAGCCAACUAC | 4485 | |
| AD-1181488.1 | csusucCfuUfGfAfCfAfagccaacuauL96 | 4128 | asUfsagdTu(G2p)gcuucadAgdGaagsusc | 4307 | GAGACUUCCCUGAAGCCAACUAC | 4486 | |
| AD-1181489.1 | gsascuucCfudTgdAagccaacuauL96 | 4129 | asUfsagdTu(G2p)gcuucadAfgGaagucscsc | 4308 | GAGACUUCCCUGAAGCCAACUAC | 4487 | |
| AD-1181490.1 | gsascuucCfudCudTgdAagccaacuauL96 | 4130 | asUfsagdTu(G2p)gcuucadAgdGaagucscsc | 4309 | GAGACUUCCCUGAAGCCAACUAC | 4488 | |
| AD-1181491.1 | gsascuucdCudTgdAagccaacuauL96 | 4131 | asUfsagdTu(G2p)gcuucadAgdGaagucscsc | 4310 | GAGACUUCCCUGAAGCCAACUAC | 4489 | |
| AD-1181492.1 | gsascuucdCudTgdAdAgccaacuauL96 | 4132 | asUfsagdTu(G2p)gcuucadAgdGaagucscsc | 4311 | GAGACUUCCCUGAAGCCAACUAC | 4490 | |
| AD-567315.8 | asgsccaaCfuAfCfAfAfugaaccuacuaL96 | 4133 | asGfsuagg(Tgn)ucauguAfgUfuggcususc | 4312 | GAAGCCAACUACAUGAACCUACA | 4491 | |
| AD-1181493.1 | asgsccaaCfuAfCfAfAfugaaccuacuaL96 | 4134 | asdGsuagg(Tgn)ucauguAfgUfuggcususc | 4313 | GAAGCCAACUACAUGAACCUACA | 4492 | |
| AD-1181494.1 | asgsccaaCfuAfCfAfAfugaaccuacuaL96 | 4135 | asdGsuadGg(Tgn)ucauguAfgUfuggcususc | 4314 | GAAGCCAACUACAUGAACCUACA | 4493 | |
| AD-1181495.1 | asgsccaaCfuAfCfAfAfugaaccuacuaL96 | 4136 | asdGsuadGg(Tgn)ucaugudAgUfuggcususc | 4315 | GAAGCCAACUACAUGAACCUACA | 4494 | |
| AD-1181496.1 | asgsccaaCfuAfCfAfAfugaaccuacuaL96 | 4137 | asdGsuadGg(Tgn)ucaugudAgUfuggcuscsc | 4316 | GAAGCCAACUACAUGAACCUACA | 4495 | |
| AD-1181497.1 | cscsaaCfuAfCfCfAfugaaccuacuaL96 | 4138 | asdGsuadGg(Tgn)ucaugudAgUfuggscsu | 4317 | GAAGCCAACUACAUGAACCUACA | 4496 | |

TABLE 31-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-1181498.1 | asgsccaaCfudAcdAugaaccuacuL96 | 4139 | asdGsuadGg(Tgn)ucaugudAgUfuggcuscsc | 4318 | GAAGCCAACUACAUGACCUACA | 4497 |
| AD-1181499.1 | asgsccaadCudAcdAugaaccuacuL96 | 4140 | asdGsuadGg(Tgn)ucaugudAgUfuggcuscsc | 4319 | GAAGCCAACUACAUGACCUACA | 4498 |
| AD-1181500.1 | asgsccaadCudAcdAugaaccuacuL96 | 4141 | asdGsuadGg(U2p)ucaugudAgUfuggcuscsc | 4320 | GAAGCCAACUACAUGACCUACA | 4499 |
| AD-1181501.1 | asgsccaadCudAcdAUfgaaccuacuL96 | 4142 | asdGsuadGg(Tgn)ucaugudAgUfuggcuscsc | 4321 | GAAGCCAACUACAUGACCUACA | 4500 |
| AD-1181502.1 | asgsccaadCudAcdAUfgaaccuacuL96 | 4143 | asdGsuagg(Tgn)ucauguAfgUfuggcuscsc | 4322 | GAAGCCAACUACAUGACCUACA | 4501 |
| AD-568586.5 | gsasgaaccfaGfAfAfacaaugccauL96 | 4144 | asUfsggca(Tgn)uguuucUfgGfuucucsusu | 4323 | AAGAGAACCAGAAACAAUGCCAG | 4502 |
| AD-1181503.1 | gsasgaaccfaGfAfAfacaaugccauL96 | 4145 | asUfsggdCa(Tgn)uguuucUfgdGuucucsusu | 4324 | AAGAGAACCAGAAACAAUGCCAG | 4503 |
| AD-1181504.1 | gsasgaaccfaGfAfAfacaaugccauL96 | 4146 | asUfsggdCa(Tgn)uguuucUfgdGuucucsusu | 4325 | AAGAGAACCAGAAACAAUGCCAG | 4504 |
| AD-1181505.1 | gsasgaaccCfgGfAfAfacaaugccauL96 | 4147 | asUfsggdCa(Tgn)uguuucUfgdGuucucsusu | 4326 | AAGAGAACCAGAAACAAUGCCAG | 4505 |
| AD-1181506.1 | gsasaccCfgGfAfAfacaaugccauL96 | 4148 | asUfsggdCa(Tgn)uguuucUfgdGuucucsusu | 4327 | AAGAGAACCAGAAACAAUGCCAG | 4506 |
| AD-1181507.1 | gsasgaaccCadGadAacaaugccauL96 | 4149 | asdTsggdCa(Tgn)uguuucUfgdGuucucscsu | 4328 | AAGAGAACCAGAAACAAUGCCAG | 4507 |
| AD-1181508.1 | gsasgaaccCadGadAacaaugccauL96 | 4150 | asUfsggdCa(Tgn)uguuucUfgdGuucucscsu | 4329 | AAGAGAACCAGAAACAAUGCCAG | 4508 |
| AD-1181509.1 | gsasgaaccCadGadAAcaaugccauL96 | 4151 | asUfsggdCa(Tgn)uguuucUfgdGuucucscsu | 4330 | AAGAGAACCAGAAACAAUGCCAG | 4509 |
| AD-1181510.1 | gsasgaaccCadGadAdAcaaugccauL96 | 4152 | asUfsggdCa(Tgn)uguuucUfgdGuucucscsu | 4331 | AAGAGAACCAGAAACAAUGCCAG | 4510 |
| AD-568978.5 | ascsagacAfaGfAfCfcaucuacacuL96 | 4153 | asGfsuguAfgAfUfgguUfUfgfucuguscsu | 4332 | AGACAGACAAGACCAUCUACACC | 4511 |
| AD-1181511.1 | ascsagacAfaGfAfCfcaucuacacuL96 | 4154 | asdGsuguAfgAfUfgguUfUfgducuguscsu | 4333 | AGACAGACAAGACCAUCUACACC | 4512 |
| AD-1181513.1 | ascsagacAfaGfAfCfcaucuacacuL96 | 4155 | asdGsugdTadGaugguUfudGucuguscsu | 4334 | AGACAGACAAGACCAUCUACACC | 4513 |
| AD-1181514.1 | ascsagacAfaGfAfCfcaucuacacuL96 | 4156 | asdGsugdTadGaugguUfudGucugsgsu | 4335 | AGACAGACAAGACCAUCUACACC | 4514 |
| AD-1181515.1 | ascsagacAadGadCcaucuacacuL96 | 4157 | asdGsugdTadGaugguUfudGucuguscsu | 4336 | AGACAGACAAGACCAUCUACACC | 4515 |
| AD-1181516.1 | ascsagacAadGadCCfaucuacacuL96 | 4158 | asdGsugdTadGaugguUfudGucuguscsu | 4337 | AGACAGACAAGACCAUCUACACC | 4516 |
| AD-1181517.1 | ascsagacAadGacfcaucuacacuL96 | 4159 | asdGsugdTadGaugguUfudGucuguscsu | 4338 | AGACAGACAAGACCAUCUACACC | 4517 |
| AD-569164.9 | asgsauccGfaGfCfCfuacuaugaauL96 | 4160 | asUfsucaUfaGfUfaggcUfcGfaucususc | 4339 | GAAGCCGAGCCUACUAUGAAA | 4518 |
| AD-1181518.1 | asgsauccGfaGfCfCfuacuaugaauL96 | 4161 | asUfsucaUfaguaggcUfcGgaucususc | 4340 | GAAGCCGAGCCUACUAUGAAA | 4519 |

TABLE 31-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-1181519.1 | asgsauccGfaGfCfCfuacuaugaauL96 | 4162 | asUfsucaUfaguaggcUfcdGgaucuscsc | 4341 | GAAGAUCCGAGCCUACUAUGAAA | 4520 |
| AD-1181520.1 | asusccGfaGfCfCfuacuaugaauL96 | 4163 | asUfsucaUfaguaggcUfcdGgauscsu | 4342 | GAAGAUCCGAGCCUACUAUGAAA | 4521 |
| AD-1181521.1 | asgsauccdGagCfCfuacuaugaauL96 | 4164 | asUfsucaUfaguaggcUfcdGgaucususc | 4343 | GAAGAUCCGAGCCUACUAUGAAA | 4522 |
| AD-1181522.1 | asgsauccdGadGcdCuacuaugaauL96 | 4165 | asUfsucaUfaguaggcUfcdGgaucususc | 4344 | GAAGAUCCGAGCCUACUAUGAAA | 4523 |
| AD-1181523.1 | asgsauccdGagCfCfUfacuaugaauL96 | 4166 | asUfsucaUfaguaggcUfcdGgaucususc | 4345 | GAAGAUCCGAGCCUACUAUGAAA | 4524 |
| AD-1181524.1 | asgsauccdGagCfCfuacuaugaauL96 | 4167 | asUfsucdAudAguaggcUfcdGgaucususc | 4346 | GAAGAUCCGAGCCUACUAUGAAA | 4525 |
| AD-570712.3 | cscsgagcCfgUfUfCfucucaauuuL96 | 4168 | asAfsauuGfuAfGfagaaCfgGfcucggsasu | 4347 | AUCCGAGCCGUUCUCUACAAUUA | 4526 |
| AD-1181525.1 | cscsgagcCfgUfUfCfucucaauuuL96 | 4169 | asAfsauuGfuagagaaCfgdGcucggsasu | 4348 | AUCCGAGCCGUUCUCUACAAUUA | 4527 |
| AD-1181526.1 | cscsgagcCfgUfUfCfucucaauuuL96 | 4170 | asdAsauuGfuagagaaCfgdGcucggsasu | 4349 | AUCCGAGCCGUUCUCUACAAUUA | 4528 |
| AD-1181527.1 | cscsgagcCfgUfUfCfucucaauuuL96 | 4171 | asdAsauuTgdTagagaaCfgdGcucggsasu | 4350 | AUCCGAGCCGUUCUCUACAAUUA | 4529 |
| AD-1181528.1 | cscsgagcCfgUfUfCfucucaauuuL96 | 4172 | asAfsaudTgdTagagaaCfgdGcucggsasu | 4351 | AUCCGAGCCGUUCUCUACAAUUA | 4530 |
| AD-1181529.1 | cscsgagcCfgUfUfCfucucaauuuL96 | 4173 | asAfsaudTgdTagagaaCfgdGcucggsgsc | 4352 | AUCCGAGCCGUUCUCUACAAUUA | 4531 |
| AD-1181530.1 | gsaagcCfgUfUfCfucucaauuuL96 | 4174 | asAfsaudTgdTagagaaCfgdGcucgsgsg | 4353 | AUCCGAGCCGUUCUCUACAAUUA | 4532 |
| AD-1181531.1 | cscsgagcCfgdTudCucucaauuuL96 | 4175 | asdAsauuTgdTagagaaCfgdGcucggsgsc | 4354 | AUCCGAGCCGUUCUCUACAAUUA | 4533 |
| AD-1181532.1 | cscsgagcCfgdTudCUfucacaauuuL96 | 4176 | asdAsauuTgdTagagaaCfgdGcucggsgsc | 4355 | AUCCGAGCCGUUCUCUACAAUUA | 4534 |
| AD-1181533.1 | cscsgagcdCgdTudCUfucacaauuuL96 | 4177 | asdAsauuTgdTagagaaCfgdGcucggsgsc | 4356 | AUCCGAGCCGUUCUCUACAAUUA | 4535 |
| AD-570713.3 | csgsagccGfuUfCfUfcuacaauuauL96 | 4178 | asUfsaauUfgUfAfgagaaAfcGfgcucggsa | 4357 | UCCGAGCCGUUCUCUACAAUUAC | 4536 |
| AD-1181534.1 | csgsagccGfuUfCfUfcuacaauuauL96 | 4179 | asUfsaauUfguagagaAfcdGgcucgsgsa | 4358 | UCCGAGCCGUUCUCUACAAUUAC | 4537 |
| AD-1181535.1 | csgsagccGfuUfCfUfcuacaauuauL96 | 4180 | asUfsaauUfguagagadAcdGgcucgsgsa | 4359 | UCCGAGCCGUUCUCUACAAUUAC | 4538 |
| AD-1181536.1 | csgsagccGfuUfCfUfcuacaauuauL96 | 4181 | asUfsaauUfguagagadAcdGgcucgsgsc | 4360 | UCCGAGCCGUUCUCUACAAUUAC | 4539 |
| AD-1181537.1 | csgsagccGfuUfCfUfcuacaauuauL96 | 4182 | asUfsaadTudGuagagadAcdGgcucgsgsc | 4361 | UCCGAGCCGUUCUCUACAAUUAC | 4540 |
| AD-1181538.1 | asgsccGfuUfCfUfcuacaauuauL96 | 4183 | asUfsaadTudGuagagadAcdGcucscsg | 4362 | UCCGAGCCGUUCUCUACAAUUAC | 4541 |
| AD-1181539.1 | csgsagccGuUfCfUfcuacaauuauL96 | 4184 | asUfsaauUfguagagadAfcdGgcucgsgsc | 4363 | UCCGAGCCGUUCUCUACAAUUAC | 4542 |
| AD-1181540.1 | csgsagccGuUfCfUfcuacaauuauL96 | 4185 | asUfsaauUfguagagadAcdGgcucgsgsc | 4364 | UCCGAGCCGUUCUCUACAAUUAC | 4543 |

TABLE 31-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-1181541.1 | csgsagccdGudTcdTcuacaauuauL96 | 4186 | asUfsaauUfguagagadAcdGgcucgsgsc | 4365 | UCCGAGCCGUUCUCUACAAUUAC | 4544 |
| AD-1181542.1 | csgsagccdGudTcdTCfuacaauuauL96 | 4187 | asUfsaauUfguagagadAcdGgcucgsgsc | 4366 | UCCGAGCCGUUCUCUACAAUUAC | 4545 |
| AD-570714.4 | gsasgccgUfuCfUfCfuacaauuacuL96 | 4188 | asGfsuaaUfuGfUfagagAfaCfggcucsgsg | 4367 | CCGAGCCGUUCUCUACAAUUACC | 4546 |
| AD-1181543.1 | gsasgccgUfuCfUfCfuacaauuacuL96 | 4189 | asdGsuaaUfuguagagAfaCfggcucsgsg | 4368 | CCGAGCCGUUCUCUACAAUUACC | 4547 |
| AD-1181544.1 | gsasgccgUfuCfUfCfuacaauuacuL96 | 4190 | asdGsuaaUfuguagadAaCfggcucsgsg | 4369 | CCGAGCCGUUCUCUACAAUUACC | 4548 |
| AD-1181545.1 | gsasgccgUfuCfUfCfuacaauuacuL96 | 4191 | asdGsuaaUfuguagagdAaCfggcucsgsg | 4370 | CCGAGCCGUUCUCUACAAUUACC | 4549 |
| AD-1181546.1 | gscscgUfuCfUfCfuacaauuacuL96 | 4192 | asdGsuaaUfuguagagdAaCfggcucscsu | 4371 | CCGAGCCGUUCUCUACAAUUACC | 4550 |
| AD-1181547.1 | gsasgccgUfuCfudCudCuacaauuacuL96 | 4193 | asdGsuaaUfuguagagdAaCfggcucsgsg | 4372 | CCGAGCCGUUCUCUACAAUUACC | 4551 |
| AD-1181548.1 | gsasgccgUfudCudCUfuacaauuacuL96 | 4194 | asdGsuaaUfuguagagdAaCfggcucsgsg | 4373 | CCGAGCCGUUCUCUACAAUUACC | 4552 |
| AD-1181549.1 | gsasgccgdTudCudCUfuacaauuacuL96 | 4195 | asdGsuaaUfuguagagdAaCfggcucsgsg | 4374 | CCGAGCCGUUCUCUACAAUUACC | 4553 |
| AD-571826.5 | csasagccUfuGfGfCfucaauaccauL96 | 4196 | asUfsgguAfuUfGfagcAfaGfgcuugsgsa | 4375 | UCCAAGCCUUGGCUCAAUACCAA | 4554 |
| AD-1181550.1 | csasagccUfuGfGfCfucaauaccauL96 | 4197 | asUfsgguAfuugagccdAaGgcuugsgsa | 4376 | UCCAAGCCUUGGCUCAAUACCAA | 4555 |
| AD-1181551.1 | csasagccUfuGfGfCfucaauaccauL96 | 4198 | asUfsgguAfuugagccdAaGgcuugsgsc | 4377 | UCCAAGCCUUGGCUCAAUACCAA | 4556 |
| AD-1181552.1 | csasagccUfuGfGfCfucaauaccauL96 | 4199 | asUfsggdTadTugagccdAadGgcuugsgsc | 4378 | UCCAAGCCUUGGCUCAAUACCAA | 4557 |
| AD-1181553.1 | asgscCfuGfGfCfucaauaccauL96 | 4200 | asUfsggdTadTugagccdAadGgcusus | 4379 | UCCAAGCCUUGGCUCAAUACCAA | 4558 |
| AD-1181554.1 | csasagccUfudGgdCucaauaccauL96 | 4201 | asUfsggdTadTugagccdAadGgcuugsgsc | 4380 | UCCAAGCCUUGGCUCAAUACCAA | 4559 |
| AD-1181555.1 | csasagccUfudGgdCUfcaauaccauL96 | 4202 | asUfsggdTadTugagccdAadGgcuugsgsc | 4381 | UCCAAGCCUUGGCUCAAUACCAA | 4560 |
| AD-572040.6 | ascsucaccUfuGfUfAfauaaauucguL96 | 4203 | asCfsgaaUfuUfAfuuacAfgGfugagususg | 4382 | CAACUCACCUGUAAUAAAUUCGA | 4561 |
| AD-1181556.1 | ascsucaccUfuGfUfAfauaaauucguL96 | 4204 | asCfsgaaUfuuauuacdAgdGugagususg | 4383 | CAACUCACCUGUAAUAAAUUCGA | 4562 |
| AD-1181557.1 | ascsucaccUfuGfUfAfauaaauucguL96 | 4205 | asCfsgadAudTuauuacdAgdGugagususg | 4384 | CAACUCACCUGUAAUAAAUUCGA | 4563 |
| AD-1181558.1 | ascsucaccUfuGfUfAfauaaauucguL96 | 4206 | asCfsgaaUfuuauuacdAgdGugaguscsc | 4385 | CAACUCACCUGUAAUAAAUUCGA | 4564 |
| AD-1181559.1 | uscsacCfuGfUfAfauaaauucguL96 | 4207 | asCfsgaaUfuuauuacdAgdGugasgsu | 4386 | CAACUCACCUGUAAUAAAUUCGA | 4565 |
| AD-1181560.1 | ascsucaccCfudGudAauuaauucguL96 | 4208 | asCfsgaaUfuuauuacdAgdGugagususg | 4387 | CAACUCACCUGUAAUAAAUUCGA | 4566 |

TABLE 31-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-1181561.1 | ascsucaCfudGudAdAuaaauucguL96 | 4209 | asCfsgaaUfuuauuacdAgdGugagususg | 4388 | CAACUCACCUGUAAUAAAUUCGA | 4567 |
| AD-1181562.1 | ascsucaCfudGudAAuaaauucguL96 | 4210 | asCfsgaaUfuuauuacdAgdGugagususg | 4389 | CAACUCACCUGUAAUAAAUUCGA | 4568 |
| AD-1181560.2 | ascsucaCfudGudAauaaauucguL96 | 4211 | asCfsgaaUfuuauuacdAgdGugagususg | 4390 | CAACUCACCUGUAAUAAAUUCGA | 4569 |
| AD-572110.5 | gsasugcCfaGfAfAfcacuaugauuL96 | 4212 | asAfsucaUfaGfUfguucUfuGfgcaucscsu | 4391 | AGGAUGCCAAGACACUAUGAUC | 4570 |
| AD-1181563.1 | gsasugcCfaGfAfAfcacuaugauuL96 | 4213 | asAfsucaUfagcguucUfudGgcaucscsu | 4392 | AGGAUGCCAAGACACUAUGAUC | 4571 |
| AD-1181564.1 | gsasugcCfaGfAfAfcacuaugauuL96 | 4214 | asdAsucdAdAgcguucUfudGgcaucscsu | 4393 | AGGAUGCCAAGACACUAUGAUC | 4572 |
| AD-1181565.1 | gsasugcCfaGfAfAfcacuaugauuL96 | 4215 | asdAsucaUfagcguucUfudGgcaucscsu | 4394 | AGGAUGCCAAGACACUAUGAUC | 4573 |
| AD-1181566.1 | gsasugcCfaGfAfAfcacuaugauuL96 | 4216 | asdAsucaUfagcguucUfudGgcaucsgsg | 4395 | AGGAUGCCAAGACACUAUGAUC | 4574 |
| AD-1181567.1 | usgsccAfaGfAfAfcacuaugauuL96 | 4217 | asdAsucaUfagcguucUfudGgcasusc | 4396 | AGGAUGCCAAGACACUAUGAUC | 4575 |
| AD-1181568.1 | gsasugcCfaadGadACfacuaugauuL96 | 4218 | asAfsucaUfagcguucUfudGgcaucscsu | 4397 | AGGAUGCCAAGACACUAUGAUC | 4576 |
| AD-1181569.1 | gsasugcCfadGadAcacuaugauuL96 | 4219 | asAfsucaUfagcguucUfudGgcaucscsu | 4398 | AGGAUGCCAAGACACUAUGAUC | 4577 |
| AD-1181570.1 | gsasugcCfadGadAdacacuaugauuL96 | 4220 | asAfsucaUfagcguucUfudGgcaucscsu | 4399 | AGGAUGCCAAGACACUAUGAUC | 4578 |
| AD-1181571.1 | gsasugcCfaadGadACfacuaugauuL96 | 4221 | asAfsucaUfagcguucUfudGgcaucscsu | 4400 | AGGAUGCCAAGACACUAUGAUC | 4579 |
| AD-1181572.1 | gsasugcCfaadGadACfacuaugauuL96 | 4222 | asdAsucaUfagcguucUfudGgcaucscsu | 4401 | AGGAUGCCAAGACACUAUGAUC | 4580 |
| AD-572387.6 | uscsaaggUfcUfAfCfgccuauuacuL96 | 4223 | asGfsuaaUfaGfGfcguaGfaCfcuugascsu | 4402 | AGUCAAGGUCUACGCCUAUUACA | 4581 |
| AD-1181573.1 | uscsaaggUfcUfAfCfgccuauuacuL96 | 4224 | asdGsuaaUfaggcguaGfaCfcuugascsu | 4403 | AGUCAAGGUCUACGCCUAUUACA | 4582 |
| AD-1181574.1 | uscsaaggUfcUfAfCfgccuauuacuL96 | 4225 | asdGsuaaUfaggcguadGaCfcuugascsu | 4404 | AGUCAAGGUCUACGCCUAUUACA | 4583 |
| AD-1181575.1 | uscsaaggUfcUfAfCfgccuauuacuL96 | 4226 | asdGsuaaUfaggcguadGaCfcuugascsc | 4405 | AGUCAAGGUCUACGCCUAUUACA | 4584 |
| AD-1181576.1 | asaaggUfcUfAfCfgccuauuacuL96 | 4227 | asdGsuaaUfaggcguadGaCfcuugasgsa | 4406 | AGUCAAGGUCUACGCCUAUUACA | 4585 |
| AD-1181577.1 | uscsaaggUfcUfacCfgccuauuacuL96 | 4228 | asdGsuaaUfaggcguadGaCfcuugascsu | 4407 | AGUCAAGGUCUACGCCUAUUACA | 4586 |
| AD-1181578.1 | uscsaaggUfcUfdACfgccuauuacuL96 | 4229 | asdGsuaaUfaggcguadGaCfcuugascsu | 4408 | AGUCAAGGUCUACGCCUAUUACA | 4587 |
| AD-1181579.1 | uscsaaggUfcUfACfgccuauuacuL96 | 4230 | asdGsuaaUfaggcguadGaCfcuugascsu | 4409 | AGUCAAGGUCUACGCCUAUUACA | 4588 |
| AD-1181580.1 | uscsaaggUfcdTadCgccuauuacuL96 | 4231 | asdGsuaaUfaggcguadGaCfcuugascsu | 4410 | AGUCAAGGUCUACGCCUAUUACA | 4589 |
| AD-1181581.1 | uscsaaggUfcdTacdGccuauuacuL96 | 4232 | asdGsuaaUfaggcguadGaCfcuugascsu | 4411 | AGUCAAGGUCUACGCCUAUUACA | 4590 |

TABLE 31-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-569272.6 | asasuucuAfcUfAfCfuaucuauaaacuL96 | 4233 | asGfsuuaUfaGfAfuguaGfuAfgaauususc | 4412 | GAAAUUCUACUACAUCUAUAACG | 4591 |
| AD-1181582.1 | asasuucuAfcUfAfCfuaucuauaaacuL96 | 4234 | asdGsuuaUfagauguaGfuAfgaauususc | 4413 | GAAAUUCUACUACAUCUAUAACG | 4592 |
| AD-1181583.1 | asasuucuAfcUfAfCfuaucuauaaacuL96 | 4235 | asdGsuuaUfagauguaGfuAfgaauususc | 4414 | GAAAUUCUACUACAUCUAUAACG | 4593 |
| AD-1181584.1 | asasuucuAfcUfAfCfuaucuauaaacuL96 | 4236 | asdGsuuaUfagauguaTadGudAgaauususc | 4415 | GAAAUUCUACUACAUCUAUAACG | 4594 |
| AD-1181585.1 | asasuucuAfcUfAfCfuaucuauaaacuL96 | 4237 | asdGsuuaUfagauguaGfuAfgaauusgsg | 4416 | GAAAUUCUACUACAUCUAUAACG | 4595 |
| AD-1181586.1 | asasuucuAfcUfAfCfuaucuauaaacuL96 | 4238 | asdGsuuaUfagaugdTadGudAgaauusgsg | 4417 | GAAAUUCUACUACAUCUAUAACG | 4596 |
| AD-1181587.1 | asasuucuAfcUfAfCfuaucuauaaacuL96 | 4239 | asdGsuuaUfagauguadGuAfgaasusu | 4418 | AAUUCUACUACAUCUAUAACG | 4597 |
| AD-1181588.1 | asasuucuAfcUfAfCfuaucuauaaacuL96 | 4240 | asdGsuuaUfagaugdTadGudAgaasusu | 4419 | AAUUCUACUACAUCUAUAACG | 4598 |
| AD-1181589.1 | asasuucuAfcUfAfCfuaucuauaaacuL96 | 4241 | asGfsuuaUfaGfAfuguaGfuAfgaaususc | 4420 | AAUUCUACUACAUCUAUAACG | 4599 |
| AD-1181590.1 | asasuucudAcUfAfCfuaucuauaaacuL96 | 4242 | asdGsuuaUfagauguadGuAfgaaususc | 4421 | AAUUCUACUACAUCUAUAACG | 4600 |
| AD-1181591.1 | asasuucudAcUfAfCfuaucuauaaacuL96 | 4243 | asdGsuuaUfagauguaTadGudAgaauusgsg | 4422 | AAUUCUACUACAUCUAUAACG | 4601 |
| AD-1181592.1 | asasuucudAcUfAfCfuaucuauaaacuL96 | 4244 | asdGsuuaUfagaugdTadGudAgfaasusu | 4423 | AAUUCUACUACAUCUAUAACG | 4602 |
| AD-1181593.1 | asasuucudAcUfAfCfuaucuauaaacuL96 | 4245 | asdGsuuaUfagaugdTadGudAgaasusu | 4424 | AAUUCUACUACAUCUAUAACG | 4603 |
| AD-565034.2 | csasgagaAfaUfUfCfuacuacaucuL96 | 4246 | asGfsaugu(Agn)guagaaUfuUfcucugsusa | 4425 | UACAGAGAAAUUCUACUACAUCU | 4604 |
| AD-1181594.1 | csasgagadAaUfUfCfuacuacaucuL96 | 4247 | asdGsaudGu(Agn)guagaaUfuUfcucugsusc | 4426 | UACAGAGAAAUUCUACUACAUCU | 4605 |
| AD-1181595.1 | csasgagadAaUfUfCfuacuacaucuL96 | 4248 | asdGsaudGu(A2p)guagaaUfuUfcucugsusc | 4427 | UACAGAGAAAUUCUACUACAUCU | 4606 |
| AD-565035.2 | asgsagaaAfuUfCfUfuacuacaucuuL96 | 4249 | asAfsgaug(Tgn)aguagaAfuUfucucusgsu | 4428 | ACAGAGAAAUUCUACUACAUCUA | 4607 |
| AD-1181596.1 | asgsagaadAuUfCfUfuacuacaucuuL96 | 4250 | asAfsgadTg(Tgn)aguagaAfuUfucucusgsu | 4429 | ACAGAGAAAUUCUACUACAUCUA | 4608 |
| AD-1181597.1 | asgsagaadAuUfCfUfuacuacaucuuL96 | 4251 | asAfsgadTg(U2p)aguagaAfuUfucucusgsu | 4430 | ACAGAGAAAUUCUACUACAUCUA | 4609 |
| AD-1181598.1 | asgsagaaUfcUfCfUfuacuacauaucuuL96 | 4252 | asAfsgadTadTaguagaAfuUfucucuscsu | 4431 | ACAGAGAAAUUCUACUACAUCUA | 4610 |
| AD-565037.2 | asgsaaauUfcUfAfCfuacaucuauuL96 | 4253 | asAfsuaga(Tgn)guaguagfaAfuuucuscsu | 4432 | AGAGAAAUUCUACUACAUCUAUA | 4611 |
| AD-1181599.1 | asgsaaaudUfcUfAfCfuacaucuauuL96 | 4254 | asAfsuadGa(Tgn)guagdTadGaAfuuucuscsu | 4433 | AGAGAAAUUCUACUACAUCUAUA | 4612 |
| AD-1181600.1 | asgsaaauUfcUfAfCfuacaucuauuL96 | 4255 | asAfsuadGa(U2p)guagdTadGaAfuuucuscsu | 4434 | AGAGAAAUUCUACUACAUCUAUA | 4613 |

TABLE 31-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: | SEQ ID NO: |
|---|---|---|---|---|---|---|---|
| AD-1181601.1 | asgsaaauUfcUfAfCfuacaucuauuL96 | 4256 | asAfsuadGadT guagdTadGaAfuuucucsu | 4435 | AGAGAAAUUCUACUACAUCUAUA | 4614 | |
| AD-567072.2 | csasagguCfuUfCfUfcucuggcuguL96 | 4257 | asCfsagcc(Agn)gagagaAfgAfccuugsasc | 4436 | GUCAAGGUCUUCUCUCUGGCUGU | 4615 | |
| AD-1181602.1 | csasagguCfuUfCfUfcucuggcuguL96 | 4258 | asCfsagdCc(Agn)gagagaAfgAfccuugsgsc | 4437 | GUCAAGGUCUUCUCUCUGGCUGU | 4616 | |
| AD-1181603.1 | csasagguCfuUfCfUfcucuggcuguL96 | 4259 | asCfsagdCc(A2p)gagagaAfgAfccuugsgsc | 4438 | GUCAAGGUCUUCUCUCUGGCUGU | 4617 | |
| AD-1181604.1 | csasagguCfuUfCfUfcucuggcuguL96 | 4260 | asCfsagdCcdAgagagaAfgAfccuugsgsc | 4439 | GUCAAGGUCUUCUCUCUGGCUGU | 4618 | |
| AD-1181605.1 | asgggagaCfuUfCfCfuugaagccauL96 | 4261 | asUfsggcu(Tgn)caaggaAfgUfcuccusgsc | 4440 | GCAGGAGACUUCCUUGAAGCCAA | 4619 | |
| AD-1181606.1 | asgggagaCfuUfCfCfuugaagccauL96 | 4262 | asUfsggdCu(Tgn)caaggaAfgUfcuccusgsc | 4441 | GCAGGAGACUUCCUUGAAGCCAA | 4620 | |
| AD-567301.2 | gsggagacUfuCfCfUfugaagccaaL96 | 4263 | asUfsggdCu(U2p)caaggaAfgUfcuccsusg | 4442 | CAGGAGACUUCCUUGAAGCCAAC | 4621 | |
| AD-1181607.1 | gsggagacUfuCfCfUfugaagccaaL96 | 4264 | asUfsuggc(Tgn)ucaaggAfaGfucuccsusg | 4443 | CAGGAGACUUCCUUGAAGCCAAC | 4622 | |
| AD-1181608.1 | gsggagacUfuCfCfUfugaagccaaL96 | 4265 | asUfsugdGc(Tgn)ucaadGgAfadGucuccsusg | 4444 | CAGGAGACUUCCUUGAAGCCAAC | 4623 | |
| AD-569262.2 | cscsuacadGagaAfaAfauucuacuacL96 | 4266 | asUfsugdGc(U2p)ucaadGgAfadGucuccsusg | 4445 | AGCCUACAGAGAAAUUCUACUAC | 4624 | |
| AD-1181609.1 | cscsuacadGagaAfaAfauucuacuacL96 | 4267 | asUfsaguAfgAfAfauucUfcUfguaggscsu | 4446 | AGCCUACAGAGAAAUUCUACUAC | 4625 | |
| AD-1181610.1 | cscsuacadGagaAfaAfauucuacuacL96 | 4268 | asUfsagdTadGaauuucUfcUfguaggscsu | 4447 | AGCCUACAGAGAAAUUCUACUAC | 4626 | |
| AD-569265.2 | ascsagagaAfaAfUfUfcuacuacuacL96 | 4269 | asUfsagdTa(G2p)aauuucUfcUfguaggscsu | 4448 | CUACAGAGAAAUUCUACUACAUC | 4627 | |
| AD-1181611.1 | ascsagagaAfaAfUfUfcuacuacuacL96 | 4270 | asAfsuguAfgUfAfgaauUfcCfucuguasag | 4449 | CUACAGAGAAAUUCUACUACAUC | 4628 | |
| AD-1181612.1 | ascsagagaAfaAfUfUfcuacuacuacL96 | 4271 | asAfsugdTadGuagaaUfuCfucugusgsg | 4450 | CUACAGAGAAAUUCUACUACAUC | 4629 | |
| AD-569268.2 | ascsagagAfaaUfUfcuacuacaucuL96 | 4272 | asdAsugdTadGuagaaUfuCfucugusgsg | 4451 | CAGAGAAAUUCUACUACAUCUAU | 4630 | |
| AD-1181613.1 | gsasgaaaUfUfcUfAfcuacuacaucuL96 | 4273 | asUfsagaUfgUfAfguagaAfaUfuucucsusg | 4452 | CAGAGAAAUUCUACUACAUCUAU | 4631 | |
| AD-1181614.1 | gsasgaaaUfUfcUfAfcuacuacaucuL96 | 4274 | asUfsagdAudGuaguaGfaGaUfuucucsusg | 4453 | CAGAGAAAUUCUACUACAUCUAU | 4632 | |
| AD-569269.2 | gsasgaaaUfUfcUfAfcuacaucuauuL96 | 4275 | asAfsuagdAfaUfUfaguaGfaAfuuucucsu | 4454 | CAGAGAAAUUCUACUACAUCUAU | 4633 | |
| AD-1181615.1 | asgsaaauUfcUfAfCfuacaucuauuL96 | 4276 | asAfsuagAfuGfUfAfguagdTadGaAfuuucucsu | 4455 | AGAGAAAUUCUACUACAUCUAUA | 4634 | |
| AD-1181616.1 | asgsaaauUfcUfAfCfuacaucuauuL96 | 4277 | asAfsuagAfuguagdTadGaDfuuuucsu | 4456 | AGAGAAAUUCUACUACAUCUAUA | 4635 | |
| AD-1181617.1 | asgsaaauUfcCfuacaucuauuL96 | 4278 | asdAsuadGadTguagdTadGaDfauuucscsu | 4457 | AGAGAAAUUCUACUACAUCUAUA | 4636 | |
| AD-569270.2 | gsasaauCfuAfCfUfacaucuauauaL96 | 4279 | asUfsauaGfauFgfuaguAfgAfauuucscsuc | 4458 | GAGAAAUUCUACUACAUCUAUAA | 4637 | |

TABLE 31-continued

Modified Sense and Antisense Strand Sequences of Complement Component C3 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-1181617.1 | gsasaauuCfuAfCfUfacaucuauauL96 | 4280 | asUfsaudAgdAguguaguAfgAfauuucsusc | 4459 | GAGAAAUUCUACUACAUCUAUAA | 4638 |
| AD-1181618.1 | gsasaauuCfuaCfUfacaucuauauL96 | 4281 | asUfsaudAgdAguguadGudAgdAauuucsusc | 4460 | GAGAAAUUCUACUACAUCUAUAA | 4639 |
| AD-570676.2 | ascsccuaCfuCfUfGfuuguucgaauL96 | 4282 | asUfsucgAfaCfAfacagAfgUfagguusasg | 4461 | CUACCCUACUCUGUUGUUCGAAA | 4640 |
| AD-1181619.1 | ascsccuaCfuCfUfdGuuguucgaauL96 | 4283 | asUfsucdGadAcaacagAfgUfagguusgsg | 4462 | CUACCCUACUCUGUUGUUCGAAA | 4641 |
| AD-1181620.1 | ascsccuaCfuCfUfdGuuguucgaauL96 | 4284 | asUfsucdGa(Agn)caacagAfgUfagguusgsg | 4463 | CUACCCUACUCUGUUGUUCGAAA | 4642 |
| AD-571304.2 | csasagguCfuUfCfUfcucuggcuguL96 | 4285 | asCfsagcCfaGfAfagagaAfgAfccuugsasc | 4464 | GUCAAGGUCUUCUCUCUGGCUGU | 4643 |
| AD-1181604.2 | csasagguCfuUfCfUfcucuggcuguL96 | 4286 | asCfsagdCcdAgagagaAfgAfccuugsgsc | 4465 | GUCAAGGUCUUCUCUCUGGCUGU | 4644 |
| AD-1181621.1 | csasagguCfuUfCfUfcucuggcuguL96 | 4287 | asCfsagdCc(Agn)gagadGadAgdAccuugsgsc | 4466 | GUCAAGGUCUUCUCUCUGGCUGU | 4645 |
| AD-1181946.2 | usgsgcucAfaUfGfAfacagagauauL96 | 4288 | asUfsaucu(C2p)uguucaUfuGfagcaasasc | 4467 | GUUGGCUCAAUGAACAGAGAUAC | 4646 |
| AD-1181622.1 | usgsgcucAfaUfgdAacagagauauL96 | 4289 | asUfsaudCu(C2p)uguudCaUfudGagcaasgsc | 4468 | GUUGGCUCAAUGAACAGAGAUAC | 4647 |
| AD-1181623.1 | usgsgcucdAaUfgdAacagagauauL96 | 4290 | asUfsaudCu(C2p)uguudCaUfudGagcaasgsc | 4469 | GUUGGCUCAAUGAACAGAGAUAC | 4648 |
| AD-1181624.1 | usgsgcucdAaUfgdAacagagauauL96 | 4291 | asUfsaudCu(Cgn)uguudCaUfudGagcaasgsc | 4470 | GUUGGCUCAAUGAACAGAGAUAC | 4649 |
| AD-1069956.2 | gscsugagGfaGfAfAfuugcuucauuL96 | 4292 | asAfsugaa(G2p)caauucUfcCfucagcsasc | 4471 | GUGCUGAGGAGAAUUGCUUCAUA | 4650 |
| AD-1181625.1 | gscsugagGfadGfAfAfuugcuucauuL96 | 4293 | asAfsugdAa(G2p)caauucUfcCfucagcsgsc | 4472 | GUGCUGAGGAGAAUUGCUUCAUA | 4651 |
| AD-1181626.1 | gscsugagGfadGfadAfAfuugcuucauuL96 | 4294 | asdAsugdAa(G2p)caauucUfcCfucagcsgsc | 4473 | GUGCUGAGGAGAAUUGCUUCAUA | 4652 |

TABLE 32

C3 Free Uptake Single Dose Screens in PCH cells (% C3 mRNA Remaining)

| Duplex | 500 nM Dose Avg | SD | 100 nm Dose Avg | SD | 10 nM Dose Avg | SD | 1 nM Dose Avg | SD |
|---|---|---|---|---|---|---|---|---|
| AD-564742.5 | 55 | 5 | 50 | 6 | 70 | 7 | 87 | 30 |
| AD-1181478.1 | 51 | 6 | 37 | 6 | 81 | 15 | 95 | 25 |
| AD-1181479.1 | 54 | 4 | 48 | 10 | 77 | 12 | 127 | 4 |
| AD-1181480.1 | 40 | 0 | 53 | 2 | 88 | 0 | 107 | 14 |
| AD-1181481.1 | 54 | 5 | 50 | 10 | 89 | 2 | 143 | 36 |
| AD-1181482.1 | 48 | 19 | 46 | 10 | 81 | 18 | 151 | 58 |
| AD-1181483.1 | 97 | 4 | 82 | 19 | 113 | 33 | 175 | 36 |
| AD-1181484.1 | 52 | 9 | 55 | 3 | 88 | 13 | 97 | 6 |
| AD-567304.4 | 51 | 9 | 70 | 5 | 82 | 12 | 89 | 19 |
| AD-1181485.1 | 58 | 4 | 56 | 13 | 79 | 8 | 74 | 8 |
| AD-1181486.1 | 56 | 7 | 46 | 5 | 62 | 9 | 97 | 11 |
| AD-1181487.1 | 55 | 5 | 56 | 10 | 81 | 8 | 95 | 19 |
| AD-1181488.1 | 45 | 1 | 47 | 2 | 72 | 6 | 97 | 4 |
| AD-1181489.1 | 67 | 5 | 81 | 9 | 89 | 9 | 118 | 16 |
| AD-1181490.1 | 95 | 2 | 103 | 13 | 123 | 7 | 138 | 17 |
| AD-1181491.1 | 71 | 8 | 95 | 21 | 111 | 11 | 170 | 28 |
| AD-1181492.1 | 62 | 13 | 91 | 11 | 92 | 7 | 77 | 5 |
| AD-567315.8 | 41 | 13 | 54 | 12 | 77 | 2 | 73 | 18 |
| AD-1181493.1 | 50 | 9 | 64 | 7 | 69 | 2 | 110 | 6 |
| AD-1181494.1 | 24 | 3 | 36 | 4 | 62 | 8 | 90 | 6 |
| AD-1181495.1 | 45 | 6 | 69 | 10 | 80 | 12 | 124 | 17 |
| AD-1181496.1 | 58 | 4 | 83 | 26 | 90 | 3 | 105 | 7 |
| AD-1181497.1 | 60 | 7 | 108 | 9 | 100 | 8 | 140 | 5 |
| AD-1181498.1 | 48 | 5 | 62 | 16 | 86 | 3 | 88 | 23 |
| AD-1181499.1 | 64 | 2 | 73 | 5 | 85 | 4 | 122 | 0 |
| AD-1181500.1 | 51 | 4 | 55 | 4 | 87 | 10 | 91 | 11 |
| AD-1181501.1 | 72 | 7 | 75 | 8 | 98 | 19 | 129 | 7 |
| AD-1181502.1 | 55 | 14 | 67 | 5 | 107 | 13 | 133 | 2 |
| AD-568586.5 | 40 | 3 | 64 | 4 | 95 | 18 | 146 | 13 |
| AD-1181503.1 | 49 | 2 | 74 | 2 | 95 | 20 | 139 | 18 |
| AD-1181504.1 | 57 | 12 | 57 | 10 | 85 | 10 | 71 | 14 |
| AD-1181505.1 | 41 | 7 | 49 | 6 | 87 | 3 | 84 | 23 |
| AD-1181506.1 | 36 | 0 | 43 | 2 | 81 | 2 | 73 | 3 |
| AD-1181507.1 | 85 | 13 | 83 | 10 | 124 | 5 | 110 | 12 |
| AD-1181508.1 | 56 | 8 | 59 | 1 | 89 | 13 | 118 | 27 |
| AD-1181509.1 | 47 | 7 | 53 | 1 | 89 | 14 | 112 | 15 |
| AD-1181510.1 | 55 | 6 | 56 | 8 | 92 | 12 | 135 | 7 |
| AD-568978.5 | 144 | 90 | 77 | 2 | 110 | 12 | 158 | 25 |
| AD-1181511.1 | 72 | 9 | 87 | 15 | 93 | 8 | 79 | 8 |
| AD-1181513.1 | 46 | 2 | 60 | 0 | 100 | 5 | 84 | 2 |
| AD-1181514.1 | 44 | 3 | 52 | 7 | 125 | 18 | 93 | 1 |
| AD-1181515.1 | 86 | 10 | 75 | 4 | 123 | 6 | 135 | 10 |
| AD-1181516.1 | 65 | 3 | 83 | 8 | 92 | 10 | 110 | 18 |
| AD-1181517.1 | 61 | 7 | 81 | 10 | 103 | 10 | 131 | 27 |
| AD-569164.9 | 48 | 5 | 44 | 3 | 64 | 10 | 80 | 4 |
| AD-1181518.1 | 39 | 4 | 44 | 5 | 61 | 4 | 83 | 13 |
| AD-1181519.1 | 24 | 3 | 30 | 1 | 70 | 3 | 106 | 4 |
| AD-1181520.1 | 24 | 2 | 28 | 2 | 79 | 10 | 112 | 15 |
| AD-1181521.1 | 51 | 4 | 64 | 7 | 119 | 18 | 134 | 11 |
| AD-1181522.1 | 75 | 6 | 76 | 6 | 117 | 7 | 114 | 5 |
| AD-1181523.1 | 58 | 9 | 60 | 12 | 81 | 8 | 122 | 11 |
| AD-1181524.1 | 50 | 5 | 53 | 10 | 80 | 6 | 108 | 1 |
| AD-570712.3 | 37 | 3 | 37 | 4 | 58 | 4 | 71 | 3 |
| AD-1181525.1 | 34 | 9 | 44 | 5 | 70 | 7 | 81 | 2 |
| AD-1181526.1 | 35 | 5 | 47 | 8 | 70 | 2 | 81 | 4 |
| AD-1181527.1 | 35 | 7 | 29 | 4 | 88 | 15 | 106 | 21 |
| AD-1181528.1 | 29 | 0 | 30 | 3 | 99 | 19 | 136 | 8 |
| AD-1181529.1 | 34 | 2 | 36 | 6 | 73 | 7 | 98 | 4 |
| AD-1181530.1 | 34 | 3 | 39 | 13 | 64 | 16 | 84 | 8 |
| AD-1181531.1 | 75 | 10 | 91 | 35 | 110 | 17 | 107 | 26 |
| AD-1181532.1 | 66 | 1 | 77 | 5 | 73 | 16 | 92 | 19 |
| AD-1181533.1 | 61 | 5 | 78 | 8 | 81 | 9 | 81 | 13 |
| AD-570713.3 | 48 | 8 | 52 | 11 | 98 | 22 | 110 | 28 |
| AD-1181534.1 | 44 | 6 | 52 | 9 | 96 | 27 | 105 | 15 |
| AD-1181535.1 | 82 | 12 | 74 | 10 | 97 | 5 | 112 | 9 |
| AD-1181536.1 | 75 | 11 | 94 | 26 | 108 | 15 | 133 | 9 |
| AD-1181537.1 | 48 | 4 | 69 | 11 | 89 | 12 | 105 | 4 |
| AD-1181538.1 | 45 | 10 | 70 | 6 | 65 | 12 | 89 | 2 |
| AD-1181539.1 | 45 | 6 | 73 | 5 | 71 | 3 | 74 | 13 |
| AD-1181540.1 | 90 | 4 | 86 | 6 | 84 | 8 | 89 | 9 |
| AD-1181541.1 | 78 | 9 | 116 | 20 | 111 | 24 | 101 | 19 |
| AD-1181542.1 | 86 | 19 | 104 | 15 | 96 | 8 | 108 | 2 |
| AD-570714.4 | 37 | 10 | 50 | 9 | 58 | 8 | 94 | 16 |
| AD-1181543.1 | 37 | 5 | 57 | 14 | 61 | 15 | 87 | 20 |
| AD-1181544.1 | 51 | 1 | 60 | 18 | 93 | 16 | 114 | 12 |
| AD-1181545.1 | 62 | 6 | 65 | 9 | 67 | 9 | 71 | 12 |
| AD-1181546.1 | 55 | 6 | 73 | 13 | 85 | 9 | 87 | 7 |
| AD-1181547.1 | 95 | 11 | 88 | 2 | 82 | 1 | 103 | 35 |
| AD-1181548.1 | 89 | 6 | 86 | 8 | 91 | 18 | 103 | 16 |
| AD-1181549.1 | 83 | 13 | 104 | 43 | 87 | 3 | 147 | 62 |
| AD-571826.5 | 40 | 3 | 55 | 13 | 76 | 12 | 145 | 36 |
| AD-1181550.1 | 74 | 24 | 78 | 12 | 71 | 6 | 230 | 26 |
| AD-1181551.1 | 70 | 7 | 73 | 7 | 84 | 15 | 68 | 2 |
| AD-1181552.1 | 33 | 6 | 51 | 9 | 80 | 18 | 96 | 20 |
| AD-1181553.1 | 34 | 5 | 50 | 12 | 82 | 19 | 97 | 12 |
| AD-1181554.1 | 68 | 10 | 80 | 17 | 91 | 12 | 100 | 20 |
| AD-1181555.1 | 69 | 17 | 79 | 16 | 109 | 4 | 110 | 21 |
| AD-572040.6 | 32 | 4 | 60 | 8 | 91 | 15 | 115 | 19 |
| AD-1181556.1 | 74 | 8 | 121 | 31 | 115 | 19 | 129 | 34 |
| AD-1181557.1 | 64 | 8 | 56 | 5 | 106 | 20 | 89 | 12 |
| AD-1181558.1 | 103 | 6 | 104 | 4 | 150 | 16 | 135 | 14 |
| AD-1181559.1 | 64 | 3 | 86 | 4 | 138 | 21 | 167 | 37 |
| AD-1181560.1 | 99 | 2 | 121 | 26 | 154 | 14 | 155 | 10 |
| AD-1181561.1 | 78 | 7 | 104 | 33 | 137 | 2 | 191 | 35 |
| AD-1181562.1 | 94 | 7 | 81 | 30 | 105 | 20 | 176 | 53 |
| AD-1181560.2 | 122 | 34 | 104 | 9 | 177 | 46 | 161 | 40 |
| AD-572110.5 | 41 | 9 | 44 | 7 | 72 | 5 | 139 | 24 |
| AD-1181563.1 | 24 | 5 | 44 | 4 | 97 | 18 | 107 | 11 |
| AD-1181564.1 | 57 | 7 | 50 | 17 | 93 | 14 | 107 | 11 |
| AD-1181565.1 | 42 | 10 | 47 | 7 | 88 | 6 | 133 | 7 |
| AD-1181566.1 | 56 | 6 | 64 | 4 | 95 | 13 | 113 | 17 |
| AD-1181567.1 | 30 | 3 | 46 | 11 | 85 | 5 | 146 | 23 |
| AD-1181568.1 | 88 | 8 | 77 | 2 | 92 | 5 | 148 | 15 |
| AD-1181569.1 | 58 | 12 | 72 | 22 | 134 | 18 | 156 | 5 |
| AD-1181570.1 | 62 | 3 | 83 | 29 | 153 | 50 | 147 | 32 |
| AD-1181571.1 | 25 | 1 | 64 | 8 | 120 | 24 | 86 | 9 |
| AD-1181572.1 | 92 | 10 | 77 | 12 | 114 | 22 | 105 | 12 |
| AD-572387.6 | 93 | 18 | 78 | 9 | 91 | 8 | 136 | 33 |
| AD-1181573.1 | 82 | 8 | 91 | 20 | 99 | 7 | 119 | 14 |
| AD-1181574.1 | 102 | 4 | 106 | 5 | 140 | 36 | 132 | 17 |
| AD-1181575.1 | 119 | 12 | 111 | 26 | 100 | 11 | 157 | 17 |
| AD-1181576.1 | 112 | 7 | 124 | 38 | 116 | 8 | 145 | 16 |
| AD-1181577.1 | 91 | 10 | 111 | 16 | 107 | 9 | 95 | 3 |
| AD-1181578.1 | 94 | 13 | 94 | 13 | 109 | 5 | 97 | 8 |
| AD-1181579.1 | 102 | 1 | 97 | 22 | 90 | 10 | 113 | 8 |
| AD-1181580.1 | 102 | 12 | 102 | 6 | 101 | 10 | 122 | 9 |
| AD-1181581.1 | 102 | 13 | 80 | 12 | 91 | 7 | 143 | 9 |
| AD-569272.6 | 68 | 10 | 45 | 2 | 65 | 7 | 121 | 17 |
| AD-1181582.1 | 115 | 38 | 97 | 13 | 94 | 16 | 153 | 60 |
| AD-1181583.1 | 82 | 3 | 83 | 8 | 106 | 21 | 90 | 17 |
| AD-1181584.1 | 88 | 2 | 78 | 5 | 93 | 5 | 94 | 24 |
| AD-1181585.1 | 97 | 7 | 94 | 26 | 97 | 5 | 115 | 22 |
| AD-1181586.1 | 98 | 5 | 99 | 21 | 92 | 8 | 128 | 22 |
| AD-1181587.1 | 93 | 14 | 101 | 22 | 90 | 6 | 159 | 49 |
| AD-1181588.1 | 97 | 7 | 89 | 16 | 86 | 24 | 120 | 21 |
| AD-1181589.1 | 52 | 7 | 54 | 15 | 71 | 13 | 134 | 19 |
| AD-1181590.1 | 86 | 7 | 110 | 13 | 101 | 30 | 192 | 56 |
| AD-1181591.1 | 86 | 8 | 87 | 18 | 104 | 6 | 83 | 11 |
| AD-1181592.1 | 89 | 5 | 78 | 7 | 101 | 11 | 87 | 15 |
| AD-1181593.1 | 91 | 3 | 89 | 12 | 97 | 8 | 121 | 32 |
| AD-565034.2 | 41 | 1 | 41 | 1 | 63 | 5 | 92 | 5 |
| AD-1181594.1 | 29 | 1 | 36 | 3 | 53 | 3 | 97 | 1 |
| AD-1181595.1 | 25 | 4 | 29 | 4 | 55 | 19 | 100 | 25 |
| AD-565035.2 | 30 | 2 | 48 | 17 | 58 | 16 | 127 | 21 |
| AD-1181596.1 | 50 | 2 | 47 | 6 | 88 | 15 | 77 | 10 |
| AD-1181597.1 | 26 | 5 | 29 | 3 | 56 | 3 | 85 | 10 |
| AD-1181598.1 | 61 | 10 | 60 | 1 | 80 | 4 | 103 | 9 |
| AD-565037.2 | 35 | 3 | 41 | 1 | 57 | 7 | 133 | 55 |
| AD-1181599.1 | 56 | 7 | 49 | 9 | 60 | 8 | 106 | 13 |
| AD-1181600.1 | 22 | 6 | 23 | 3 | 51 | 20 | 86 | 6 |
| AD-1181601.1 | 20 | 4 | 25 | 9 | 28 | 0 | 84 | 15 |
| AD-567072.2 | 64 | 12 | 75 | 6 | 69 | 9 | 112 | 14 |
| AD-1181602.1 | 69 | 4 | 77 | 13 | 115 | 34 | 92 | 11 |
| AD-1181603.1 | 66 | 17 | 55 | 4 | 105 | 18 | 96 | 10 |
| AD-1181604.1 | 54 | 11 | 66 | 16 | 91 | 13 | 106 | 15 |
| AD-567300.2 | 51 | 3 | 56 | 4 | 85 | 12 | 137 | 43 |

TABLE 32-continued

C3 Free Uptake Single Dose Screens
in PCH cells (% C3 mRNA Remaining)

| Duplex | 500 nM Dose Avg | SD | 100 nm Dose Avg | SD | 10 nM Dose Avg | SD | 1 nM Dose Avg | SD |
|---|---|---|---|---|---|---|---|---|
| AD-1181605.1 | 46 | 3 | 47 | 4 | 62 | 9 | 114 | 22 |
| AD-1181606.1 | 58 | 7 | 65 | 14 | 63 | 15 | 111 | 23 |
| AD-567301.2 | 45 | 15 | 41 | 12 | 52 | 2 | 101 | 9 |
| AD-1181607.1 | 29 | 0 | 43 | 2 | 78 | 18 | 128 | 14 |
| AD-1181608.1 | 36 | 6 | 35 | 2 | 95 | 21 | 79 | 9 |
| AD-569262.2 | 18 | 2 | 23 | 2 | 45 | 6 | 78 | 9 |
| AD-1181609.1 | 20 | 5 | 21 | 1 | 47 | 12 | 106 | 25 |
| AD-1181610.1 | 19 | 2 | 27 | 1 | 37 | 1 | 140 | 5 |
| AD-569265.2 | 41 | 7 | 32 | 5 | 44 | 7 | 108 | 12 |
| AD-1181611.1 | 16 | 3 | 24 | 8 | 38 | 8 | 115 | 34 |
| AD-1181612.1 | 28 | 1 | 37 | 13 | 72 | 29 | 164 | 55 |
| AD-569268.2 | 21 | 2 | 24 | 3 | 54 | 13 | 60 | 11 |
| AD-1181613.1 | 32 | 5 | 26 | 4 | 45 | 9 | 60 | 9 |
| AD-1181614.1 | 28 | 6 | 30 | 4 | 44 | 9 | 77 | 10 |
| AD-569269.2 | 19 | 4 | 16 | 3 | 25 | 0 | 67 | 9 |
| AD-1181615.1 | 16 | 1 | 18 | 3 | 26 | 0 | 95 | 27 |
| AD-1181616.1 | 36 | 6 | 26 | 3 | 51 | 25 | 105 | 15 |
| AD-569270.2 | 43 | 8 | 51 | 13 | 68 | 15 | 105 | 32 |
| AD-1181617.1 | 24 | 1 | 40 | 6 | 59 | 11 | 99 | 24 |
| AD-1181618.1 | 38 | 3 | 39 | 7 | 64 | 8 | 77 | 4 |
| AD-570676.2 | 67 | 19 | 39 | 1 | 49 | 4 | 117 | 7 |
| AD-1181619.1 | 36 | 10 | 35 | 5 | 41 | 6 | 87 | 2 |
| AD-1181620.1 | 68 | 10 | 58 | 9 | 57 | 3 | 127 | 14 |
| AD-571304.2 | 70 | 1 | 66 | 11 | 60 | 2 | 215 | 100 |
| AD-1181604.2 | 69 | 5 | 63 | 8 | 101 | 39 | 162 | 36 |
| AD-1181621.1 | 108 | 12 | 150 | 48 | 105 | 5 | 188 | 54 |
| AD-1069946.2 | 83 | 15 | 91 | 14 | 149 | 44 | 67 | 8 |
| AD-1181622.1 | 70 | 4 | 85 | 26 | 137 | 21 | 124 | 17 |
| AD-1181623.1 | 70 | 11 | 76 | 22 | 120 | 48 | 120 | 17 |
| AD-1181624.1 | 95 | 12 | 83 | 10 | 119 | 3 | 129 | 22 |
| AD-1069956.2 | 51 | 9 | 57 | 15 | 102 | 23 | 130 | 16 |
| AD-1181625.1 | 55 | 1 | 46 | 13 | 80 | 27 | 138 | 29 |
| AD-1181626.1 | 60 | 7 | 48 | 10 | 98 | 20 | 128 | 31 |

TABLE 33

C3 Transfection Single Dose Screens
in PCH cells (% C3 mRNA Remaining)

| Duplex | 50 nM Dose Avg | SD | 10 nM Dose Avg | SD | 1 nM Dose Avg | SD | 0.1 nm Dose Avg | SD |
|---|---|---|---|---|---|---|---|---|
| AD-564742.5 | 4 | 0 | 6 | 4 | 54 | 2 | 64 | 7 |
| AD-1181478.1 | 4 | 0 | 4 | 3 | 134 | 8 | 55 | 3 |
| AD-1181479.1 | 5 | 1 | 4 | 3 | 137 | 33 | 73 | 17 |
| AD-1181480.1 | 4 | 0 | 4 | 3 | 137 | 8 | 78 | 15 |
| AD-1181481.1 | 6 | 1 | 4 | 2 | 118 | 21 | 77 | 6 |
| AD-1181482.1 | 5 | 1 | 4 | 2 | 98 | 14 | 38 | 3 |
| AD-1181483.1 | 8 | 2 | 7 | 3 | 107 | 10 | 105 | 17 |
| AD-1181484.1 | 6 | 0 | 4 | 1 | 27 | 5 | 58 | 15 |
| AD-567304.4 | 6 | 1 | 7 | 1 | 44 | 12 | 63 | 0 |
| AD-1181485.1 | 3 | 1 | 6 | 0 | 23 | 5 | 60 | 8 |
| AD-1181486.1 | 4 | 1 | 10 | 5 | 45 | 9 | 55 | 10 |
| AD-1181487.1 | 5 | 2 | 9 | 5 | 49 | 7 | 70 | 2 |
| AD-1181488.1 | 4 | 1 | 5 | 1 | 44 | 7 | 64 | 9 |
| AD-1181489.1 | 7 | 2 | 7 | 2 | 103 | 30 | 76 | 2 |
| AD-1181490.1 | 7 | 3 | 6 | 3 | 105 | 12 | 108 | 19 |
| AD-1181491.1 | 8 | 2 | 6 | 1 | 90 | 20 | 81 | 17 |
| AD-1181492.1 | 6 | 2 | 9 | 2 | 75 | 14 | 89 | 14 |
| AD-567315.8 | 4 | 1 | 10 | 1 | 76 | 5 | 48 | 7 |
| AD-1181493.1 | 6 | 1 | 7 | 0 | 105 | 24 | 60 | 8 |
| AD-1181494.1 | 5 | 0 | 5 | 0 | 112 | 21 | 44 | 4 |
| AD-1181495.1 | 7 | 1 | 6 | 1 | 129 | 28 | 65 | 18 |
| AD-1181496.1 | 9 | 1 | 5 | 2 | 133 | 31 | 75 | 11 |
| AD-1181497.1 | 6 | 1 | 2 | 3 | 93 | 12 | 61 | 2 |
| AD-1181498.1 | 7 | 1 | 16 | 5 | 120 | 28 | 70 | 12 |
| AD-1181499.1 | 6 | 1 | 15 | 3 | 101 | 20 | 74 | 11 |
| AD-1181500.1 | 8 | 0 | 10 | 2 | 107 | 7 | 72 | 6 |
| AD-1181501.1 | 9 | 1 | 13 | 1 | 109 | 1 | 71 | 8 |

TABLE 33-continued

C3 Transfection Single Dose Screens
in PCH cells (% C3 mRNA Remaining)

| Duplex | 50 nM Dose Avg | SD | 10 nM Dose Avg | SD | 1 nM Dose Avg | SD | 0.1 nm Dose Avg | SD |
|---|---|---|---|---|---|---|---|---|
| AD-1181502.1 | 11 | 2 | 14 | 2 | 125 | 19 | 76 | 2 |
| AD-568586.5 | 7 | 2 | 5 | 2 | 78 | 26 | 54 | 10 |
| AD-1181503.1 | 7 | 3 | 5 | 0 | 82 | 11 | 36 | 3 |
| AD-1181504.1 | 5 | 1 | 7 | 2 | 81 | 7 | 39 | 10 |
| AD-1181505.1 | 5 | 1 | 8 | 2 | 77 | 6 | 37 | 1 |
| AD-1181506.1 | 5 | 0 | 9 | 1 | 86 | 10 | 41 | 3 |
| AD-1181507.1 | 22 | 2 | 29 | 3 | 89 | 1 | 90 | 9 |
| AD-1181508.1 | 9 | 2 | 10 | 2 | 94 | 5 | 62 | 3 |
| AD-1181509.1 | 6 | 0 | 7 | 1 | 97 | 4 | 55 | 4 |
| AD-1181510.1 | 7 | 2 | 6 | 1 | 49 | 8 | 46 | 5 |
| AD-568978.5 | 8 | 0 | 9 | 3 | 101 | 18 | 74 | 23 |
| AD-1181511.1 | 8 | 1 | 14 | 5 | 67 | 11 | 69 | 11 |
| AD-1181513.1 | 6 | 0 | 11 | 3 | 81 | 7 | 59 | 5 |
| AD-1181514.1 | 6 | 0 | 7 | 1 | 24 | 4 | 55 | 9 |
| AD-1181515.1 | 65 | 8 | 62 | 1 | 25 | 4 | 99 | 5 |
| AD-1181516.1 | 37 | 2 | 31 | 3 | 17 | 5 | 94 | 14 |
| AD-1181517.1 | 41 | 5 | 38 | 5 | 19 | 3 | 88 | 12 |
| AD-569164.9 | 4 | 1 | 7 | 1 | 19 | 1 | 36 | 4 |
| AD-1181518.1 | 6 | 1 | 7 | 1 | 12 | 1 | 46 | 6 |
| AD-1181519.1 | 6 | 1 | 7 | 1 | 33 | 6 | 48 | 6 |
| AD-1181520.1 | 6 | 0 | 7 | 1 | 25 | 2 | 53 | 5 |
| AD-1181521.1 | 12 | 1 | 15 | 1 | 24 | 4 | 74 | 3 |
| AD-1181522.1 | 32 | 3 | 31 | 1 | 11 | 2 | 83 | 6 |
| AD-1181523.1 | 14 | 1 | 9 | 1 | 14 | 4 | 68 | 5 |
| AD-1181524.1 | 7 | 1 | 6 | 1 | 78 | 2 | 51 | 5 |
| AD-570712.3 | 5 | 1 | 6 | 0 | 50 | 9 | 47 | 2 |
| AD-1181525.1 | 5 | 0 | 6 | 1 | 43 | 4 | 62 | 12 |
| AD-1181526.1 | 7 | 0 | 5 | 1 | 50 | 11 | 63 | 10 |
| AD-1181527.1 | 6 | 1 | 6 | 1 | 35 | 4 | 54 | 9 |
| AD-1181528.1 | 5 | 1 | 5 | 1 | 19 | 5 | 51 | 3 |
| AD-1181529.1 | 6 | 1 | 5 | 1 | 23 | 4 | 62 | 12 |
| AD-1181530.1 | 5 | 1 | 5 | 0 | 18 | 5 | 40 | 5 |
| AD-1181531.1 | 22 | 1 | 18 | 5 | 13 | 1 | 89 | 7 |
| AD-1181532.1 | 12 | 1 | 10 | 3 | 16 | 3 | 74 | 17 |
| AD-1181533.1 | 15 | 1 | 17 | 1 | 13 | 2 | 76 | 7 |
| AD-570713.3 | 6 | 0 | 6 | 1 | 16 | 2 | 56 | 6 |
| AD-1181534.1 | 8 | 1 | 7 | 1 | 21 | 4 | 66 | 8 |
| AD-1181535.1 | 23 | 4 | 16 | 1 | 19 | 4 | 104 | 20 |
| AD-1181536.1 | 25 | 5 | 16 | 2 | 10 | 1 | 113 | 57 |
| AD-1181537.1 | 8 | 2 | 5 | 1 | 15 | 1 | 77 | 50 |
| AD-1181538.1 | 2 | 1 | 5 | 1 | 8 | 2 | 44 | 5 |
| AD-1181539.1 | 4 | 0 | 8 | 2 | 10 | 0 | 58 | 2 |
| AD-1181540.1 | 30 | 2 | 40 | 3 | 13 | 3 | 93 | 3 |
| AD-1181541.1 | 122 | 20 | 89 | 5 | 10 | 1 | 99 | 12 |
| AD-1181542.1 | 88 | 12 | 79 | 12 | 8 | 0 | 97 | 13 |
| AD-570714.4 | 6 | 1 | 5 | 0 | 11 | 6 | 47 | 5 |
| AD-1181543.1 | 4 | 1 | 4 | 0 | 19 | 1 | 41 | 6 |
| AD-1181544.1 | 6 | 1 | 10 | 2 | 15 | 2 | 66 | 10 |
| AD-1181545.1 | 5 | 1 | 10 | 1 | 16 | 2 | 74 | 3 |
| AD-1181546.1 | 9 | 0 | 17 | 4 | 17 | 5 | 79 | 7 |
| AD-1181547.1 | 77 | 15 | 62 | 4 | 14 | 0 | 85 | 7 |
| AD-1181548.1 | 66 | 9 | 65 | 7 | 40 | 4 | 87 | 2 |
| AD-1181549.1 | 35 | 2 | 49 | 19 | 91 | 25 | 87 | 6 |
| AD-571826.5 | 5 | 0 | 6 | 1 | 39 | 1 | 55 | 2 |
| AD-1181550.1 | 8 | 1 | 8 | 0 | 72 | 9 | 70 | 13 |
| AD-1181551.1 | 7 | 2 | 7 | 1 | 36 | 3 | 79 | 4 |
| AD-1181552.1 | 4 | 0 | 5 | 2 | 37 | 10 | 59 | 2 |
| AD-1181553.1 | 3 | 2 | 7 | 1 | 40 | 14 | 50 | 6 |
| AD-1181554.1 | 27 | 9 | 25 | 6 | 68 | 10 | 89 | 2 |
| AD-1181555.1 | 24 | 10 | 17 | 1 | 25 | 7 | 120 | 34 |
| AD-572040.6 | 5 | 2 | 8 | 3 | 26 | 15 | 72 | 6 |
| AD-1181556.1 | 22 | 4 | 42 | 1 | 20 | 1 | 122 | 22 |
| AD-1181557.1 | 5 | 0 | 17 | 4 | 54 | 2 | 97 | 9 |
| AD-1181558.1 | 40 | 3 | 79 | 10 | 134 | 8 | 92 | 14 |
| AD-1181559.1 | 16 | 5 | 59 | 2 | 137 | 33 | 113 | 17 |
| AD-1181560.1 | 45 | 28 | 77 | 3 | 137 | 8 | 102 | 10 |
| AD-1181561.1 | 22 | 12 | 60 | 4 | 118 | 21 | 91 | 5 |
| AD-1181562.1 | 119 | 96 | 63 | 1 | 98 | 14 | 99 | 10 |
| AD-1181560.2 | 113 | 110 | 71 | 11 | 107 | 10 | 117 | 7 |
| AD-572110.5 | 3 | 0 | 10 | 2 | 27 | 5 | 106 | 21 |
| AD-1181563.1 | 4 | 0 | 14 | 3 | 44 | 12 | 94 | 18 |
| AD-1181564.1 | 5 | 0 | 9 | 1 | 23 | 5 | 54 | 17 |
| AD-1181565.1 | 6 | 1 | 13 | 3 | 45 | 9 | 84 | 3 |

TABLE 33-continued

C3 Transfection Single Dose Screens
in PCH cells (% C3 mRNA Remaining)

| Duplex | 50 nM Dose Avg | SD | 10 nM Dose Avg | SD | 1 nM Dose Avg | SD | 0.1 nm Dose Avg | SD |
|---|---|---|---|---|---|---|---|---|
| AD-1181566.1 | 7 | 1 | 14 | 2 | 49 | 7 | 84 | 3 |
| AD-1181567.1 | 5 | 1 | 16 | 4 | 44 | 7 | 89 | 18 |
| AD-1181568.1 | 21 | 4 | 35 | 0 | 103 | 30 | 108 | 14 |
| AD-1181569.1 | 21 | 8 | 52 | 7 | 105 | 12 | 108 | 16 |
| AD-1181570.1 | 14 | 4 | 36 | 3 | 90 | 20 | 104 | 7 |
| AD-1181571.1 | 9 | 4 | 22 | 1 | 75 | 14 | 95 | 12 |
| AD-1181572.1 | 18 | 1 | 23 | 1 | 76 | 5 | 83 | 12 |
| AD-572387.6 | 26 | 3 | 53 | 7 | 105 | 24 | 118 | 9 |
| AD-1181573.1 | 44 | 10 | 64 | 2 | 112 | 21 | 112 | 27 |
| AD-1181574.1 | 66 | 15 | 80 | 1 | 129 | 28 | 141 | 25 |
| AD-1181575.1 | 91 | 9 | 89 | 12 | 133 | 31 | 132 | 20 |
| AD-1181576.1 | 71 | 22 | 99 | 9 | 93 | 12 | 104 | 7 |
| AD-1181577.1 | 88 | 21 | 94 | 12 | 120 | 28 | 83 | 6 |
| AD-1181578.1 | 88 | 9 | 95 | 13 | 101 | 20 | 93 | 12 |
| AD-1181579.1 | 99 | 17 | 102 | 13 | 107 | 7 | 102 | 16 |
| AD-1181580.1 | 88 | 3 | 100 | 1 | 109 | 1 | 122 | 8 |
| AD-1181581.1 | 87 | 11 | 104 | 12 | 125 | 19 | 115 | 16 |
| AD-569272.6 | 8 | 0 | 17 | 2 | 78 | 26 | 110 | 3 |
| AD-1181582.1 | 22 | 4 | 33 | 4 | 82 | 11 | 99 | 6 |
| AD-1181583.1 | 57 | 8 | 80 | 3 | 81 | 7 | 76 | 11 |
| AD-1181584.1 | 41 | 3 | 64 | 10 | 77 | 6 | 100 | 20 |
| AD-1181585.1 | 69 | 3 | 82 | 9 | 86 | 10 | 93 | 11 |
| AD-1181586.1 | 67 | 4 | 75 | 13 | 89 | 1 | 136 | 3 |
| AD-1181587.1 | 65 | 6 | 83 | 5 | 94 | 5 | 117 | 24 |
| AD-1181588.1 | 63 | 6 | 80 | 8 | 97 | 4 | 117 | 4 |
| AD-1181589.1 | 8 | 2 | 16 | 5 | 49 | 8 | 110 | 21 |
| AD-1181590.1 | 68 | 13 | 62 | 6 | 101 | 18 | 106 | 10 |
| AD-1181591.1 | 60 | 5 | 78 | 4 | 67 | 11 | 85 | 8 |
| AD-1181592.1 | 83 | 2 | 89 | 8 | 83 | 4 | 98 | 8 |
| AD-1181593.1 | 80 | 1 | 89 | 8 | 81 | 7 | 99 | 4 |
| AD-565034.2 | 7 | 1 | 9 | 2 | 24 | 4 | 82 | 11 |
| AD-1181594.1 | 5 | 1 | 8 | 1 | 25 | 4 | 73 | 15 |
| AD-1181595.1 | 5 | 1 | 8 | 1 | 17 | 5 | 69 | 11 |
| AD-565035.2 | 5 | 1 | 10 | 1 | 19 | 3 | 69 | 28 |
| AD-1181596.1 | 6 | 1 | 9 | 1 | 19 | 1 | 40 | 11 |
| AD-1181597.1 | 5 | 1 | 8 | 1 | 12 | 1 | 42 | 6 |
| AD-1181598.1 | 9 | 0 | 14 | 0 | 33 | 6 | 92 | 11 |
| AD-565037.2 | 5 | 1 | 7 | 1 | 25 | 2 | 62 | 3 |
| AD-1181599.1 | 6 | 0 | 9 | 0 | 24 | 4 | 70 | 9 |
| AD-1181600.1 | 4 | 1 | 6 | 1 | 11 | 2 | 50 | 15 |
| AD-1181601.1 | 4 | 0 | 6 | 2 | 14 | 4 | 32 | 6 |
| AD-567072.2 | 20 | 2 | 40 | 4 | 78 | 2 | 119 | 6 |
| AD-1181602.1 | 11 | 3 | 22 | 2 | 50 | 9 | 85 | 22 |
| AD-1181603.1 | 10 | 1 | 19 | 5 | 43 | 4 | 81 | 5 |
| AD-1181604.1 | 12 | 0 | 19 | 2 | 50 | 11 | 100 | 9 |
| AD-567300.2 | 7 | 1 | 14 | 3 | 35 | 4 | 102 | 14 |
| AD-1181605.1 | 4 | 1 | 7 | 1 | 19 | 5 | 62 | 1 |
| AD-1181606.1 | 5 | 1 | 11 | 2 | 23 | 4 | 105 | 5 |
| AD-567301.2 | 4 | 0 | 6 | 0 | 18 | 5 | 72 | 12 |
| AD-1181607.1 | 4 | 0 | 6 | 1 | 13 | 1 | 82 | 46 |
| AD-1181608.1 | 4 | 1 | 8 | 0 | 16 | 3 | 32 | 5 |
| AD-569262.2 | 4 | 1 | 7 | 1 | 13 | 2 | 41 | 5 |
| AD-1181609.1 | 4 | 1 | 9 | 2 | 16 | 2 | 51 | 3 |
| AD-1181610.1 | 4 | 0 | 7 | 1 | 21 | 4 | 71 | 9 |
| AD-569265.2 | 5 | 1 | 9 | 1 | 19 | 4 | 54 | 12 |
| AD-1181611.1 | 3 | 1 | 5 | 1 | 10 | 1 | 55 | 21 |
| AD-1181612.1 | 5 | 0 | 7 | 1 | 15 | 1 | 51 | 9 |
| AD-569268.2 | 3 | 1 | 5 | 1 | 8 | 2 | 18 | 2 |
| AD-1181613.1 | 4 | 0 | 6 | 0 | 10 | 0 | 25 | 5 |
| AD-1181614.1 | 4 | 0 | 7 | 1 | 13 | 3 | 37 | 4 |
| AD-569269.2 | 3 | 0 | 5 | 1 | 10 | 1 | 31 | 8 |
| AD-1181615.1 | 3 | 1 | 6 | 0 | 8 | 0 | 28 | 7 |
| AD-1181616.1 | 5 | 0 | 8 | 1 | 11 | 6 | 34 | 4 |
| AD-569270.2 | 3 | 1 | 9 | 2 | 19 | 1 | 74 | 16 |
| AD-1181617.1 | 4 | 0 | 5 | 1 | 15 | 2 | 34 | 10 |
| AD-1181618.1 | 6 | 1 | 8 | 1 | 16 | 2 | 37 | 3 |
| AD-570676.2 | 6 | 0 | 8 | 1 | 17 | 5 | 36 | 9 |
| AD-1181619.1 | 6 | 0 | 7 | 1 | 14 | 0 | 38 | 5 |
| AD-1181620.1 | 8 | 1 | 14 | 4 | 40 | 4 | 75 | 10 |
| AD-571304.2 | 16 | 5 | 25 | 8 | 91 | 25 | 130 | 30 |
| AD-1181604.2 | 10 | 2 | 18 | 4 | 39 | 1 | 107 | 22 |
| AD-1181621.1 | 26 | 4 | 89 | 30 | 72 | 9 | 86 | 37 |
| AD-1069946.2 | 9 | 0 | 19 | 9 | 36 | 3 | 61 | 14 |
| AD-1181622.1 | 5 | 2 | 7 | 3 | 37 | 10 | 58 | 10 |
| AD-1181623.1 | 9 | 2 | 11 | 4 | 40 | 14 | 81 | 16 |
| AD-1181624.1 | 16 | 2 | 17 | 3 | 68 | 10 | 91 | 14 |
| AD-1069956.2 | 6 | 0 | 6 | 1 | 25 | 7 | 70 | 9 |
| AD-1181625.1 | 5 | 0 | 6 | 3 | 26 | 15 | 59 | 7 |
| AD-1181626.1 | 5 | 1 | 10 | 1 | 20 | 1 | 60 | 10 |

Example 6. In Vivo Screening of dsRNA Duplexes in Mice

Duplexes of interest, identified from the above in vitro studies were evaluated in vivo. In particular, at pre-dose day −14 groups of wild-type mice (C57BL/6) (n=3) were transduced by intravenous administration of $2 \times 10^{10}$ viral particles of an adeno-associated virus 8 (AAV8) vector encoding human complement component C3. In particular, mice were administered an AAV8 encoding a portion of human complement component C3 mRNA spanning nucleotides 94-2892 of NM_000064.3.

At day 0, groups of three mice were subcutaneously administered a single 10 mg/kg dose of the agents of interest or PBS control. At day 14 post-dose animals were sacrificed, liver samples were collected and snap-frozen in liquid nitrogen. Tissue mRNA was extracted and analyzed by the RT-QPCR method.

Figure 4:
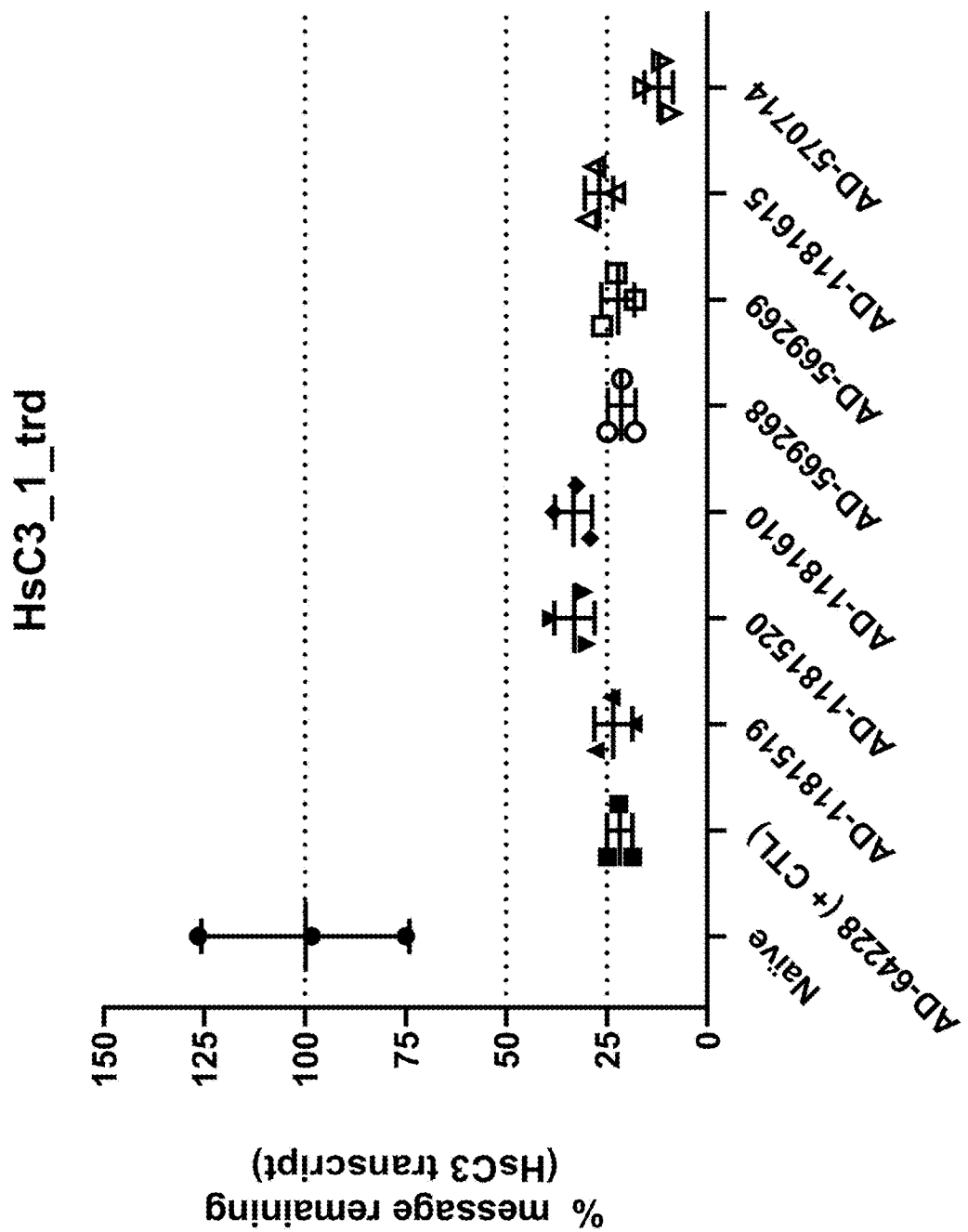
FIG. 4 is a graph showing C3 mRNA levels in mice (n=3 per group) subcutaneously administered a single 2 mg/kg dose of the indicated dsRNA duplexes, on day 14 post-dose. C3 mRNA levels are shown relative to control levels detected with PBS treatment.

Human C3 mRNA levels were compared to housekeeping gene GAPDH. The values were then normalized to the average of PBS vehicle control group. The data were expressed as percent of baseline value, and presented as mean plus standard deviation. The results, presented in FIG. 4, demonstrate that the exemplary duplex agents tested effectively reduce the level of the human C3 messenger RNA in vivo.

Example 7. In Vivo Analysis of Duplexes of Interest in Non-Human Primates

Duplexes of interest, identified from the above in vitro and in vivo studies, were evaluated in vivo. In particular, female *Cynomolgus* monkeys were subcutaneously administered a single dose of the agents of interest. FIG. 5 provides the treatment groups and the duplexes of interest. Serum was collected weekly to the end of the study and C3 protein levels were determined by ELISA assay (C3 Human ELISA: Hycult HK366). Briefly, this human C3 ELISA assay was previously validated for cross reactivity to *cynomolgus* monkey and the instructions provided with the kit were followed with the exceptions that samples were diluted 1:50,000 or 1:20,000 for samples with high silencing expected in order to keep ODs within the standard curve. ELISA assays were performed at interim time points, and any data that was reproduced twice was averaged at the g/ml level then normalized to average pre-dose.

Figure 6:
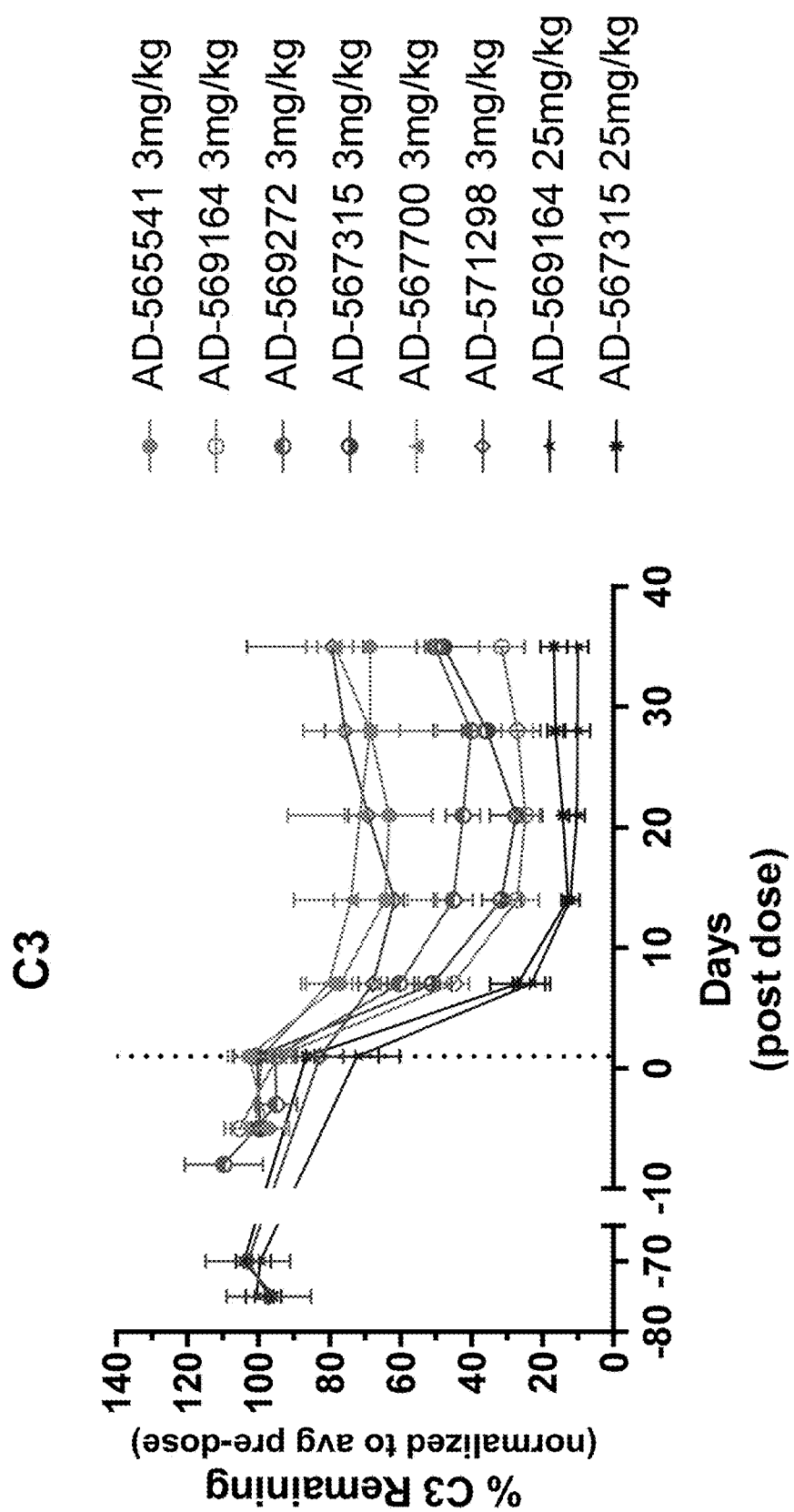
FIG. 6 is a graph showing the effect of subcutaneous administration of a single 3 mg/kg or 25 mg/kg dose of the indicated dsRNA duplexes on % C3 protein levels remaining normalized to average predose C3 protein level in the serum of Cynmologous. The baseline was adjusted to day 1 dosing for all groups.

The results, shown in FIG. 6, demonstrate that the exemplary duplex agents tested potently and durably reduce the level of the *Cynomolgus* C3 protein in vivo.

Additional duplexes of interest, identified from the above in vitro and in vivo studies, were also evaluated in vivo. In particular, nine Groups of female *Cynomolgus* monkeys were subcutaneously administered a single dose of the agents of interest (Groups 1-5 and 7-10) and one Group of emale *Cynomolgus* monkeys was subcutaneously administered two doses of a duplex of interest on Day 1 and Day 55. FIG. 7 provides the treatment groups and the duplexes of interest. Serum was collected weekly to the end of the study and C3 protein levels were determined by ELISA assay (C3 Human ELISA: Hycult HK366). Briefly, this human C3 ELISA assay was previously validated for cross reactivity to *cynomolgus* monkey and the instructions provided with the kit were followed with the exceptions that samples were diluted 1:50,000 or 1:15,000 for samples with high silencing expected in order to keep ODs within the standard curve. ELISA assays were performed at interim time points, and any data that was reproduced twice was averaged at the g/ml level then normalized to average pre-dose.

Figure 8:
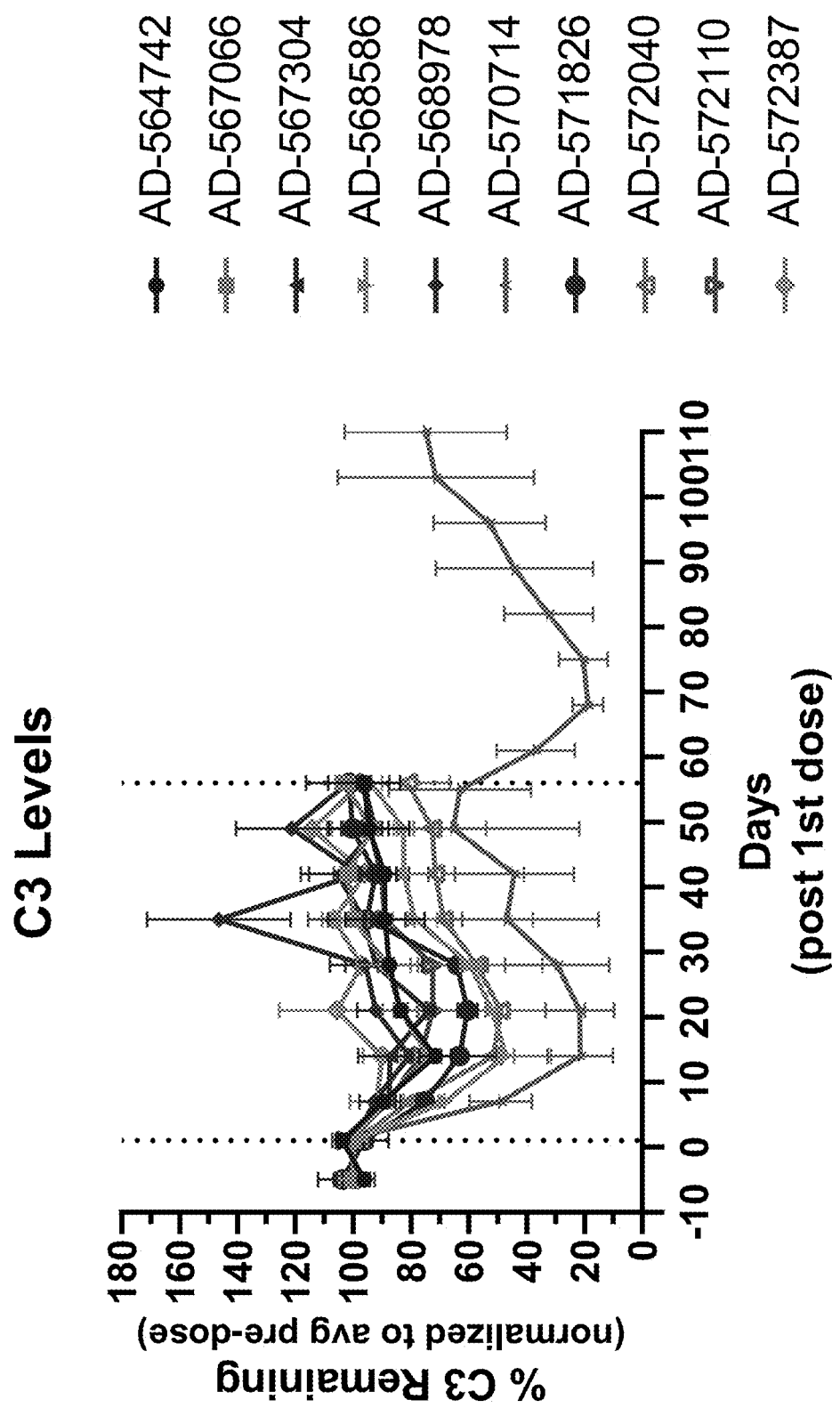
FIG. 8 is a graph showing the effect of subcutaneous administration of a single 3 mg/kg or 25 mg/kg dose of the indicated dsRNA duplexes on % C3 protein levels remaining normalized to average predose C3 protein level in the serum of Cynmologous.

The results, shown in FIG. 8, demonstrate that the exemplary duplex agents tested potently and durably reduce the level of the *Cynomolgus* C3 protein in vivo.

In another study, additional duplexes of interest, identified from the above in vitro and in vivo studies, were evaluated in vivo. In particular, three Groups of female *Cynomolgus* monkeys were subcutaneously administered a single 3 mg/kg dose of AD-1181519, AD-569268, or AD-570714 (Groups 1, 4, and 7), three Groups of female *Cynomolgus* monkeys were subcutaneously administered a single 9 mg/kg dose of AD-1181519, AD-569268, or AD-570714 (Groups 2, 5, and 8), one Group of female *Cynomolgus* monkeys was subcutaneously administered a single 25 mg/kg dose of AD-570714 (Group 10), and three Groups of female *Cynomolgus* monkeys were subcutaneously administered three 3 mg/kg dose of AD-1181519, AD-569268, or AD-570714 on Days 1, 29, and 57 (Groups 3, 6, and 9; 3×3 mg/kg) (see FIG. 8). Serum was collected weekly to the end of the study. C3 protein levels were determined by ELISA assay (C3 Human ELISA: Hycult HK366) and hemolytic activity was evaluated to determine the functional activity of the alternative pathway, e.g., alternative hemolysis assay Wieslsab Complement Alternative Pathway (CAP) assay. For the C3 ELISA assays, the assay used was previously validated for cross reactivity to *cynomolgus* monkey and the instructions provided with the kit were followed with the exceptions that samples were diluted 1:39,067. ELISA assays were performed at interim time points, and any data that was reproduced twice was averaged at the µg/ml level then normalized to average pre-dose. In addition, liver biopsies were performed on 3 animals administered 25 mg/kg of AD-570714 at Days −21 and Day 29 (see FIG. 9).

Figure 10:
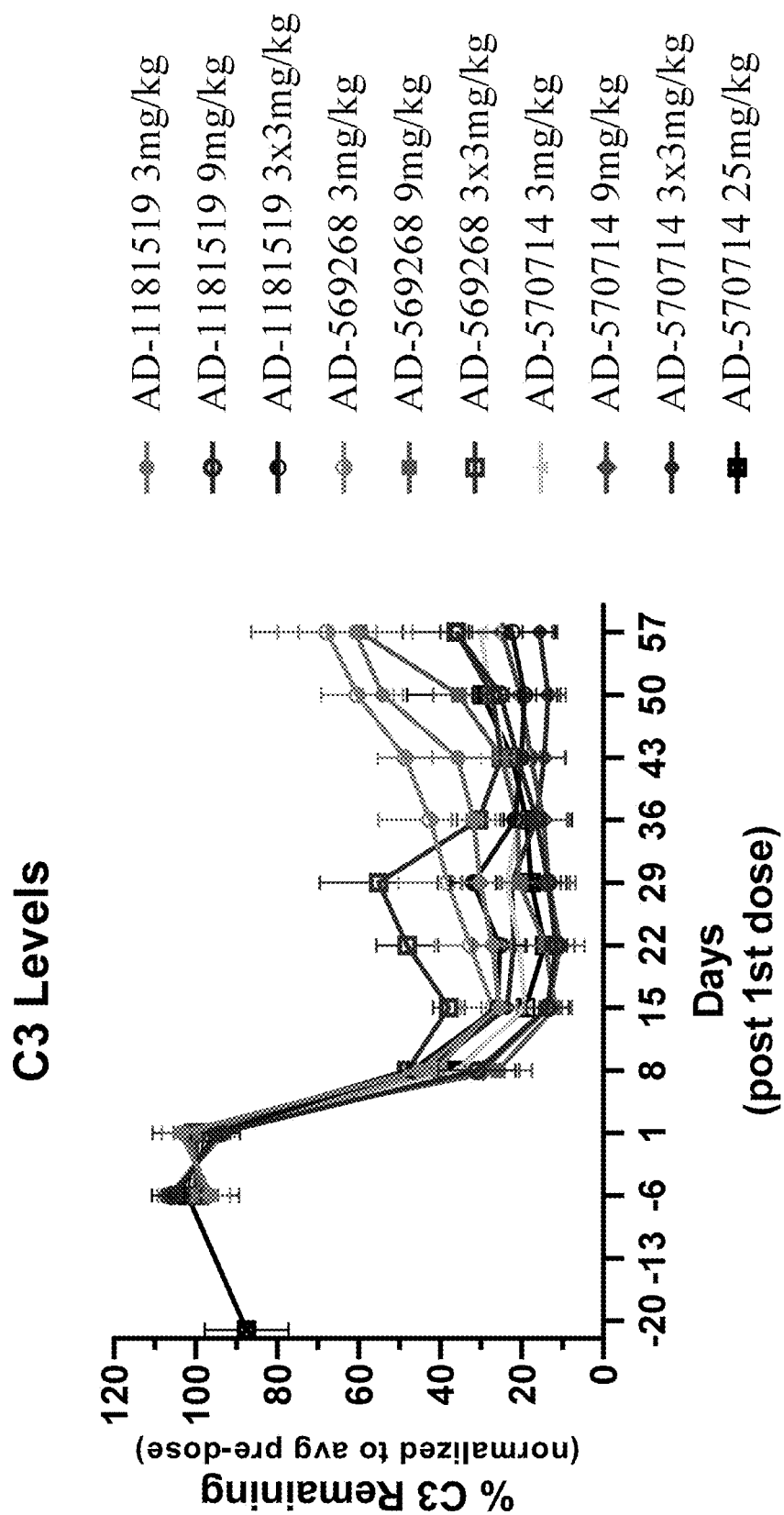
FIG. 10 is a graph showing the effect of subcutaneous administration of a single 3 mg/kg or 25 mg/kg dose of the indicated dsRNA duplexes on % C3 protein levels remaining normalized to average predose C3 protein level in the serum of Cynmologous. For Group 2, Day −6 on the graph corresponds to Day −27 and Day 1 is the day on which the duplex was administered.

The results, shown in FIG. 10, demonstrate that the exemplary duplex agents tested potently and durably reduce the level of the *Cynomolgus* C3 protein in vivo.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

SEQUENCE LISTING

The patent contains a lengthy sequence listing. A copy of the sequence listing is available in electronic form from the USPTO web site (https://seqdata.uspto.gov/?pageRequest=docDetail&DocID=US12258565B2). An electronic copy of the sequence listing will also be available from the USPTO upon request and payment of the fee set forth in 37 CFR 1.19(b)(3).

We claim:

1. A double stranded ribonucleic acid (dsRNA) agent for inhibiting expression of complement component C3 in a cell, or a pharmaceutically acceptable salt thereof, comprising a sense strand differing by no more than 4 bases from the nucleotide sequence 5'-gsasgccgUfuCfUfCfuacaauuacu-3' of SEQ ID NO:4188 and an antisense strand differing by no more than 4 bases from the nucleotide sequence 5'-asGfsuaaUfuGfUfagagAfaCfggcucsgsg-3' of SEQ ID NO:4367, wherein a, g, c and u are 2'-O-methyl (2'-OMe) A, G, C, and U, respectively; Af, Gf, Cf, and Uf are 2'-fluoro A, G, C and U, respectively; and s is a phosphorothioate linkage.

2. The dsRNA agent, or a pharmaceutically acceptable salt thereof, of claim 1, comprising a sense strand differing by no more than 3 bases from the nucleotide sequence 5'-gsasgccgUfuCfUfCfuacaauuacu-3' of SEQ ID NO:4188 and an antisense strand differing by no more than 3 bases from the nucleotide sequence 5'-asGfsuaaUfuGfUfagagAfaCfggcucsgsg-3' of SEQ ID NO:4367.

3. The dsRNA agent, or a pharmaceutically acceptable salt thereof, of claim 1, comprising a sense strand differing by no more than 2 bases from the nucleotide sequence 5'-gsasgccgUfuCfUfCfuacaauuacu-3' of SEQ ID NO:4188 and an antisense strand differing by no more than 2 bases from the nucleotide sequence 5'-asGfsuaaUfuGfUfagagAfaCfggcucsgsg-3' of SEQ ID NO:4367.

4. The dsRNA agent, or a pharmaceutically acceptable salt thereof, of claim 1, comprising a sense strand differing by no more than 1 base from the nucleotide sequence 5'-gsasgccgUfuCfUfCfuacaauuacu-3' of SEQ ID NO:4188 and an antisense strand differing by no more than 1 base from the nucleotide sequence 5'-asGfsuaaUfuGfUfagagAfaCfggcucsgsg-3' of SEQ ID NO:4367.

5. The dsRNA agent, or a pharmaceutically acceptable salt thereof, of claim 1, comprising a sense strand comprising the nucleotide sequence 5'-gsasgccgUfuCfUfCfuacaauuacu-3' of SEQ ID NO:4188 and an antisense strand comprising the nucleotide sequence 5'-asGfsuaaUfuGfUfagagAfaCfggcucsgsg-3' of SEQ ID NO:4367.

6. The dsRNA agent, or a pharmaceutically acceptable salt thereof, of claim 1, comprising a sense strand consisting of the nucleotide sequence 5'-gsasgccgUfuCfUfCfuacaauuacu-3' of SEQ ID NO:4188 and an antisense strand consisting of the nucleotide sequence 5'-asGfsuaaUfuGfUfagagAfaCfggcucsgsg-3' of SEQ ID NO:4367.

7. The dsRNA agent, or a pharmaceutically acceptable salt thereof, of claim 1, further comprising a ligand.

8. The dsRNA agent, or a pharmaceutically acceptable salt thereof, of claim 7, wherein the ligand is conjugated to the 3' end of the sense strand of the dsRNA agent.

9. The dsRNA agent, or a pharmaceutically acceptable salt thereof, of claim 7, wherein the ligand is an N-acetyl-galactosamine (GalNAc) derivative.

10. The dsRNA agent, or a pharmaceutically acceptable salt thereof, of claim 9, wherein the ligand is one or more GalNAc derivatives attached through a monovalent, bivalent, or trivalent linker.

11. The dsRNA agent, or a pharmaceutically acceptable salt thereof, of claim 10, wherein the ligand is

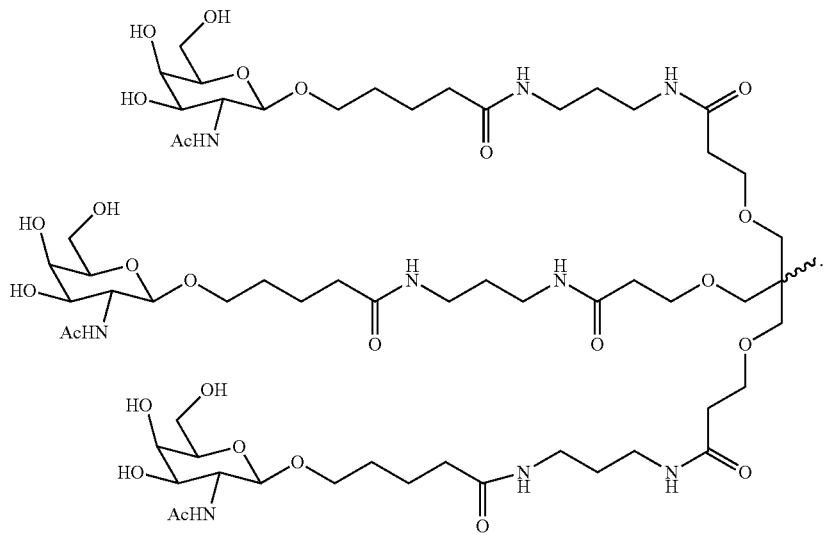 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

12. The dsRNA agent, or a pharmaceutically acceptable salt thereof, of claim 11, wherein the dsRNA agent, or a pharmaceutically acceptable salt thereof, is conjugated to the ligand as shown in the following schematic

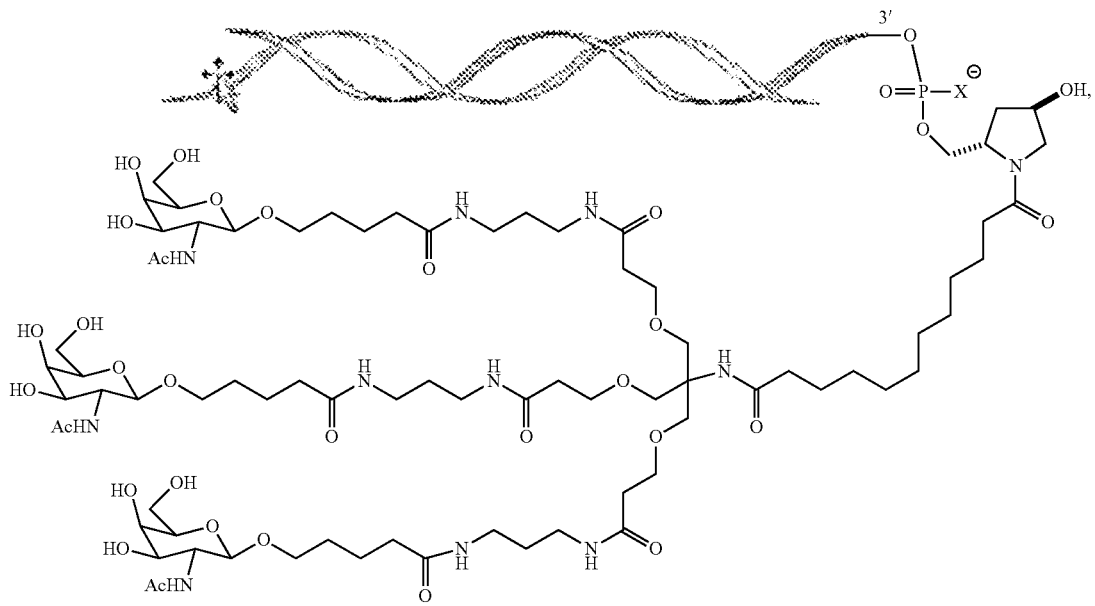

wherein X is O or S.

13. The dsRNA agent, or a pharmaceutically acceptable salt thereof, of claim 12, wherein X is O.

14. An isolated cell containing the dsRNA agent, or a pharmaceutically acceptable salt thereof, of claim 1.

15. A pharmaceutical composition comprising the dsRNA agent, or a pharmaceutically acceptable salt thereof, of claim 1.

16. The pharmaceutical composition of claim 15, wherein the dsRNA agent, or a pharmaceutically acceptable salt thereof, is in an unbuffered solution.

17. The pharmaceutical composition of claim 16, wherein the unbuffered solution is saline or water.

18. The pharmaceutical composition of claim 15, wherein the dsRNA agent, or a pharmaceutically acceptable salt thereof, is in a buffer solution.

19. The pharmaceutical composition of claim 18, wherein the buffer solution comprises acetate, citrate, prolamine, carbonate, or phosphate or any combination thereof.

20. The pharmaceutical composition of claim 19, wherein the buffer solution is phosphate buffered saline (PBS).

21. A double stranded ribonucleic acid (dsRNA) agent for inhibiting expression of complement component C3 in a cell, or a pharmaceutically acceptable salt thereof, comprising a sense strand comprising the nucleotide sequence 5'-gsasgccgUfuCfUfCfuacaauuacu-3' of SEQ ID NO:4188 and an antisense strand comprising the nucleotide sequence 5'-asGfsuaaUfuGfUfagagAfaCfggcucsgsg-3' of SEQ ID NO:4367, wherein a, g, c and u are 2'-O-methyl (2'-OMe) A, G, C, and U, respectively; Af, Gf, Cf, and Uf are 2'-fluoro A, G, C and U, respectively; and s is a phosphorothioate linkage, wherein the 3'-end of the sense strand of the dsRNA agent, or a pharmaceutically acceptable salt thereof, is conjugated to a ligand as shown in the following schematic

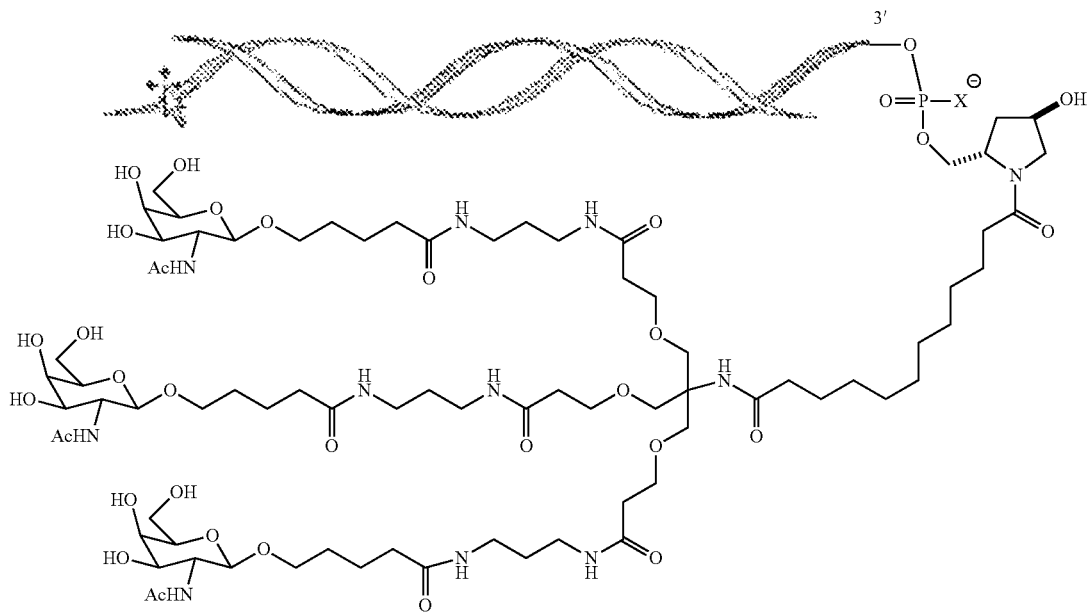

wherein X is O.

22. The dsRNA agent, or a pharmaceutically acceptable salt thereof, of claim 21, which is in a sodium salt form.

23. An isolated cell containing the dsRNA agent, or a pharmaceutically acceptable salt thereof, of claim 21.

24. A pharmaceutical composition comprising the dsRNA agent, or a pharmaceutically acceptable salt thereof, of claim 21.

25. A double stranded ribonucleic acid (dsRNA) agent for inhibiting expression of complement component C3 in a cell, or a pharmaceutically acceptable salt thereof, consisting of a sense strand consisting of the nucleotide sequence 5'-gsasgccgUfuCfUfCfuacaauuacu-3' of SEQ ID NO:4188 and an antisense strand consisting of the nucleotide sequence 5'-asGfsuaaUfuGfUfagagAfaCfggcucsgsg-3' of SEQ ID NO:4367, wherein a, g, c and u are 2'-O-methyl (2'-OMe) A, G, C, and U, respectively; Af, Gf, Cf, and Uf are 2'-fluoro A, G, C and U, respectively; and s is a phosphorothioate linkage, wherein the 3'-end of the sense strand of the dsRNA agent, or a pharmaceutically acceptable salt thereof, is conjugated to a ligand as shown in the following schematic

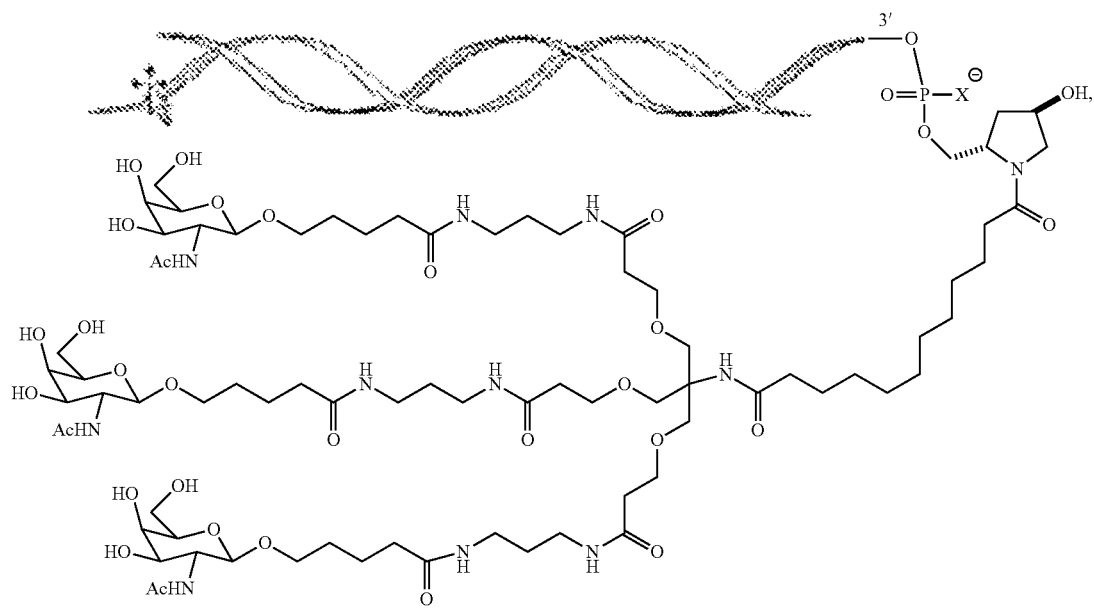
wherein X is O.
26. The dsRNA agent, or a pharmaceutically acceptable salt thereof, of claim 25, which is in a sodium salt form.
27. An isolated cell containing the dsRNA agent, or a pharmaceutically acceptable salt thereof, of claim 25.
28. A pharmaceutical composition comprising the dsRNA agent, or a pharmaceutically acceptable salt thereof, of claim 25.
* * * * *